(12) United States Patent
Li et al.

(10) Patent No.: US 11,813,334 B2
(45) Date of Patent: Nov. 14, 2023

(54) POLYETHYLENE GLYCOL CONJUGATE DRUG, AND PREPARATION METHOD THEREFOR AND USE THEREOF

(71) Applicant: CHONGQING UPGRA BIOTECHNOLOGY CO., LTD., Chongqing (CN)

(72) Inventors: Gaoquan Li, Chongqing (CN); Dajun Li, Chongqing (CN); Qian Zhang, Chongqing (CN); Diedie Li, Chongqing (CN); Chengzhi Gao, Chongqing (CN); Yue Liu, Chongqing (CN); Xiaoling Ding, Chongqing (CN); Yusong Wei, Chongqing (CN); Xiangwei Yang, Chongqing (CN); Yongchen Peng, Chongqing (CN); Jia Gao, Chongqing (CN); Qiang Luo, Chongqing (CN); Yanxia Heng, Chongqing (CN); Mei Liu, Chongqing (CN); Yuyang Yi, Chongqing (CN); Xiafan Zeng, Chongqing (CN); Tao Tu, Chongqing (CN); Xiao Tang, Chongqing (CN); Xi Liu, Chongqing (CN); Jianhuan Li, Chongqing (CN); Zhaojie Wang, Chongqing (CN); Bin Wang, Chongqing (CN); Jinping Wan, Chongqing (CN); Mingyang Hou, Chongqing (CN); Jiao Liu, Chongqing (CN); Huiyu Chen, Chongqing (CN); Jie Lou, Chongqing (CN); Yue Yang, Chongqing (CN); Yuanqiang Wang, Chongqing (CN)

(73) Assignee: CHONGQING UPGRA BIOTECHNOLOGY CO., LTD., Chongqing (CN)

( * ) Notice: Subject to any disclaimer, the term of this patent is extended or adjusted under 35 U.S.C. 154(b) by 40 days.

(21) Appl. No.: 17/779,825

(22) PCT Filed: Mar. 11, 2020

(86) PCT No.: PCT/CN2020/078713
§ 371 (c)(1),
(2) Date: May 25, 2022

(87) PCT Pub. No.: WO2021/103342
PCT Pub. Date: Jun. 3, 2021

(65) Prior Publication Data
US 2023/0101564 A1    Mar. 30, 2023

(30) Foreign Application Priority Data
Nov. 28, 2019    (CN) .......................... 201911192038.2

(51) Int. Cl.
A61K 47/60    (2017.01)
A61P 35/00    (2006.01)
A61K 47/64    (2017.01)

(52) U.S. Cl.
CPC ............ *A61K 47/60* (2017.08); *A61K 47/641* (2017.08); *A61P 35/00* (2018.01)

(58) Field of Classification Search
None
See application file for complete search history.

(56) References Cited

U.S. PATENT DOCUMENTS

| 2014/0363371 A1 | 12/2014 | Luo et al. |
| 2020/0261588 A1 | 8/2020 | Li et al. |

(Continued)

FOREIGN PATENT DOCUMENTS

| CN | 1876187 A | 12/2006 |
| CN | 104105508 A | 10/2014 |

(Continued)

OTHER PUBLICATIONS

International Search Report, International Application No. PCT/CN2020/078713, dated Aug. 20, 2021 (6 pages).

(Continued)

*Primary Examiner* — Karl J Puttlitz
(74) *Attorney, Agent, or Firm* — Ware, Fressola, Maguire & Barber LLP

(57) ABSTRACT

The present invention relates to the technical field of medicines, and relates to a polyethylene glycol conjugated drug, a preparation method therefor and the use thereof. In particular, the present invention relates to a polyethylene glycol conjugated drug as shown in formula I or a pharmaceutically acceptable salt thereof. The present invention also relates to a method for preparing the polyethylene glycol conjugated drug or the pharmaceutically acceptable salt thereof, a (Continued)

pharmaceutical composition comprising the polyethylene glycol conjugated drug or the pharmaceutically acceptable salt thereof, and the use thereof in the preparation of a drug.

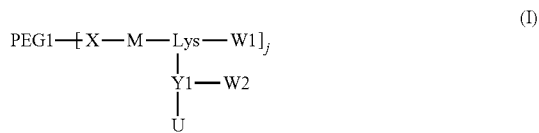

(I)

23 Claims, 4 Drawing Sheets

(56) References Cited

U.S. PATENT DOCUMENTS

| 2021/0023231 A1* | 1/2021 | Yoshioka | C07K 7/06 |
| 2021/0147624 A1* | 5/2021 | Yoshioka | C08L 71/02 |

FOREIGN PATENT DOCUMENTS

| CN | 104987504 A | 10/2015 |
| CN | 105601903 A | 5/2016 |
| CN | 107670048 A | 2/2018 |
| CN | 107670050 A | 2/2018 |

OTHER PUBLICATIONS

Written Opinion, International Application No. PCT/CN2020/078713, dated Aug. 20, 2021 (3 pages).

* cited by examiner

POLYETHYLENE GLYCOL CONJUGATE DRUG, AND PREPARATION METHOD THEREFOR AND USE THEREOF

TECHNICAL FIELD

The disclosure belongs to the technical field of medicine, and relates to a polyethylene glycol conjugated drug, and a preparation method therefor and use thereof.

BACKGROUND

Compared with the original drug, PEGylated drugs have huge advantages. They can increase the water solubility of drug molecules and this is important for molecules with extremely low solubility such as paclitaxel, camptothecin, or platinum derivatives. They also can prevent or reduce the agglomeration, immunogenicity and antigenicity of drugs. Most small-molecule drugs can only stay in the blood circulation for a few minutes, while polymer-(anticancer drug) conjugates can stay for tens, hundreds of hours or even longer, which is conducive to "enhanced penetration and retention" effect, i.e., EPR effect, caused by leakage of tumor capillaries. Due to increase in hydrodynamic volume, the renal elimination of the drug can be weakened, the drug can be protected from enzymatic degradation, the half-life of the drug in the plasma can be extended, and the bioavailability of the drug can be increased. The anticancer drugs can be highly enriched in cancerous organs, tissues or cells through passive or active targeting of the polymer-(anticancer drug) conjugates, thus greatly reducing the toxic side effects caused by small molecule drugs spreading all over the body. The cell absorption of drugs can be limited to the endocytic pathway, which is conducive to drug delivery to the lysosome, thereby avoiding drug resistance caused by p-glycoprotein pumping. The polymer-(anticancer drug) conjugates can also stimulate or restore immune function, which is conducive to killing cancer cells.

The polyethylene glycol conjugated drug technology of NEKTAR and ENZON of the United States has achieved great success. So far, 15 drugs have been approved by the US FDA to enter the market. In addition, 36 new clinical drugs are undergoing phase I, phase II, and phase III clinical trials or entering the NDA phase. However, all of the above PEGylated drugs are single-dose PEGylated drugs.

As disclosed in Chinese patent ZL201510996205.4, a chemotherapeutic drug gemcitabine and a Chk1 inhibitor AZD7762 are simultaneously grafted onto a four-arm polyethylene glycol carrier. The Chk1 inhibitor itself has no anti-cancer effect, but it can enhance the efficacy of the chemotherapeutic drug when combined with the chemotherapy drug gemcitabine. As disclosed in Chinese patents ZL201710761441.7 and ZL201710761572.5, two anticancer drugs are simultaneously grafted onto a grafting site of polyethylene glycol to achieve inhibition of cancer cells through different biological signal pathways or targets, as well as free combination of different treatment modalities.

SUMMARY

The existing polyethylene glycol conjugated drugs have the following problems: with the increase of drug loading, the dissolution of polyethylene glycol conjugated drugs (especially four-arm or eight-arm polyethylene glycol conjugated drugs) in saline will usually be severely deteriorated, or even become completely insoluble, which limits the concentration in the liquid formulation (e.g., injections with saline as a carrier), thus bringing inconvenience to the application of the drug.

According to the disclosure, by coupling a single-arm polyethylene glycol to a specific position on polyethylene glycol conjugated drugs (such as four-arm or eight-arm polyethylene glycol conjugated drugs), the solubility of polyethylene glycol conjugated drugs in saline can be greatly improved, and thus the above technical problems can be solved.

BRIEF SUMMARY

In one aspect, the disclosure relates to a polyethylene glycol conjugated drug of formula (I) or a pharmaceutically acceptable salt thereof;

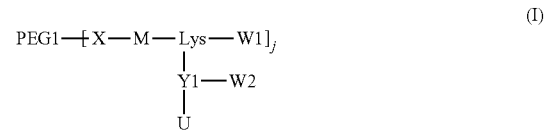

wherein PEG1 is a single-arm or multi-arm polyethylene glycol segment, j represents the number of arms of PEG1, X, M, Y1, U, W1, and W2 are defined as follows, and Lys represents a lysine residue.

In one aspect, the disclosure provides a pharmaceutical composition, including the polyethylene glycol conjugated drug of the disclosure or a pharmaceutically acceptable salt thereof in a therapeutically and/or prophylactically effective amount.

In one aspect, the disclosure provides use of the polyethylene glycol conjugated drug of the disclosure or a pharmaceutically acceptable salt thereof in the preparation of a medicament for treating and/or preventing a disease (such as a cancer). The disease refers to a disease treated by an active ingredient in the polyethylene glycol conjugated drug.

In one aspect, the disclosure further provides an injection solution, comprising the polyethylene glycol conjugated drug of the disclosure or a pharmaceutically acceptable salt thereof, or the pharmaceutical composition of the disclosure.

The disclosure further provides a method for preparing the polyethylene glycol conjugated drug of the disclosure or a pharmaceutically acceptable salt thereof.

DETAILED SUMMARY

1. Polyethylene Glycol Conjugated Drug or Pharmaceutically Acceptable Salt Thereof In one aspect, the disclosure relates to a polyethylene glycol conjugated drug of formula (I) or a pharmaceutically acceptable salt thereof;

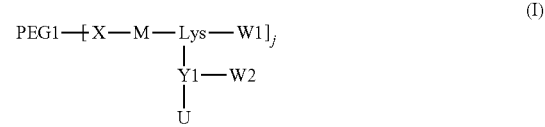

wherein Lys represents a lysine residue, PEG1 is a single-arm or multi-arm polyethylene glycol segment, and j represents the number of arms of PEG1;

X represents carbonyl; M represents GFLG;

Y1 is selected from:

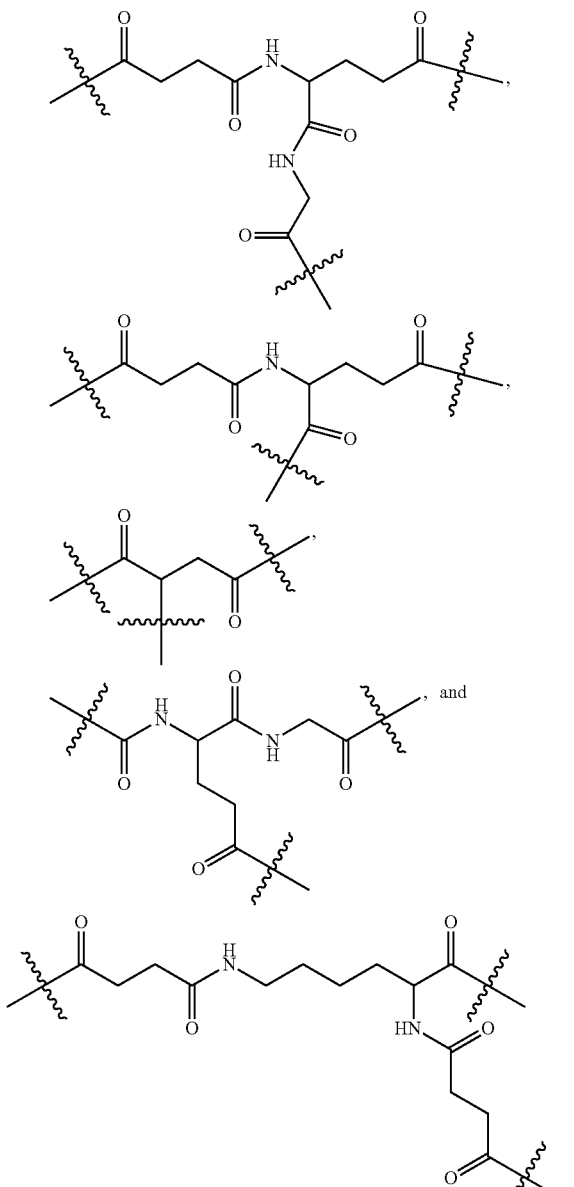

when j is greater than 1 (such as, 4 or 8), there will be multiple (such as, 4 or 8) Y1s at the same time, and in this case, the Y1s may be the same or different;
W1 is selected from:

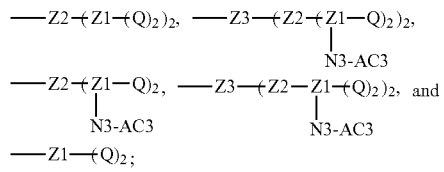

when j is greater than 1 (such as, 4 or 8), there will be multiple (such as, 4 or 8) W1s at the same time, and in this case, the W1s may be the same or different;

Q represents

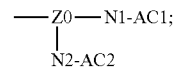

each of Z0, Z1, Z2 and Z3 is independently selected from

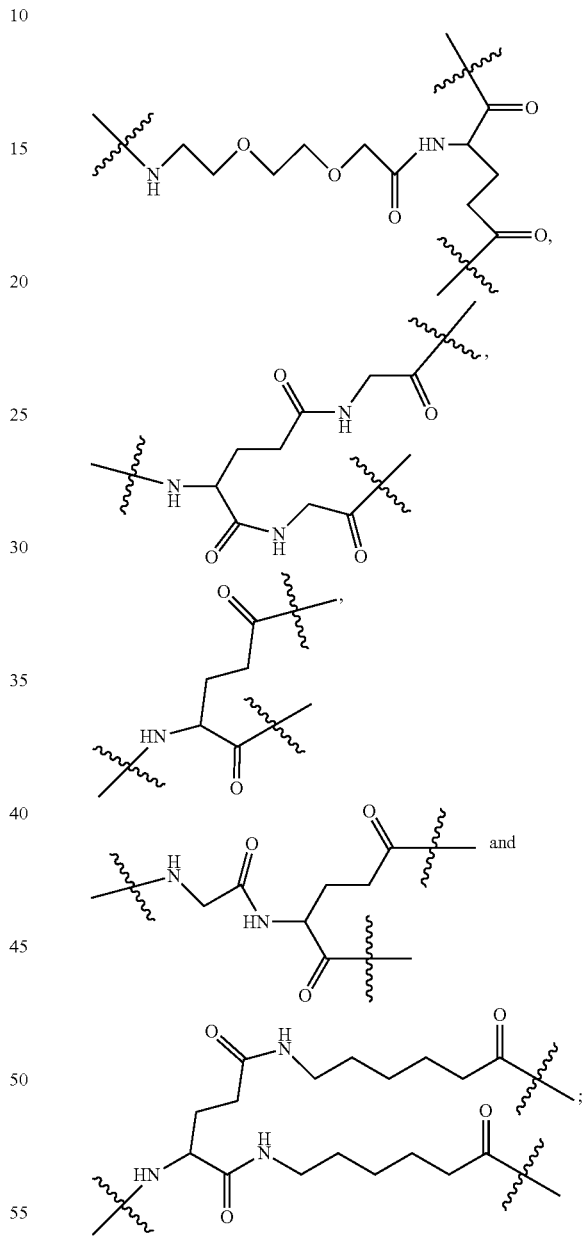

Z0, Z1, Z2, and Z3 may be the same or different, and when there are multiple Z0s, multiple Z1s, multiple Z2s, or multiple Z3s at the same time, the Z0s are the same or different, the Z1s are the same or different, the Z2s are the same or different, or the Z3s are the same or different;

each of N1, N2 and N3 independently is G or GFLG; N1, N2 and N3 are the same or different, and when there are multiple N1s, multiple N2s or multiple N3s at the same time, the N1s are the same or different, the N2s are the same or different, or the N3s are the same or different;

AC1, AC2 and AC3 are drug molecules (for example, drug molecules with anti-tumor activity); AC1, AC2 and AC3 are the same or different, and when there are multiple AC1s, multiple AC2s or multiple AC3s at the same time, the AC1s are the same or different, the AC2s are the same or different, or the AC3s are the same or different;

W2 is selected from H, N1'-AC1', Q',

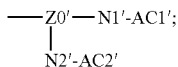 and Z2'—(Z1'—(Q')$_2$)$_2$;

when j is greater than 1 (such as, 4 or 8), there will be multiple (such as, 4 or 8) W2s at the same time, and in this case, the W2s may be the same or different;

Q' represents

—Z0'—N1'-AC1';
   |
   N2'-AC2' each of Z0', Z1' and Z2' is independently selected from:

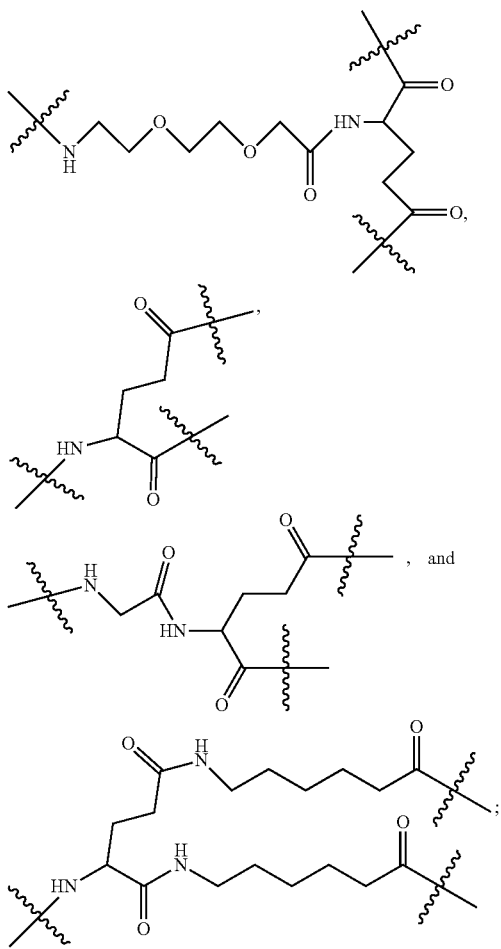

Z0', Z1' and Z2' may be the same or different, and when there are multiple Z0's, multiple Z1's or multiple Z2's at the same time, the Z0's are the same or different, the Z1's are the same or different, or the Z2's are the same or different;

each of N1' and N2' independently is G or GFLG; N1' and N2' are the same or different, and when there are multiple N1's or multiple N2's at the same time, the N1's are the same or different or the N2's are the same or different;

AC1' and AC2' are drug molecules (for example, drug molecules with anti-tumor activity); AC1' and AC2' are the same or different, and when there are multiple AC1's or multiple AC2's at the same time, the AC1's are the same or different or the AC2's are the same or different;

U represents PEG2 or

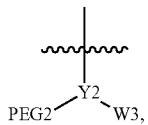

wherein PEG2 represents a single-arm polyethylene glycol segment, which is linked to Y1 or Y2 through an amide bond;

Y2 represents

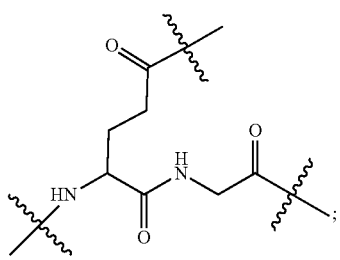 [SMILES: *NC(CCC(*)=O)C(=O)NCC(*)=O]

W3 represents N1"-AC1", wherein N1" is GFLG and AC1" is a drug molecule (for example, a drug molecule with anti-tumor activity).

In some embodiments, the polyethylene glycol conjugated drug of the disclosure or a pharmaceutically acceptable salt thereof is characterized in one or more of the following:

(1) PEG1 is a four-arm or eight-arm polyethylene glycol segment;
(2) PEG1 has a number-average molecular weight of 5 k-10 k, 10 k-20 k or 20 k-40 k;
(3) PEG2 has a number-average molecular weight of 5 k-10 k or 10 k-20 k;
(4) each of AC1, AC2, AC3, AC1', AC2', and AC1" is independently selected from MK2, LPT, PCB, SB7, PKI, and NPB;
(5) M is linked to an α-amino group on Lys;
(6) M is linked to an ε-amino group on Lys;
(7) N1, N2 and N3 are all GFLG;
(8) N1 and N2 are both GFLG;
(9) N1 and N2 are both G; and
(10) N1' and N2' are both GFLG.

In some embodiments, in the polyethylene glycol conjugated drug of the disclosure or a pharmaceutically acceptable salt thereof, AC1 and AC2 are selected from:

(1) a combination in which AC1 is MK2 and AC2 is PCB;
(2) a combination in which AC1 and AC2 are both PCB;

(3) a combination in which AC1 and AC2 are both LPT;
(4) a combination in which AC1 is PCB and AC2 is SB7;
(5) a combination in which AC1 and AC2 are both SB7;
(6) a combination in which AC1 and AC2 are both PKA;
(7) a combination in which AC1 and AC2 are both SN38; and
(8) a combination in which AC1 is LPT and AC2 is PCB.

In some embodiments, in the polyethylene glycol conjugated drug of the disclosure or a pharmaceutically acceptable salt thereof, AC1, AC2 and AC3 are selected from:
(1) a combination in which AC1, AC2 and AC3 are all LPT; and
(2) a combination in which AC1 and AC2 are both PCB and AC3 is SB7.

In some embodiments, in the polyethylene glycol conjugated drug of the disclosure or a pharmaceutically acceptable salt thereof, AC1' and AC2' are selected from:
(1) a combination in which AC1' and AC2' are both PCB;
(2) a combination in which AC1' is PCB and AC2' is SB7;
(3) a combination in which AC1' and AC2' are both LPT; and
(4) a combination in which AC1' is LPT and AC2' is PCB.

In some embodiments, the polyethylene glycol conjugated drug of the disclosure has a structure of formula (II):

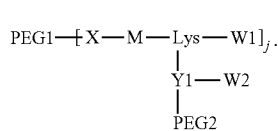

(II)

In some embodiments, in the polyethylene glycol conjugated drug of formula (II),

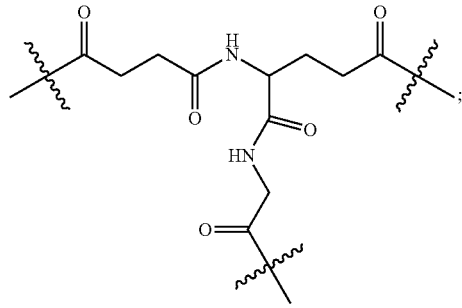 [SMILES: *C(=O)CCC(=O)NC(CCC(*)=O)C(=O)NCC(*)=O]

Y1 is

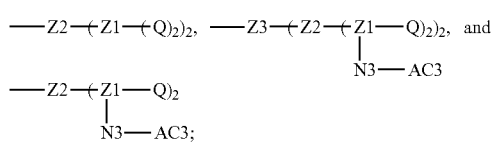

W1 is selected from
W2 is N1'-AC1';

In some embodiments, PEG1 is a four-arm polyethylene glycol segment with a number-average molecular weight of 10 k-20 k or 20 k-40 k;

In some embodiments, the number-average molecular weight of PEG2 is 10 k-20 k;

In some embodiments, N1' is GFLG;

In some embodiments, AC1' is SB7;

In some embodiments, W1 is selected from:

(1)

wherein Z2 is

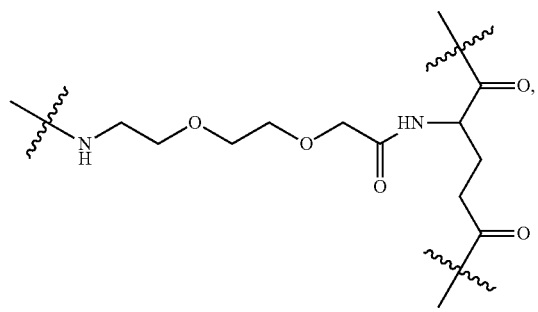 [SMILES: *NCCOCCOCC(=O)NC(CCC(*)=O)C(*)=O]

Z1 is

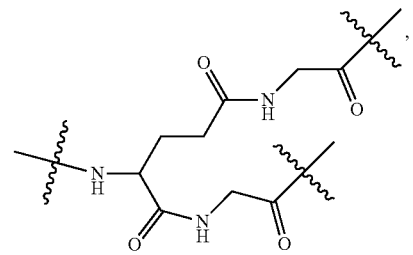 [SMILES: *NC(CCC(=O)NCC(*)=O)C(=O)NCC(*)=O]

and Z0 is

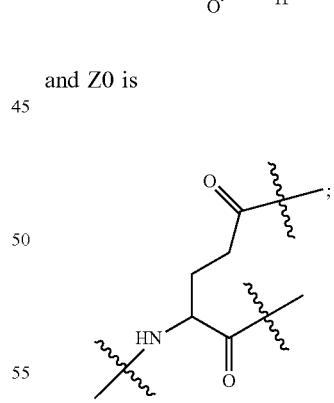

in some embodiments, N1 and N2 are both GFLG, AC1 is MK2, and AC2 is PCB;

(2)

wherein Z3 and Z1 are both

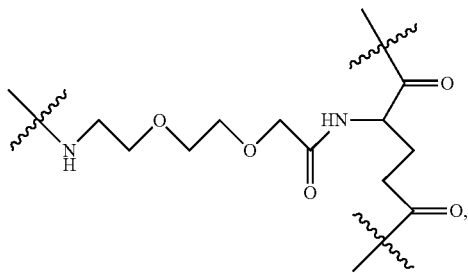 [SMILES: *NCCOCCOCC(=O)NC(CCC(*)=O)C(*)=O]

and Z2 and Z0 are both

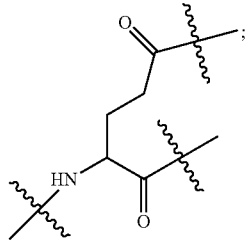 [SMILES: *NC(CCC(*)=O)C(*)=O]

in some embodiments, N1, N2 and N3 are all GFLG and AC1, AC2 and AC3 are all LPT;

$$—Z2—(Z1—Q)_2 \atop \ \ \ \ \ \ \ \ \ \ \ |\ \ \ \ \ N3—AC3,$$ (3)

wherein Z2 is

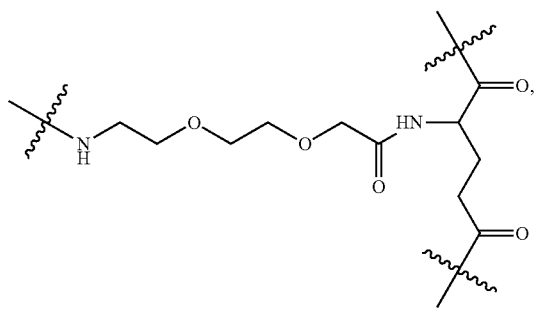 [SMILES: *NCCOCCOCC(=O)NC(CCC(*)=O)C(*)=O]

and Z1 and Z0 are both

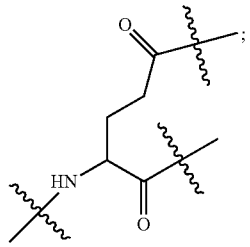 [SMILES: *NC(CCC(*)=O)C(*)=O]

in some embodiments, N1, N2 and N3 are all GFLG and AC1, AC2 and AC3 are all LPT; and $$—Z2—(Z1—(Q)_2)_2,$$ (4)

wherein Z2 is

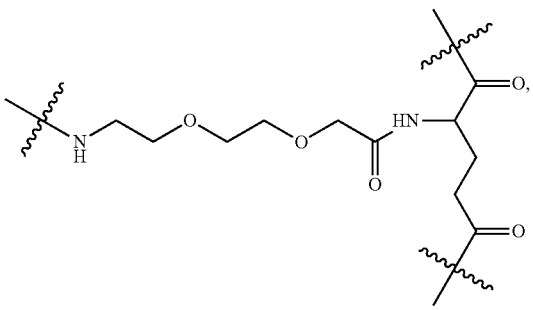 [SMILES: *NCCOCCOCC(=O)NC(CCC(*)=O)C(*)=O]

Z1 is

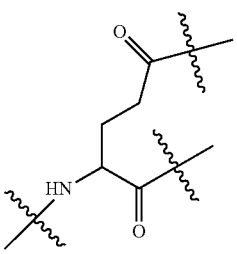 [SMILES: *NC(CCC(*)=O)C(*)=O]

and Z0 is

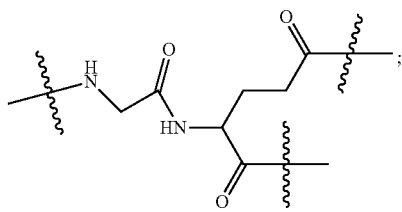 [SMILES: *NCC(=O)NC(CCC(*)=O)C(*)=O]

in some embodiments, N1 and N2 are both GFLG and AC1 and AC2 are both PCB;

In some embodiments, the polyethylene glycol conjugated drug has a structure selected from:

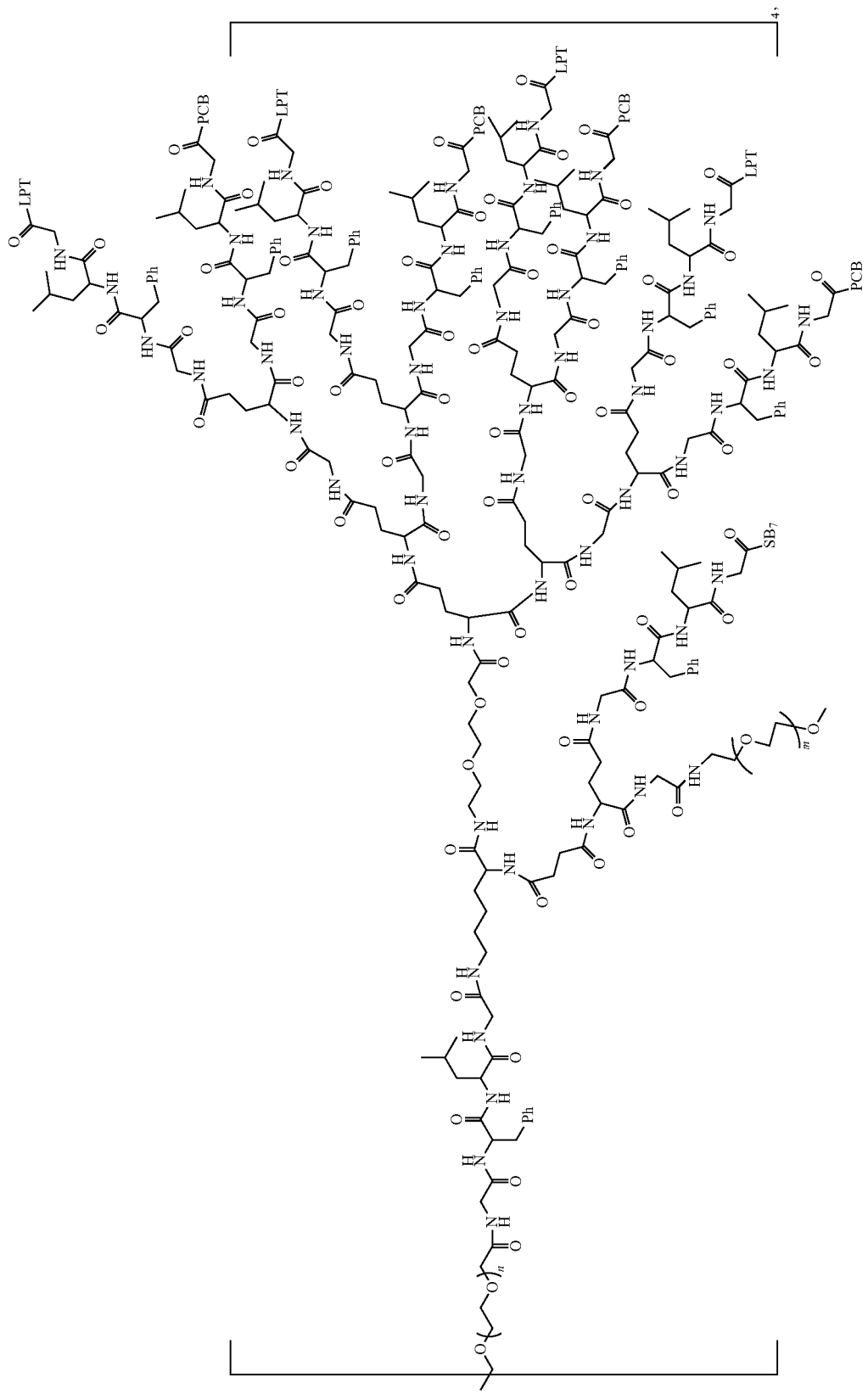

-continued
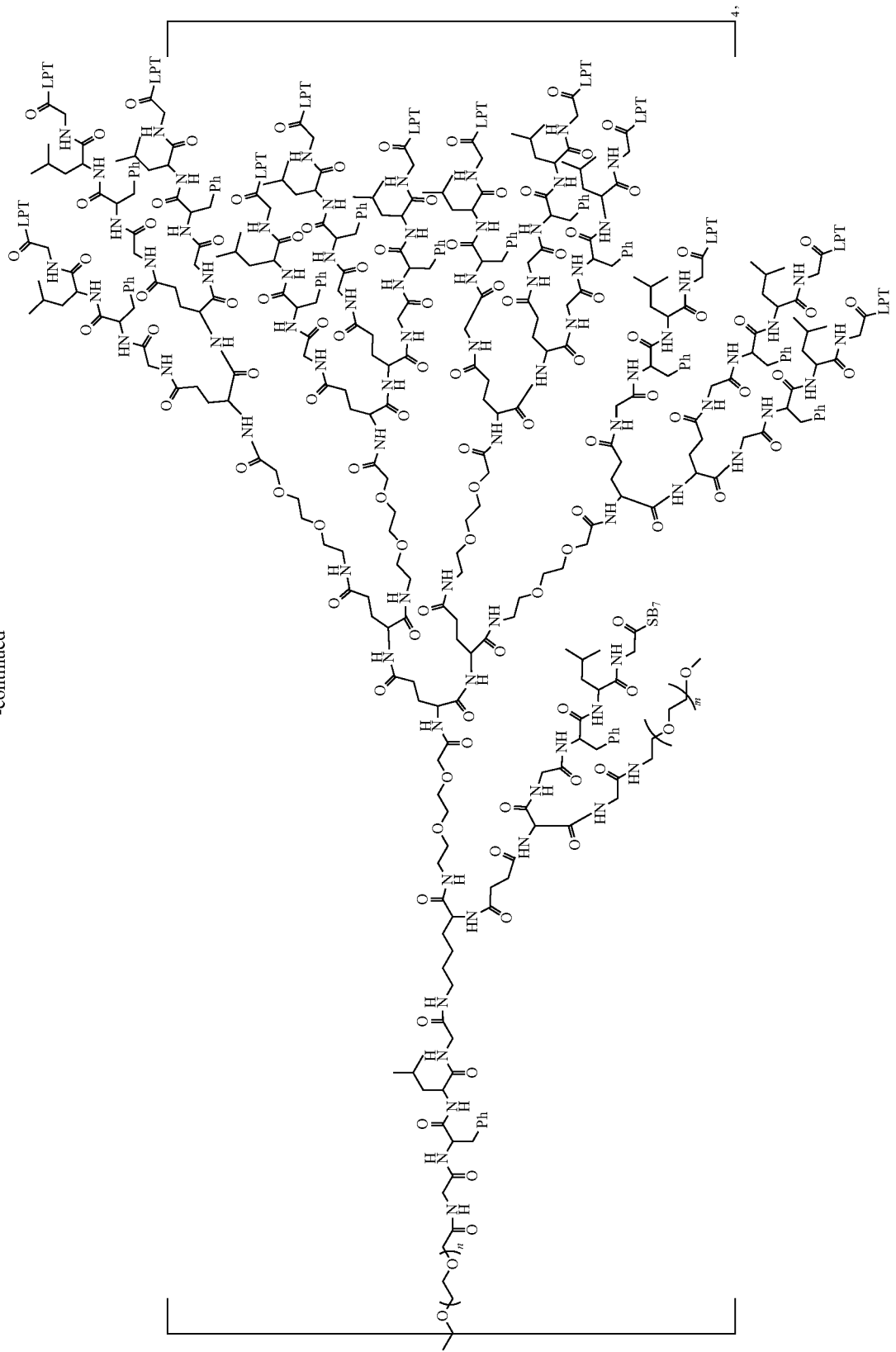

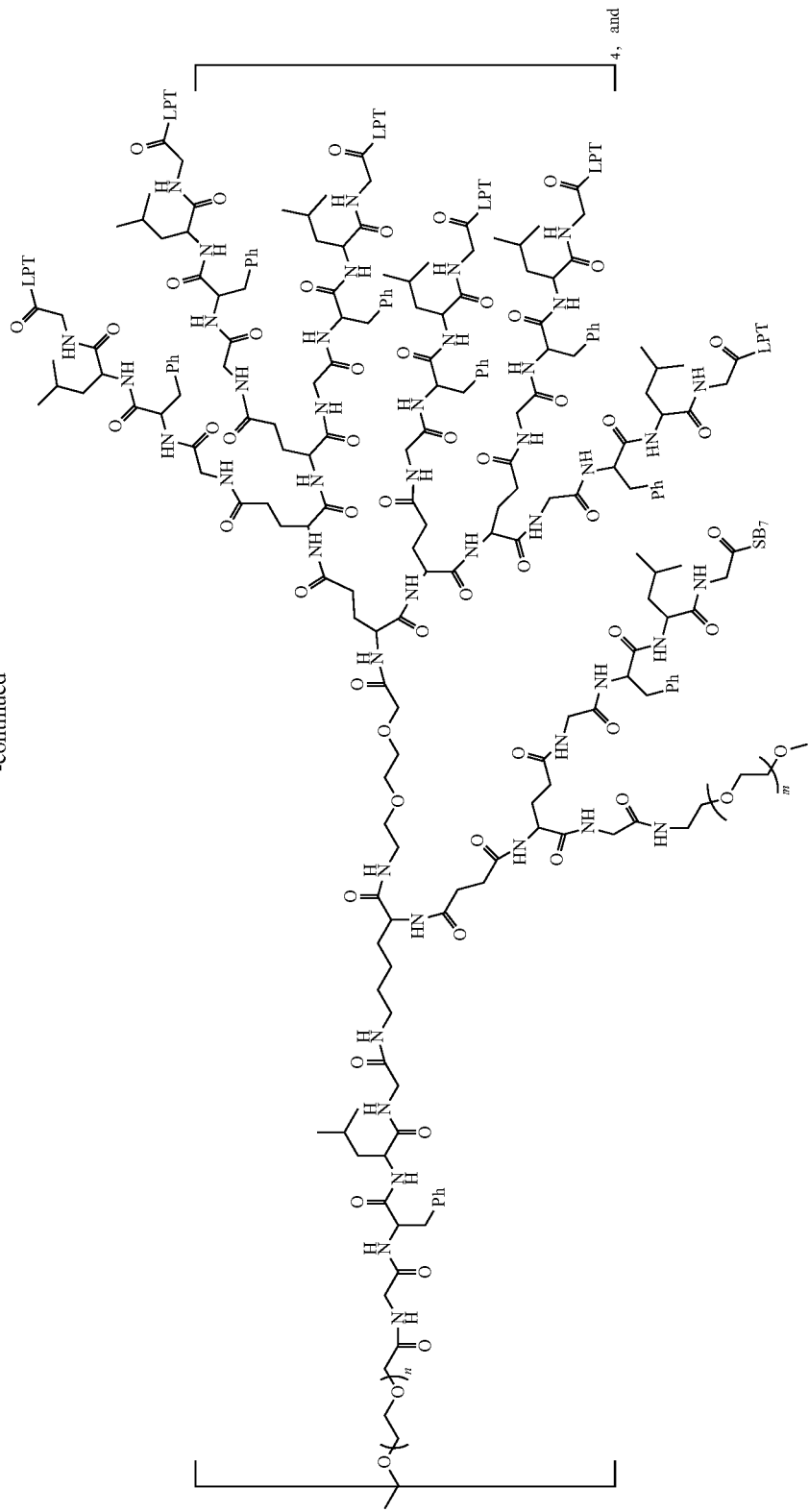

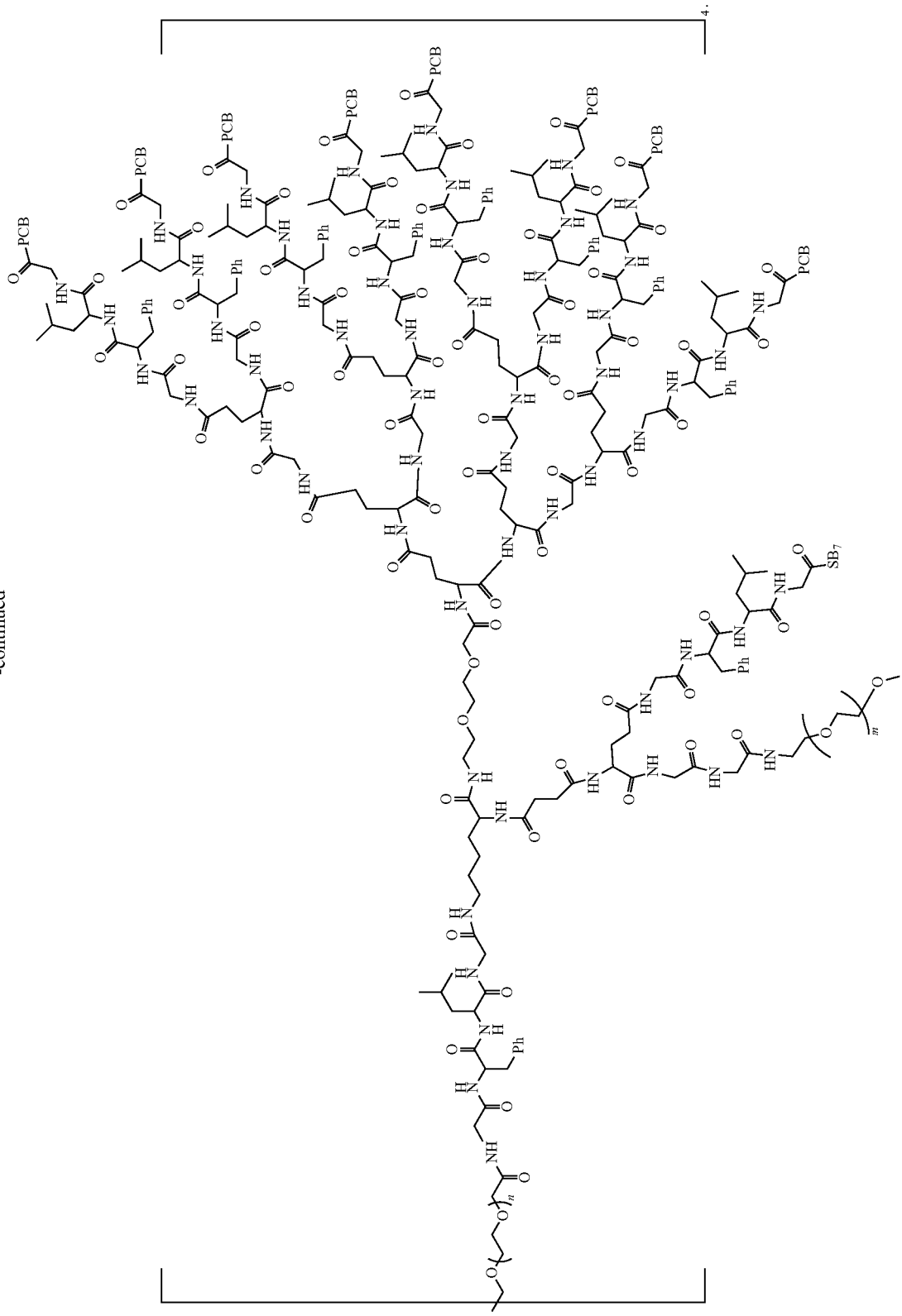

In some embodiments, in the polyethylene glycol conjugated drug of formula (II), Y1 is

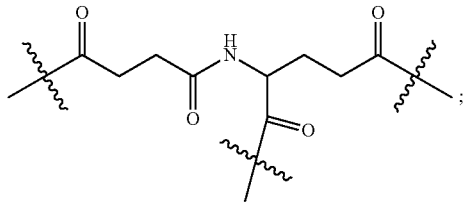 [SMILES: *C(=O)CCC(=O)NC(CCC(*)=O)C(*)=O]

W1 is selected from

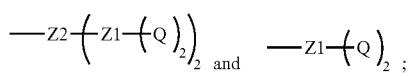

W2 is selected from N1'-AC1',

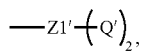

and Q';

In some embodiments, PEG1 is a four-arm or eight-arm polyethylene glycol segment with a number-average molecular weight of 10 k-20 k or 20 k-40 k;

In some embodiments, the number-average molecular weight of PEG2 is 5 k-10 k or 10 k-20 k;

In some embodiments, W1 is selected from:

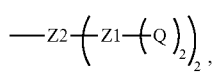 (1)

wherein Z2 is

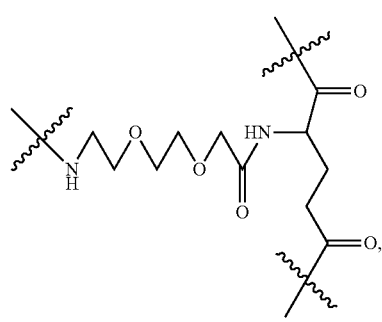 [SMILES: *NCCOCCOCC(=O)NC(CCC(*)=O)C(*)=O]

Z1 is

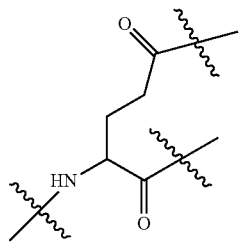 [SMILES: *NC(CCC(*)=O)C(*)=O]

and Z0 is

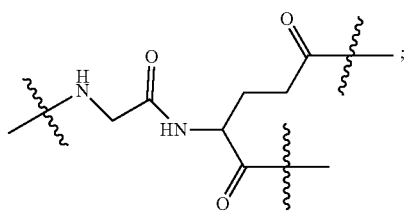 [SMILES: *NCC(=O)NC(CCC(*)=O)C(*)=O]

in some embodiments, N1 and N2 are both GFLG and AC1 and AC2 are both LPT; and

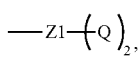 (2)

wherein Z1 is

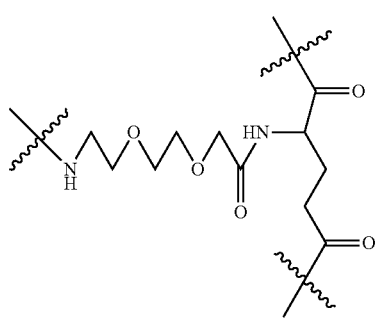 [SMILES: *NCCOCCOCC(=O)NC(CCC(*)=O)C(*)=O]

and Z0 is

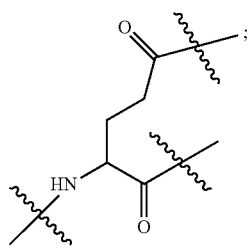 [SMILES: *NC(CCC(*)=O)C(*)=O]

in some embodiments, N1 and N2 are both GFLG and AC1 and AC2 are both PKA.

In some embodiments, W2 is selected from:
N1'-AC1', wherein N1' is GFLG and AC1' is PCB;
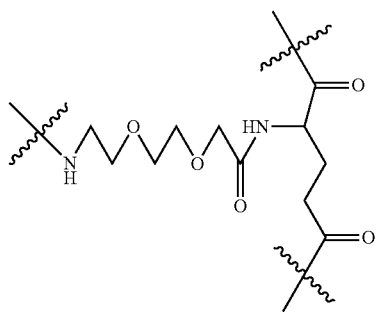 [SMILES: *NCCOCCOCC(=O)NC(CCC(*)=O)C(*)=O]
wherein Z1' is
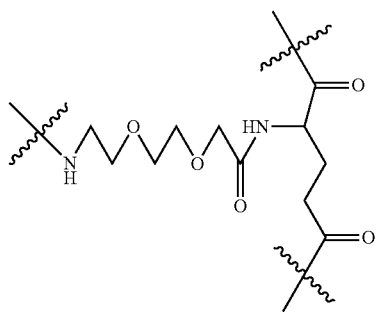 [SMILES: *NCCOCCOCC(=O)NC(CCC(*)=O)C(*)=O]
and Z0' is
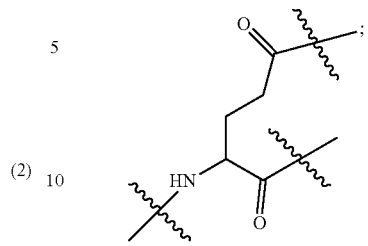
in some embodiments, N1' and N2' are both GFLG and AC1' and AC2' are both PCB;
(3) Q', wherein Z0' is
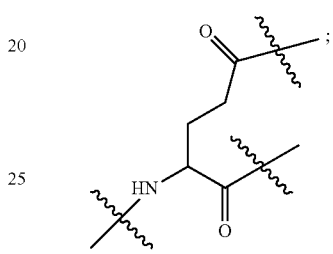
in some embodiments, N1' and N2' are both GFLG, AC1' and AC2' are both PCB;
In some embodiments, the polyethylene glycol conjugated drug has a structure selected from:

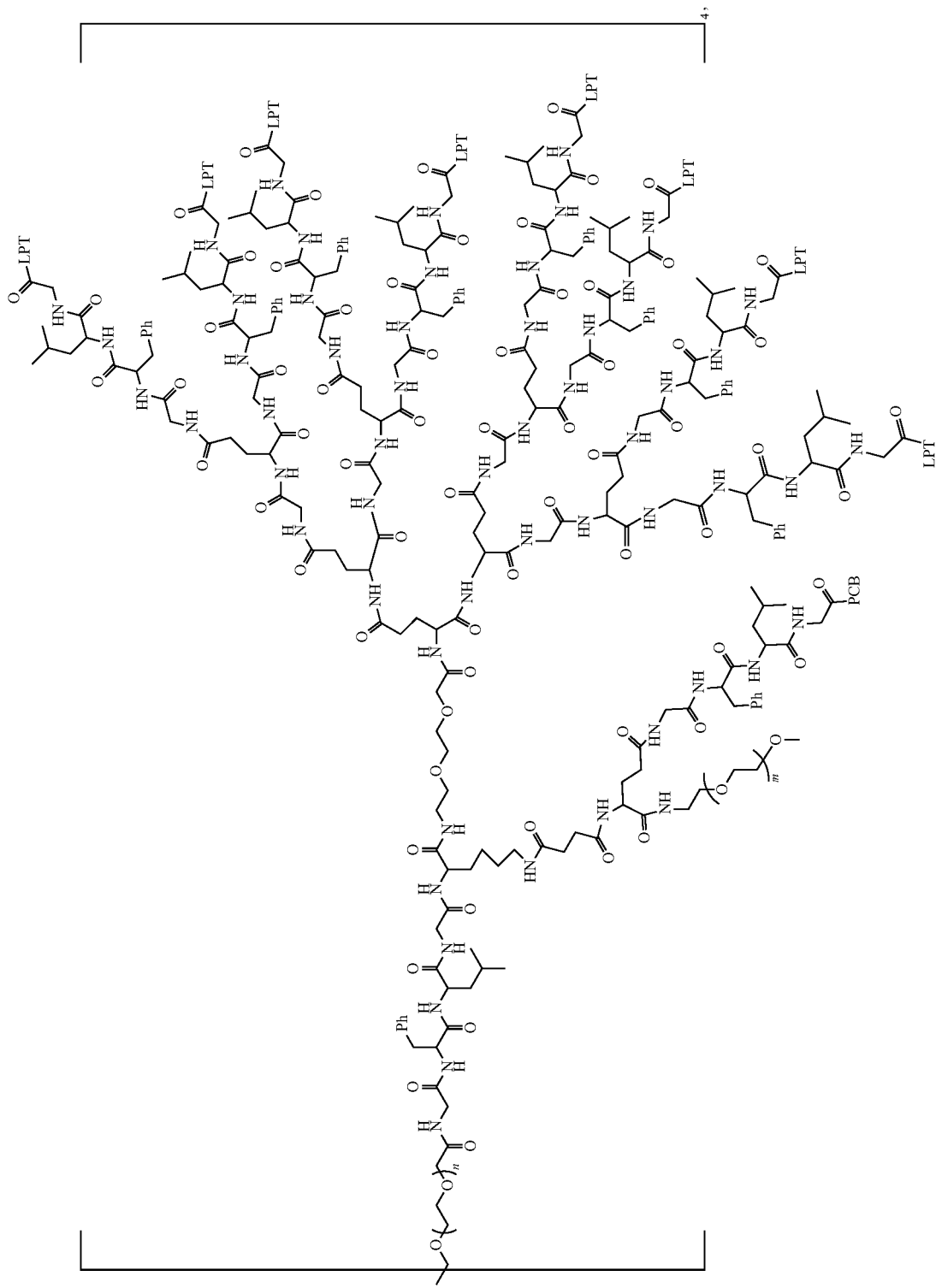

-continued
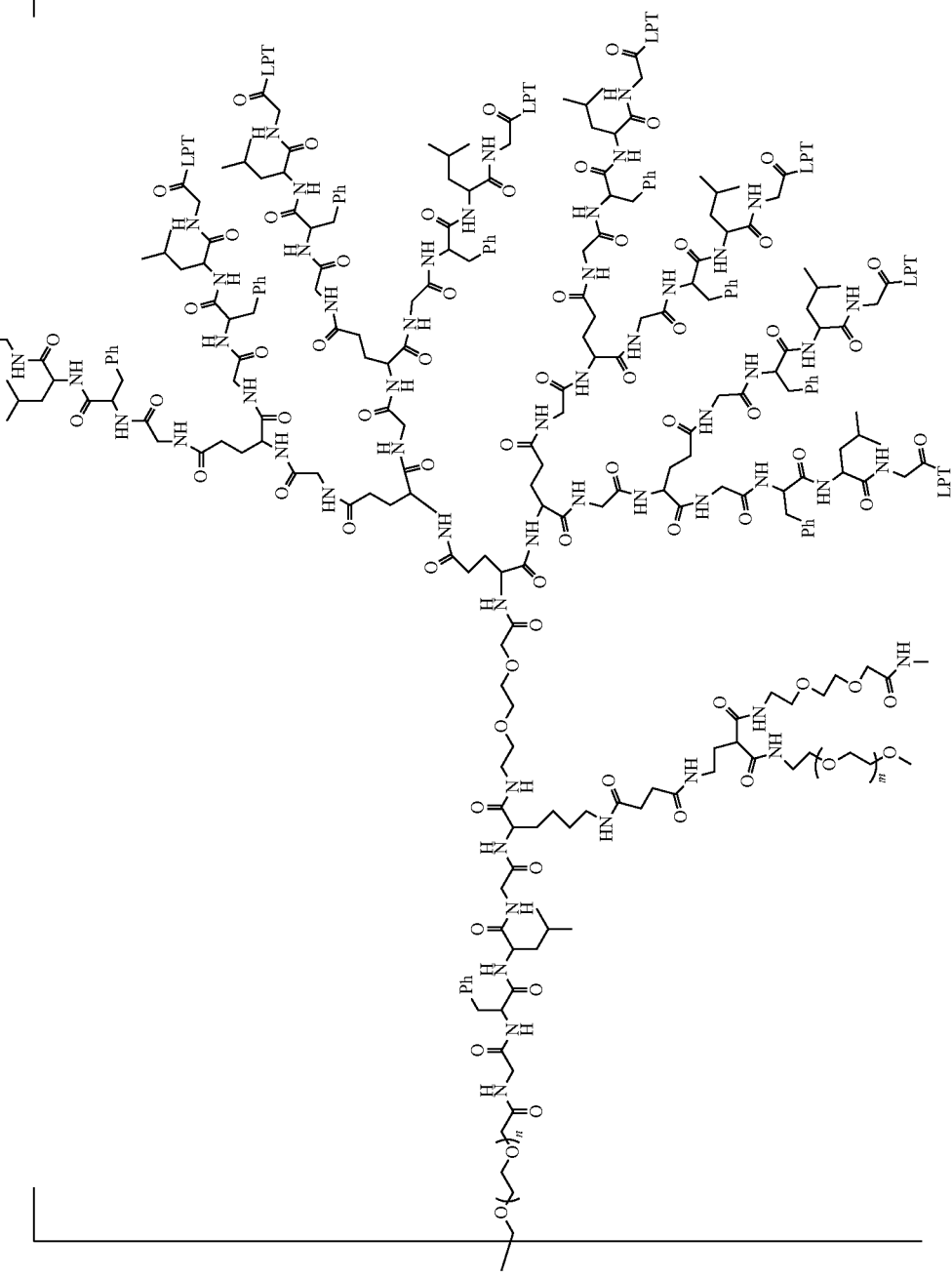

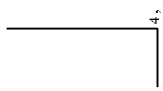
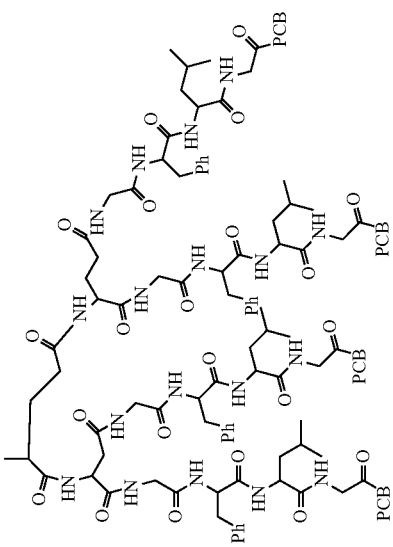

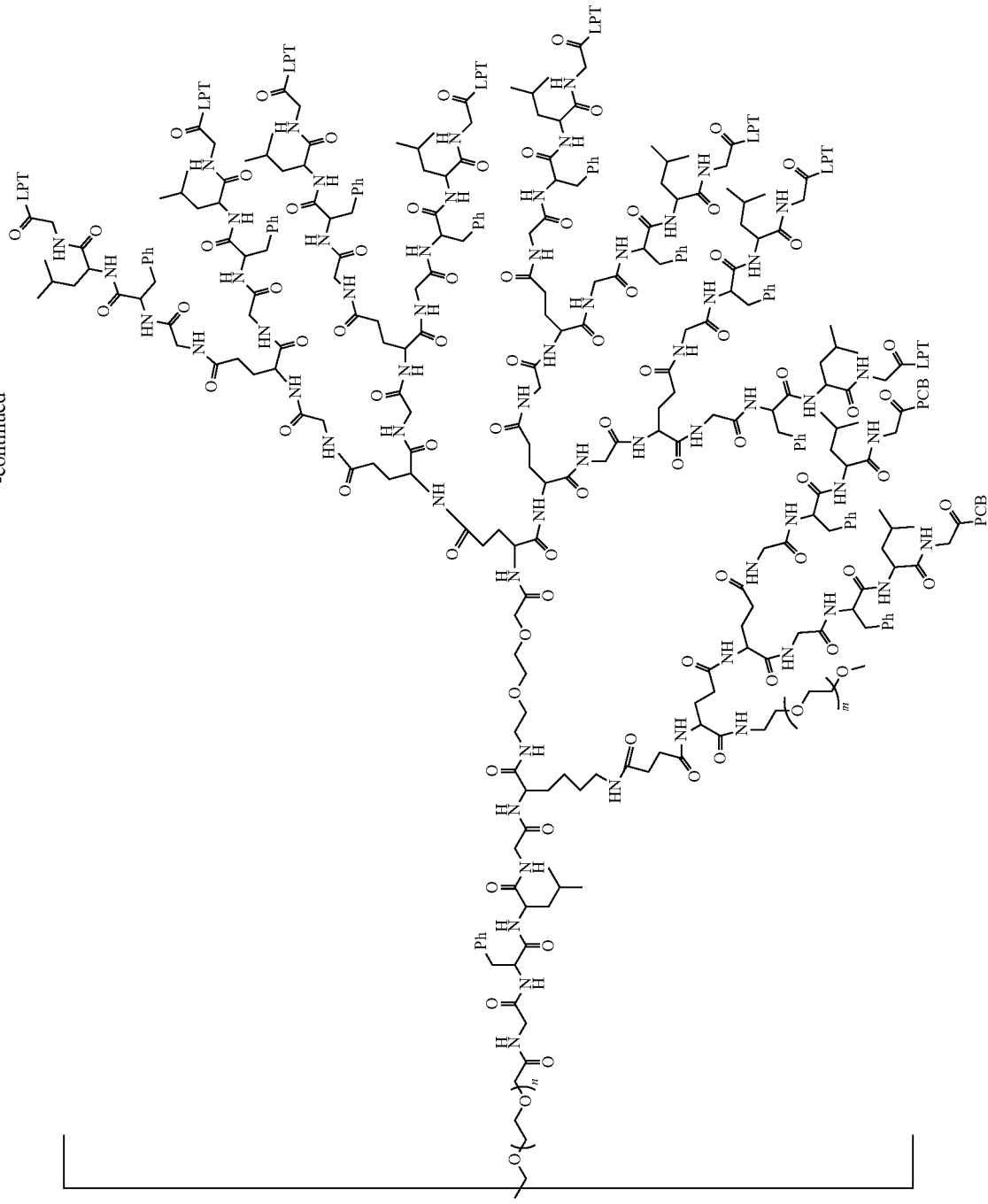

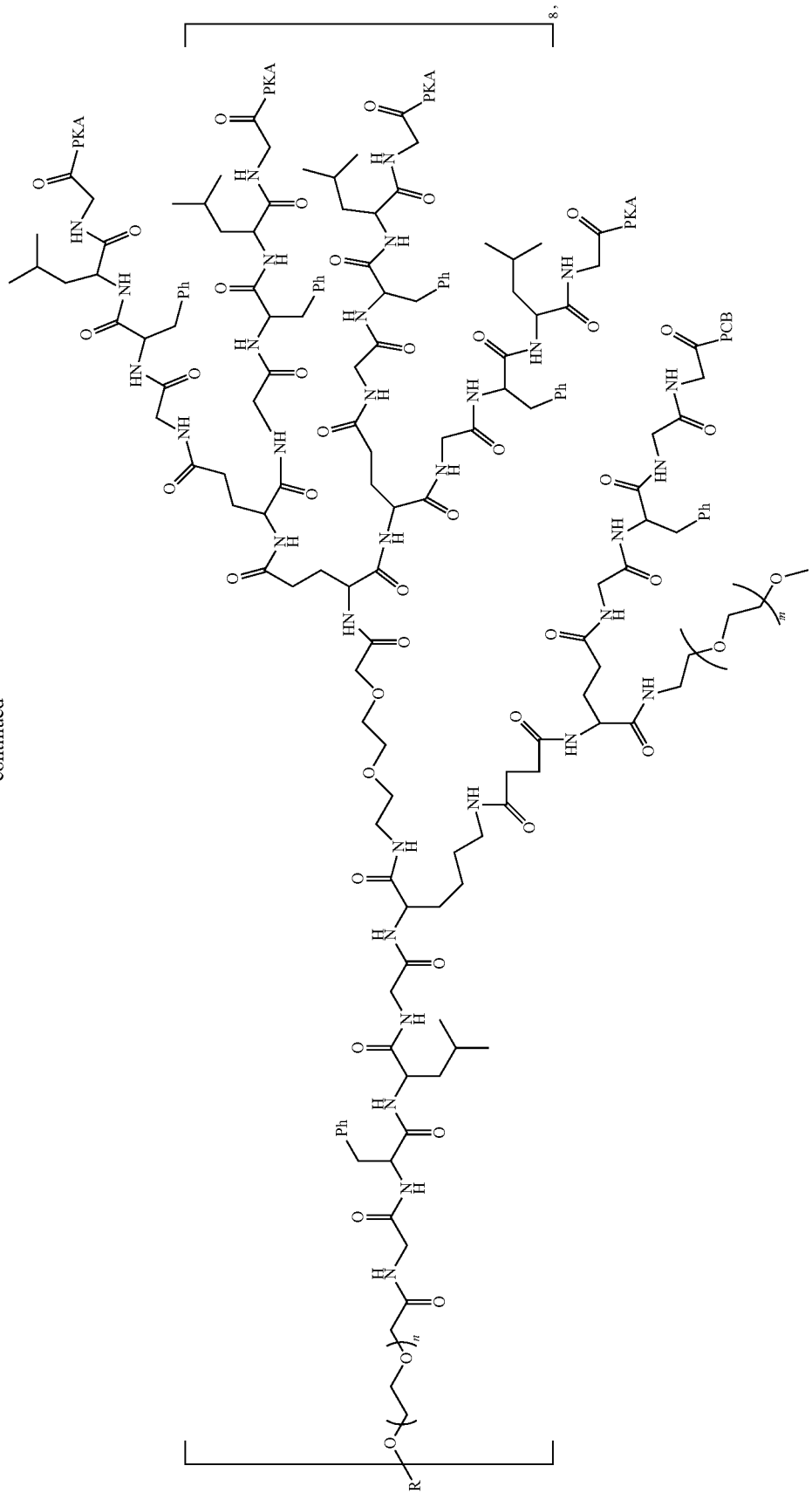

wherein R is a core structure of an eight-arm polyethylene glycol.

In some embodiments, in the polyethylene glycol conjugated drug of formula (II), Y1 is

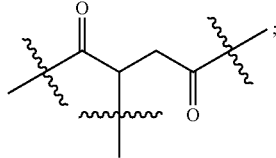 [SMILES: *C(=O)CC(*)C(*)=O]

W1 is selected from

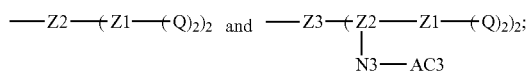

and W2 is H;

In some embodiments, PEG1 is a four-arm polyethylene glycol segment with a number-average molecular weight of 10 k-20 k or 20 k-40 k;

In some embodiments, the number-average molecular weight of PEG2 is 5 k-10 k or 10 k-20 k;

In some embodiments, W1 is selected from:

—Z2—(Z1—(Q)$_2$)$_2$,  (1)

wherein Z2 is

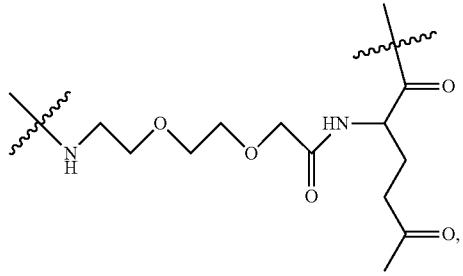 [SMILES: *NCCOCCOCC(=O)NC(CCC(C)=O)C(*)=O]

Z1 is

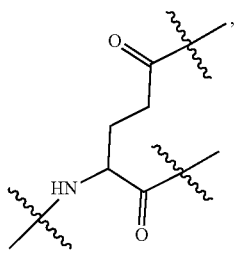 [SMILES: *NC(CCC(*)=O)C(*)=O]

and Z0 is

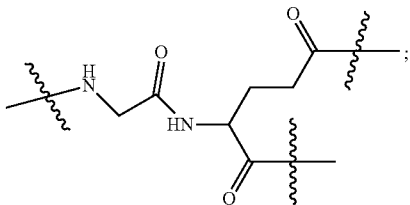 [SMILES: *NCC(=O)NC(CCC(*)=O)C(*)=O]

in some embodiments, N1 and N2 are both GFLG and AC1 and AC2 are both PCB; or N1 and N2 are both GFLG, AC1 is PCB, and AC2 is SB7; or N1 and N2 are both GFLG, and AC1 and AC2 are both SB7;

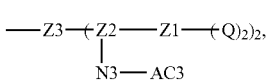    (2)

wherein Z3 and Z1 are both

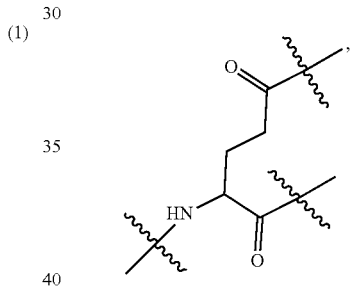

Z2 and Z0 are both

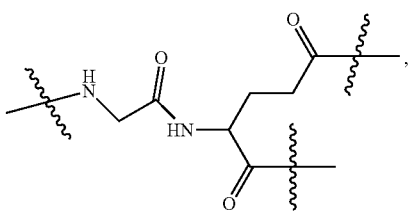 [SMILES: *NCC(=O)NC(CCC(*)=O)C(*)=O]

N1, N2 and N3 are all GFLG, AC1 and AC2 are both PCB, and AC3 is SB7;

In some embodiments, the polyethylene glycol conjugated drug has a structure selected from:

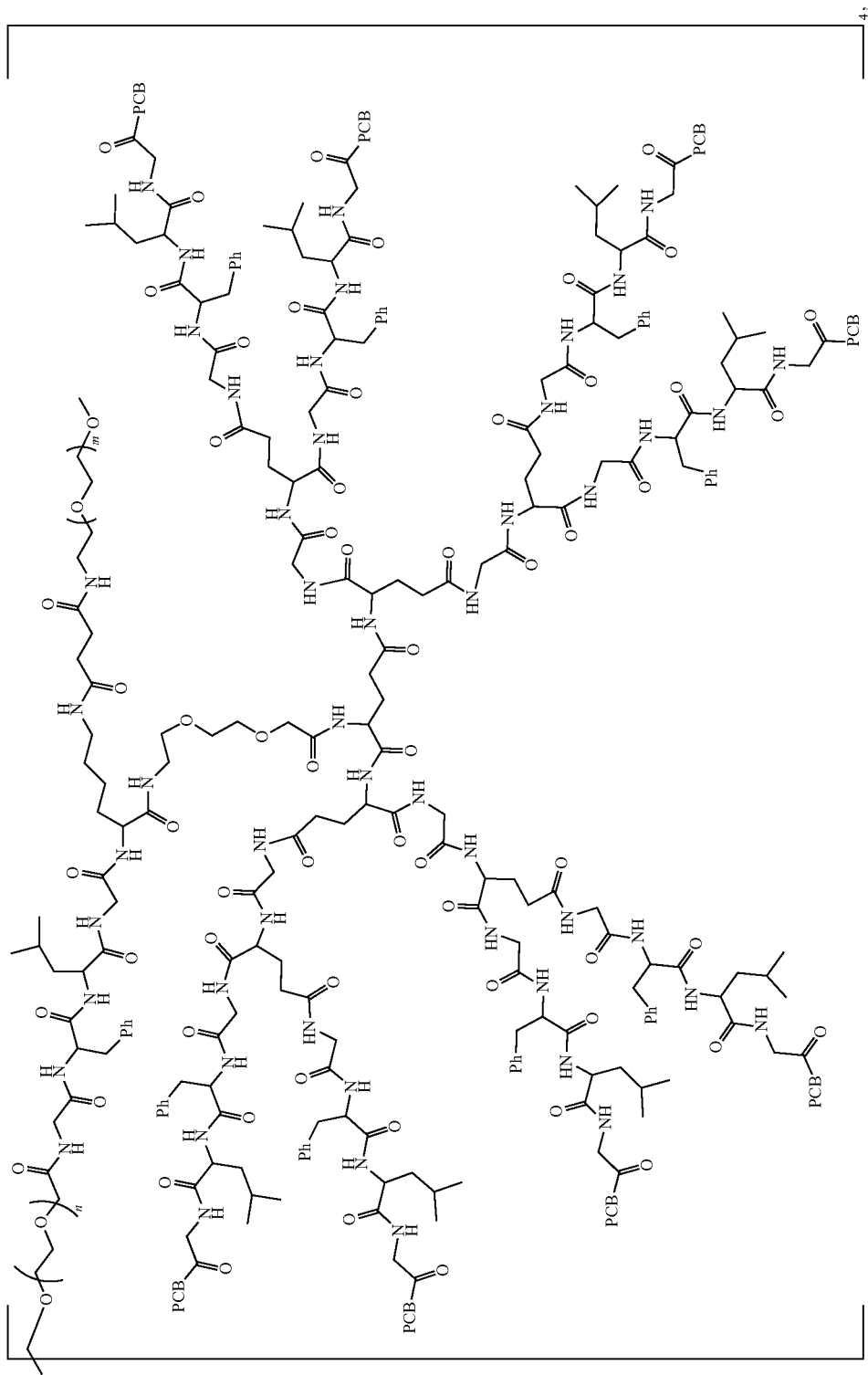

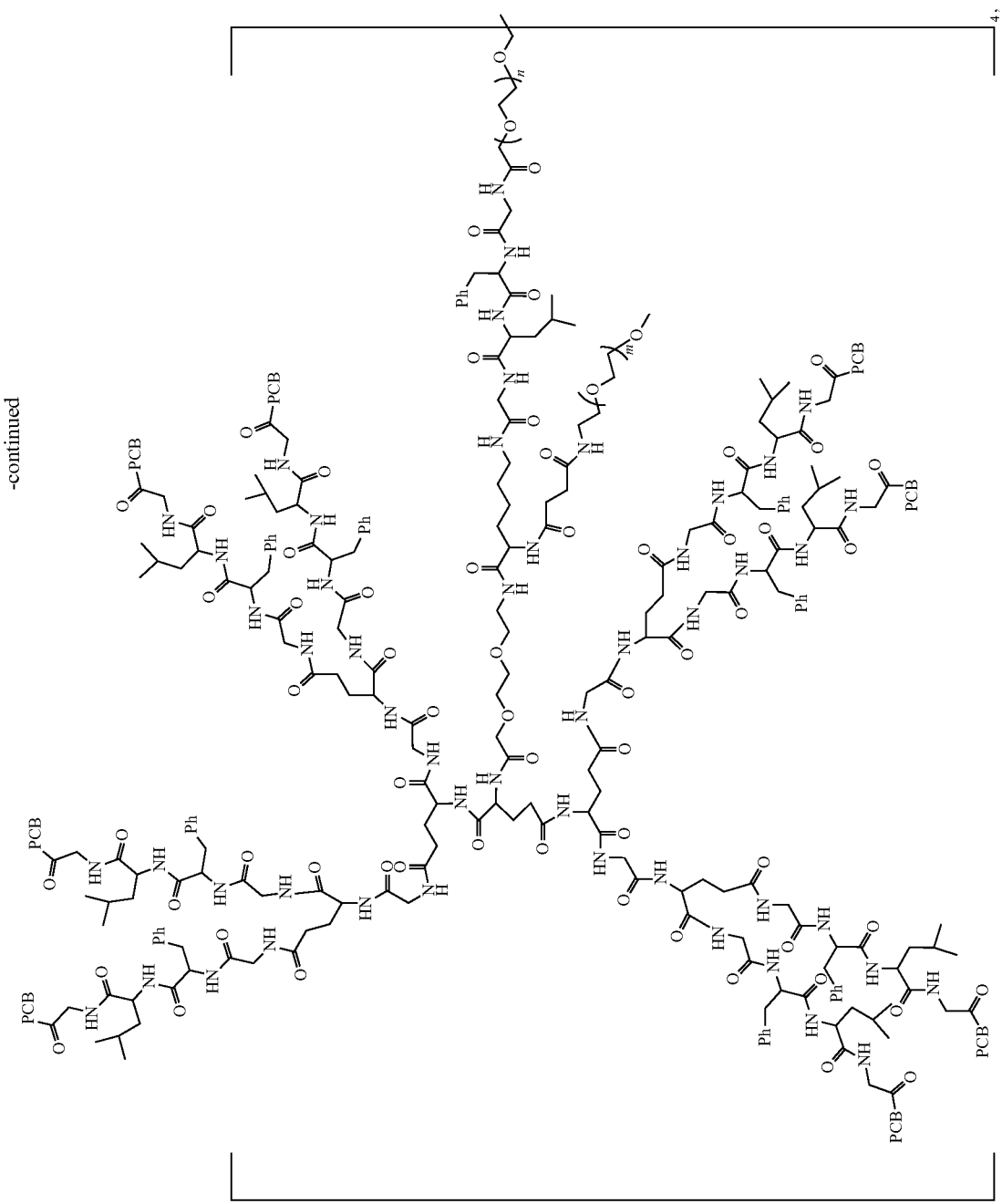

-continued
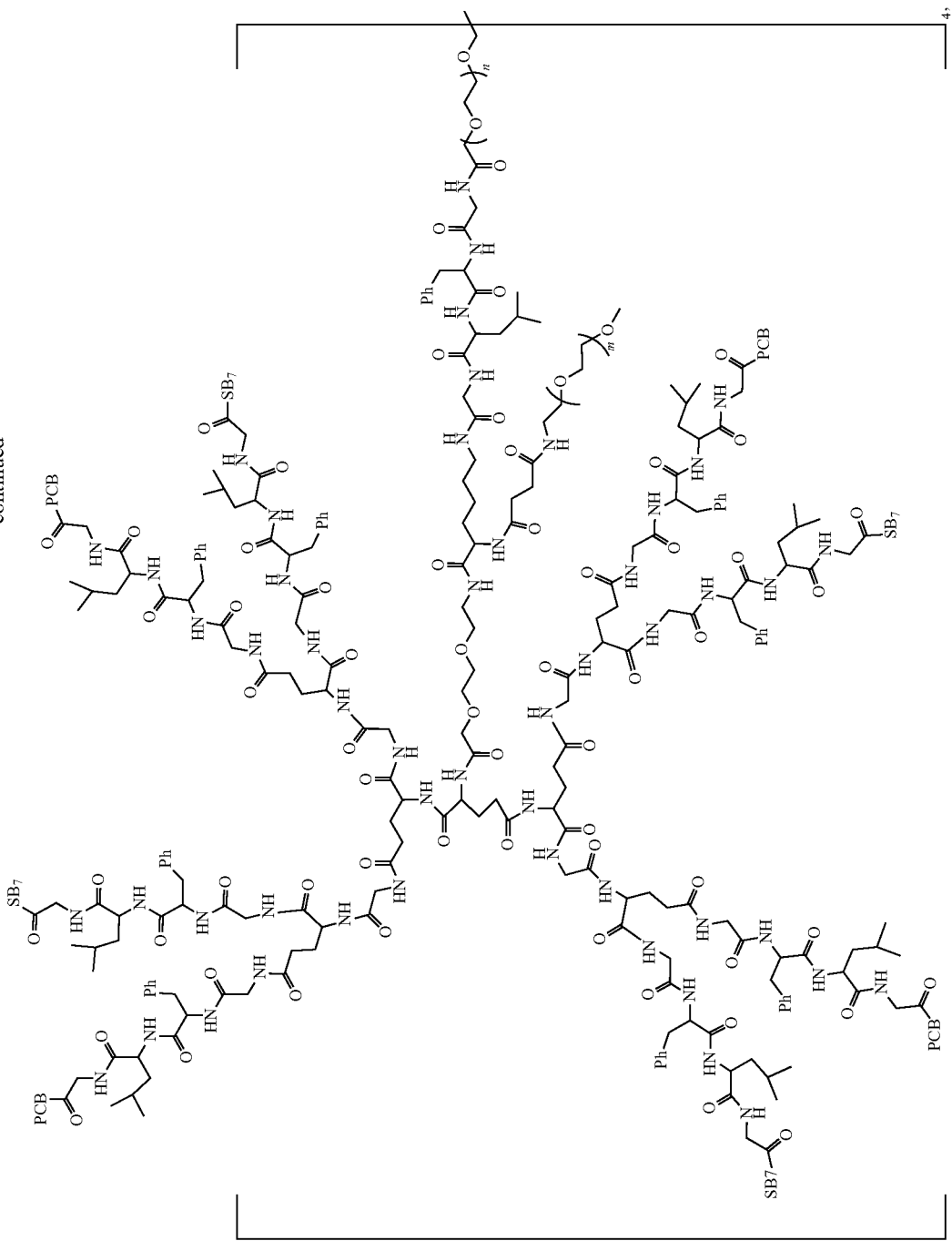

-continued
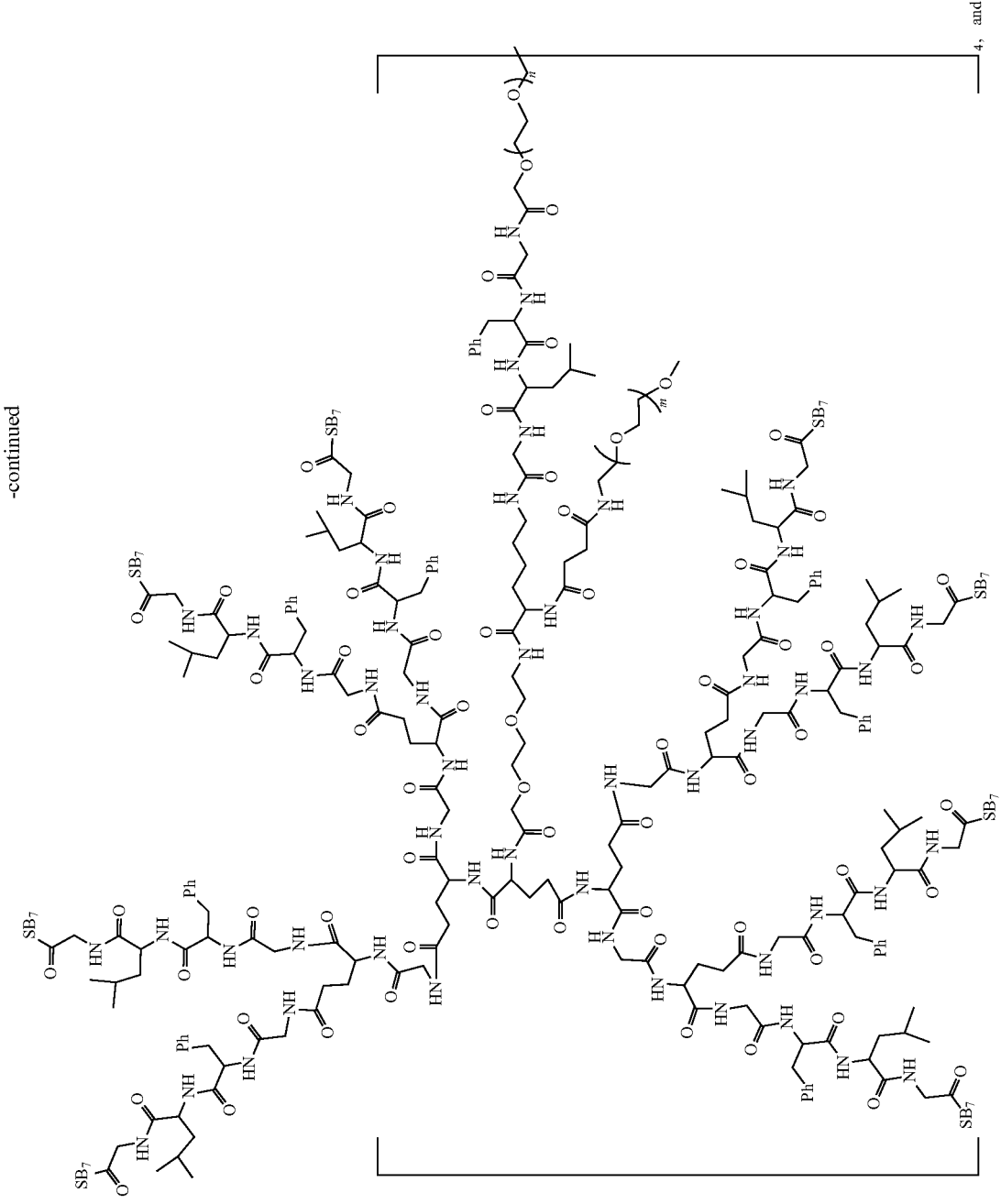
4, and

-continued
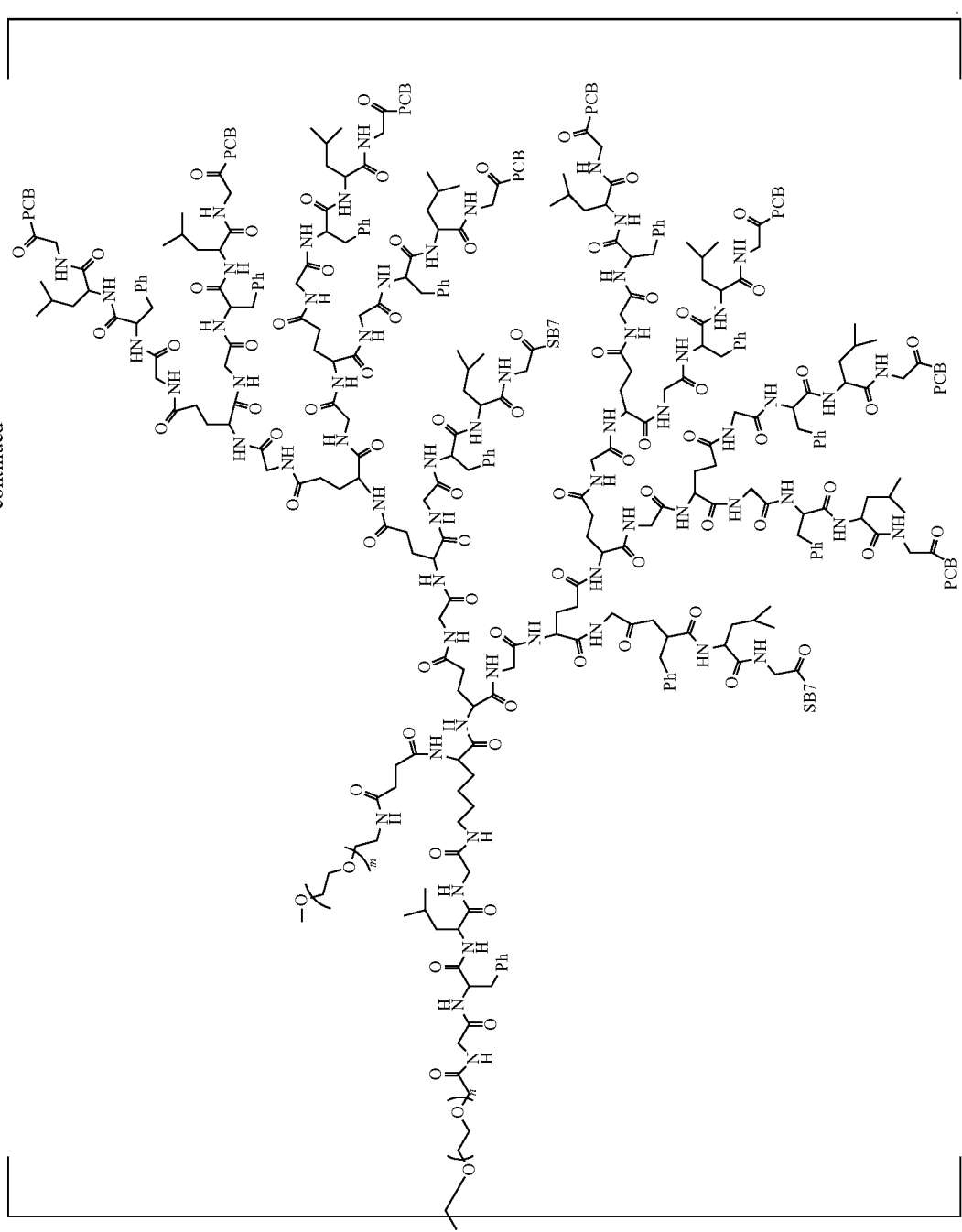

In some embodiments, in the polyethylene glycol conjugated drug of formula (II), Y1 is

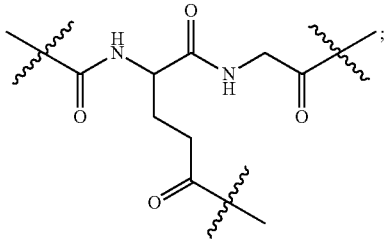 [SMILES: *C(=O)CCC(NC(*)=O)C(=O)NCC(*)=O]

W1 is

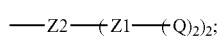

W2 is

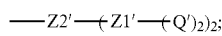

In some embodiments, PEG1 is a four-arm polyethylene glycol segment with a number-average molecular weight of 5 k-10 k or 10 k-40 k;

In some embodiments, the number-average molecular weight of PEG2 is 10 k-20 k;

In some embodiments, Z2 is

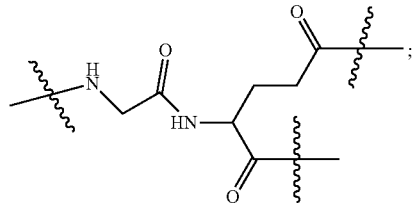 [SMILES: *NCC(=O)NC(CCC(*)=O)C(*)=O]

Z1 is

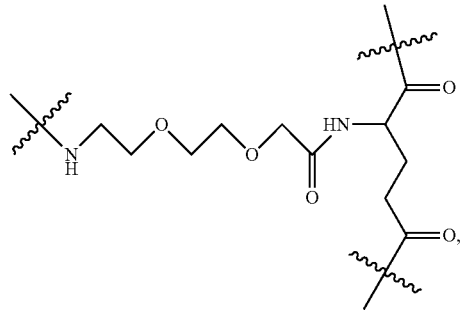 [SMILES: *NCCOCCOCC(=O)NC(CCC(*)=O)C(*)=O]

and Z0 is

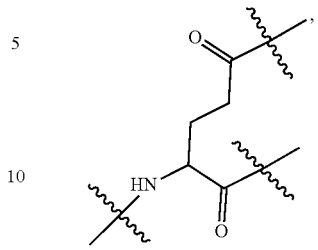

In some embodiments, N1 and N2 are both GFLG, AC1 is PCB, and AC2 is SB7;

In some embodiments, Z2' is

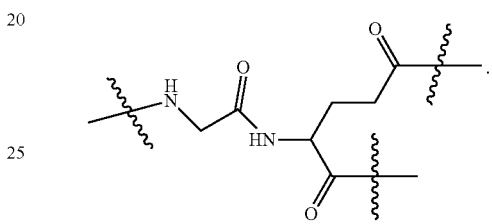

Z1' is

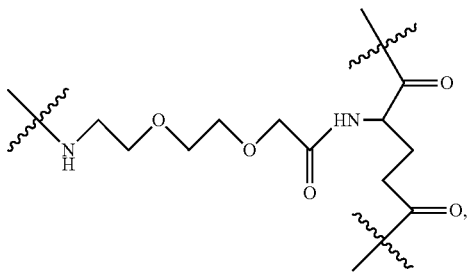 [SMILES: *NCCOCCOCC(=O)NC(CCC(*)=O)C(*)=O]

and Z0' is

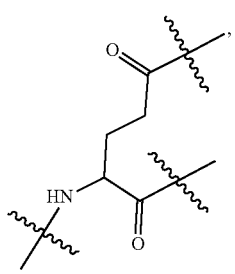 [SMILES: *NC(CCC(*)=O)C(*)=O]

In some embodiments, N1' and N2' are both GFLG, AC1' is PCB, and AC2' is SB7;

In some embodiments, the polyethylene glycol conjugated drug has a structure selected from:

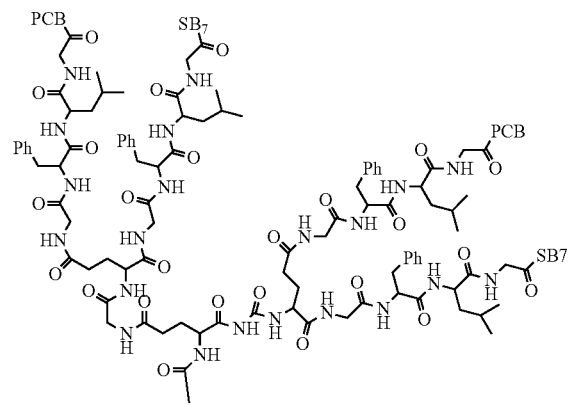
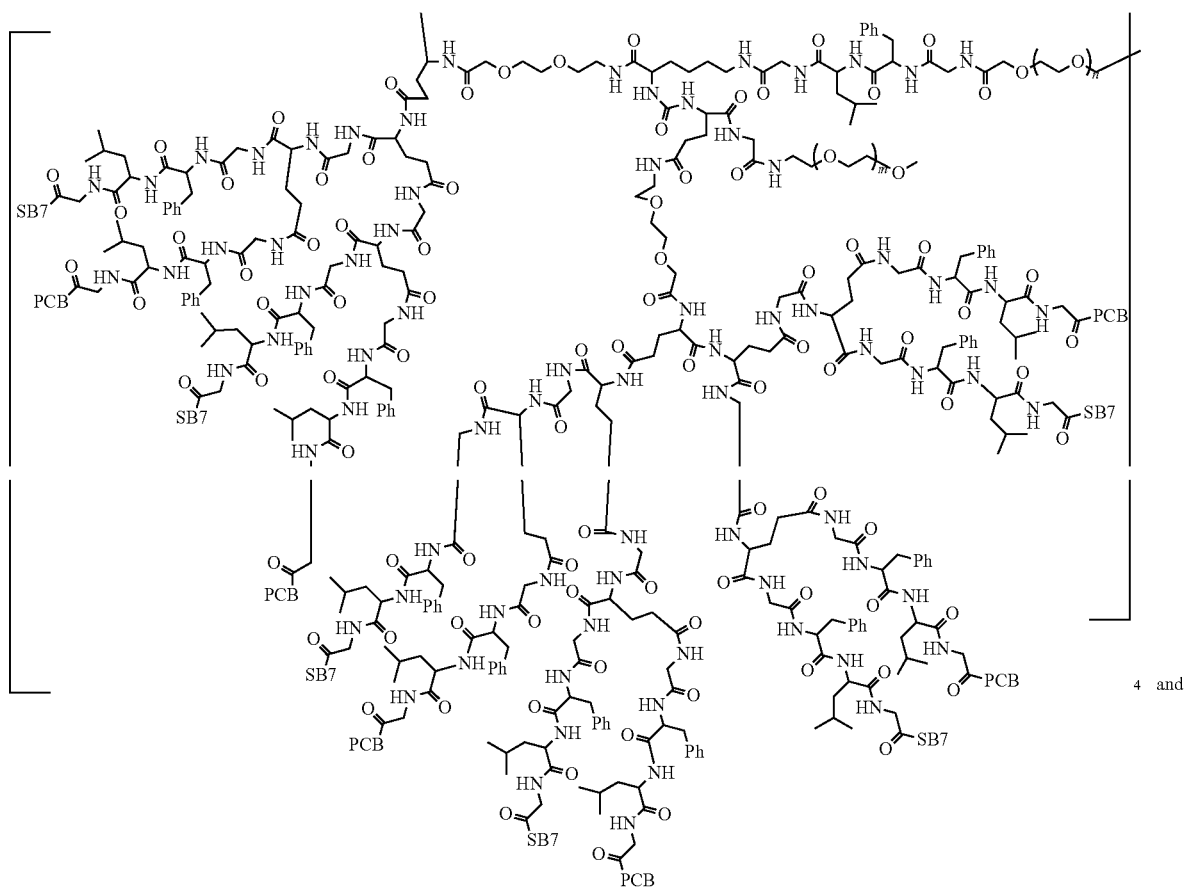

-continued
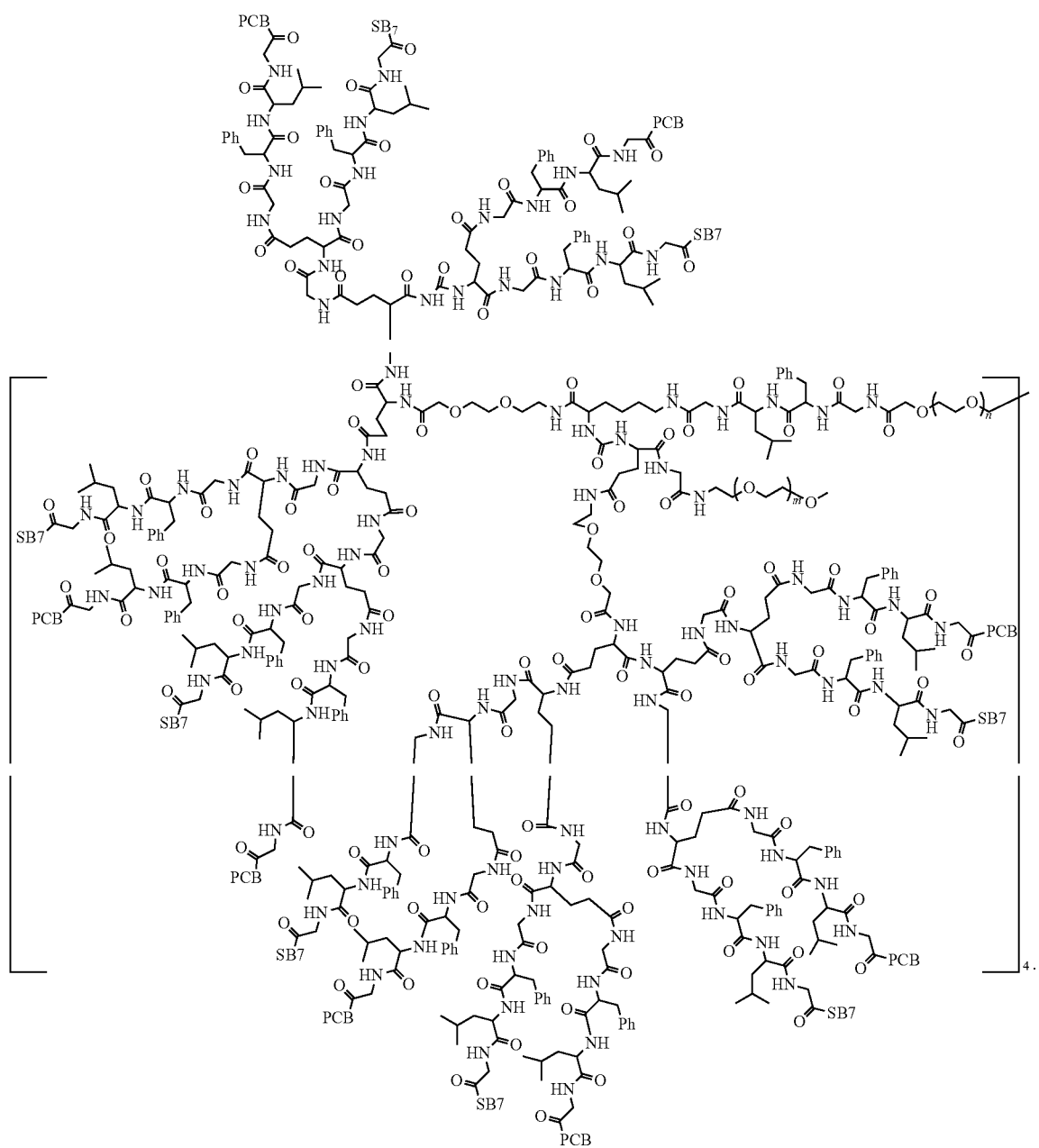

In some embodiments, in the polyethylene glycol conjugated drug of formula (II), Y1 is

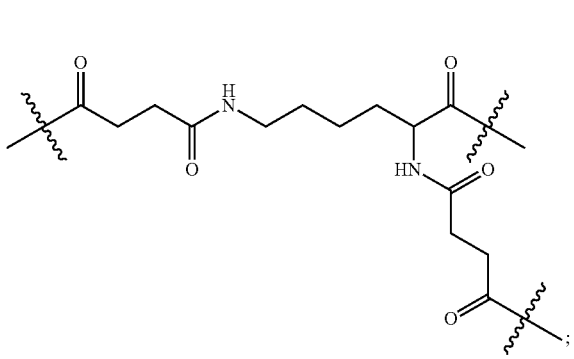 [SMILES: *C(=O)CCC(=O)NCCCCC(NC(=O)CCC(*)=O)C(*)=O]

W1 is

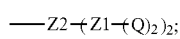

W2 is

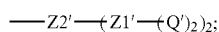

In some embodiments, PEG1 is a four-arm polyethylene glycol segment with a number-average molecular weight of 10 k-40 k;

In some embodiments, the number-average molecular weight of PEG2 is 10 k-20 k;

In some embodiments, Z2 is

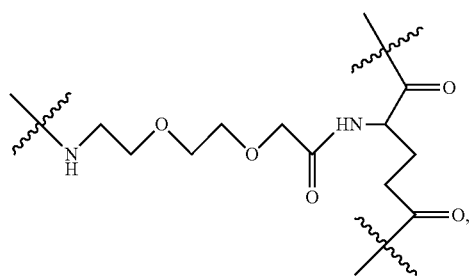 [SMILES: *NCCOCCOCC(=O)NC(CCC(*)=O)C(*)=O]

Z1 is

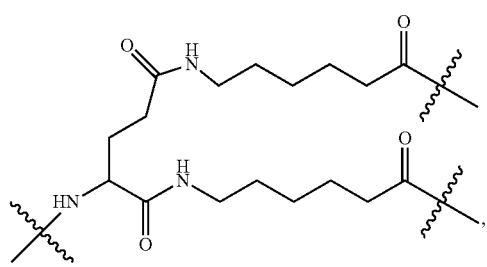 [SMILES: *NC(CCC(=O)NCCCCCC(*)=O)C(=O)NCCCCCC(*)=O]

and Z0 is

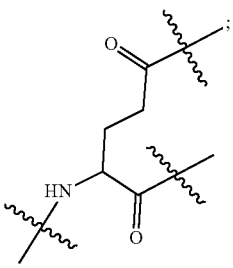 [SMILES: *NC(CCC(*)=O)C(*)=O]

In some embodiments, N1 and N2 are both GFLG and AC1 and AC2 are both LPT;

In some embodiments, Z2' is

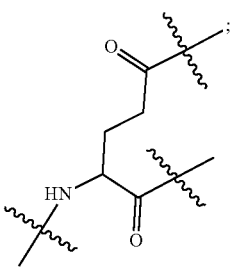 [SMILES: *NC(CCC(*)=O)C(*)=O]

Z1' is

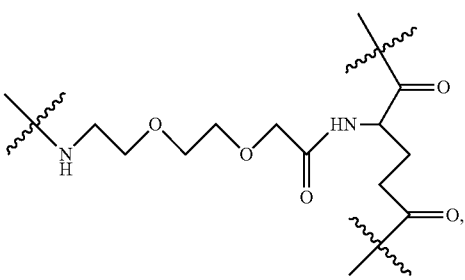 [SMILES: *NCCOCCOCC(=O)NC(CCC(*)=O)C(*)=O]

and Z0' is

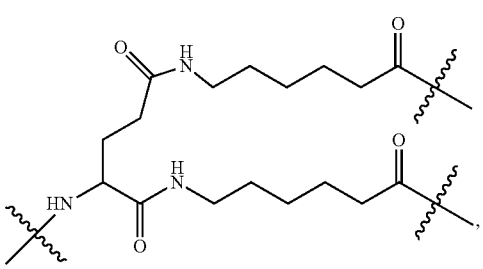 [SMILES: *NC(CCC(=O)NCCCCCC(*)=O)C(=O)NCCCCCC(*)=O]

In some embodiments, N1' and N2' are both GFLG, AC1' is PCB, and AC2' is LPT;

In some embodiments, the polyethylene glycol conjugated drug has a structure as follows:

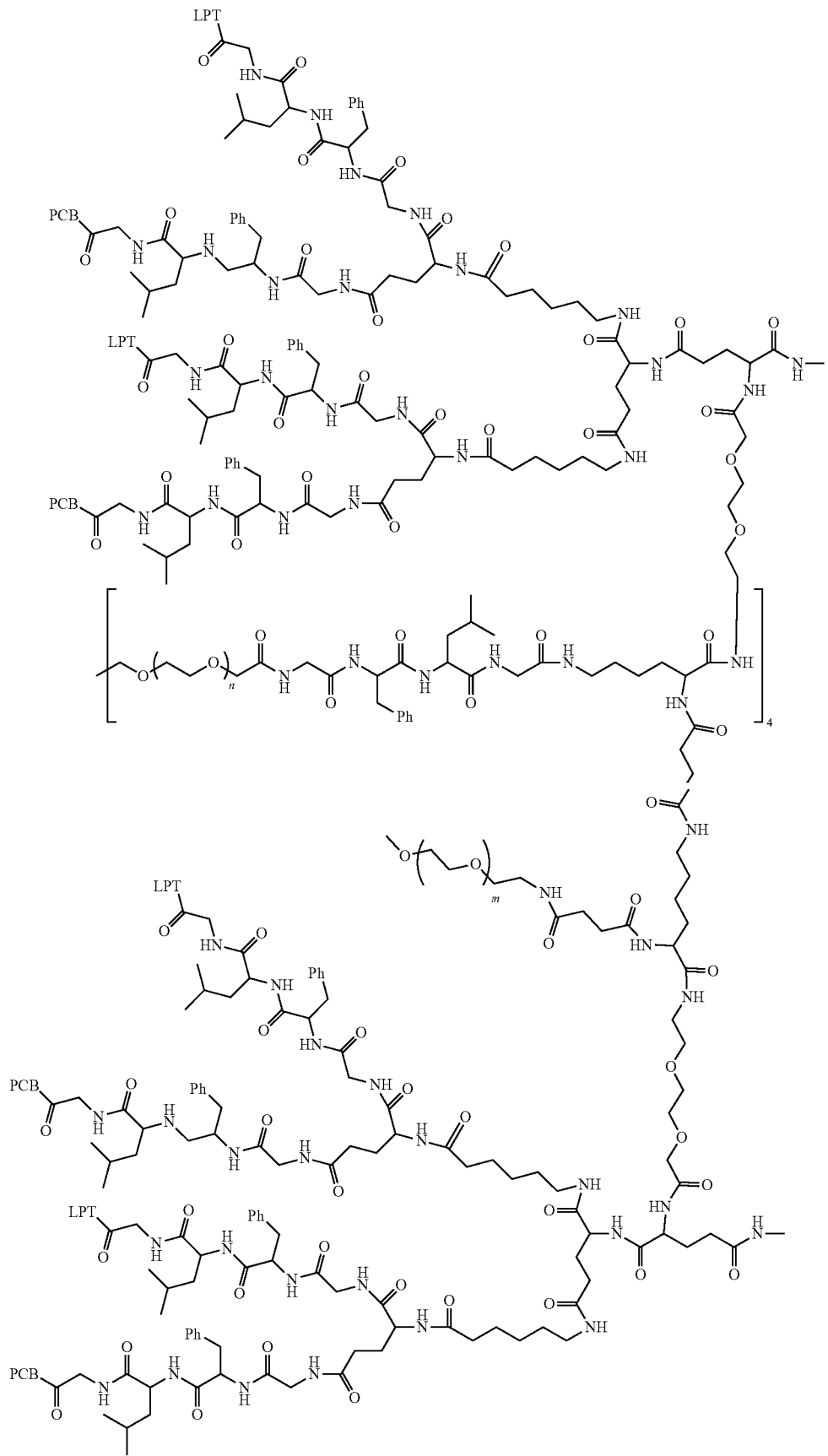

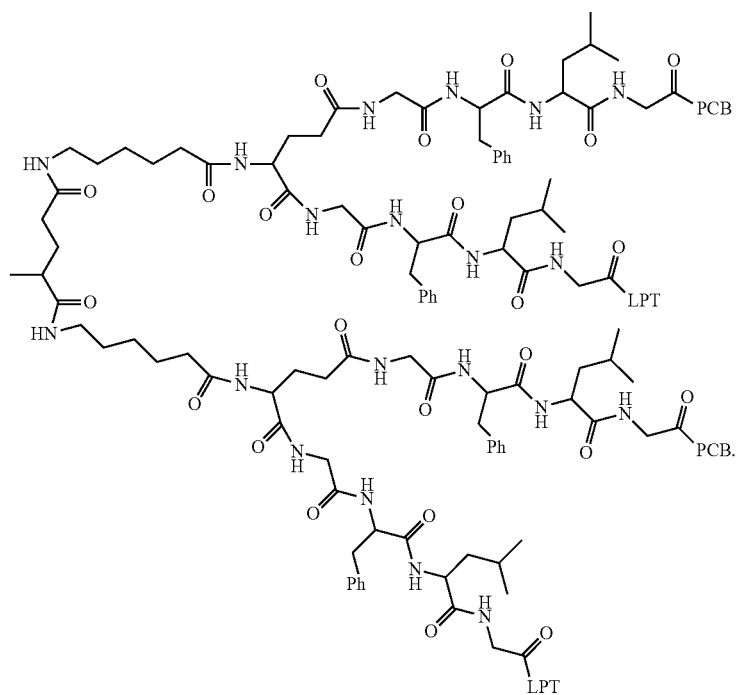
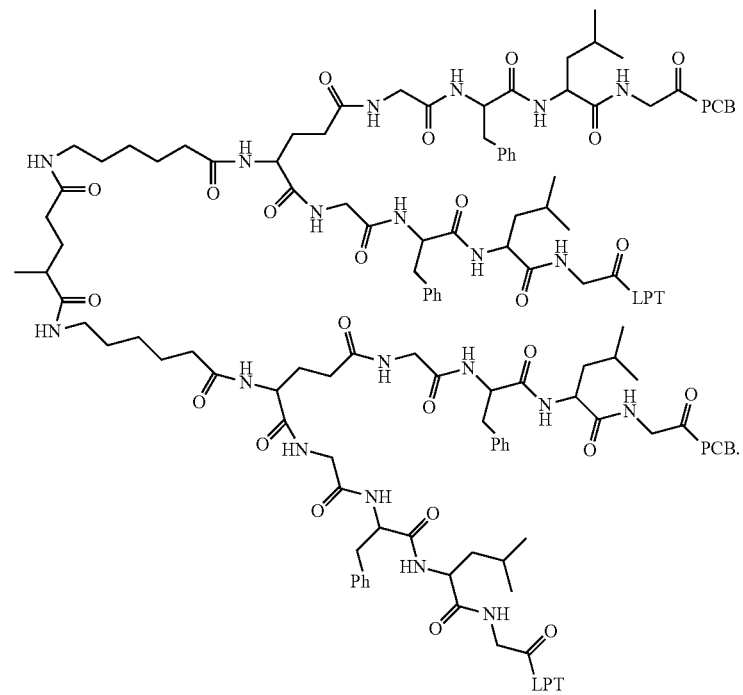

In some embodiments, in the polyethylene glycol conjugated drug of formula (II), Y1 is

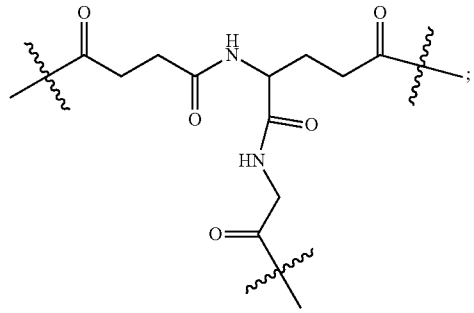 [SMILES: *C(=O)CCC(=O)NC(CCC(*)=O)C(=O)NCC(*)=O]

W1 is

—Z1—(Q)$_2$;

W2 is

—Z1'—(Q')$_2$;

In some embodiments, PEG1 is a four-arm polyethylene glycol segment with a number-average molecular weight of 10 k-40 k;

In some embodiments, the number-average molecular weight of PEG2 is 10 k-20 k;

In some embodiments, Z1 is

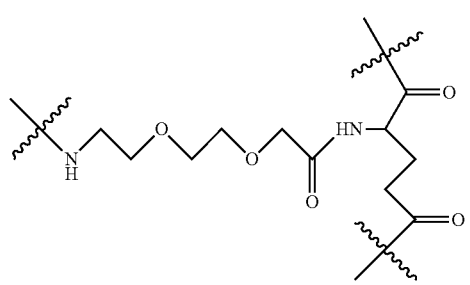 [SMILES: *NCCOCCOCC(=O)NC(CCC(*)=O)C(*)=O]

and Z0 is

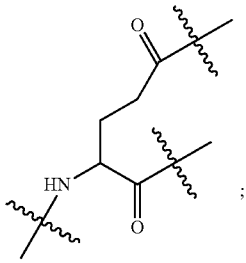 [SMILES: *NC(CCC(*)=O)C(*)=O]

In some embodiments, N1 and N2 are both G and AC1 and AC2 are both SN38;

In some embodiments, Z1' is

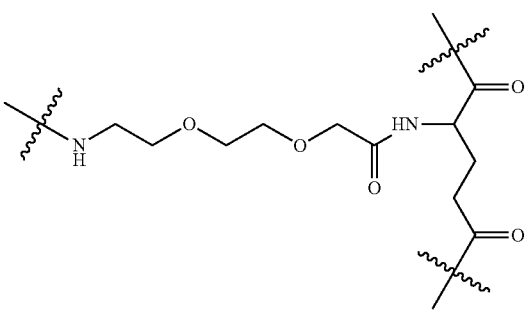 [SMILES: *NCCOCCOCC(=O)NC(CCC(*)=O)C(*)=O]

and Z0' is

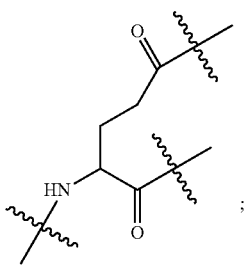 [SMILES: *NC(CCC(*)=O)C(*)=O]

in some embodiments, N1' and N2' are both G and AC2' are both SN38;

In some embodiments, the polyethylene glycol conjugated drug has a structure as follows:

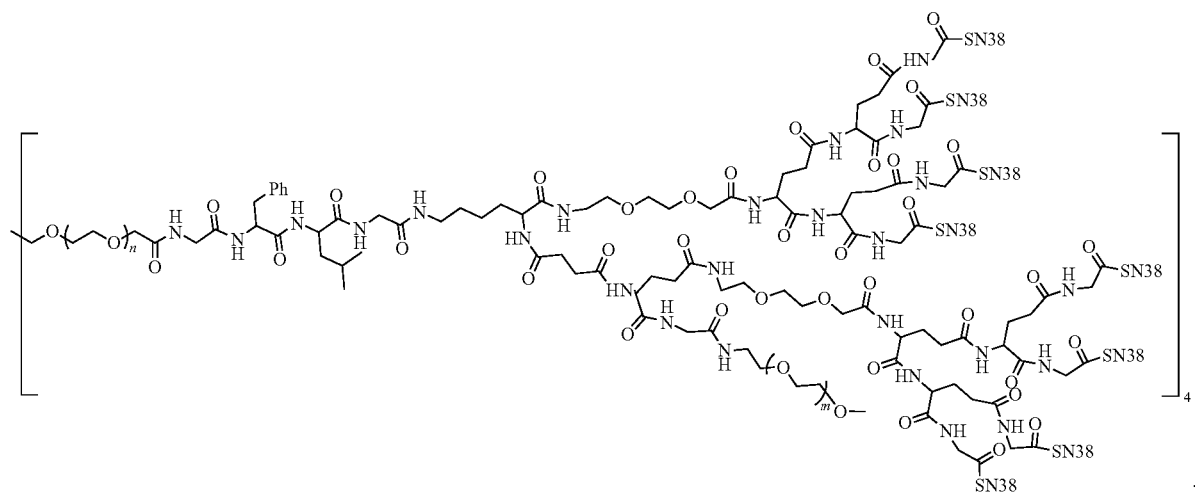

In some embodiments, the polyethylene glycol conjugated drug of the disclosure has a structure of formula (III):

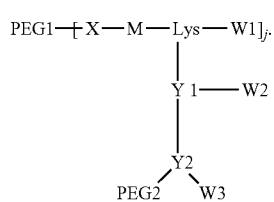

In some embodiments, in the polyethylene glycol conjugated drug of formula (III),
Y1 is

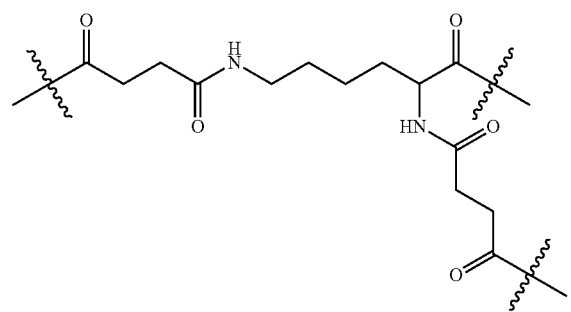

Y2 is

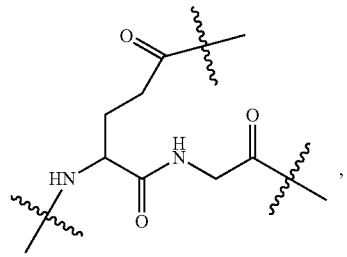 [SMILES: *NC(CCC(*)=O)C(=O)NCC(*)=O]

W1 is selected from

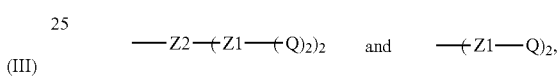

and W2 is selected from

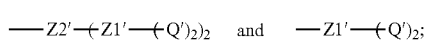

In some embodiments, PEG1 is a four-arm polyethylene glycol segment with a number-average molecular weight of 10 k-40 k;

In some embodiments, the number-average molecular weight of PEG2 is 5 k-10 k or 10 k-20 k;

In some embodiments, W1 is selected from:

wherein Z2 is

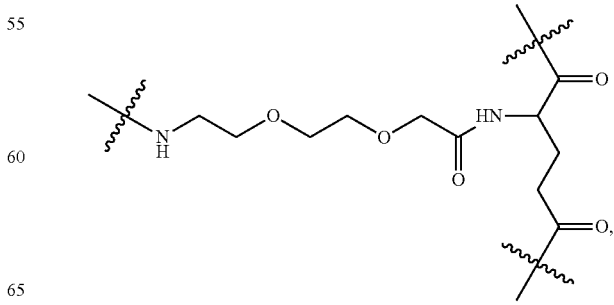

Z1 is

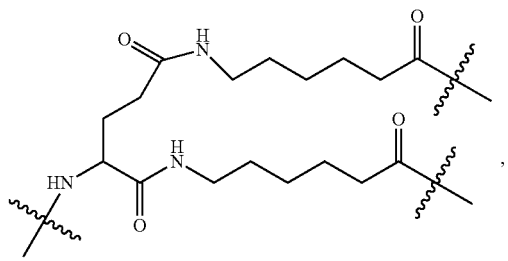 [SMILES: *NC(CCC(=O)NCCCCCC(*)=O)C(=O)NCCCCCC(*)=O]

and Z0 is

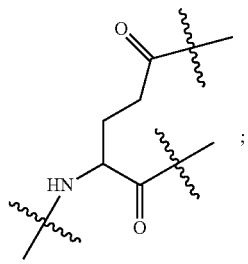 [SMILES: *NC(CCC(*)=O)C(*)=O]

In some embodiments, N1 and N2 are both GFLG and AC1 and AC2 are both LPT; or N1 and N2 are both GFLG, AC1 is LPT, and AC2 is PCB;

$$—Z1—(Q)_2, \quad (2)$$

wherein Z1 is

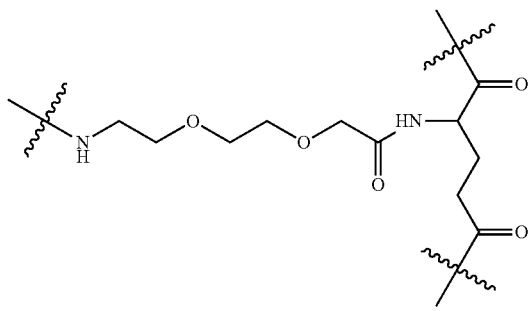 [SMILES: *NCCOCCOCC(=O)NC(CCC(*)=O)C(*)=O]

and Z0 is

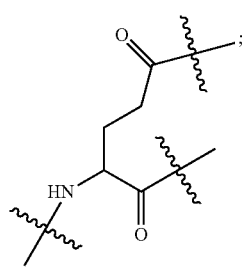 [SMILES: *NC(CCC(*)=O)C(*)=O]

In some embodiments, N1 and N2 are both GFLG and AC1 and AC2 are both LPT; or N1 and N2 are both GFLG and AC1 and AC2 are both PCB;

In some embodiments, W2 is selected from:

$$—Z2'—(Z1'—(Q')_2)_2, \quad (1)$$

wherein Z2' is

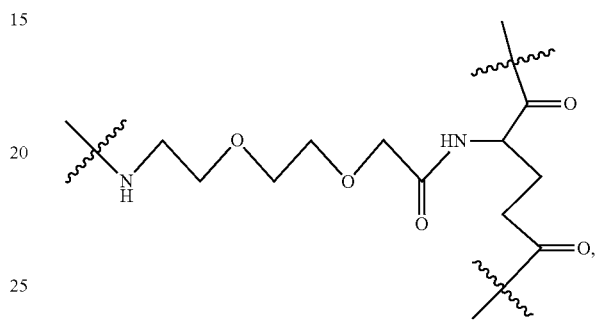

Z1' is

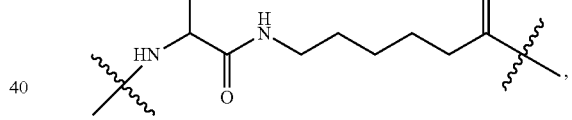

and Z0' is

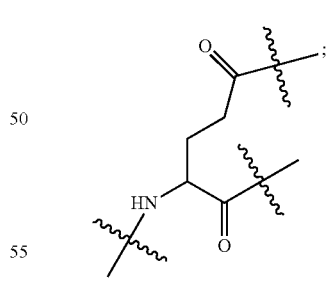

In some embodiments, N1' and N2' are both GFLG and AC1' and AC2' are both LPT; or N1' and N2' are both GFLG, AC1' is LPT, and AC2' is PCB;

$$—Z1'—(Q')_2, \quad (2)$$

wherein Z1' is
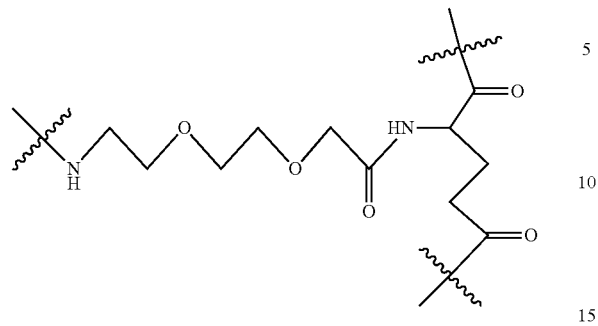
and Z0' is
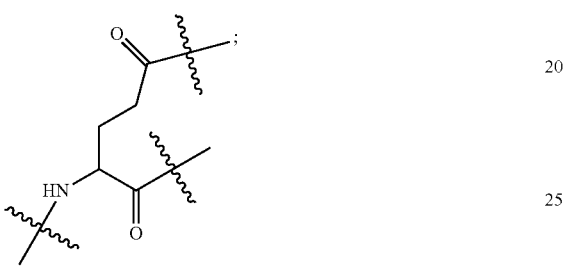
In some embodiments, N1' and N2' are both GFLG and AC1' and AC2' are both LPT; or N1' and N2' are both GFLG and AC1' and AC2' are both PCB;
In some embodiments, W3 is GFLG-SB7.
In some embodiments, the polyethylene glycol conjugated drug has a structure selected from:

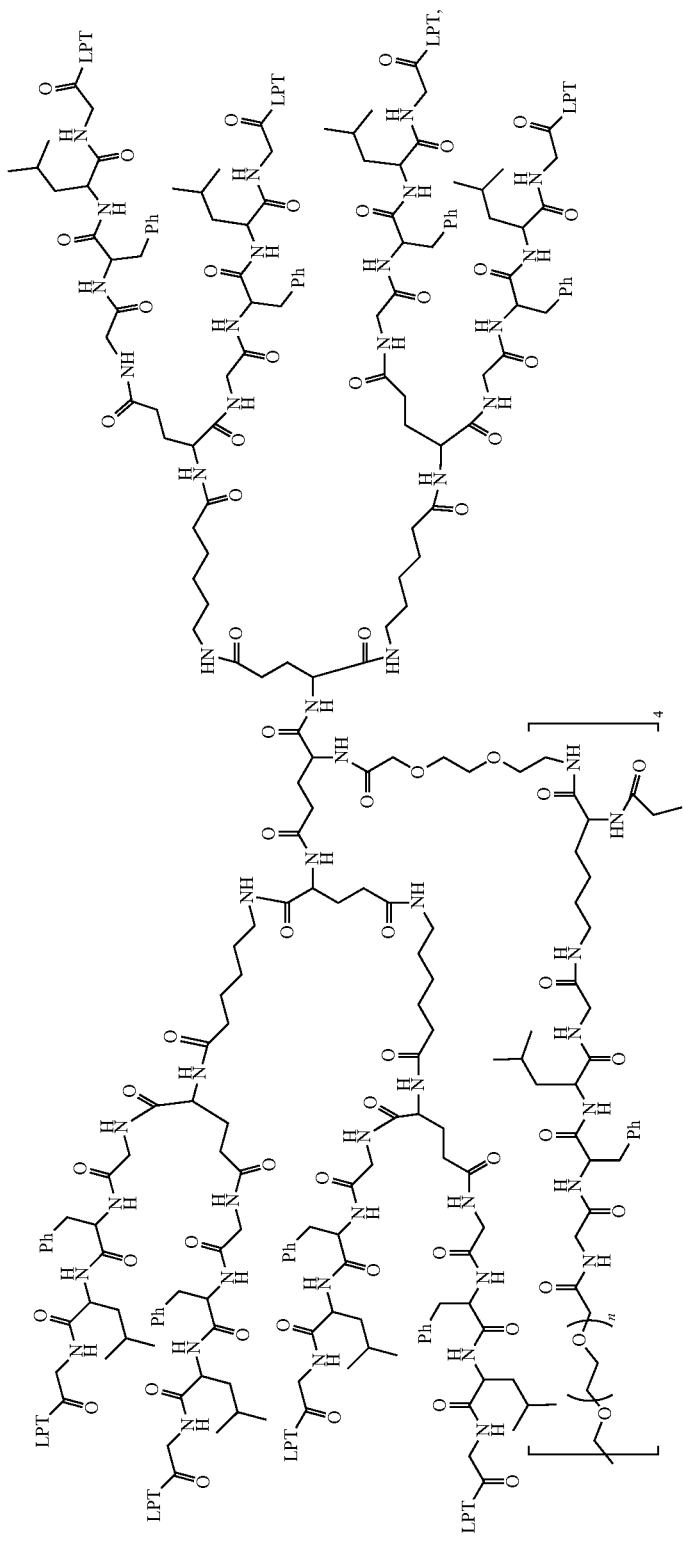

-continued
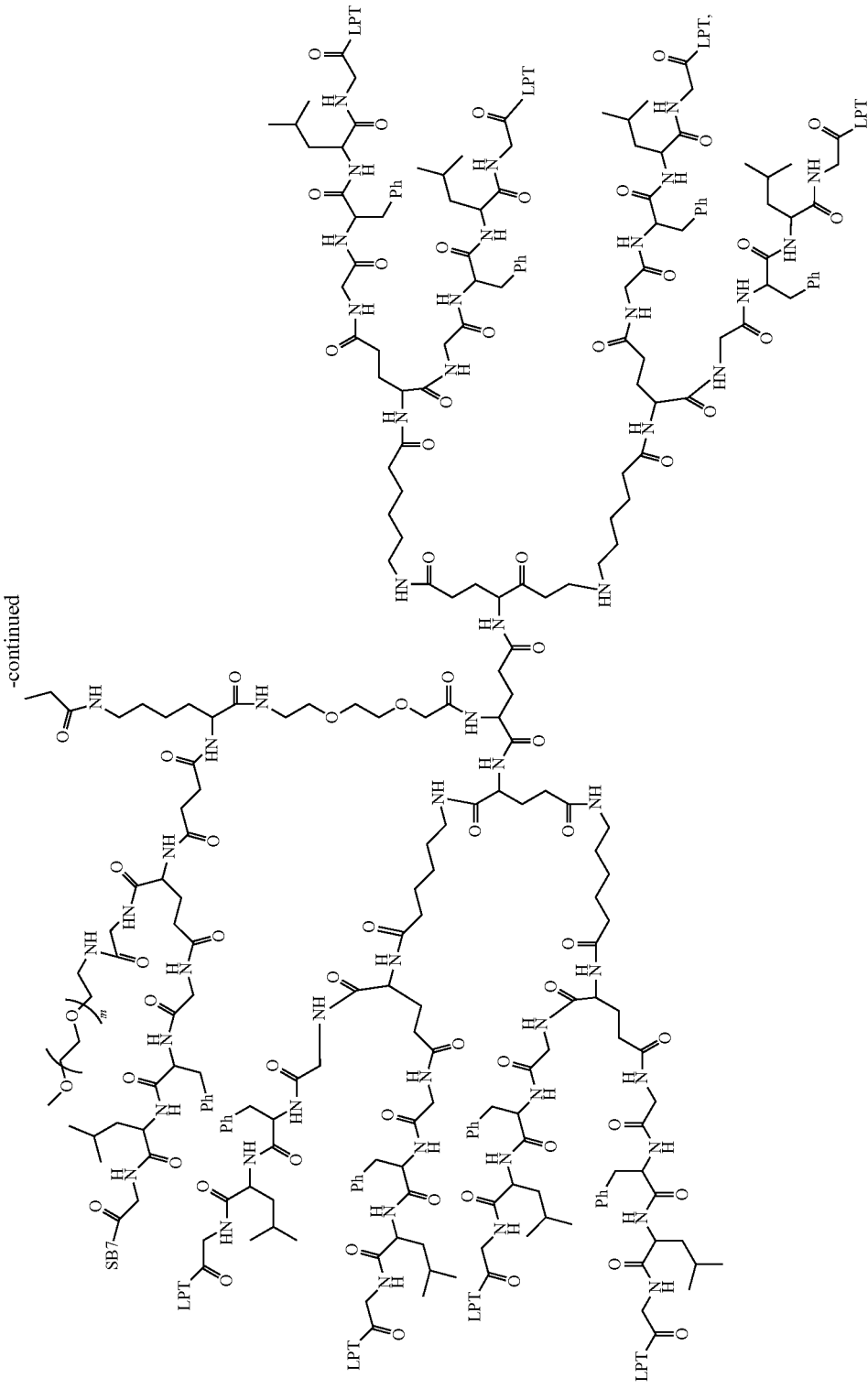

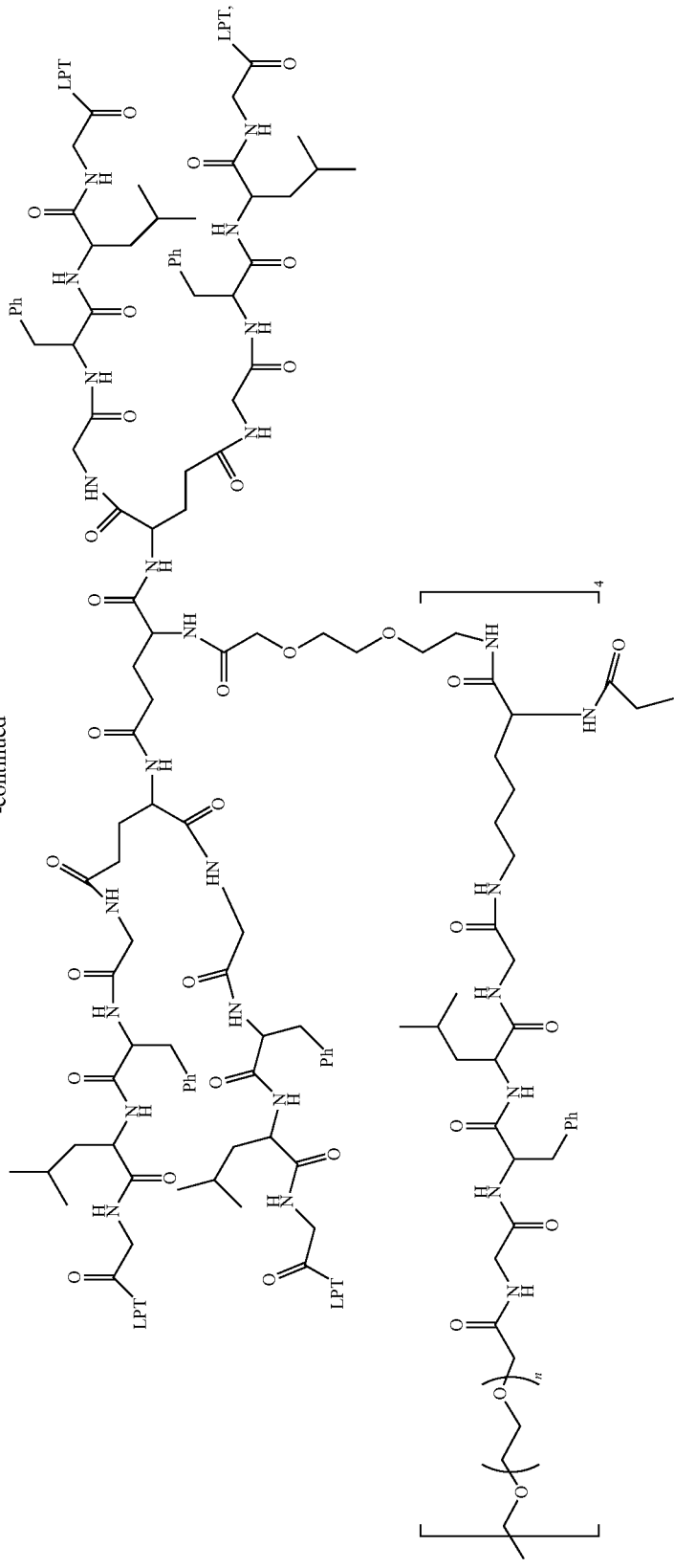

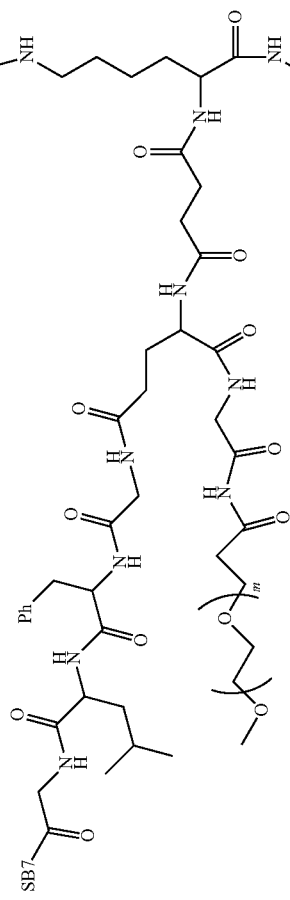
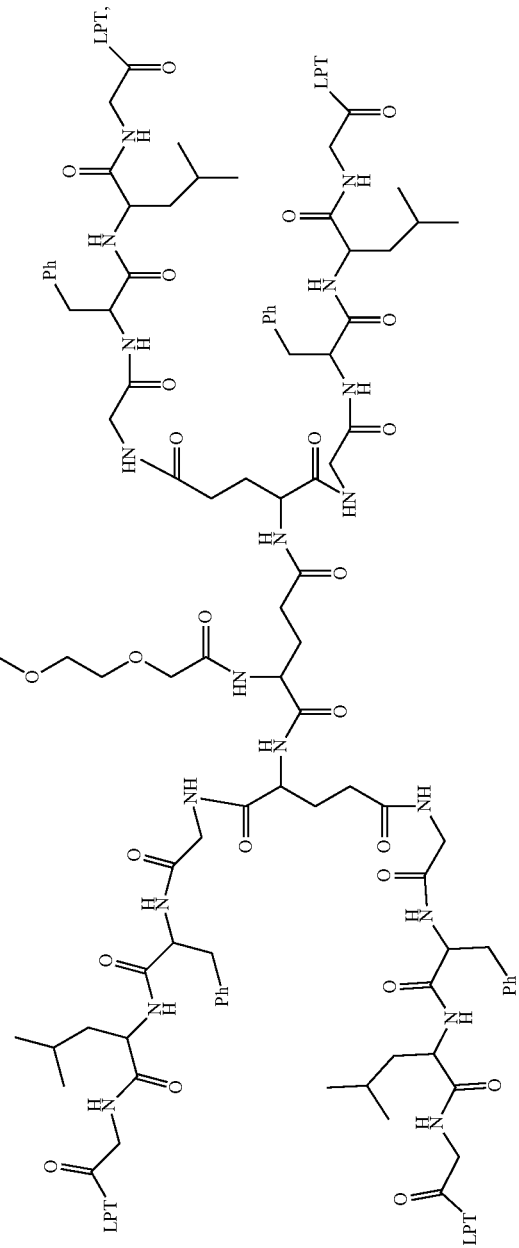

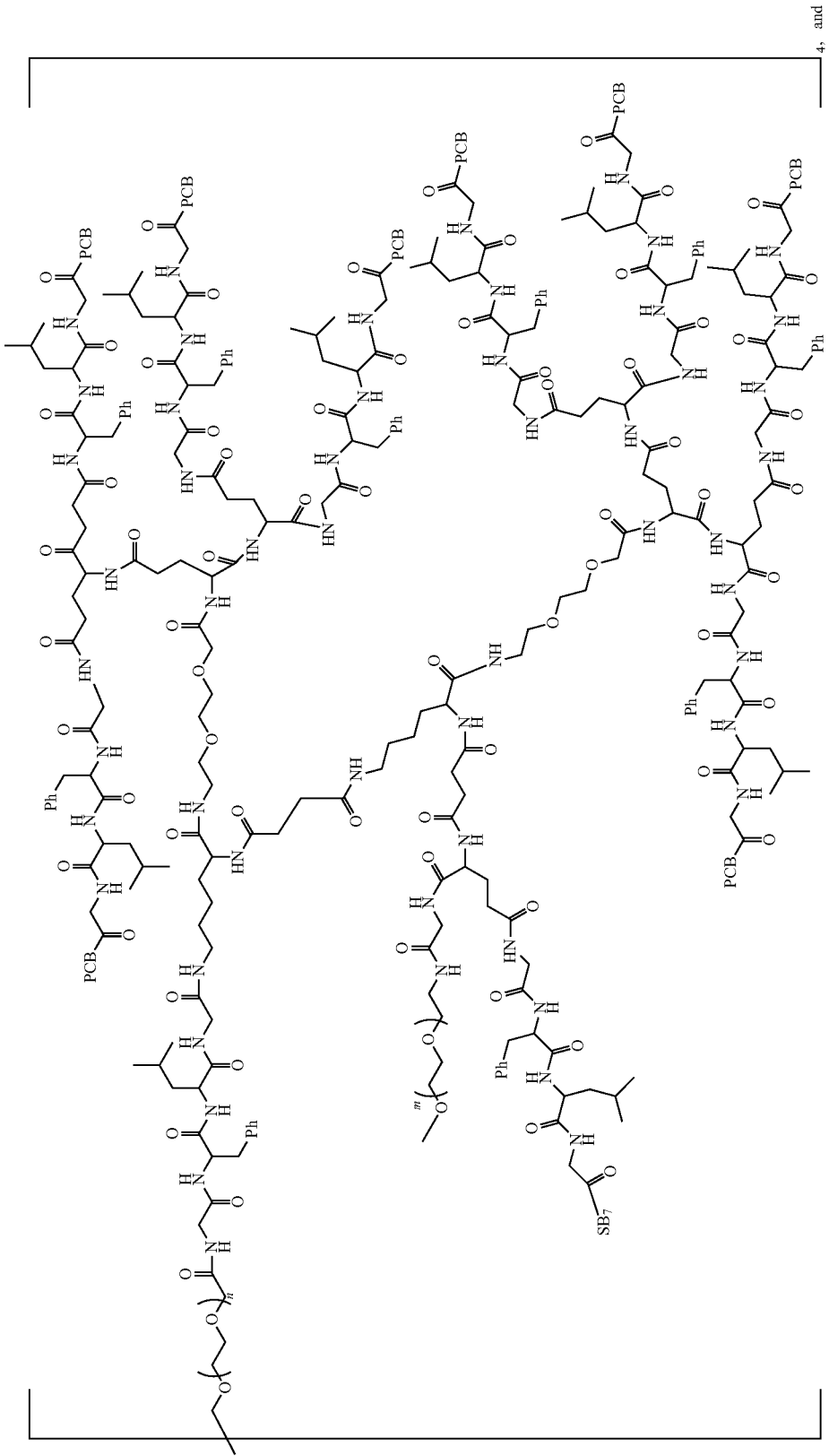

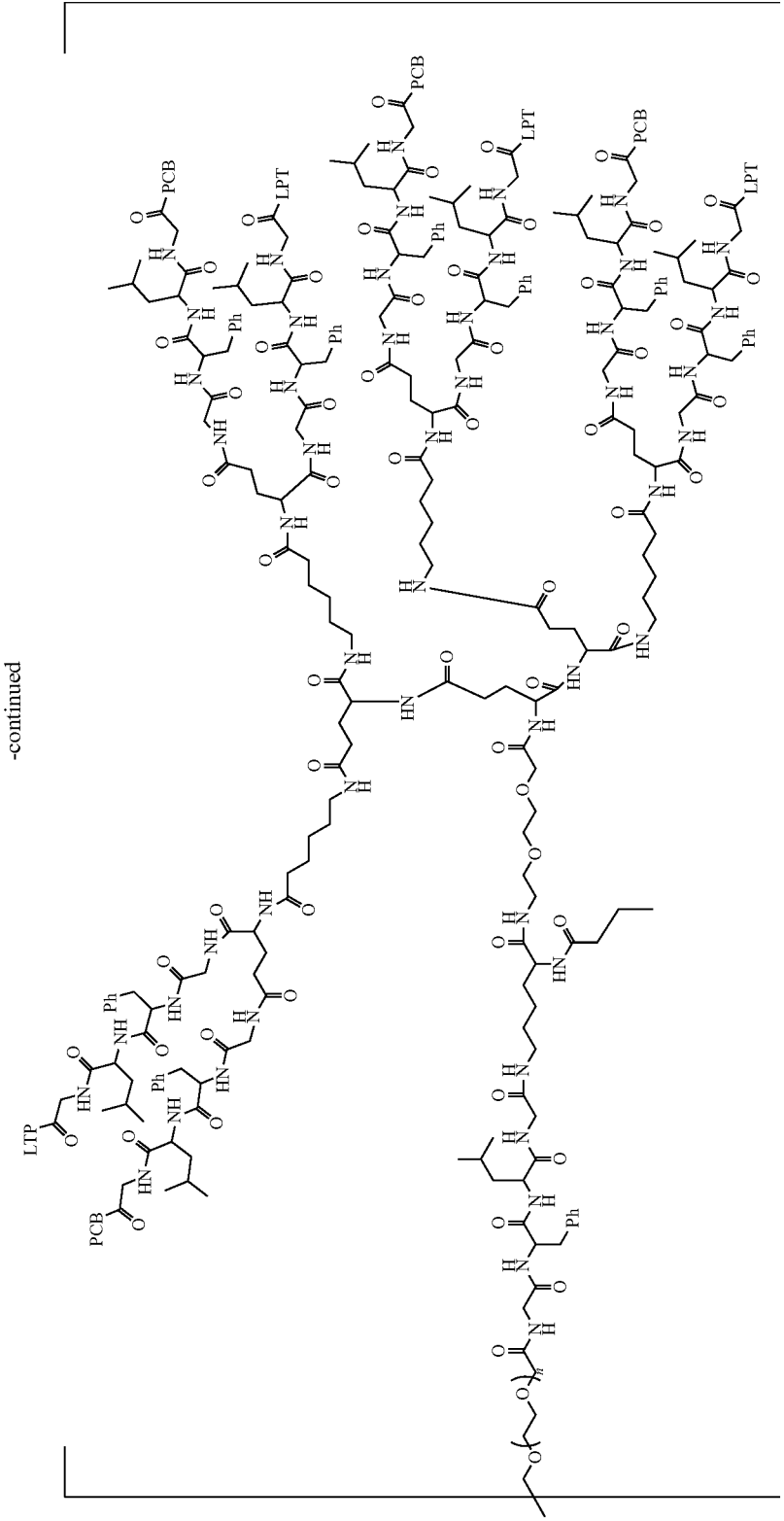

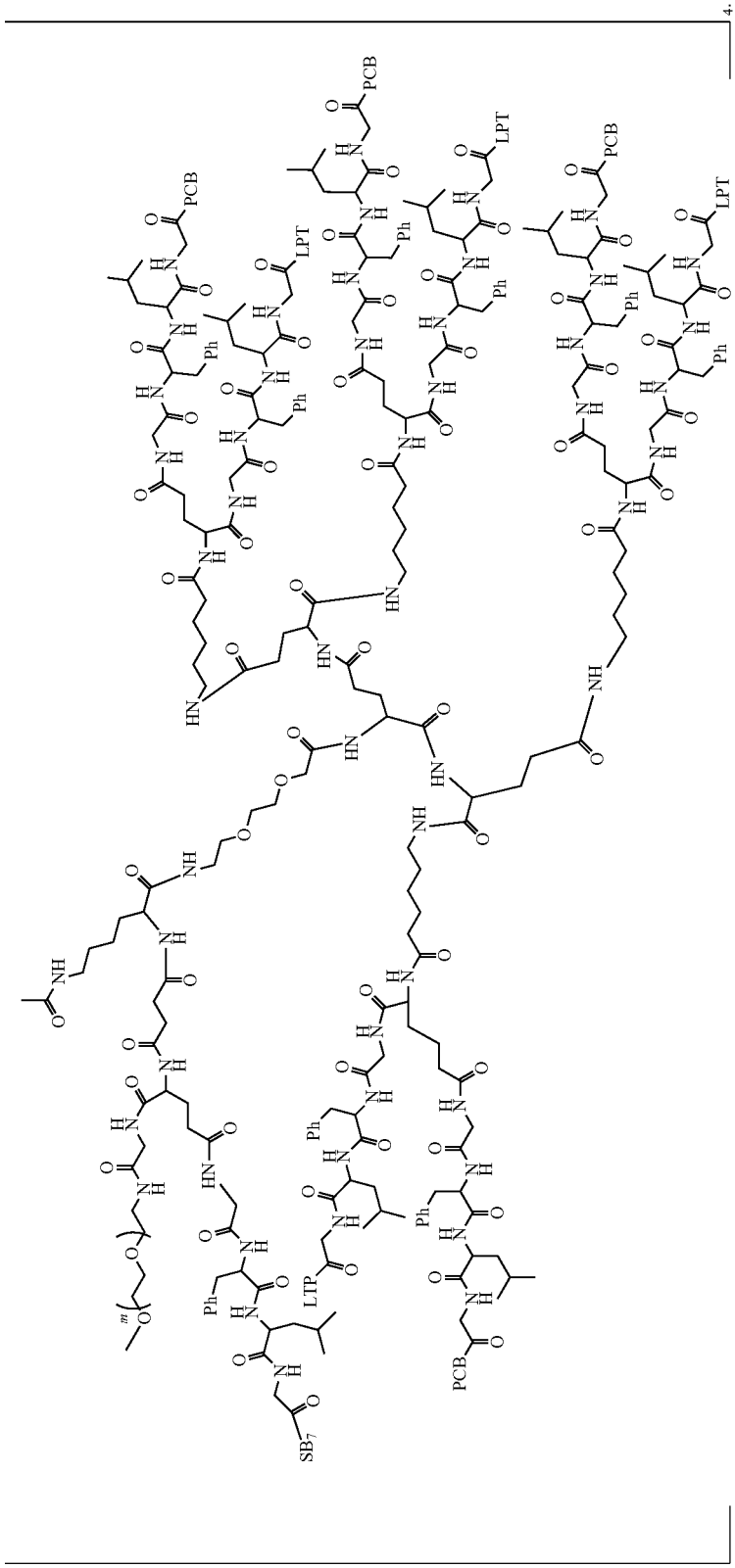

The polyethylene glycol conjugated drug of the disclosure includes but is not limited to:

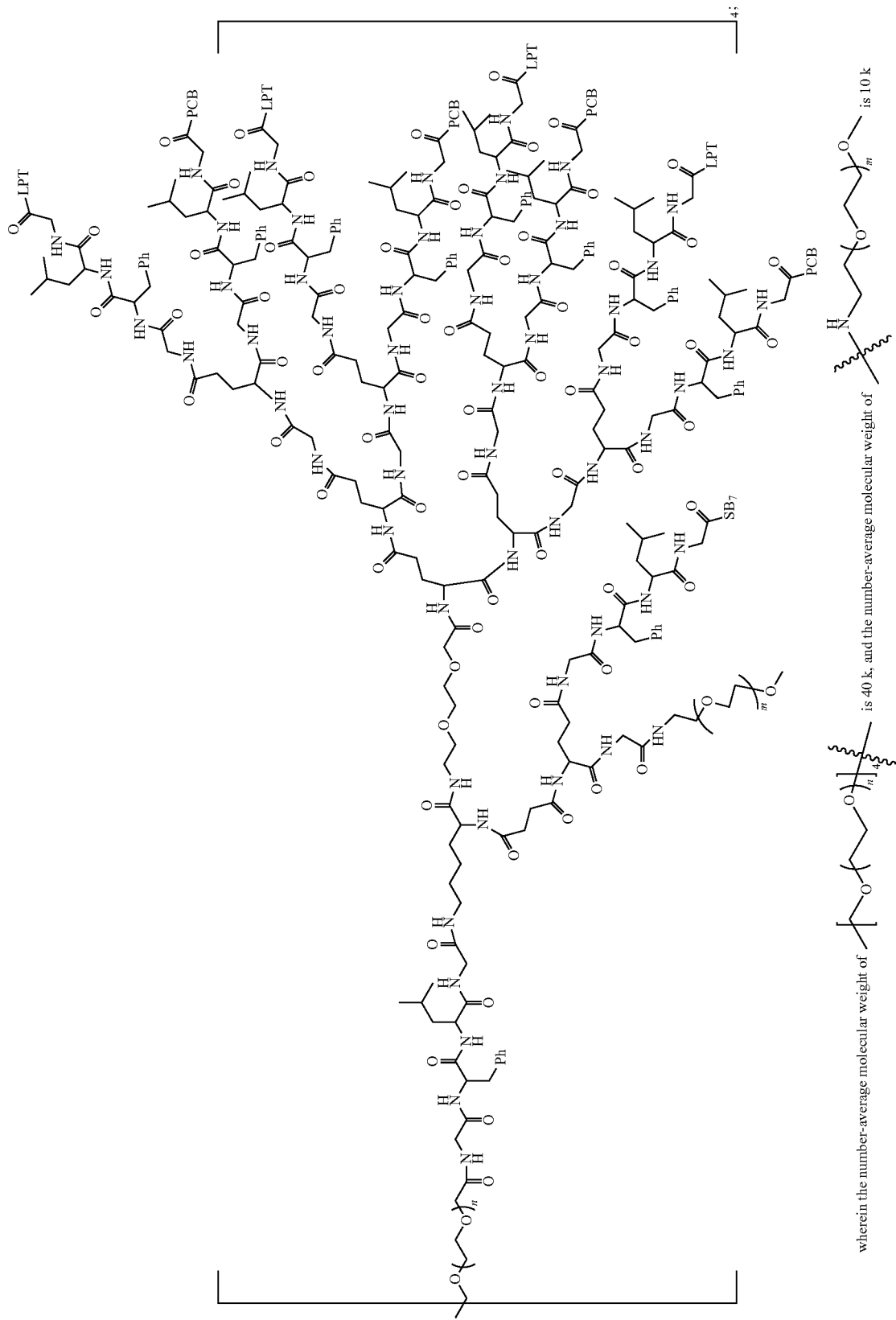

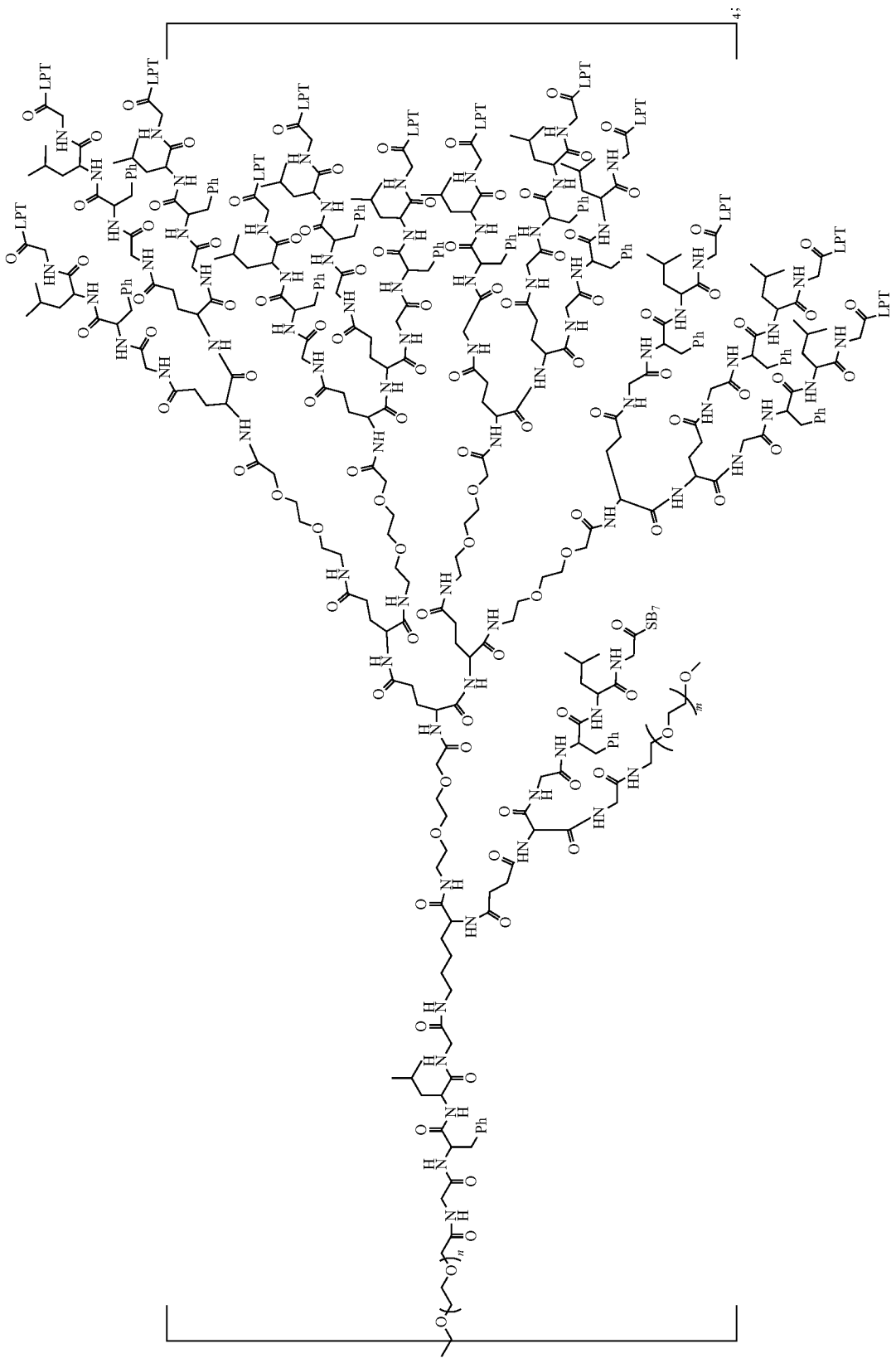

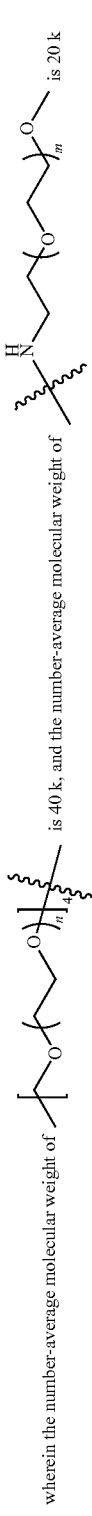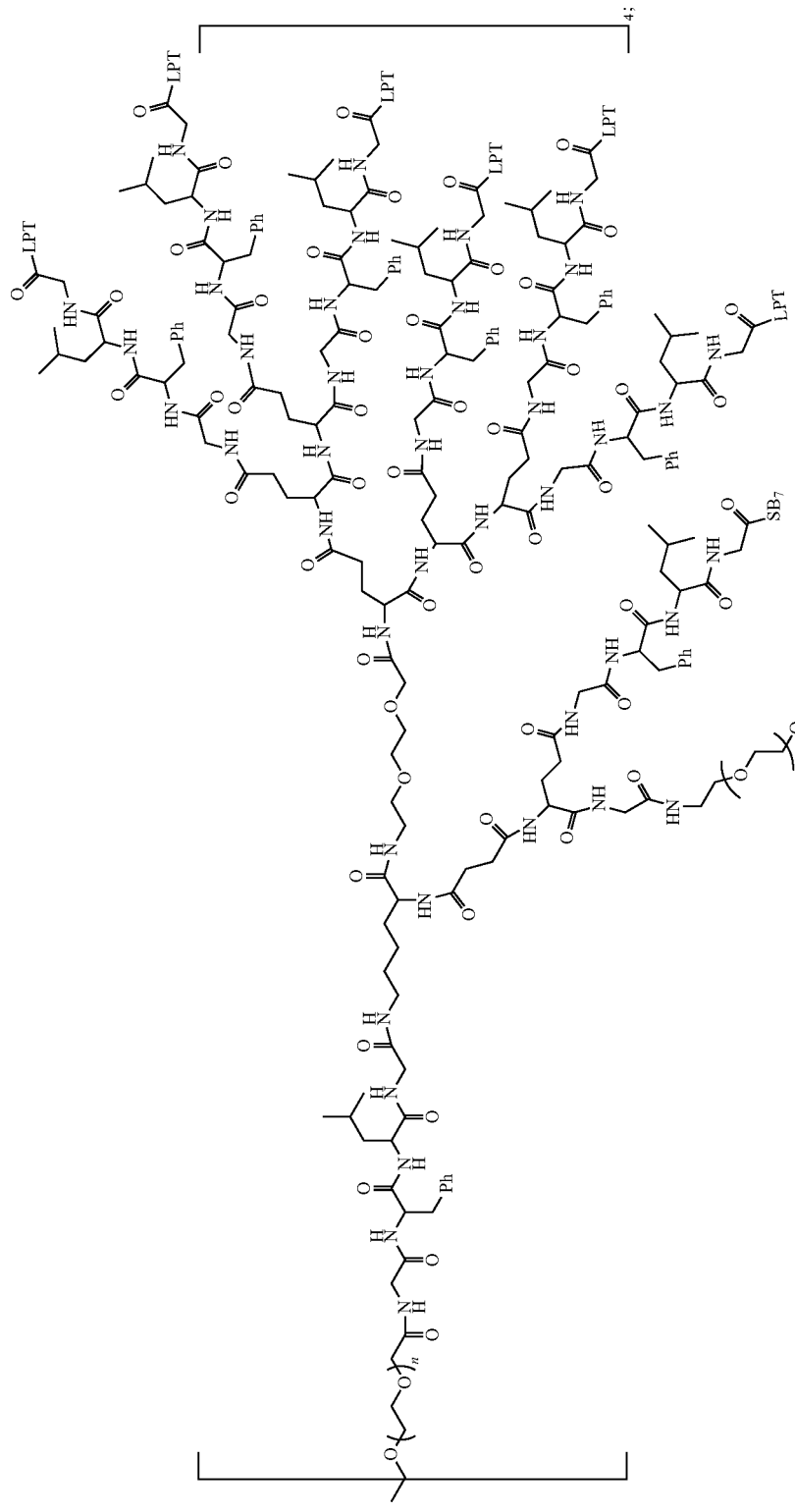

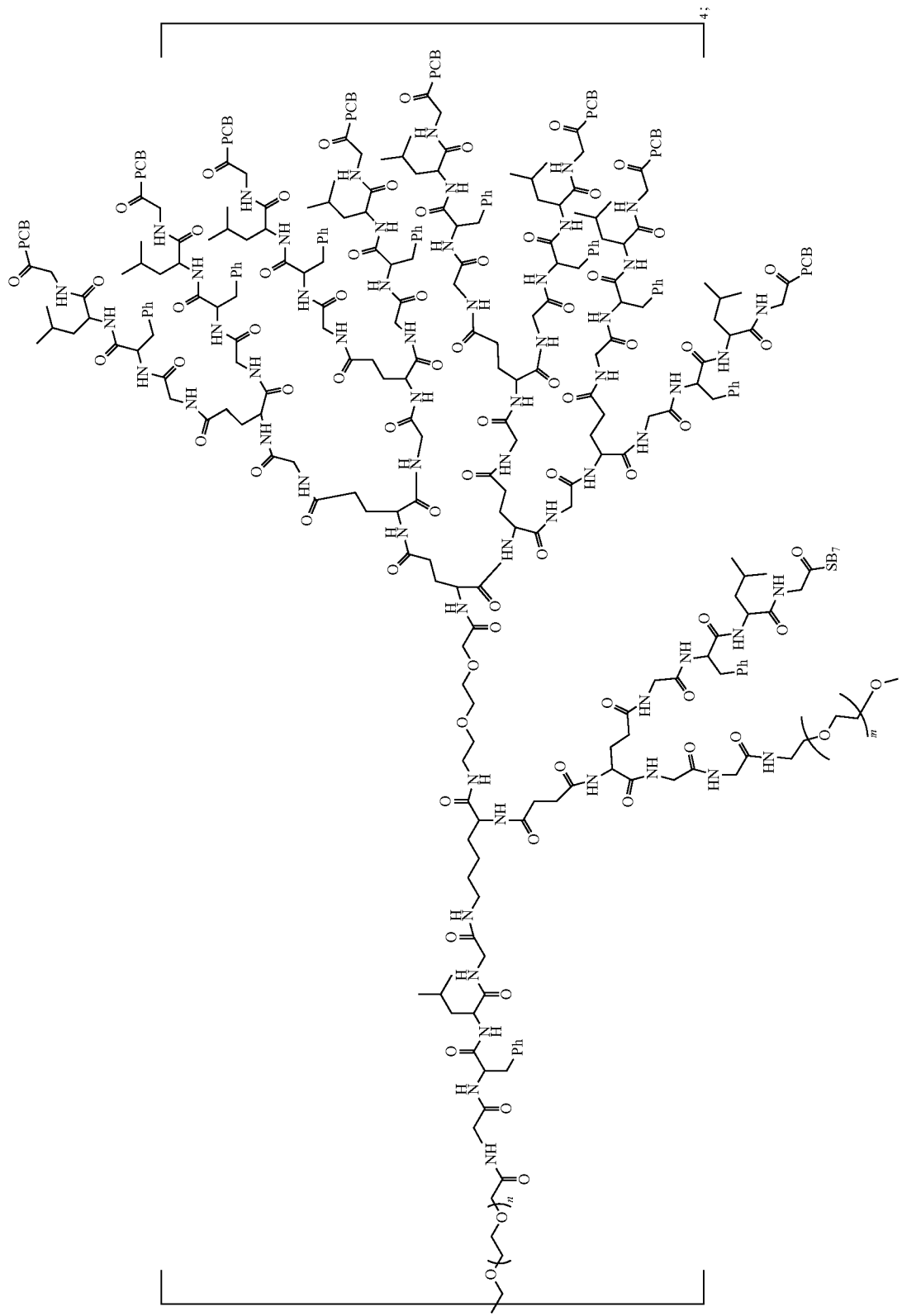

-continued
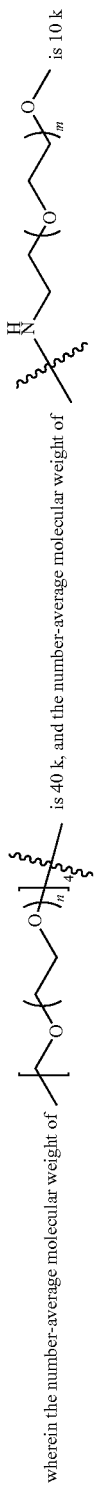
wherein the number-average molecular weight of [structure] is 40 k, and the number-average molecular weight of [structure] is 10 k

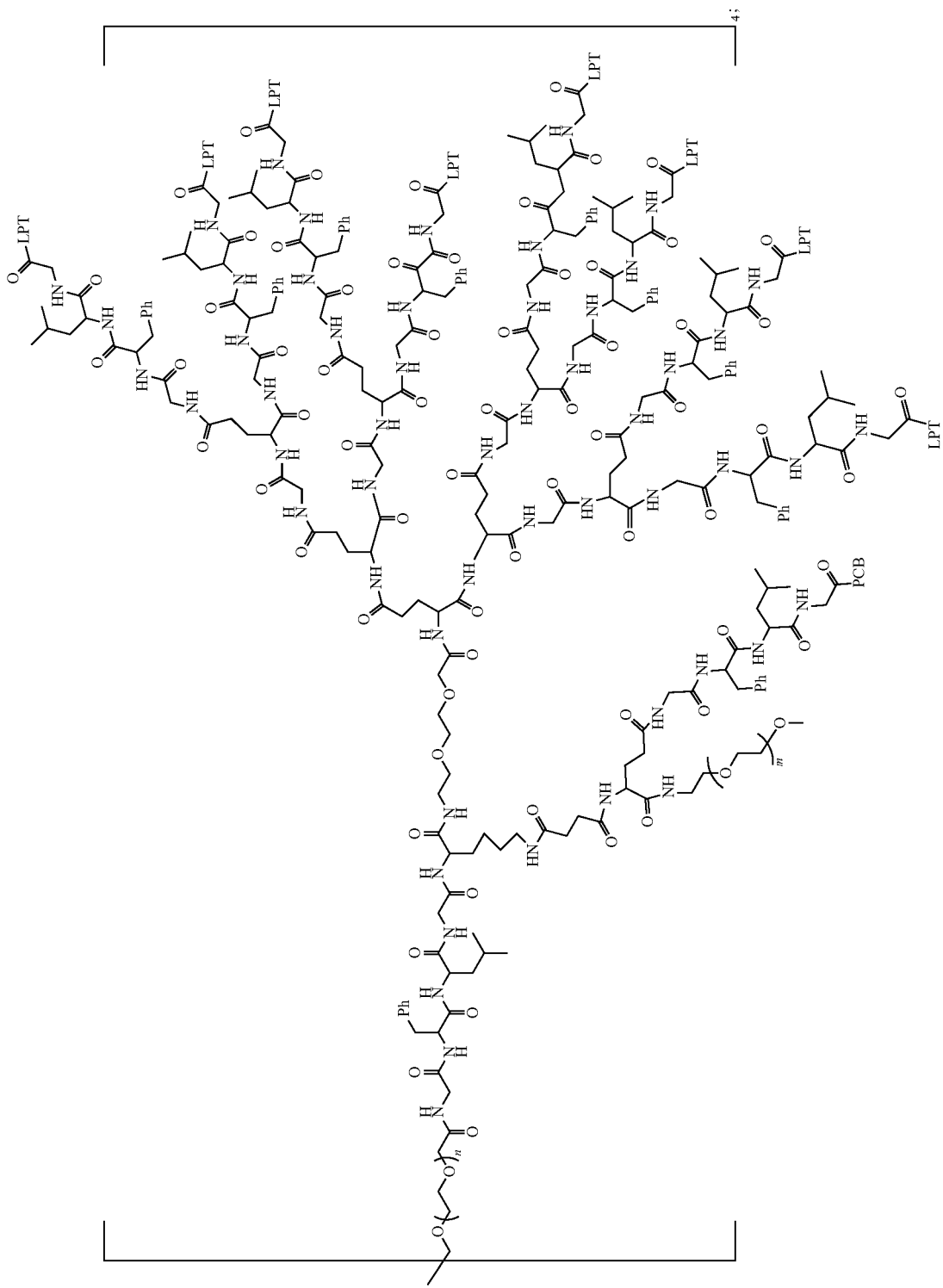

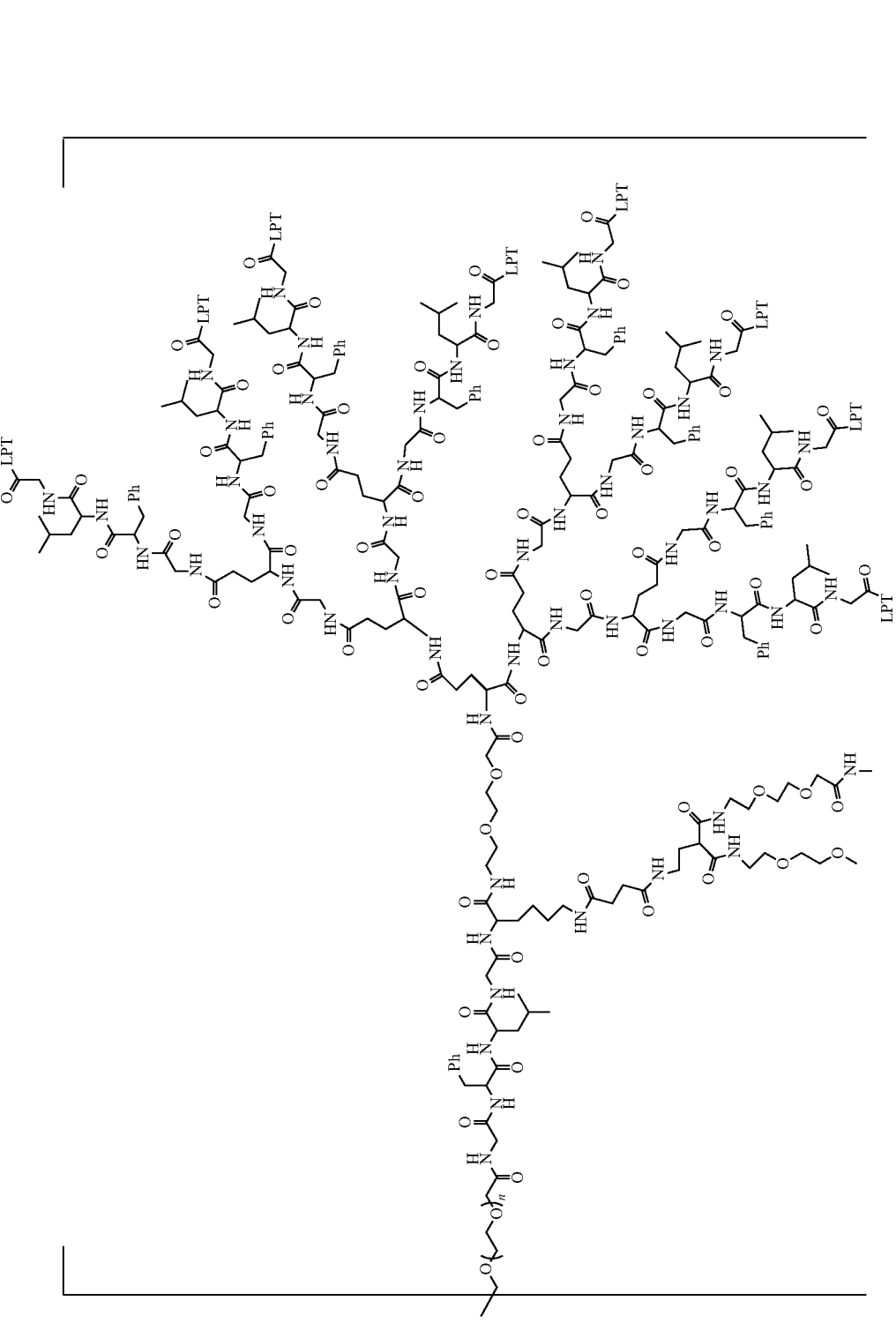

-continued
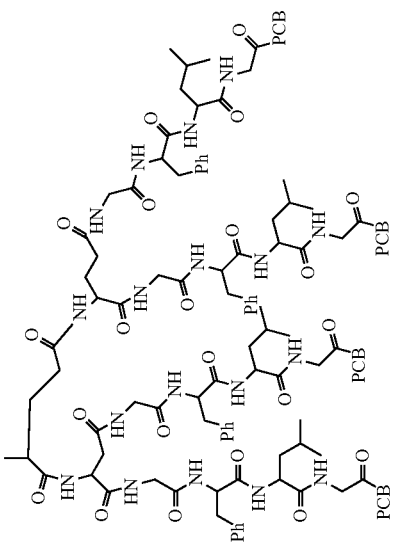
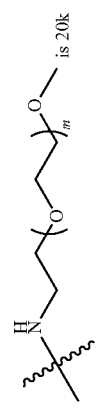
wherein the number-average molecular weight of [structure] is 40k, and the number-average molecular weight of [structure] is 20k.

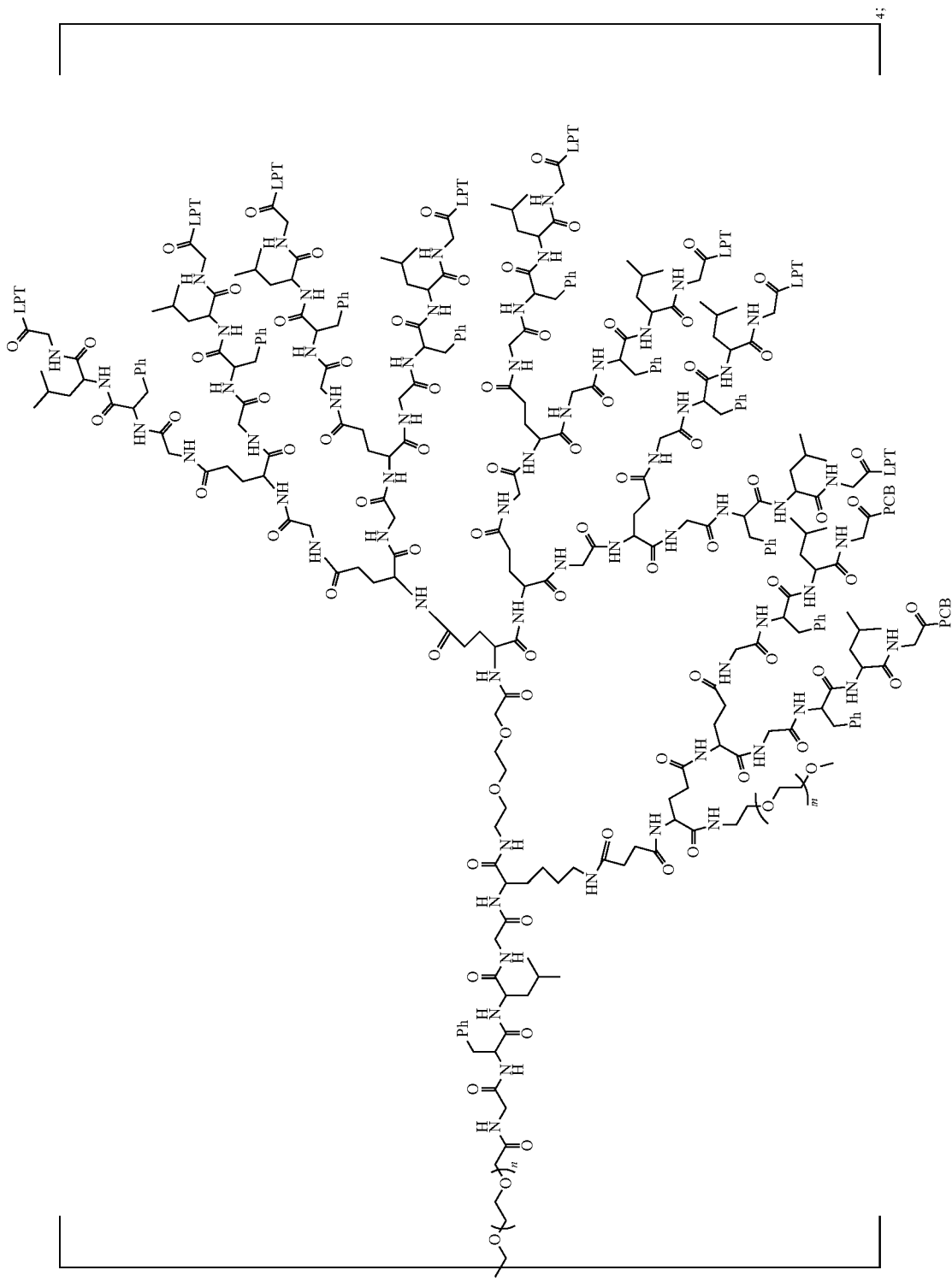

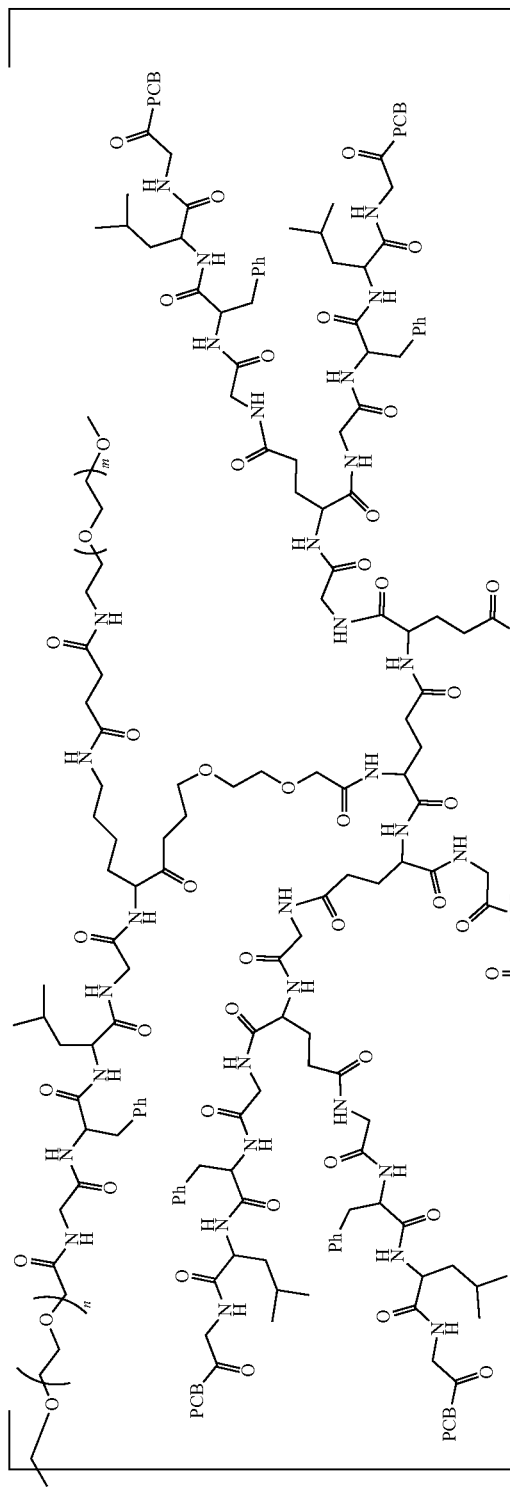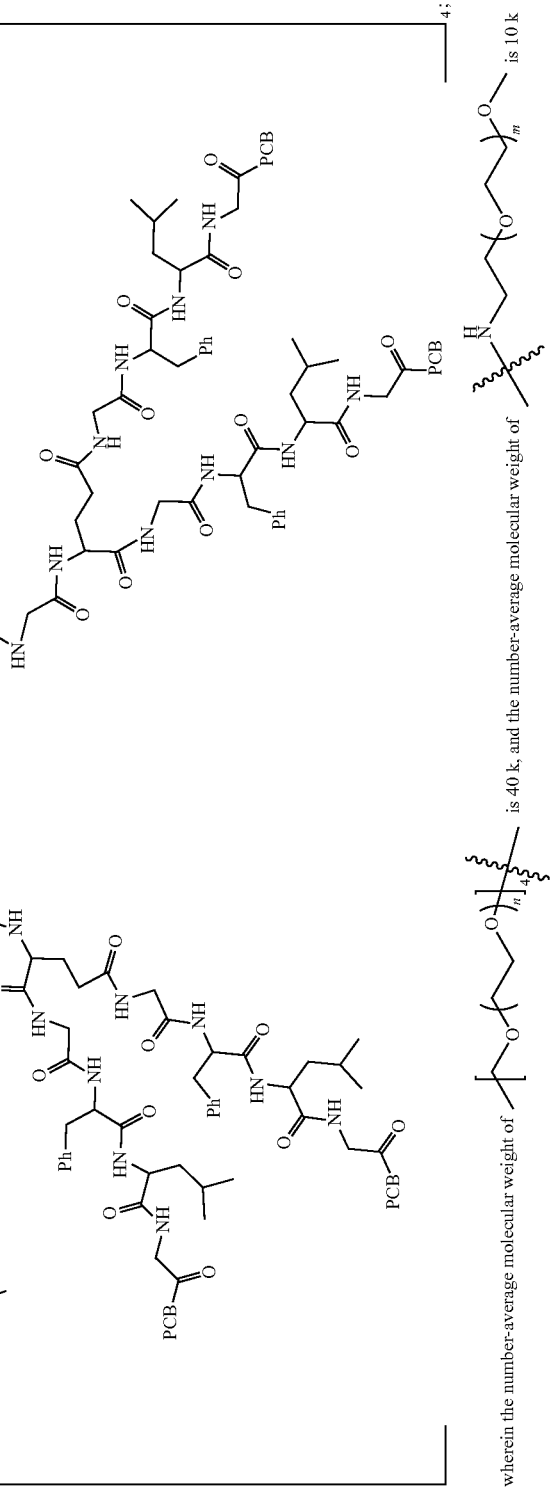

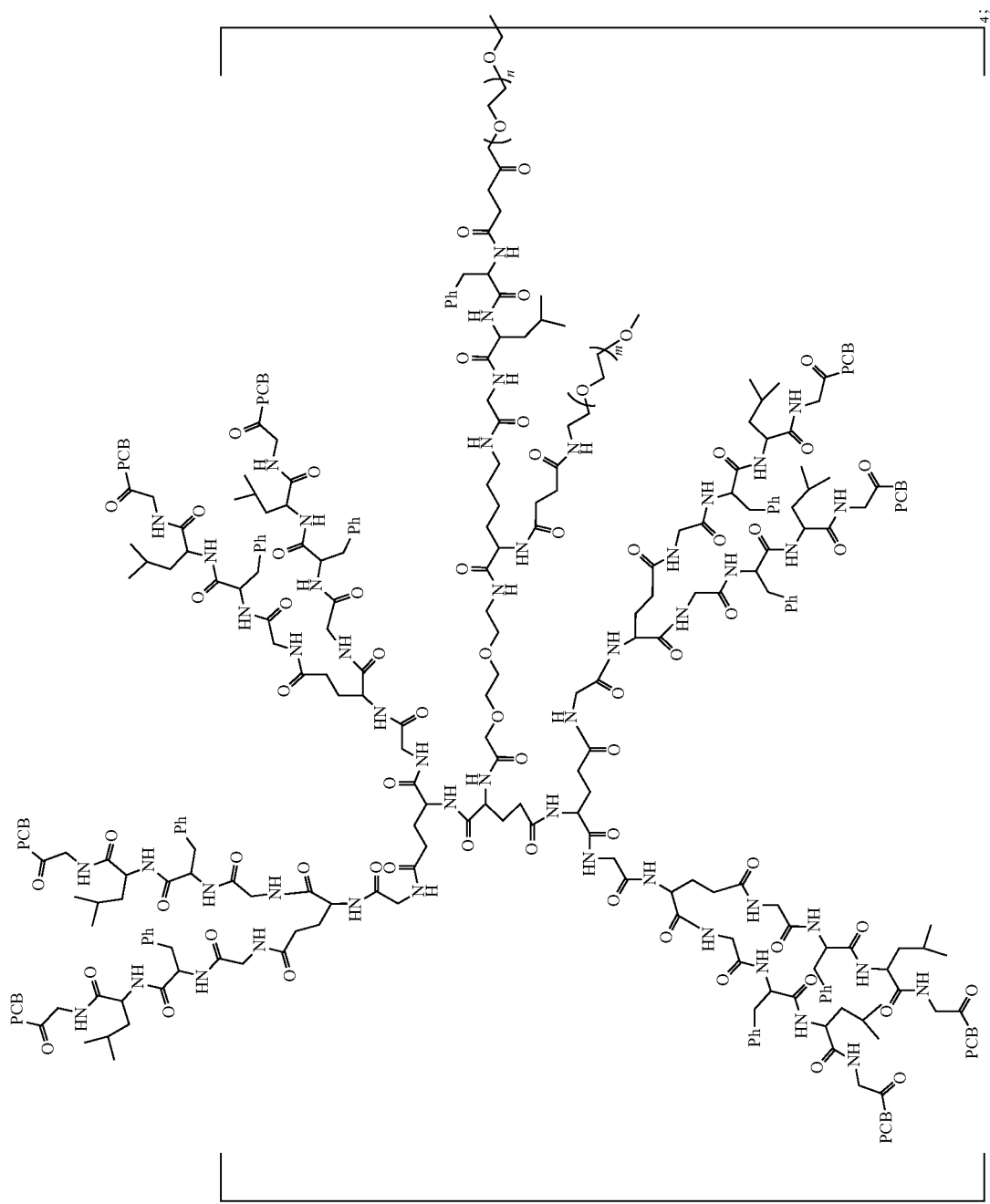

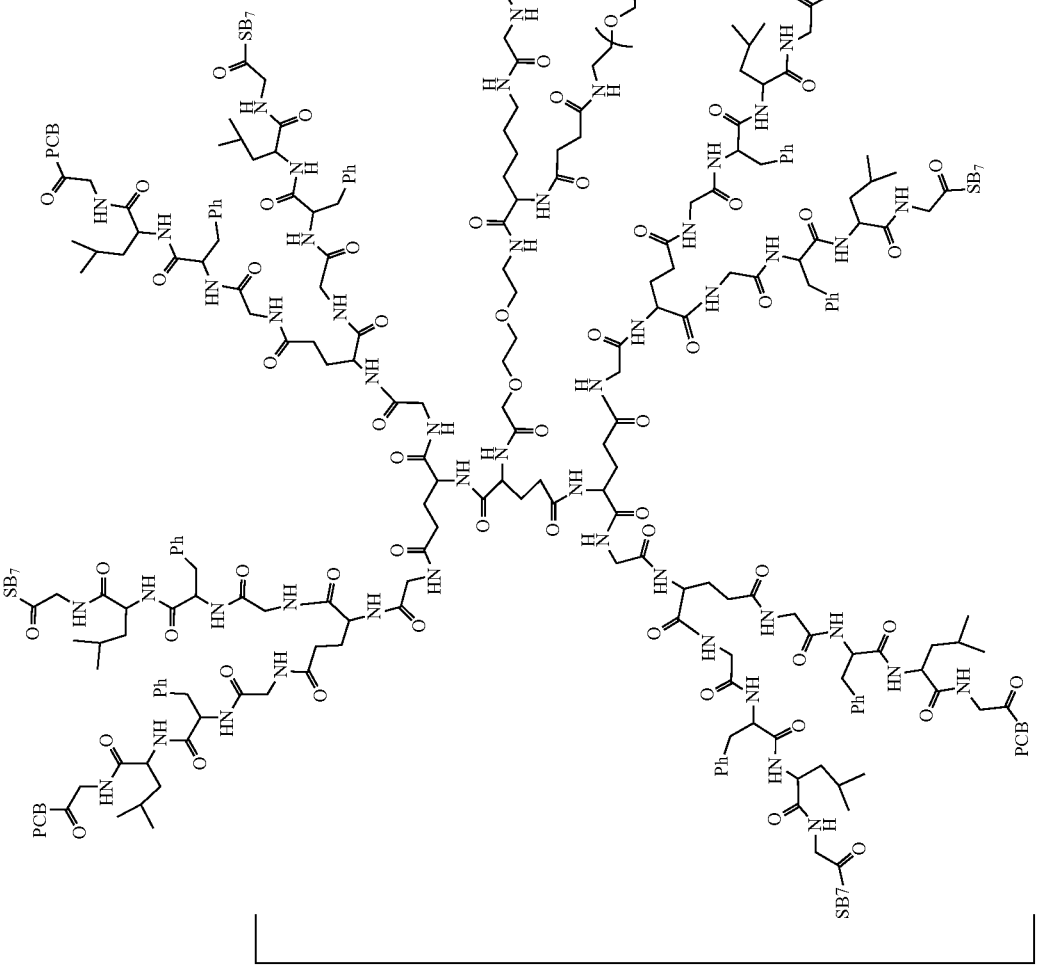

-continued
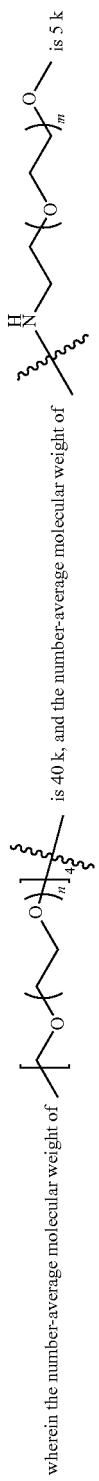

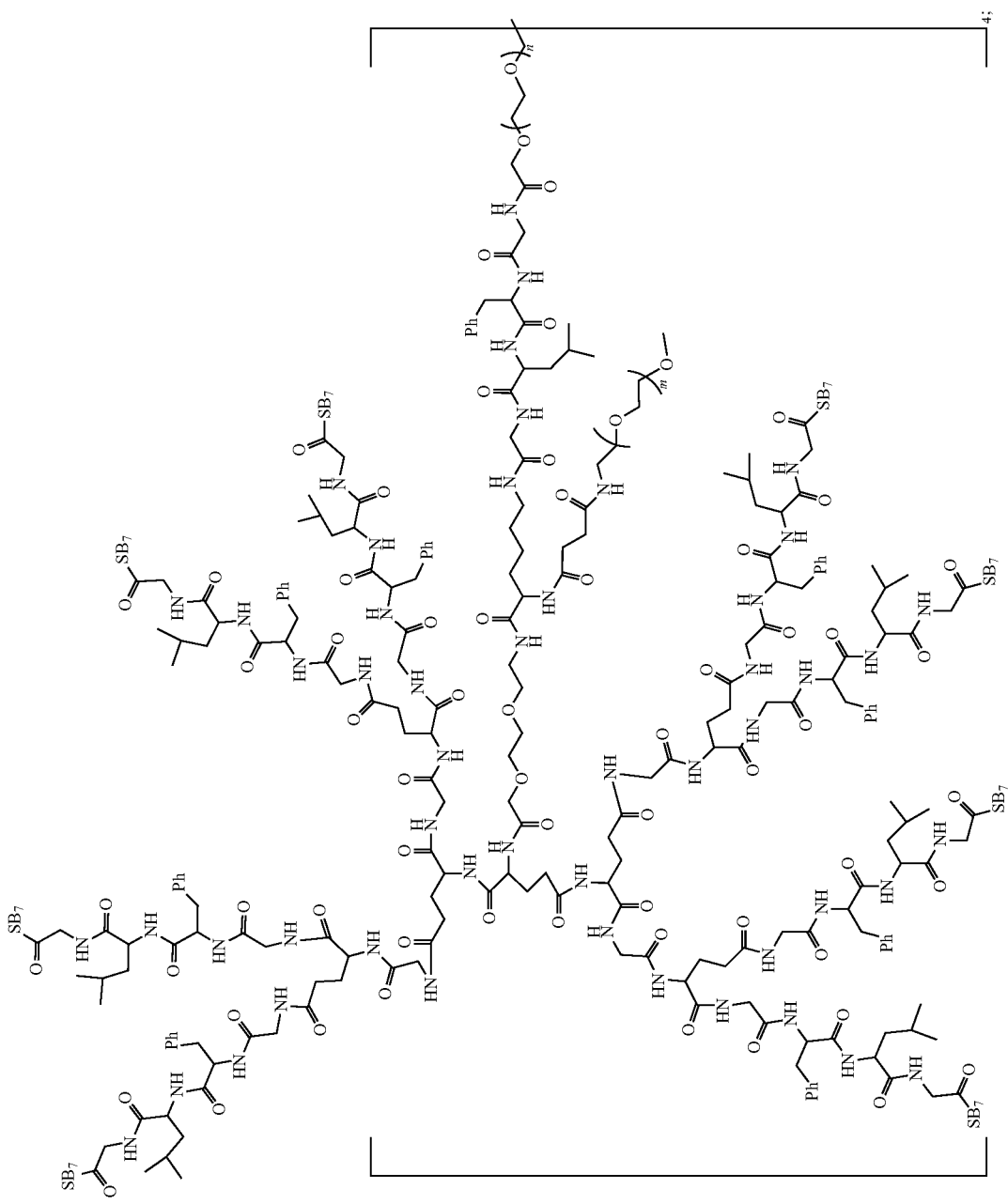

-continued
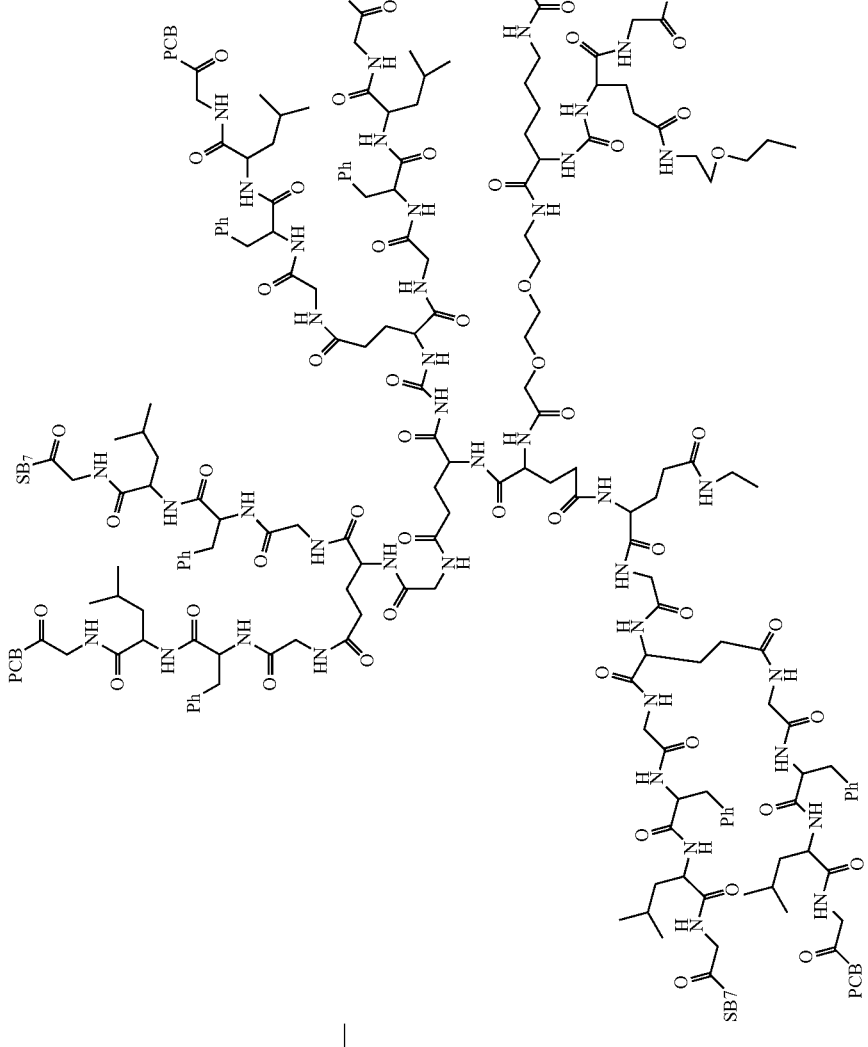
wherein the number-average molecular weight of 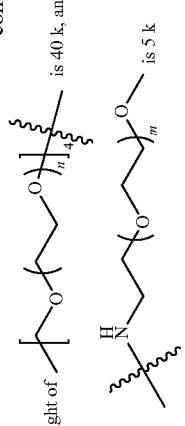 is 40 k, and the number-average molecular weight of 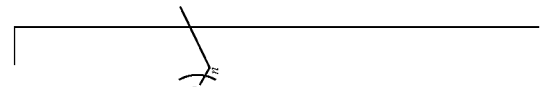 is 5 k

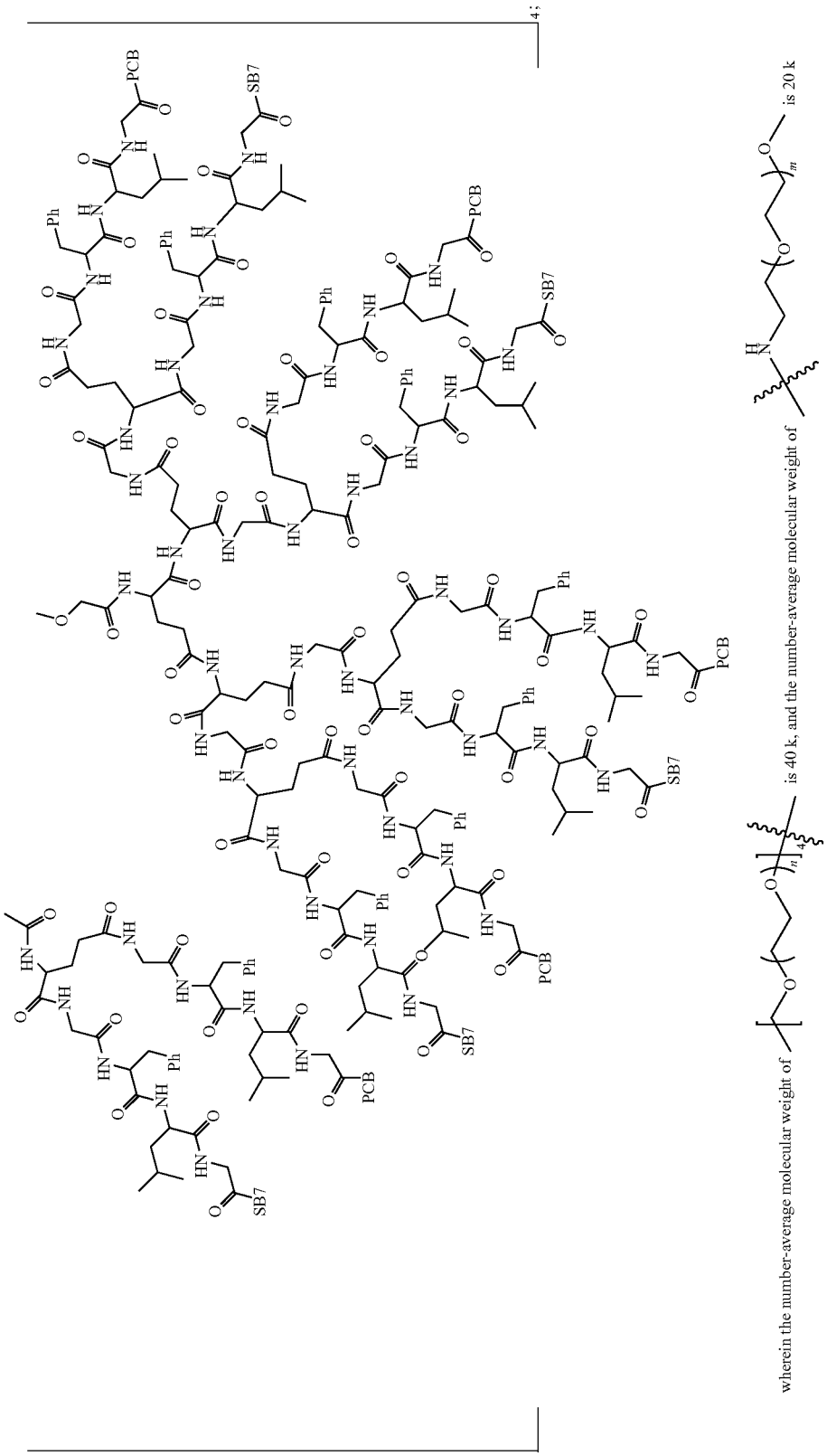

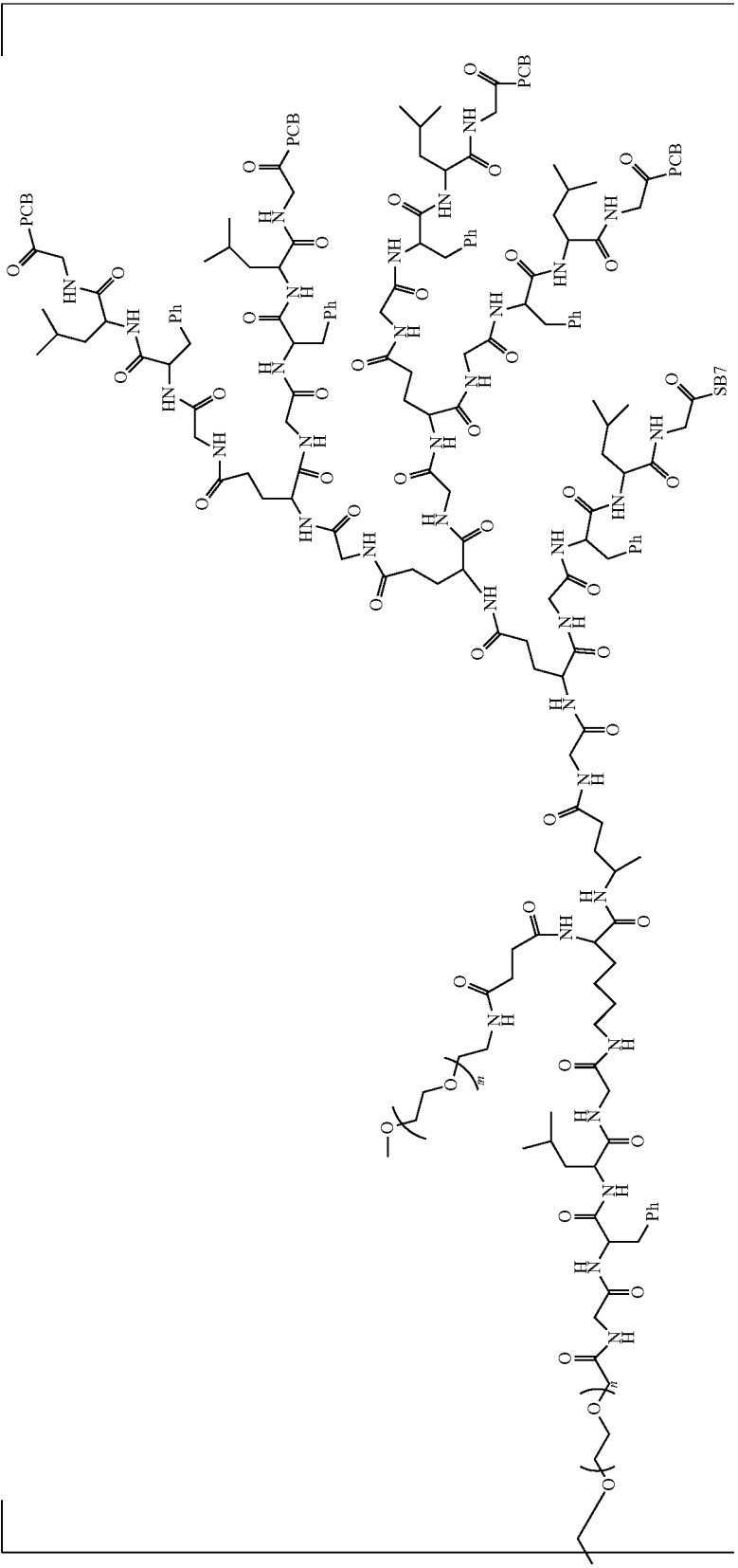

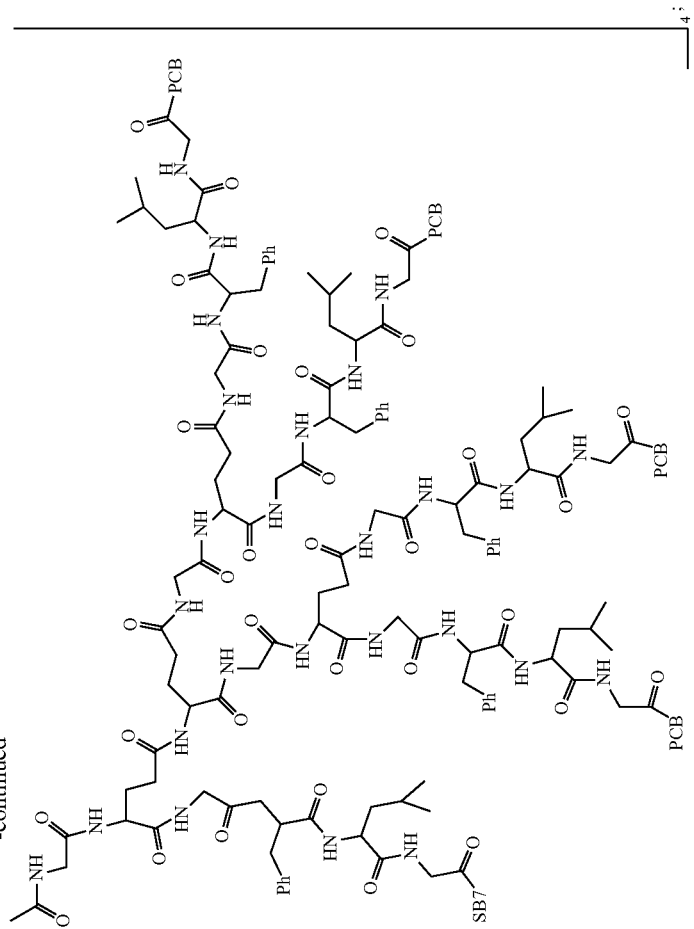

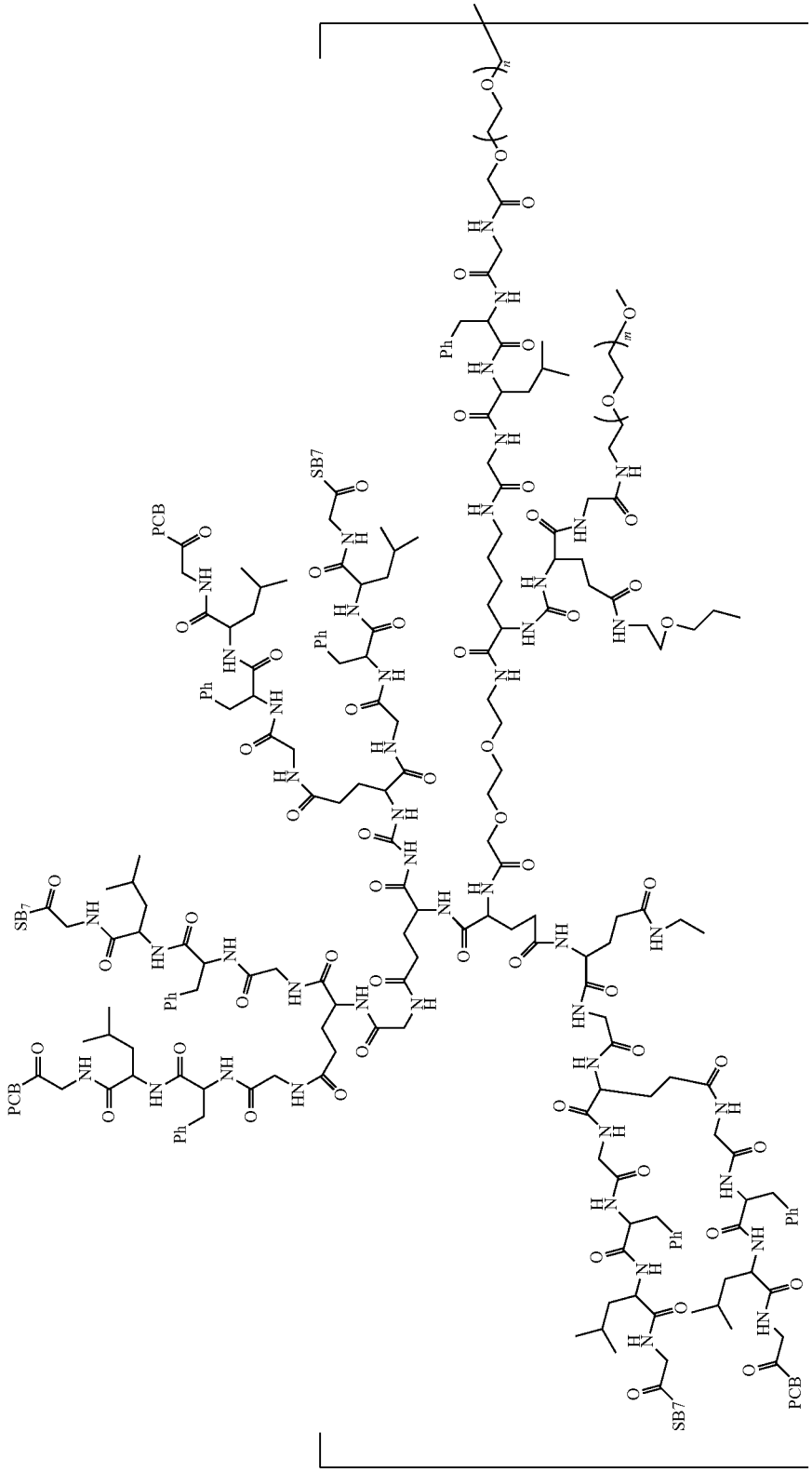

-continued
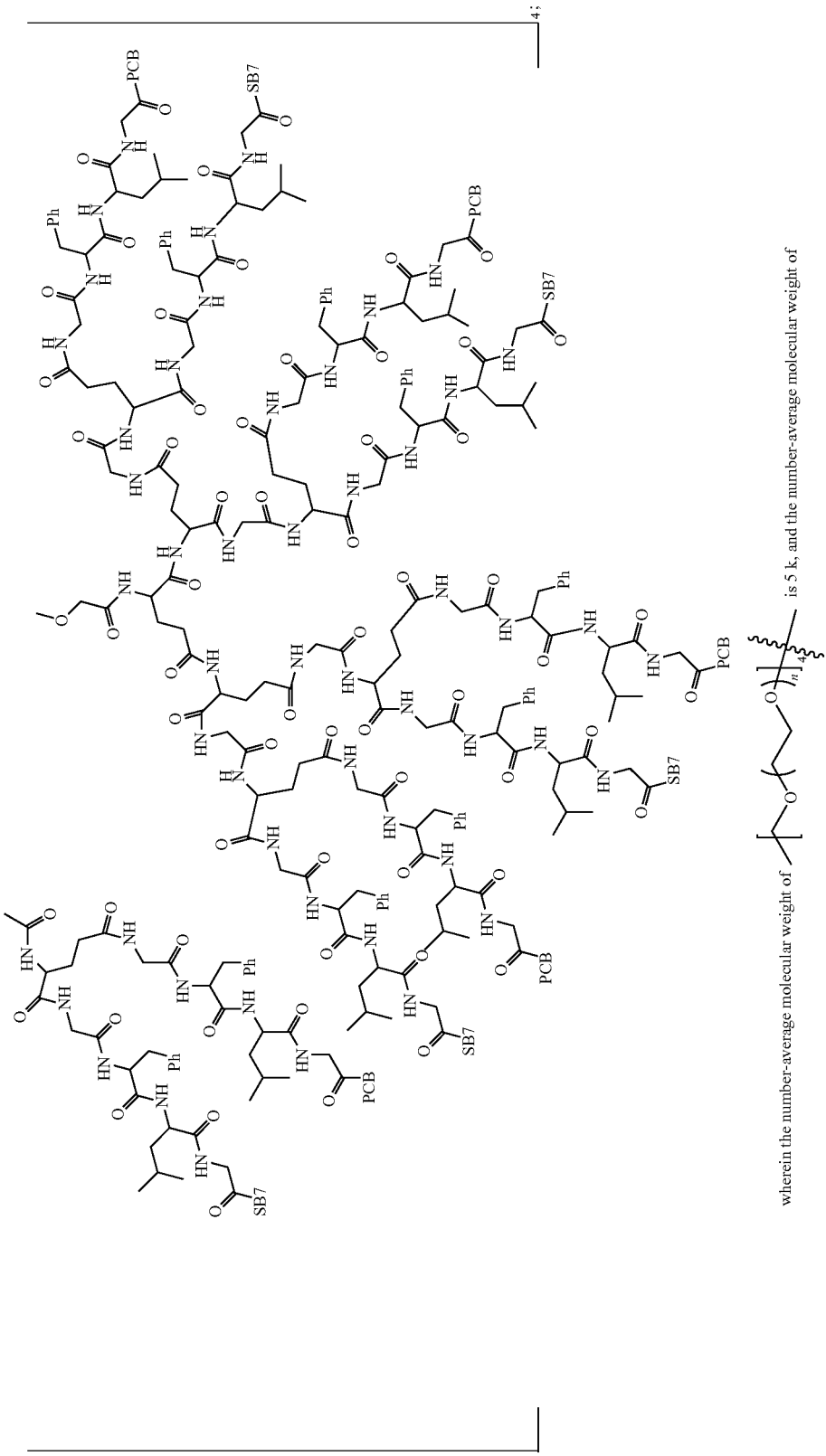
wherein the number-average molecular weight of 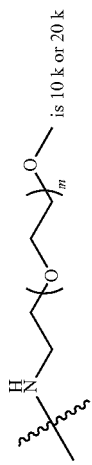 is 5 k, and the number-average molecular weight of $\phantom{x}$ is 10 k or 20 k

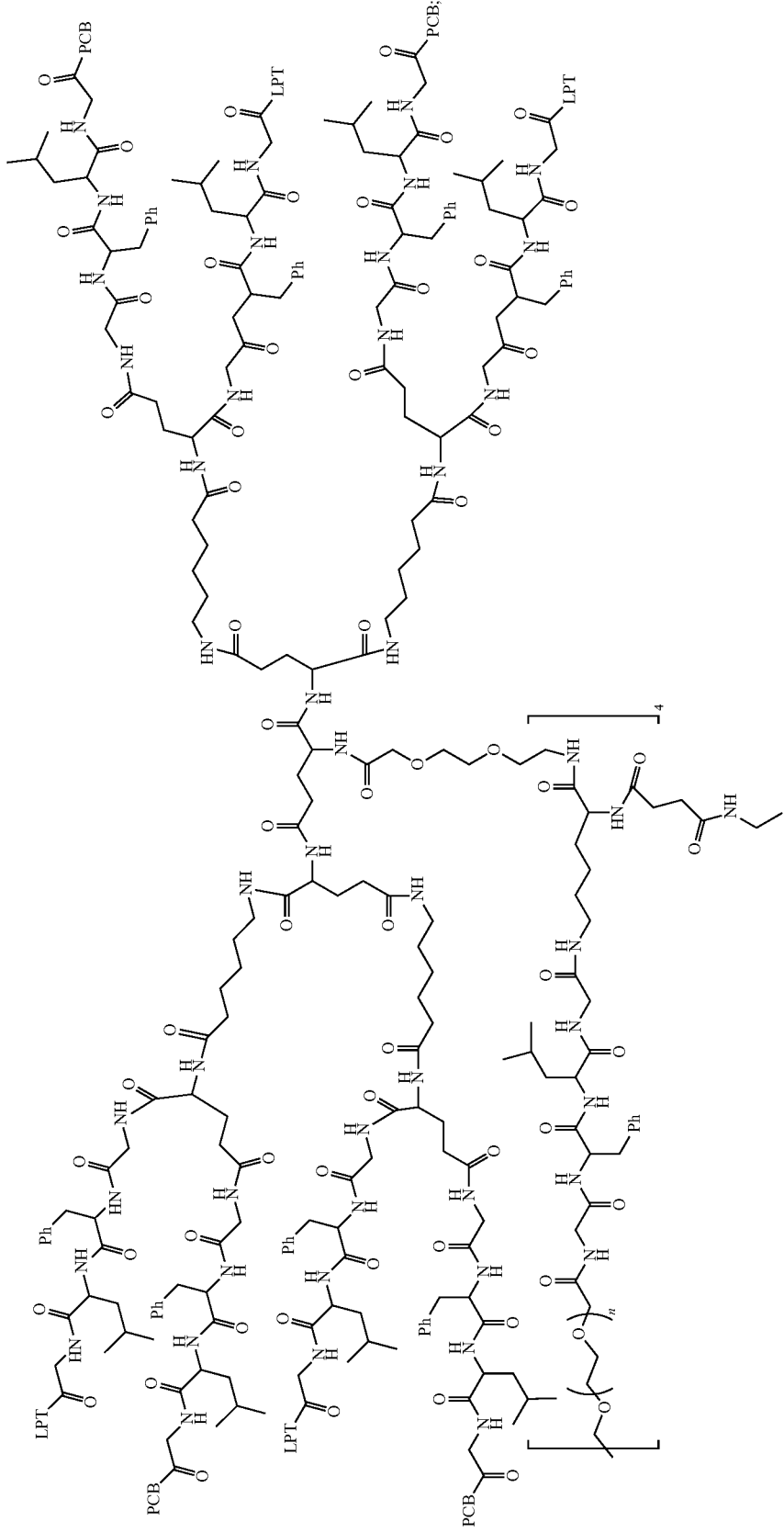

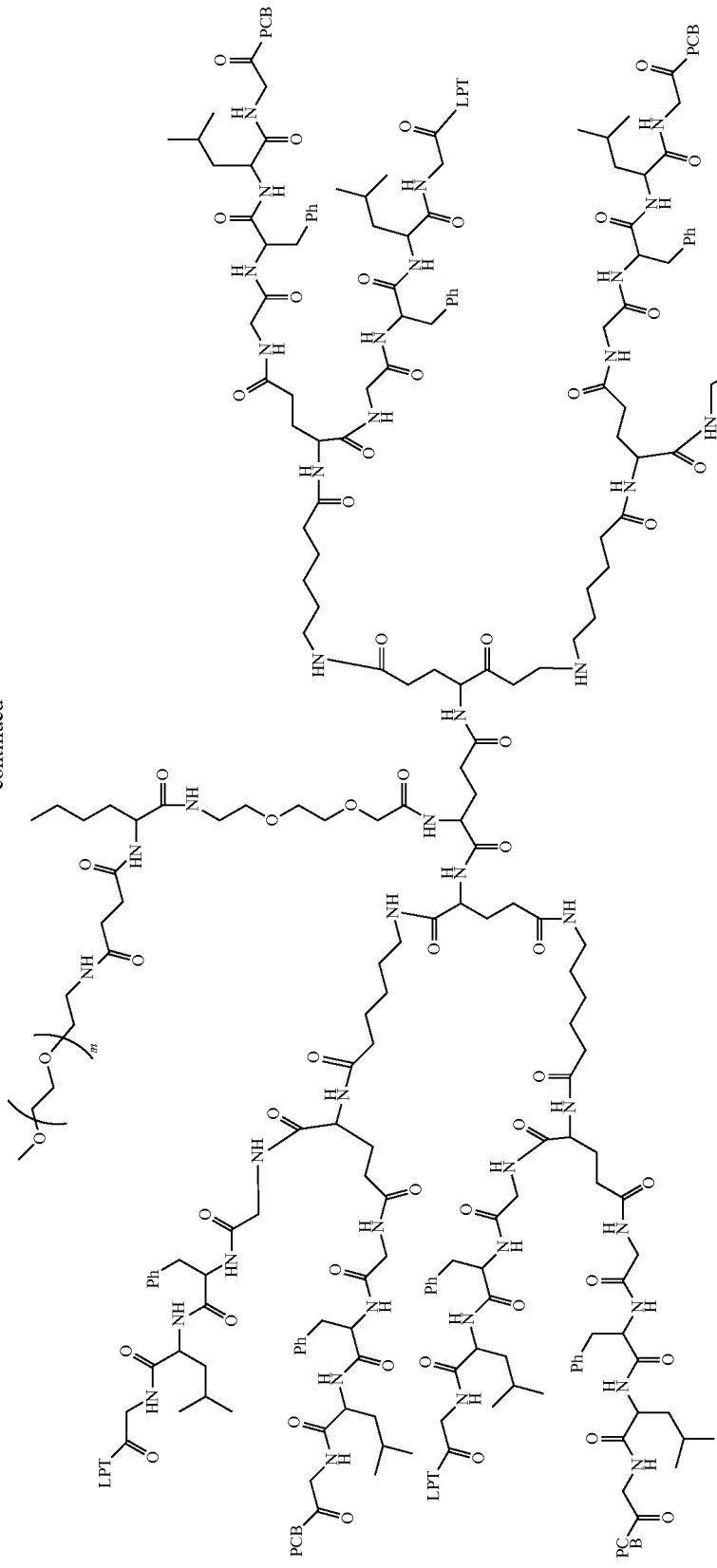
-continued
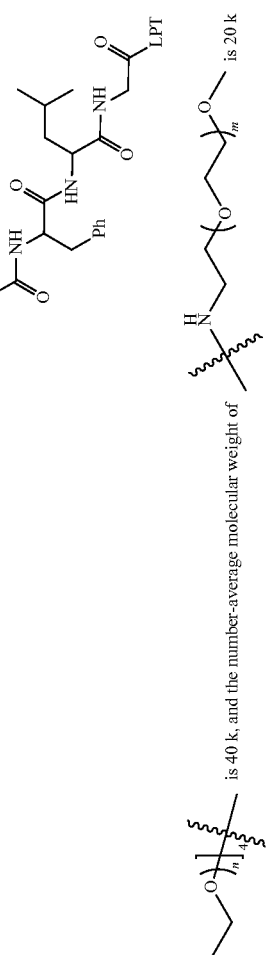
wherein the number-average molecular weight of  is 40 k, and the number-average molecular weight of -O{-}$_m$- is 20 k -continued
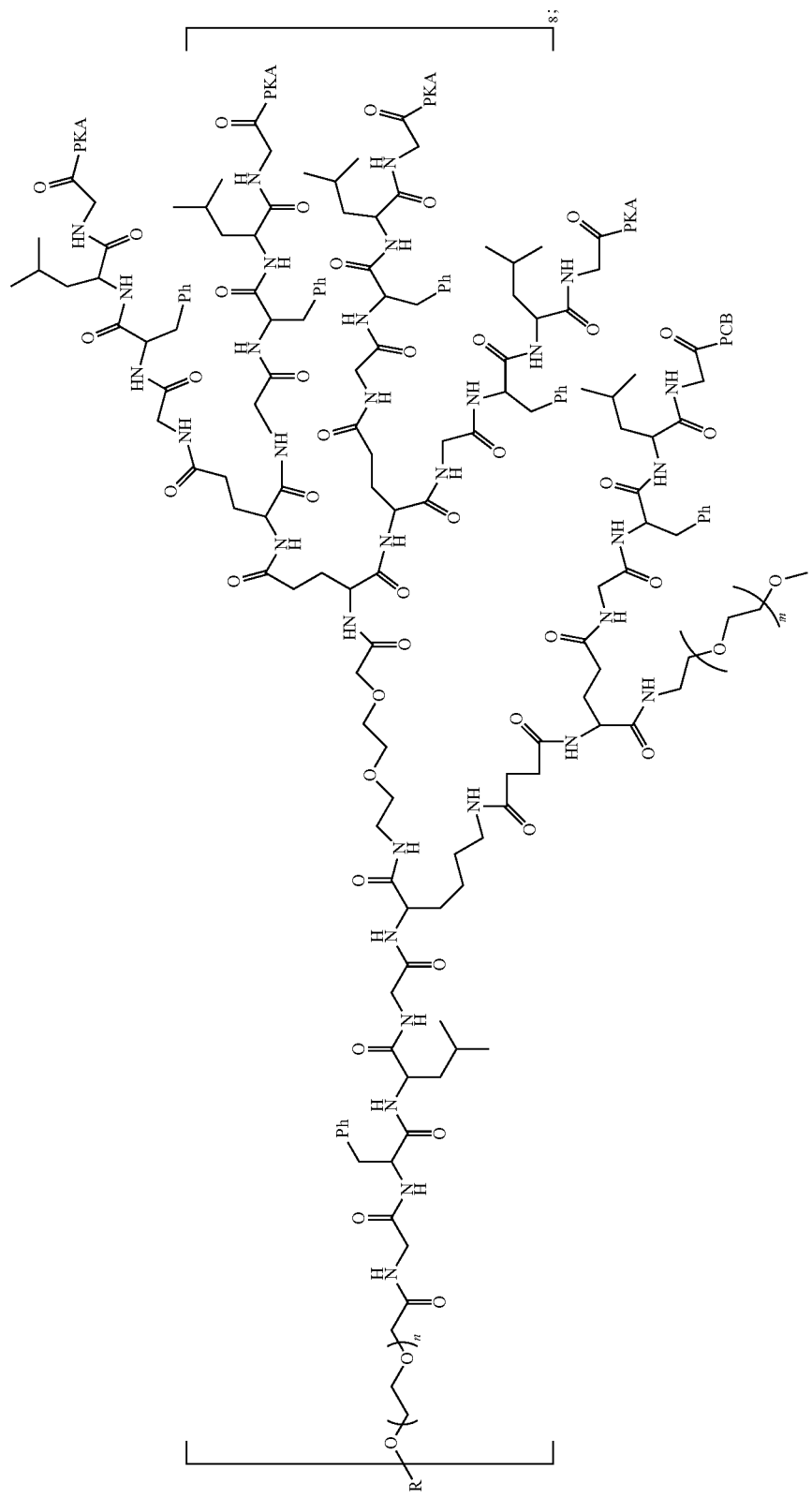
when R is a core structure of an eight-arm polyethylene glycol; the number-average molecular weight of  is 40 k, and the number-average molecular weight of is 5 k -continued
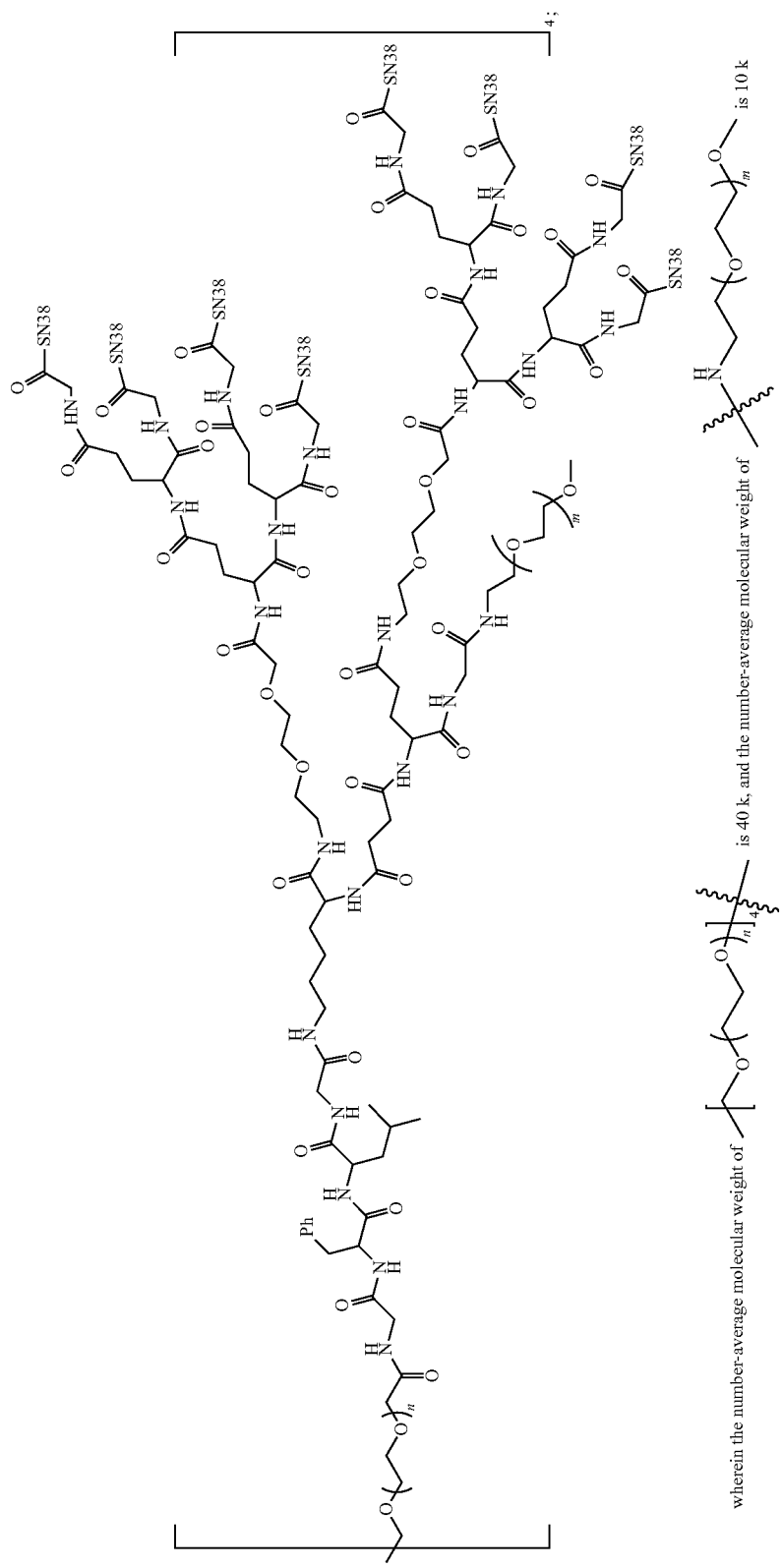

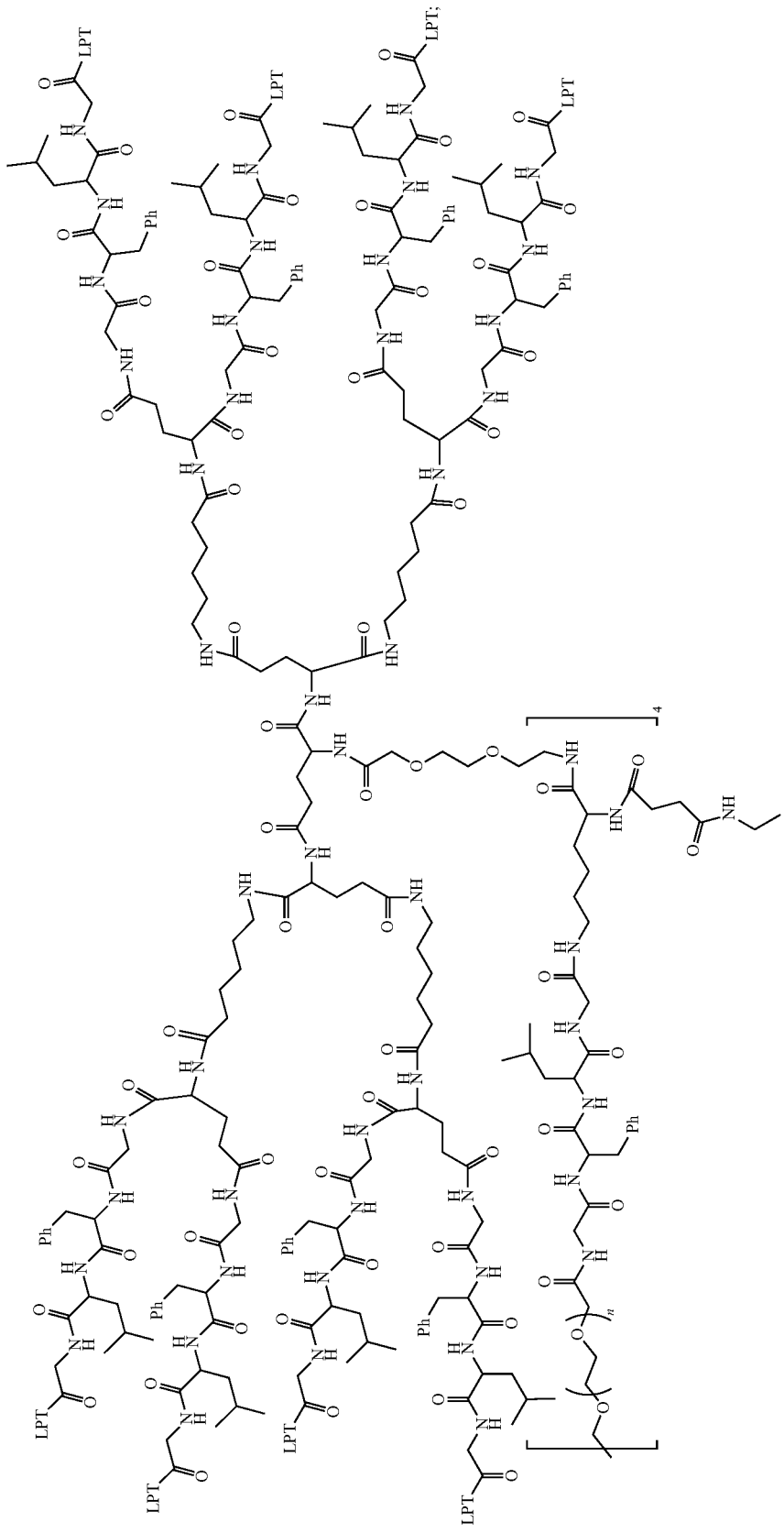

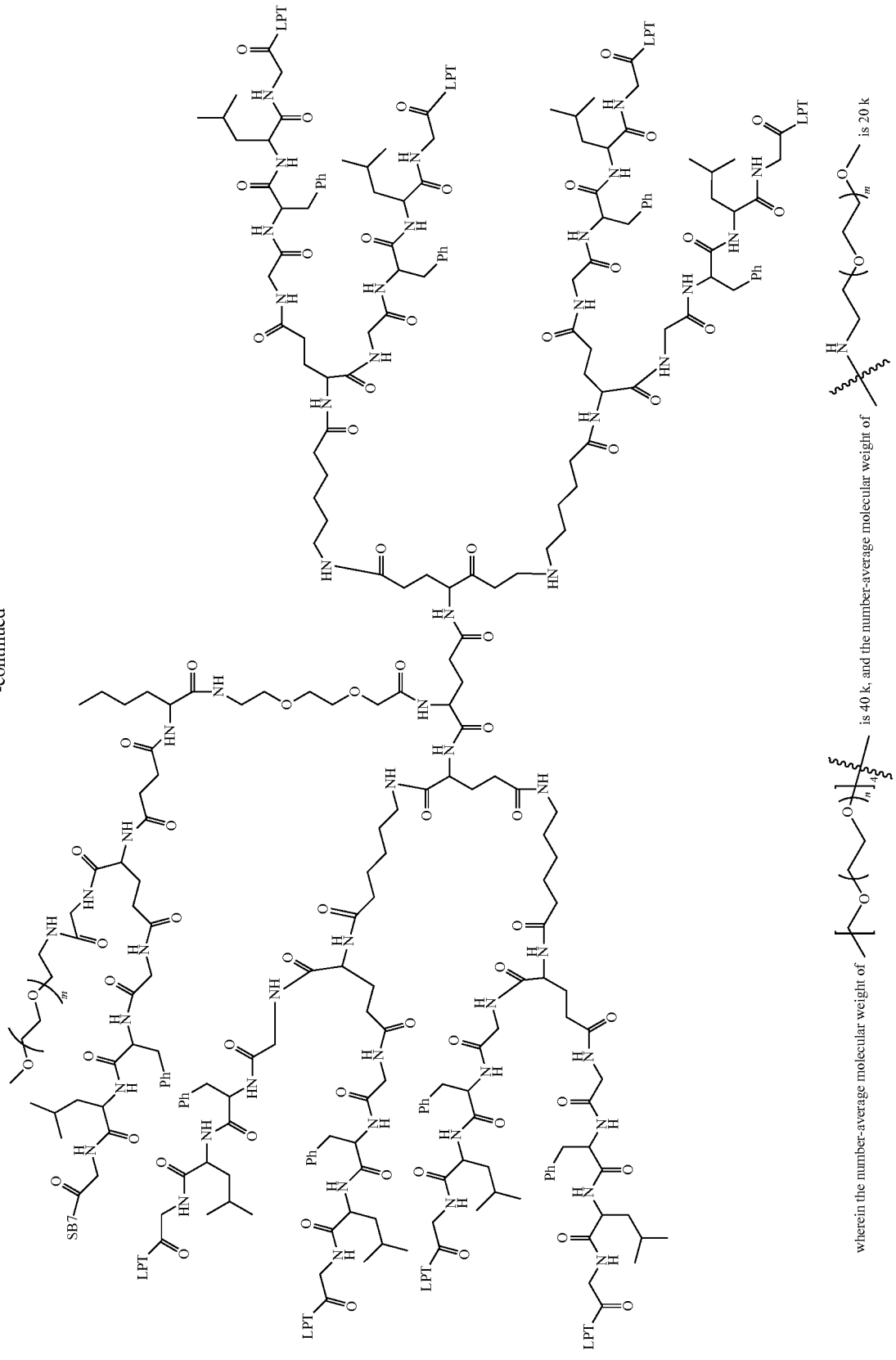

-continued
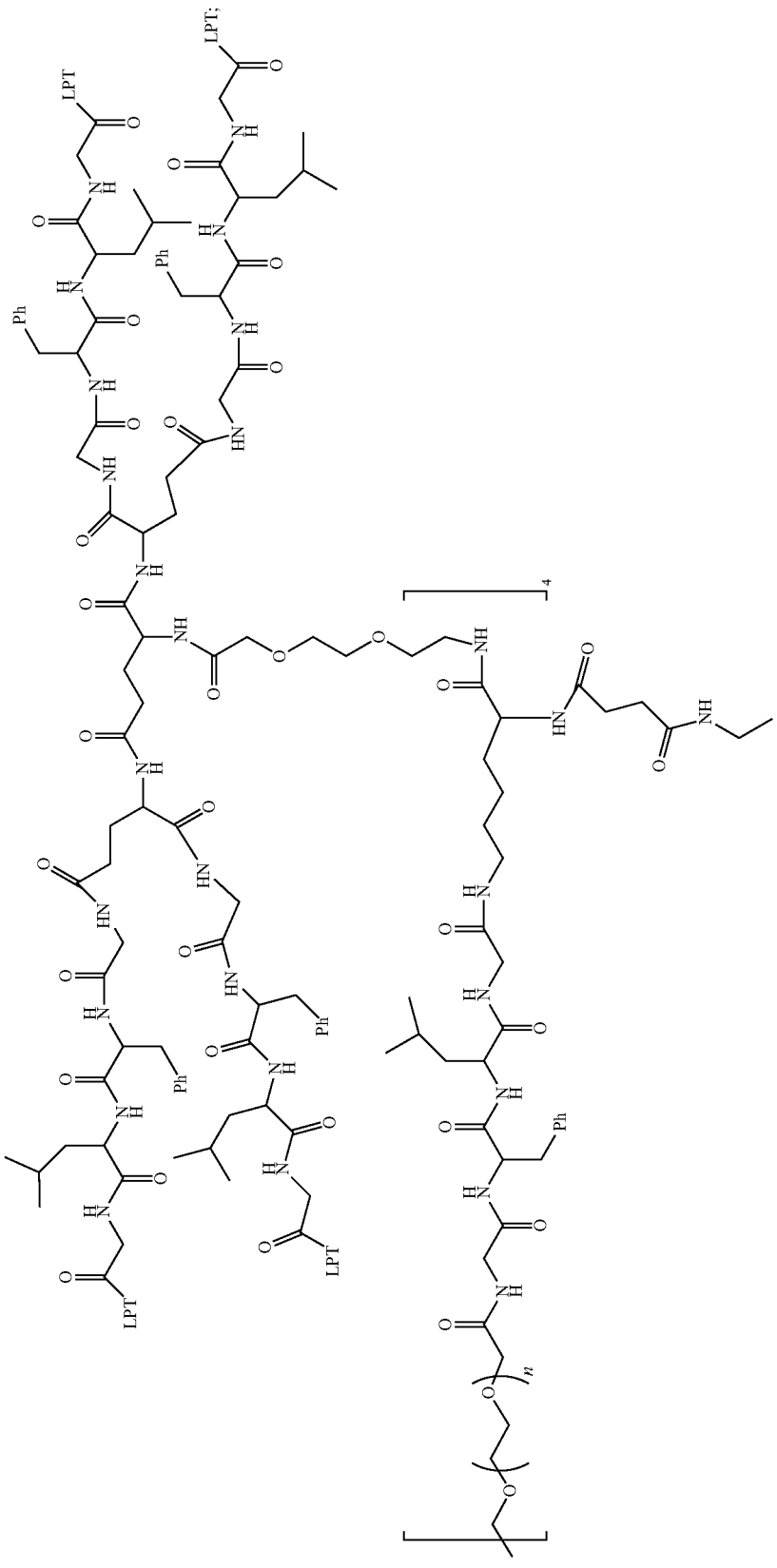

-continued
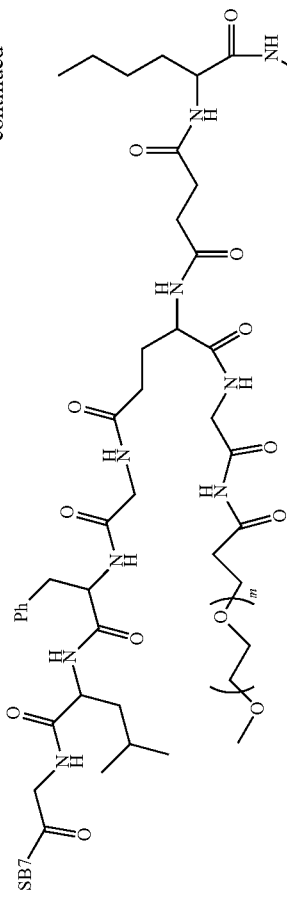
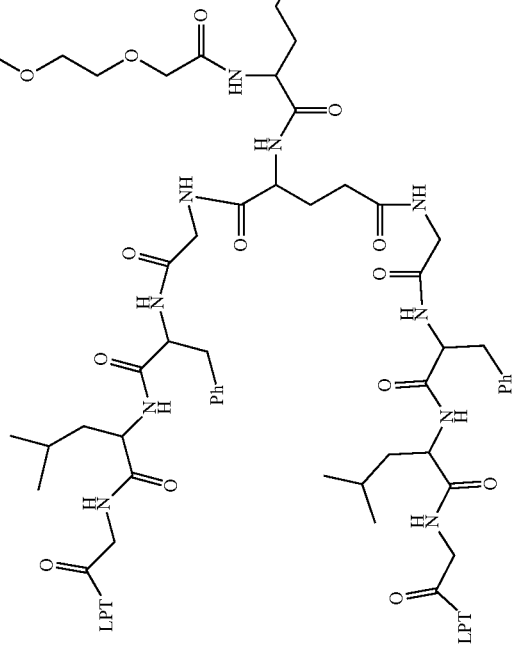
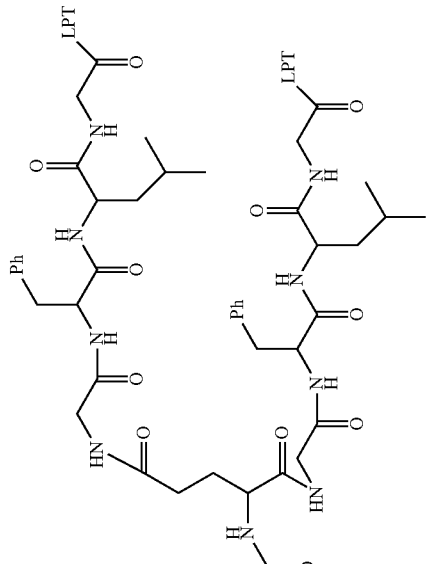
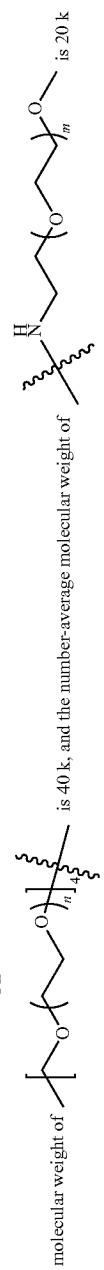
wherein the number-average molecular weight of ⁓⁓⁓(OCH₂CH₂)ₙ₄O⁓ is 40 k, and the number-average molecular weight of ⁓⁓⁓(OCH₂CH₂)ₘO⁓ is 20 k

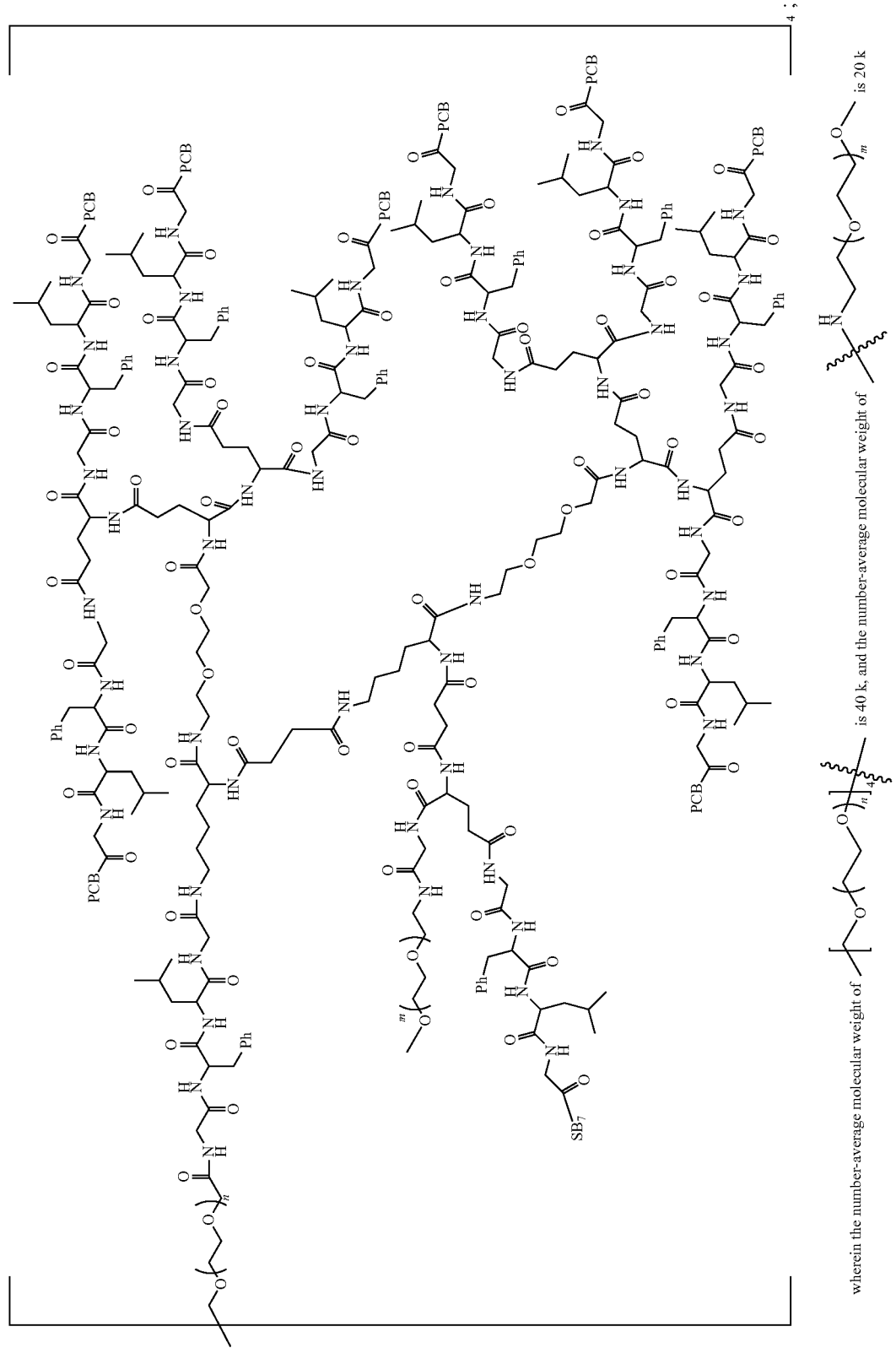

wherein the number-average molecular weight of $\underset{\text{\textasciitilde}}{\overset{}{\longleftarrow}}\!\!\left[\!\!\overset{}{\underset{}{\bigcirc}}\!\!\right]_{n}\!\!\underset{\text{\textasciitilde}}{\overset{}{\longleftarrow}}$ is 40 k, and the number-average molecular weight of $\underset{\text{\textasciitilde}}{\overset{}{\longleftarrow}}\!\!\overset{}{\underset{}{\bigcirc}}\!\!\underset{m}{}$ is 20 k;

-continued
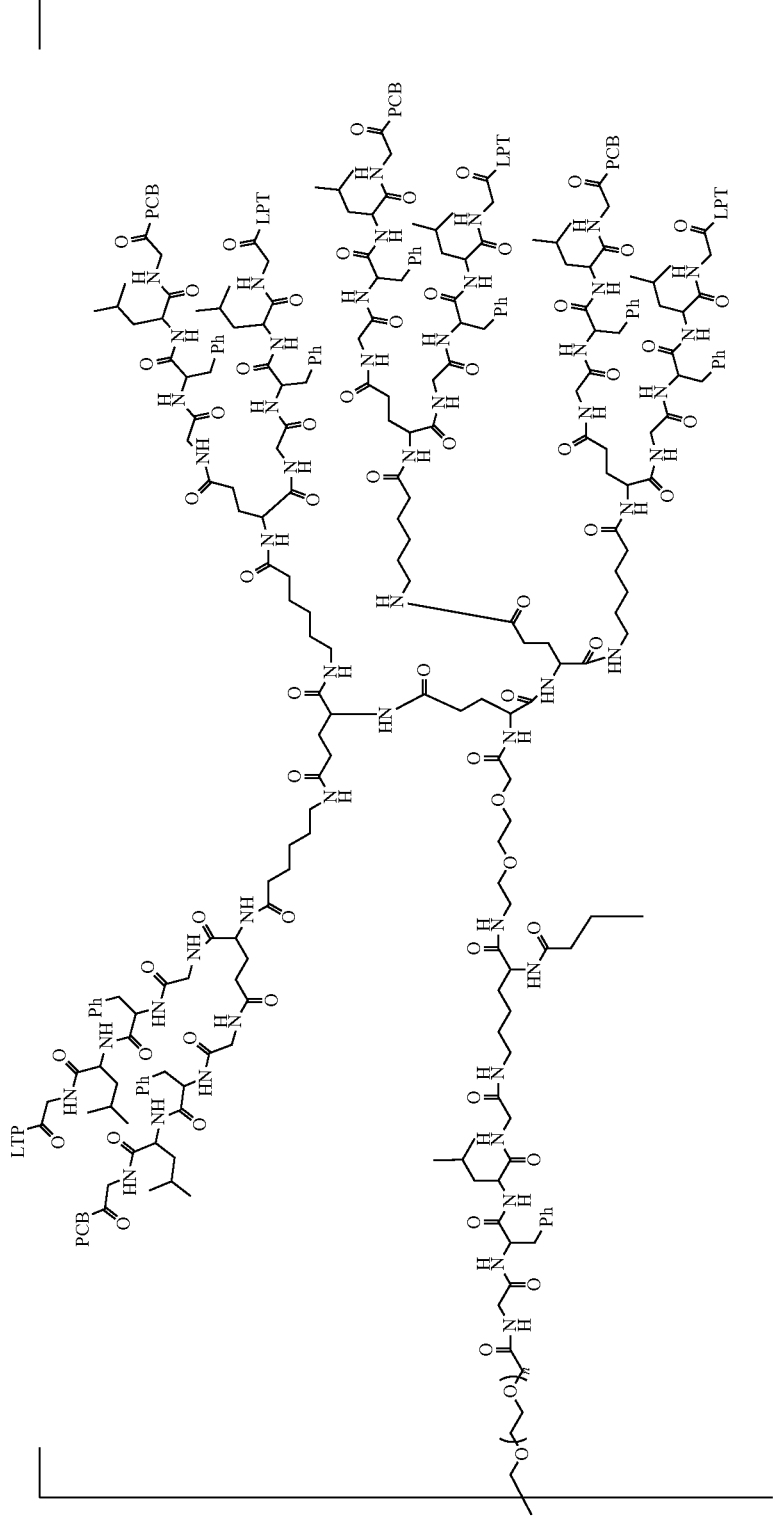

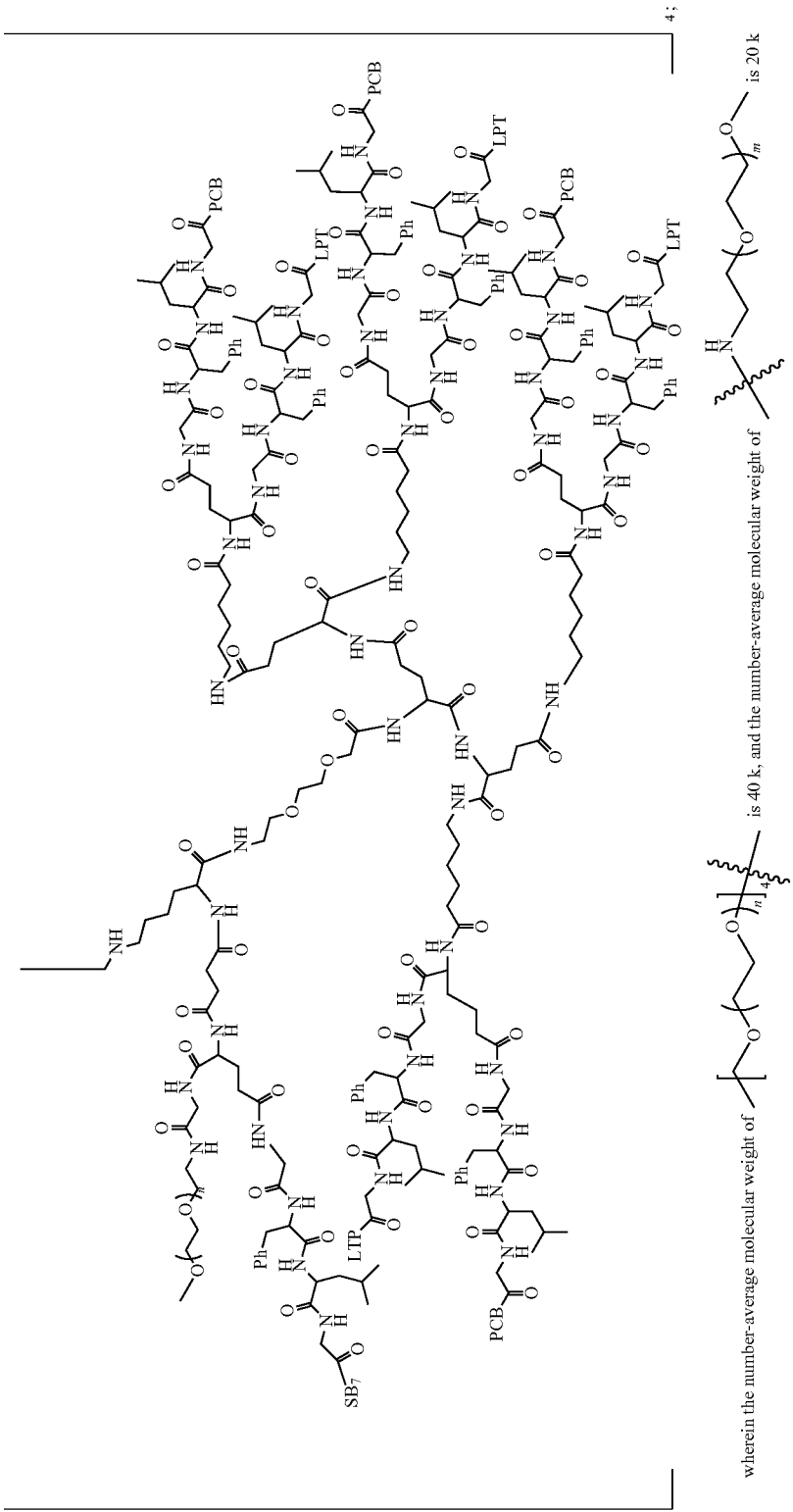

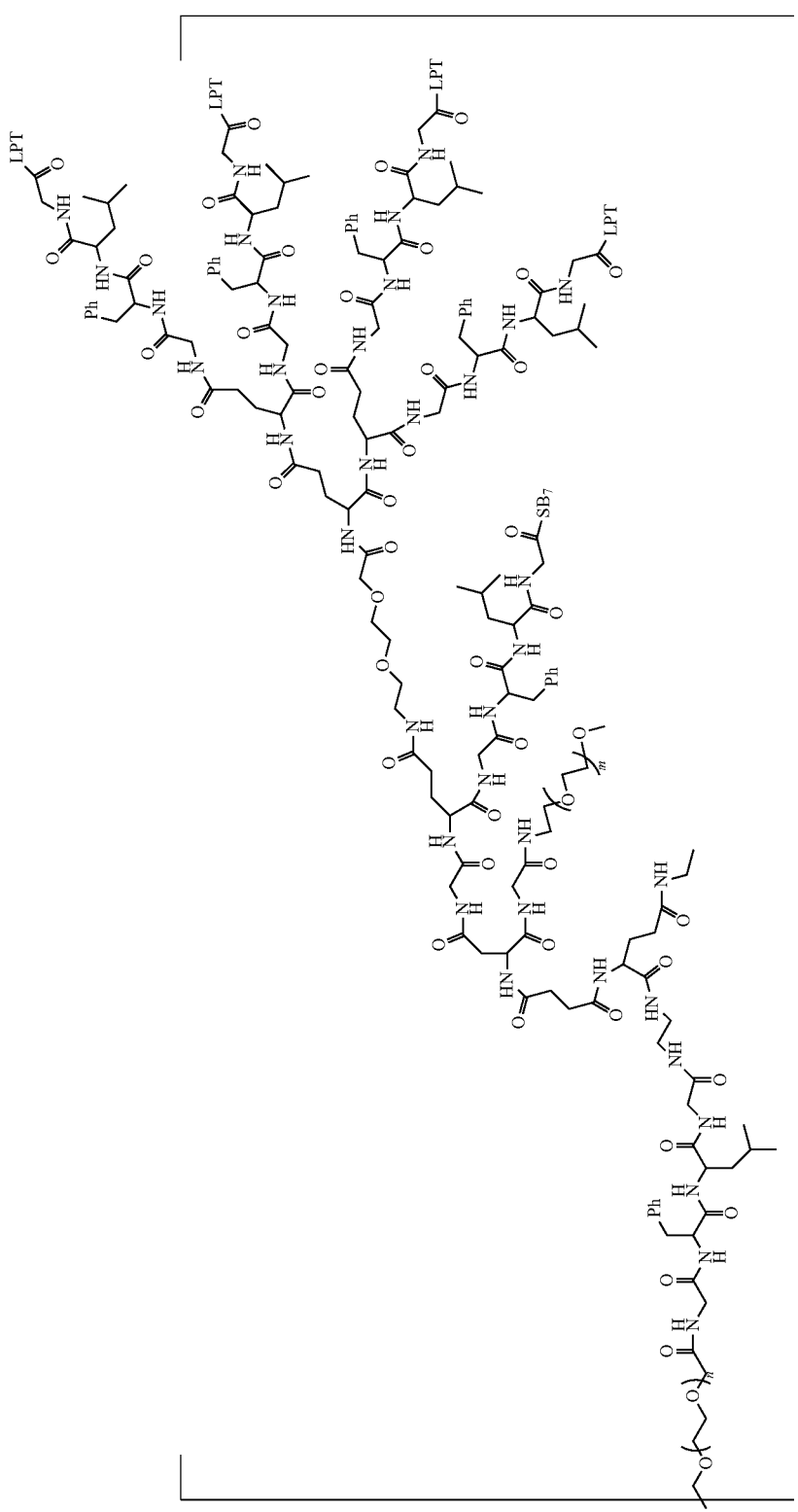

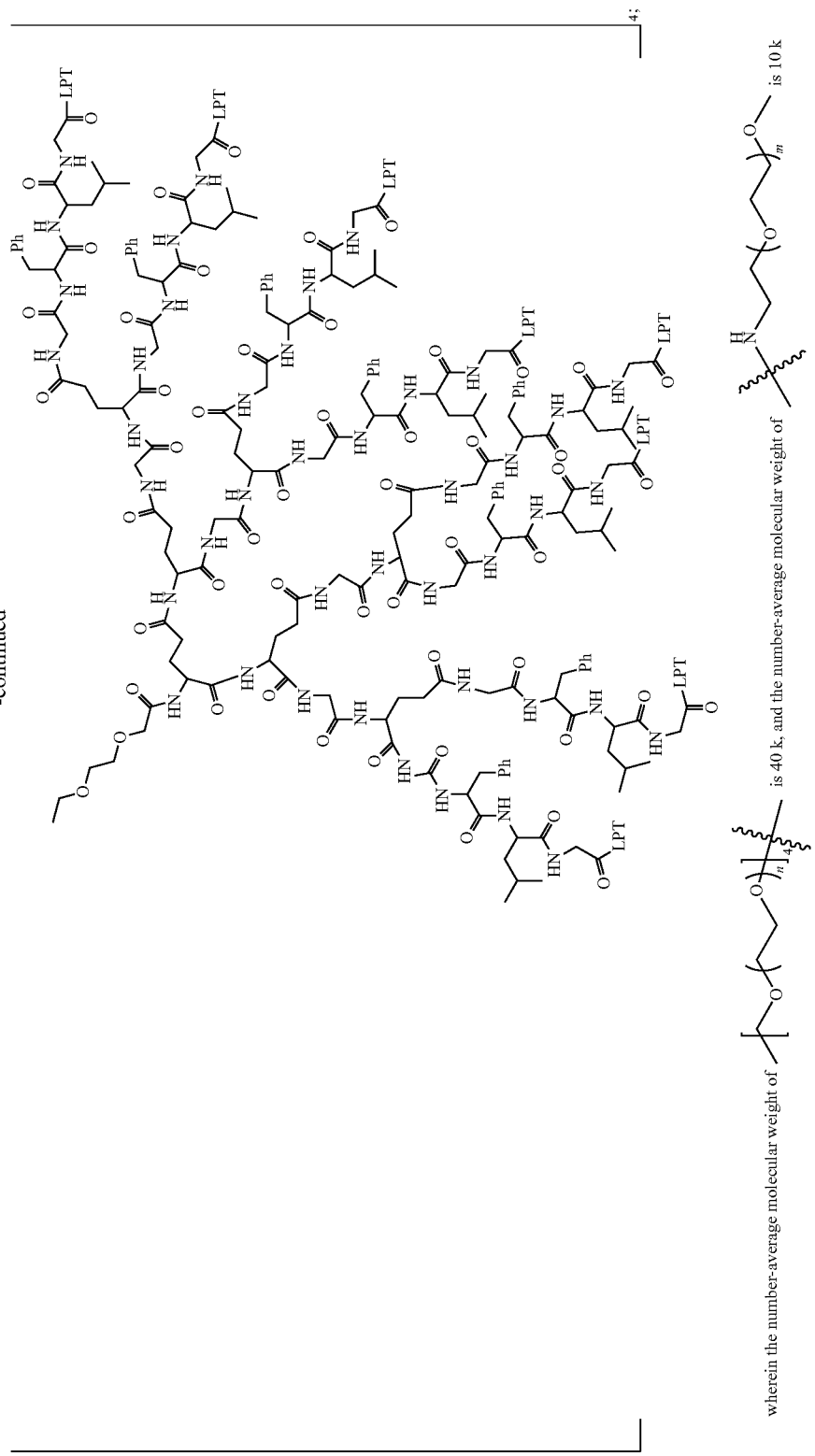

23
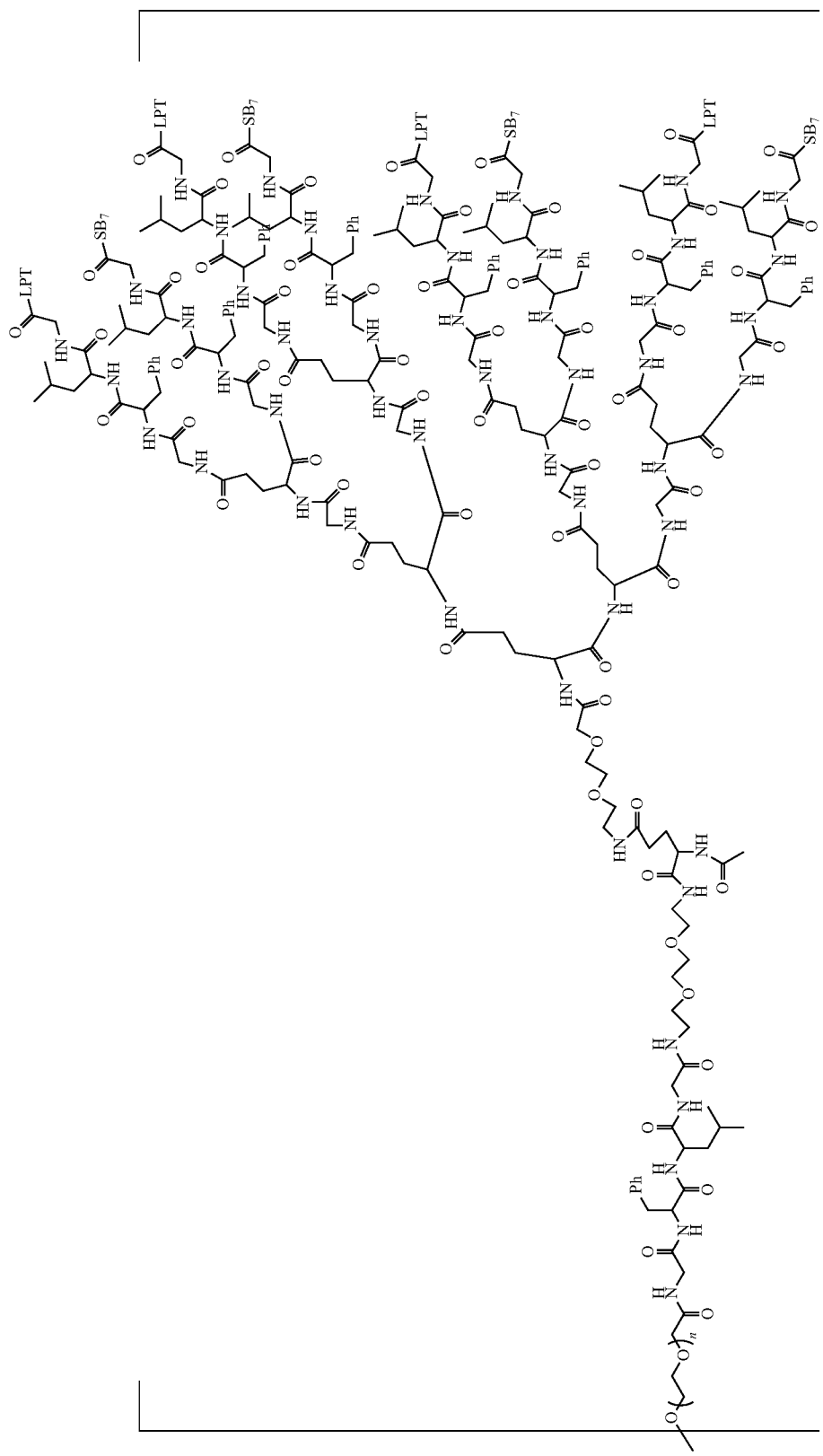

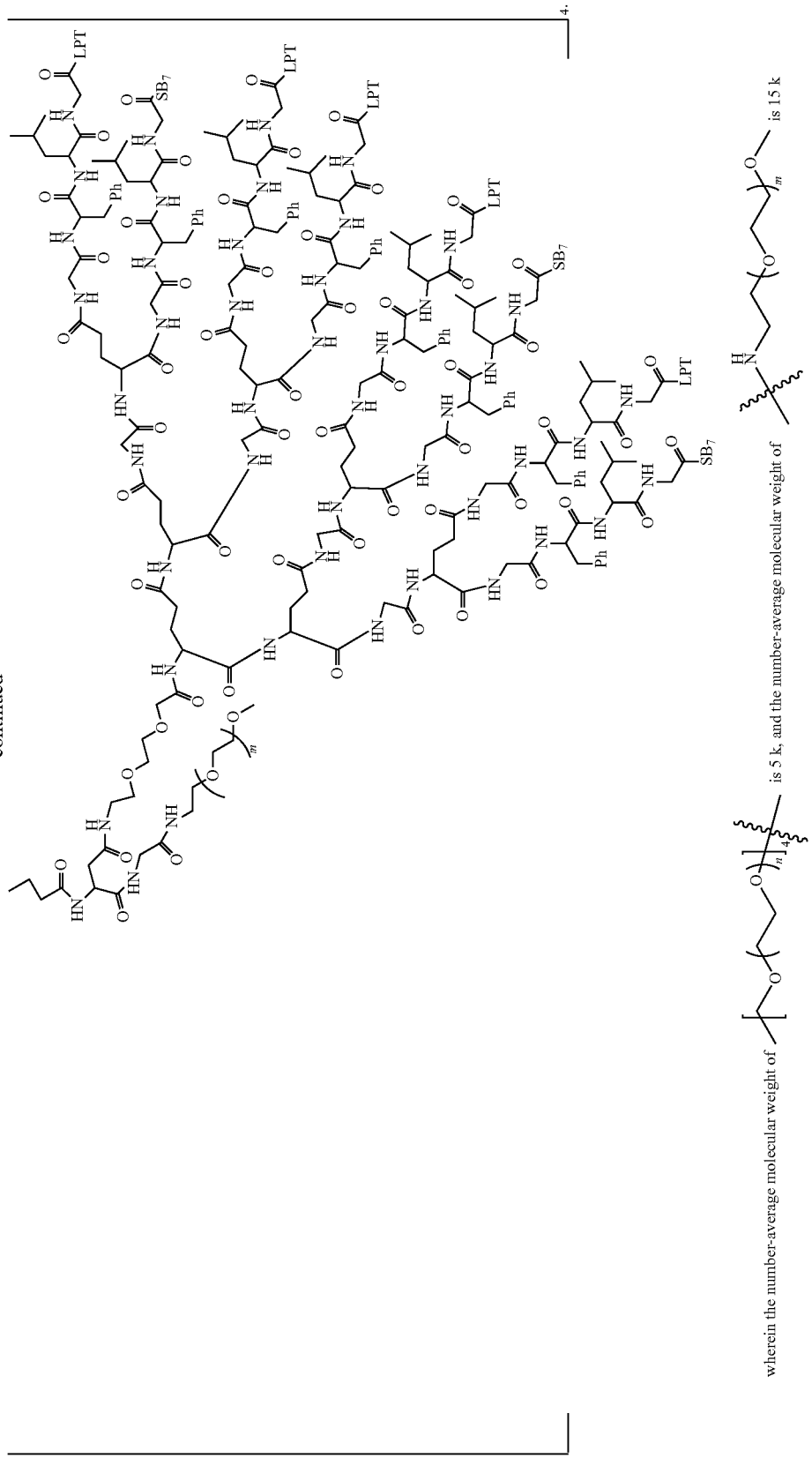

2. Pharmaceutical Composition and its Use and Preparations

In one aspect, this application provides a pharmaceutical composition, including an effective amount of the polyethylene glycol conjugated drug or a pharmaceutically acceptable salt thereof according to the disclosure for treating and/or preventing diseases; in some embodiments, the composition also includes one or more pharmaceutically acceptable excipients.

The pharmaceutical composition of the disclosure may be prepared into any pharmaceutically acceptable dosage form. For example, the pharmaceutical composition of the disclosure may be prepared into tablets, capsules, pills, granules, solutions, suspensions, syrups, injection preparations (including injection solutions, sterile powders for injection, and concentrated solutions for injection), suppositories, inhalants or sprays.

In addition, the pharmaceutical composition of the disclosure may also be applied to patients or subjects in need of such treatment in any suitable way of administration, such as oral, parenteral, rectal or pulmonary administration. In the case of oral administration, the pharmaceutical composition may be prepared into oral preparations, for example, oral solid preparations, such as tablets, capsules, pills, granules, etc.; it may also be prepared into oral liquid preparations, such as oral solutions oral suspensions, syrups, etc. When the pharmaceutical composition is prepared into oral preparations, suitable fillers, binders, disintegrants, lubricants, etc. may be added. In the case of parenteral administration, the pharmaceutical composition may be prepared into injection preparations, including injection solutions, sterile powders for injection, and concentrated solutions for injection. When the pharmaceutical composition is prepared into injection preparations, they may be produced by a conventional method in the current pharmaceutical field. In the case of preparation of injection preparations, it is not required to add additives, or appropriate additives may be added according to the nature of the drug. In the case of rectal administration, the pharmaceutical composition may be prepared into suppositories and the like. In the case of pulmonary administration, the pharmaceutical composition can be made into an inhalant or a spray.

The subjects of the disclosure are mammals, such as bovines, equines, ovines, swines, canines, felines, rodents, and primates; more preferably, the subjects are humans.

In some embodiments, the pharmaceutical composition is prepared in the form of an injection.

In some embodiments, the pharmaceutical composition is used to treat and/or prevent cancers.

In one aspect, the disclosure provides use of the polyethylene glycol conjugated drug of the disclosure or a pharmaceutically acceptable salt thereof in the preparation of a medicament for treating and/or preventing a disease (such as a cancer). The disease refers to a disease treated by an active ingredient in the polyethylene glycol conjugated drug.

In one aspect, the disclosure provides a method for treating and/or preventing a cancer, including administering an effective amount of the polyethylene glycol conjugated drug of the disclosure or a pharmaceutically acceptable salt thereof to subjects in need.

In some embodiments, the cancer is selected from colon cancer, leukemia, lymphoma, bladder cancer, bone cancer, brain tumor, medulloblastoma, glioma, breast cancer, adenoma/carcinoid, adrenal cortical cancer, pancreatic islet cell cancer, cervical cancer, endometrial cancer, ovarian cancer, colorectal cancer, skin cancer, esophageal cancer, eye cancer, gallbladder cancer, stomach cancer, head and neck cancer, liver cancer, melanoma, Kaposi's sarcoma, kidney cancer, oral cancer, lung cancer, nasopharyngeal cancer, neuroblastoma, ovarian cancer, pancreatic cancer, thyroid cancer, parathyroid penile cancer, prostate cancer, urethral cancer, vaginal cancer, vulvar cancer, anal cancer, and sarcoma, as well as metastasis of these cancers.

In one aspect, the disclosure further provides an injection solution, including the polyethylene glycol conjugated drug of the disclosure or a pharmaceutically acceptable salt thereof, or the pharmaceutical composition of the disclosure. In some embodiments, saline (normal saline) is used as a carrier for the injection solution.

3. Preparation Method and Intermediates

In one aspect, the disclosure provides a method for preparing the polyethylene glycol conjugated drug of the disclosure or a pharmaceutically acceptable salt thereof. The polyethylene glycol conjugated drug has a structure shown as formula (II), and the method includes the following steps:

step 1: preparing an intermediate

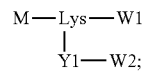

step 2: carrying out an amidation reaction so that PEG1 with carboxyl group(s) or activated carboxyl group(s) is linked to M to obtain an intermediate

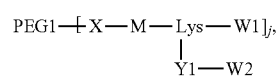

wherein Y1 has a free carboxyl group; and step 3: carrying out an amidation reaction so that PEG2 with free amino group(s) or activated amino group(s) is linked to Y1 in the intermediate

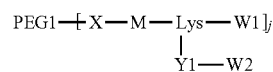

obtain a polyethylene glycol conjugated drug of formula (II);
    wherein PEG1, PEG2, Lys, X, Y1, W1, W2, M, and j are defined as above.

In one aspect, the disclosure provides a method for preparing the polyethylene glycol conjugated drug of the disclosure or a pharmaceutically acceptable salt thereof. The polyethylene glycol conjugated drug has a structure of formula (III), and the method includes the following steps:

step 1: preparing an intermediate

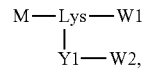

wherein an amino group on a glycine residue in M is protected, and Y1 has a free amino group; preparing an intermediate Y2-W3, wherein Y2 has a free carboxyl group and a protected carboxyl group;

step 2: carrying out an amidation reaction between the free amino group on Y1 and the free carboxyl group on Y2 so that the intermediate

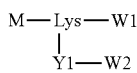

is linked to Y2-W3 to obtain an intermediate

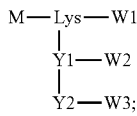

step 3: removing a protecting group of carboxyl on Y2 and a protecting group of amino on M in the intermediate

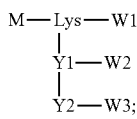

step 4: carrying out an amidation reaction so that the intermediate

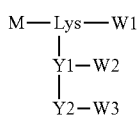

from step 3 is linked to PEG1 with free carboxyl group(s) or activated carboxyl group(s) to obtain an intermediate

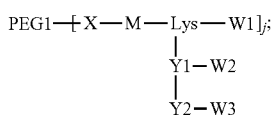

and step 5: carrying out an amidation reaction so that the intermediate

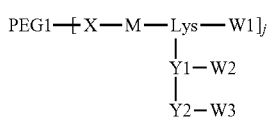

is linked to PEG2 with free amino group(s) or activated amino group(s) to obtain a polyethylene glycol conjugated drug of formula (III);

wherein PEG1, PEG2, Lys, X, Y1, Y2, W1, W2, W3, M, and j are defined as above.

In one aspect, the disclosure further provides a compound having any one of the following structures:

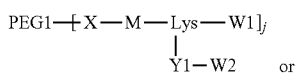 or

-continued

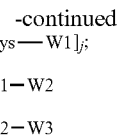

wherein PEG1, PEG2, Lys, X, Y1, Y2, W1, W2, W3, M, and j are defined as above.

The disclosure provides use of those compounds as intermediates in preparation of the polyethylene glycol conjugated drug of the disclosure or a pharmaceutically acceptable salt thereof.

Definition of Terms

Unless otherwise defined below, the meanings of all technical and scientific terms used herein are intended to be the same as those commonly understood by those skilled in the art. The reference to the technology used herein is intended to refer to the technology generally understood in the art, including those technical changes or equivalent technology substitutions that are obvious to those skilled in the art. Although it is believed that the following terms are well understood by those skilled in the art, the following definitions are still set forth to better explain the disclosure.

As used herein, "PEG" is an abbreviation for polyethylene glycol, which refers to a homopolymer with a repeating unit of $-CH_2CH_2O-$, including single-arm polyethylene glycol, is multi-arm polyethylene glycol and their derivatives, such as derivatives with reactive functional groups such as amino or carboxyl group at the terminal. In the disclosure, the arms of the multi-arm polyethylene glycol preferably have the same degree of polymerization. When referring to the molecular weight of the multi-arm polyethylene glycol, the molecular weight means the total molecular weight of each arm. In the structural formula of the disclosure, the letter m or n in the subscript of the polyethylene glycol repeating unit represents the degree of polymerization of polyethylene glycol. When the polyethylene glycol is a multi-arm polyethylene glycol, the letter m or n represents the degree of polymerization of each arm.

As used herein, the "pharmaceutically acceptable salt" of the polyethylene glycol conjugated drug includes an acid addition salt and base addition salt of the polyethylene glycol conjugated drug, such as hydrochloride, hexafluorophosphate, and meglumine salt.

As used herein, the wavy line "/" in the structural formula means the position where other groups are bonded to the structure represented by the structural formula.

As used herein, the term "effective amount" refers to the amount of a compound that will relieve one or more symptoms of the disease being treated to a certain extent after being administered.

As used herein, the term "treating" means reversing, alleviating, or inhibiting the disease or condition to which such term is applied or the progression of one or more symptoms of such a disease or condition, or preventing such a disease or condition or one or more symptoms of such a disease or condition.

Beneficial Effect

The polyethylene glycol conjugated drug of the disclosure can achieve high drug loading capacity and good solubility. Through the preparation method of the disclosure, the polyethylene glycol conjugated drug of the disclosure can be prepared efficiently and conveniently and the ratio and position of the drug can be adjusted flexibly.

The embodiments of the disclosure will be described in detail below in conjunction with the accompanying drawings and examples. However, those skilled in the art will understand that the following drawings and examples are only used to illustrate the disclosure, not to limit the scope of the disclosure. Various objectives and advantageous aspects of the disclosure will become apparent to those skilled in the art based on the accompanying drawings and the following detailed description of the preferred embodiments.

DETAILED DESCRIPTION

Figure 1:
FIG. 1 shows the state of a 10 mg/mL solution of Compound 24-184 in Example 25.

The embodiments of the disclosure will be described in detail below in conjunction with examples. However, those skilled in the art will understand that the following examples are only used to illustrate the disclosure, not to limit the scope of the disclosure. Those without specific conditions in the examples are generally implemented under conventional conditions or conditions recommended by the manufacturers. The reagents or instruments used without specifying the manufacturers are all conventional products that can be purchased commercially.

The meanings of abbreviations in the examples are as follows:

| | | | |
|---|---|---|---|
| G | Glycine residue | L | Leucine residue |
| F | Phenylalanine residue | Asp | Aspartic acid residue |
| E | Glutamate residue | Glu | Glutamate residue |
| DMF | N,N-dimethylformamide | TFA | Trifluoroacetate |
| t-Bu | Tert-butyl | Bn | Benzyl |
| Boc | Tert-butoxycarbonyl | Fmoc | Fluorenyl methoxycarbonyl |
| HOBT | 1-hydroxybenzotriazole | Ts | P-toluenesulfonyl |
| HBTU | O-benzotriazole-tetramethylurea hexafluorophosphate | LPT | Lapatinib |
| DIEA | N,N-diisopropylethylamine | SB7 | SB-743921 |
| EA | Ethyl acetate | PCB | Palbociclib |
| TMP | 2,4,6-trimethylpyridine | NPB | Niraparib |
| PyAOP | (3H-1,2,3-triazolo[4,5-b]pyridin-3-oxy)tris-1-pyrrolidinylphosphonium hexafluorophosphate | | |
| LC | $NH_2-CH_2CH_2O-CH_2CH_2O-CH_2-COOH$ or $-NH-CH_2CH_2O-CH_2CH_2O-CH_2-CO-$ | | |

The source and structure of some raw materials are as follows:

M-NH$_2$HCl-5K
JenKem, mPEG-CH$_2$CH$_2$—NH$_2$HCl
M-SCM-10K
JenKem,

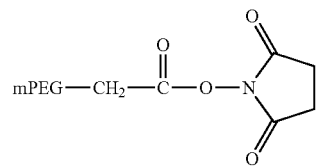

4ARM-SCM-40K/5K
JenKem,

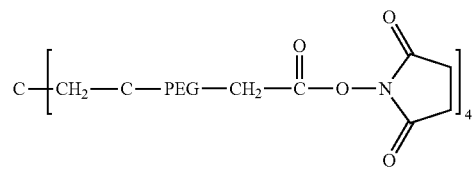

Example 1: Synthesis of Compound 31-91

30-28

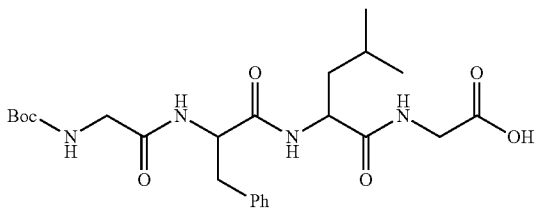

Raw material Boc-GFLG-OBn (19.0 g, 32.6 mmol, home-made) and 10% Pd/C catalyst (300 mg) were added into a hydrogenation reaction device and then dissolved with DMF (50 mL). The hydrogenation reaction device was then sealed and H$_2$ (18 psi) was introduced. The mixed solution was stirred overnight at room temperature. After the reaction was found to be completed from the monitoring of the TLC, the reaction solution was taken out and evenly dropwise added to a sand core funnel filled with compacted diatomaceous earth and suction filtering was carried out; the diatomaceous earth was then washed with DMF (90 mL) until there was no product in the diatomaceous earth. A reaction product solution was thus obtained.

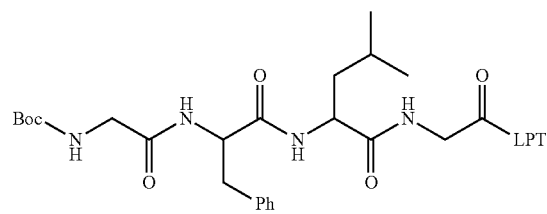

30-29

Compound 30-28 (17.9 mmol), LPT (8 g, 13.77 mmol), HBTU (7.83 g, 20.65 mmol) and HOBT (2.79 g, 20.65 mmol) were added in a 500 mL round-bottomed flask and then dissolved with DMF (100 mL), and the mixed solution was stirred at −5° C. for 30 min. Then DIEA (10.24 mL, 61.96 mmol) was slowly added dropwise, and then the mixed solution reacted at a low temperature for 2 h; then, the reaction device was placed at room temperature and the reaction solution in the reaction flask was stirred overnight. At the end of the reaction, deionized water (1000 mL) was added to precipitate a pale yellow solid, suction filtering was then carried out, and the solid was then washed with deionized water and dried. 14.53 g of the product was obtained.

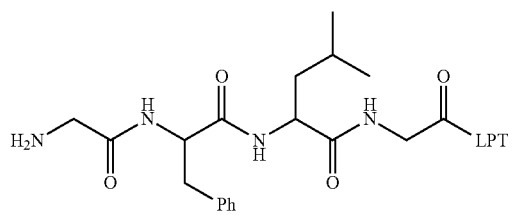

14-128

Compound 30-29 (14.53 g, 13.77 mmol) was added in a 500 mL round-bottomed flask, and then dissolved with dichloromethane (150 mL), and then TFA (15.34 mL, 206.55 mmol) was added and the obtained solution was stirred at room temperature to react overnight. When the reaction was stopped, the reaction solution was concentrated under reduced pressure, a saturated sodium bicarbonate solution (200 mL) was added to neutralize the TFA, the product in the aqueous phase was extracted three times with ethyl acetate (150 mL×3), and the obtained organic phases were combined, then dried with anhydrous sodium sulfate, filtered out by suction, and concentrated; the operations of dry sample loading, column chromatography, and elution with 5% methanol/0.5% ammonia water/dichloromethane were carried out, and then the elution product was collected, concentrated, and dried. 13.15 g of the product was obtained.

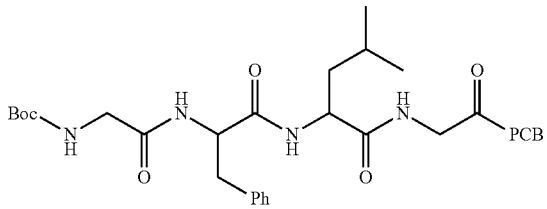

30-30

The solution of Compound 30-28 (13.97 mmol), PCB (5 g, 11.17 mmol), HBTU (6.35 g, 16.76 mmol), and HOBT (2.26 g, 16.76 mmol) were added in a 500 mL round-bottomed flask and then dissolved with DMF (100 mL), and the mixed solution was stirred at −5° C. for 30 min; DIEA (8.31 mL, 50.28 mmol) was then slowly added dropwise and the obtained solution reacted at this temperature for 2 h; the reaction solution in the reaction flask was then stirred at room temperature overnight. At the end of the reaction, deionized water (1000 mL) was added to precipitate a yellow solid, suction filtering was then carried out, and the solid was then washed with deionized water and dried. 10.3 g of the product was obtained.

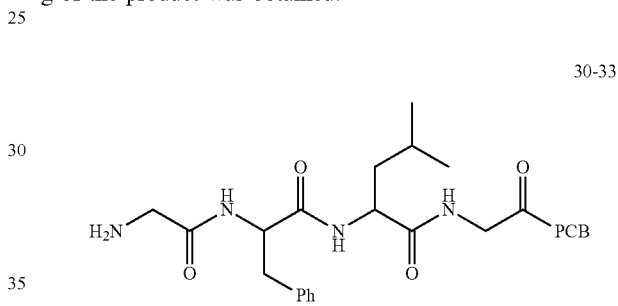

30-33

Compound 30-30 (10.3 g, 11.17 mmol) was added in a 500 mL round-bottomed flask and then dissolved with dichloromethane (50 mL), TFA (12.45 mL, 167.55 mmol) was then added and the obtained solution was stirred at room temperature to react overnight; after the reaction was completed, the reaction solution was concentrated at reduced pressure and then precipitated with n-hexane (50 mL) and methyl tert-butyl ether (400 mL), the supernatant was discarded, n-hexane and methyl tert-butyl ether were added again for precipitation, and the operation of precipitation was repeated three times; suction filtering was then carried out to obtain a solid product; the obtained solid product was dissolved with dichloromethane and methanol; the operations of dry sample loading, column chromatography and elution with 5% methanol/1% ammonia/dichloromethane were carried out; the elution product was then collected, concentrated, and dried. 8.6 g of the product was obtained with a yield of 94%.

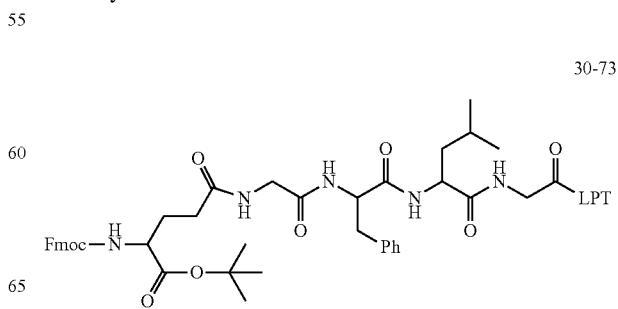

30-73

Fmoc-Glu-OtBu (3.47 g, 8.16 mmol, purchased from Innochem), Compound 14-128 (6.0 g, 6.27 mmol), HBTU (3.6 g, 9.42 mmol), and HOBT (1.27 g, 9.42 mmol) were added in a 500 mL round-bottomed flask and then dissolved with DMF (50 mL), and the mixed solution was stirred at −5° C. for 30 min. Then DIEA (4.67 mL, 28.3 mmol) was slowly added dropwise, and then the mixed solution reacted at a low temperature for 2 h; then, the reaction device was placed at room temperature and the reaction solution was stirred overnight. At the end of the reaction, deionized water (1000 mL) was added to precipitate a pale yellow solid, suction filtering was then carried out, and the solid was then washed with deionized water and dried. 8.54 g of the product was obtained.

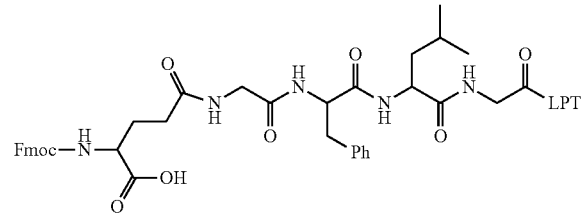

30-77

Compound 30-73 (8.54 g, 6.27 mmol) was added in a 500 mL round-bottomed flask and then dissolved with dichloromethane (50 mL), TFA (6.98 mL, 94.05 mmol) was then added and the obtained solution was stirred at room temperature to react overnight; after the reaction was completed, the reaction solution was concentrated at reduced pressure and then precipitated with n-hexane (100 mL) and methyl tert-butyl ether (300 mL), the supernatant was discarded, n-hexane and methyl tert-butyl ether were added again, and the operation of precipitation was repeated three times; suction filtering was then carried out to obtain a solid product; the obtained solid product was then dried. 8.19 g of the product was obtained.

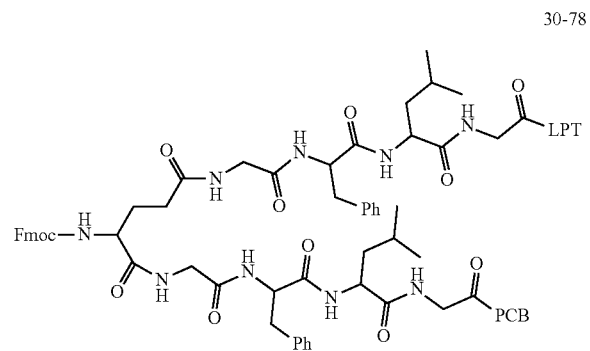

30-78

Compound 30-77 (7.37 g, 5.64 mmol), Compound 30-33 (4.86 g, 5.92 mmol), HBTU (3.2 g, 8.46 mmol) and HOBT (1.14 g, 8.46 mmol) were added in a 500 mL round-bottomed flask and then dissolved with DMF (50 mL), and the mixed solution was stirred at −5° C. for 30 min. Then DIEA (8.13 mL, 25.38 mmol) was slowly added dropwise, and then the mixed solution reacted at a low temperature for 2 h; then, the reaction device was placed at room temperature and the reaction solution in the reaction flask was stirred overnight. At the end of the reaction, the reaction solution was precipitated with n-hexane (100 mL) and methyl tert-butyl ether (400 mL) and the filter cake was washed with methyl tert-butyl ether (100 mL) to obtain a solid product; the solid product was then dried. 11.89 g of the product was obtained.

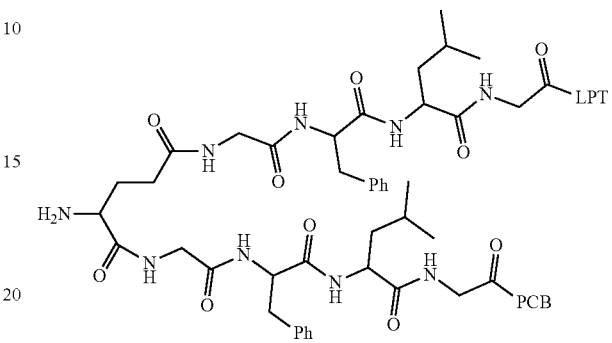

30-79

Compound 30-78 (11.89 g, 5.64 mmol) was added in a 500 mL round-bottomed flask and then dissolved with DMF (30 mL), morpholine (14.72 mL, 169.2 mmol) was then added and the obtained solution was stirred at room temperature for 60 min to react; at the end of the reaction, n-hexane (50 mL) and methyl tert-butyl ether (400 mL) were added for precipitation, and the filter cake was washed with n-hexane (100 mL) to obtain a solid product; and the obtained solid product was then dried. 10.65 g of the product was obtained, including extra-quota.

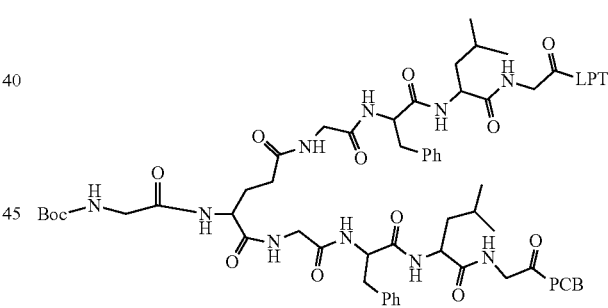

30-86

Compound 30-79 (4.8 g, 2.54 mmol), Boc-Gly-OH (0.67 g, 3.81 mmol), HBTU (1.45 g, 3.81 mmol), and HOBT (0.51 g, 3.81 mmol) were added in a 500 mL round-bottomed flask and then dissolved with DMF (50 mL), and the mixed solution was stirred at −5° C. for 30 min. Then DIEA (1.89 mL, 11.43 mmol) was slowly added dropwise, and then the mixed solution reacted at a low temperature for 2 h; then, the reaction device was placed at room temperature and the reaction solution in the reaction flask was stirred overnight. At the end of the reaction, the reaction solution was precipitated with n-hexane (100 mL) and methyl tert-butyl ether (400 mL) and the filter cake was washed with methyl tert-butyl ether (100 mL) to obtain a solid product; the solid product was then dried. 5.19 g of the product was obtained, including extra-quota.

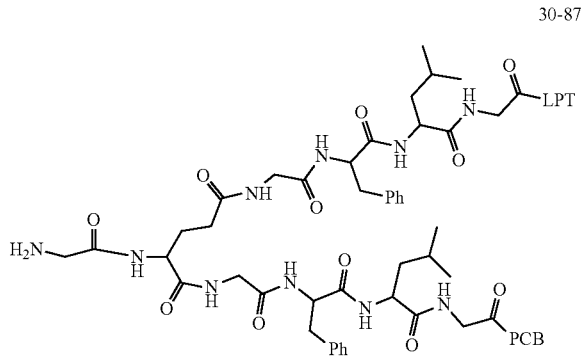

30-87

Compound 30-86 (5.19 g, 5.54 mmol) was added in a 500 mL round-bottomed flask and then dissolved with dichloromethane (30 mL), TFA (2.83 mL, 38.1 mmol) was then added and the obtained solution was stirred at room temperature to react overnight; when the reaction was stopped, the reaction solution was concentrated at reduced pressure and then precipitated with n-hexane (50 mL) and methyl tert-butyl ether (400 mL), and the operation of precipitation was repeated three times; filtering was then carried out to obtain a solid product; the obtained solid product was dissolved with dichloromethane and methanol; the operations of dry sample loading, column chromatography and elution with 5% methanol/1% ammonia water/dichloromethane were carried out; the elution product was then collected, concentrated, and dried. 4.0 g of the product was obtained with a yield of 82%.

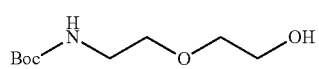

16-34

2-(2-aminoethoxy) ethanol (18.8680 g, 190.2226 mmoL) was weighed and poured into a 500 mL round-bottomed flask and then diluted with dichloromethane (100 mL), triethylamine (38.4972 mL, 380.4452 mmoL) was then added, and (Boc)₂O (49.8261 g, 228.2671 mmoL) was then added slowly with stirring, and the obtained solution was stirred at room temperature to react. At the end of the reaction, the reaction solution was evaporated to dryness, then sodium bicarbonate powder was added, the obtained mixture was diluted with dichloromethane, silica gel powder was added, and the operations of evaporating, dry sample loading, and column chromatography were carried out. Elution with 50% ethyl acetate/petroleum ether was carried out. 27.3 g of the product was obtained with a yield of 70%.

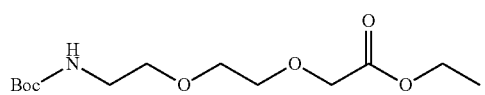

16-36

Compound 16-34 (27.3 g, 132.8144 mmoL) was added in a 500 mL flask, nitrogen was introduced in the flask for protective purpose, the THF solution of potassium tert-butoxide was added, the mixed solution was placed at 0° C. to react, ethyl bromoacetate (17.6265 mL, 159.3773 mmoL) was then added, and the obtained solution was first stirred for 3 h, and then further reacted at room temperature. At the end of the reaction, the reaction solution was first evaporated to dryness, then deionized water and ethyl acetate were added, and the organic phase was separated; the aqueous phase was extracted with ethyl acetate until there was no product in the aqueous phase; the organic phases were combined, dried with anhydrous sodium sulfate powder, and filtered out by suction. The filtrate was subjected to dry sample loading and column chromatography. Gradient elution with 30%-100% ethyl acetate/petroleum ether was carried out. 20 g of the product was obtained with a yield of 52%.

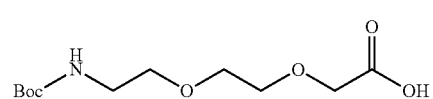

24-36

Compound 16-36 (17.9 g, 61.4402 mmoL) was added in a 250 mL flask, 1,4-dioxane (50 mL) was added, and lithium hydroxide (3.2386 g, 135.1685 mmoL) was further added with stirring, and 30 min later, deionized water (100 mL) was added, and the obtained solution was then stirred at room temperature to react. At the end of the reaction, the reaction solution was extracted three times with a mixed solution of methyl tert-butyl ether and n-hexane (1:1) (100 mL×3). The aqueous phase was adjusted to pH=1 with concentrated hydrochloric acid, and then extracted three times with ethyl acetate (300 mL×3), the ethyl acetate phases were combined, the washing with saturated sodium chloride was carried out three times (100 mL×3), the obtained solution was concentrated, and the operations of dry sample loading, column chromatography, and then elution with 40%-100% ethyl acetate/petroleum ether were carried out. 10.1 g of the product was obtained with a yield of 62%.

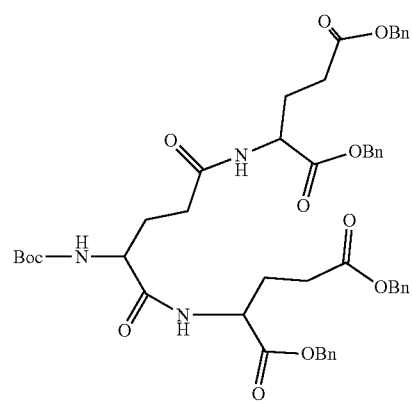

14-154

Compound Boc-Glu-OH (10 g, 40.5 mmol), H-Glu-(OBn)₂·TsOH (42.5 g, 85.1 mmol), HOBT (16.5 g, 121.5 mmol) and HBTU (46.1 g, 121.5 mmol) were added in a 500 mL round-bottomed flask and then dissolved with DMF (100 mL), and the mixed solution was stirred at −5° C. for 30 min. Then DIEA (66.2 mL, 400.5 mmol) was slowly added dropwise and then the reaction solution in the reaction flask was first stirred for 2 h at −5° C. and then further stirred overnight at room temperature. At the end of the reaction, a saturated sodium bicarbonate solution (300 mL) and ethyl acetate (200 mL) were added for extraction, the organic phase was separated, the aqueous phase was extracted three times with ethyl acetate (100 mL×3), and the organic phases were combined and washed twice with a saturated sodium chloride solution (200 mL×2), and then dried with anhydrous sodium sulfate powder; suction filtering was carried out and the filtrate was concentrated and dried. 35.07 g of the product was obtained.

14-155

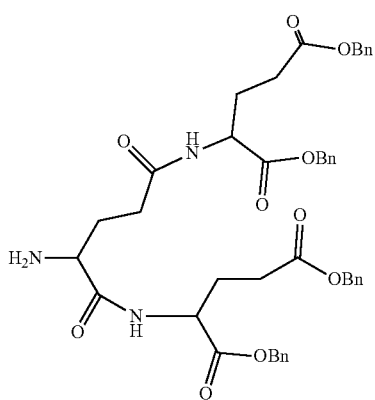

Compound 14-154 (35.1 g, 40.5 mmol) was added in a 500 mL round-bottomed flask and then dissolved with $CH_2Cl_2$ (50 mL), and the mixed solution was stirred at room temperature. TFA (45 mL, 607.5 mmol) was then added dropwise, and the mixed solution reacted at room temperature for 2 h. At the end of the reaction, the reaction solution was evaporated to dryness. A saturated sodium bicarbonate solution (300 mL) and ethyl acetate (200 mL) were added for extraction, the organic phase was separated, the aqueous phase was extracted three times with ethyl acetate (100 mL×3), and the organic phases were combined and washed twice with a saturated sodium chloride solution (200 mL×2), and then dried with anhydrous sodium sulfate powder; suction filtering was carried out and the filtrate was concentrated. The operations of dry sample loading, column chromatography, and elution with a 70% EA/PE solution were carried out; the elution product was then collected and concentrated. 13.28 g of the product was obtained.

14-163

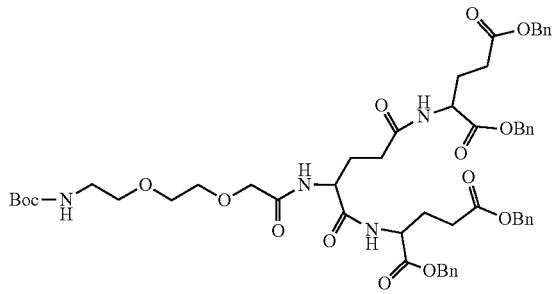

Compound 14-155 (31.06 g, 40.6 mmol), Compound 10-102 (synthesized according to the synthesis method of Compound 24-36) (13.90 g, 52.8 mmol), HOBT (8.23 g, 60.9 mmol) and HBTU (23.10 g, 60.9 mmol) were added in a 500 mL round-bottomed flask and then dissolved with DMF (150 mL), and the mixed solution was stirred at −5° C. for 30 min. Then DIEA (30.20 mL, 182.7 mmol) was slowly added dropwise and then the reaction device was placed at −5° C. and the reaction solution was stirred to react for 2 h; and then the reaction solution was further stirred overnight at room temperature to react. At the end of the reaction, a saturated sodium bicarbonate solution (300 mL) and ethyl acetate (100 mL) were added for extraction, and this extraction operation was repeated three times. The organic phases were combined, washed twice with a saturated sodium chloride solution, and then evaporated to dryness. The operations of dry sample loading, column chromatography, and elution with 0.2%-10% methanol/dichloromethane were carried out and the elution product was then collected, concentrated and dried. 22.63 g of the product was obtained with a yield of 55.1%.

30-74

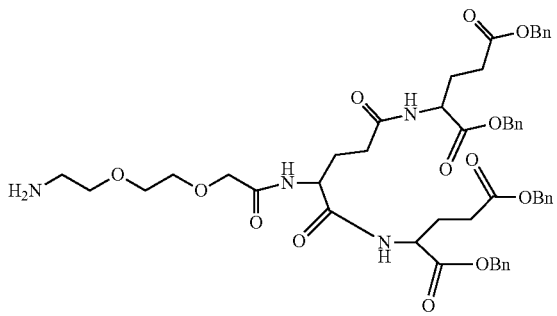

Compound 14-163 (5.0 g, 4.95 mmol) was added in a 500 mL round-bottomed flask and then dissolved with dichloromethane (30 mL). TFA (5.5 mL, 74.2 mmol) was added to the obtained solution and stirred overnight at room temperature to react. At the end of the reaction, a saturated sodium bicarbonate solution (300 mL) and ethyl acetate (200 mL) were added for extraction, the organic phase was separated, the aqueous phase was extracted three times with ethyl acetate (100 mL×3), and the organic phases were combined and washed twice with a saturated sodium chloride solution (200 mL×2), and then dried with anhydrous sodium sulfate powder; suction filtering was carried out and the filtrate was dried. The product was thus obtained.

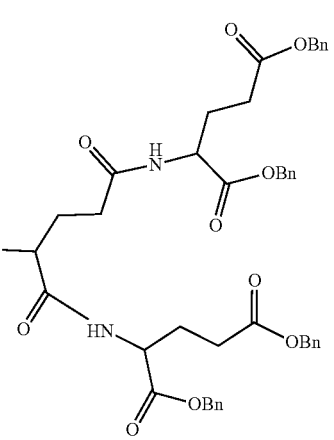

30-75

Compound 30-74 (4.51 g, 4.95 mmol), N-α-Fmoc-N-ε-Boc-L-lysine (purchased from Aladdin, 2.89 g, 6.18 mmol), HBTU (2.81 g, 7.42 mmol), and HOBT (1.0 g, 7.42 mmol) were added in a 500 mL round-bottomed flask and then dissolved with DMF (50 mL), and the mixed solution was stirred at −5° C. for 30 min. Then DIEA (3.67 mL, 22.2 mmol) was slowly added dropwise, and then the mixed solution was stirred for 2 h at −5° C. to react; then, the reaction solution in the reaction flask was stirred overnight at room temperature. At the end of the reaction, deionized water (300 mL) and ethyl acetate (200 mL) were added for extraction, the organic phase was separated, the aqueous phase was extracted three times with ethyl acetate (100 mL×3), and the organic phases were combined and washed twice with a saturated sodium chloride solution (200 mL×2), and then dried with anhydrous sodium sulfate powder. The organic phase was collected, concentrated and dried. 6.73 g of the product was obtained, including extra-quota.

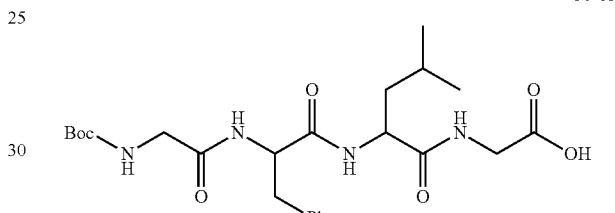

30-82

Compound 30-75 (6.73 g, 4.95 mmol) was added in a 500 mL round-bottomed flask and then dissolved with dichloromethane (20 mL), TFA (3.68 mL, 49.5 mmol) was then added and the obtained solution was stirred at room temperature to react overnight; after the reaction was completed, the reaction solution was concentrated and then precipitated with n-hexane (50 mL) and methyl tert-butyl ether (400 mL), the supernatant was discarded, the lower solution was precipitated again with n-hexane (50 mL) and methyl tert-butyl ether (400 mL), and the operation of precipitation was repeated three times to obtain a solid product; the obtained solid product was then dried. 6.24 g of the product was obtained with a yield of 100%.

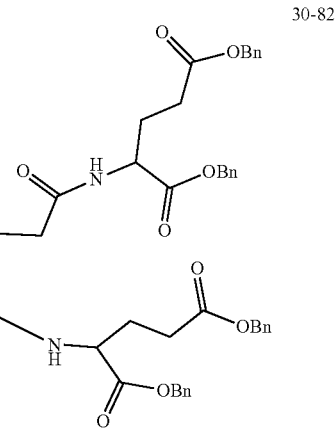

30-83

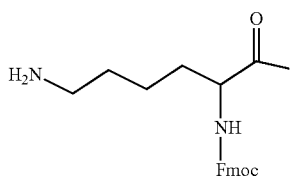

The raw material Boc-GFLG-OBn (home-made) (3.75 g, 6.43 mmol) and 10% Pd/C catalyst (100 mg) were added into a hydrogenation reactor and then dissolved with DMF (30 mL); $H_2$ was then charged until the pressure on the hydrogenation reaction device was read as 18 Psi, and then the obtained solution reacted overnight at room temperature. At the end of the reaction, the reaction solution was taken out and evenly added dropwise to a sand core funnel filled with compacted diatomaceous earth and suction filtering was carried out. The diatomaceous earth was washed with DMF (90 mL) until it did not contain any product, and then the reaction product solution was obtained.

30-84

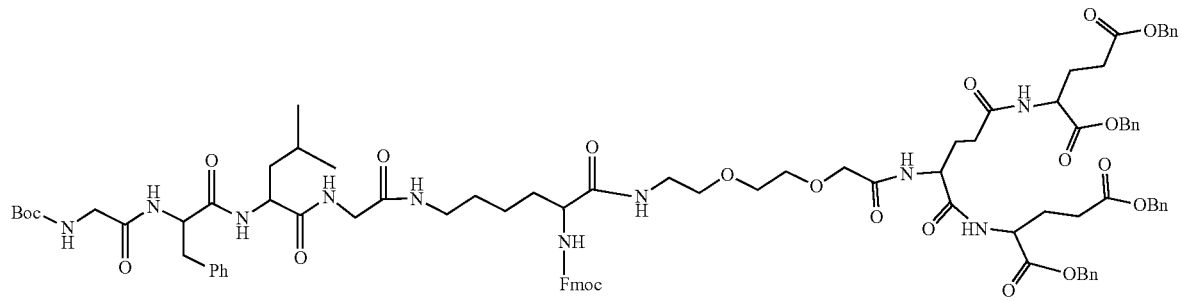

Compound 30-82 (6.24 g, 4.95 mmol), the solution of Compound 30-83 (6.43 mmol), HBTU (2.82 g, 7.43 mmol) and HOBT (1.0 g, 7.43 mmol) were added in a 500 mL round-bottomed flask and then dissolved with DMF (50 mL), and the mixed solution was stirred at −5° C. for 30 min. Then DIEA (3.68 mL, 22.3 mmol) was slowly added dropwise, and then the mixed solution was stirred for 2 h at −5° C. to react; then, the reaction solution in the reaction flask was stirred overnight at room temperature. At the end of the reaction, deionized water (300 mL) and ethyl acetate (200 mL) were added for extraction, the organic phase was separated, the aqueous phase was extracted three times with ethyl acetate (100 mL×3), and the organic phases were combined and washed twice with a saturated sodium chloride solution (200 mL×2), and then dried with anhydrous sodium sulfate powder. The organic phase was collected, concentrated and dried. The operations of dry sample loading, column chromatography, and elution with 5% methanol/dichloromethane were carried out and the elution product was then collected, concentrated, evaporated to dryness and dried in a vacuum oven. 6.1 g of the product was obtained with a yield of 71%.

MALDI-TOF MS: [M+Na$^+$] 1758.48

30-113

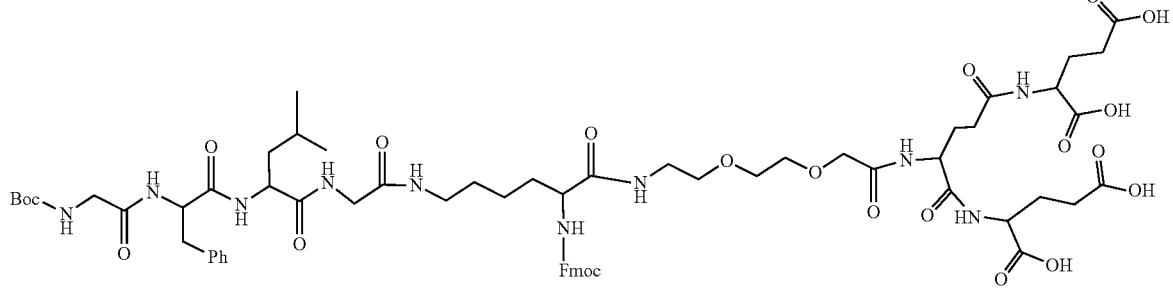

The raw material Compound 30-84 (0.85 g, 0.494 mmol) and 10% Pd/C catalyst (100 mg) were added into a hydrogenation reactor and then dissolved with DMF (30 mL); $H_2$ was then charged until the pressure on the hydrogenation reaction device was read as 18 Psi, and then the obtained solution reacted overnight at room temperature. At the end of the reaction, the reaction solution was taken out and evenly added dropwise to a sand core funnel filled with compacted diatomaceous earth and suction filtering was carried out. The diatomaceous earth was washed with DMF (90 mL) until it did not contain any product, and then the reaction product solution was obtained.

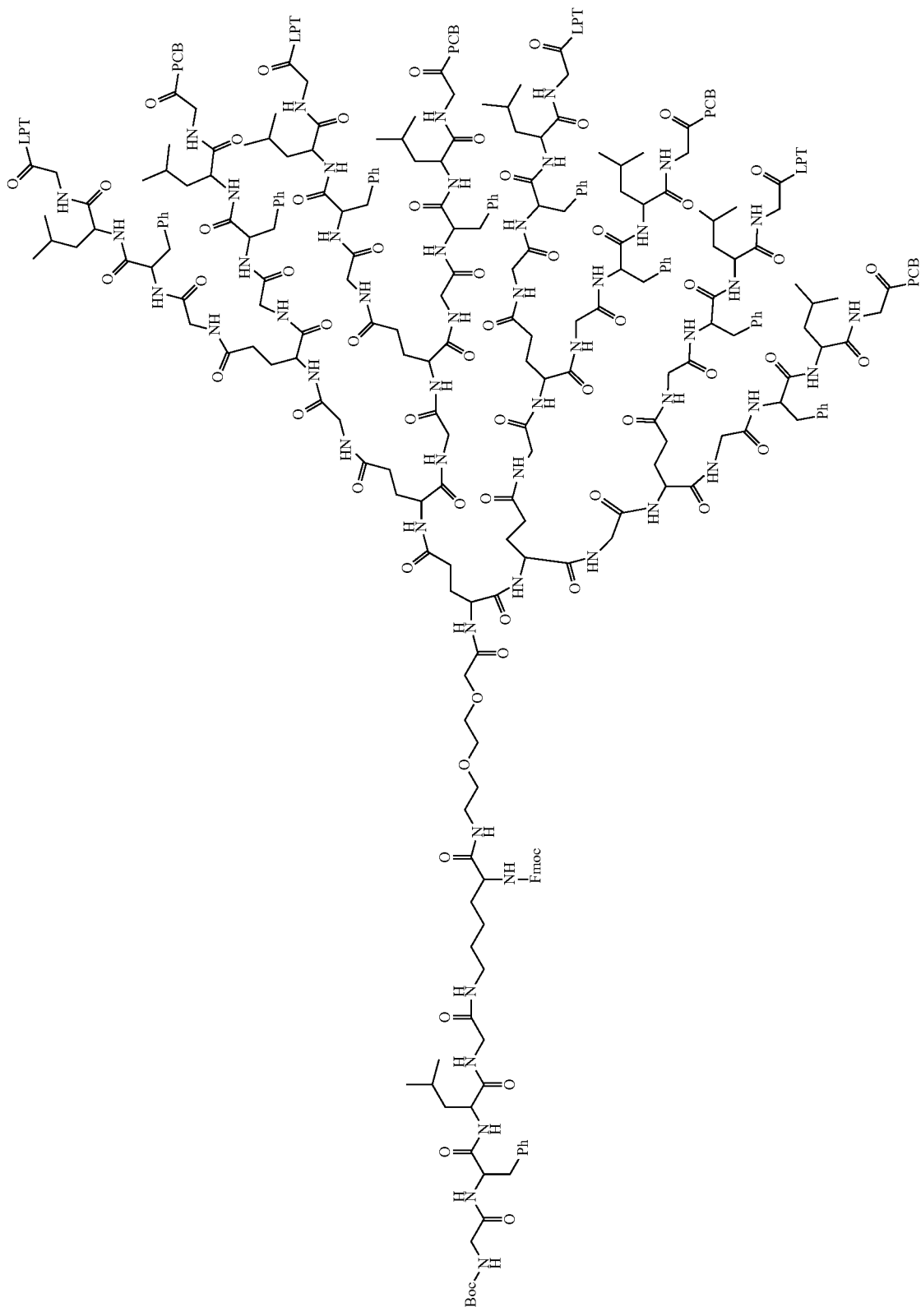

Compound 30-87 (5.0 g, 2.57 mmol), the solution of Compound 30-113 (0.494 mmol), HBTU (1.12 g, 2.97 mmol) and HOBT (0.4 g, 2.97 mmol) were added in a 500 mL round-bottomed flask and then dissolved with DMF (50 mL), and the mixed solution was stirred at −5° C. for 30 min. Then DIEA (1.47 mL, 8.89 mmol) was slowly added dropwise, and then the mixed solution reacted at a low temperature (−5° C.) for 2 h; then, the reaction solution in the reaction flask was stirred overnight at room temperature. At the end of the reaction, n-hexane (100 mL) and methyl tert-butyl ether (400 mL) were added for precipitation, the supernatant was then discarded, the lower solution was precipitated again with n-hexane (50 mL) and methyl tert-butyl ether (400 mL), and such precipitation was repeated three times to obtain a solid product; the solid product was then filtered out and then dissolved with dichloromethane (100 mL) and methanol (10 mL); silica gel powder was then added, and the operations of evaporation, dry sample loading, column chromatography, and elution with 5% methanol/dichloromethane were carried out; the elution product was collected, concentrated, evaporated to dryness, and dried in a vacuum oven. 3.0 g of the product was obtained with a yield of 67%.

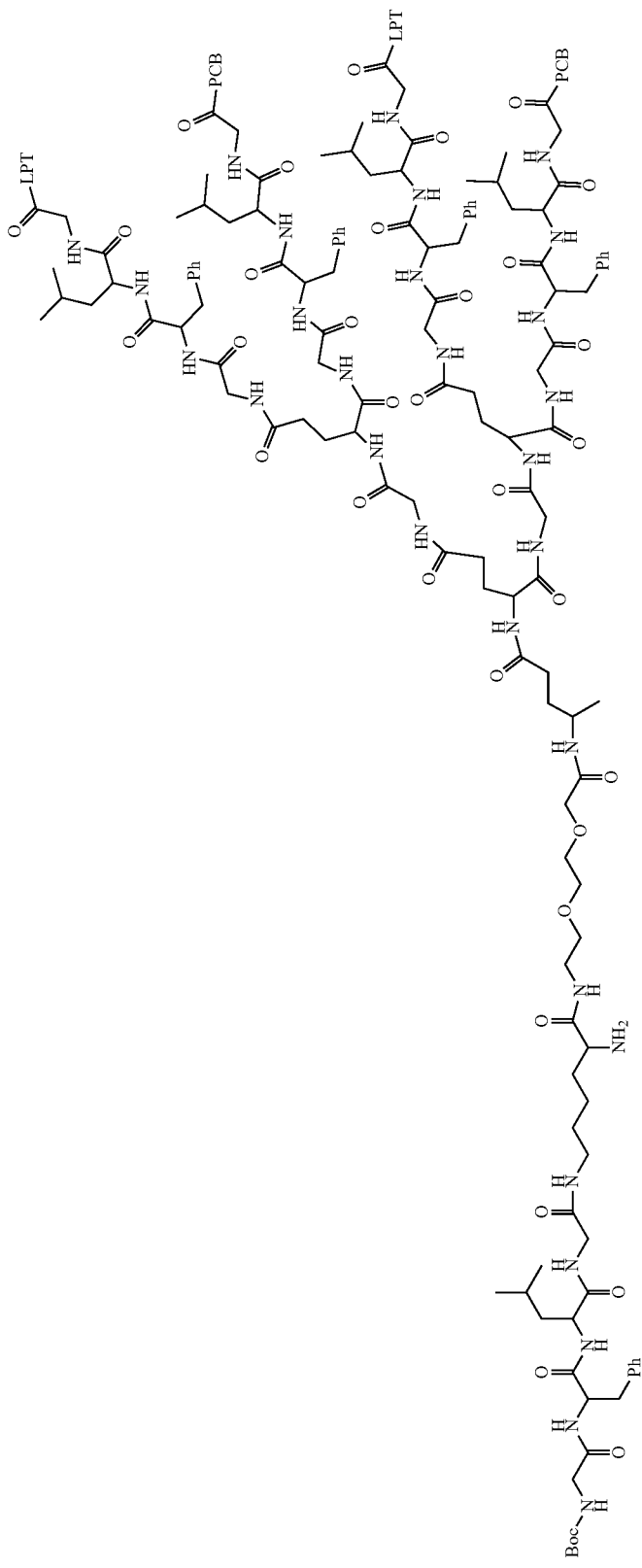

-continued
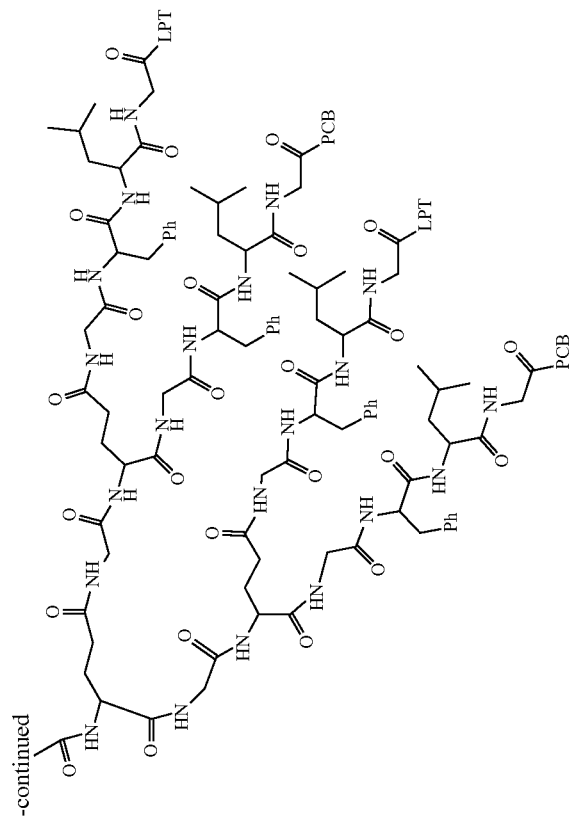

Product 30-114 (3.0 g, 0.33 mmol) was added in a 500 mL round-bottomed flask and dissolved with DMF (45 mL), morpholine (0.86 mL, 9.91 mmol) was then added and the obtained solution was stirred at room temperature to react for 60 min; at the end of the reaction, n-hexane (50 mL) and methyl tert-butyl ether (400 mL) were added for precipitation, suction filtering was then carried out, the filter cake was washed with methyl tert-butyl ether (100 mL) to obtain a solid product, and then the solid product was dissolved with dichloromethane (100 mL) and methanol (10 mL); silica gel powder was added to the obtained solution; and the operations of evaporation to dryness, dry sample loading, column chromatography and elution with 6% methanol/0.5% ammonia water/dichloromethane were carried out; the elution product was then collected, concentrated, evaporated to dryness, and dried in a vacuum oven. 2.7 g of the product was obtained with a yield of 93%.

29-48

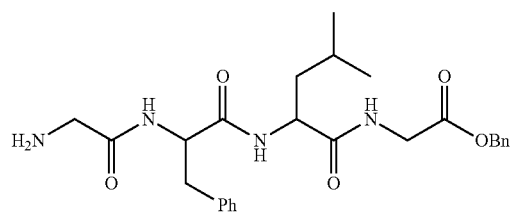

The raw material Boc-GFLG-OBn (7.5 g, 12.9 mmol) was added in a 500 mL round-bottomed flask and then dissolved with CH$_2$Cl$_2$ (10 mL), and the mixed solution was stirred at room temperature to react. TFA (14.4 mL, 193.9 mmol) was then added dropwise, and the mixed solution reacted overnight at room temperature. At the end of the reaction, the reaction solution was evaporated to dryness, a saturated sodium bicarbonate solution (300 mL) and ethyl acetate (200 mL) were then added for extraction, the organic phase was separated, the aqueous phase was extracted three times with ethyl acetate (100 mL×3), and the organic phases were combined and washed twice with a saturated sodium chloride solution (200 mL×2), and then dried with anhydrous sodium sulfate powder; suction filtering was carried out and the filtrate was dried. 6.4 g of the product was obtained.

29-47

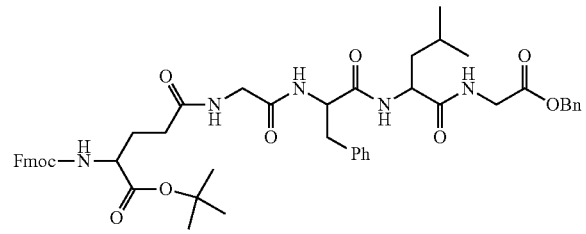

Fmoc-Glu-OtBu (5 g, 11.75 mmol), Compound 29-48 (6.4 g, 12.9 mmol), HBTU (6.68 g, 18 mmol), and HOBT (2.4 g, 18 mmol) were added in a 500 mL round-bottomed flask and then dissolved with DMF (40 mL), and the mixed solution was stirred at −5° C. for 30 min. Then DIEA (8.7 mL, 52 mmol) was slowly added dropwise to further react, and 2 h later, the reaction solution was taken out and stirred at room temperature to react. At the end of the reaction, a saturated sodium chloride solution (300 mL) and ethyl acetate (200 mL) were added for extraction, the organic phase was separated, the aqueous phase was extracted three times with ethyl acetate (100 mL×3), and the organic phases were combined and dried with anhydrous sodium sulfate powder; suction filtering was carried out and the filtrate was dried in vacuum to obtain the product.

29-52

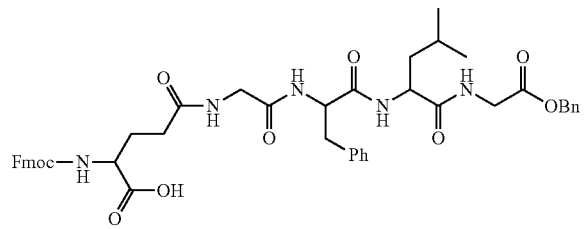

Compound 29-47 (3.82 g, 4.29 mmol) was added in a 500 mL round-bottomed flask and then dissolved with CH$_2$Cl$_2$ (20 mL), and the mixed solution was stirred at room temperature. TFA (4.78 mL, 64.35 mmol) was then added dropwise, and the mixed solution reacted at room temperature for 2 h. At the end of the reaction, a saturated sodium bicarbonate solution (300 mL) and ethyl acetate (200 mL) were added for extraction, the organic phase was separated, the aqueous phase was extracted three times with ethyl acetate (100 mL×3), and the organic phases were combined and washed twice with a saturated sodium chloride solution (200 mL×2), and then dried with anhydrous sodium sulfate powder; silica gel powder was added; and the operations of suction filtering, dry sample loading, column chromatography, and elution with a 3% methanol/dichloromethane solution were carried out; the elution product was then collected and concentrated. 6.7 g of the product was obtained with a yield of 68.6%.

31-31

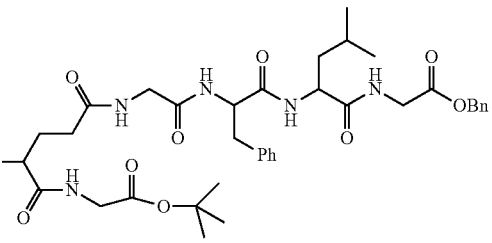

Compound 29-52 (6.7 g, 8.03 mmol), NH$_2$-Gly-OtBu·HCl (1.62 g, 9.64 mmol), HOBT (1.63 g, 12.04 mmol) and HBTU (4.57 g, 12.04 mmol) were added in a 500 mL round-bottomed flask and then dissolved with DMF (20 mL), and the mixed solution was stirred at 0° C. for 30 min. Then DIEA (5.97 mL, 36.14 mmol) was slowly added dropwise and then the solution in the reaction flask was stirred overnight at a low temperature (0° C.) to react. At the end of the reaction, a saturated sodium chloride solution (300 mL) and ethyl acetate (200 mL) were added for extraction, the organic phase was separated, the aqueous phase was extracted three times with ethyl acetate (100 mL×3), the organic phases were combined and dried with anhydrous sodium sulfate powder; silica gel powder was added; and the operations of suction filtering, dry sample loading, column chromatography, and elution with a 2% methanol/dichloromethane solution were carried out; the elution product was then collected and concentrated. 3.8 g of the product was obtained with a yield of 50.0%.

31-37

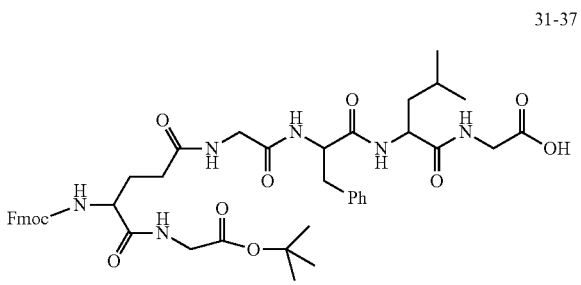

Raw material Compound 31-31 (3.8 g, 4.01 mmol) and 10% Pd/C catalyst (300 mg) were added into a hydrogenation reaction device and then dissolved with DMF (40 mL). The hydrogenation reaction device was then sealed and $H_2$ (18 psi) was introduced. The mixed solution was stirred overnight at room temperature. After the reaction was found to be completed from the monitoring of the TLC, the reaction solution was taken out and evenly dropwise added to a sand core funnel filled with compacted diatomaceous earth and suction filtering was carried out; the diatomaceous earth was then washed with DMF (90 mL) until there was no product in the diatomaceous earth. The reaction product solution was thus obtained.

31-45

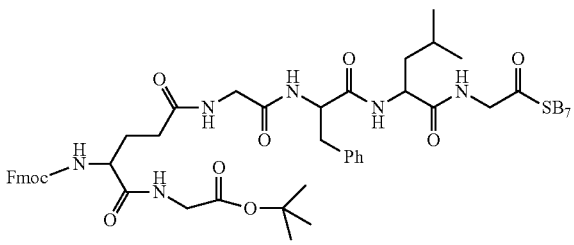

Compound 31-37 (2.86 g, 4.01 mmol), SB7 (1.15 g, 2.22 mmol), HOBT (0.45 g, 3.34 mmol) and HBTU (1.27 g, 3.34 mmol) were added in a 250 mL round-bottomed flask and then dissolved with DMF (130 mL), and the mixed solution was stirred at 0° C. for 30 min. Then DIEA (1.65 mL, 10.01 mmol) was slowly added dropwise and then the solution in the reaction device was stirred overnight at a low temperature (0° C.) to react. At the end of the reaction, n-hexane (400 mL) and methyl tert-butyl ether (700 mL) were added to the reaction solution to precipitate a solid product, and then suction filtering was carried out; the solid was taken, and then dried for later use. The operations of dry sample loading, column chromatography, and elution with 3% methanol/dichloromethane were carried out and the elution product was then collected and concentrated. 4.7 g of the pure product was obtained, including extra-quota.

31-55

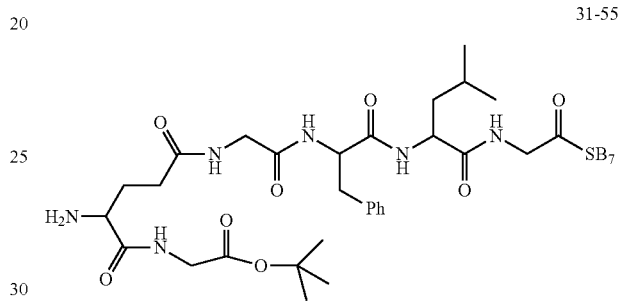

Compound 31-45 (3.02 g, 2.22 mmol) was added in a 250 mL round-bottomed flask and then dissolved with DMF (20 mL), and the mixed solution was stirred at room temperature. Morpholine (5.80 mL, 66.6 mmol) was then added dropwise, and the mixed solution reacted at room temperature for 2 h. At the end of the reaction, n-hexane (200 mL) and methyl tert-butyl ether (400 mL) were added to the reaction solution to precipitate a solid product, and then suction filtering was carried out; the solid was taken, and then dried for later use. The operations of dry sample loading, column chromatography, and elution with 2% methanol/0.5% ammonia water/dichloromethane were carried out and the elution product was then collected and concentrated. 3.1 g of the product was obtained, including extra-quota.

31-56

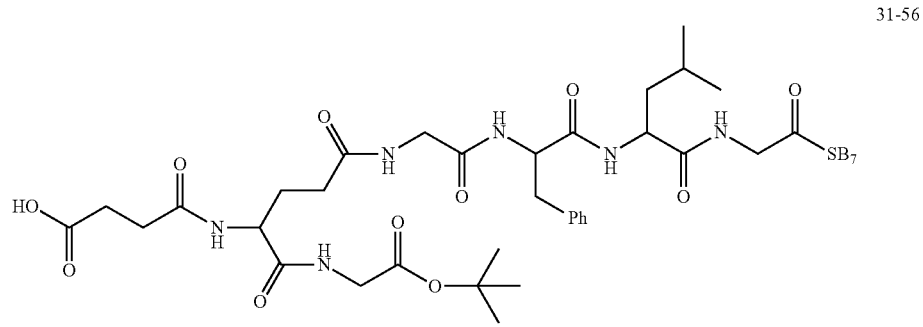

Compound 31-55 (2.52 g, 2.22 mmol) was added in a 250 mL round-bottomed flask and then dissolved with DMF (15 mL), the mixed solution was then stirred at room temperature, and then succinic anhydride (0.67 g, 6.66 mmol) was added quickly. After reaction for 0.5 h, DIEA (1.47 mL, 8.88 mmol) was slowly added dropwise and then the mixed solution in the reaction device was stirred overnight at room temperature to react. At the end of the reaction, n-hexane (100 mL) and methyl tert-butyl ether (400 mL) were added to the reaction solution to precipitate a solid product, and then suction filtering was carried out; the solid was taken. The operations of dry sample loading, column chromatography, and elution with 5% methanol/dichloromethane-10% methanol/dichloromethane were carried out. The elution product was collected and concentrated. 2.73 g of the product was obtained with a yield of 99.6%, mL), and the mixed solution was stirred at −5° C. for 30 min. Then DIEA (0.23 mL, 1.37 mmol) was slowly added dropwise, and then the mixed solution reacted at a low temperature (−5° C.) for 2 h; then, the reaction solution in the reaction device was stirred overnight at room temperature to react. At the end of the reaction, n-hexane (100 mL) and methyl tert-butyl ether (400 mL) were added for precipitation, the supernatant was then discarded, the lower solution was precipitated again with n-hexane (50 mL) and methyl tert-butyl ether (400 mL), and such precipitation was repeated three times to obtain a solid product; the solid product was then filtered out and dissolved with dichloromethane (100 mL) and methanol (10 mL); the operations of dry sample loading, column chromatography, and elution with 6% methanol/1% ammonia/dichloromethane were car-

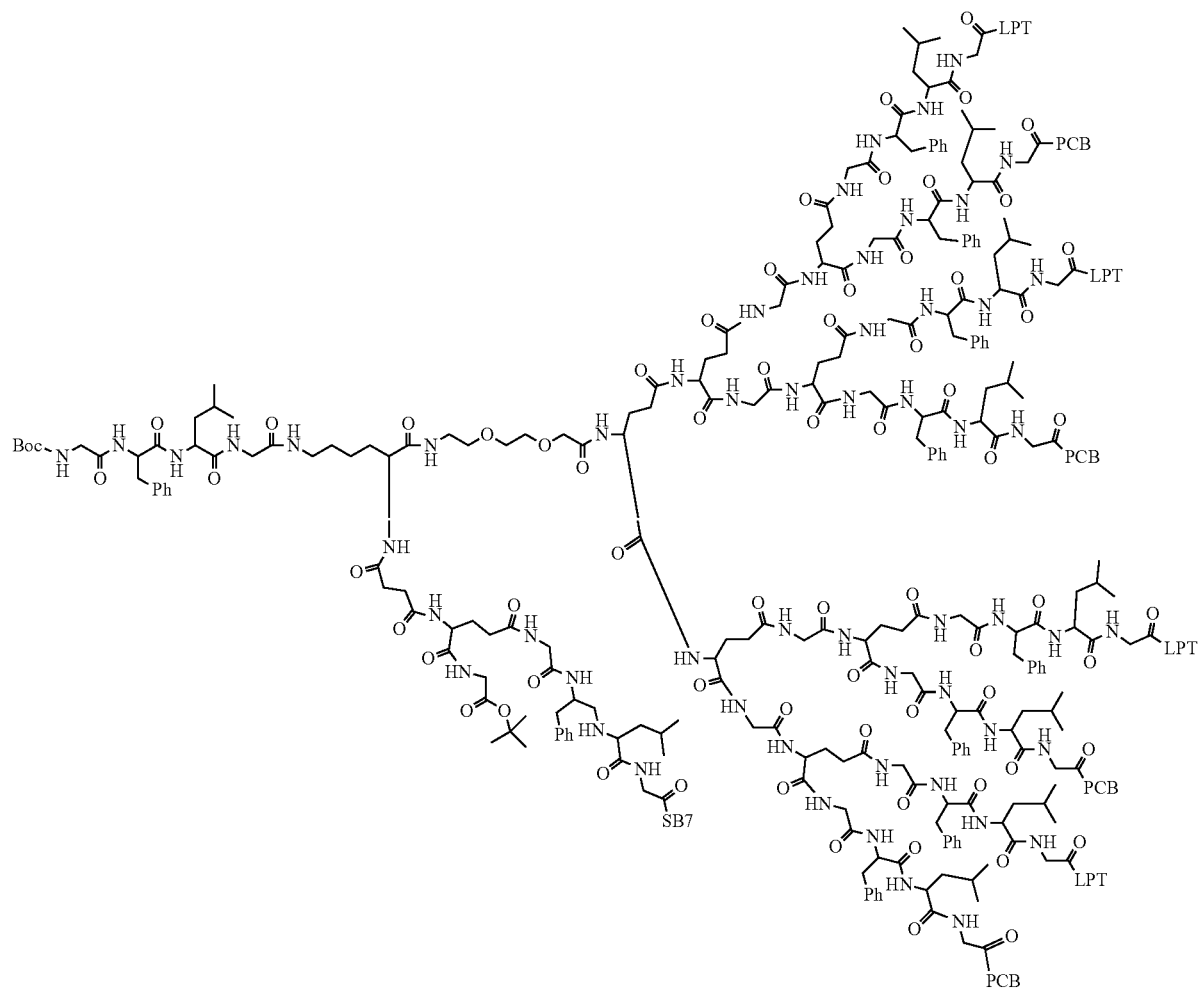

30-124

Compound 30-122 (2.7 g, 0.304 mmol), Compound 31-56 (0.45 g, 0.365 mmol), HOBT (0.062 g, 0.456 mmol) and HBTU (0.17 g, 0.456 mmol) were added in a 500 mL round-bottomed flask and then dissolved with DMF (50 ried out; the elution product was collected, concentrated, evaporated to dryness, and dried in a vacuum oven. 2.0 g of the product was obtained with a yield of 65%.

MALDI-TOF MS: [M+H$^+$] 10079.74 [M−H$^+$] 10078.14

30-129

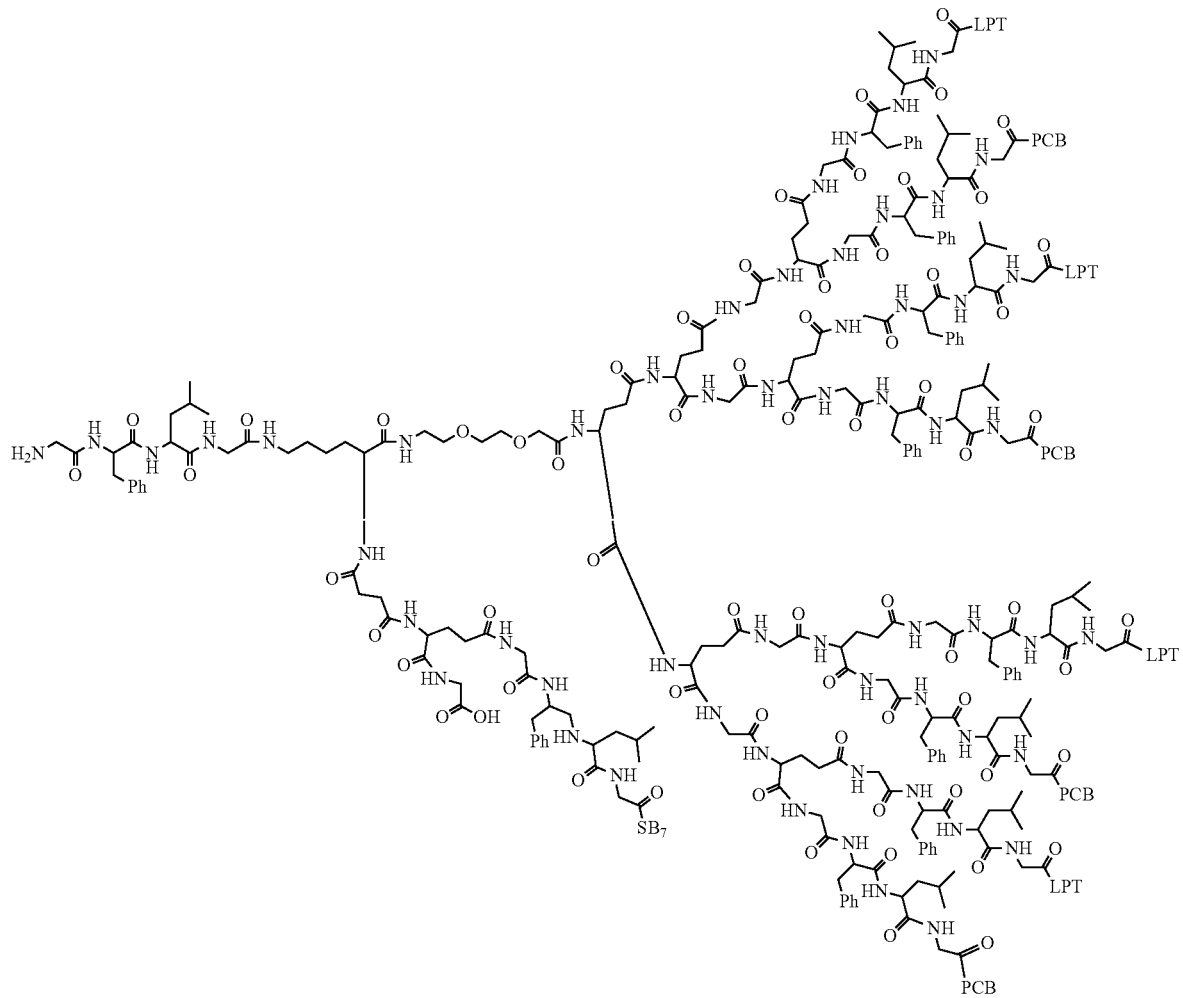

Compound 30-124 (2.0 g, 0.198 mmol) was added in a 500 mL round-bottomed flask and then dissolved with dichloromethane (30 mL), TFA (0.22 mL, 2.98 mmol) was then added and the obtained solution was stirred overnight at room temperature to react; after the reaction was completed, n-hexane (50 mL) and methyl tert-butyl ether (400 mL) were added to precipitate a solid; suction filtering was then carried out to obtain a solid product; the obtained solid product was dissolved with dichloromethane (100 mL) and methanol (10 mL); the operations of dry sample loading, column chromatography and elution with 8% methanol/dichloromethane were carried out; the elution product was then collected, concentrated, evaporated to dryness and dried in a vacuum oven. 1.1 g of the product was obtained.

$^1$H-NMR (400 MHz, DMSO-$d_6$) δ 10.11-9.98 (m, 6H), 8.93 (s, 3H), 8.76-8.75 (m, 3H), 8.61-8.57 (m, 4H), 8.20-7.99 (m, 60H), 7.88-7.85 (m, 12H), 7.80-7.70 (m, 10H), 7.48-7.43 (m, 10H), 7.34-7.06 (m, 86H), 6.98 (s, 6H), 6.67-6.53 (m, 3H), 5.25 (s, 6H), 4.74-4.57 (m, 13H), 4.36-4.22 (d, 20H), 4.02-3.98 (m, 4H), 3.32-3.38 (m, 68H), 3.11-3.01 (m, 41H), 2.89 (s, 1H), 2.75-2.69 (m, 15H), 2.41-2.37 (m, 24H), 2.33-2.13 (m, 50H), 1.99-1.74 (m, 41H), 1.56-1.48 (m, 46H), 0.86-0.77 (m, 66H).

MALDI-TOF MS: [M+H$^+$] 9916.38

30-131

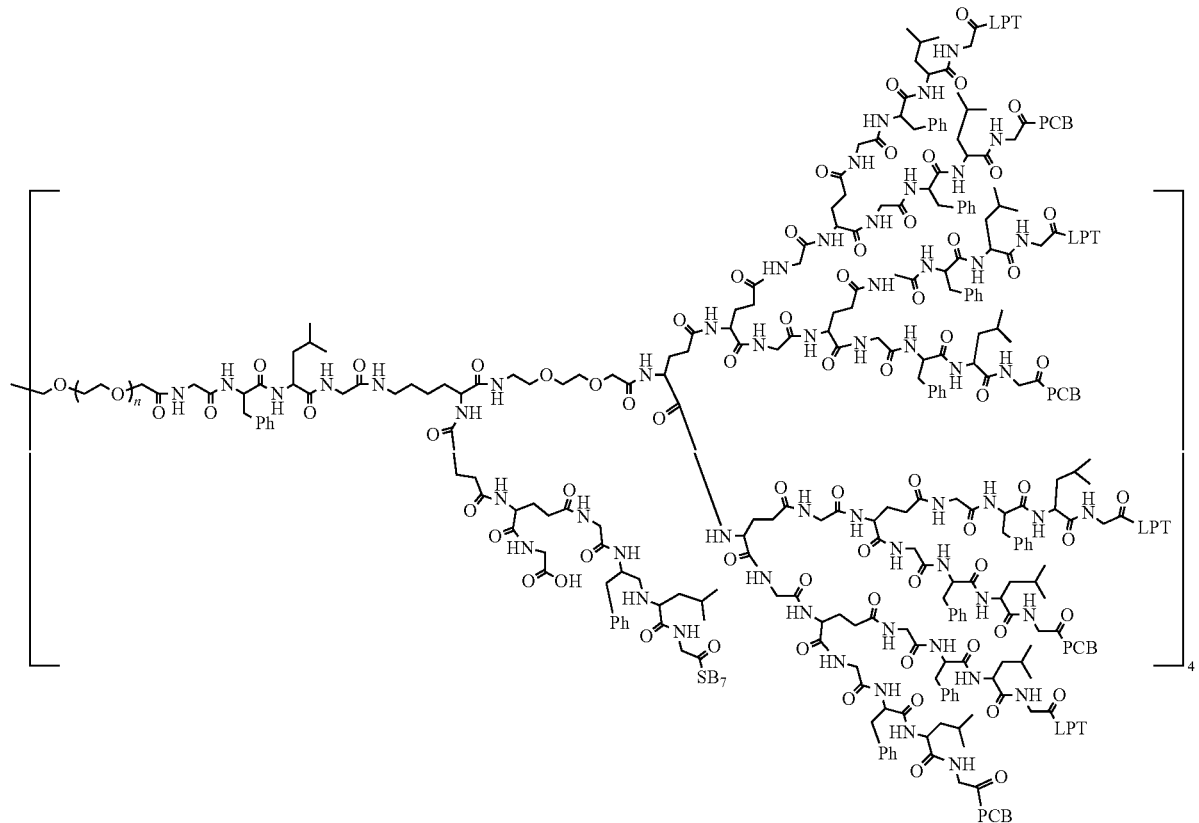

Compound 30-129 (1.1 g, 0.11 mmol) was added in a 500 mL round-bottomed flask and then dissolved with dichloromethane (10 mL) and DMF (50 mE), and then DIEA (0.1 mL, 0.63 mmol) was added, and finally high-molecular 4ARM-SCM-40K (1.01 g, 0.024 mmol, purchased from JenKem, Lot No: ZZ322P074) was added, and the mixed solution was stirred in the dark at the lowest speed at room temperature for 6 days. At the end of the reaction, the reaction solution was concentrated and then precipitated with n-hexane (100 mL) and methyl tert-butyl ether (300 mE), the supernatant was then discarded, the lower solution was precipitated again with n-hexane (50 mL) and methyl tert-butyl ether (400 mL), and such precipitation was repeated three times to obtain a solid product; the solid product was then filtered out, the filter cake was washed with methyl tert-butyl ether (100 mL), and the obtained solid product was dissolved with dichloromethane (100 mL) and methanol (10 mL); the operations of dry sample loading, column chromatography, and elution with 5% methanol/dichloromethane were carried out; the elution product was collected, concentrated, evaporated to dryness, and dried in a vacuum oven. The product was thus obtained.

$^1$H-NMR (400 MHz, DMSO-d$_6$) δ 10.11-9.91 (m, 18H), 8.93 (s, 12H), 8.80-8.79 (m, 12H), 8.55-8.54 (m, 16H), 8.21-7.97 (m, 191H), 7.88-7.86 (m, 21H), 7.79-7.79 (m, 26H), 7.47-7.43 (m, 32H), 7.35-7.14 (m, 415H), 7.05-7.03 (m, 30H), 6.92 (s, 5H), 6.70-6.67 (m, 6H), 5.33-5.24 (m, 38H), 5.15-5.08 (m, 4H), 4.74-4.69 (m, 22H), 4.57-4.49 (m, 46H), 4.38-4.15 (m, 104H), 3.99-3.81 (m, 8H), 3.51 (s, 158H), 3.76-347 (m, 3768H), 3.11-3.01 (m, 95H), 2.75-2.54 (m, 178H), 2.49-2.40 (m, 102H), 2.33-2.29 (m, 49H), 2.23-2.12 (m, 60H), 2.02-1.95 (m, 64H), 1.87-1.75 (m, 64H), 1.57-1.35 (s, 284H), 0.87-0.81 (m, 264H).

MALDI-TOF MS: from 79280.63 to 85210.73

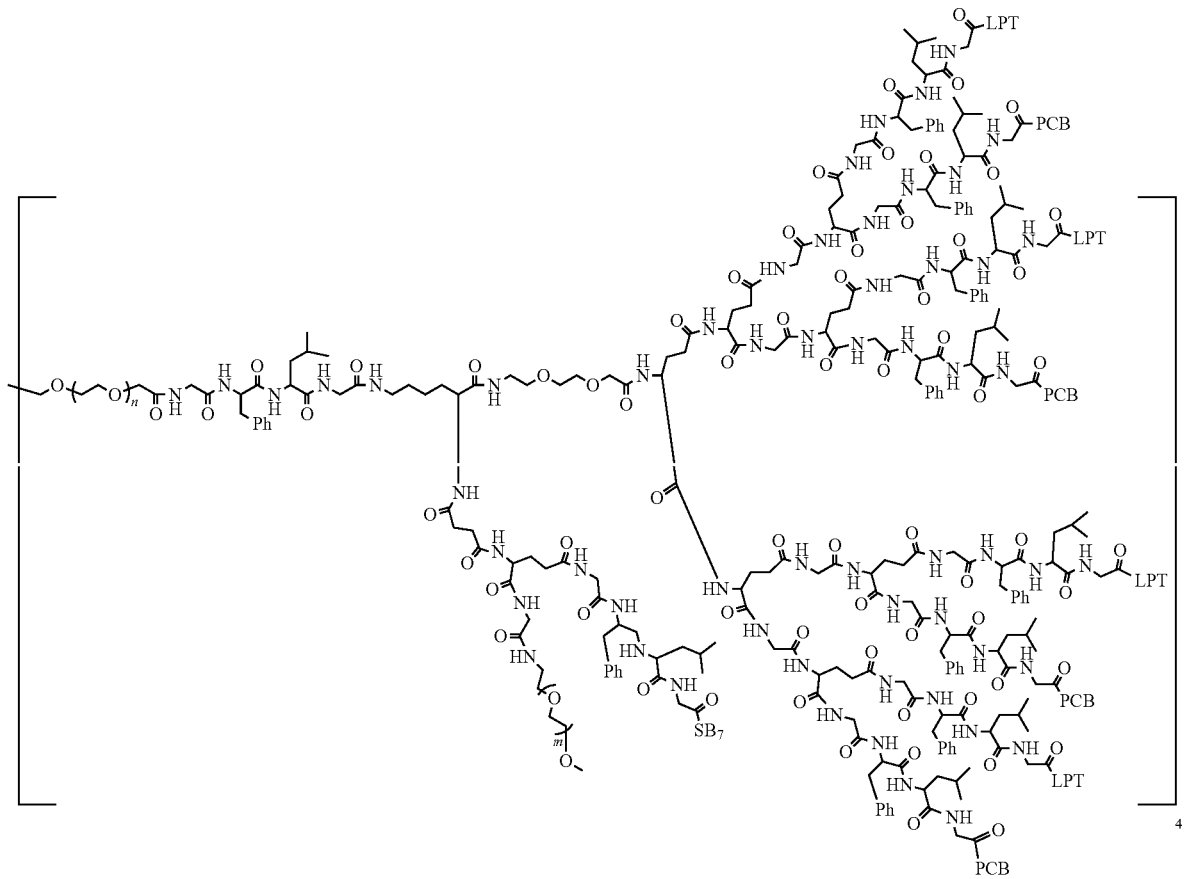

31-91

The reactants Compound 30-131 (0.85 g, 0.010 mmol), M-NH₂HCl-10K (0.66 g, 0.063 mmol), HOBT (0.25 g, 1.85 mmol) and HBTU (0.53 g, 1.40 mmol) were added in a 250 mL round-bottomed flask and then dissolved with DMF (50 mL), and the solution was stirred at 0° C. for 30 min. Then DIEA (0.20 mL, 1.21 mmol) was slowly added dropwise, and then the mixed solution was stirred for 2 h at 0° C. to react; then, the reaction solution was slowly stirred at room temperature for one week to react. At the end of the reaction, n-hexane (200 mL) and methyl tert-butyl ether (400 mL) were added to the reaction solution to precipitate a solid product; suction filtering was then carried out and the solid product was then dissolved with dichloromethane (50 mL); silica gel powder was then added to the resulting solution and the solution was then evaporated to dryness; the operations of dry sample loading, column chromatography, and gradient elution with 5% methanol/dichloromethane to 12% methanol/dichloromethane were carried out; the elution product was then collected and concentrated. 0.76 g of the product was obtained. The product was dried and then dissolved with a mixed solution of DMF (2 mL), ethyl acetate (2 mL), and absolute ethanol (30 mL). The resulting solution was precipitated with n-hexane (50 mL) and methyl tert-butyl ether (100 mL) and then filtered out by suction; the solid was taken, and then dried for later use. The weight of the obtained product was 0.65 g.

¹H-NMR (400 MHz, DMSO-d₆) δ 9.98 (d, J=104 Hz, 18H), 8.93 (s, 12H), 8.75 (s, 16H), 8.54 (s, 20H), 8.19-8.01 (m, 265H), 7.88-7.73 (m, 45H), 7.47-7.20 (m, 413H), 5.25 (s, 26H), 4.74-4.47 (m, 90H), 4.35-4.23 (m, 178H), 3.99-3.51 (m, 7568H), 3.17-3.01 (m, 258H), 2.89 (s, 67H), 2.73-2.67 (m, 70H), 2.48-2.41 (m, 189H), 2.29-2.22 (m, 130H), 1.87-1.75 (m, 64H), 1.57-1.48 (m, 64H), 1.10 (s, 284H), 0.85-0.81 (m, 264H).

Example 2: Synthesis of Compound 31-162

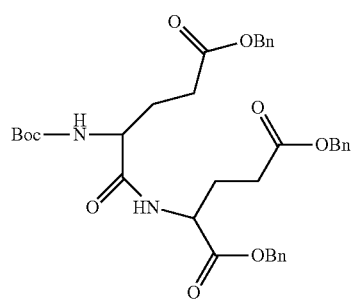

23-210

Boc-Glu(OH)—OBn (10 g, 29.64 mmol), NH₂-Glu-(OBn)₂·TsOH (16.3 g, 32.61 mmol), HBTU (16.9 g, 44.46 mmol) and HOBT (6.1 g, 44.46 mmol) were added in a 500 mL round-bottomed flask and then dissolved with DMF (200 mL), and the mixed solution was stirred at −5° C. for 30 min. Then DIEA (22 mL, 133.4 mmol) was slowly added dropwise, and then the mixed solution reacted at a low temperature (−5° C.) for 2 h; then, the reaction solution in the reaction flask was stirred overnight at room temperature to react. At the end of the reaction, a saturated sodium chloride solution (300 mL) and ethyl acetate (200 mL) were added for extraction, the organic phase was separated, the aqueous phase was extracted three times with ethyl acetate (100 mL×3), and the organic phases were combined and dried with anhydrous sodium sulfate powder; suction filtering was carried out and the obtained liquid was evaporated to dryness and concentrated. 31.4 g of the product was obtained, including extra-quota.

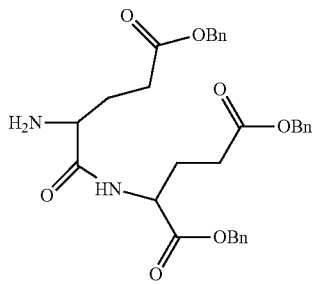

29-1

Compound 23-210 (31.4 g, 29.64 mmol) was added in a 500 mL round-bottomed flask and then dissolved with dichloromethane (100 mL). TFA (33 mL, 444.6 mmol) was then added to the obtained solution and stirred overnight at room temperature to react. When the reaction was stopped, the reaction solution was concentrated and evaporated to dryness and then extracted with a saturated sodium chloride solution (300 mL) and ethyl acetate (200 mL); then, the organic phase was separated, the aqueous phase was extracted three times with ethyl acetate (100 mL×3), and the organic phases were combined and dried with anhydrous sodium sulfate powder; suction filtering was carried out and the obtained liquid was evaporated to dryness and concentrated.

29-3

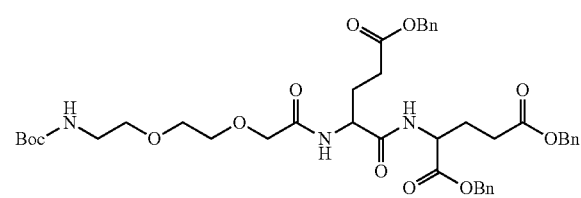

Compound 29-1 (16.2 g, 29.64 mmol), Compound 10-102 (synthesized according to the synthesis method of Compound 24-36, 38.5 g, 38.5 mmol), HBTU (16.8 g, 44.4 mmol) and HOBT (6 g, 44.4 mmol) were added in a 500 mL round-bottomed flask and then dissolved with DMF (200 mL), and the mixed solution was stirred at −5° C. for 30 min. Then DIEA (22 mL, 133.2 mmol) was slowly added dropwise, and then the mixed solution reacted at a low temperature (−5° C.) for 2 h; then, the reaction solution in the reaction device was stirred overnight at room temperature to react. At the end of the reaction, a saturated sodium chloride solution (300 mL) and ethyl acetate (200 mL) were added to the reaction solution for extraction, the organic phase was separated, the aqueous phase was extracted three times with ethyl acetate (100 mL×3), and the organic phases were combined and dried with anhydrous sodium sulfate powder; suction filtering was carried out, and the obtained liquid was evaporated to dryness and concentrated; the operations of dry sample loading, column chromatography and elution with 45% ethyl acetate were carried out; the product was then collected, concentrated and evaporated to dryness. 11.1 g of the product was obtained.

30-70

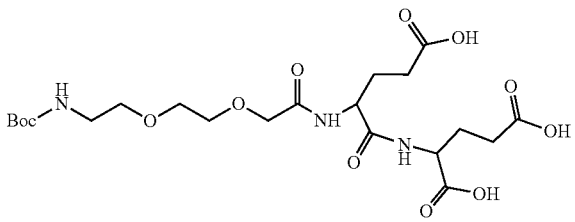

Raw material Compound 29-3 (1.13 g, 1.43 mmol) and 10% Pd/C catalyst (100 mg) were added into a hydrogenation reaction device and then dissolved with DMF (30 mL). The hydrogenation reaction device was then sealed and $H_2$ (18 psi) was introduced. The mixed solution was stirred overnight at room temperature. After the reaction was found to be completed from the monitoring of the TLC, the reaction solution was taken out and evenly dropwise added to a sand core funnel filled with compacted diatomaceous earth and suction filtering was carried out; the diatomaceous earth was then washed with DMF (90 mL) until there was no product in the diatomaceous earth. The reaction product solution was thus obtained.

30-71

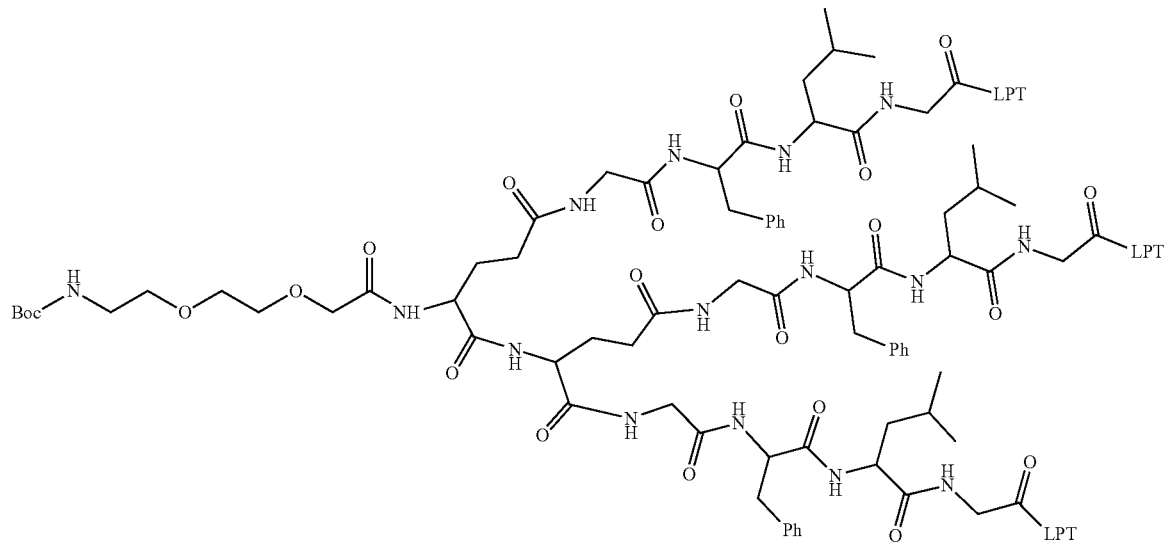

Compound 30-70 (1.43 mmol), Compound 14-128 (4.5 g, 4.71 mmol), HOBT (0.86 g, 6.42 mmol) and HBTU (2.44 g, 6.42 mmol) were added in a 500 mL round-bottomed flask and then dissolved with DMF (50 mL), and the mixed solution was stirred at −5° C. for 30 min. Then DIEA (3.18 mL, 19.3 mmol) was slowly added dropwise, and then the mixed solution reacted at a low temperature (−5° C.) for 2 h; then, the reaction solution in the reaction flask was stirred overnight at room temperature. At the end of the reaction, the reaction solution was precipitated with n-hexane (100 mL) and methyl tert-butyl ether (400 mL), the supernatant was discarded, n-hexane and methyl tert-butyl ether were added again for precipitation, and such precipitation operation was repeated 3 times; then filtering was carried out to obtain a solid product and the solid product was dried. 4.76 g of the product was obtained with a yield of 100%.

Compound 30-71 (4.76 g, 1.43 mmol) was added in a 500 mL round-bottomed flask and then dissolved with dichloromethane (20 mL), TFA (1.59 mL, 21.45 mmol) was then added and the obtained solution was stirred overnight at room temperature to react; after the reaction was completed, n-hexane (50 mL) and methyl tert-butyl ether (400 mL) were added to precipitate a solid; suction filtering was then carried out to obtain a solid product; the obtained solid product was dissolved with dichloromethane (50 mL) and methanol (10 mL); the operations of dry sample loading, column chromatography and elution with 5% methanol/1% ammonia water/dichloromethane were carried out; the elution product was then collected, concentrated, evaporated to dryness and dried in a vacuum oven. 2.3 g of the desired product was obtained and the undissolved part weighed 1.7 g, totaling 4.0 g.

MALDI-TOF MS: [M+H⁺] 3232.31, [M+Na⁺] 3256.24

30-80

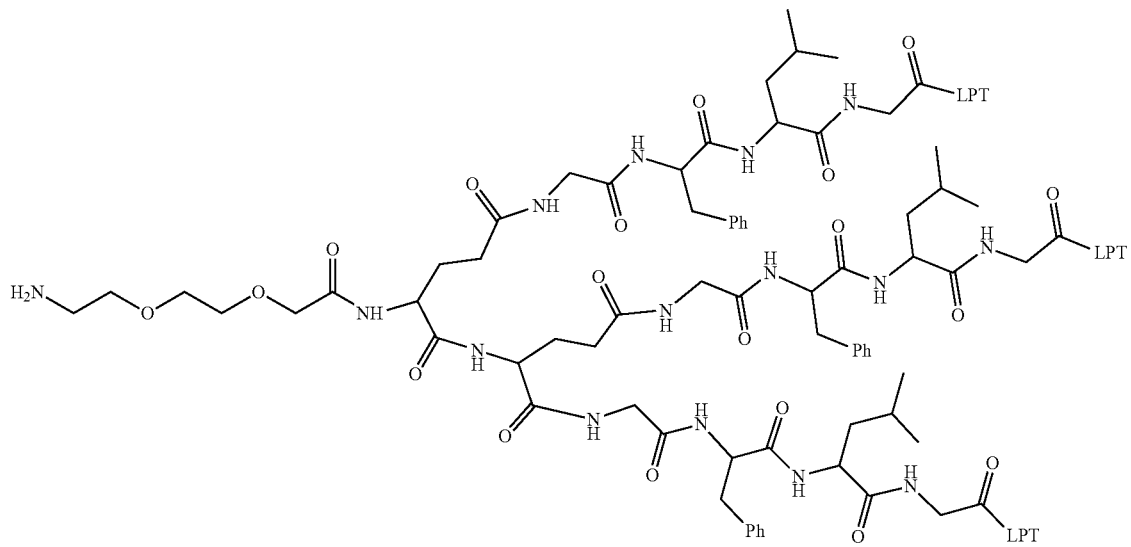

30-90

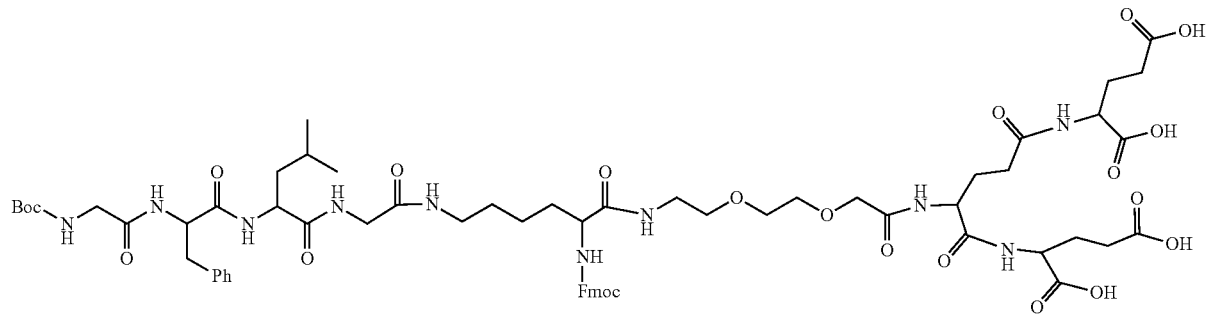

Raw material Compound 30-84 (0.26 g, 0.15 mmol) and 10% Pd/C catalyst (100 mg) were added into a hydrogenation reaction device and then dissolved with DMF (30 mL). The hydrogenation reaction device was then sealed and $H_2$ (18 psi) was introduced. The mixed solution was stirred overnight at room temperature. After the reaction was found to be completed from the monitoring of the TLC, the reaction solution was taken out and evenly dropwise added to a sand core funnel filled with compacted diatomaceous earth and suction filtering was carried out; the diatomaceous earth was then washed with DMF (90 mL) until there was no product in the diatomaceous earth. The reaction product solution was thus obtained.

30-93

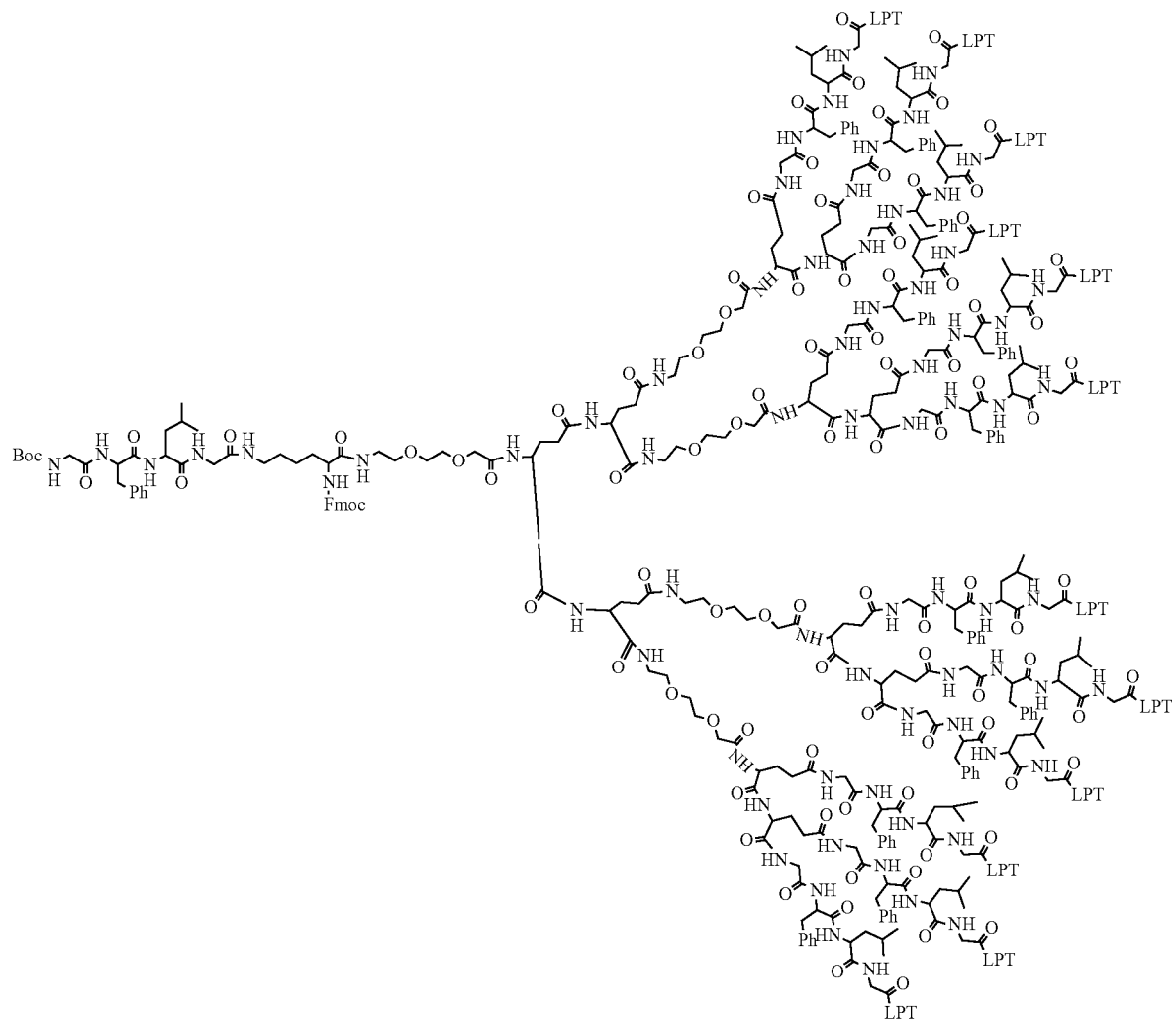

Compound 30-90 (0.15 mmol), Compound 30-80 (2.5 g, 0.77 mmol), HOBT (0.12 g, 0.89 mmol) and HBTU (0.34 g, 0.89 mmol) were added in a 500 mL round-bottomed flask and then dissolved with DMF (50 mL), and the mixed solution was stirred at −5° C. for 30 min. Then DIEA (0.45 mL, 2.67 mmol) was slowly added dropwise, and then the mixed solution reacted at a low temperature (−5° C.) for 2 h; then, the reaction solution in the reaction device was stirred overnight at room temperature. At the end of the reaction, the reaction solution was precipitated with n-hexane (100 mL) and methyl tert-butyl ether (400 mL), the supernatant was discarded, n-hexane and methyl tert-butyl ether were added again for precipitation, and such precipitation operation was repeated 3 times; then the solid product was then filtered out and dried. 2.13 g of the product was obtained with a yield of 1000%.

MALDI-TOF MS: [M+H$^+$] 14148.00

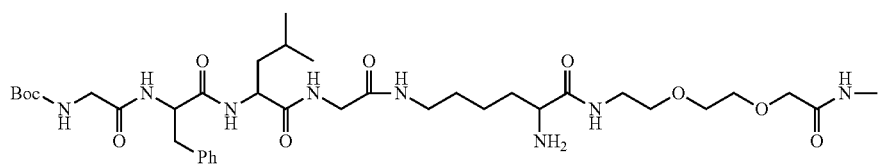

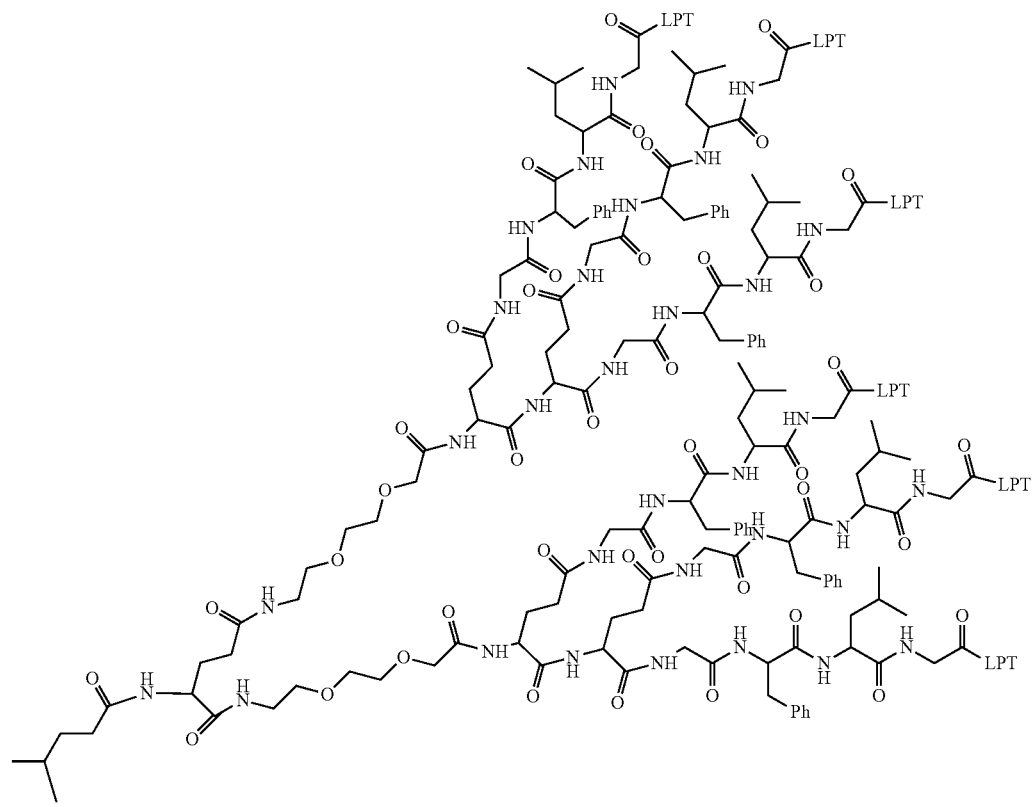

30-103

-continued

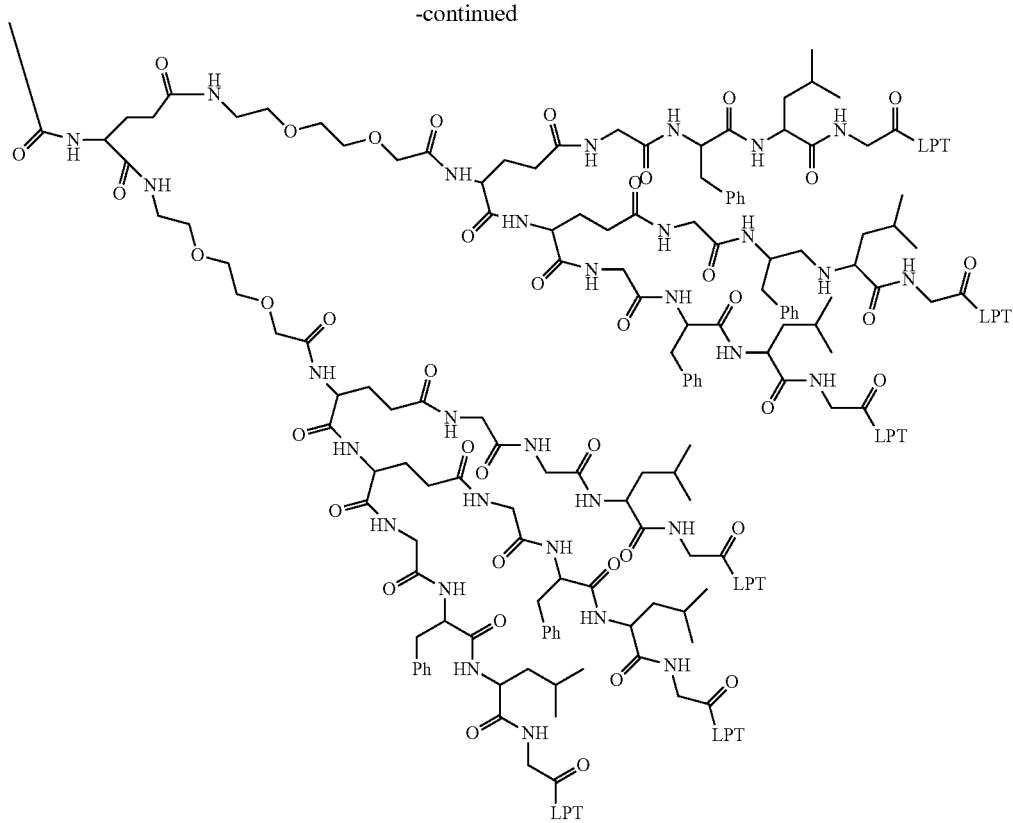

Product 30-93 (2.13 g, 0.15 mmol) was added in a 500 mL round-bottomed flask and dissolved with DMF (30 mL), morpholine (0.39 mL, 4.5 mmol) was then added and the obtained solution was stirred at room temperature to react for 60 min; at the end of the reaction, n-hexane (50 mL) and methyl tert-butyl ether (300 mL) were added for precipitation and the solid product was then filtered out by suction; the filter cake was washed with n-hexane (100 mL) to obtain a solid product, and then the solid product was dissolved with dichloromethane (100 mL) and methanol (10 mL); and the operations of dry sample loading, column chromatography and elution with 8% methanol/1% ammonia water/ dichloromethane were carried out; the elution product was then collected, concentrated, evaporated to dryness, and dried in a vacuum oven. 1.85 g of the product was obtained with a yield of 88%.

30-133

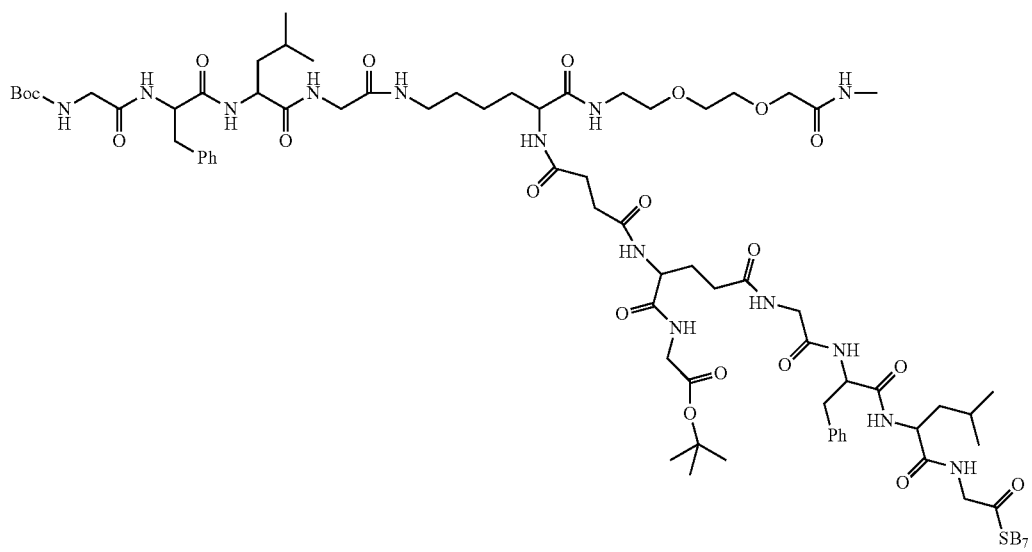

-continued
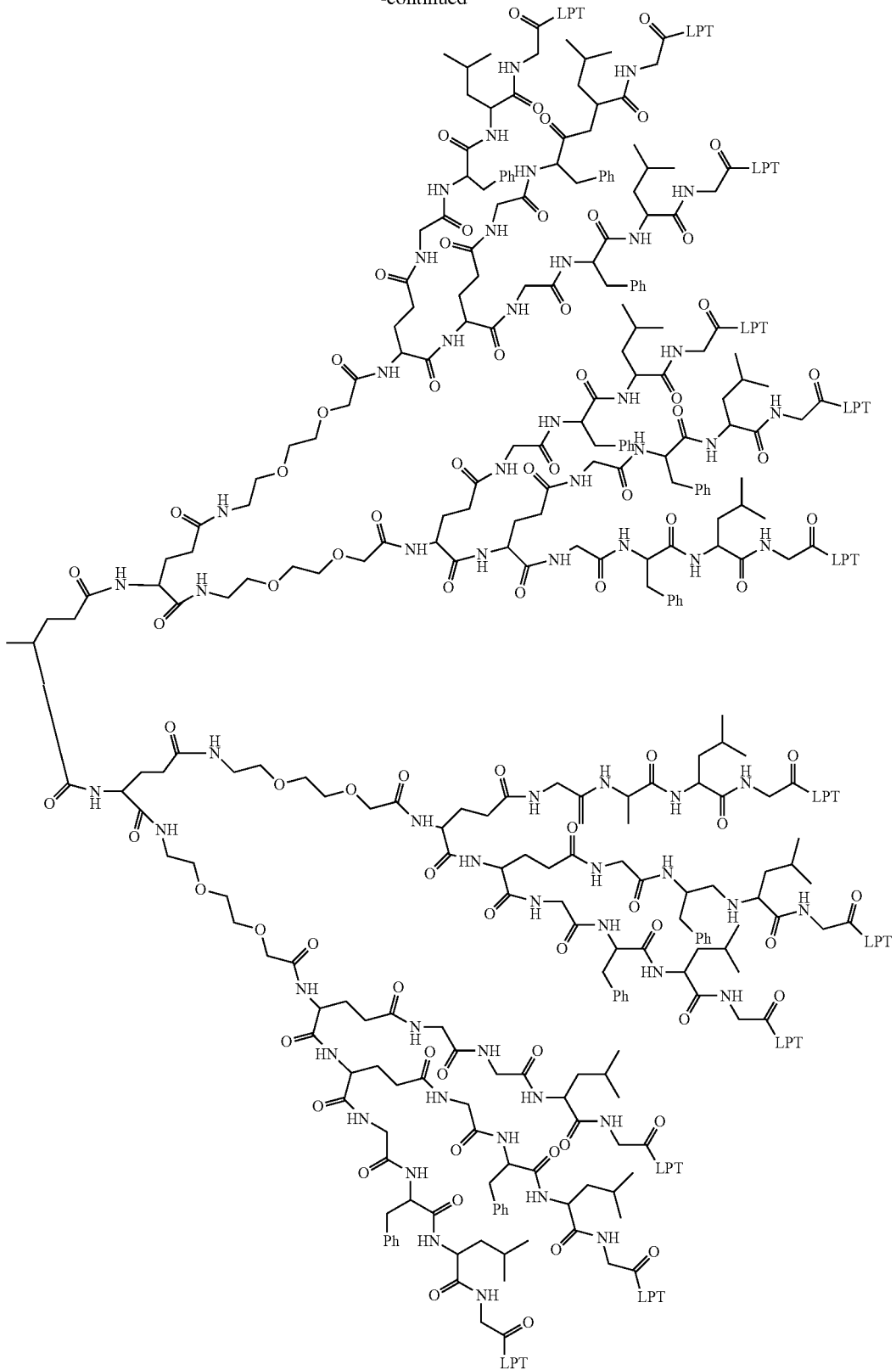
Compound 30-103 (1.85 g, 0.13 mmol), Compound 31-56 (0.195 g, 0.158 mmol), HOBT (0.027 g, 0.197 mmol) and HBTU (0.075 g, 0.197 mmol) were added in a 500 mL round-bottomed flask and then dissolved with DMF (50 mL), and the mixed solution was stirred at −5° C. for 30 min. Then DIEA (0.1 mL, 0.593 mmol) was slowly added dropwise, and then the mixed solution reacted at a low temperature (−5° C.) for 2 h; then, the reaction solution in the reaction flask was stirred overnight at room temperature. At the end of the reaction, n-hexane (100 mL) and methyl tert-butyl ether (400 mL) were added for precipitation, the supernatant was then discarded, n-hexane and methyl tert-butyl ether were added again for precipitation, and such precipitation was repeated three times to obtain a solid product; the solid product was then filtered out and dissolved with dichloromethane (100 mL) and methanol (10 mL); the operations of dry sample loading, column chromatography, and elution with 8% methanol/1 ammonia water/dichloromethane were carried out; the elution product was collected, concentrated, evaporated to dryness, and dried in a vacuum oven. 1.2 g of the product was obtained.

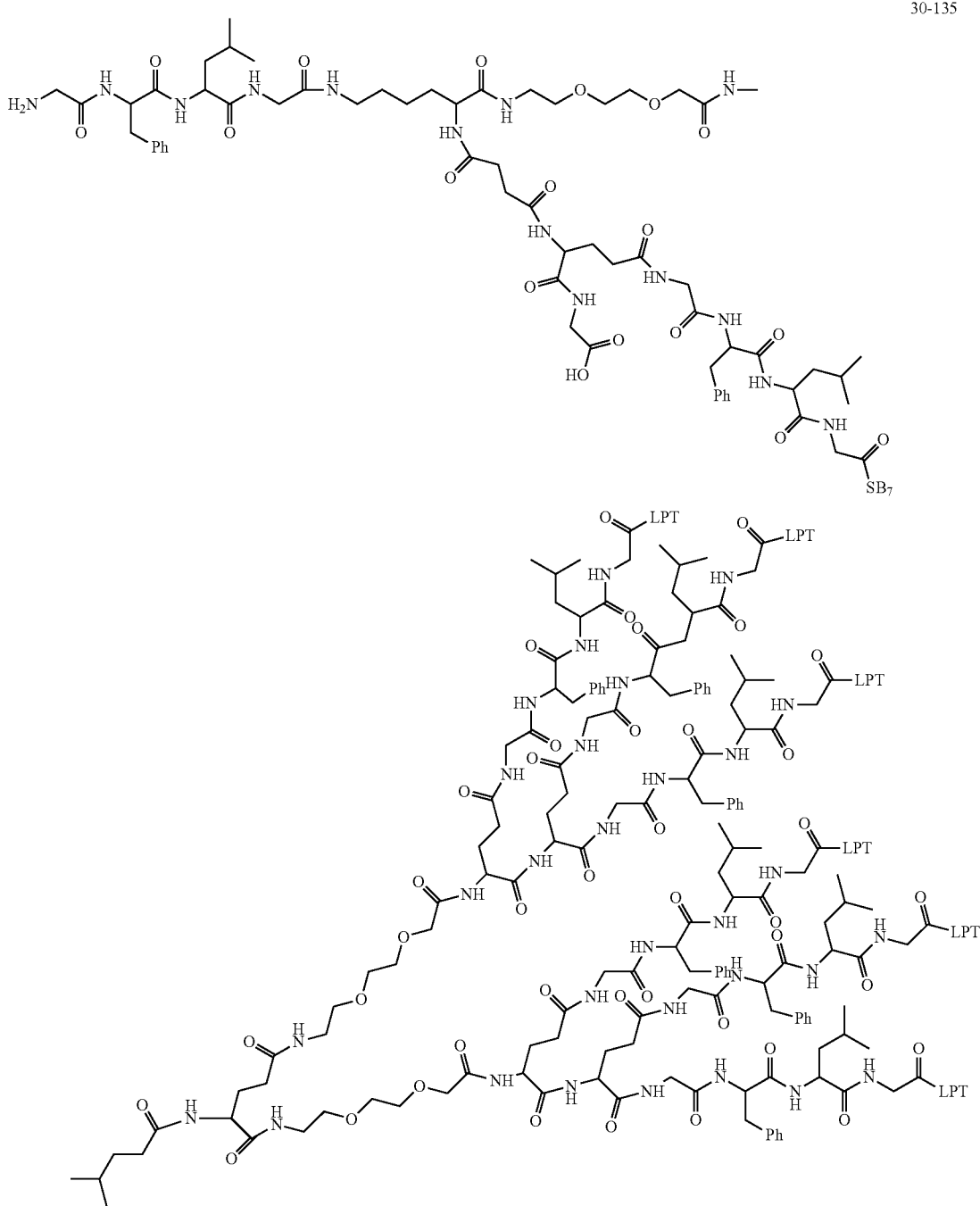

30-135

-continued

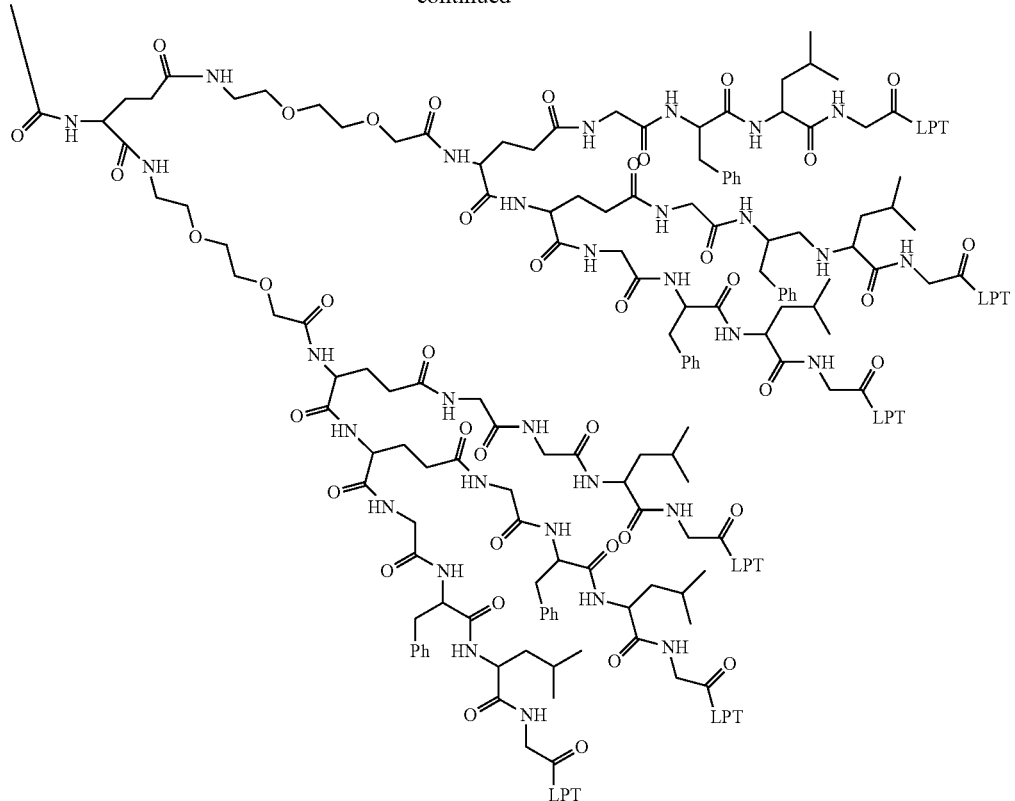

Product 30-133 (1.2 g, 0.078 mmol) was added in a 500 mL round-bottomed flask and dissolved with dichloromethane (20 mL), TFA (3.0 mL, 40.39 mmol) was then added and the obtained solution was stirred at room temperature to react for 60 min; at the end of the reaction, the reaction solution was subjected to rotary evaporation, n-hexane (50 mL) and methyl tert-butyl ether (100 mL) were then added for precipitation and the solid product was then filtered out by suction; the filter cake was washed with methyl tert-butyl ether (50 mL) to obtain a solid product, and then the solid product was dissolved with dichloromethane (100 mL) and methanol (10 mL); and the operations of dry sample loading, column chromatography and elution with 8% methanol/dichloromethane were carried out; the elution product was then collected, concentrated, evaporated to dryness, and dried in a vacuum oven. 0.77 g of the product was obtained with a yield of 65%.

MALDI-TOF MS: [M+H$^+$] 15060.71, [M+K$^+$] 15097.40

205 206
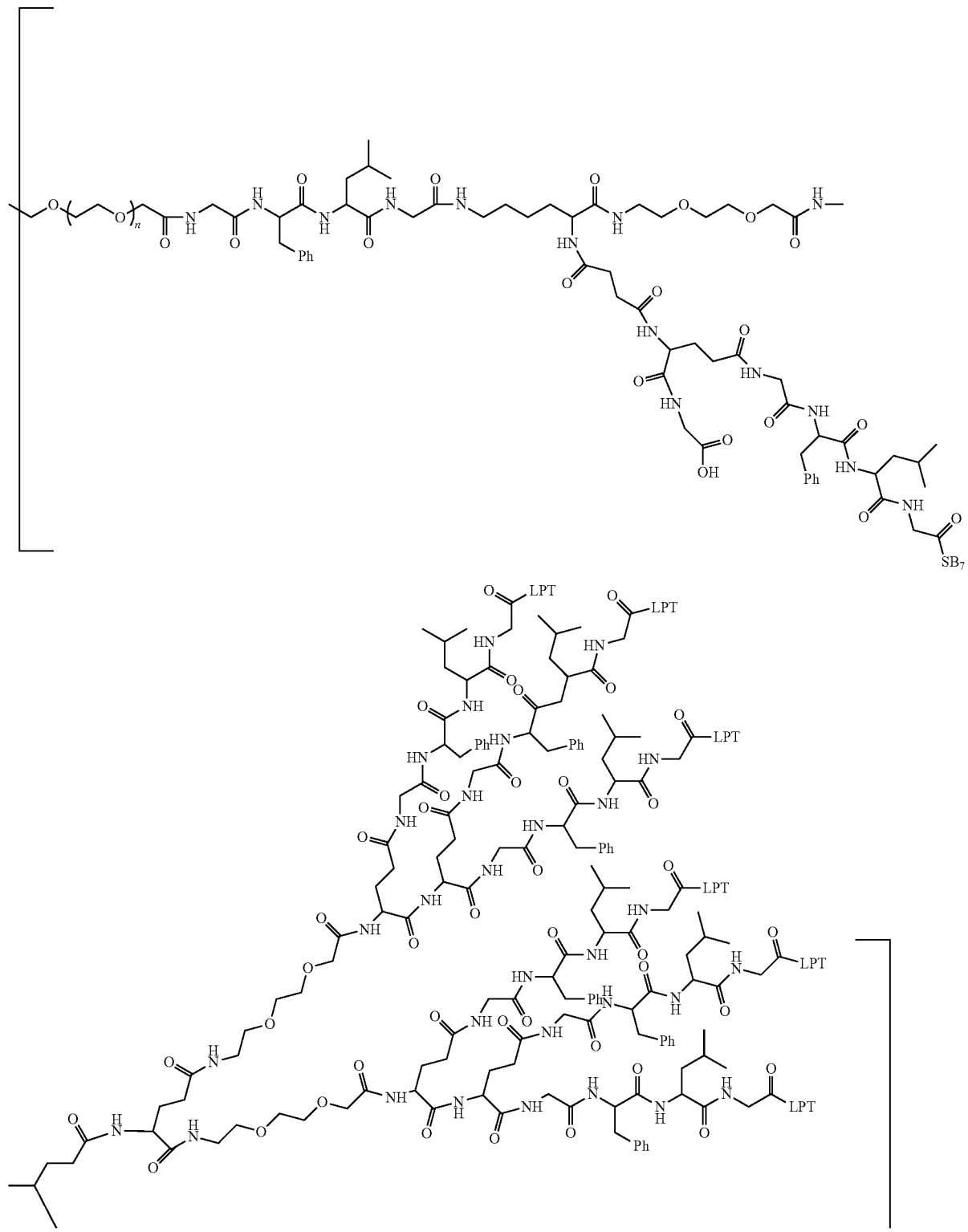

-continued

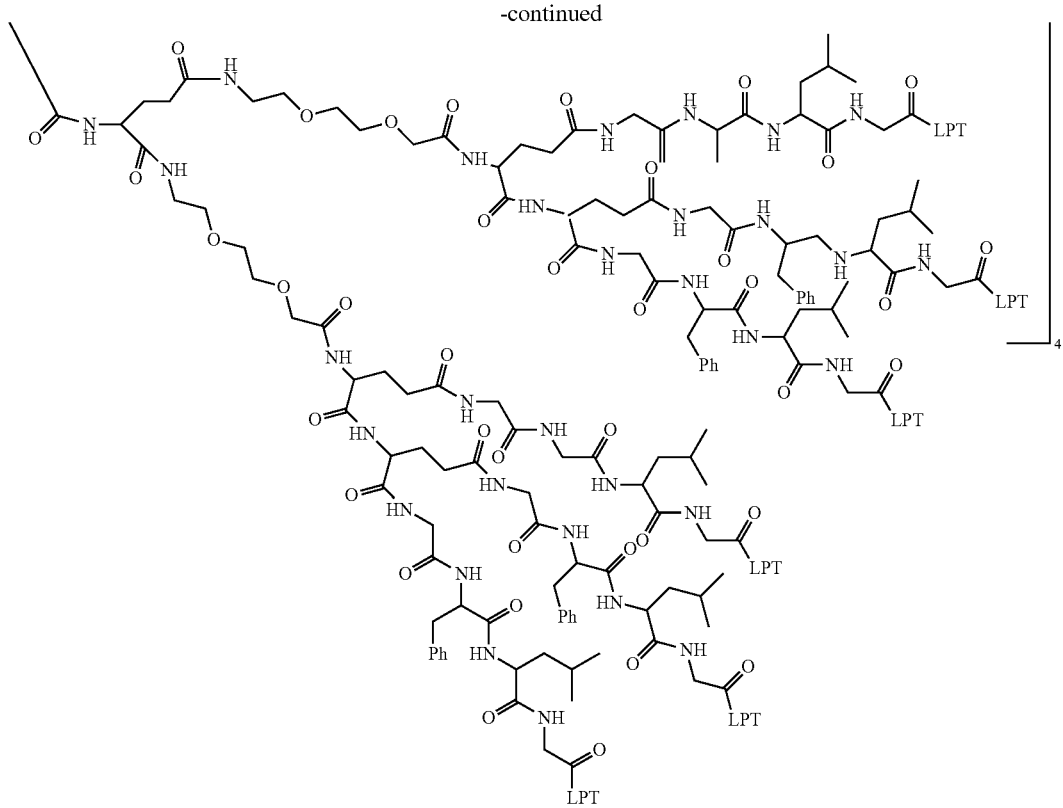

Compound 30-135 (0.77 g, 0.05 mmol) was added in a 250 mL round-bottomed flask and then dissolved with DMF (20 mL), and the solution was stirred at −5° C. for 30 min. Then, DIEA (0.20 mL, 1.21 mmol) was slowly added dropwise and the reaction continued for 30 m; then, the reaction solution was stirred at room temperature to react; 4ARM-SCM-40K (0.49 g, 0.01 mmol, purchased from Jenkem) was then added to the reaction solution and dissolved by ultrasonic. The obtained solution was slowly stirred for one week to react. At the end of the reaction, n-hexane (100 mL) and methyl tert-butyl ether (150 mL) were added to the reaction solution to precipitate a solid product, and then suction filtering was carried out; the solid was taken and then dried in an oven. The operations of dry sample loading, column chromatography, and elution with 800 methanol/1% ammonia water/dichloromethane were carried out. The elution product was then collected, concentrated, evaporated to dryness with a rotary evaporator, and dried in an oven. 0.27 g of the product was obtained.

209 210
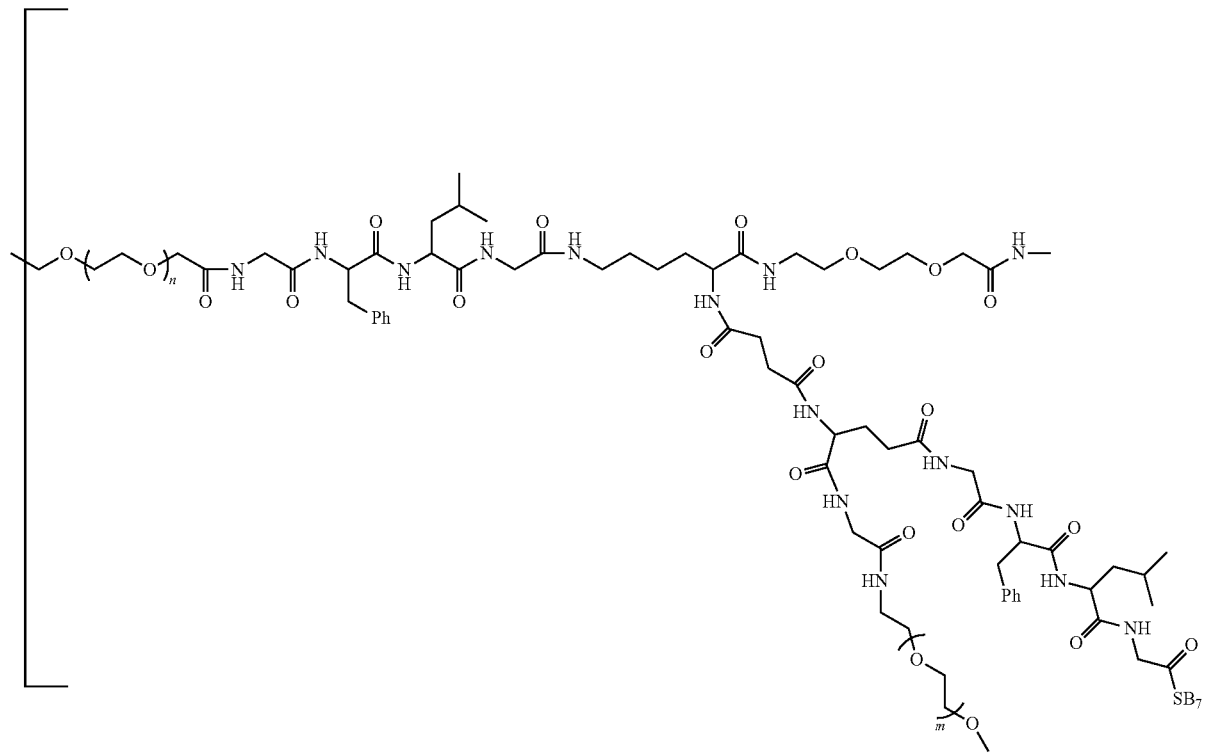
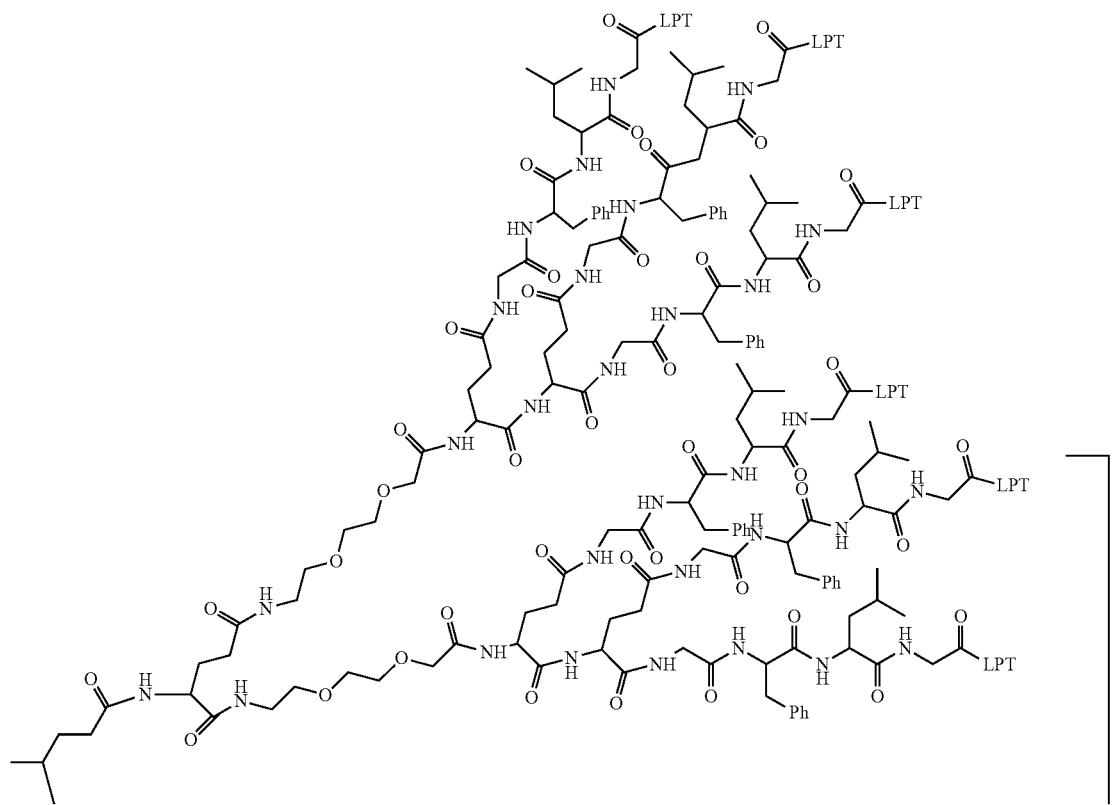

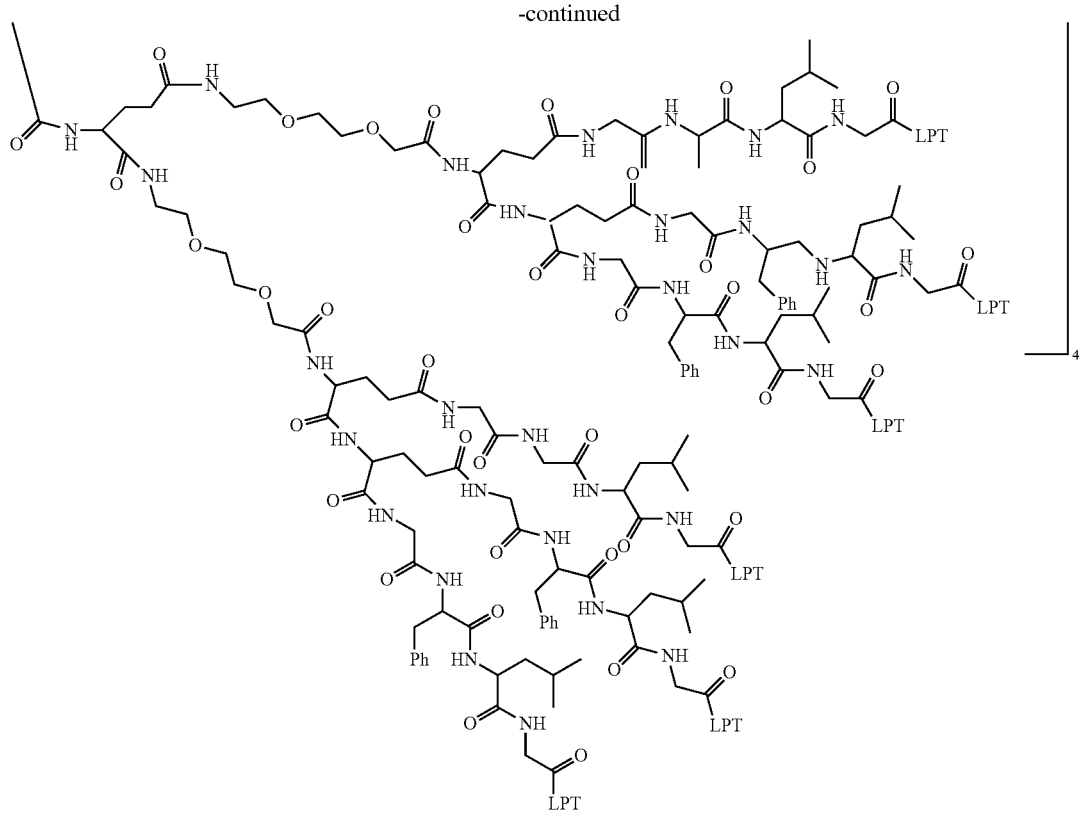

The Compound 31-142 (0.27 g, 0.003 mmol), M-NH₂HCl-20K (0.32 g, 0.016 mmol), HOBT (0.05 g, 0.37 mmol) and HBTU (0.12 g, 0.32 mmol) were added in a 250 mL round-bottomed flask and then dissolved with DMF (12 mL), and the solution was stirred at 0° C. for 30 min. Then DIEA (0.20 mL, 1.21 mmol) was slowly added dropwise, and the solution further reacted for 30 min; then, the reaction solution was slowly stirred at room temperature for one week to react. At the end of the reaction, n-hexane (50 mL) and methyl tert-butyl ether (100 mL) were added to the reaction solution to precipitate a solid product; suction filtering was then carried out and the solid product was then subjected to dry sample loading, column chromatography, and gradient elution with 500 methanol/1% ammonia water/dichloromethane-3000 methanol/1% ammonia water/dichloromethane; the elution product was then collected and concentrated. 76 mg of the product 31-162 was obtained.

$^1$H-NMR (400 MHz, DMSO-d$_6$) δ 8.89 (s, 92H), 8.67 (s, 68H), 8.29-7.98 (m, 344H), 7.84-7.66 (m, 172H), 7.54-7.44 (m, 108H), 7.34-7.09 (m, 472H), 6.99 (s, 40H), 5.27 (s, 128H), 4.76-4.33 (m, 564H), 3.50 (s, 11218H), 3.06-2.97 m, 168H), 2.85 (s, 180H), 2.10 (s, 96H), 1.82-1.12 (m, 592H), 1.01-0.67 (m, 336H).

Example 3: Synthesis of Compound 31-136

14-143

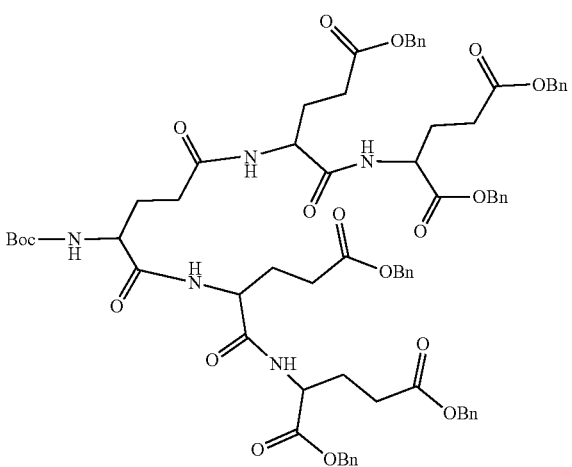

Compound 14-138 (synthesized according to the synthesis route of Compound 29-1, 15.65 g, 28.64 mmol), Boc-Glu-OH (3.47 g, 14.07 mmol), HOBT (5.70 g, 42.21 mmol), and HBTU (16.01 g, 42.21 mmol) were added in a 500 mL round-bottomed flask and then dissolved with DMF (100 mL), and the mixed solution was stirred at −5° C. for 30 min. Then DIEA (20.93 mL, 126.63 mmol) was slowly added dropwise and then the reaction device was placed at −5° C. and the reaction solution was stirred to react for 2 h; and then the reaction solution was further stirred overnight at room temperature. At the end of the reaction, a saturated sodium bicarbonate solution (300 mL) and ethyl acetate (200 mL) were added for extraction, the organic phase was separated, the aqueous phase was extracted three times with ethyl acetate (100 mL×3), and the organic phases were combined and washed twice with a saturated sodium chloride solution (200 mL×2), and then dried with anhydrous sodium sulfate powder. Suction filtering was then carried out and the obtained liquid was evaporated to dryness. 18.31 g of the product was obtained.

$CH_2Cl_2$ (30 mL), and the mixed solution was stirred at room temperature. TFA (15.64 mL, 210.55 mmol) was then added dropwise, and the mixed solution reacted at room temperature for 2 h. At the end of the reaction, the reaction solution was evaporated to dryness. After the reaction was completed, a saturated sodium bicarbonate solution (300 mL) and ethyl acetate (200 mL) were then added for extraction, the organic phase was separated, the aqueous phase was extracted three times with ethyl acetate (100 mL×3), and the organic phases were combined and washed twice with a saturated sodium chloride solution (200 mL×2), and then dried with anhydrous sodium sulfate powder; suction filtering was carried out and the obtained liquid was evaporated to dryness. 16.90 g of the product was obtained with a yield of 78.1%.

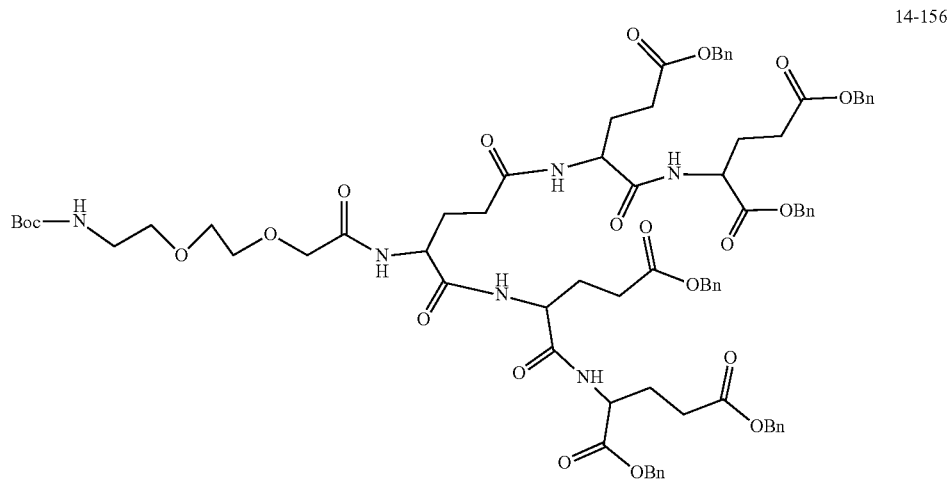 [SMILES: CC(C)(C)OC(=O)NCCOCCOCC(=O)NC(CCC(=O)NC(CCC(=O)OCc1ccccc1)C(=O)NC(CCC(=O)OCc1ccccc1)C(=O)OCc1ccccc1)C(=O)NC(CCC(=O)OCc1ccccc1)C(=O)NC(CCC(=O)OCc1ccccc1)C(=O)OCc1ccccc1]

14-156

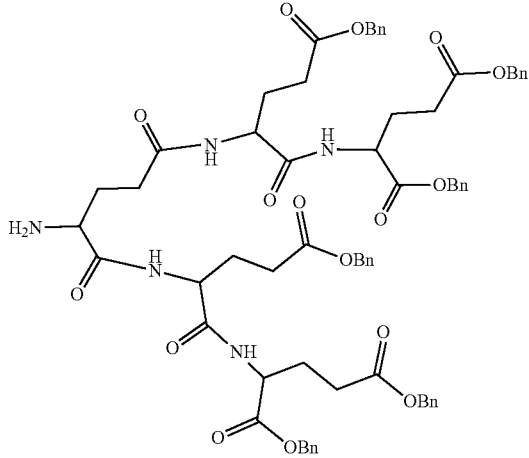

14-144

Compound 14-143 (13.81 g, 14.04 mmol) was added in a 500 mL round-bottomed flask and then dissolved with Compound 14-144 (13.2 g, 10.96 mmol), Compound 10-102 (synthesized according to the synthesis method of Compound 24-36, 3.17 g, 12.06 mmol), HOBT (2.22 g, 16.44 mmol) and HBTU (6.24 g, 16.44 mmol) were added in a 500 mL round-bottomed flask and then dissolved with DMF (70 mL), and the mixed solution was stirred at −5° C. for 30 min. Then DIEA (8.15 mL, 49.32 mmol) was slowly added dropwise and then the reaction device was placed at −5° C. and the reaction solution was stirred to react for 2 h; then the reaction solution further reacted overnight at room temperature. At the end of the reaction, deionized water (300 mL) and ethyl acetate (200 mL) were added for extraction, the organic phase was separated, the aqueous phase was extracted three times with ethyl acetate (100 mL×3), and the organic phases were combined and washed twice with a saturated sodium chloride solution (200 mL×2), and then dried with anhydrous sodium sulfate powder. Suction filtering was then carried out and the obtained liquid was evaporated to dryness and dried in an oven. The operations of dry sample loading, column chromatography, and elution with 1.5% methanol/dichloromethane were carried out. 10.02 g of the product was obtained with a yield of 63.15%.

14-221

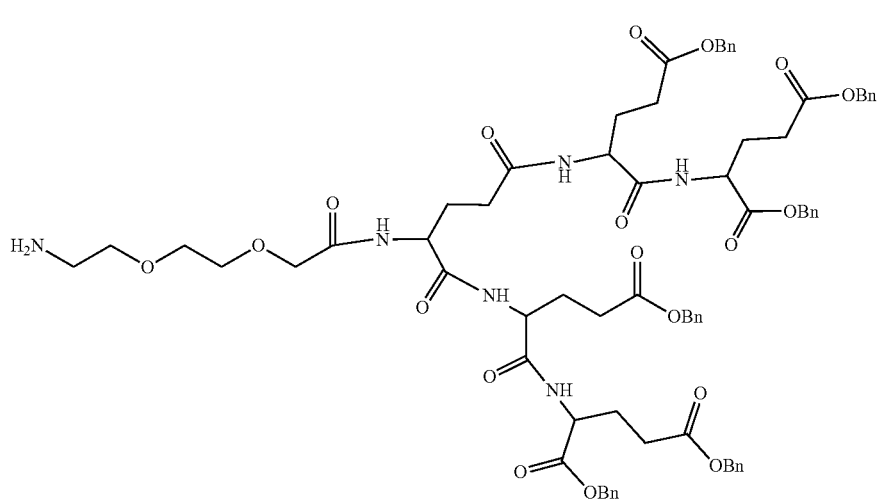

Compound 14-156 (1.5 g, 0.83 mmol) was added in a 250 mL round-bottomed flask and then dissolved with CH$_2$Cl$_2$ (10 mL), and the mixed solution was stirred at room temperature. TFA (0.92 mL, 12.42 mmol) was then added dropwise, and the mixed solution reacted at room temperature for 2 h. At the end of the reaction, the reaction solution was evaporated to dryness, a saturated sodium bicarbonate solution (300 mL) and ethyl acetate (200 mL) were then added for extraction, the organic phase was separated, the aqueous phase was extracted three times with ethyl acetate (100 mL×3), and the organic phases were combined and washed twice with a saturated sodium chloride solution (200 mL×2), and then dried with anhydrous sodium sulfate powder; suction filtering was carried out and the obtained liquid was evaporated to dryness. The product was obtained.

Compound 14-221 (1.12 g, 0.83 mmol), Fmoc-Lys(Boc)-OH (0.47 g, 1.00 mmol), HOBT (0.17 g, 1.25 mmol) and HBTU (0.47 g, 1.25 mmol) were added in a 250 mL round-bottomed flask and then dissolved with DMF (25 mL), and the mixed solution was stirred at 0° C. for 30 min. Then DIEA (0.62 mL, 3.75 mmol) was slowly added dropwise and then the solution in the reaction device was stirred overnight at a low temperature (0° C.) to react. At the end of the reaction, a saturated sodium chloride solution (300 mL) and ethyl acetate (200 mL) were added for extraction, the organic phase was separated, the aqueous phase was extracted three times with ethyl acetate (100 mL×3), and the organic phases were combined and washed twice with a saturated sodium chloride solution (200 mL×2), and then dried with anhydrous sodium sulfate powder; suction filtering was carried out and the filtrate was concentrated and dried. The product was obtained.

14-222

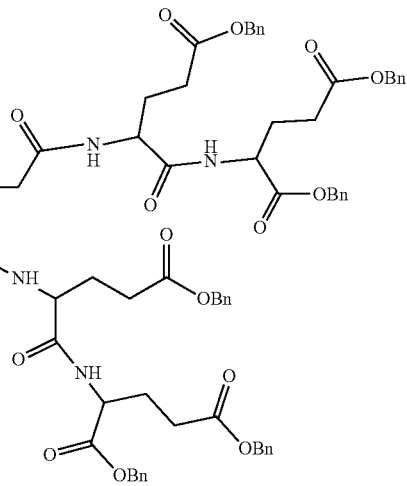

14-227

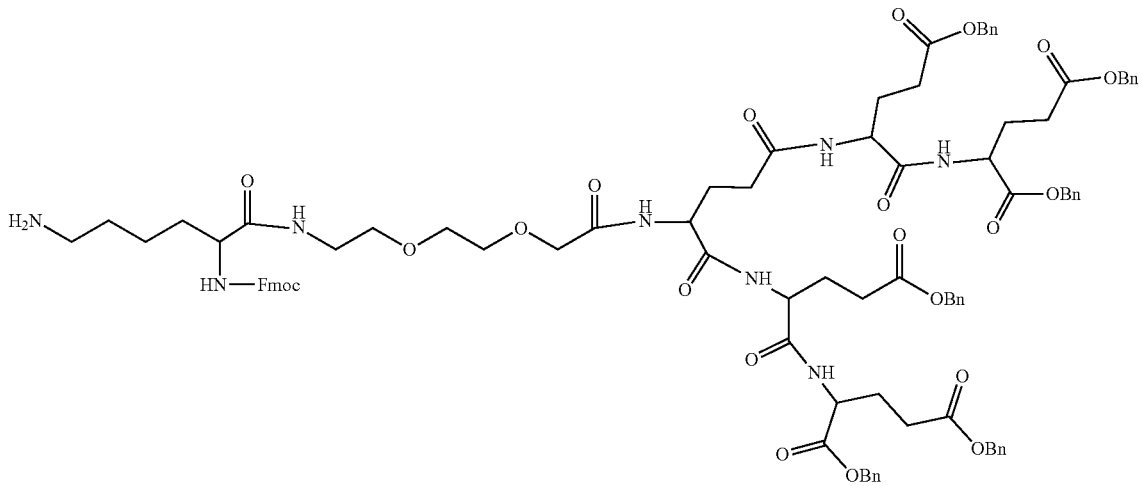

Compound 14-222 (1.49 g, 0.83 mmol) was added in a 250 mL round-bottomed flask and then dissolved with $CH_2Cl_2$ (10 mL), and the mixed solution was stirred at room temperature. TFA (0.92 mL, 12.42 mmol) was then added dropwise, and the mixed solution reacted at room temperature for 2 h. At the end of the reaction, a saturated sodium bicarbonate solution (300 mL) and ethyl acetate (200 mL) were added for extraction, the organic phase was separated, the aqueous phase was extracted three times with ethyl acetate (100 mL×3), and the organic phases were combined and washed twice with a saturated sodium chloride solution (200 mL×2), and then dried with anhydrous sodium sulfate powder; suction filtering was carried out and the filtrate was concentrated and dried. The product was obtained.

31-1

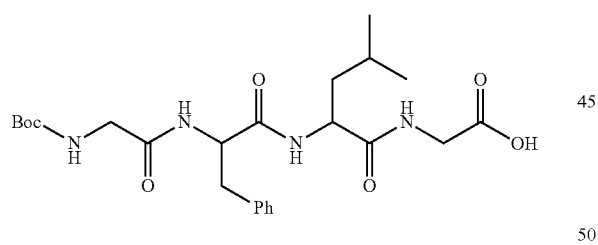

Raw material Boc-GFLG-OBn (0.63 g, 1.08 mmol, home-made) and 10% Pd/C catalyst (50 mg) were added into a hydrogenation reaction device and then dissolved with DMF (30 mL). The hydrogenation reaction device was then sealed and $H_2$ (18 psi) was introduced. The mixed solution was stirred overnight at room temperature. After the reaction was found to be completed from the monitoring of the TLC, the reaction solution was taken out and evenly dropwise added to a sand core funnel filled with compacted diatomaceous earth and suction filtering was carried out; the diatomaceous earth was then washed with DMF (90 mL) until there was no product in the diatomaceous earth. A reaction product solution was thus obtained.

31-2

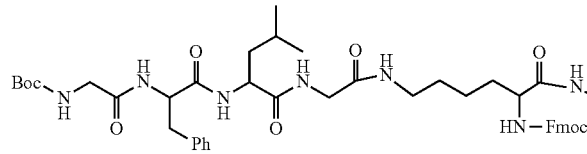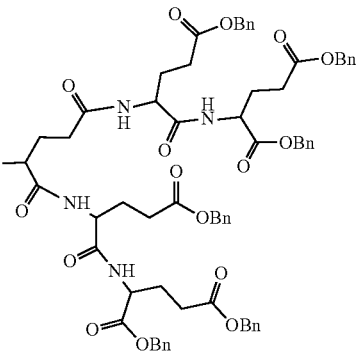

The solution of Compound 14-227 (1.18 g, 0.68 mmol), the solution of Compound 31-1 (0.53 g, 1.08 mmol), HOBT (0.14 g, 1.02 mmol) and HBTU (0.39 g, 1.02 mmol) were added in a 500 mL round-bottomed flask and then dissolved with DMF (80 mL), and the mixed solution was stirred at 0° C. for 30 min. Then DIEA (0.51 mL, 3.06 mmol) was slowly added dropwise and then the solution in the reaction device was stirred overnight at a low temperature (0° C.) to react. Deionized water (300 mL) and ethyl acetate (200 mL) were then added for extraction, the organic phase was separated, the aqueous phase was extracted three times with ethyl acetate (100 mL×3), and the organic phases were combined and washed twice with a saturated sodium chloride solution (200 mL×2), and then dried with anhydrous sodium sulfate powder. Suction filtering was then carried out and the obtained liquid was evaporated to dryness to obtain a product. The operations of dry sample loading, column chromatography, and elution with 3% methanol/dichloromethane were carried out. 1.22 g of the pure product was obtained with a yield of 82.4%.

31-86

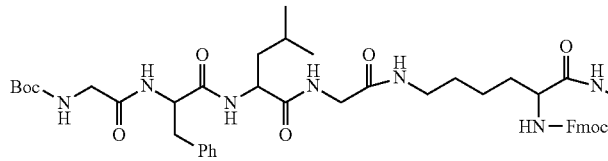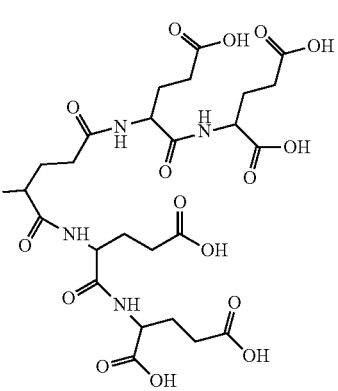

Raw material Compound 31-2 (0.33 g, 0.15 mmol) and 10% Pd/C catalyst (60 mg) were added into a hydrogenation reaction device and then dissolved with DMF (30 mL). The hydrogenation reaction device was then sealed and H$_2$ (18 psi) was introduced. The mixed solution was stirred overnight at room temperature. After the reaction was found to be completed from the monitoring of the TLC, the reaction solution was taken out and evenly dropwise added to a sand core funnel filled with compacted diatomaceous earth and suction filtering was carried out; the diatomaceous earth was then washed with DMF (90 mL) until there was no product in the diatomaceous earth. The reaction product solution was thus obtained.

31-87

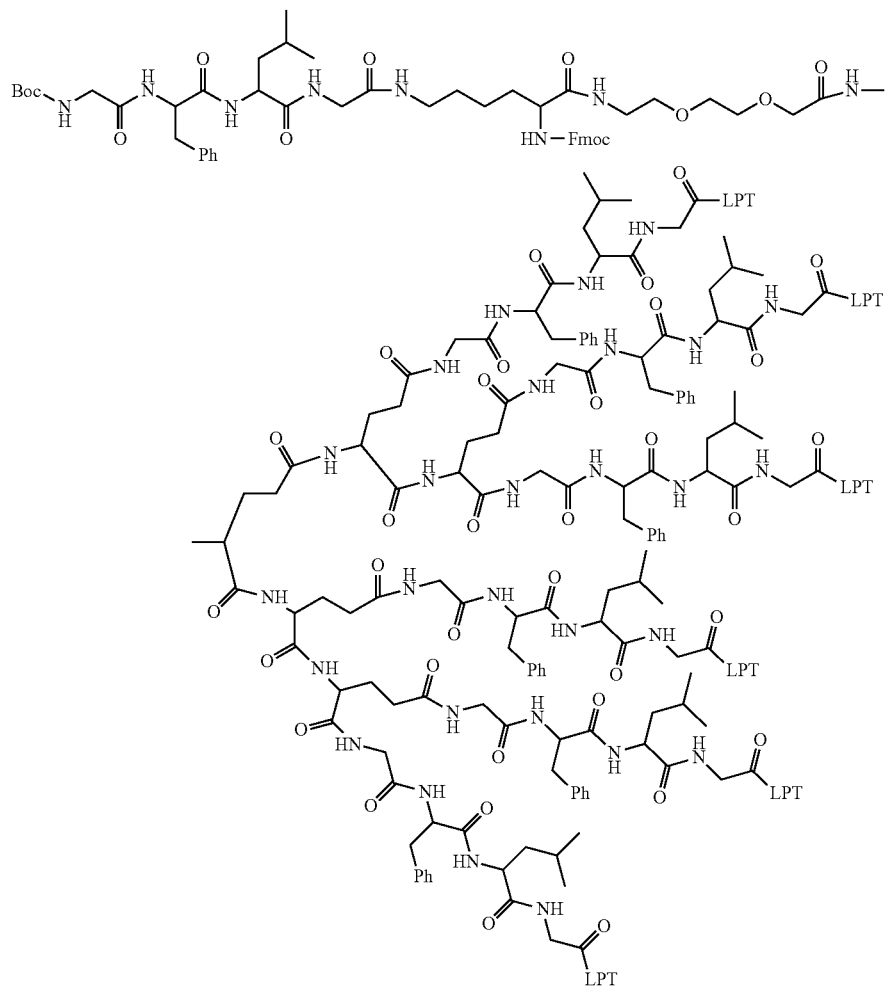

Compound 31-86 (0.24 g, 0.15 mmol), Compound 14-128 (synthesized according to the synthesis route of Compound 14-128) (1.03 g, 1.08 mmol), HOBT (0.18 g, 1.35 mmol) and HBTU (0.51 g, 1.35 mmol) were added in a 250 mL round-bottomed flask and then dissolved with DMF (80 mL), and the mixed solution was stirred at 0° C. for 30 min. Then DIEA (0.67 mL, 4.05 mmol) was slowly added dropwise and then the solution in the reaction device was stirred overnight at a low temperature (0° C.) to react. At the end of the reaction, n-hexane (200 mL) and methyl tert-butyl ether (800 mL) were added to the reaction solution to precipitate a solid, and then suction filtering was carried out to obtain a solid product. The operations of dry sample loading, column chromatography, and gradient elution with 5% methanol/dichloromethane-10% methanol/dichloromethane were carried out. The elution product was collected and concentrated. 0.96 g of the product was obtained with a yield of 88.1%.

MALDI-TOF MS: [M+H$^+$] 7177.76.

31-98

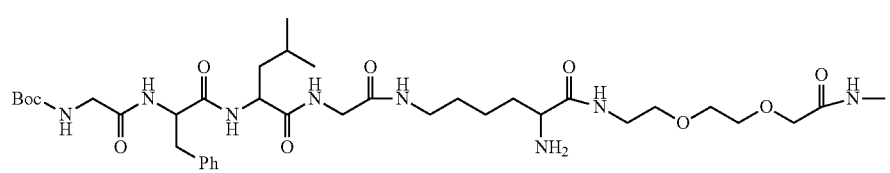

-continued

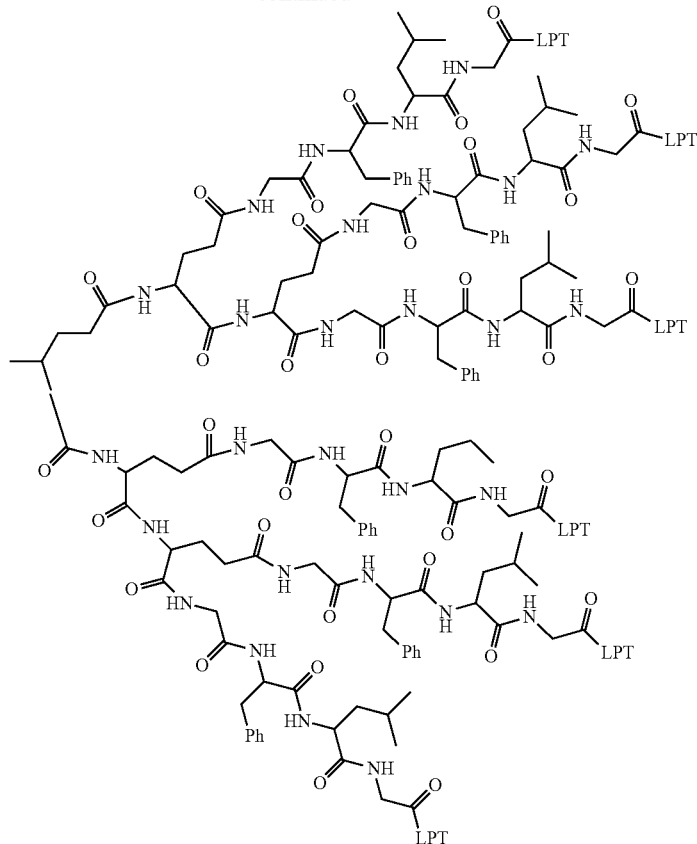

Compound 31-87 (0.96 g, 0.13 mmol) was added in a 250 mL round-bottomed flask and then dissolved with DMF (10 mL), and the mixed solution was stirred at room temperature. Morpholine (0.34 mL, 3.90 mmol) was then added dropwise, and the mixed solution reacted at room temperature for 2 h. At the end of the reaction, n-hexane (50 mL) and methyl tert-butyl ether (600 mL) were added to the reaction solution to precipitate a solid, and then suction filtering was carried out to obtain a solid product. The operations of dry sample loading, column chromatography, and gradient elution with 5% methanol/1% ammonia water/dichloromethane-12% methanol/1% ammonia water/dichloromethane were carried out. The elution product was collected and concentrated. 1.08 g of the product was obtained with a yield of 86.4%.

MALDI-TOF MS: [M+H$^+$] 6473.96.

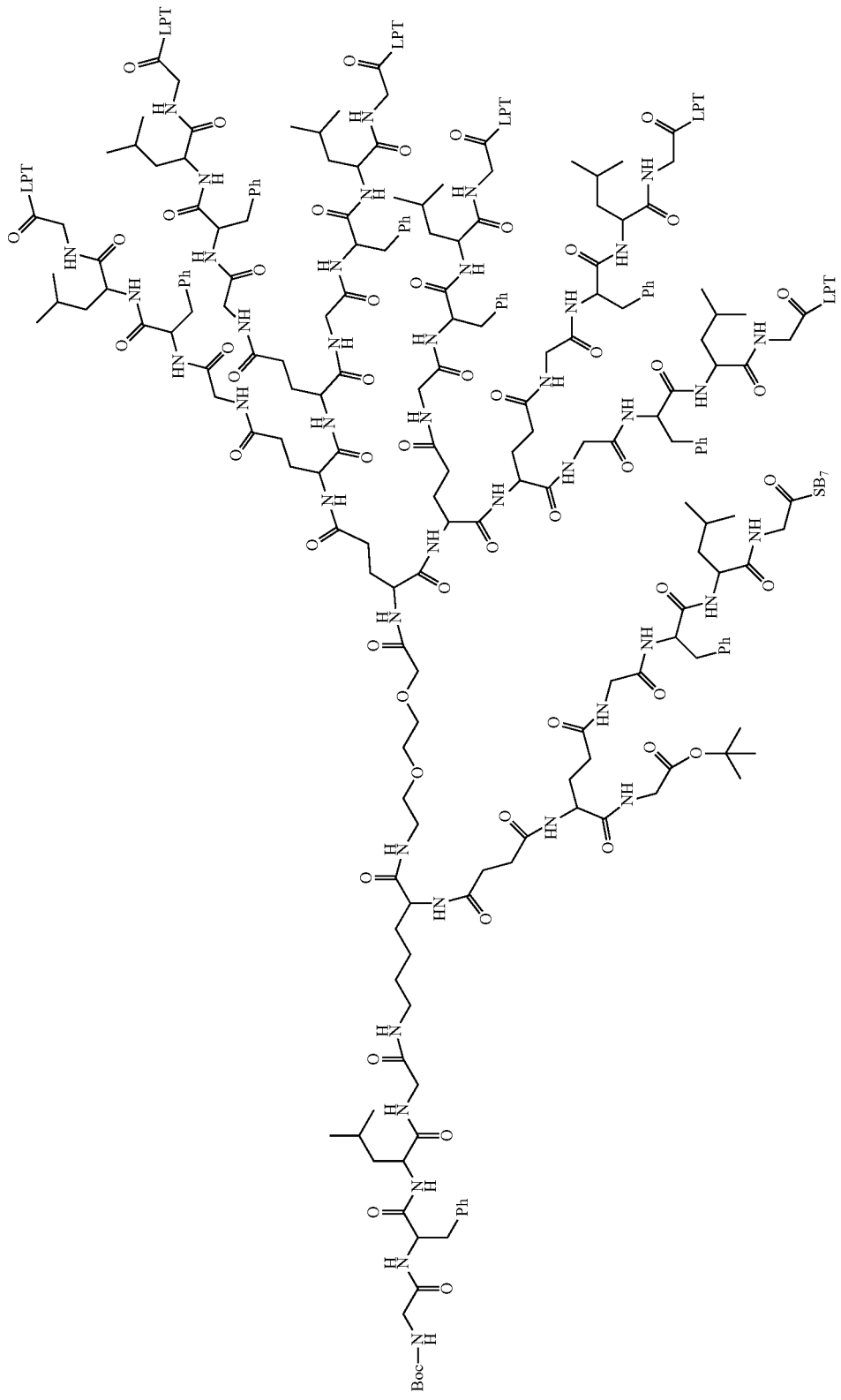

Compound 31-98 (1.08 g, 0.15 mmol), Compound 31-56 (0.22 g, 0.18 mmol), HOBT (0.03 g, 0.22 mmol) and HBTU (0.08 g, 0.22 mmol) were added in a 250 mL round-bottomed flask and then dissolved with DMF (30 mL), and the mixed solution was stirred at −5° C. for 30 min. Then DIEA (0.11 mL, 0.68 mmol) was slowly added dropwise and then the reaction device was placed at −5° C. and the reaction solution was stirred to react for 2 h; and then the reaction solution was further stirred overnight at room temperature to react. At the end of the reaction, the reaction solution was precipitated with n-hexane (50 mL) and methyl tert-butyl ether (300 mL) and then rested for about 30 min in a refrigerator with a temperature of 2° C. to precipitate a solid, and then suction filtering was carried out; the solid product was obtained. The operations of dry sample loading, column chromatography, and gradient elution with 5% methanol/dichloromethane-10% methanol/dichloromethane were carried out. The elution product was collected and concentrated. 0.92 g of the product was obtained with a yield of 74.2%.

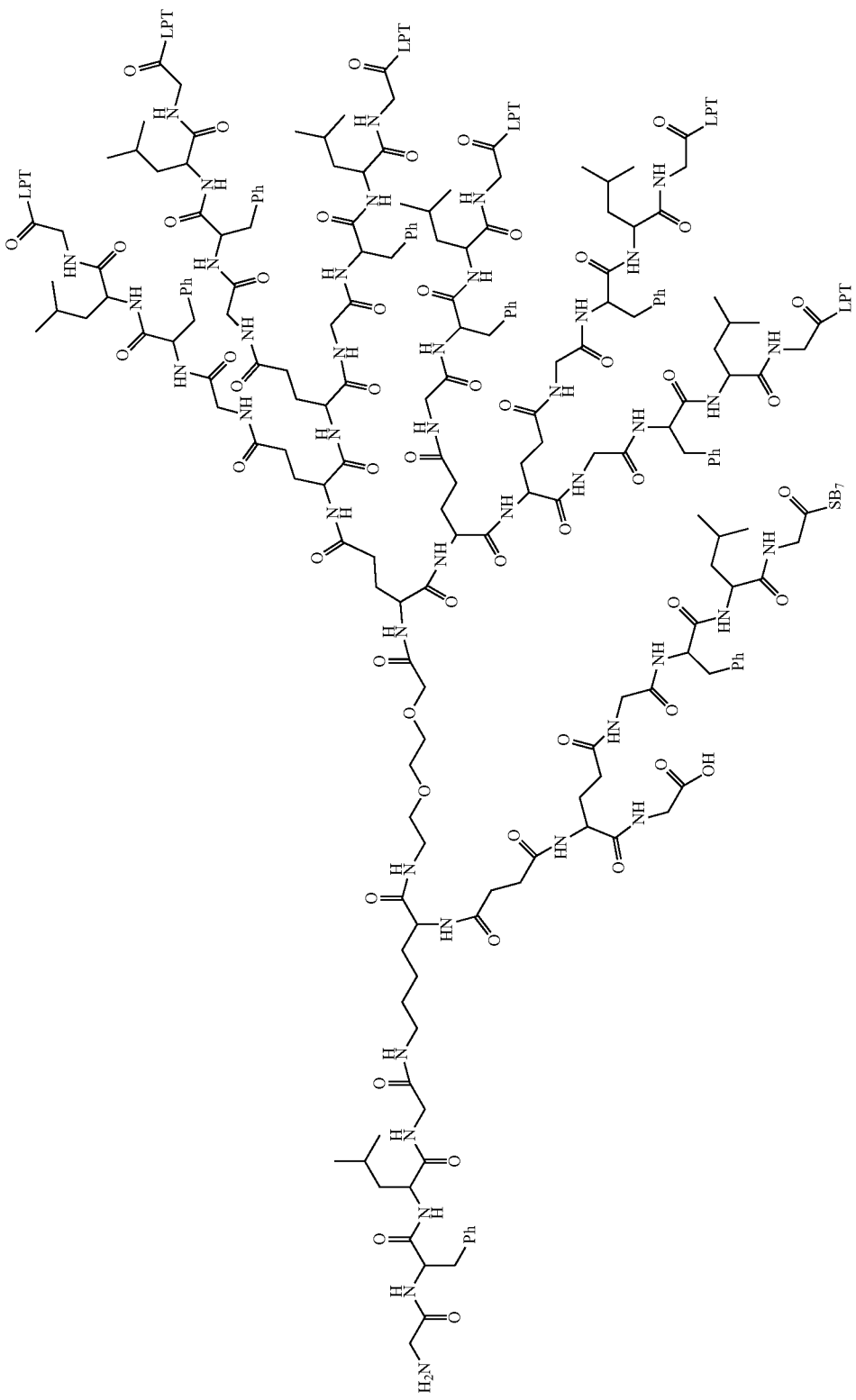

Compound 31-102 (0.92 g, 0.11 mmol) was added in a 250 mL round-bottomed flask and then dissolved with $CH_2Cl_2$ (10 mL), and the mixed solution was stirred at room temperature. TFA (3.00 mL, 40.39 mmol) was then added dropwise, and the mixed solution reacted at room temperature for 2 h. At the end of the reaction, the reaction solution was evaporated to dryness and then precipitated with methyl tert-butyl ether (50 mL) and the obtained solution was then rested for about 30 min in a refrigerator with a temperature of 2 to 8° C. to precipitate a solid, and then suction filtering was carried out; the solid product was obtained. The operations of dry sample loading, column chromatography, and gradient elution with 6% methanol/1% ammonia water/dichloromethane-10% methanol/1% ammonia water/dichloromethane were carried out. The elution product was collected and concentrated. 0.57 g of the product was obtained.

MALDI-TOF MS: $[M+H^+]$ 8087.56, $[M+Na^+]$ 8110.20, $[M+K^+]$ 8126.30.

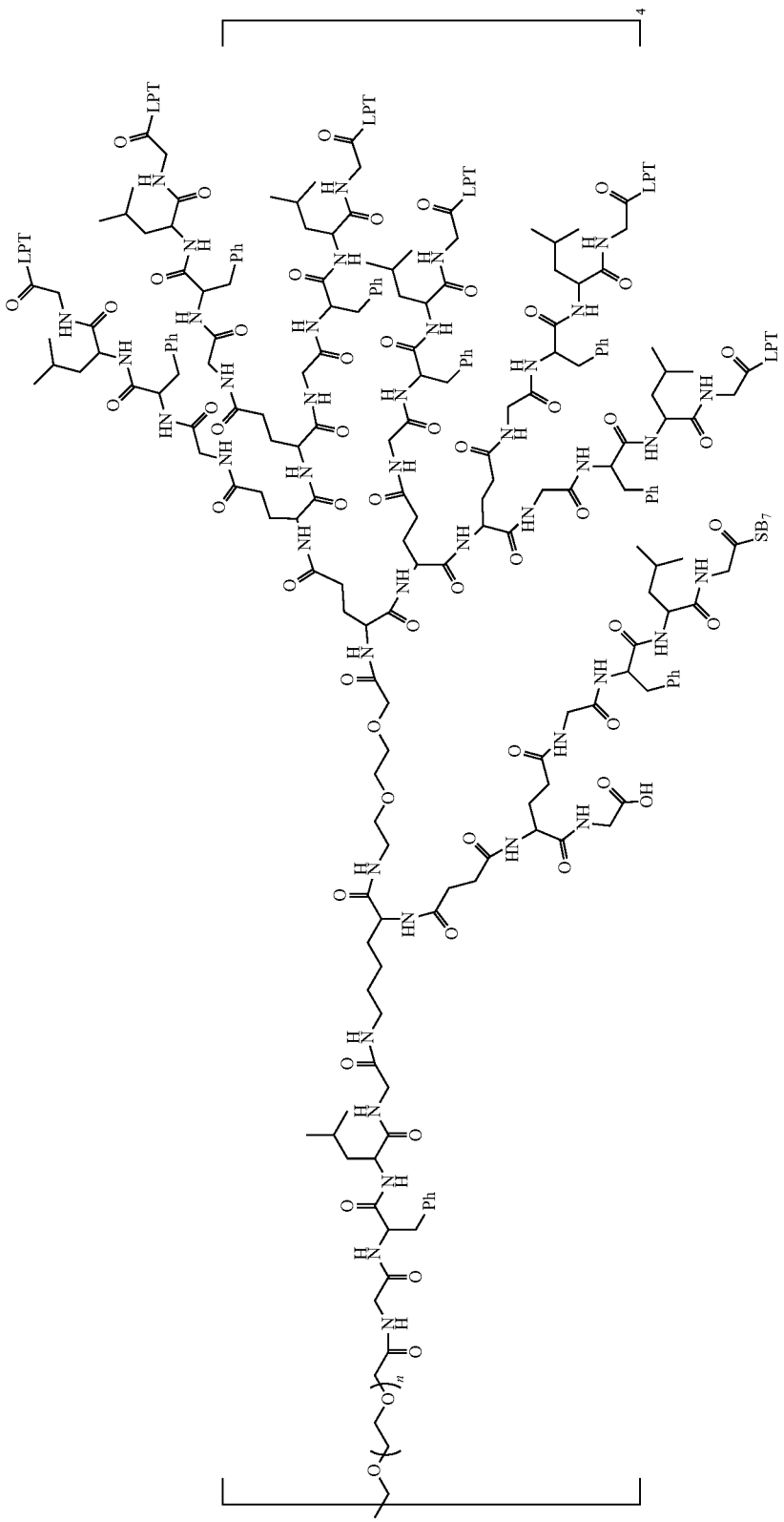

Compound 31-108 (0.57 g, 0.070 mmol) was added in a 250 mL round-bottomed flask and then dissolved with DMF (20 mL), and the solution was stirred at −5° C. for 30 min. Then, DIEA (0.20 mL, 1.21 mmol) was slowly added dropwise and the reaction continued for 30 min; then, the reaction solution was then taken out and stirred at room temperature to react; 4ARM-SCM-40K (0.67 g, 0.016 mmol) was then added to the reaction solution and dissolved by ultrasonic. The obtained solution was slowly stirred for one week to react. The reaction was monitored every day by TLC. At the end of the reaction, n-hexane (50 mL) and methyl tert-butyl ether (200 mL) were added to the reaction solution to precipitate a solid, and then suction is filtering was carried out to obtain a solid product. The operations of dry sample loading, column chromatography, and elution with 6% a ammonia water/dichloromethane were carried out. The elution product was then collected, concentrated, evaporated to dryness with a rotary evaporator, and dried in an oven. 0.47 g of the product was obtained.

$^1$H-NMR (400 MHz, DMSO-$d_6$) δ 9.83 (s, 20H), 8.73 (s, 26H), 8.54 (s, 26H), 8.21-8.11 (m, 139H), 7.79-7.70 (m, 72H), 7.49-7.43 (m, 37H), 7.33-7.26 (m, 131H), 7.19-7.03 (m, 269H), 6.60 (d, J=40 Hz, 31H), 5.32-52-0.25 (m, 78H), 4.74-4.59 (m, 136H), 4.36-4.08 (m, 214H), 3.81-3.01 (m, 3768H), 2.89 (s, 14H), 2.75-2.52 (m, 157H), 2.37-2.33 (m, 20H), 2.12-2.11 (m, 58H), 1.82-1.74 (m, 32H), 1.59-1.47 (m, 92H), 1.40-1.34 (m, 56H), 0.85-0.79 (m, 216H).

MALDI-TOF MS: from 73650.24 to 74008.79.

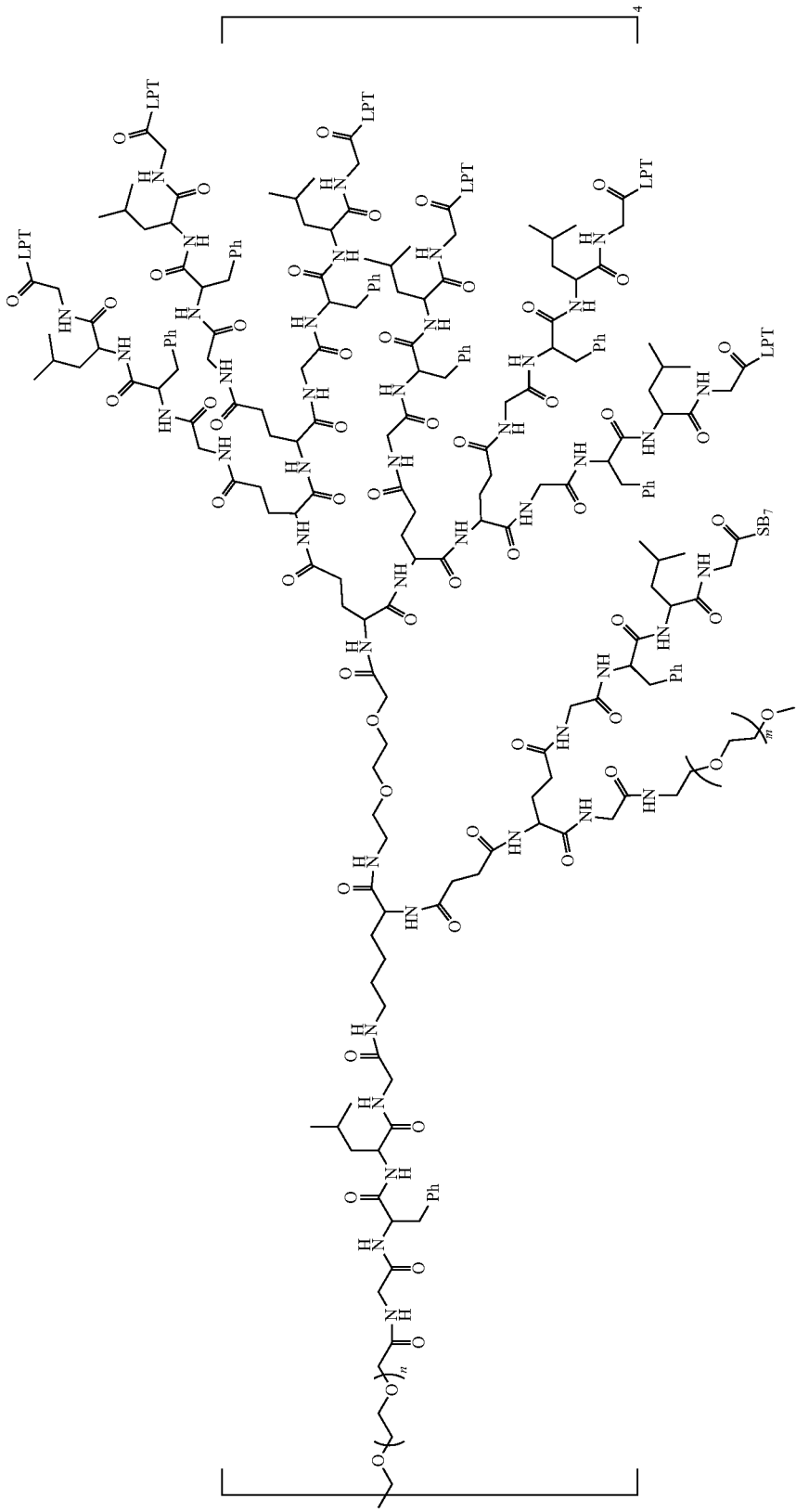

The Compound 31-113 (0.47 g, 0.006 mmol), M-NH₂HCl-10K (0.40 g, 0.038 mmol), HOBT (0.10 g, 0.74 mmol) and HBTU (0.28 g, 0.74 mmol) were added in a 250 mL round-bottomed flask and then dissolved with DMF (20 mL), and the solution was stirred at 0° C. for 30 min. Then DIEA (0.20 mL, 1.21 mmol) was slowly added dropwise, and the solution further reacted for 30 min; then, the reaction solution was slowly stirred at room temperature for one week to react. The reaction was monitored every day by TLC. At the end of the reaction, n-hexane (50 mL) and methyl tert-butyl ether (150 mL) were added to the reaction solution to precipitate a solid; suction filtering was then carried out to obtain a solid product; the operations of dry sample loading, column chromatography, and elution with 5% methanol/1% ammonia/dichloromethane were carried out; the elution product was then collected and concentrated. 0.65 g of the product 31-136 was obtained.

¹H-NMR (400 MHz, DMSO-d₆) δ 8.85-8.45 (d, 40H), 8.35-7.62 (m, 264H), 7.56-6.93 (m, 368H), 6.78-6.47 (m, 52H), 4.79-4.48 (m, 94H), 4.38-4.09 (m, 130H), 3.81-3.12 (m, 4728H), 3.07-2.97 (m, 131H), 2.95-2.83 (m, 137H), 2.75-2.64 (m, 140H), 2.17-2.05 (s, 56H), 1.60-1.43 (m, 113H), 1.38-1.34 (m, 17H), 1.24-1.15 (m, 43H), 1.11-1.09 (s, 7H), 0.96-0.69 (m, 216H).

Example 4: Synthesis of Compound 31-167 mL), and the mixed solution was stirred at −5° C. for 30 min. Then DIEA (5.85 mL, 35.37 mmol) was slowly added dropwise, and then the mixed solution reacted at a low temperature (−5° C.) for 2 h; then, the reaction solution in the reaction device was stirred overnight at room temperature to react. At the end of the reaction, deionized water (1000 mL) was added to precipitate a pale yellow solid, suction filtering was then carried out, and the filter cake was then washed with n-hexane (100 mL) and dried in vacuum. 7.29 g of the solid product was obtained.

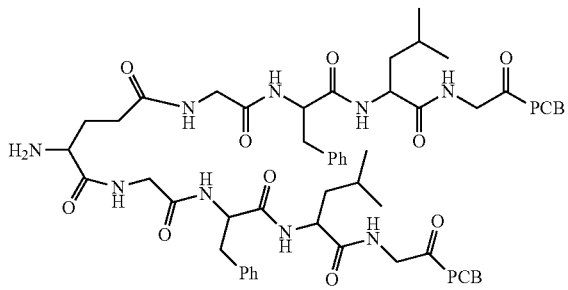

31-82

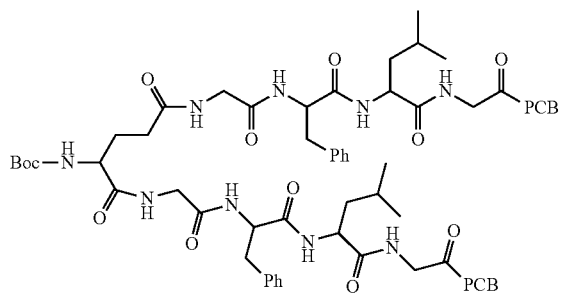

31-81

Compound 31-81 (7.29 g, 3.93 mmol) was added in a 500 mL round-bottomed flask and then dissolved with dichloromethane (20 mL), TFA (5.48 mL, 73.78 mmol) was then added and the obtained solution was stirred overnight at room temperature to react; at the end of the reaction, the reaction solution was concentrated and then precipitated with methyl tert-butyl ether (200 mL); the solid product was then filtered out and dried in vacuum. 6.90 g of the product was obtained.

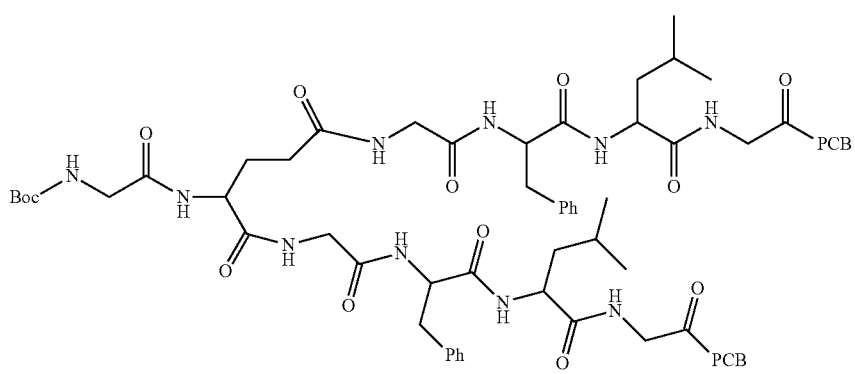

30-105

Boc-Glu-OH (0.97 g, 3.93 mmol), GFLG-PCB (synthesized according to the synthesis method of Compound 30-33, 7.0 g, 8.52 mmol), HBTU (4.47 g, 11.79 mmol) and HOBT (1.59 g, 11.79 mmol) were added in a 500 mL round-bottomed flask and then dissolved with DMF (100

Compound 31-82 (6.90 g, 3.93 mmol), Boc-Gly-OH (2.07 g, 11.82 mmol), HBTU (2.24 g, 5.90 mmol), and HOBT (0.80 g, 5.90 mmol) were added in a 500 mL round-bottomed flask and then dissolved with DMF (100 mL), and the mixed solution was stirred at −5° C. for 30 min. Then DIEA (3.89 mL, 23.54 mmol) was slowly added dropwise, and then the mixed solution reacted at a low temperature (−5° C.) for 2 h; then, the reaction solution in the reaction device was stirred overnight at room temperature. At the end of the reaction, the reaction solution was precipitated with n-hexane (100 mL) and methyl tert-butyl ether (600 mL); the solid product was then filtered out by suction and dried in vacuum. 7.52 g of the product was obtained.

31-84

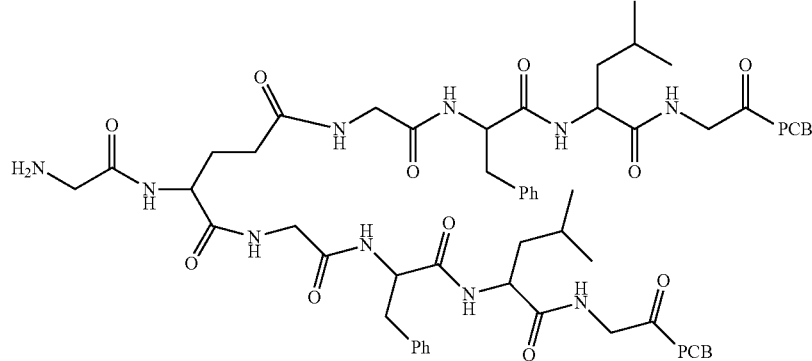

Compound 30-105 (7.52 g, 3.93 mmol) was added in a 500 mL round-bottomed flask and then dissolved with dichloromethane (20 mL), and then TFA (4.38 mL, 58.95 mmol) was added and the obtained solution was stirred at room temperature. 2 h later, the reaction was completed, the reaction solution was concentrated and then precipitated with methyl tert-butyl ether (100 mL); the solid product was then filtered out by suction and dissolved with dichloromethane (80 mL) and methanol (20 mL); silica gel powder was then added and the obtained solution was then evaporated to dryness. The operations of dry sample loading, column chromatography, and gradient elution with 4% methanol/1% ammonia water/dichloromethane-8% methanol/1% ammonia water/dichloromethane were carried out. The elution product was collected, concentrated and dried. 6.51 g of the product was obtained with a yield of 91.4%.

31-95

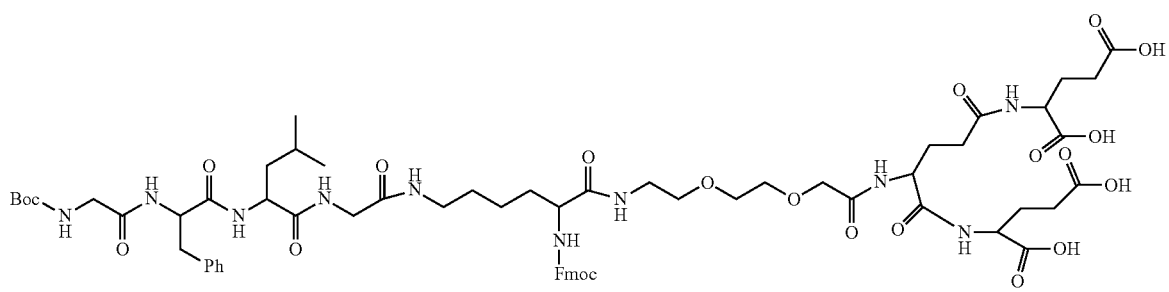

Raw material Compound 30-55 (0.95 g, 0.55 mmol) (synthesized according to the synthesis method of Compound 30-84) and 10% Pd/C catalyst (100 mg) were added into a hydrogenation reaction device and then dissolved with DMF (40 mL). $H_2$ (18 psi) was then introduced in the device. The mixed solution was stirred overnight at room temperature. After the reaction was found to be completed from the monitoring of the TLC, the reaction solution was taken out and evenly dropwise added to a sand core funnel filled with compacted diatomaceous earth and suction filtering was carried out; the diatomaceous earth was then washed with DMF (90 mL) until there was no product in the diatomaceous earth. The reaction product solution was thus obtained.

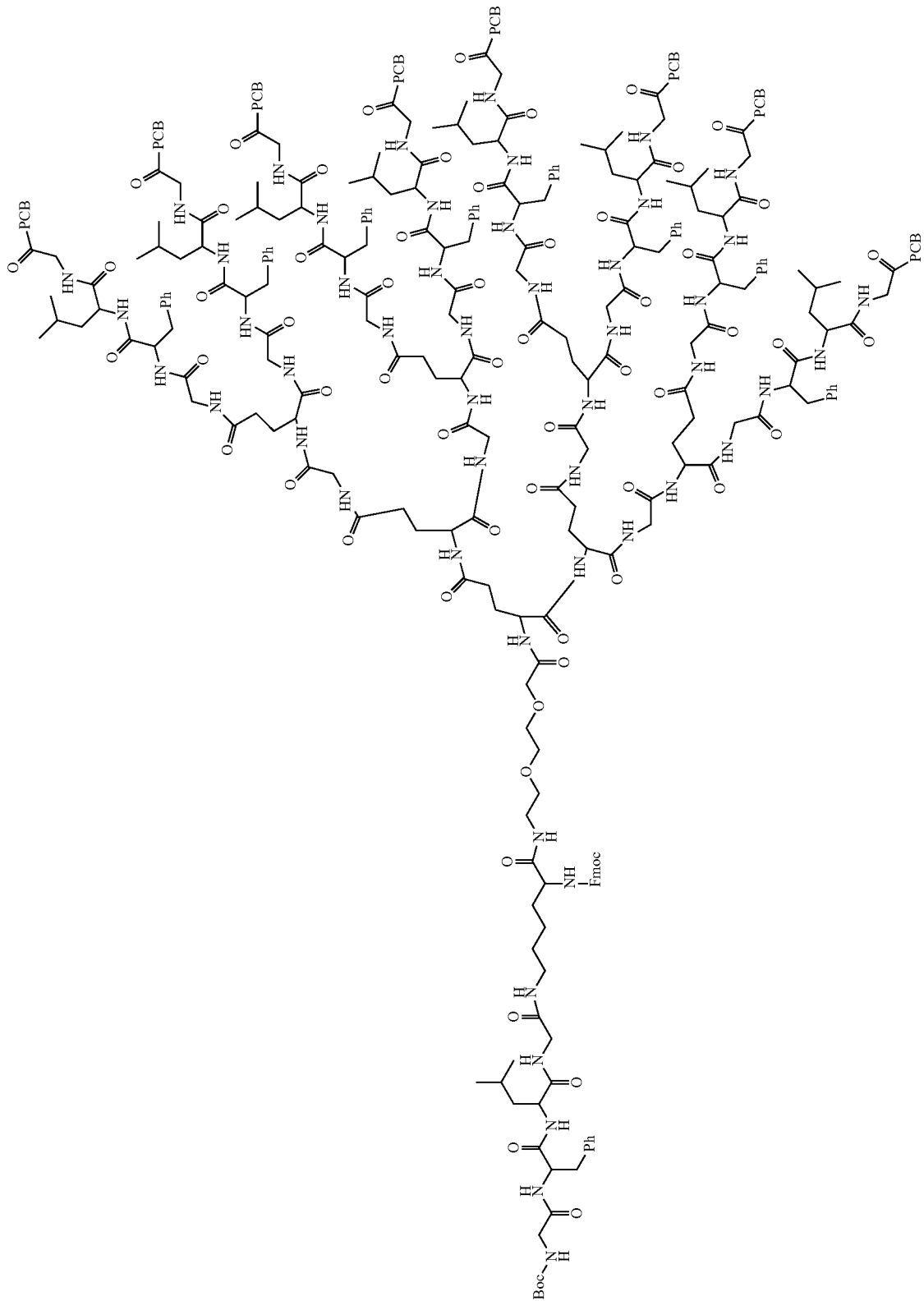

Compound 31-95 (0.76 g, 0.55 mmol), Compound 31-84 (5.2 g, 2.87 mmol), HBTU (1.25 g, 3.30 mmol) and HOBT (0.44 g, 3.30 mmol) were added in a 500 mL round-bottomed flask and then dissolved with DMF (140 mL), and the mixed solution was stirred at −5° C. for 30 min. Then DIEA (1.63 mL, 9.90 mmol) was slowly added dropwise, and then the mixed solution reacted at a low temperature (−5° C.) for 2 h; then, the reaction solution in the reaction device was stirred overnight at room temperature to react. At the end of the reaction, n-hexane (100 mL) and methyl tert-butyl ether (1000 mL) were added for precipitation; the solid product was then filtered out by suction and dissolved with dichloromethane (100 mL) and methanol is (10 mL); the operations of dry sample loading, column chromatography, and elution with 500 methanol/dichloromethane-1200 methanol/dichloromethane were carried out; the elution product was collected, concentrated, evaporated to dryness, and dried in a vacuum oven. 2.1 g of the product was obtained with a yield of 45%.

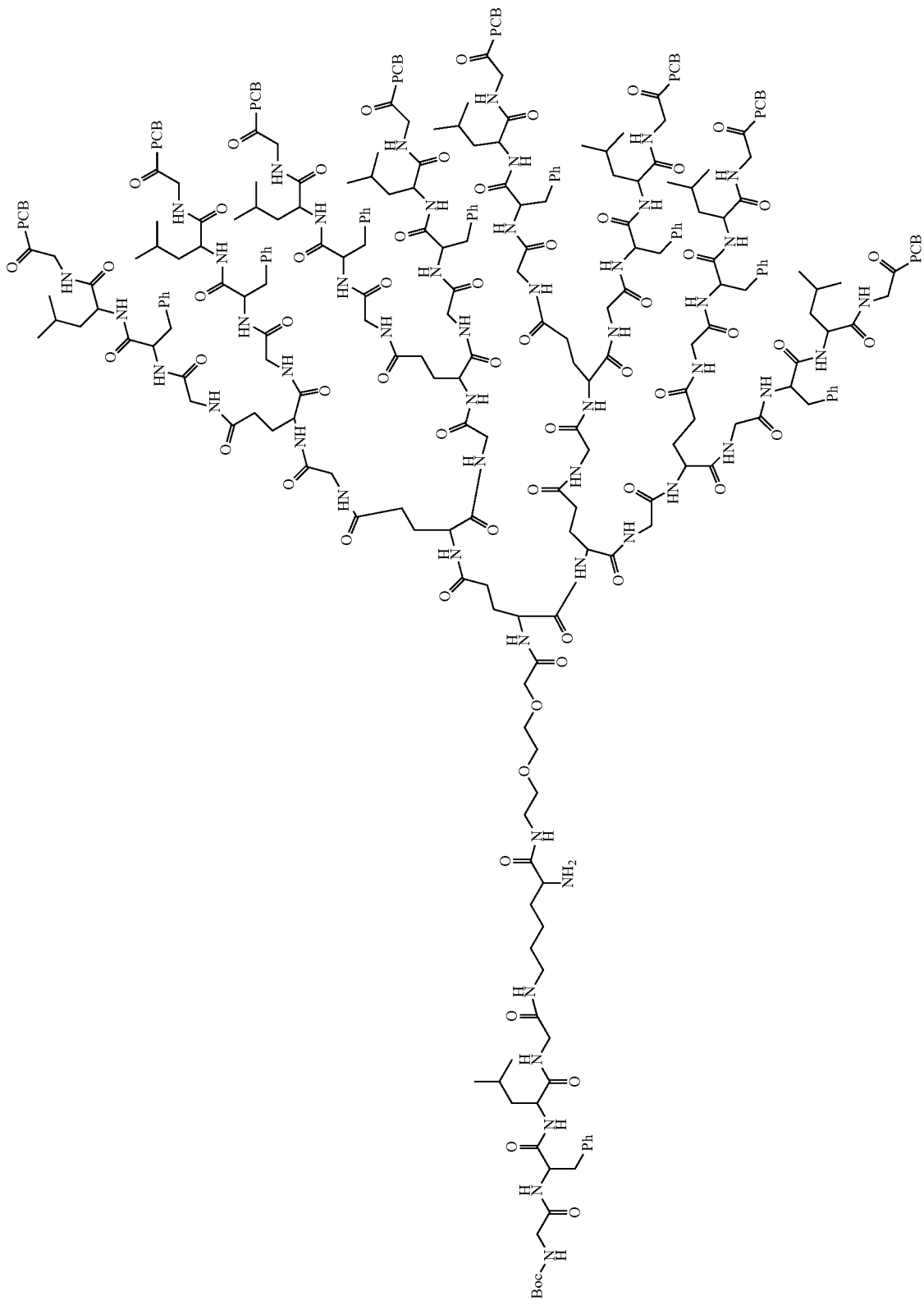

Compound 31-96 (2.1 g, 0.24 mmol) was added in a 500 mL round-bottomed flask and dissolved with DMF (60 mL), morpholine (0.63 mL, 7.2 mmol) was then added and the obtained solution was stirred for 2 h at room temperature to react; at the end of the reaction, n-hexane (100 mL) and methyl tert-butyl ether (400 mL) were added for precipitation; the solid product was then filtered out by suction and dissolved with dichloromethane (100 mL) and methanol (10 mL); and silica gel powder was then added and the obtained solution was then evaporated to dryness. The operations of dry sample loading, column chromatography, and gradient elution with 8% methanol/dichloromethane-12% methanol/1% ammonia water/dichloromethane were carried out and the elution product was then collected, concentrated, evaporated to dryness and dried in a vacuum oven. 0.93 g of the product was obtained with a yield of 46.5%.

MALDI-TOF MS: [M+K$^+$] 8363.53

31-119

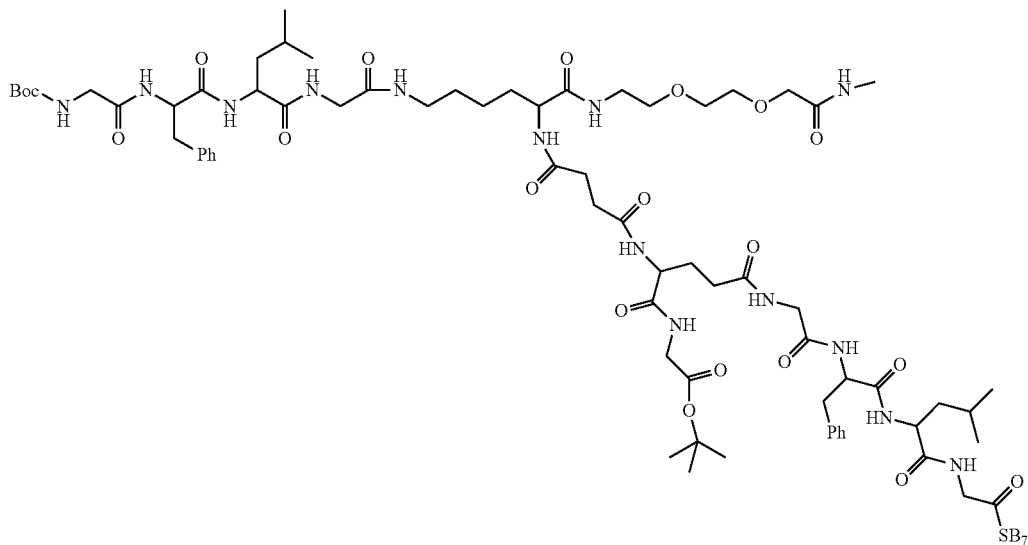

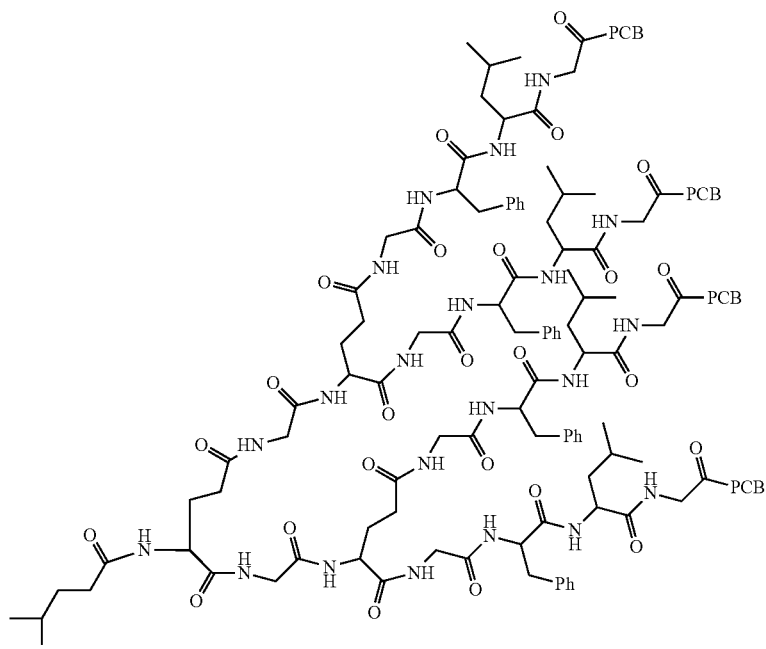

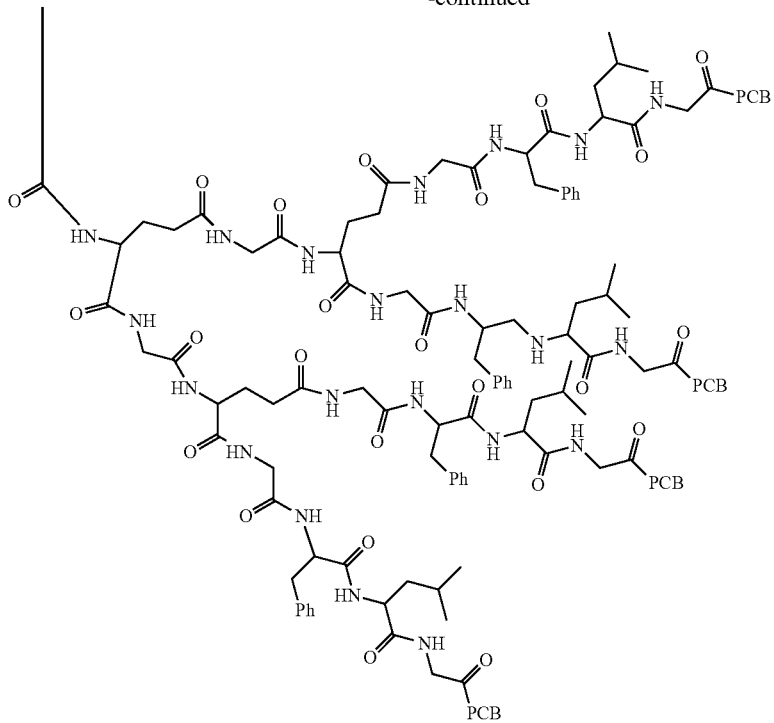

30

Compound 31-100 (0.93 g, 0.11 mmol), Compound 31-56 (0.26 g, 0.21 mmol), HOBT (0.10 g, 0.74 mmol) and HBTU (0.21 g, 0.55 mmol) were added in a 250 mL round-bottomed flask and then dissolved with DMF (30 mL), and the mixed solution was stirred at −5° C. for 30 min. Then DIEA (0.20 mL, 1.21 mmol) was slowly added dropwise, and then the mixed solution reacted at a low temperature (−5° C.) for 2 h; then, the reaction solution in the reaction flask was stirred overnight at room temperature to react. At the end of the reaction, n-hexane (50 mL) and methyl tert-butyl ether (200 mL) were added for precipitation; the solid product was then filtered out by suction and dissolved with dichloromethane (100 mL) and methanol (10 mE); silica gel powder was then added and the obtained solution was evaporated to dryness. The operations of dry sample loading, column chromatography, and gradient elution with 5% methanol/0.5% ammonia water/dichloromethane-8% methanol/0.5% ammonia water/dichloromethane were carried out and the elution product was then collected, concentrated, evaporated to dryness and dried in a vacuum oven. 0.85 g of the product was is obtained with a yield of 80.2%.

MALDI-TOF MS: [M+H⁺] 9539.80, [M+Na⁺] 9561.82

31-123

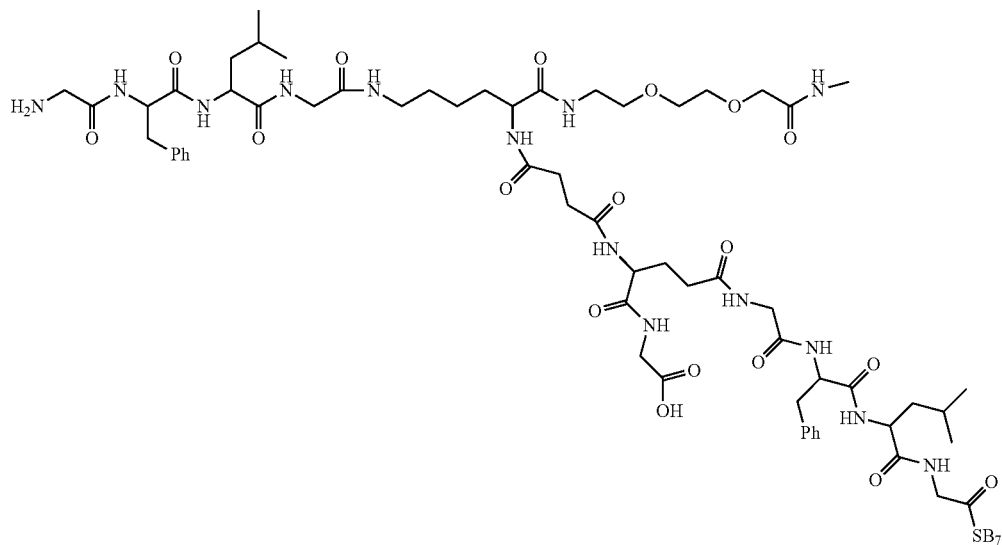

-continued

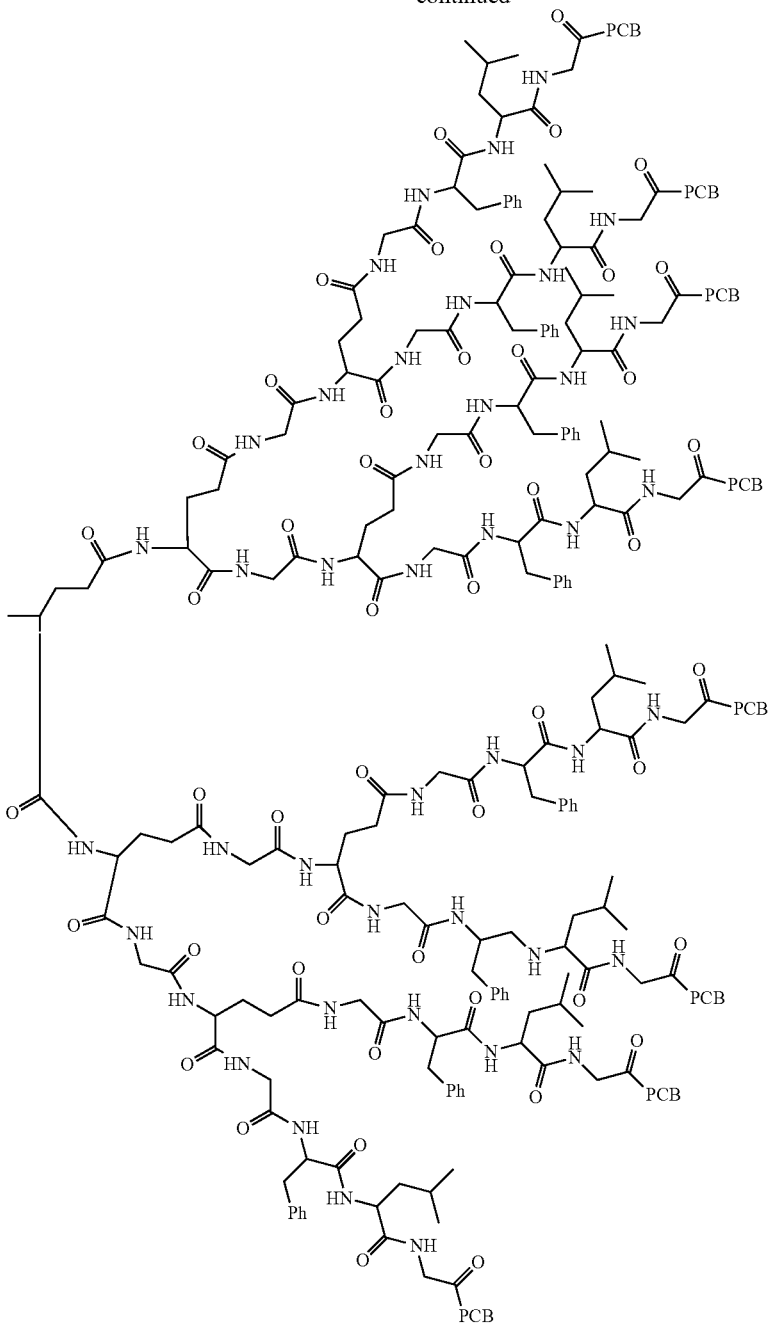

Compound 31-119 (0.87 g, 0.089 mmol) was added in a 250 mL round-bottomed flask and then dissolved with dichloromethane (20 mL), TFA (2.0 mL, 26.93 mmol) was then added and the obtained solution was stirred for 2 h at room temperature to react; at the end of the reaction, the reaction solution was evaporated to dryness with a rotary evaporator and then precipitated with methyl tert-butyl ether (50 mL); the solid product was then filtered out by suction and dissolved with dichloromethane (100 mL) and methanol (10 mL); silica gel powder was then added and the obtained solution was then evaporated to dryness. The operations of dry sample loading, column chromatography, and gradient elution with 5% methanol/1% ammonia water/dichloromethane-7% methanol ammonia water/dichloromethane were carried out and the elution product was then collected, concentrated, evaporated to dryness and dried in a vacuum oven. 0.38 g of the product was obtained with a yield of 45.2%.

MALDI-TOF MS: [M+H$^+$] 9378.50

255
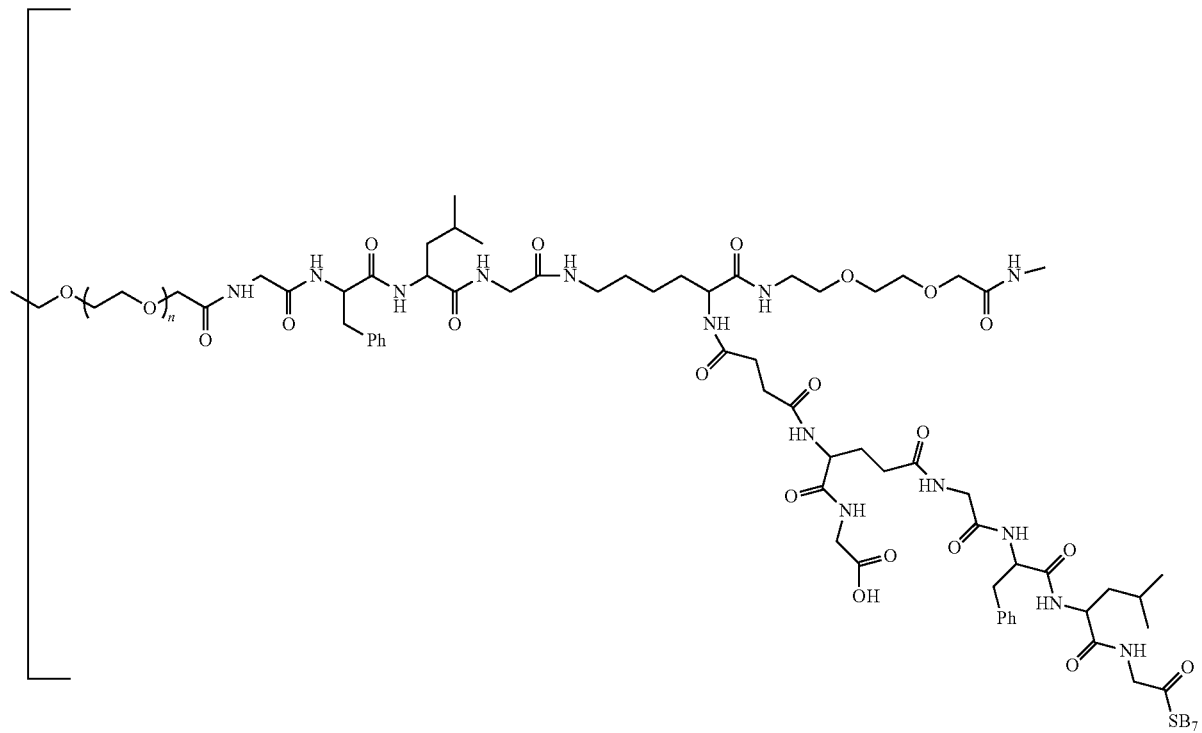
256
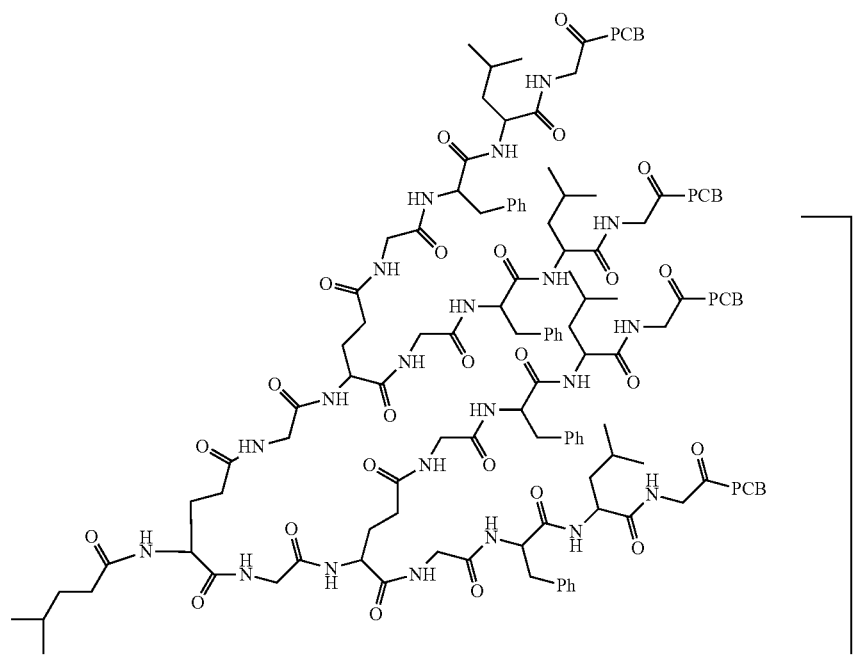

-continued

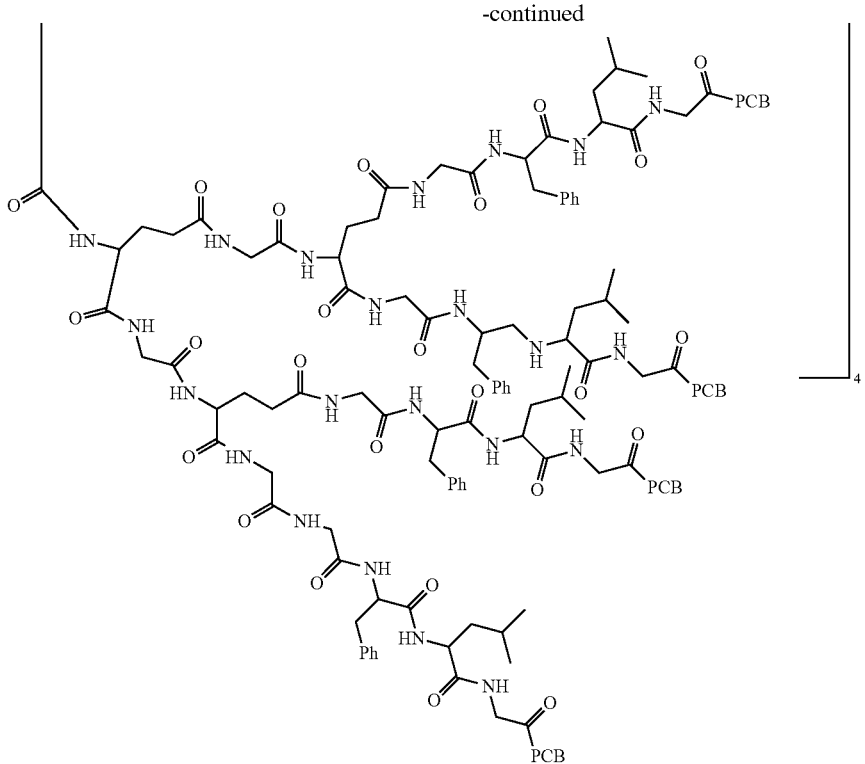

Compound 31-123 (0.38 g, 0.04 mmol) was added in a 250 mL round-bottomed flask and then dissolved with DMF (20 mL), and the solution was stirred at −5° C. for 20 min. Then, DIEA (0.20 mL, 1.21 mmol) was slowly added dropwise and the reaction continued for 10 min; then, the reaction solution was then taken out and stirred at room temperature to react; 4RM-SCM-40K (0.38 g, 0.009 mmol) was then added to the reaction solution and dissolved by ultrasonic. The obtained solution was slowly stirred for one week to react. The reaction was monitored every day by TLC. At the end of the reaction, n-hexane (100 mL) and methyl tert-butyl ether (200 mL) were added to the reaction solution to precipitate a solid, and then suction filtering was carried out to obtain a solid product. The operations of dry sample loading, column chromatography, and elution with 7% methanol/1% ammonia water/dichloromethane were carried out. The elution product was then collected, concentrated, evaporated to dryness with a rotary evaporator, and dried in an oven. 0.57 g of the product was obtained.

31-167
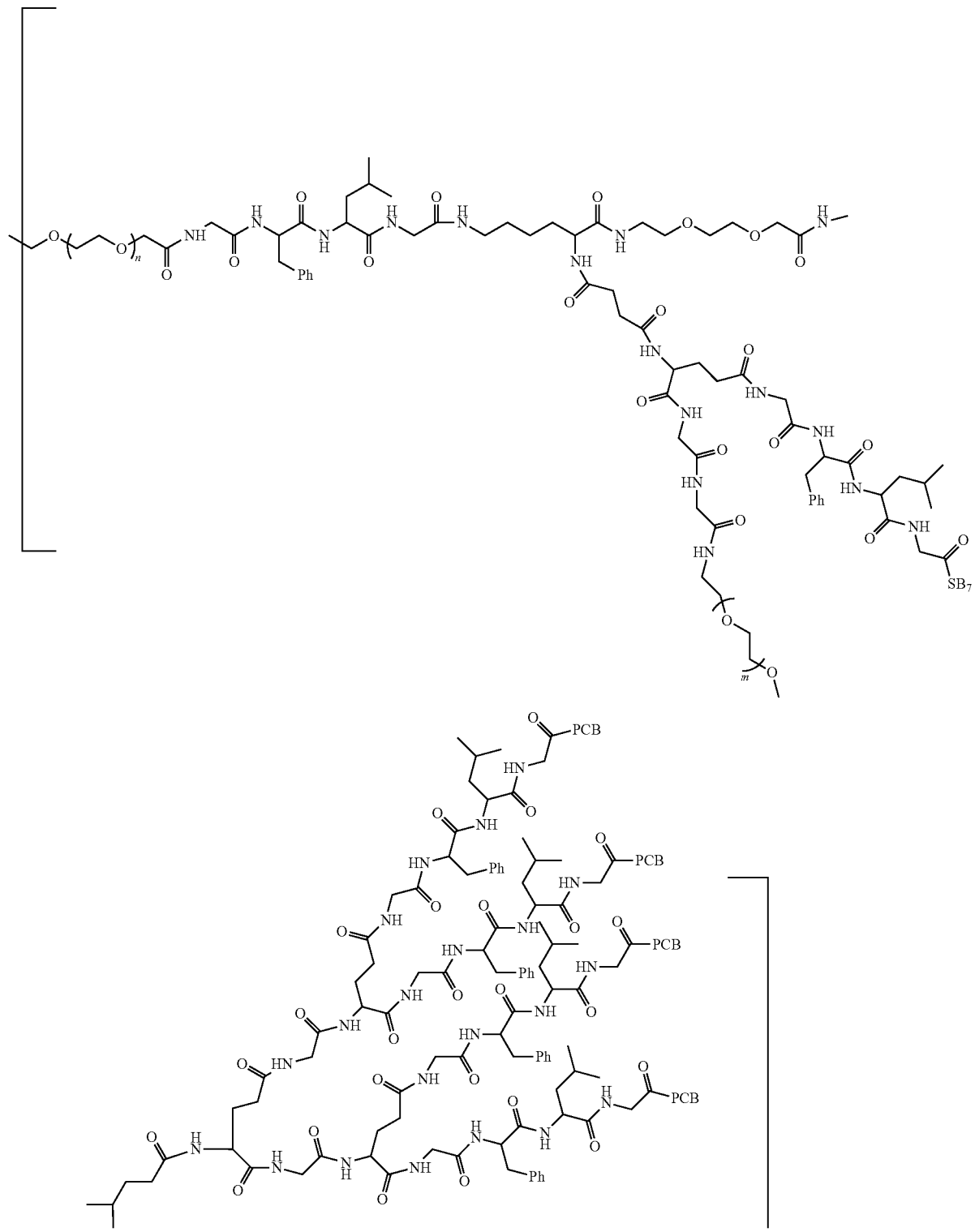

-continued

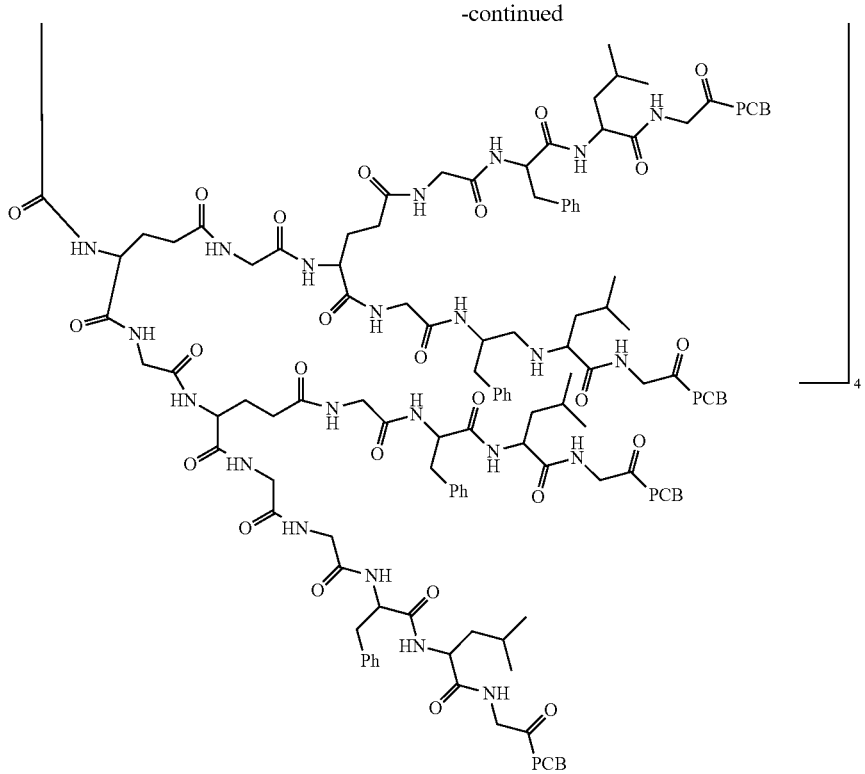

The Compound 31-147 (0.57 g, 0.007 mmol), M-NH$_2$·HCl-10K (0.56 g, 0.043 mmol), HOBT (0.05 g, 0.37 mmol), and HBTU (0.15 g, 0.40 mmol) were added in a 250 mL round-bottomed flask and then dissolved with DMF (40 mL), and the solution was stirred at 0° C. for 30 min. Then DIEA (0.20 mL, 1.21 mmol) was slowly added dropwise, and the solution further reacted for 30 min; then, the reaction solution was slowly stirred at room temperature for one week to react. The reaction was monitored every day by TLC. At the end of the reaction, n-hexane (100 mL) and methyl tert-butyl ether (100 mL) were added to the reaction solution to precipitate a solid; suction filtering was then carried out to obtain a solid product; the operations of dry sample loading, column chromatography, and gradient elution with 5% methanol/1% ammonia water/dichloromethane-10% methanol/1% ammonia water/dichloromethane were carried out; the elution product was then collected and concentrated. 76 mg of the product 31-167 was obtained.

$^1$H-NMR (400 MHz, DMSO-d$_6$) δ 10.26 (s, 45H), 8.94 (s, 42H), 8.23-7.84 (m, 296H), 7.25-7.07 (m, 228H), 6.96 (s, 23H), 4.46-4.29 (m, 210H), 3.63-3.50 (s, 4728H), 2.97-2.69 (m, 336H), 2.34-2.16 (m, 250H), 1.95-1.09 (m, 764H), 0.92-0.72 (m, 240H).

Example 5: Synthesis of Compound 33-8

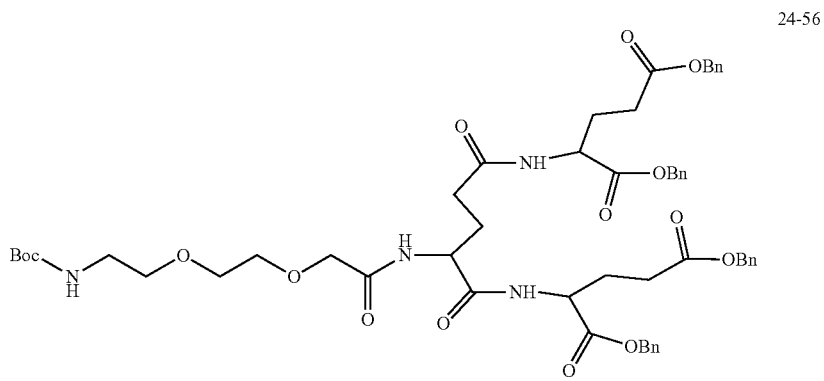 [SMILES: CC(C)(C)OC(=O)NCCOCCOCC(=O)NC(CCC(=O)NC(CCC(=O)OCc1ccccc1)C(=O)OCc1ccccc1)C(=O)NC(CCC(=O)OCc1ccccc1)C(=O)OCc1ccccc1]

24-56

Boc-LC-OH (synthesized according to the synthesis method of Compound 24-36) (15 g, 57.67 mmol), E[E(OBn)$_2$]$_2$ (synthesized according to the synthesis method of Compound 14-155) (53 g, 69.204 mmol), HBUT (30.6190 g, 80.738 mmol), and HOBT (10.9093 g, 80.738 mmol) were weighed and added in a 500 mL reaction flask and dissolved with DMF (200 mL); the obtained solution was stirred for 30 min at −5° C., DIEA (42 mL, 259.515 mmol) was added dropwise, and the mixed solution was first stirred at a low temperature (−5° C.) for 2 h and then reacted at room temperature. At the end of the reaction, the reaction solution was transferred in a 2 L separatory funnel, a saturated sodium bicarbonate solution (400 mL) and ethyl acetate (300 mL) were then added, the organic phase was then separated, the aqueous phase was extracted twice with ethyl acetate (150 mL×2), the obtained organic phases were combined, and washing with a saturated sodium chloride solution was carried out twice (200 mL×2); the obtained solution was then concentrated and evaporated to dryness, and the operations of dry sample loading and column chromatography were carried out. Elution with 50% ethyl acetate/petroleum ether was carried out and the elution product was then evaporated to dryness and dried in vacuum. 22 g of the product was obtained.

dissolved; the mixed solution was stirred at room temperature to react. At the end of the reaction, the reaction solution was evaporated to dryness, the dichloromethane was removed, and then the obtained solid was dissolved with ethyl acetate (100 mL), and a saturated sodium bicarbonate solution was added until the aqueous phase became alkaline; then, the organic phase was separated, and the aqueous phase was extracted with ethyl acetate three times (50 mL×3) until there was no product in the aqueous phase; the organic phases were combined, and washing with a saturated sodium chloride solution (50 mL) was carried out once; the obtained solution was concentrated and evaporated to dryness. 3.2 g of the product was obtained with a yield of 100%.

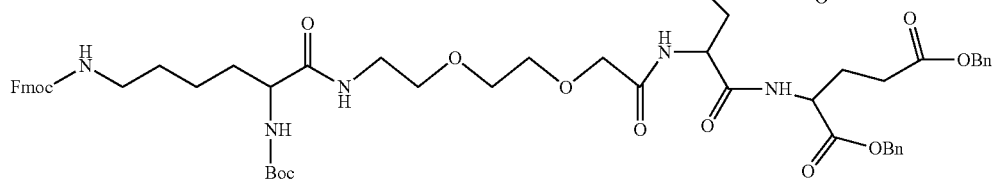

24-91

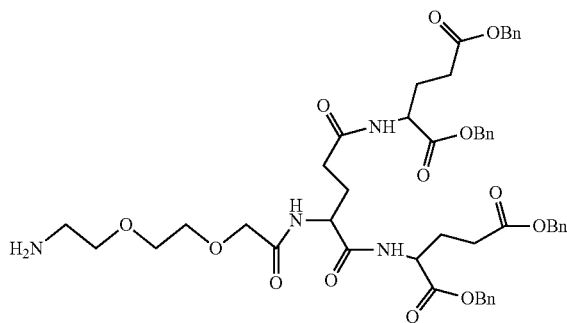

24-90

Compound 24-56 (2 g, 1.9782 mmol) was weighed, dichloromethane (10 mL) and TFA (4.4 mL, 59.346 mmol) were then added sequentially, and the obtained solution was treated by ultrasonic until Compound 24-56 was completely The reactants Boc-L-Lys-(Fmoc)-OH (0.9258 g, 1.9759 mmol), Compound 24-90 (1.8 g, 1.9759 mmol), HBUT (1.1240 g, 2.9639 mmol), and HOBT (0.4005 g, 2.9639 mmol) were added in a 100 mL reaction flask and then dissolved with a small amount of DMF and the resulting solution was stirred at −5° C. for 0.5 h; DIEA (1.4752 mL, 8.8911 mmol) was slowly added dropwise to the mixed solution; 2 h later, the reaction solution further reacted at room temperature. At the end of the reaction, deionized water (100 mL) and ethyl acetate (100 mL) were added for extraction, the organic phase was separated, the aqueous phase was extracted three times with ethyl acetate (500 mL×3), and the organic phases were combined and washed twice with a saturated sodium chloride solution (50 mL×2), and then dried with anhydrous sodium sulfate. Suction filtration was then carried out, the liquid was concentrated to 10 mL, petroleum ether (70 mL) was added, the resulting solution was treated by ultrasonic for 10 min and then rested for 30 min, and the solid was precipitated. The filter cake was washed three times with petroleum ether (50 mL×3) and then dried in vacuum. 3.7 g of the product was obtained with a yield of 100%.

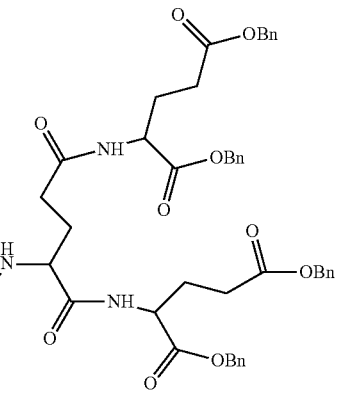

24-93

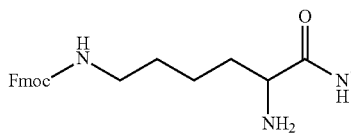

Compound 24-91 (2.69 g, 1.9757 mmol) was weighed, dichloromethane (15 mL) and TFA (4.4023 mL, 59.271 mmol) were then added sequentially, and the obtained solution was treated by ultrasonic until Compound 24-91 was completely dissolved; the mixed solution was stirred at room temperature to react. At the end of the reaction, the reaction solution was evaporated to dryness and petroleum ether (70 mL) was then added, the resulting solution was treated by ultrasonic for 10 min and then rested for 30 min, and the solid was precipitated. The filter cake was washed three times with petroleum ether (50 mL×3) and then dried in vacuum. 4 g of the product was obtained with a yield of 100%.

Boc-GFLG-OBn (home-made, 1.2664 g, 2.1733 mmol) and 10% Pd/C catalyst (20 mg) were added into a microreactor, DMF (25 mL) was then added, the device was then set up and $H_2$ (18 psi) was introduced in the device. The mixed solution was then stirred overnight at room temperature. After the reaction was found to be completed from the monitoring of the TLC, the reaction solution was taken out and evenly dropwise added to a sand core funnel filled with compacted diatomaceous earth and suction filtering was carried out; the diatomaceous earth was then washed with DMF (90 mL) until there was no product in the diatomaceous earth. A reaction product solution was thus obtained.

24-95

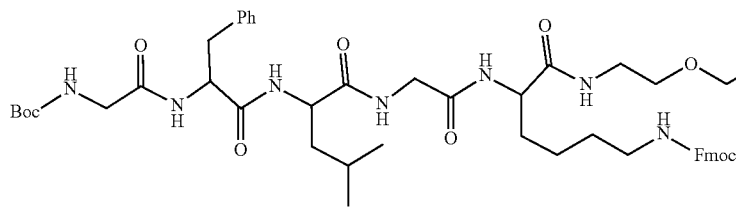

24-94

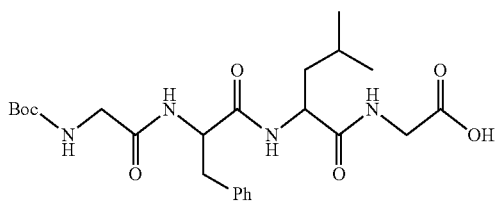

Compound 24-93 (2.4922 g, 1.9757 mmol), HBTU (1.1239 g, 2.9636 mmol), and HOBT (0.4004 g, 2.9636 mmol) were added in a round-bottomed flask and then dissolved with a DMF solution (2.1733 mmol) of Compound 24-94 and the resulting solution was stirred at −5° C. for 0.5 h; DIEA (2.4697 mL) was then slowly added dropwise to the mixed solution and the obtained solution reacted at a low temperature (−5° C.). At the end of the reaction, ethyl acetate (100 mL) and pure water (70 mL) were added for extraction, the organic phase was separated, the aqueous phase was extracted three times with ethyl acetate (50 mL×3), and the obtained organic phases were combined, washed once with a saturated sodium chloride solution (50 mL), and then concentrated to 50 mL; silica gel powder was then added and the obtained solution was evaporated to dryness. The operations of column chromatography and gradient elution with 3%-5% methanol/dichloromethane were carried out. 1 g of the product was obtained with a yield of 29%.

$^1$H-NMR (400 MHz, DMSO-$d_6$) δ 8.51 (m, 1H), 8.31 (m, 1H), 8.16 (m, 1H), 7.98 (m, 2H), 7.87 (m, 1H) 4, 7.66 (m, 3H), 7.50 (m, 1H), 7.32 (m, 23H), 7.20 (m, 6H), 6.92 (m, 1H), 5.06 (m, 7H), 4.56 (m, 1H), 4.37-4.17 (m, 7H), 3.89 (s, 2H), 3.71 (s, 1H), 3.51 (m, 4H), 3.16 (m, 2H), 2.94 (m, 3H), 2.40 (m, 4H), 2.17 (m, 2H), 1.89 (m, 6H), 1.47 (m, 5H), 1.35 (s, 9H), 1.23 (m, 9H), 0.82 (m, 6H).

MALDI-TOFMS: [M+H$^+$] 1735.75, [M–H$^+$] 1733.41, [M+Na$^+$] 1757.43.

24-136

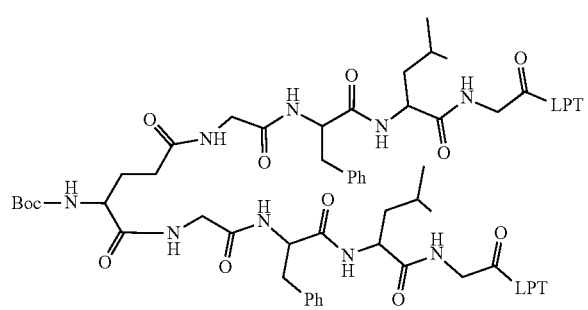

GFLG-LPT (synthesized according to the synthesis route of Compound 14-128) (6.4 g, 6.6981 mmol), Boc-Glu-(OH) (0.7886 g, 3.1896 mmol), HBTU (3.6289 g, 9.5688 mmol), and HOBT (1.2929 g, 9.5688 mmol) were weighed and added in a 500 mL reaction flask and then completely dissolved with DMF in a condition of ultrasonic. The obtained solution was stirred at −5° C. for 30 min. DIEA (4.7446 mL, 28.7064 mmol) was then slowly added dropwise, and the mixed solution was stirred at a low temperature (−5° C.) for 2 h and then taken out and placed at room temperature to react. At the end of the reaction, ethyl acetate (20 mL) and n-hexane (250 mL) were added to the reaction solution, the resulting solution was then rested for 20 min in a refrigerator, the supernatant was discarded, ethyl acetate (20 mL), n-hexane (250 mL) were added again for precipitation; the solid product was then filtered out by suction and dried in vacuum. 8 g of the product was obtained with a yield of 100%, 1.3 g being extra-quota product.

24-138

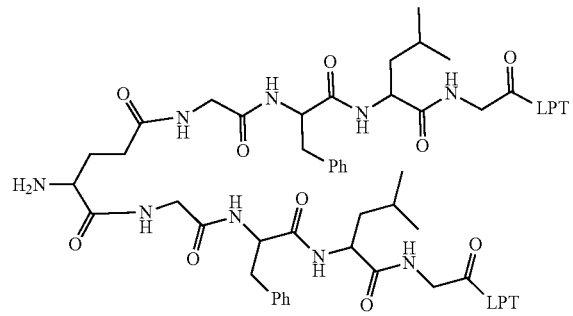

Compound 24-136 (6.7 g, 3.1896 mmol) was weighed, dichloromethane (10 mL) and TFA (5.9227 mL, 79.74 mmol) were then added sequentially, and the obtained solution was treated by ultrasonic until Compound 24-136 was completely dissolved; the mixed solution was stirred at room temperature to react. At the end of the reaction, the reaction solution was evaporated to dryness, and methyl tert-butyl ether (100 mL) and n-hexane (150 mL) were then added for precipitation to separate out a product; suction filtering was then carried out and ethyl acetate (30 mL) was added to the filter cake and the resulting solution was treated by ultrasonic to be uniform; n-hexane (200 mL) was then added, and suction filtering and drying in vacuum were carried out. 7 g of the product was obtained with a yield of 100%, 0.6 g being extra-quota product.

24-112

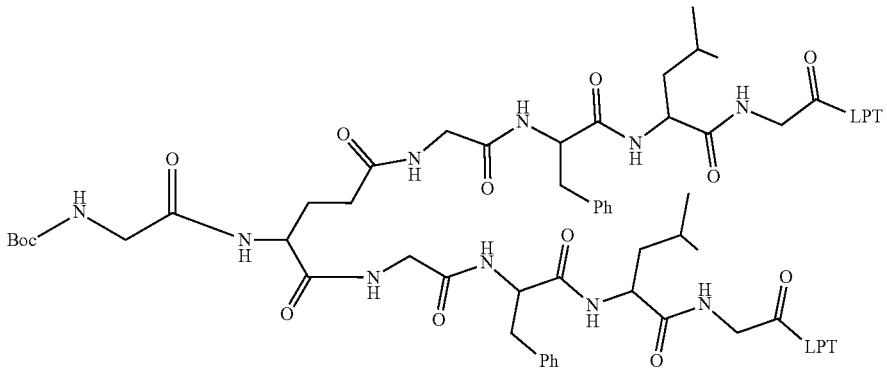

Compound 24-138 (3.3 g, 1.6330 mmol), Boc-Gly-OH (0.3147 g, 1.7964 mmol), HBTU (0.9289 g, 2.4495 mmol), and HOBT (0.3310 g, 2.4495 mmol) were weighed and added in a 500 mL flask and then completely dissolved with DMF (30 mL) in a condition of ultrasonic. The obtained solution was stirred at −5° C. for 30 min. DIEA (1.2193 mL, 7.3485 mmol) was then slowly added dropwise, and the mixed solution was stirred at a low temperature (−5° C.) for 2 h and then taken out and placed at room temperature to react to the end. At the end of the reaction, ethyl acetate (200 mL) and pure water (300 mL) were added for extraction, the organic phase was separated, the aqueous phase was extracted twice with ethyl acetate (100 mL×2), and the organic phases were combined, washed once with a saturated sodium chloride solution (150 mL), and then concentrated to 150 mL; silica gel powder (10 g) was then added and the obtained solution was evaporated to dryness. The operations of column chromatography and elution with 1% ammonia water+4% methanol/dichloromethane were carried out. The elution product was then evaporated to dryness and dried in vacuum. 2.6 g of the product was obtained with a yield of 77%.

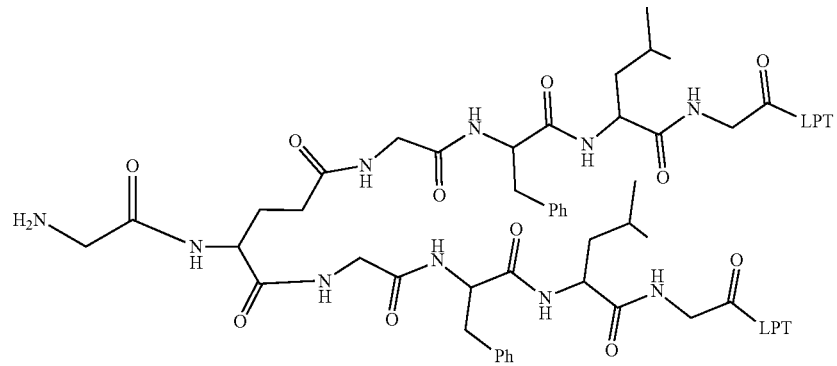

24-115

Compound 24-112 (2.7 g, 1.2390 mmol) was weighed, dichloromethane (10 mL) and TFA (1.8405 mL, 24.7800 mmol) were then added sequentially, and the obtained solution was treated by ultrasonic until Compound 24-112 was completely dissolved; the mixed solution was stirred at room temperature to react. At the end of the reaction, the reaction solution was evaporated to dryness, ethyl acetate (10 mL) n-hexane (200 mL) were then added, and the obtained solution was rested in a refrigerator for 30 min; the supernatant was discarded, the lower solution was oily liquid, dichloromethane (10 mL) was added and the obtained solution was treated by ultrasonic to be uniform; n-hexane (200 mL) was then added and the obtained solution to precipitate a product; the product was filtered out by suction; the obtained solid is product was completely dissolved with 20% methanol/dichloromethane (200 mL), silica gel powder (10 g) was then added, and the obtained solution was evaporated to dryness with a rotary evaporator. The operations of column chromatography and gradient elution with 1% ammonia water+4%-5% methanol/dichloromethane were carried out. The elution product was then evaporated to dryness and dried in vacuum. 1.7 g of the product was obtained with a yield of 68%.

MALDI-TOFMS: [M−H$^+$] 2077.97, [M+H$^+$] 2081.05, [M+Na$^+$] 2100.95.

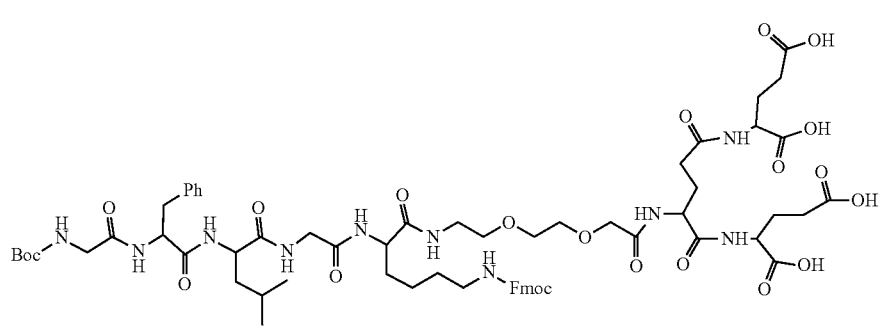

24-119

The reactant Compound 24-95 (0.2609 g, 0.1503 mmol) and 10% Pd/C (50 mg) were added into a hydrogenation reactor and then dissolved with DMF (30 mL); the hydrogenation reactor was then sealed and H₂ (18 psi) was introduced in the reactor. The mixed solution was then stirred overnight at room temperature. After the reaction was found to be completed from the monitoring of the TLC, the reaction solution was taken out and evenly dropwise added to a sand core funnel filled with compacted diatomaceous earth and suction filtering was carried out; the diatomaceous earth was then washed with DMF (90 mL) until there was no product in the diatomaceous earth. A reaction product solution was thus obtained.

ture (−5° C.) to the end. At the end of the reaction, methyl tert-butyl ether (100 mL) and n-hexane (200 mL) were added to the reaction solution, the resulting solution was rested in the refrigerator for 30 min, the supernatant was discarded and there was no product in the supernatant; ethyl acetate (50 mL) was added to the lower liquid, and the obtained solution was treated to be uniform by ultrasonic; methyl tert-butyl ether (100 mL) and n-hexane (200 mL) were added to the solution to precipitate a solid product; the solid product was then filtered out by suction and dissolved with a solvent (20% methanol/dichloromethane); silica gel

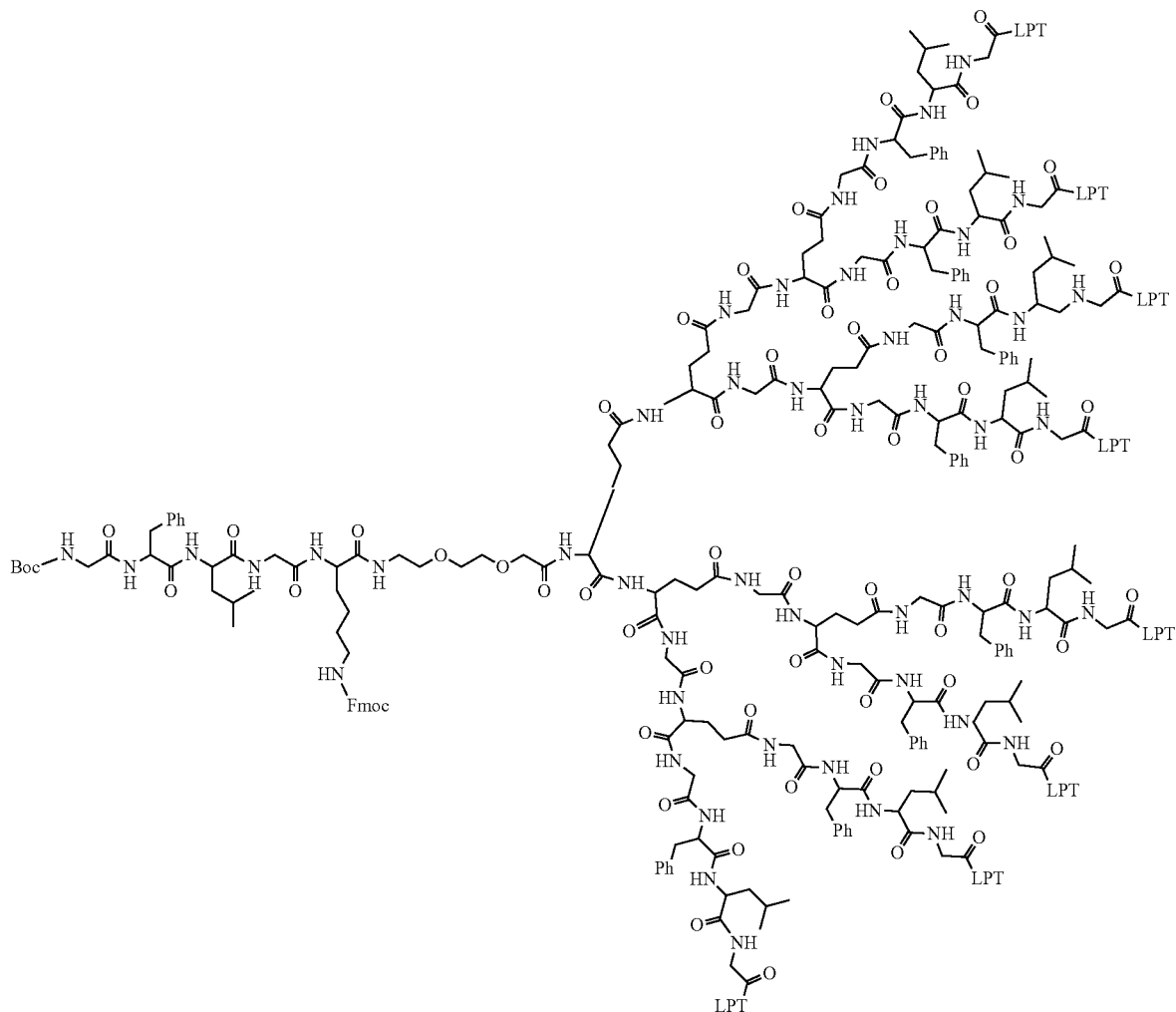

24-120

Compound 24-115 (1.5 g, 0.9619 mmol), HBTU (0.3420 g, 0.9018 mmol), HOBT (0.1219 g, 0.9018 mmol) were weighed and added into a 250 mL flask and then completely dissolved with the DMF solution of Compound 24-119 by ultrasonic, the resulting solution was stirred at −5° C. for 30 min, DIEA (0.4489 mL, 2.7054 mmol) was slowly added dropwise, and the mixed solution reacted at a low temperapowder was then added to the obtained solution and the operations of evaporation, column chromatography, and gradient elution with 1% ammonia water:5% methanol-1% ammonia water:8% methanol/dichloromethane were carried out; the elution product was then evaporated to dryness and dried in vacuum. 1.1 g of the product was obtained with a yield of 80%.

24-122

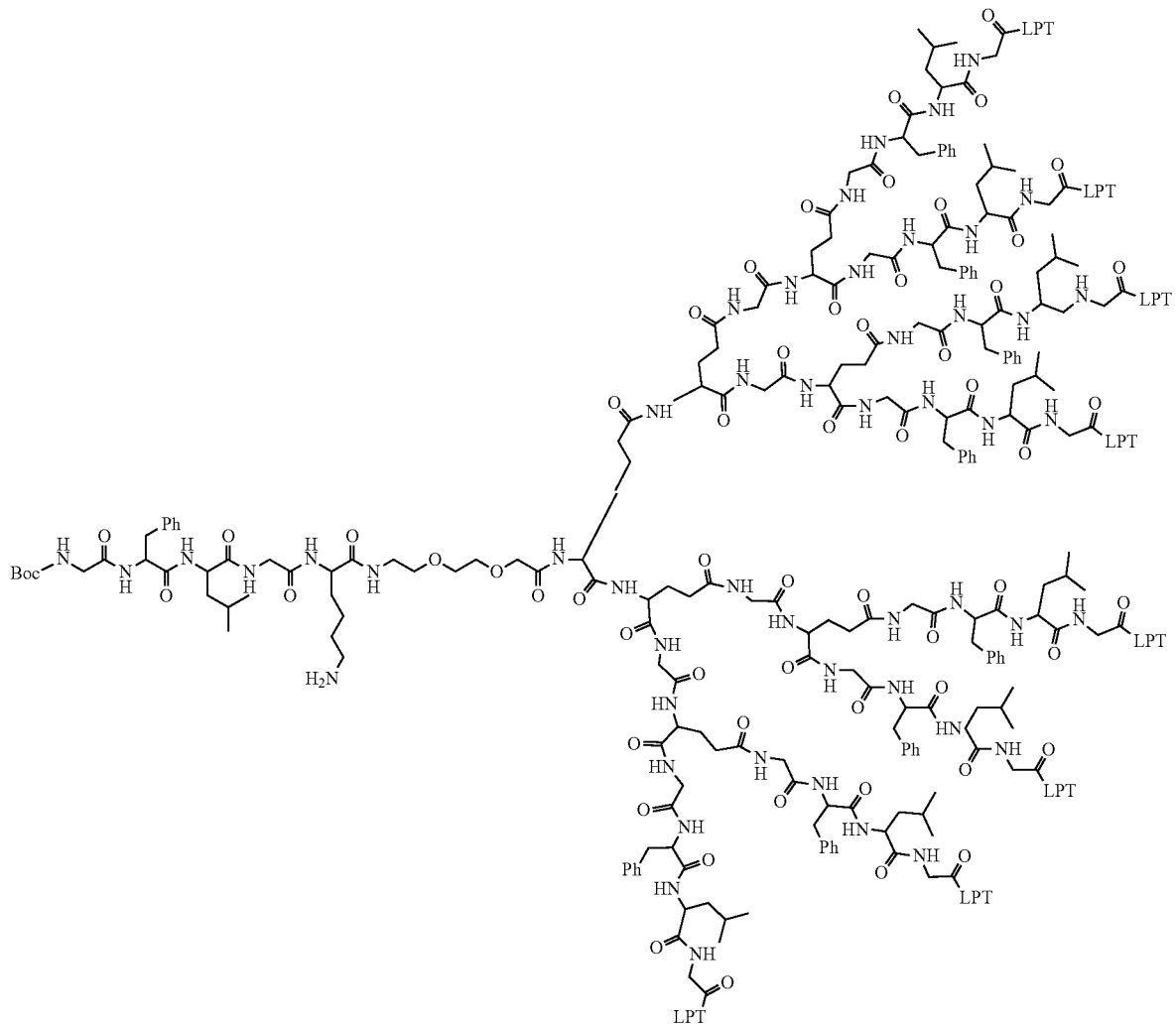

The reactant Compound 24-120 (1.1 g, 0.1143 mmol) was added in a 250 mL round-bottomed flask and dissolved with DMF (10 mL), morpholine (0.2988 mL, 3.4304 mmol) was then added, and the obtained solution was stirred at room temperature to react. At the end of the reaction, methyl tert-butyl ether (150 mL) and n-hexane (70 mL) were added to the reaction solution to precipitate a solid product; the solid product was then filtered out by suction and dissolved with a solvent (20% methanol/dichloromethane); silica gel powder was then added to the obtained solution and the operations of evaporation, column chromatography, and gradient elution with 1% ammonia water:5%-1% ammonia water:8% methanol/dichloromethane were carried out; the elution product was then evaporated to dryness and dried in vacuum. 0.8 g of the product was obtained with a yield of 80%.

MALDI-TOF MS: [M+H⁺] 9498.36, [M+K⁺] 9536.73.

19-173

Fmoc-Glu-OtBu (1.19 g, 2.79 mmol), GFLG-PCB (synthesized according to the synthesis method of Compound 30-33) (2.3 g, 2.79 mmol), HOBT (0.56 g, 4.185 mmol), and HBTU (1.58 g, 4.185 mmol) were weighed and added in a 250 mL flask and then dissolved with a DMF solution (50 mL); the obtained solution was placed in a low-temperature constant temperature bath (−5° C.) and stirred for 30 min, DIEA (2.0 mL, 12.5 mmol) was added dropwise, and the mixed solution first reacted at a low temperature for 2 h and was then stirred at room temperature to react. At the end of the reaction, the reaction solution was precipitated with methyl tert-butyl ether (50 mL) and n-hexane (100 mL).

19-174

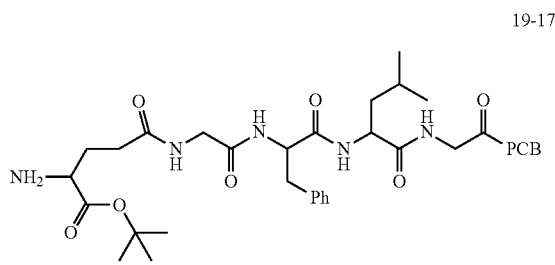

Compound 19-173 was weighed and added into a 250 mL flask and then DMF solution (20 mL) and morpholine (7.29 mL, 83.7 mmol) were added sequentially; the resulting solution was stirred at room temperature to react. 3 h later, the reaction ended. Methyl tert-butyl ether (100 mL) and n-hexane (200 mL) were added to precipitate the solution, thus obtaining a powder; then, suction filtering was carried out to obtain a solid product. The operations of column chromatography, dry sample loading and elution with 1% ammonia water:3% methanol/dichloromethane were carried out. The elution product was evaporated to dryness and dried in vacuum. 1.8 g of the product was obtained with a yield of 64%.

19-175

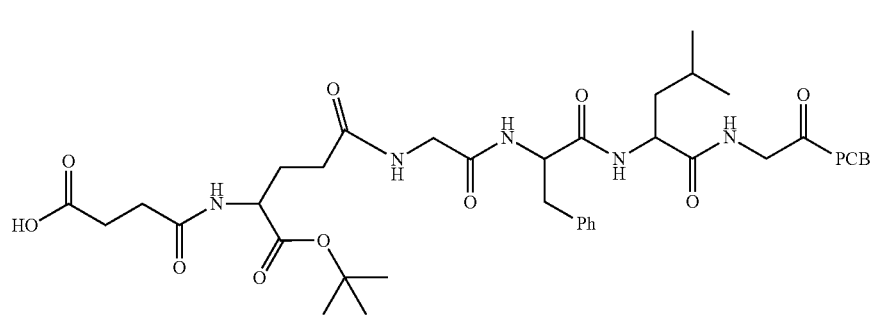

Compound 19-174 was added in a 250 mL flask and then placed in a low-temperature constant temperature bath (−5° C.); DIEA (0.32 mL, 6.4 mmol) was then added dropwise to the mixed solution, and 30 min later, succinic anhydride was added. The obtained solution was stirred to react. At the end of the reaction, methyl tert-butyl ether (100 mL) and n-hexane (200 mL) were added to precipitate the solution, thus obtaining a powder. Suction filtering was then carried out to obtain a solid product.

19-176

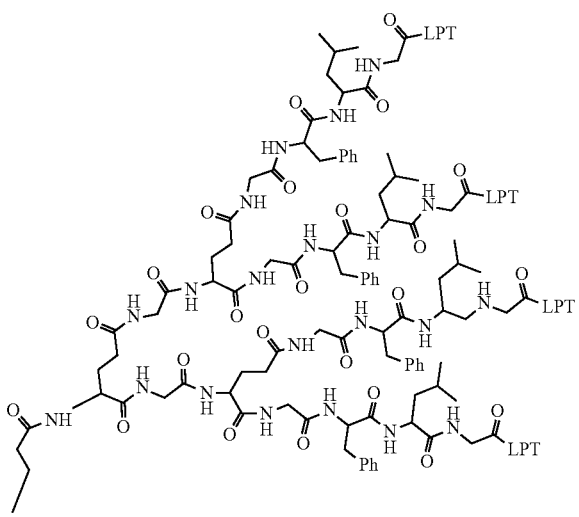

277

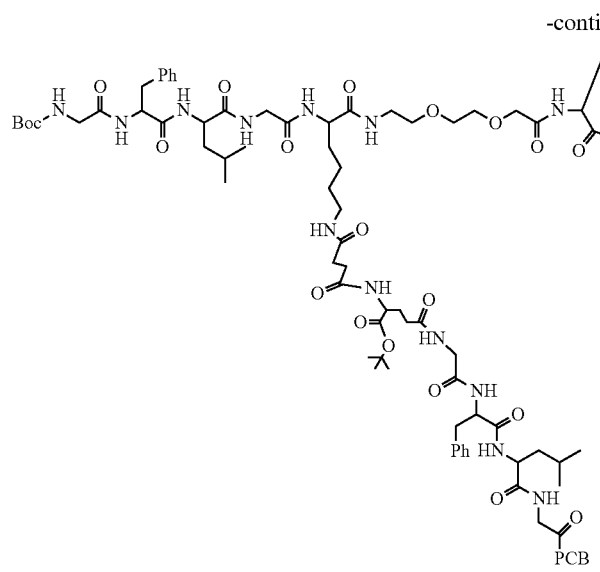

278

-continued

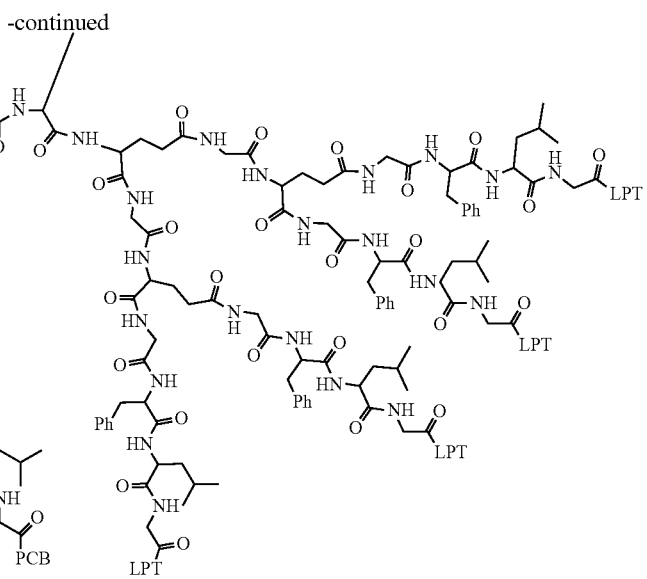

Compound 24-122 (0.8 g, 0.0854 mmol), Compound 19-175 (0.098 g, 0.089 mmol), HOBT (0.017 g, 0.127 mmol), and HBTU (0.048 g, 0.127 mmol) were weighed and added in a 250 mL flask and then dissolved with a DMF solution (20 mL); the obtained solution was placed in a low-temperature constant temperature bath (−5° C.) and stirred for 30 min, DIEA (0.069 mL, 0.383 mmoL) was added dropwise, and the mixed solution first reacted at a low temperature (−5° C.) for 2 h and was then stirred at room temperature to react. At the end of the reaction, methyl tert-butyl ether (50 mL) and n-hexane (100 mL) were then added to the reaction solution to precipitate a solid. Suction filtering was then carried out to obtain a solid product.

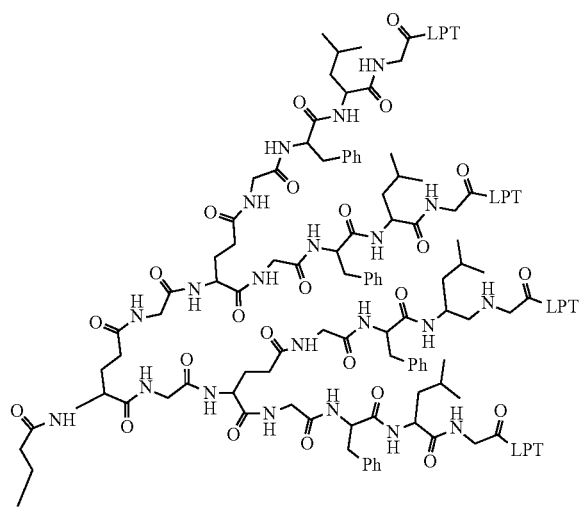

19-177

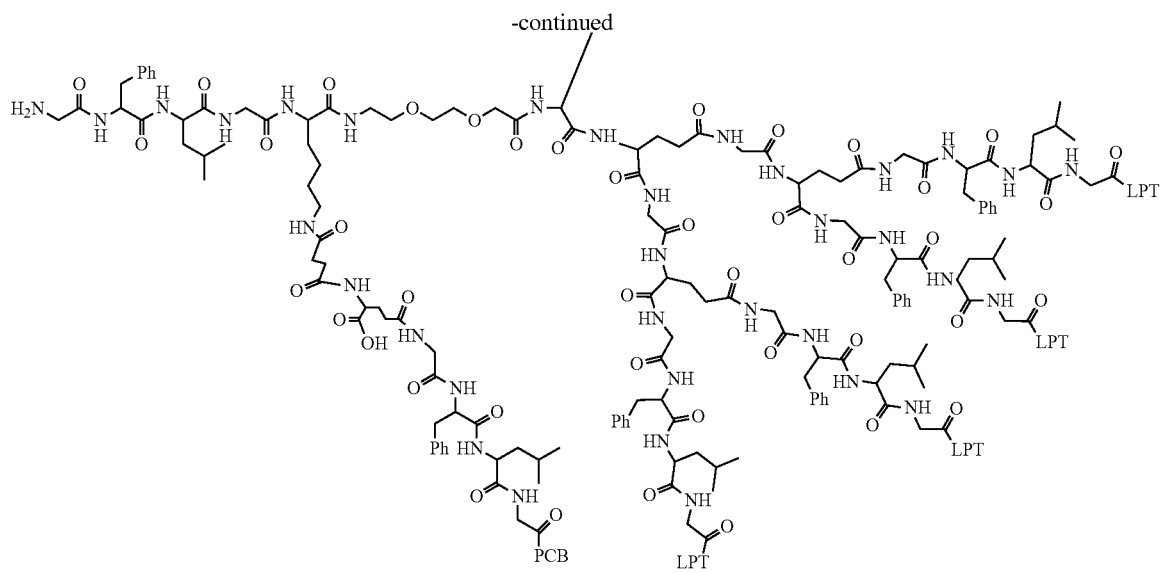
-continued

Dichloromethane (5 mL) and TFA (0.187 mL, 2.55 mmol) were added to the reactant Compound 19-176 sequentially and the obtained solution was treated by ultrasonic until the Compound 19-176 was dissolved. The obtained solution was stirred at room temperature to react. At the end of the reaction, the reaction solution was concentrated and methyl tert-butyl ether (50 mL) and n-hexane (100 mL) were then added to the reaction solution to precipitate a solid. Suction filtering was then carried out to obtain a solid product. The operations of column chromatography, dry sample loading and gradient elution with 1% ammonia water:7% methanol/dichloromethane-1% ammonia water:8% methanol/dichloromethane were carried out. The elution product was evaporated to dryness and then dried in vacuum. 0.5 g of the product was obtained.

$^1$H-NMR (400 MHz, DMSO-d$_6$) δ 9.84 (s, 6H), 8.73 (s, 6H), 8.54 (s, 6H), 8.38-8.14 (m, 19H), 8.13-7.90 (m, 32H), 7.89-7.66 (m, 9H), 7.54-7.45 (m, 8H), 7.39-7.25 (m, 26H), 7.20 (s, 48H), 7.13-7.02 (m, 11H), 6.67 (s, 4H), 6.53 (s, 2H), 5.24 (s, 15H), 4.80-4.49 (m, 27H), 4.42-4.04 (m, 45H), 3.85-3.56 (m, 60H), 3.55-3.44 (m, 20H), 3.26-3.13 (m, 17H), 3.11-3.02 (m, 32H), 2.89 (m, 2H), 2.78-2.6.3 (m, 15H), 2.35-2.02 (m, 16H), 1.63-1.54 (m, 12H), 1.52-1.46 (m, 19H), 1.38-1.20 (m, 21H), 0.89-0.76 (m, 60H).

MALDI-TOF MS: [M+Na$^+$] 10343.69, [M+K$^+$] 10357.54

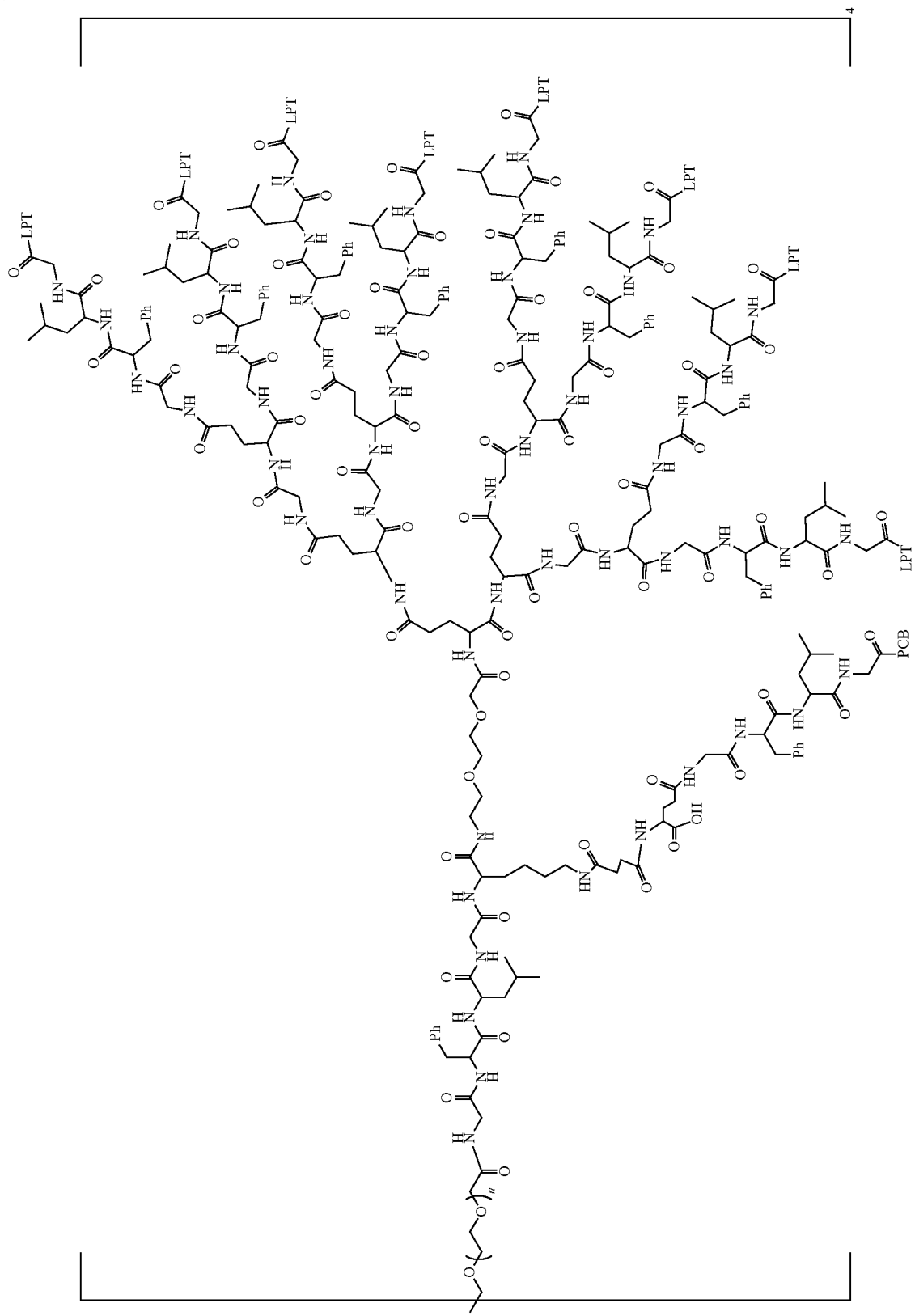

Compound 19-177 (0.5 g) was dissolved in DMF (20 mL) in a 250 mL flask, and then the flask was placed in a low-temperature constant temperature bath (−5° C.). The mixed solution was stirred for 30 min and DIEA (0.033 mL) was then added dropwise to the solution. 4ARM-SCM-40K (0.42 g, 0.01008 mmol) was then added and dissolved in the above solution and the resulting solution was then stirred slowly at room temperature in the dark to react. At the end of the reaction, methyl tert-butyl ether (150 mL) was added in a conical flask, the reaction solution was poured into the conical flask, and then n-hexane (200 mL) was added to precipitate the product. Suction filtering and column chromatography were then carried out. With the column height of 5 cm, gradient elution with an eluent 5% methanol/dichloromethane-1% ammonia water:7% methanol/dichloromethane was carried out, and the elution product was evaporated to dryness and dried in vacuum. 0.7 g of the product was obtained.

$^1$H-NMR (400 MHz, DMSO-$d_6$) δ 10.24 (s, 21H), 8.79-8.76 (m, 30H), 8.70-8.60 (m, 35H), 8.45-8.16 (m, 123H), 8.12-8.06 (m, 124H), 7.89-7.78 (m, 47H), 7.73-7.62 (m, 31H), 7.61-7.38 (m, 50H), 7.35-7.14 (m, 201H), 7.15-7.02 (m, 61H), 7.00-6.91 (m, 10H), 6.72-6.63 (m, 16H), 6.66-6.50 (m, 6H), 5.58-5.30 (m, 8H), 4.78-4.67 (m, 48H), 4.57 (s, 34H), 4.40-4.31 (m, 44H), 4.26-4.05 (m, 108H), 4.02-3.91 (m, 44H), 3.81-3.63 (m, 132H), 3.52-3.49 (m, 3819H), 2.98-2.85 (m, 59H), 2.83-2.63 (m, 98H), 2.63-2.58 (m, 27H), 2.37-2.24 (m, 35H), 2.18-2.05 (m, 55H), 2.04-1.67 (m, 97H), 1.66-1.43 (m, 146H), 1.42-1.28 (m, 99H), 1.19-1.14 (s, 40H), 0.89-0.75 (m, 240H).

MALDI-TOFMS: 82789.90-83004.54

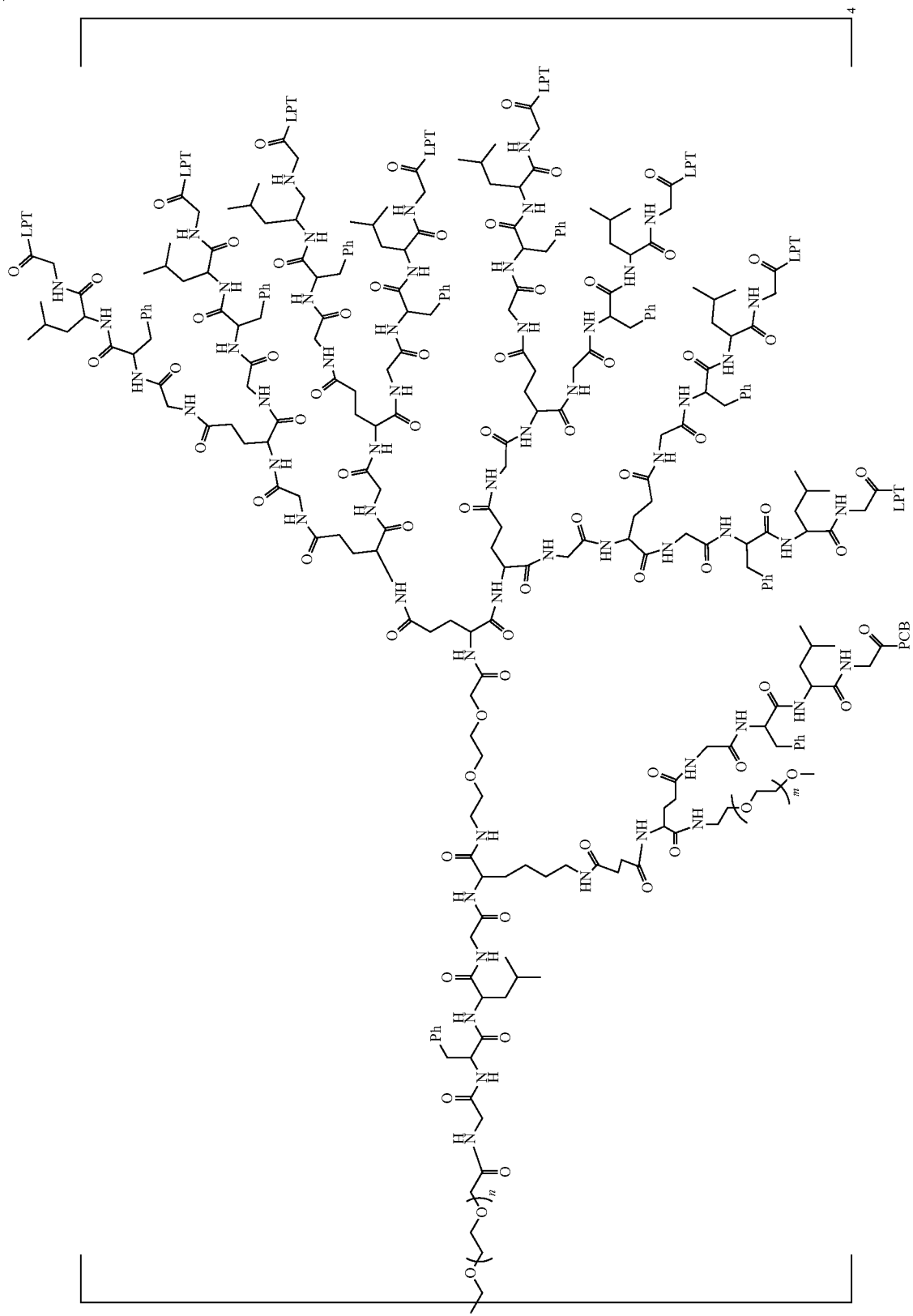

M-NH$_2$HCL-10K (0.53 g, 0.0507 mmol), Compound 19-178 (0.7 g, 0.00845 mmol), is HOBT (0.0107 g, 0.076 mmol), and HBTU (0.03 g, 0.076 mmol) were added into a 250 mL flask and a DMF solution (20 mL) was then added; the resulting solution was then placed in a low-temperature constant temperature bath (−5° C.); 30 min later, DIEA (0.04 mL) was then added dropwise; 1 h later, the mixed solution was taken out and slowly stirred in the dark at a room temperature to react. At the end of the reaction, methyl tert-butyl ether (50 mL) and n-hexane (150 mL) were then added to the reaction solution to precipitate a solid. Suction filtering was then carried out. The obtained solid was dissolved with a solution (20% methanol:80% dichloromethane) (50 mL); and then the operations of dry sample loading and column chromatography were carried out. With the column height of 5 cm, gradient elution with 6% methanol/dichloromethane-1% ammonia water:10% methanol/dichloromethane was carried out, the elution product was evaporated to dryness and then dissolved with absolute ethanol (5 mL) and dichloromethane (2 mL); the obtained solution was treated by ultrasonic to obtain a homogeneous phase; n-hexane (100 mL) was added and then suction filtering was carried out. The process of dissolution and precipitation was repeated three times, and the precipitate was dried in vacuum. 0.6 g of the product was obtained.

$^1$H-NMR (400 MHz, DMSO-d$_6$) δ11.10 (s, 7H), 8.93-8.73 (m, 42H), 8.29-7.63 (m, 334H), 7.51-7.07 (m, 452H), 6.96 (s, 15H), 6.74-6.65 (m, 7H), 6.58-6.53 (m, 3H), 5.30-5.25 (m, 44H), 3.51-3.50 (m, 7884H), 3.10-2.83 (m, 690H), 2.33 (s, 71H), 1.41-1.16 (m, 395H), 0.91-0.74 (m, 240H).

Example 6: Synthesis of Compound 33-65

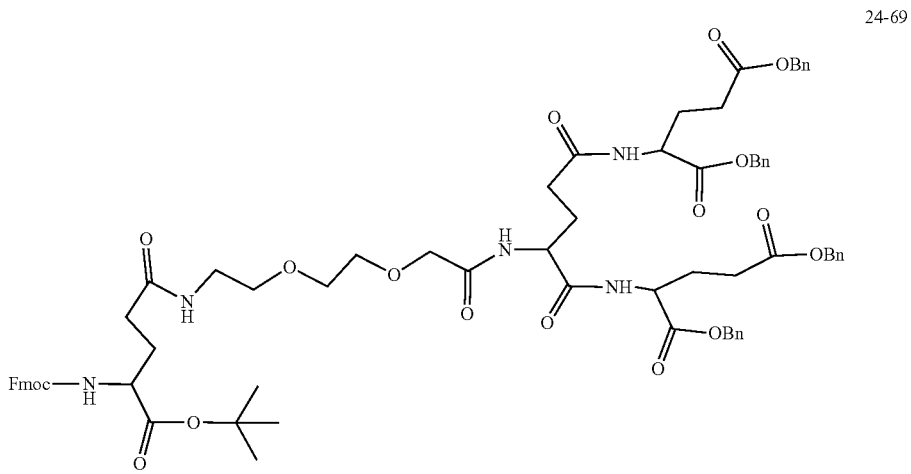

24-69

The reactants Fmoc-GLu-OtBu (14.0111 g, 32.9308 mmol), Compound 30-74 (30 g, 32.9308 mmol), HBUT (18.7330 g, 49.3962 mmol), and HOBT (6.6749 g, 49.3962 mmol) were added in a 500 mL reaction flask and then dissolved with DMF (150 mL) and the resulting solution was stirred at −5° C. for 0.5 h; DIEA (24.4928 mL, 148.1886 mmol) was slowly added dropwise to the mixed solution; 2 h later, the reaction solution further reacted at room temperature. At the end of the reaction, the reaction solution was extracted with deionized water (300 mL) and ethyl acetate (100 mL), the organic phase was then separated, the aqueous phase was extracted three times with ethyl acetate (150 mL×3), and the obtained organic phases were then combined, washed three times with a saturated sodium chloride solution (200 mL×3), and then concentrated; silica gel powder was then added and the operations of dry sample loading and column chromatography were carried out. Gradient elution with 50%-80% ethyl acetate/petroleum ether was carried out. 26 g of the product was obtained with a yield of 60%.

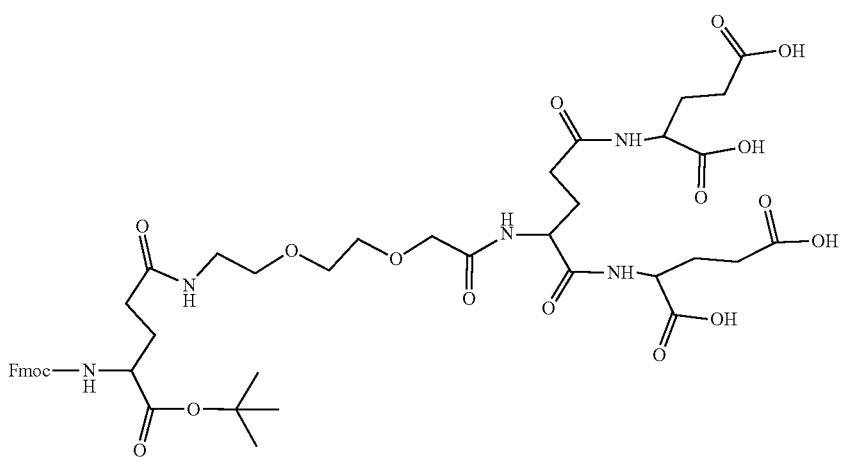

The reactant Compound 24-69 (0.835 g) was weighed and added into a hydrogenation device and then dissolved with DMF (30 mL) and then 10% Pd/C (0.1 g) was added to the resulting solution; the hydrogenation device was then set up and H$_2$ (18 psi) was introduced in the device. The mixed solution was then stirred overnight at room temperature. After the reaction was found to be completed from the monitoring of the TLC, the reaction solution was taken out and evenly dropwise added to a sand core funnel filled with compacted diatomaceous earth and suction filtering was carried out; the diatomaceous earth was then washed with DMF (90 mL) until there was no product in the diatomaceous earth. A reaction product solution was thus obtained.

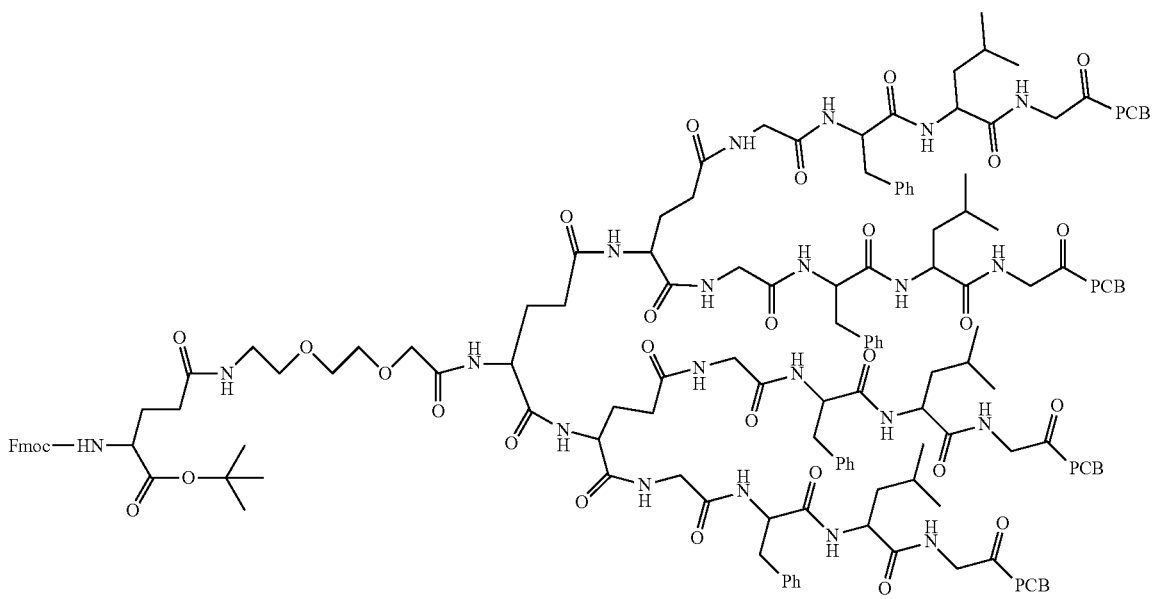

GFLG-PCB (synthesized according to the synthesis method of Compound 30-33) (2.5 g, 3.04 mmol), Compound 33-7 (0.6336 mmol), HOBT (0.513 g, 3.8 mmol), and HBTU (1.4 g, 3.8 mmol) were added into a 250 mL flask and a DMF solution (80 mL) was then to the flask; next, the flask was placed in a low-temperature constant temperature bath (−5° C.); 30 min later, DIEA (1.88 mL, 11.4 mmol) was dropwise added; 1 h later, the resulting solution was take out and stirred at room temperature to react. At the end of the reaction, deionized water (300 mL) was added to the reaction solution to precipitate a solid and the solid product was filtered out by suction and then dried in vacuum. The product was thus obtained.

33-14

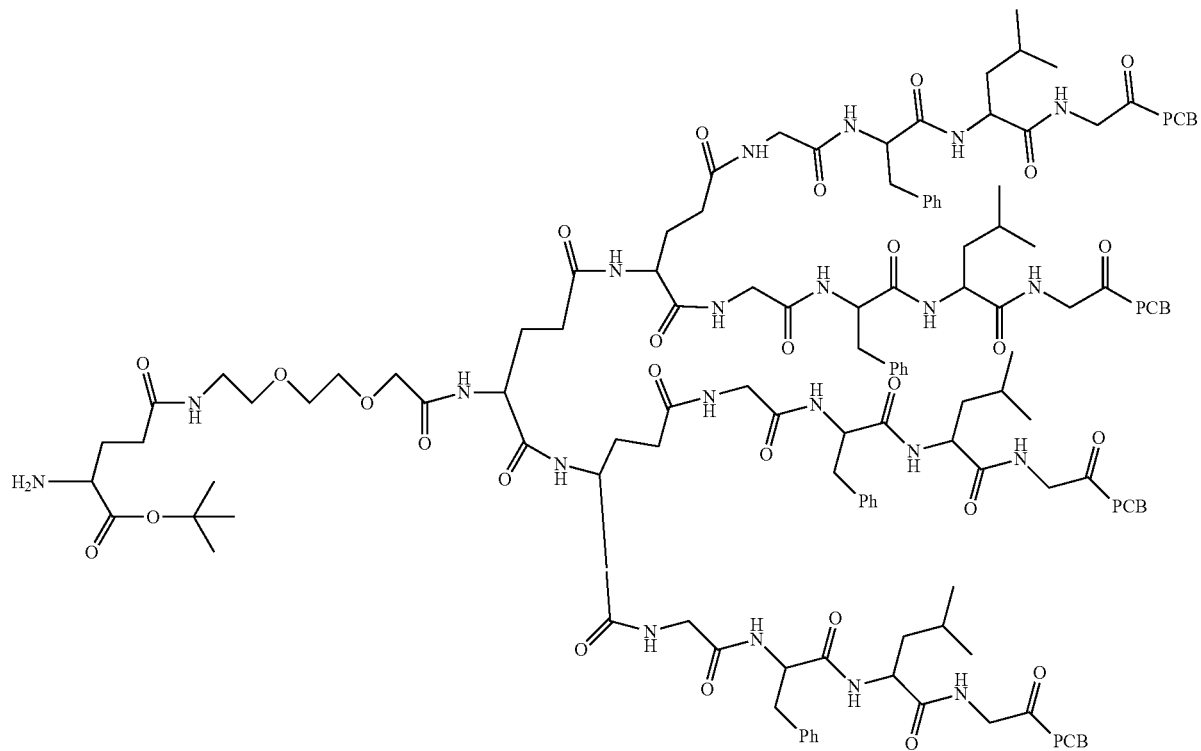

The reactant Compound 33-13 was dissolved with a DMF solution (40 mL), morpholine (3 mL) was then added to the resulting solution, and then the mixed solution was stirred at room temperature to react. At the end of the reaction, methyl tert-butyl ether (100 mL) and n-hexane (200 mL) were added to precipitate the solution, thus obtaining a powder. The powder was filtered out by suction and dried in vacuum. 0.4 g of the product was obtained.

33-18

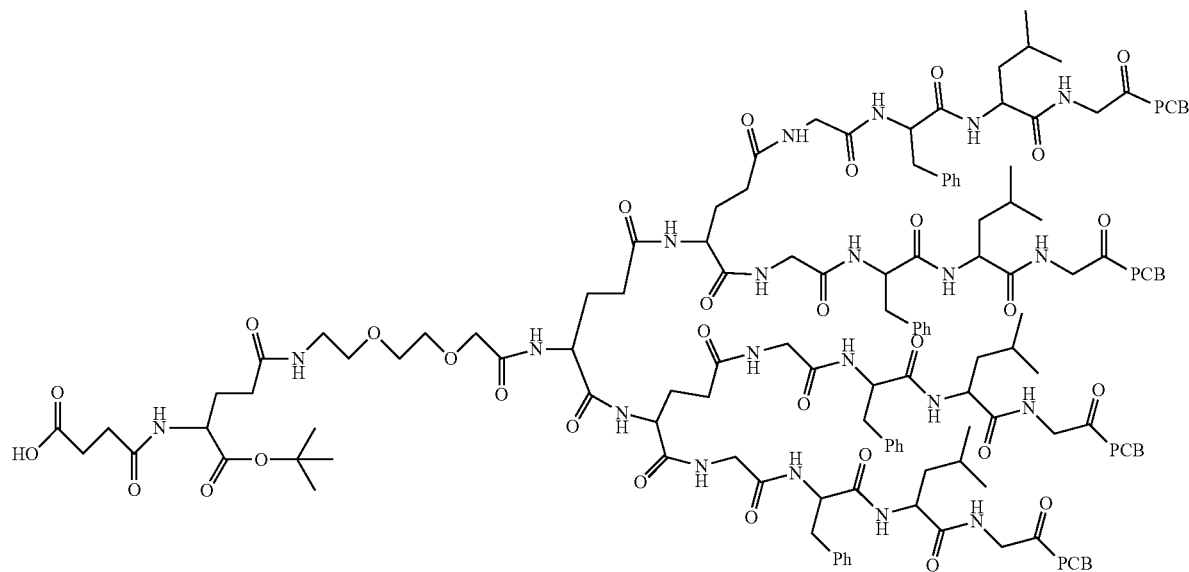

Compound 33-14 (0.4 g, 0.101 mmol) was added into a 250 mL flask and dissolved with a DMF solution (50 mL) and the resulting solution was then placed in a low-temperature constant temperature bath (−5° C.); DIEA (0.066 mL, 0.404 mmol) was then added dropwise to the mixed solution, and 30 min later, succinic anhydride (0.03 g, 0.303 mmol) was added. The obtained solution was stirred to react. At the end of the reaction, methyl tert-butyl ether (100 mL) and n-hexane (200 mL) were added to precipitate the solution, thus obtaining a powder. The powder was filtered out by suction and dried in vacuum. The product was thus obtained.

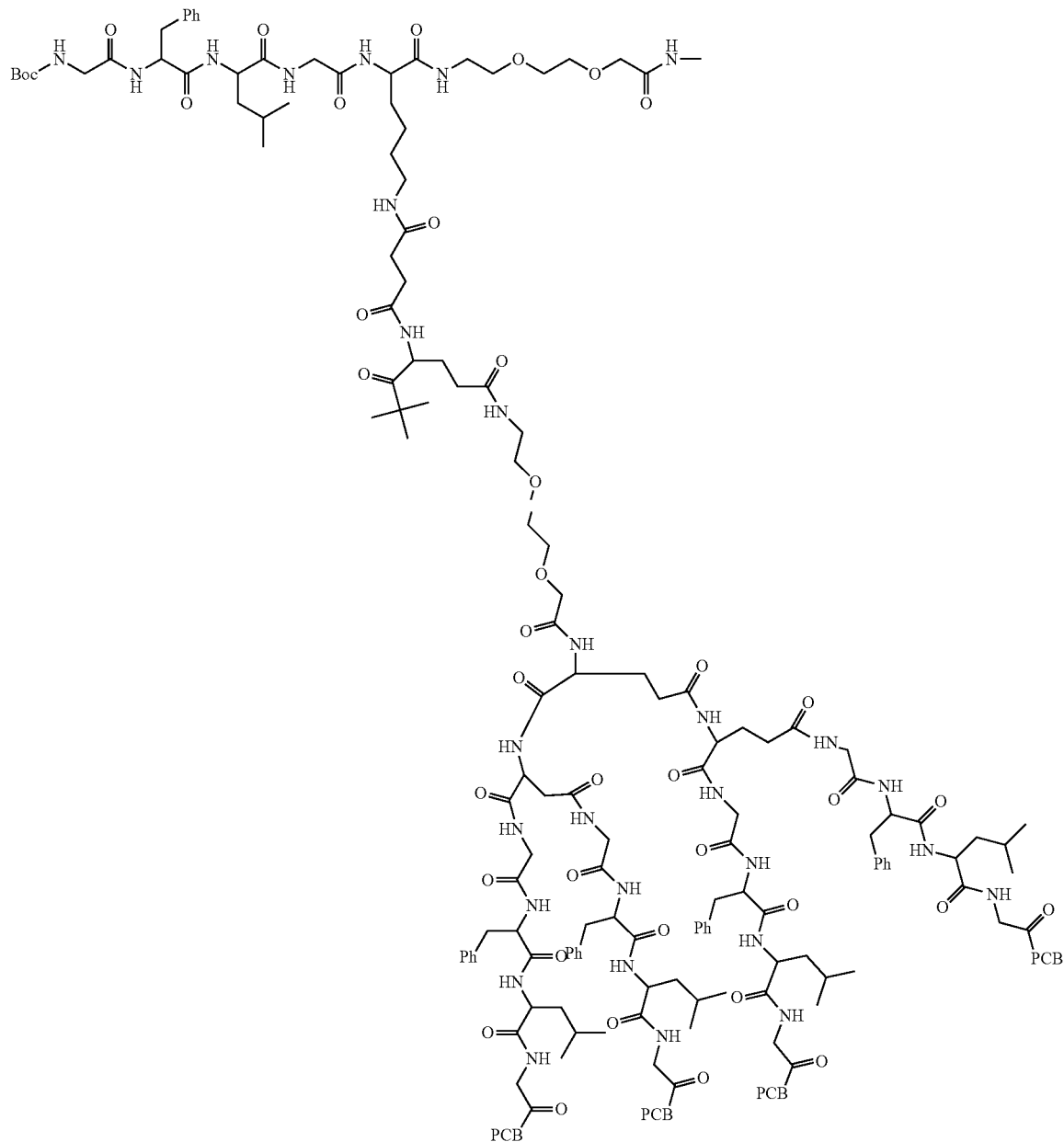

33-19

-continued

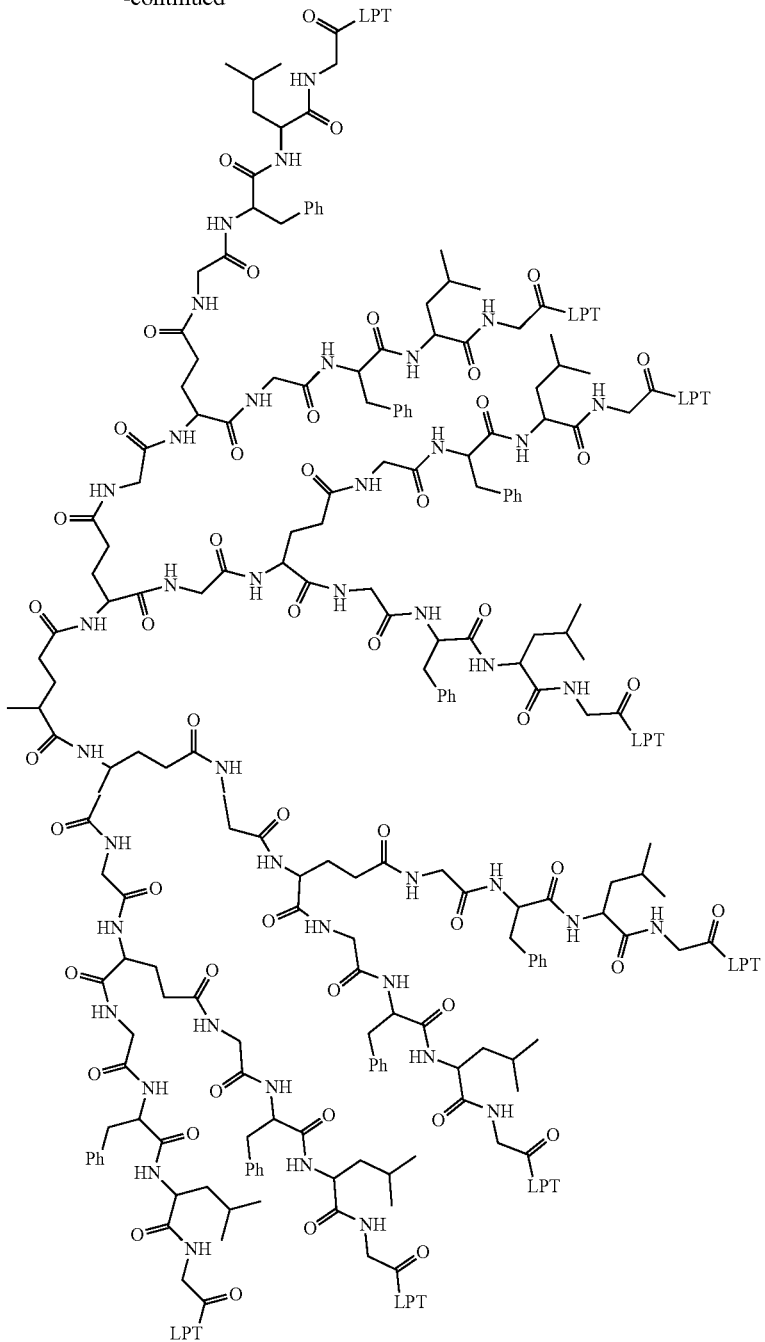

Compound 24-151 (0.8 g, 0.0851 mmol, synthesized according to the synthesis method of Compound 24-122), Compound 33-18 (0.4 g, 0.085 mmol), HOBT (0.017 g, 0.127 mmol), and HBTU (0.048 g, 0.127 mmol) were weighed and added in a 250 mL flask and then dissolved with a DMF solution (30 mL); the obtained solution was placed in a low-temperature constant temperature bath (−5° C.) and stirred for 30 min, DIEA (0.069 mL, 0.383 mmoL) was added dropwise, and the mixed solution first reacted at a low temperature (−5° C.) for 2 h and was then stirred at room temperature to react. At the end of the reaction, methyl tert-butyl ether (50 mL) and n-hexane (100 mL) were added to the reaction solution to precipitate a solid, and then suction filtering was carried out to obtain a solid product. The operations of dry sample loading, column chromatography, and gradient elution with 1% ammonia water:5% methanol/dichloromethane-1% ammonia water:8% methanol/dichloromethane were carried out. The elution product was evaporated to dryness and then dried in vacuum. 0.7 g of the product was obtained.

297 298
33-27
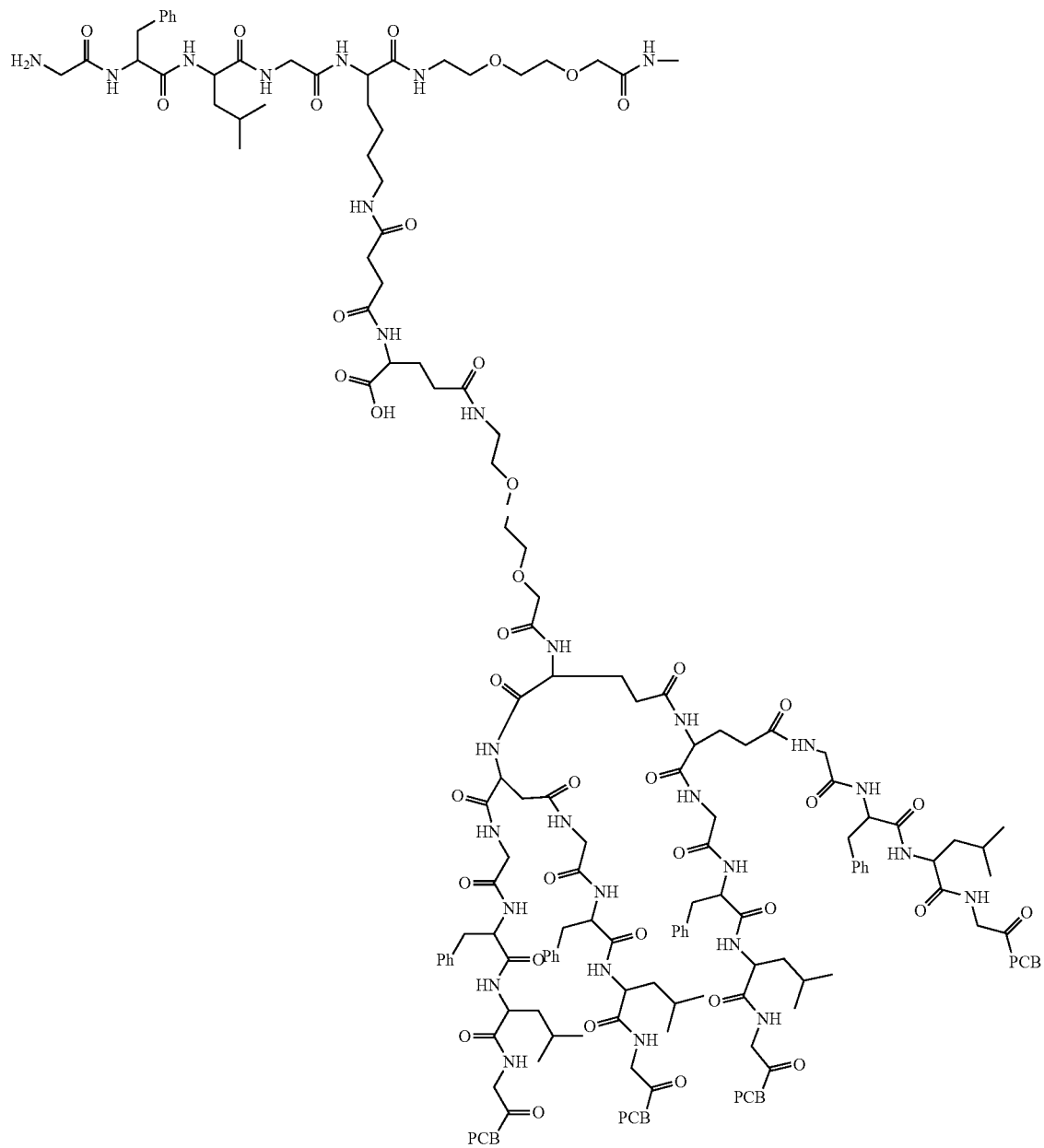

-continued

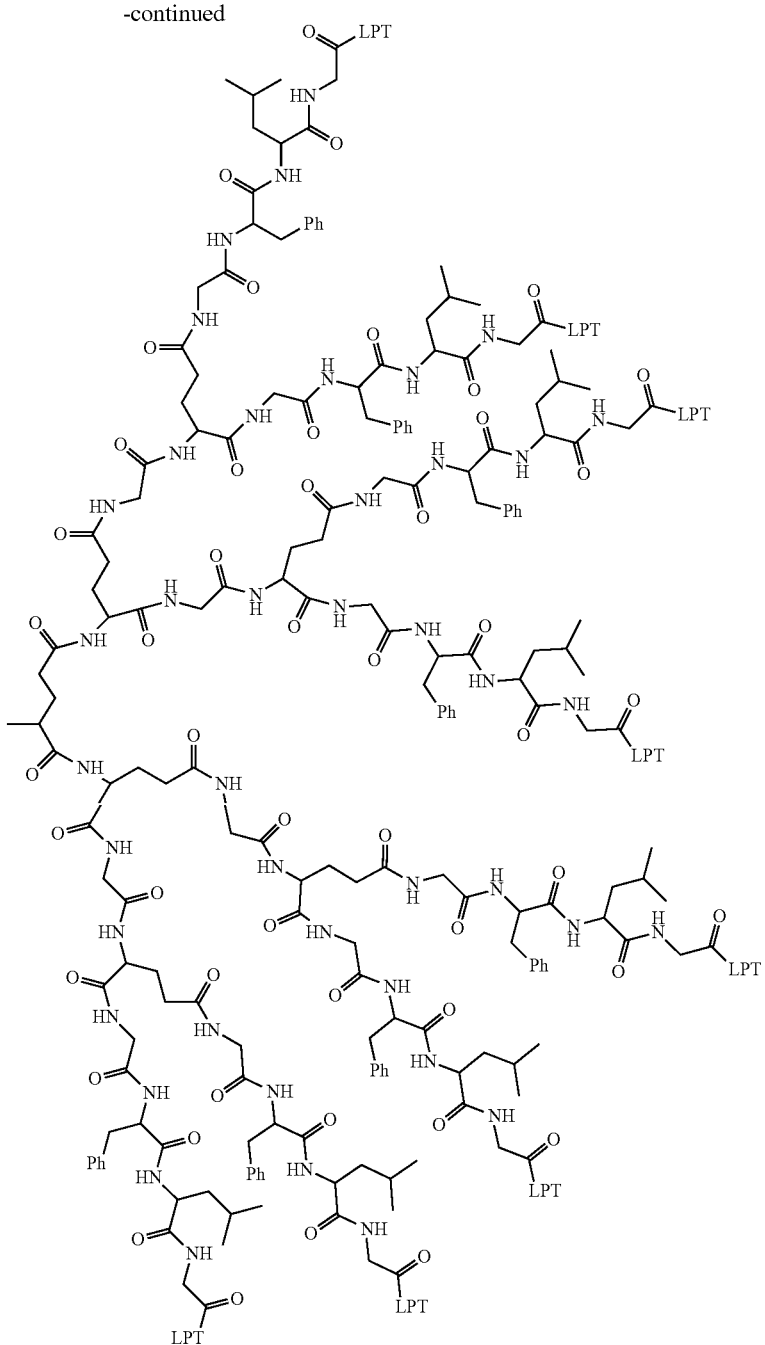

The reactant Compound 33-19 was dissolved with dichloromethane (5 mL) and TFA (0.12 mL, 1.7 mmol) by ultrasonic, and the obtained solution was stirred at room temperature to react. At the end of the reaction, the reaction solution was concentrated and then methyl tert-butyl ether (50 mL) and n-hexane (100 mL) were added to the reaction solution to precipitate a solid, and then suction filtering was carried out to obtain a solid product. The operations of dry sample loading, column chromatography, and gradient elution with 1% ammonia water:5% methanol/dichloromethane-1% ammonia water:10% methanol/dichloromethane were carried out. The elution product was then evaporated to dryness and dried in vacuum. 0.5 g of the product was obtained.

$^1$H-NMR (400 MHz, DMSO-$d_6$) δ 10.11 (s, 7H), 9.83 (s, 11H), 8.96-8.91 (m, 8H), 8.68-8.77 (m, 13H), 8.58-8.51 (m, 12H), 7.95-8.24 (m, 84H), 7.89-7.85 (m, 9H), 7.80-7.68 (m, 20H), 7.50-7.42 (m, 15H), 7.23-7.16 (m, 55H), 6.66 (s, 6H), 6.52 (s, 3H), 5.85-5.74 (m, 9H), 4.77-4.66 (m, 16H), 4.62-4.53 (m, 14H), 4.41-4.16 (m, 43H), 4.12-3.83 (s, 35H), 3.80-3.54 (m, 72H), 3.51 (s, 8H), 3.21-3.09 (m, 26H), 3.05 (s, 12H), 3.01-2.96 (m, 21H), 2.89 (s, 3H), 2.85-2.65 (m, 28H), 2.41 (s, 13H), 2.31-2.27 (m, 12H), 2.24-2.19 (m, 9H), 2.17-2.09 (m, 17H), 1.92-1.67 (m, 46H), 1.64-1.44 (m, 53H), 1.40-1.32 (m, 10H), 0.88-0.74 (m, 78H).

MALDI-TOF MS: [M+H$^+$] 13264.29

33-37

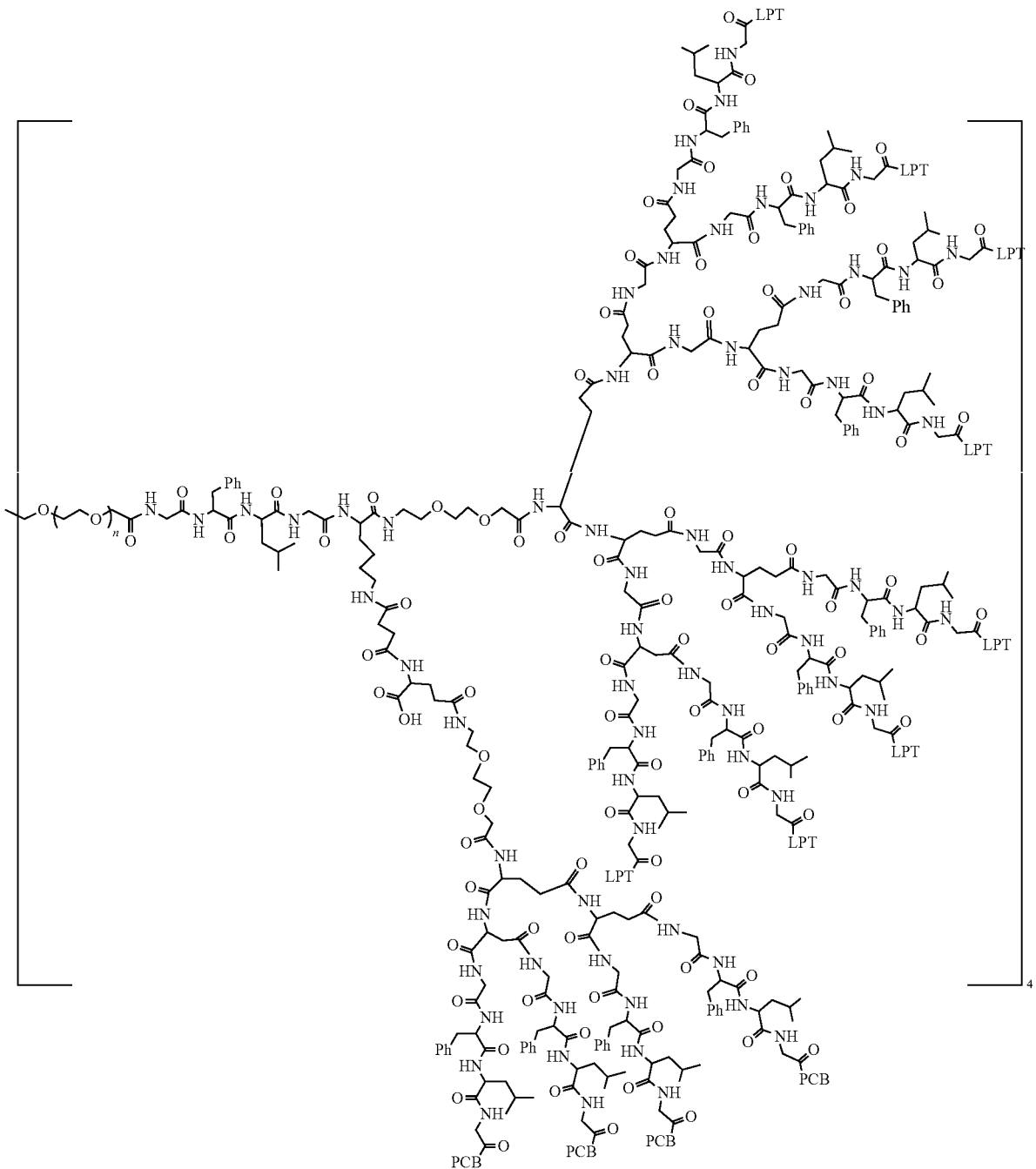

The reactant Compound 33-27 (0.5 g) was dissolved in DMF (20 mL) in a 250 mL flask, and then the flask was placed in a low-temperature constant temperature bath (−5° C.). The mixed solution was stirred for 30 min and DIEA (0.0038 mL) was then added dropwise to the solution. 4ARM-SCM-40K (0.32 g, 0.0078 mmol) was then added and dissolved in the above solution and the resulting solution was then stirred slowly at room temperature in the dark to react. 0.5 g of unreacted raw material was recovered. Dichloromethane (10 mL) and toluene (10 mL) were added and the resulting solution was treated by ultrasonic to be a homogeneous phase and then evaporated to dryness with a rotary evaporator; such operation was repeated three times. The obtained product was put into reaction again. At the end of the reaction, methyl tert-butyl ether (150 mL) was added in a conical flask, the reaction solution was poured into the conical flask, and then n-hexane (200 mL) was added to precipitate the product. Suction filtering was then carried out to obtain a solid product. The operations of dry sample loading and column chromatography were carried out. With the column height of 5 cm, gradient elution with 7% methanol/dichloromethane-1% ammonia water:10% methanol/dichloromethane was carried out, and the elution product was evaporated to dryness and dried in vacuum. 0.5 g of the product was obtained.

MALDI-TOF MS: 93854.80-95498.54

33-65

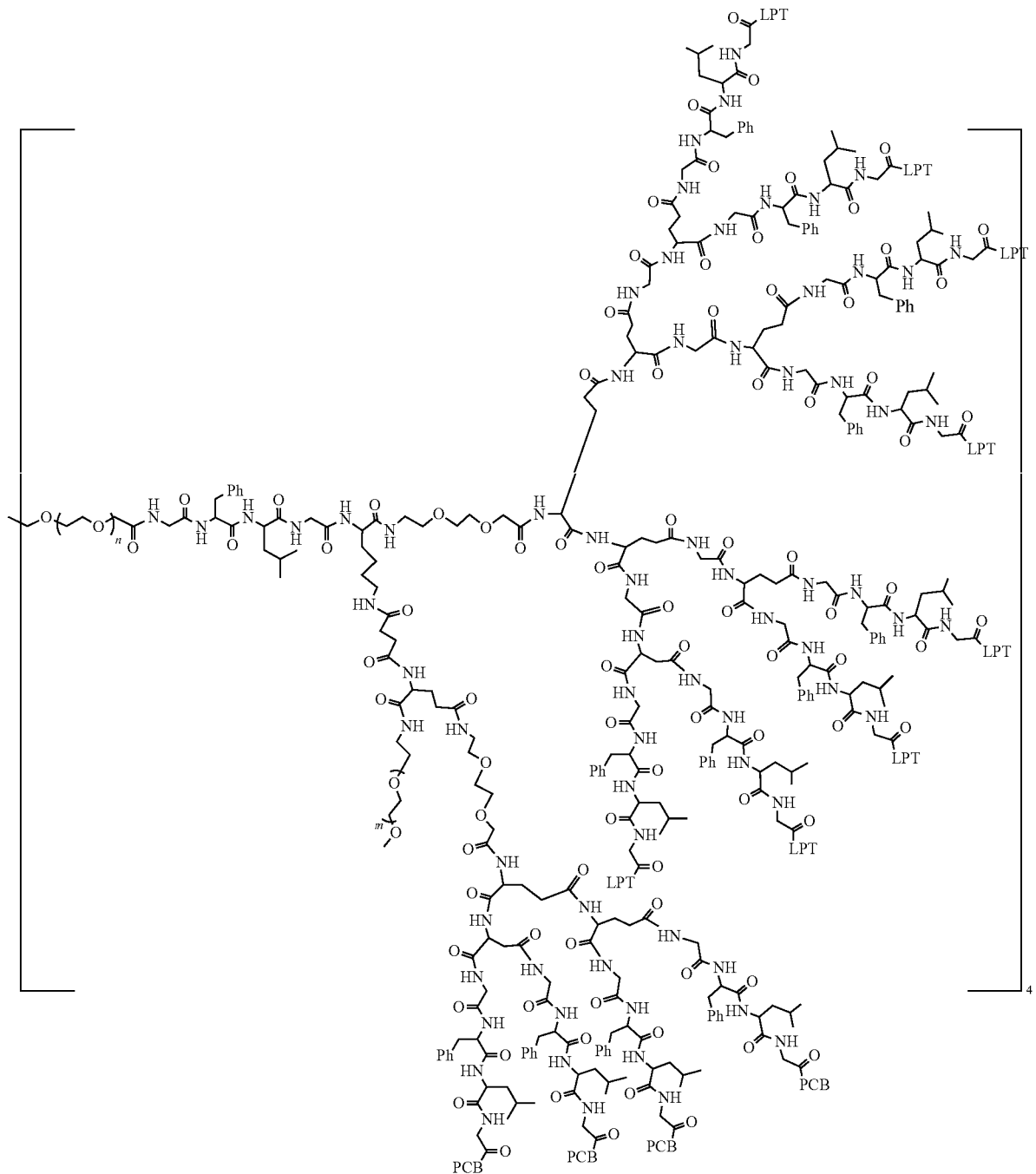

M-NH₂HCL-20K (0.64 g, 0.0317 mmol), Compound 33-37 (0.7 g, 0.00528 mmol), HOBT (0.0042 g, 0.0317 mmol), and HBTU (0.012 g, 0.0317 mmol) were added into a 250 mL flask and a DMF solution (20 mL) was then added; the resulting solution was then placed in a low-temperature constant temperature bath (−5° C.); 30 min later, DIEA (0.017 mL) was then added dropwise; 1 h later, the mixed solution was taken out and slowly stirred in the dark at a room temperature to react. At the end of the reaction, methyl tert-butyl ether (50 mL) and n-hexane (150 mL) were then added to the reaction solution to precipitate a solid and the solid product was then filtered out by suction. The obtained solid was dissolved with a solution (20% methanol:80% dichloromethane) (50 mL); and then the operations of dry sample loading and column chromatography were carried out. With the column height of 5 cm, gradient elution with 5% methanol/dichloromethane-1% ammonia water:10% methanol/dichloromethane was carried out, the elution product was evaporated to dryness and then dissolved with absolute ethanol (5 mL) and dichloromethane (2 mL); the obtained solution was treated by ultrasonic to obtain a homogeneous phase; n-hexane (100 mL) was added and then suction filtering was carried out. The process of dissolution and precipitation was repeated three times. The obtained product was dried in vacuum. 0.6 g of the product was finally obtained.

$^1$H-NMR (400 MHz, DMSO-$d_6$) δ 8.97-8.92 (m, 27H), 8.78-8.73 (m, 28H), 8.69-8.64 (m, 31H), 8.21-8.13 (m, 80H), 8.08-8.03 (m, 46H), 7.95 (s, 35H), 7.34-7.27 (m, 86H), 7.22-7.18 (m, 282H), 7.09-7.06 (m, 225H), 6.93-6.96 (m, 194H), 6.70-6.66 (m, 24H), 6.55-6.52 (m, 17H), 5.29-5.23 (m, 51H), 4.78-4.67 (m, 79H), 4.60-4.52 (m, 74H), 4.38-4.18 (m, 215H), 3.53-3.48 (m, 13966H), 3.24 (s, 51H), 3.18-3.10 (m, 176H), 3.07-3.04 (m, 44H), 3.03-2.99 (m, 74H), 2.89 (s, 81H), 2.73 (s, 50H), 2.70-2.67 (m, 33H), 2.43-2.39 is (m, 53H), 2.35-2.28 (m, 86H), 1.39-1.35 (m, 57H), 1.28-1.18 (m, 558H), 0.95-0.66 (m, 312H).

Example 7: Synthesis of Compound 24-184

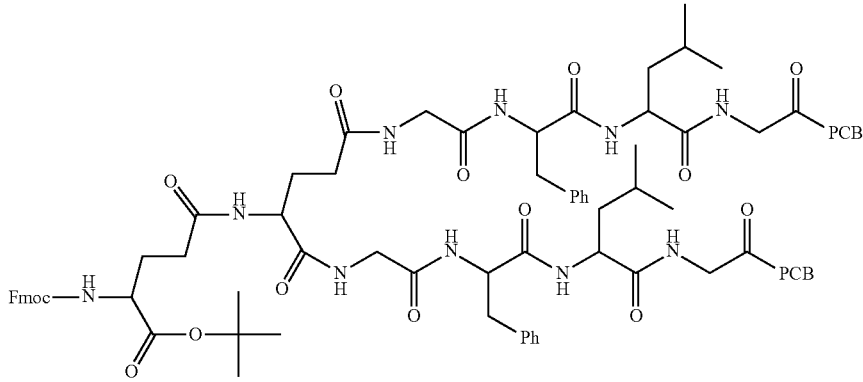

33-6

Compound 33-5 (synthesized according to the synthesis route of Compound 31-82) (3.0 g, 1.73 mmol), Fmoc-Glu-OtBu (0.72 g, 1.73 mmol), HOBT (0.34 g, 2.59 mmol), and HBTU (0.98 g, 2.59 mmol) were added into a 250 mL flask and DMF solution (35 mL) was then added; the resulting solution was placed in a low-temperature constant temperature bath (−5° C.) and stirred for 30 min, and DIEA (1.2 mL, 7.78 mmol) was then added dropwise; 1 h later, the mixed solution was taken out and stirred at room temperature to react. At the end of the reaction, methyl tert-butyl ether (50 mL) and n-hexane (150 mL), were added for precipitation, the supernatant was discarded, methyl tert-butyl ether and n-hexane were then added again; the precipitation operation was carried out three times to obtain a powder, and the powder was then filtered out by suction. The solid product was subjected to operations of dry sample loading, column chromatography and gradient elution with 3%-6% methanol/dichloromethane. 1.5 g of the product was obtained with a yield of 40%.

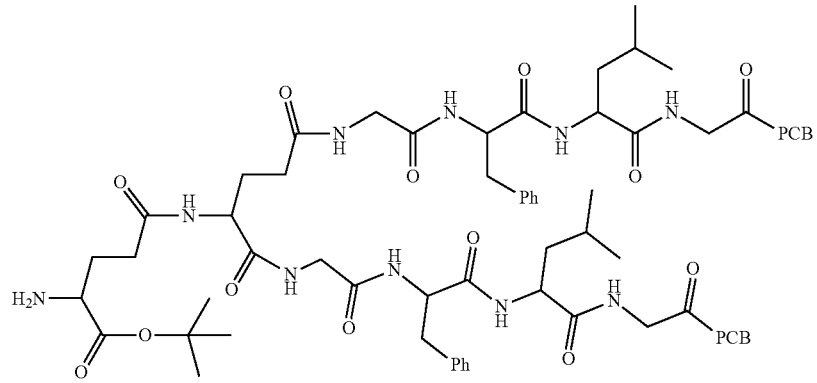

33-9

Compound 33-6 (1.5 g, 0.6936 mmol) was weighed and dissolved with DMF solution (80 mL). Morpholine (1.8 mL, 20.8 mmol) was then added to the resulting solution, and the obtained solution was stirred at room temperature to react. At the end of the reaction, methyl tert-butyl ether (50 mL) and n-hexane (150 mL), were added for precipitation, the supernatant was discarded, methyl tert-butyl ether and n-hexane were then added again; the precipitation operation was carried out three times, and suction filtering was then carried out. 1.3 g of the product was obtained with a yield of 100%.

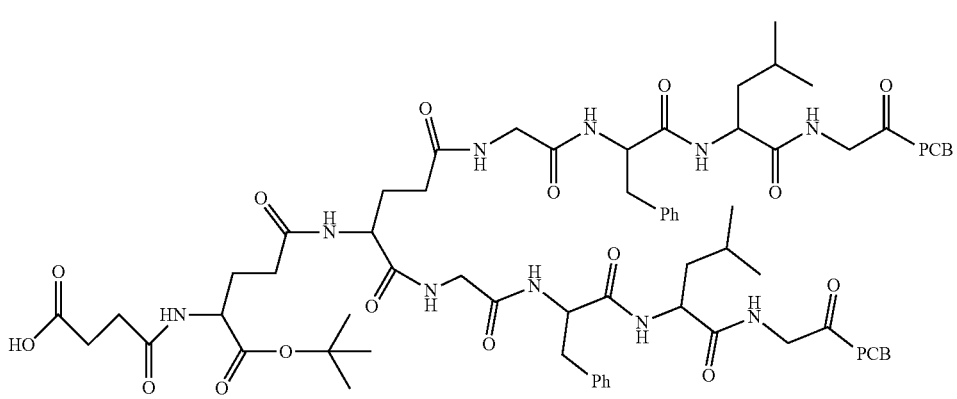

33-11

Compound 33-9 (1.3 g, 0.6936 mmol) was added into a 250 mL flask and dissolved with a DMF solution (40 mL) and the resulting solution was then placed in a low-temperature constant temperature bath (−5° C.); DIEA (0.45 mL, 2.77 mmol) was then added dropwise to the mixed solution, and 30 min later, succinic anhydride (0.208 g, 2.0808 mmol) was added; the resulting solution was stirred to react. At the end of the reaction, the reaction solution was precipitated with methyl tert-butyl ether (100 mL) and n-hexane (200 mL) to obtain a powder; suction filtering was then carried out; then, the obtained solid product was dissolved with 20% methanol/dichloromethane, silica gel powder was then added, and the obtained solution was evaporated to dryness. The operations of column chromatography and gradient elution with 1% ammonia water+6%-8% methanol/dichloromethane were carried out. 1.1 g of the product was obtained with a yield of 73%.

MALDI-TOF MS: [M+H$^+$] 2040.11, [M+Na$^+$] 2062.01.

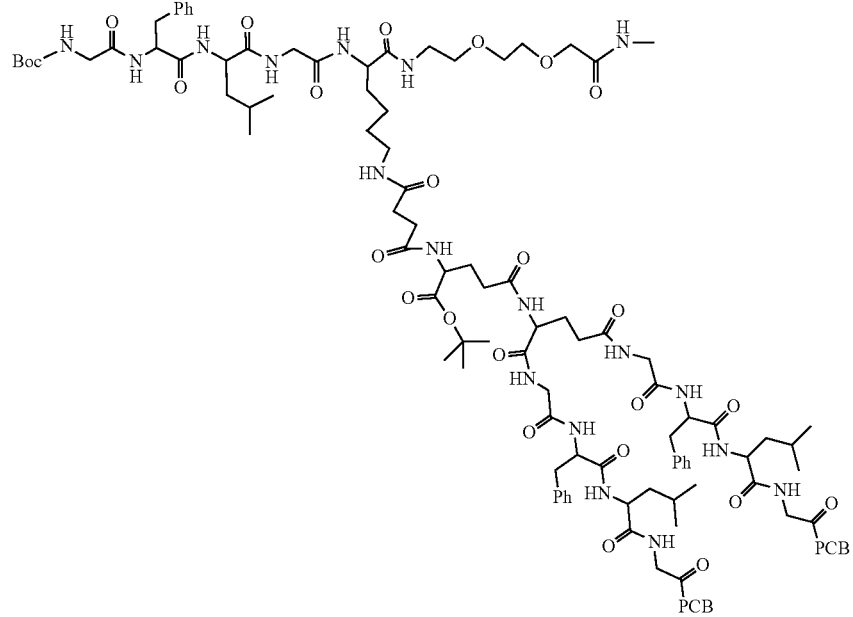

24-153

-continued

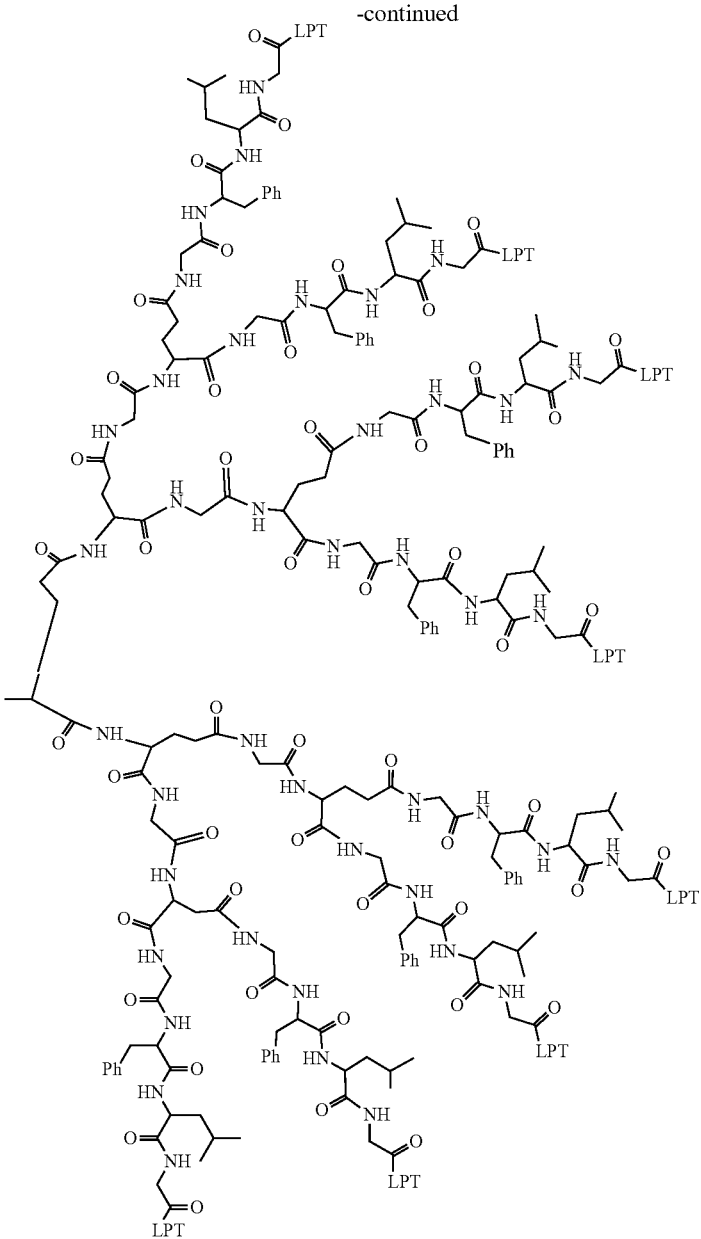

Compound 24-151 (synthesized in the same way as Compound 24-122) (0.9 g, 0.0948 mmol), Compound 33-11 (0.2108 g, 0.1043 mmol), HBTU (0.0539 g, 0.1422 mmol), and HOBT (0.0192 g, 0.1422 mmol) were weighed and added into a 250 mL flask and then completely dissolved with the DMF solution (40 mL) by ultrasonic, the resulting solution was stirred at −5° C. for 30 min, DIEA (0.0708 mL, 0.4266 mmol) was slowly added dropwise, and the mixed solution was stirred at a low temperature for 2 h and then placed at room temperature to react to the end. At the end of the reaction, methyl tert-butyl ether (200 mL) was added to the reaction solution to precipitate a solid product; the solid product was then filtered out by suction and dissolved with a solvent (20% methanol/dichloromethane); silica gel powder was then added to the obtained solution; the obtained solution was then evaporated to dryness with a rotary evaporator and the operations of column chromatography and gradient elution with 1% ammonia water+6%-7% methanol/dichloromethane were carried out. 0.8 g of the product was obtained with a yield of 80%.

311 312
24-155
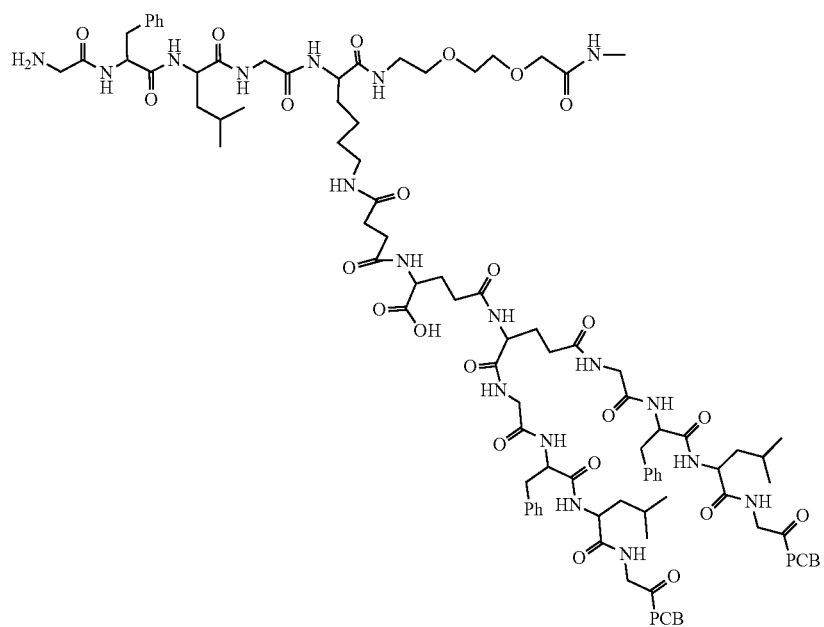
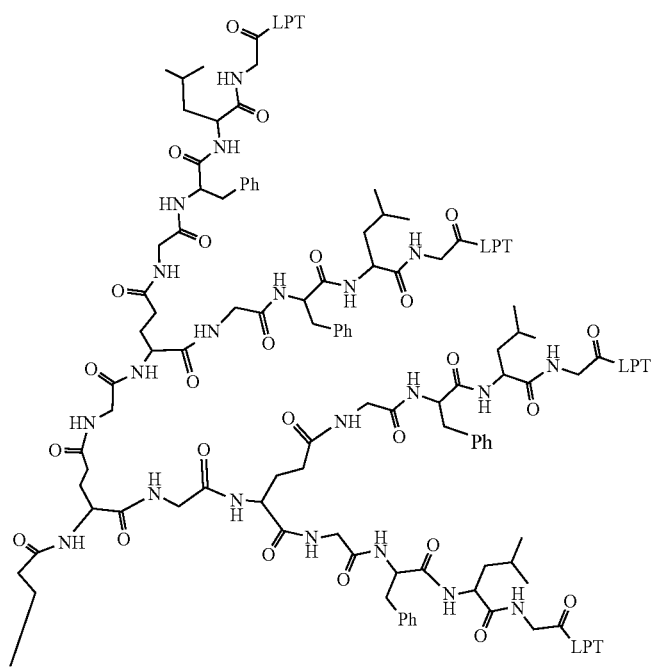

-continued

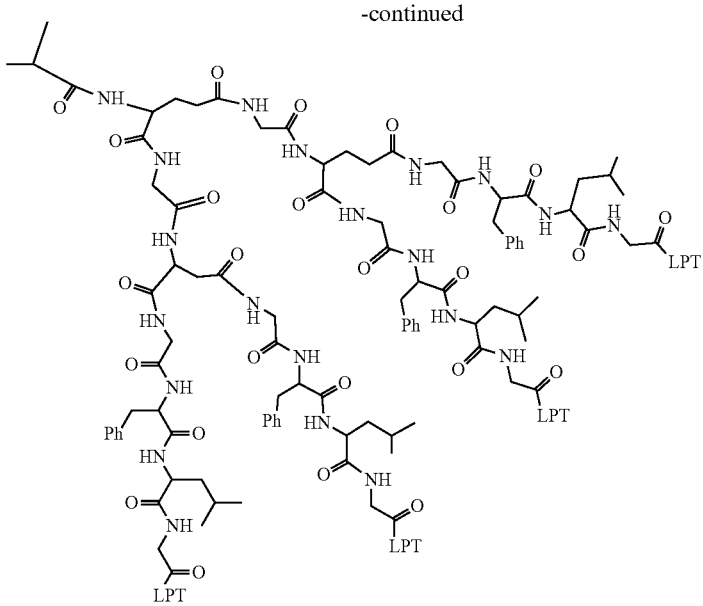

Compound 24-153 (0.8 g, 0.0701 mmol) was weighed and added into a 250 mL reaction flask, dichloromethane (5 mL) and TFA (0.2083 mL, 2.8038 mmol) were then added sequentially, and the obtained solution was treated by ultrasonic until Compound 24-153 was completely dissolved; the mixed solution was stirred at room temperature to react. At the end of the reaction, the reaction solution was evaporated to dryness and dichloromethane was removed; then, methyl tert-butyl ether (150 mL) was added to the reaction solution to precipitate a solid product; the solid product was then filtered out by suction and dissolved with a solvent (20% methanol/dichloromethane); silica gel powder (5 g) was then added to the obtained solution; the obtained solution was then evaporated to dryness with a rotary evaporator and the operations of column chromatography and gradient elution with 1% is ammonia water+5%-8% methanol/dichloromethane were carried out. 0.7 g of the product was obtained with a yield of 89%.

24-159

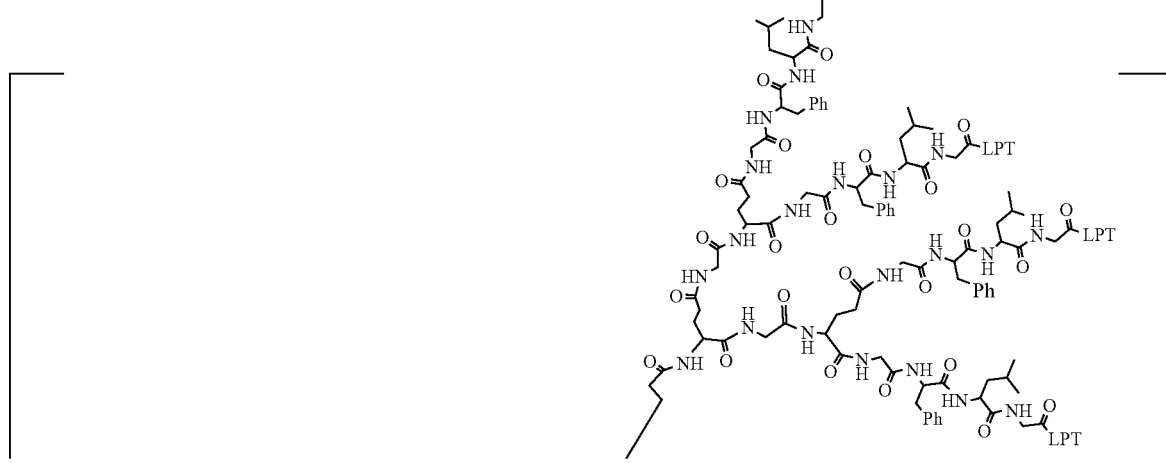

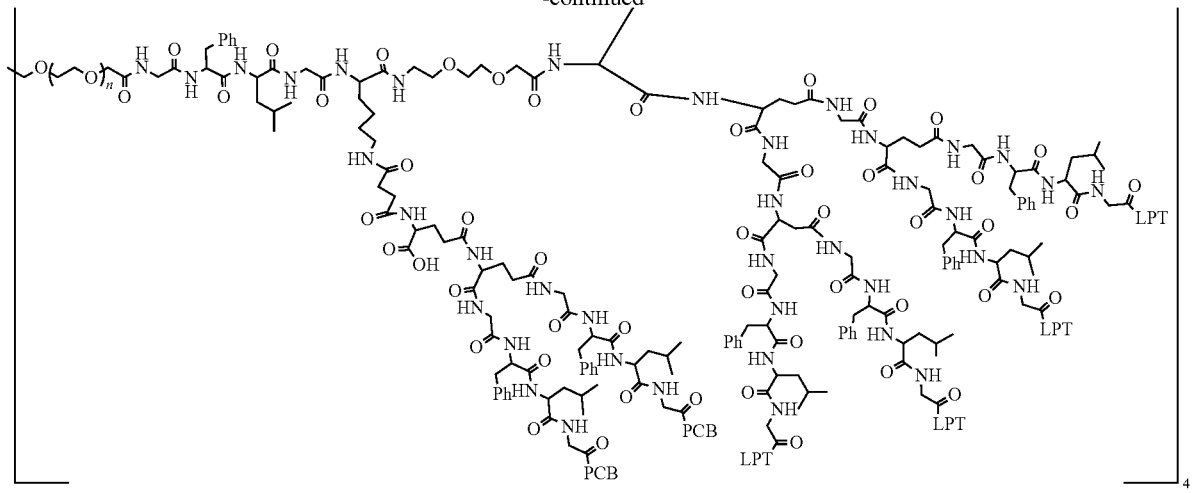

Compound 24-155 (0.5 g, 0.0444 mmol) was weighed and added into a 250 mL reaction flask and then dissolved with DMF (15 mL), DIEA (0.1800 mL, 1.7756 mmol) and 4ARM-SCM-40K (0.3880 g, 0.0092 mmol) were then added to the resulting solution sequentially and dissolved by ultrasonic. The obtained solution reacted in the dark at a low speed stirring. At the end of the reaction, methyl tert-butyl ether (200 mL) was added to the reaction solution to precipitate a solid and the solid was then filtered out by suction; the obtained solid product was then dissolved with 20% methanol/dichloromethane, silica gel powder (5 g) was then added, and the obtained solution was evaporated to dryness. The operations of column chromatography and gradient elution with 10%-30% methanol/dichloromethane were carried out. 0.4 g of the product was obtained with a yield of 50%.

$^1$H-NMR (400 MHz, DMSO-d$_6$) δ 10.00 (d, J=111.0 Hz, 27H), 8.99 (d, J=53.2 Hz, 19H), 8.74 (s, 23H), 8.54 (s, 29H), 8.10 (d, J=81.0 Hz, 233H), 7.92-7.71 (m, 55H), 7.25 (s, 383H), 6.99-6.84 (m, 16H), 6.74-6.52 (m, 3H), 5.24 (s, 56H), 4.63 (m, 40H), 4.24 (s, 102H), 3.77-3.41 (m, 3644H), 3.01 (s, 110H), 2.89 (s, 54H), 2.69 (s, 109H), 2.14 (d, J=121.5 Hz, 160H), 1.34 (m, 809H), 0.84 (s, 277H).

24-184

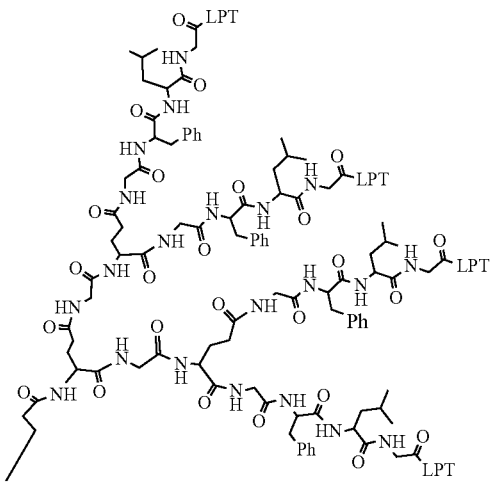

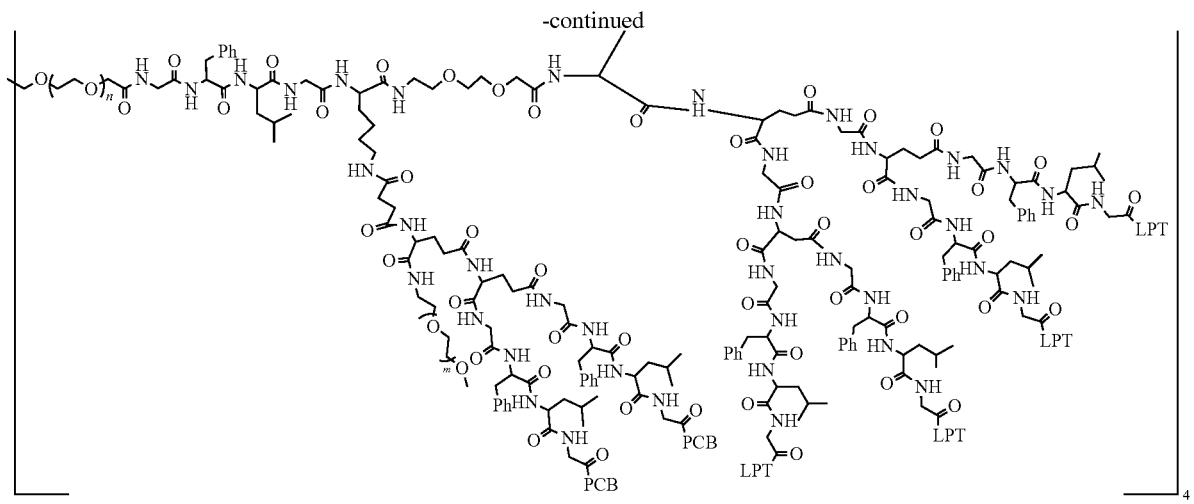

The reactants, Compound 24-159 (0.4 g, 0.0046 mmol), M-NH₂HCL-20K (0.5640 g, 0.0277 mmol), HBTU (0.0157 g, 0.0414 mmol), and HOBT (0.0056 g, 0.0414 mmol) were weighed and added in a 250 mL reaction flask and dissolved with DMF (20 mL) by ultrasonic; the obtained solution was stirred at −5° C. for 30 min; DIEA (0.0205 mL, 0.1242 mmol) was slowly added dropwise and the obtained solution was first stirred for 1 h and then slowly stirred in the dark at room temperature to react. At the end of the reaction, methyl tert-butyl ether (150 mL) and n-hexane (50 mL) were added to precipitate the reaction solution, suction filtering was carried out, and the solid product was dissolved with a mixed solvent (20% methanol/dichloromethane); silica gel was added to the obtained solution, and the operations of evaporation, dry sample loading and column chromatography were carried out. Gradient elution with 1% ammonia+ 5%-10% methanol/dichloromethane was carried out, and the pure product was collected and evaporated to dryness, and then dissolved with absolute ethanol (10 mL) and dichloromethane (10 mL) by ultrasonic treatment; next, methyl tert-butyl ether (150 mL) and n-hexane (50 mL) were added, suction filtering was carried out, and the obtained solid was further dissolved with absolute ethanol (10 mL) and dichloromethane (10 mL); the obtained solution was precipitated with methyl tert-butyl ether and n-hexane and the precipitation operation was repeated three times. 0.6 g of the product was obtained with a yield of 77.9%.

¹H-NMR (400 MHz, DMSO-d₆) δ 10.15 (s, 4H), 9.85 (s, 9H), 8.94 (s, 4H), 8.74 (s, 9H), 8.52 (s, 13H), 8.28-7.98 (m, −207H), 7.79 (s, 63H), 7.45 (s, 28H), 7.32-7.09 (m, 330H), 6.67-6.51 (s, 17H), 5.76 (s, 42H), 5.24 (s, 50H), 4.74-4.57 (m, 154H), 4.36-4.21 (m, 325H), 3.70-3.60 (m, 477H), 3.51 (s, 5459H), 3.25-3.11 (m, 37H), 3.02 (d, J=26.1 Hz, 94H), 2.89 (s, 74H), 2.70-2.66 (m, 128H), 2.35-2.29 (m, 38H), 2.11 (s, 16H), 1.85-1.48 (m, 140H), 1.25-1.23 (m, 37H), 0.82 (s, 207H).

Example 8: Synthesis of Compound 25-129

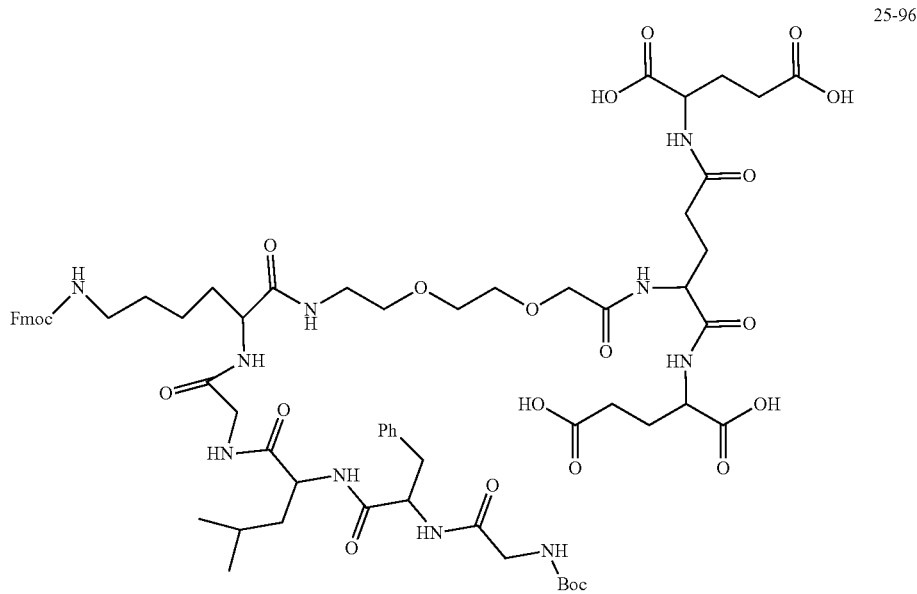

Compound 24-95 (1.1433 g, 0.6586 mmol, home-made) and 10% Pd/C (50 mg) were added into a hydrogenation reactor and then dissolved with DMF (30 mL); the hydrogenation reactor was sealed and $H_2$ was then introduced into the reactor until the pressure in the reactor reached 1.6 MPa; the obtained solution in the hydrogenation reactor was stirred overnight at room temperature. At the end of the reaction, the hydrogenation reactor was taken out, the reaction solution was evenly added dropwise to a sand core funnel filled with compacted diatomaceous earth and suction filtering was carried out. The diatomaceous earth was washed three times with DMF (20 mL×3) until there was no product in the diatomaceous earth, and then the reaction product solution was obtained.

in a 500 mL round-bottomed flask and then dissolved with DMF (65 mL), and the obtained solution was stirred for about 30 min at −5° C.; then, DIEA (1.4 mL, 8.5289 mmol) was slowly added dropwise; and then the reaction solution in the flask was further stirred for 2 h at −5° C. At the end of the reaction, n-hexane (150 mL) and methyl tert-butyl ether (30 mL) were first added to precipitate the reaction solution; the supernatant was discarded; and then n-hexane (150 mL) and methyl tert-butyl ether (30 mL) were added to the lower oily solution for precipitation, and the precipitation operation was repeated three times to obtain an oily solid. Then, the oily solid was dissolved with dichlorometh-

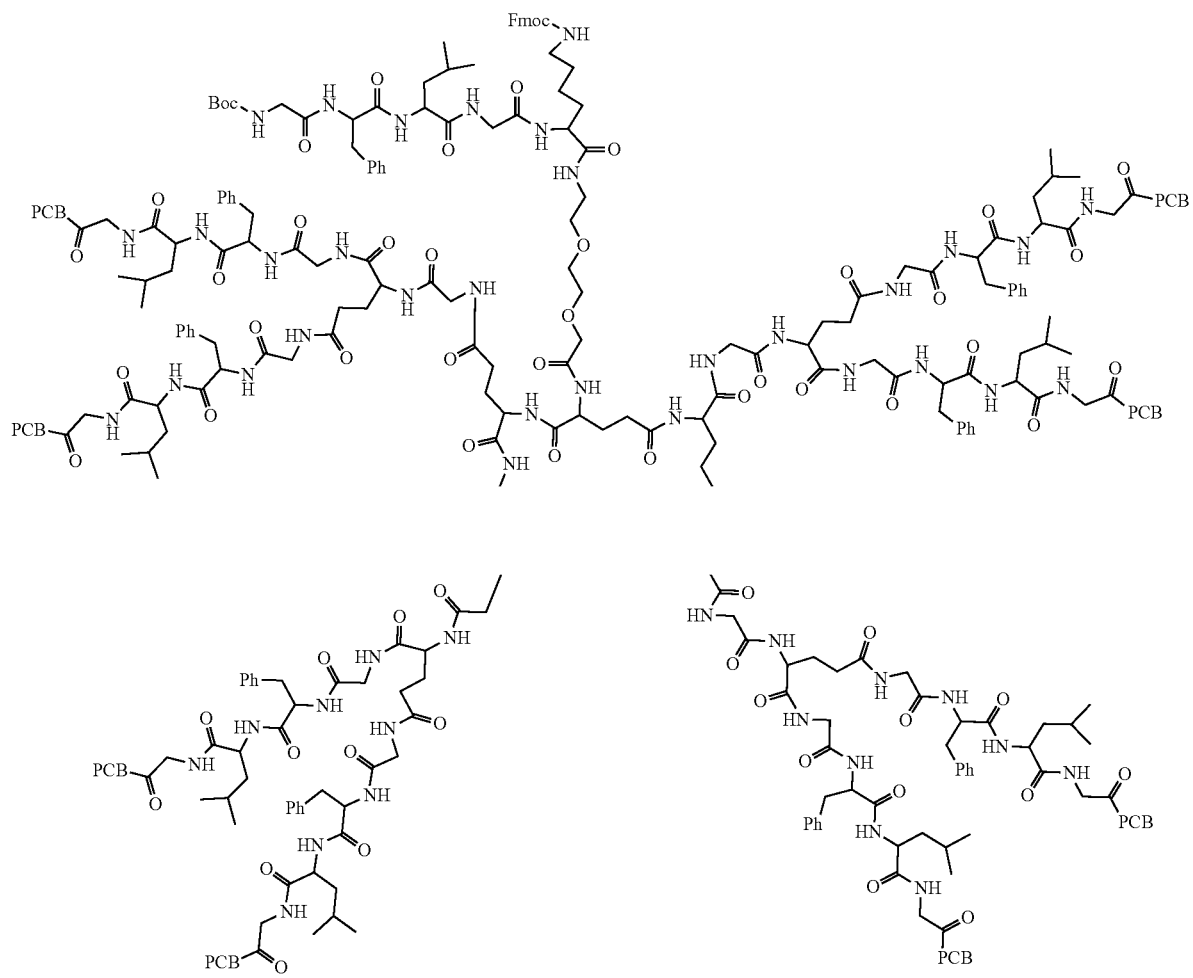

25-116

The solution of Compound 25-96 (0.69 g, 0.5017 mmol), HBTU (1.1416 g, 3.0101 mmol), HOBT (0.4067 g, 3.0101 mmol), and Compound 25-114 (4.0 g, 2.2074 mmol, synthesized in the same way as Compound 31-84) were added ane (10 mL) and then precipitated with methyl tert-butyl ether (150 mL) to obtain a powdery solid, and the solid product was then filtered out and dried. 5.6 g of Product 25-116 was obtained with a yield of 100%.

25-117

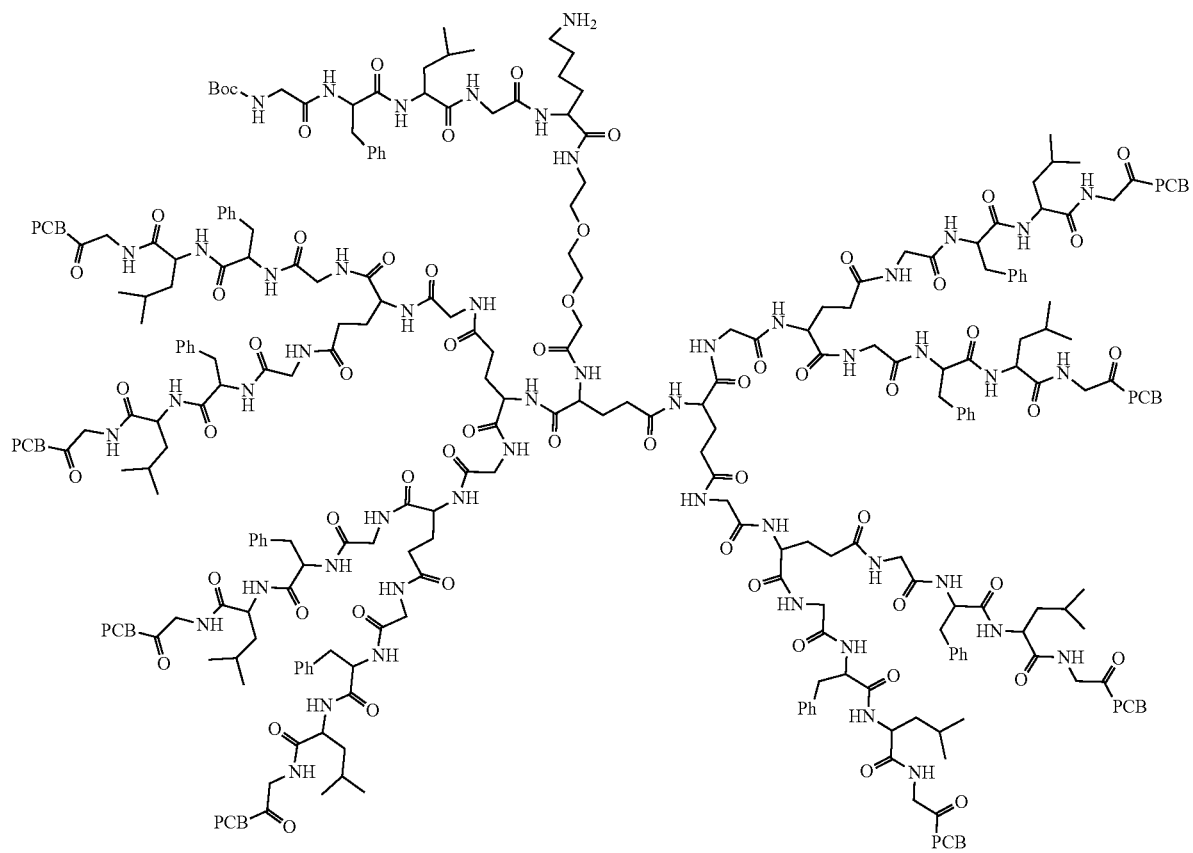

Compound 25-116 (4.2904 g, 0.5017 mmol) was added in a 500 mL round-bottomed flask and then dissolved with dichloromethane (10 mL), morpholine (0.7 mL, 7.5255 mmol) was then added with stirring, and the mixed solution was stirred for 2 h at room temperature to react. At the end of the reaction, n-hexane (150 mL) and methyl tert-butyl ether (30 mL) were first added to precipitate the reaction solution; the supernatant was discarded; and then n-hexane (150 mL) and methyl tert-butyl ether (30 mL) were added to the lower oily solution for precipitation, and the precipitation operation was repeated three times to obtain an oily solid. Then, the oily solid was dissolved with dichloromethane (10 mL) and then precipitated with methyl tert-butyl ether (150 mL) to obtain a powdery solid, and the solid product was then filtered out. The solid product was then dissolved with a mixed solvent (20% methanol/dichloromethane) (60 mL), 70 mL of silica gel powder was then added, and the obtained solution was then evaporated to dryness. The operations of dry sample loading, column chromatography and elution with eluent (1% ammonia water:5%-8% methanol:94%-91% dichloromethane) were carried out, and the elution solution was then collected, concentrated, evaporated to dryness and dried. 2.3 g of Product 25-117 was obtained with a yield of 55.04%.

$^1$H-NMR (400 MHz, DMSO-d$_6$) δ 10.17 (s, 11H), 8.98 (m, 11H), 8.06 (m, 41H), 7.93-7.80 (m, 12H), 7.72 (s, 4H), 7.48 (m, 8H), 7.38 (s, 3H), 7.18 (m, 35H), 6.94 (s, 1H), 5.98 (s, OH), 5.84-5.78 (m, 7H), 5.53 (s, 1H), 5.32 (s, 3H), 4.98 (s, 7H), 4.71-4.13 (m, 22H), 4.12-3.94 (m, 12H), 3.93-3.88 (m, 2H), 3.86-3.43 (m, 64H), 3.17 (d, J=5.2 Hz, 19H), 3.12 (s, 14H), 3.04 (m, 13H), 2.89 (s, 4H), 2.70 (m, 11H), 2.41 (s, 22H), 2.31 (m, 20H), 2.22 (s, 28H), 2.00 (m, 5H), 1.81 (m, 39H), 1.53 (m, 38H), 1.40 (s, 2H), 1.34 (s, 9H), 1.30-1.04 (m, 21H), 0.84 (m, 54H).

25-121

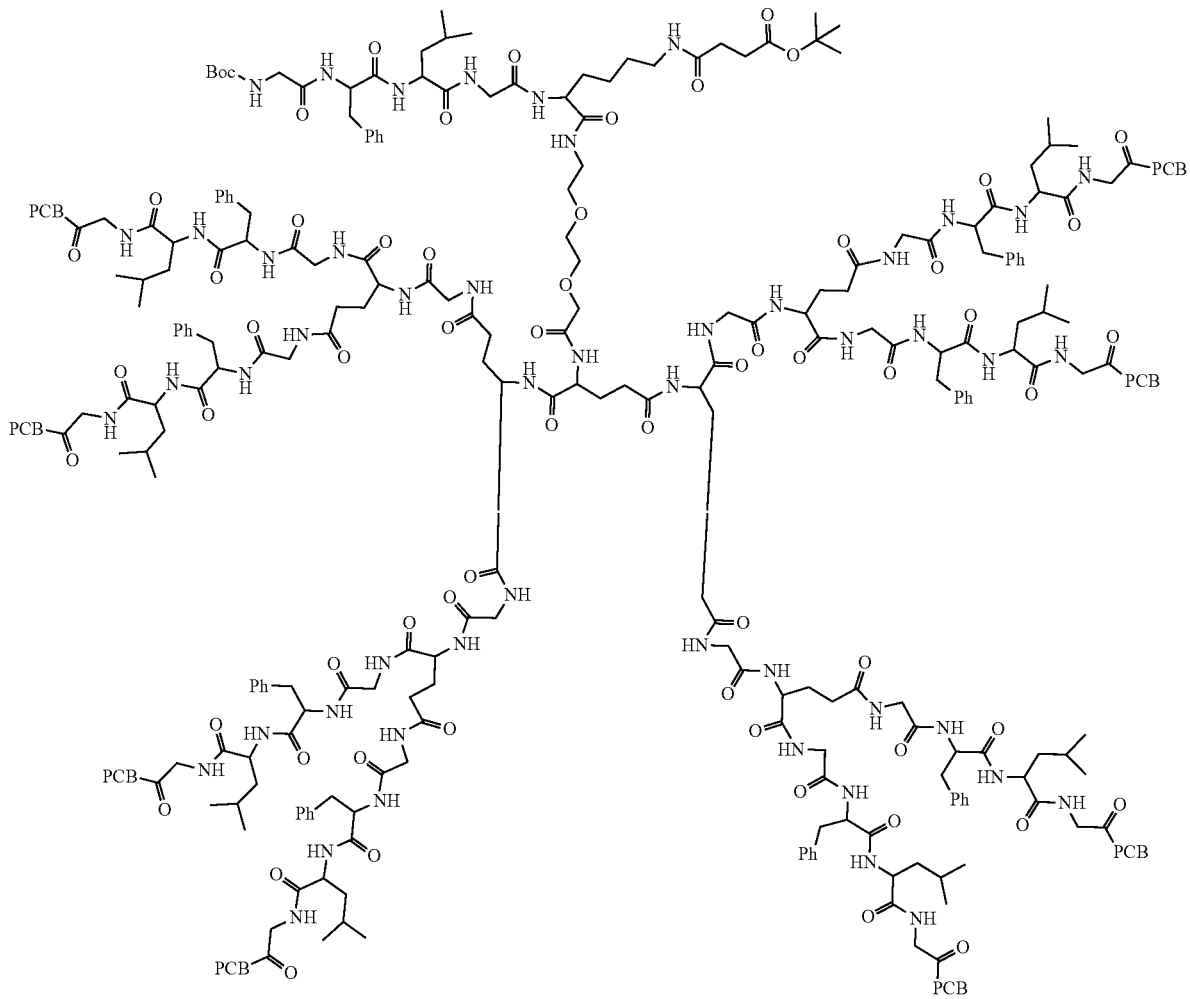

Compound 25-117 (2.3 g, 0.2761 mmol), HBTU (0.1571 g, 0.4142 mmol), HOBT (0.0560 g, 0.4142 mmol) and mono-tert-butyl succinate (0.0529 g, 0.3037 mmol) were added in a 500 mL round-bottomed flask and dissolved with DMF (30 mL), and the obtained solution in the reaction flask was stirred for about 30 min at −5° C.; then, DIEA (0.3 mL, 1.3805 mmol) was slowly added dropwise; the obtained solution was further stirred at −5° C. for 30 min to react, and then the reaction solution was placed at room temperature to react overnight. At the end of the reaction, n-hexane (100 mL) and methyl tert-butyl ether (20 mL) were added to precipitate the reaction solution; the supernatant was discarded; and then n-hexane (150 mL) and methyl tert-butyl ether (30 mL) were added to the lower oily solution for precipitation, and the precipitation operation was repeated three times to obtain an oily solid. Then, the oily solid was dissolved with dichloromethane (10 mL) and then precipitated with methyl tert-butyl ether (150 mL) to obtain a powdery solid, and the solid product was then filtered out. At last, the solid product was then dissolved with a mixed solvent (20% methanol/dichloromethane) (50 mL), 50 mL of silica gel powder was then added, and the obtained solution was then evaporated to dryness. The operations of dry sample loading, column chromatography and elution with eluent (1% ammonia water:5%-6% methanol:94%-93% dichloromethane) were carried out, and the elution solution was then collected, concentrated, evaporated to dryness and dried. 2.0 g of Product 25-121 was obtained with a yield of 85.36%.

$^1$H-NMR (400 MHz, DMSO-d$_6$) δ 10.14 (s, 11H), 8.94 (s, 11H), 8.08 (m, 41H), 7.87 (m, 11H), 7.75 (s, 4H), 7.48 (m, 8H), 7.39 (m, 3H), 7.19 (m, 35H), 6.90 (s, 2H), 5.87-5.76 (m, 9H), 5.32 (s, 1H), 5.00 (s, 6H), 4.39 (m, 31H), 4.09 (m, 4H), 3.97 (m, 14H), 3.62 (m, 50H), 3.47 (m, 12H), 3.15 (m, 30H), 3.02 (m, 14H), 2.89 (s, 4H), 2.72 (m, 17H), 2.41 (s, 26H), 2.30 (s, 19H), 2.24 (m, 19H), 2.13 (s, 9H), 2.00 (m, 3H), 1.81 (m, 41H), 1.56 (m, 38H), 1.40 (s, 1H), 1.34 (s, 18H), 1.23 (m, 14H), 0.84 (m, 48H).

25-122

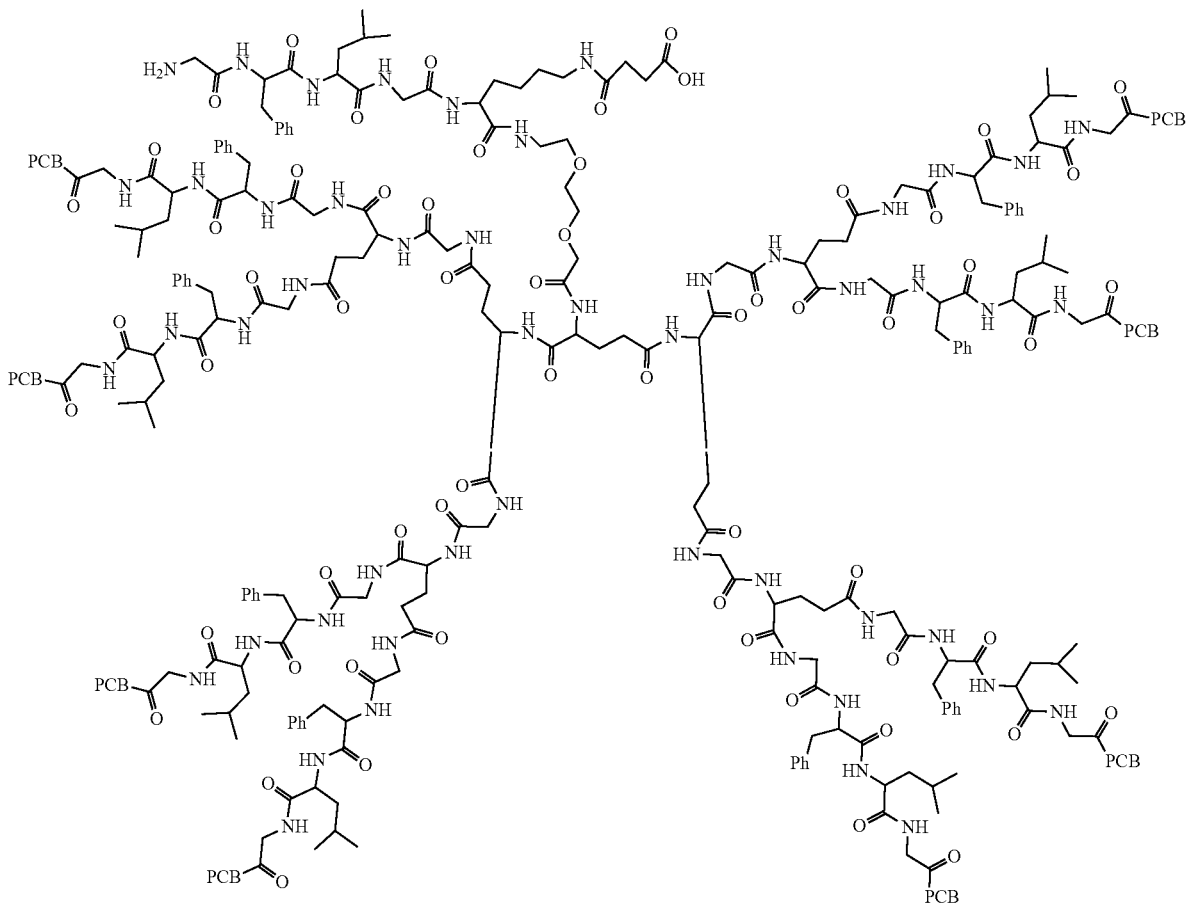

Compound 25-121 (2.0 g, 0.2357 mmol) was added in a 500 mL round-bottomed flask and then dissolved with dichloromethane (5 mL), TFA (0.3 mL, 3.5354 mmol) was then added with stirring, and the mixed solution in the reaction flask was stirred overnight at room temperature to react. At the end of the reaction, the reaction solution was first concentrated under reduced pressure and evaporated to remove dichloromethane. Then, methyl tert-butyl ether (150 mL) was added for precipitation and a powdery solid was obtained: the solid product was then filtered out, and the filter cake was washed with methyl tert-butyl ether (20 mL×3). The filter cake was then dissolved with a mixed solvent (50 mL) (20% methanol/dichloromethane), 30 mL of silica gel powder was then added, and the obtained solution was then evaporated to dryness. The operations of dry sample loading, column chromatography and elution with eluent (1% ammonia water:6%-10% methanol:93%-89% dichloromethane) were carried out, and the elution solution was then collected, concentrated, evaporated to dryness and dried. 1.5 g of Product 25-122 was obtained with a yield of 76.41%.

$^1$H-NMR (400 MHz, DMSO-$d_6$) δ 10.17 (s, 8H), 8.94 (s, 8H), 8.47-7.96 (m, 41H), 7.96 (m, 15H), 7.73 (s, 2H), 7.48 (m, 6H), 7.39 (m, 3H), 7.18 (m, 41H), 5.90-5.77 (m, 8H), 4.98 (s, 4H), 4.76-4.14 (m, 28.14H), 4.01 (m, 14H), 3.93-3.50 (m, 63H), 3.14 (m, 30H), 3.07-2.91 (m, 17H), 2.89 (s, 5H), 2.74 (m, 17H), 2.67 (s, 2H), 2.44-2.34 (m, 25H), 2.30 (s, 24H), 2.22 (s, 20H), 2.00 (m, 4H), 1.81 (m, 43H), 1.53 (m, 39H), 1.40 (s, 1H), 1.34 (d, J=6.0 Hz, 5H), 1.25 (m, 14H), 0.84 (m, 48H).

25-125

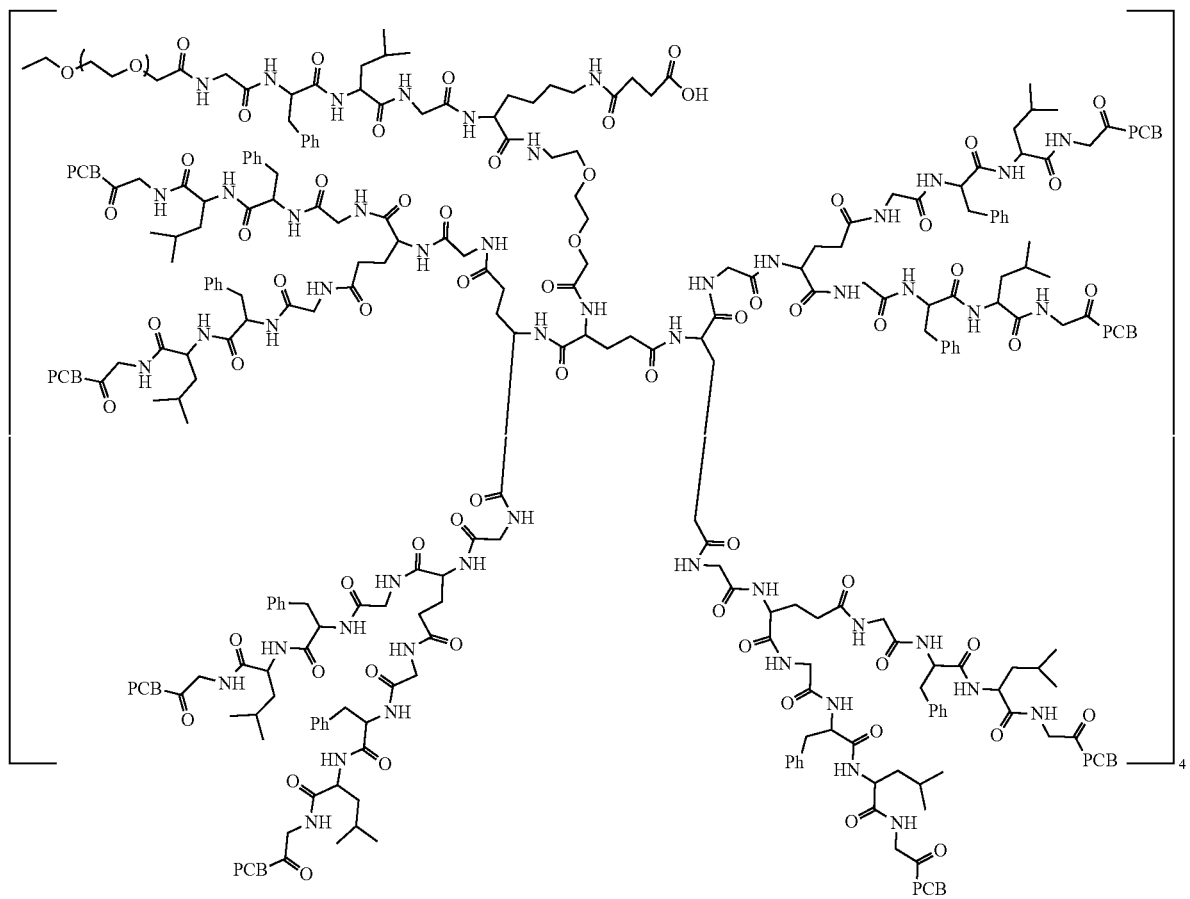

Compound 25-122 (1.5 g, 0.1801 mmol) was added in a 500 mL round-bottomed flask and dissolved with DMF (30 mL), and the obtained solution in the reaction flask was stirred for about 30 min at −5° C.; then, DIEA (0.3 mL, 1.3805 mmol) was slowly added dropwise; the obtained solution was further stirred at −5° C. for 30 min to react, and then 4ARM-SCM-40K (MW: 41958, 1.5113 g, 0.0360 mmol) was added to the reaction solution and the resulting solution was slowly stirred for one week in the dark at room temperature to react. At the end of the reaction, n-hexane (150 mL) was added to precipitate the reaction solution; the supernatant was discarded; and then methyl tert-butyl ether (150 mL) and n-hexane (30 mL) were added to the lower oily solution for precipitation, the powdery solid was obtained, and the solid product was filtered out. The solid product was then dissolved with a mixed solvent (20% methanol/dichloromethane) (60 mL), 60 mL of silica gel powder was then added, and the obtained solution was then evaporated to dryness. The operations of dry sample loading, column chromatography and elution with eluent (1% ammonia water:4%-8% methanol:95%-91% dichloromethane) were carried out, and the elution solution was then collected, concentrated, evaporated to dryness and dried. 0.6125 g of Product 25-125 was obtained with a yield of 22.74%.

$^1$H-NMR (400 MHz, DMSO-$d_6$) δ 10.13 (s, 36H), 8.94 (s, 36H), 8.08 (m, 195H), 7.93-7.74 (m, 91H), 7.48 (m, 43H), 7.31 (d, J=4.2 Hz, 41H), 7.19 (m, 155H), 7.04 (s, 30H), 6.95-6.83 (m, 37H), 5.90-5.74 (m, 68H), 5.32 (m, 36H), 5.14 (d, J=5.3 Hz, 21H), 5.00 (s, 43H), 4.69-4.46 (m, 105H), 4.30 (m, 140H), 3.98 (m, 110H), 3.84 (m, 105H), 3.71-3.66 (m, 106H), 3.51 (s, 3852H), 3.14 (m, 94H), 3.03 (m, 44H), 2.89 (s, 18H), 2.71 (m, 83H), 2.41 (s, 69H), 2.34-2.19 (m, 146H), 2.04-1.68 (m, 211H), 1.53 (m, 174H), 1.36 (m, 99H), 1.22 (m, 447H), 0.84 (m, 192H).

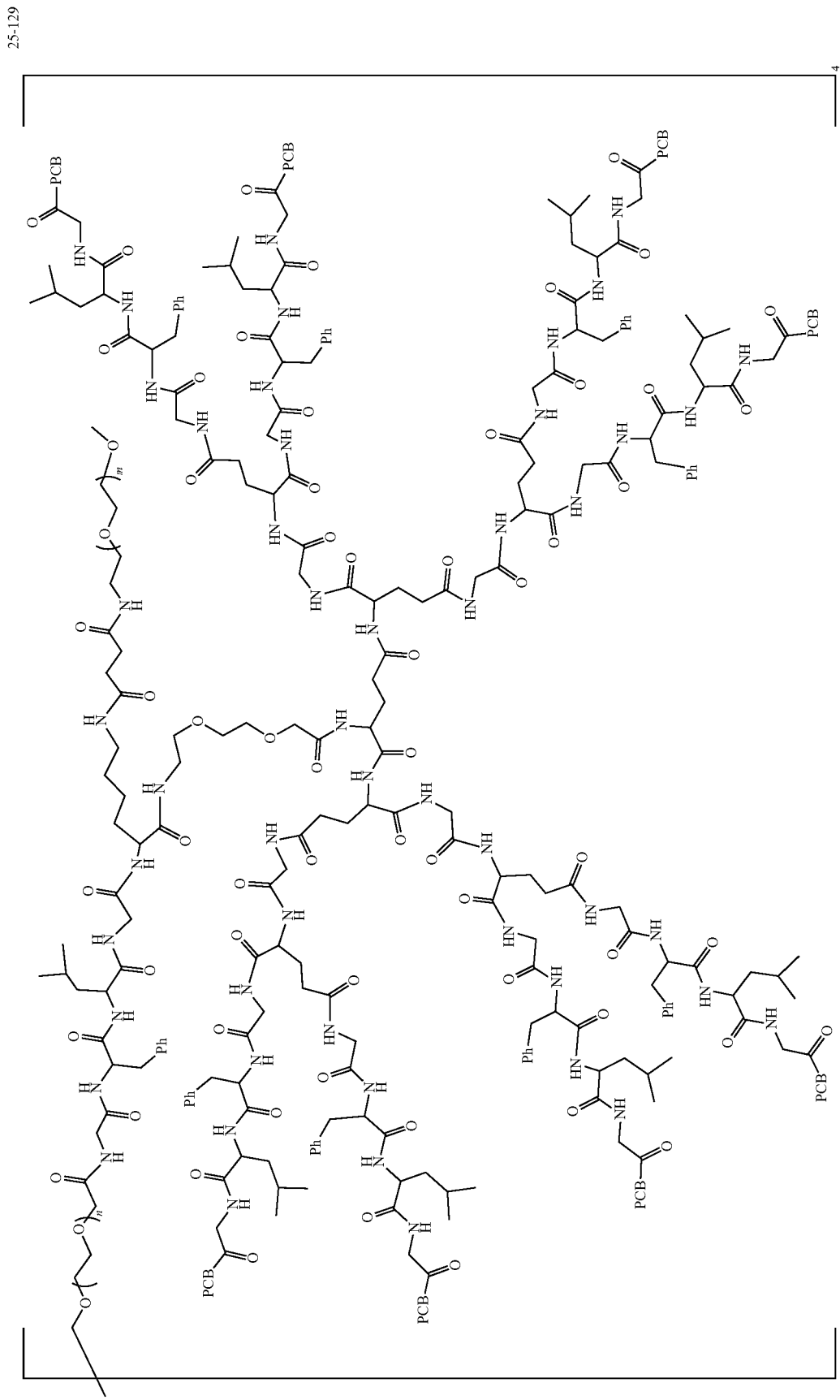

Compound 25-125 (0.6 g, 0.0080 mmol), HBTU (0.0027 g, 0.0722 mmol), HOBT (0.0010 g, 0.0722 mmol), and M-NH$_2$·HCl-10K (0.5061 g, 0.0481 mmol) were added in a 500 mL round-bottomed flask and dissolved with DMF (10 mL), and the obtained solution was stirred for about 30 min at −5° C.; then, DIEA (0.3 mL, 1.3805 mmol) was slowly added dropwise; the obtained solution was further stirred at −5° C. for 10 min to react, and then the reaction solution was placed at room temperature to react for one week. At the end of the reaction, n-hexane (60 mL) and methyl tert-butyl ether (10 mL) were added to precipitate the reaction solution; the supernatant was discarded; and then n-hexane (150 mL) and methyl tert-butyl ether (30 mL) were added to the lower oily solution for precipitation, and the precipitation operation was repeated three times to obtain an oily solid. Then, the oily solid was dissolved with dichloromethane (10 mL) and then precipitated with methyl tert-butyl ether (60 mL) to obtain a powdery solid, and the solid product was then filtered out. The filter cake was then dissolved with a mixed solvent (50 mL) (20% methanol/dichloromethane), 40 mL of silica gel powder was then added, and the obtained solution was then evaporated to dryness. Elution was then carried out with eluent (1% ammonia water:4%-8% methanol:95%-91% dichloromethane), and the elution solution was collected, concentrated and evaporated to dryness. 0.48 g of Product 25-129 was obtained with a yield of 52.0%.

$^1$H-NMR (400 MHz, DMSO-d$_6$) δ 10.16 (s, 173H), 8.99 (m, 115H), 8.09 (m, 286H), 7.88 (m, 78H), 7.81-7.64 (m, 76H), 7.63-7.33 (m, 157H), 7.22 (m, 190H), 6.95 (m, 79H), 6.80-6.60 (m, 87H), 5.95-5.78 (m, 89H), 5.50-5.25 (m, 111H), 5.01 (s, 73H), 4.76-4.31 (m, 259H), 4.31-4.17 (m, 103H), 4.16-3.41 (m, 5482H), 3.25 (m, 16H), 3.22-2.93 (m, 158H), 2.81 (m, 110H), 2.60 (m, 124H), 2.41 (s, 131H), 2.23 (m, 203H), 2.00 (m, 78H), 1.81 (m, 173H), 1.54 (m, 208H), 1.43-0.95 (m, 1092H), 0.93-0.78 (m, 248H).

Example 9: Synthesis of Compound 28-140

28-82

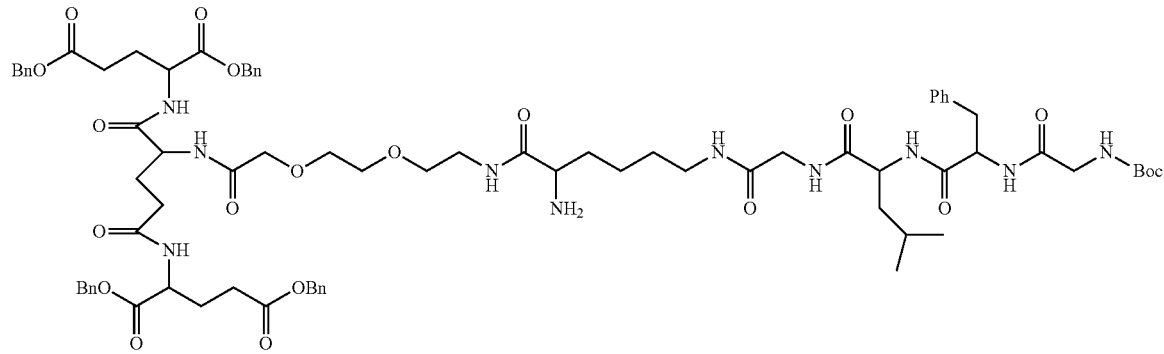

Compound 30-84 (6.9642 g, 4.0117 mmol, home-made) was added into a 500 mL flask and then dissolved with DMF; morpholine (5.2 mL, 60.175 mmol) was added to the obtained solution, and the obtained solution was stirred at room temperature for 1 h to react. At the end of the reaction, the reaction solution was transferred to a 1 L separatory funnel and extracted with deionized water (200 mL) and ethyl acetate (200 mL) to obtain an organic phase; the aqueous phase was washed with ethyl acetate (200 mL×1), and the obtained organic phases were combined, washed with saturated sodium chloride solution (200 mL), then concentrated and evaporated to dryness; 6.07 g of Product 28-82 was obtained with a yield of 100%.

28-83

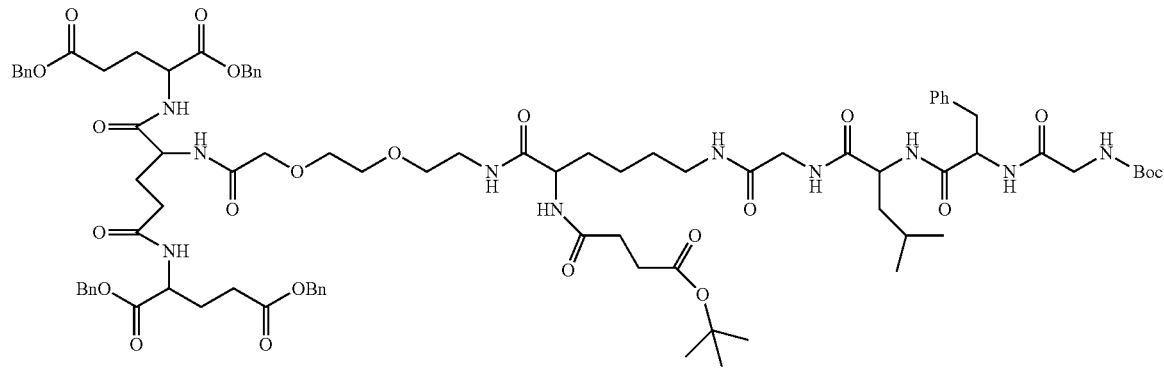

Compound 28-82 (6.0726 g, 4.0117 mmol), mono-tert-butyl succinate (0.7687 g, 4.4129 mmol, purchased from Accela), HBTU (2.2821 g, 6.0176 mmol), and HOBT (0.8132 g, 6.0176 mmol) were added into a 500 mL flask and the mixed solution was stirred at −5° C. for about 20 min to react; DIEA (2.9837 mL, 18.0527 mmol) was then slowly added dropwise, and the obtained solution further reacted at −5° C. for 1 h; and the solution in the flask was stirred overnight at room temperature to react. At the end of the reaction, the reaction solution was transferred to a 1 L separatory funnel and then extracted with a saturated sodium bicarbonate solution (200 mL) and ethyl acetate (200 mL) to obtain an organic phase; the aqueous phase was washed with ethyl acetate (150 mL×1), and the obtained organic phases were combined, washed with a saturated sodium chloride solution (200 mL×1), then concentrated and evaporated to dryness; the solid product was then dissolved with methanol (40 mL) and dichloromethane (160 mL), silica gel powder (30 g) was added to the obtained solution, and the solution was then evaporated to dryness to obtain a powdery solid; the operations of dry sample loading, column chromatography, and elution with a mixed solution (1% ammonia water:4% methanol/dichloromethane) were carried out. 5.18 g of Product 28-83 was obtained with a yield of 77%.

$^1$H-NMR (400 MHz, DMSO-d$_6$) δ 8.51 (m, 1H), 8.30 (m, 1H), 8.15 (m, 1H), 8.01-7.86 (m, 4H), 7.69 (m, 2H), 7.33 (m, 20H), 7.20 (m, 5H), 6.93 (m, 1H), 5.08 (m, 7H), 4.38-4.10 (m, 5H), 3.95-3.85 (m, 2H), 3.53 (m, 9H), 3.18 (m, 4H), 3.01 (m, 4H), 2.36 (m, 7H), 2.16 (m, 2H), 1.48 (m, 6H), 1.36 (s, 18H), 1.25 (m, 3H), 0.90-0.82 (m, 6H).

MALDI-TOF MS: [M+Na$^+$] 1691.84

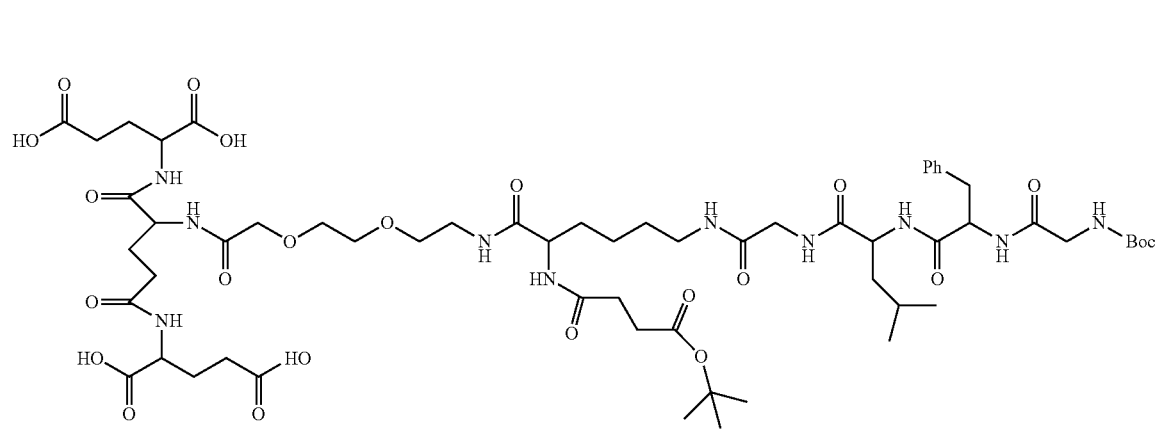

28-85

Compound 28-83 (0.5562 g, 0.3359 mmol) and 10% Pd/C (0.0200 g) were added in a reactor and then dissolved with DMF (30 mL); the reactor was then sealed and H$_2$ was introduced in the reactor to a pressure of 16 Psi; and the mixed solution was then stirred overnight at room temperature to react. At the end of the reaction, the reaction solution was filtered with diatomaceous earth, the diatomaceous earth was washed with DMF (20 mL×3), and a solution containing Product 28-85 was thus obtained.

28-86

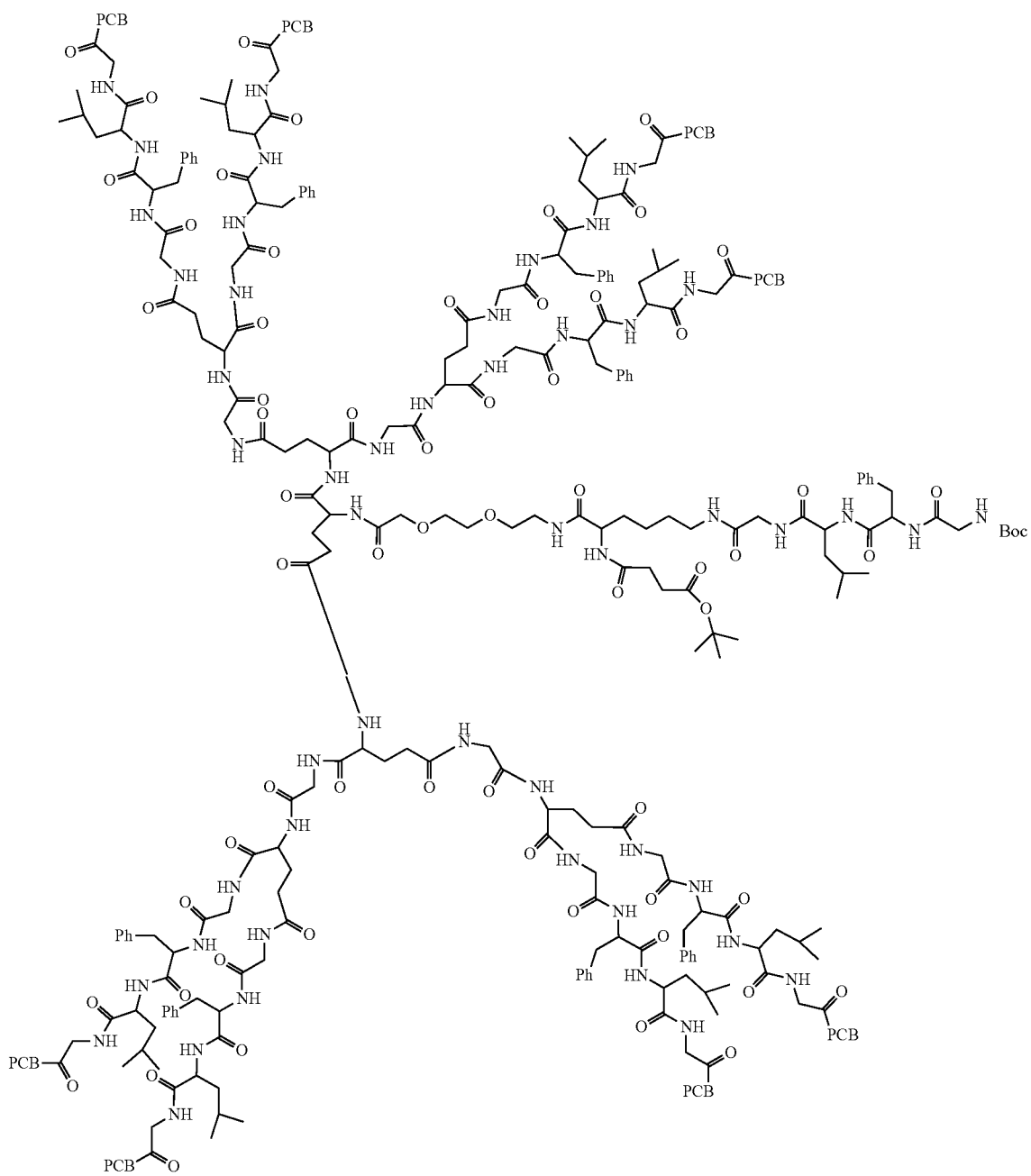

Compound 28-85 (0.4351 g, 0.3359 mmol), Compound 31-84 (home-made) (2.8 g, 1.545 mmol), HBTU (0.7643 g, 2.0154 mmol), and HOBT (0.2723 g, 2.0154 mmol) were added into a 500 mL flask and the mixed solution was stirred at −5° C. for about 20 min to react; DIEA (0.0847 mL, 0.5126 mmol) was then slowly added dropwise, and the obtained solution was further stirred at −5° C. for 1 h; and the reaction solution in the flask was then stirred overnight at room temperature. At the end of the reaction, n-hexane (150 mL) and methyl tert-butyl ether (30 mL) were added for precipitation, supernatant was discarded, and n-hexane (150 mL) and methyl tert-butyl ether (50 mL) were added to the lower oily solution; such operations were repeated three times to obtain a viscous oily product; methyl tert-butyl ether (200 mL) was added to precipitate a solid product; suction filtering was then carried out and the filter cake was washed with methyl tert-butyl ether (50 mL×3) and then dried. 2.8 g of Product 28-86 was obtained with a yield of 88%.

28-87

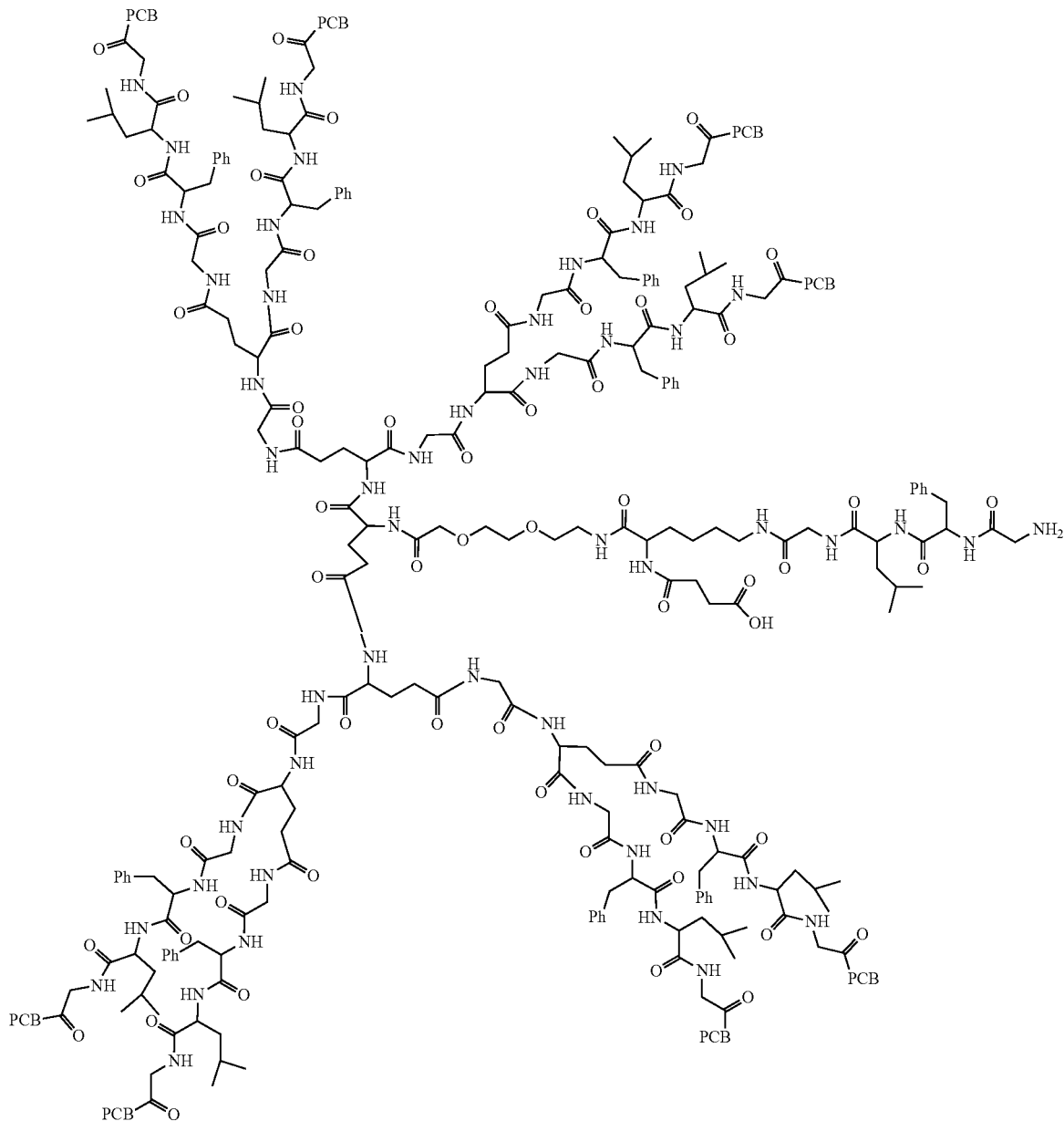

Product 28-86 (2.8 g, 0.3359 mmol) was added in a 500 mL flask and then dissolved with dichloromethane (15 mL), TFA (0.9978 mL, 13.436 mmol) was then added in the flask, and the mixed solution was stirred overnight at room temperature to react. At the end of the reaction, the reaction solution was concentrated to a small amount, methyl tert-butyl ether (200 mL) was then added and the powdery product was precipitated; suction filtering was then carried out, and the filter cake was washed with methyl tert-butyl ether (50 mL×3) and then dissolved with a mixed solution of methanol (40 mL) and dichloromethane (160 mL); silica gel powder (30 g) was added and the obtained solution was then evaporated to dryness to obtain a powdery solid; the operations of dry sample loading, column chromatography, and elution with a mixed solution (2% ammonia water:5%-8% methanol/dichloromethane) were carried out; the elution product was then collected, concentrated, and evaporated to dryness. 1.5 g of Product 28-87 was obtained with a yield of 54%.

$^1$H-NMR (400 MHz, DMSO-d$_6$) δ 10.14 (s, 1H), 10.10 (m, 6H), 8.95 (d, J=4.3 Hz, 9H), 8.38 (m, 5H), 8.29-8.06 (m, 34H), 7.99-7.80 (m, 22H), 7.50 (m, 10H), 7.27-7.13 (m, 46H), 5.82 (m, 7H), 4.56 (s, 9H), 4.31 (m, 15H), 4.00 (m, 19H), 3.62 (s, 22H), 3.13-3.04 (m, 36H), 2.95 (s, 21H), 2.80-2.67 (m, 35H), 2.42-2.32 (m, 47H), 2.24-1.93 (m, 26H), 1.88-1.78 (m, 47H), 1.65-1.51 (m, 48H), 1.24 (m, 17H), 0.89-0.84 (m, 48H).

MALDI-TOF MS: [M+H$^+$] 8325.63

28-129
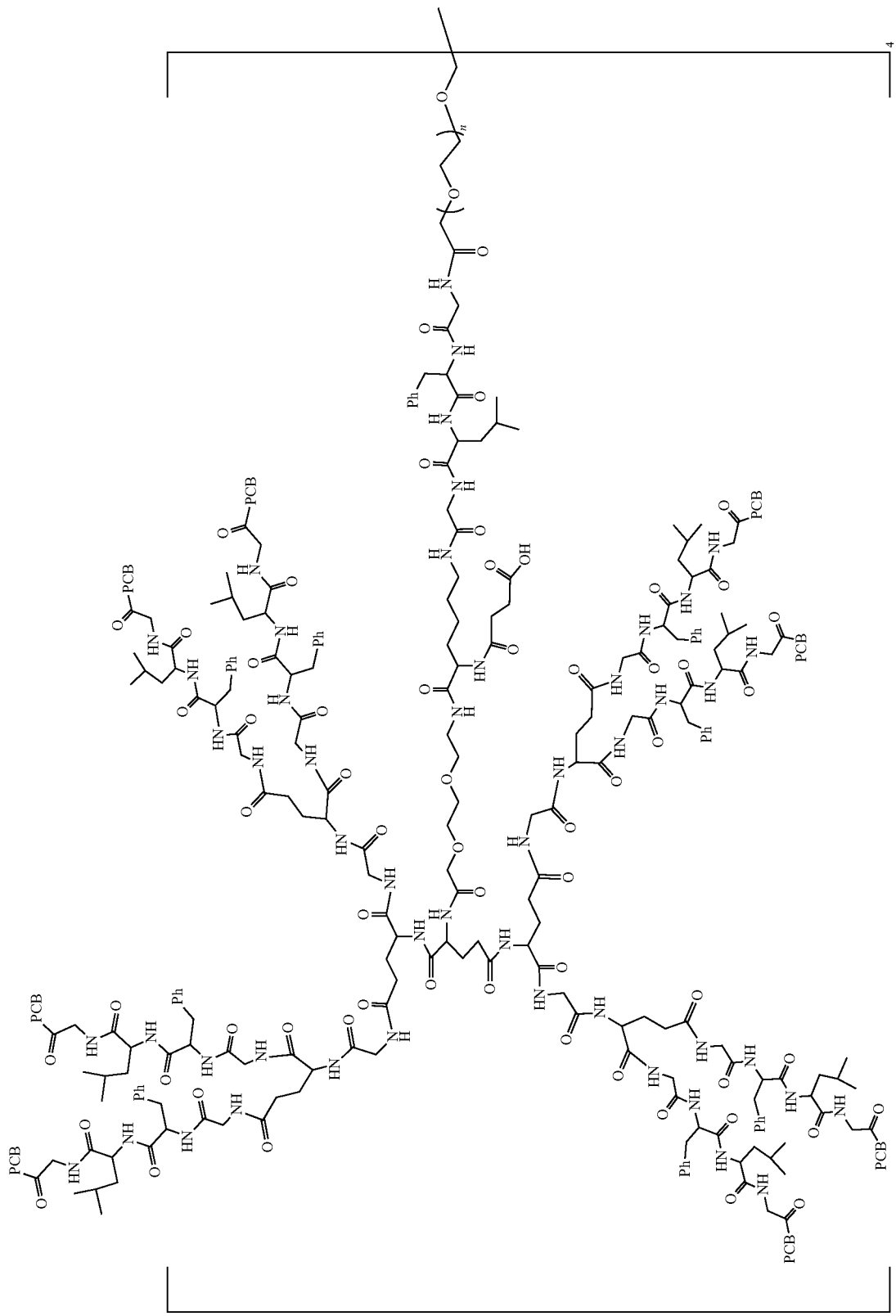

Product 28-87 (1.5 g, 0.1804 mmol) was added to a 500 mL flask and then dissolved with DMF (20 mL); the mixed solution was stirred at −5° C. at a low speed for about 10 min to react, DIEA (0.298 mL, 1.8038 mmol) was slowly added dropwise, 4ARM-SCM-40K (1.72 g, 0.0410 mmol, purchased from JenKem) was then added, and the obtained solution was stirred for a week in the dark at room temperature at a low speed to react. At the end of the reaction, n-hexane (200 mL) and methyl tert-butyl ether (50 mL) were added to layer the reaction solution, supernatant was discarded, n-hexane (200 mL) and methyl tert-butyl ether (50 mL) were further added to the lower oily solution, and such operations were repeated three times to obtain a viscous oily product; methyl tert-butyl ether (200 mL) was added to precipitate a solid product; filtering was then carried out and the filter cake was washed with methyl tert-butyl ether and methanol (60 mL×3) and then dissolved with a mixed solution of methanol (40 mL) and dichloromethane (160 mL); silica gel powder (10 g) was added to the obtained solution, and the solution was then evaporated to dryness to obtain a powdery solid; the operations of dry sample loading, column chromatography, and elution with a mixed solution (1% ammonia water:6%-10% methanol/dichloromethane) were carried out; the elution product was then collected, concentrated, and evaporated to dryness to obtain a solid product, and the solid product was then dried. 1.7 g of Product 28-129 was obtained with a yield of 57%.

$^1$H-NMR (400 MHz, DMSO-$d_6$) δ 8.95 (m, 27H), 8.37 (m, 18H), 8.20 (m, 56H), 8.10-7.82 (m, 139H), 7.50 (m, 32H), 7.32-7.10 (m, 163H), 5.85-5.79 (m, 30H), 4.56 (s, 36H), 4.31 (m, 66H), 4.07-3.99 (m, 60H), 3.78 (m, 101H), 3.32 (s, 3938H), 3.13 (s, 99H), 3.05-2.85 (m, 144H), 2.76 (m, 127H), 2.42-2.29 (m, 192H), 2.24-2.12 (m, 114H), 1.88-1.76 (m, 193H), 1.67-1.54 (m, 113H), 1.51 (s, 78H), 1.24 (m, 68H), 0.86 (m, 196H).

MALDI-TOF MS: 74277.33-75025.05

28-140

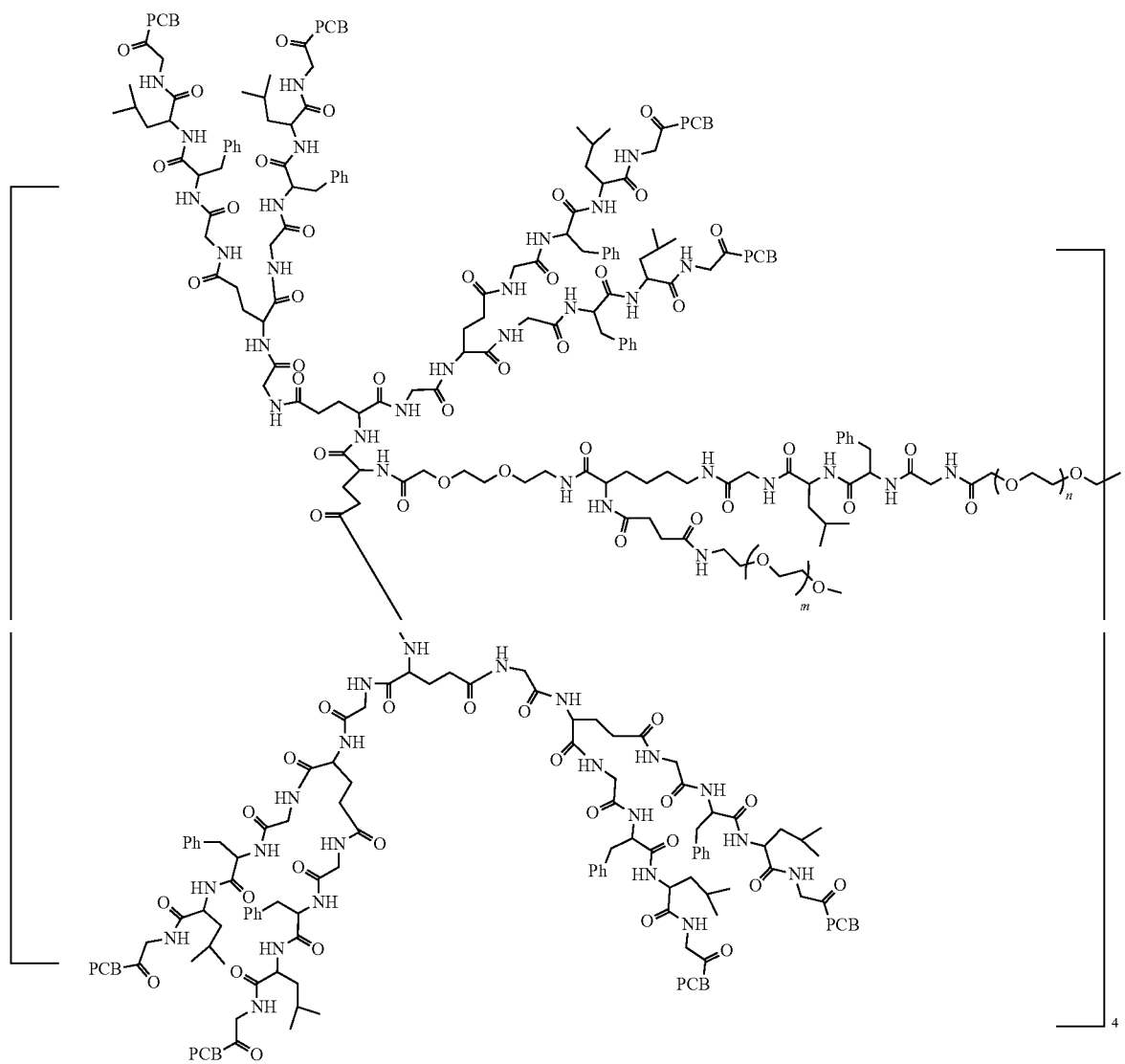

Product 28-129 (1.7 g, 0.0227 mmol) was added to a 500 mL flask and then dissolved with DMF (30 mL), and M-NH$_2$-10K·HCl (1.44 g, 0.1364 mmol, purchased from Jenkem), HBTU (0.052 g, 0.1364 mmol), and HOBT (0.018 g, 0.1364 mmol) were then added to the obtained solution; the mixed solution was slowly stirred at −5° C. for about 10 min to react, DIEA (0.067 mL, 0.4093 mmol) was then slowly added dropwise, and the obtained solution further reacted at −5° C. for 20 min; and the solution was stirred in the dark at a low speed at room temperature for 7 days. At the end of the reaction, n-hexane (100 mL) and methyl tert-butyl ether (30 mL) were added to the solution, the supernatant was discarded, and n-hexane (100 mL) and methyl tert-butyl ether (30 mL) were added to the lower liquid; such operations were repeated three times to obtain a viscous oily product; methyl tert-butyl ether (100 mL) was then added to precipitate a solid, the solid product was then filtered out and the filter cake was washed with methyl tert-butyl ether (30 mL×3) and then dissolved with a mixed solution of methanol (40 mL) and dichloromethane (160 mL); silica gel powder (15 g) was added to the obtained solution, and the solution was then evaporated to dryness to obtain a powdery solid; the operations of dry sample loading, column chromatography, and elution with a mixed solution (2% ammonia water:6%-8% methanol/dichloromethane) were carried out; the elution product was then collected, concentrated and evaporated to dryness to obtain a solid, and the solid was dried; the product was dissolved with absolute ethanol (2 mL) and dichloromethane (30 mL), and methyl tert-butyl ether (200 mL) was added to the obtained solution to obtain a solid product by precipitation; the solution was filtered and the filter cake was washed with methyl tert-butyl ether (50 mL×2) and dried. 1.6 g of Product 28-140 was obtained with a yield of 61%.

$^1$H-NMR (400 MHz, DMSO-d$_6$) δ 9.00-8.89 (m, 28H), 8.45-8.30 (m, 18H), 8.23-8.08 (m, 58H), 8.03-7.81 (m, 140H), 7.56-7.44 (m, 32H), 7.21 (s, 160H), 5.76 (s, 66H), 4.79-4.56 (m, 66H), 4.46-4.30 (m, 60H), 4.07 (s, 100H), 3.51 (s, 7541H), 3.00 (s, 99H), 2.91 (s, 144H), 2.65 (m, 128H), 2.43-2.27 (m, 192H), 2.19-1.86 (m, 116H), 1.86-1.73 (m, 193H), 1.66-1.39 (m, 113H), 1.23 (s, 78H), 1.10-1.00 (m, 65H), 0.83-0.68 (m, 198H).

MALDI-TOF MS: 110620-119019

Example 10: Synthesis of Compound 28-126

28-97

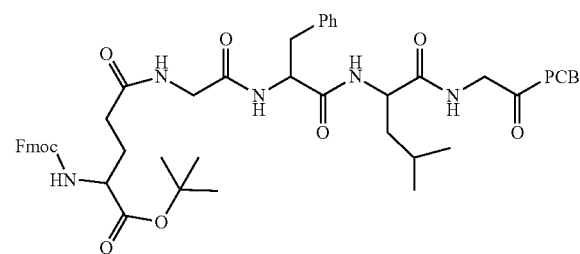

Fmoc-Glu-OtBu (11.8639 g, 27.8843 mmol, purchased from Ark pharm) was added in a 1000 mL flask and then dissolved with DMF (200 mL); the obtained solution reacted at 0° C., and the Compound 30-33 (10.0000 g, 12.1659 mmol, home-made), HBTU (13.2186 g, 34.8554 mmol), and HOBT (4.7100 g, 104.5661 mmol) were added to the reaction solution; the obtained solution was stirred for 10 min, and then DIEA (17.2828 mL, 104.5661 mmol) was slowly added dropwise; the obtained solution was stirred overnight at 0° C. to react. At the end of the reaction, n-hexane (200 mL) and methyl tert-butyl ether (70 mL) were added to the reaction solution for precipitation and the solution was layered; the supernatant was discarded; n-hexane and methyl tert-butyl ether were further added to the lower oily solution for precipitation and such operations were repeated five times to finally obtain a viscous oily product; dichloromethane (40 mL) and methyl tert-butyl ether (300 mL) were then added to precipitate a solid, the solid was filtered out and dried. 28.5681 g of Product 28-97 was obtained with a yield of 100%.

28-98

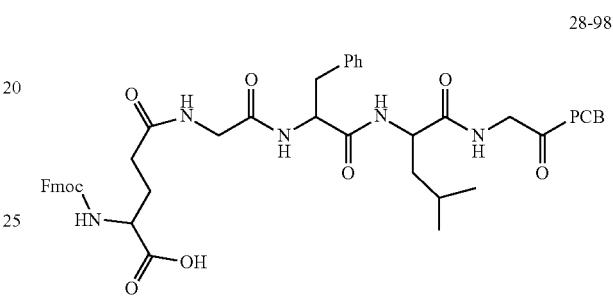

Compound 28-97 (28.5681 g, 23.2369 mmol) was added in a 1000 mL flask and then dissolved with dichloromethane (30 mL), TFA (25.6190 mL, 348.5535 mmol) was then added with stirring, and the mixed solution was stirred overnight at room temperature to react. At the end of the reaction, the reaction solution was concentrated, and methyl tert-butyl ether (400 mL) was added to precipitate a solid; the solid was then filtered out by suction and the filter cake was washed with methyl tert-butyl ether (100 mL×3) and then dried. 27.2 g of Product 28-98 was obtained with a yield of 100%.

28-143

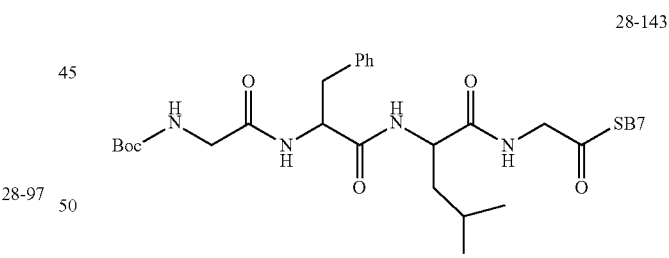

SB-743921 (8.000 g, 15.4718 mmol, also known as SB7), HBTU (8.814 g, 23.2078 mmol), and HOBT (3.136 g, 23.2078 mmol) were added to the DMF (110 mL) solution containing Product 28-142 (9.9072 g, 20.1134 mmol); the obtained solution was stirred at −5° C. for 20 min to react, and then DIEA (7.0483 mL, 42.6443 mmol) was slowly added dropwise over 10 min; the obtained solution was further stirred at −5° C. for 1 h to react, and then stirred overnight at room temperature to react. At the end of the reaction, the reaction solution was transferred to a 1 L separatory funnel and extracted with saturated sodium bicarbonate solution (250 mL) and ethyl acetate (300 mL) to obtain the organic phase; the aqueous phase was washed with ethyl acetate (200 mL×2), and the obtained organic phases were combined and washed with a saturated sodium chloride solution (200 mL×2); the obtained solution was then evaporated to dryness to obtain a solid product and the solid product was then dried for 3 h in a vacuum oven. 15 g of Product 28-143 was obtained with a yield of 100%.

28-146

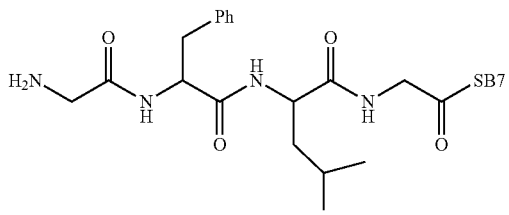

Product 28-143 (15.32 g, 15.46 mmol) was added in a 500 mL flask and then dissolved with dichloromethane (30 mL), TFA (17.2 mL, 231.9 mmol) was then added in the flask, and the mixed solution was stirred overnight at room temperature to react. At the end of the reaction, the reaction solution was concentrated and precipitated with methyl tert-butyl ether (300 mL) to obtain a powdery solid; suction filtering was then carried out, the filter cake was washed with methyl tert-butyl ether (150 mL×2) and then dissolved with a mixed solution of methanol (60 mL) and dichloromethane (240 mL), silica gel powder (50 g) was added to the obtained solution, and the solution was then evaporated to dryness to obtain a powdery solid; the operations of dry sample loading, column chromatography, and elution with a mixed solution (1% ammonia water:2%-3% methanol/dichloromethane) were carried out; the elution product was then collected, concentrated, and evaporated to obtain a solid, and the solid was dried in a vacuum oven. 12.4 g of Product 28-146 was obtained with a yield of 91%.

28-149

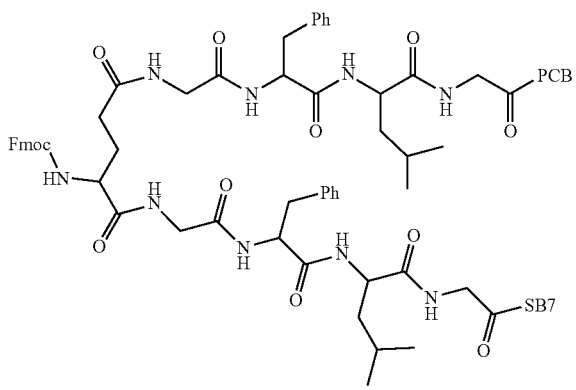

Compound 28-98 (3.9248 g, 2.9445 mmol), Compound 28-146 (2.5 g, 2.8043 mmol), HBTU (1.5953 g, 4.2065 mmol), and HOBT (0.5684 g, 4.2065 mmol) were added into a 500 mL flask and then dissolved with DMF (50 mL); the mixed solution was stirred at 0° C. for 10 min to react; DIEA (2.0858 mL, 12.6194 mmol) was then slowly added dropwise, and the obtained solution was further stirred overnight at 0° C. to react. At the end of the reaction, n-hexane (200 mL) and methyl tert-butyl ether (50 mL) were added to layer the reaction solution, supernatant was discarded, and n-hexane (200 mL) and methyl tert-butyl ether (50 mL) were further added to the lower solution; such operations were repeated three times to obtain an oily product; methyl tert-butyl ether (200 mL) was added to precipitate a solid product; the solid product was filtered out and the filter cake was washed twice with methyl tert-butyl ether and then dried. 5.7 g of Product 28-149 was obtained with a yield of 100%.

28-151

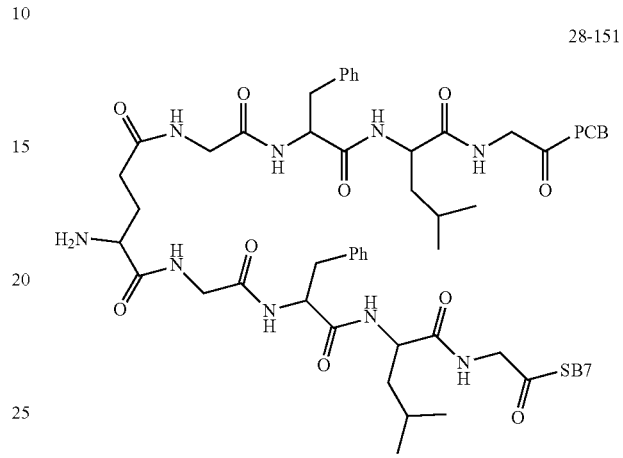

Compound 28-149 (5.7 g, 2.8043 mmol) was added in a 500 mL flask and then dissolved with DMF (20 mL) and morpholine (4.886 mL, 56.086 mmol, purchased from Macklin) was then added, and the mixed solution was stirred for 1 h at room temperature to react. At the end of the reaction, n-hexane (200 mL) and methyl tert-butyl ether (50 mL) were added to the reaction solution for precipitation to obtain a viscous oily product; the viscous oily product was then dissolved with dichloromethane (20 mL); methyl tert-butyl ether (250 mL) was then added for precipitation to obtain a solid and the solid was filtered out. 5.1 g of Product 28-151 was obtained with a yield of 100%.

28-152

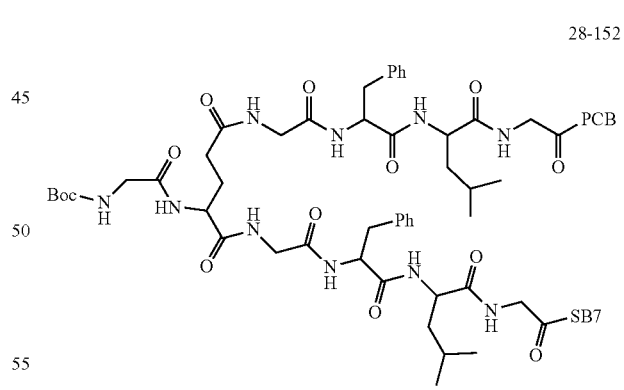

Compound 28-151 (5.1166 g, 2.8043 mmol), Boc-Gly-OH (0.6386 g, 3.6456 mmol, purchased from Aladdin), HBTU (1.5953 g, 4.2065 mmol), and HOBT (0.5684 g, 4.2065 mmol) were added in a 250 mL flask and dissolved with a DMF (35 mL), the obtained solution was stirred for 10 min at −5° C. to react; then, DIEA (2.0858 mL, 12.6194 mmol) was slowly added dropwise to further react at −5° C. for 30 min, and then the reaction solution was stirred overnight at room temperature to further react. At the end of the reaction, n-hexane (200 mL) and methyl tert-butyl ether (50 mL) were added to layer the reaction solution, supernatant was discarded, and n-hexane (200 mL) and methyl tert-butyl ether (50 mL) were further added to the lower solution; such operations were repeated four times to finally obtain a viscous oily product; dichloromethane (20 mL) and methyl tert-butyl ether (200 mL) was added to precipitate a solid product; the solid product was filtered out and the filter cake was washed with methyl tert-butyl ether (50 mL×3) and then dried. 5.5 g of Product 28-152 was obtained with a yield of 100%.

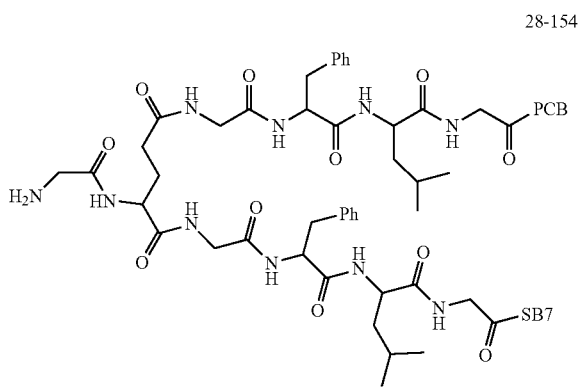

28-154

Compound 28-152 (5.5 g, 2.8043 mmol) was added in a 500 mL flask, dichloromethane (15 mL) and TFA (4.1650 mL, 56.086 mmol) were then added, and the mixed solution was stirred overnight at room temperature to react. At the end of the reaction, methyl tert-butyl ether (250 mL) was added to the reaction solution to obtain a solid; suction filtering was then carried out, the filter cake was washed with methyl tert-butyl ether (50 mL×3) and then dissolved with a mixed solution of methanol (40 mL) and dichloromethane (160 mL), silica gel powder (20 g) was added to the obtained solution, and the solution was then evaporated to dryness to obtain a powdery solid; the operations of dry sample loading, column chromatography, and gradient elution with a mixed solution (7%-8% methanol/dichloromethane) were carried out; the elution product was then collected, concentrated, evaporated to dryness to obtain a solid product, and the solid product was then dried. 3.8 g of Product 28-154 was obtained with a yield of 72%.

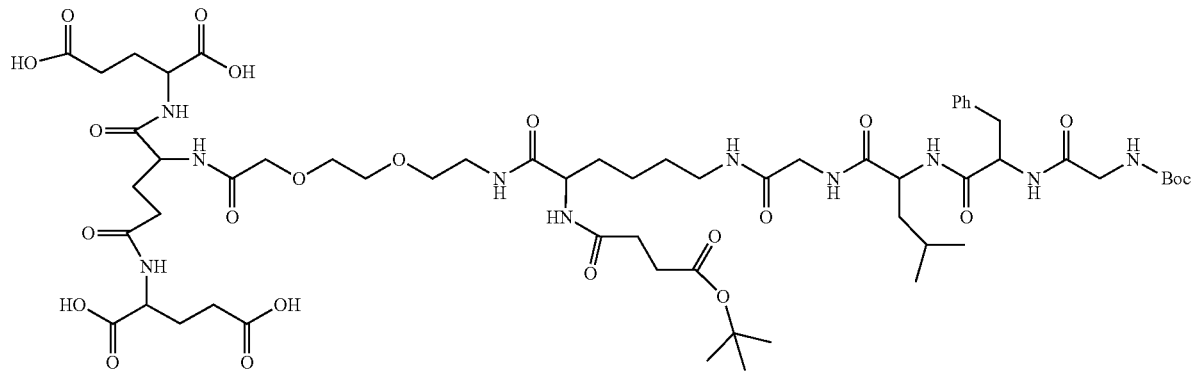

28-107

Compound 28-83 (1.1238 g, 0.6780 mmol) and 10% Pd/C (0.020 g) were added in a reactor and then dissolved with DMF (30 mL); the reactor was then sealed and $H_2$ was introduced in the reactor to a pressure of 18 psi; and the mixed solution was then stirred overnight at room temperature to react. At the end of the reaction, the reaction solution was filtered with diatomaceous earth, the diatomaceous earth was washed with DMF (20 mL×3), and a DMF solution containing Product 28-107 was thus obtained.

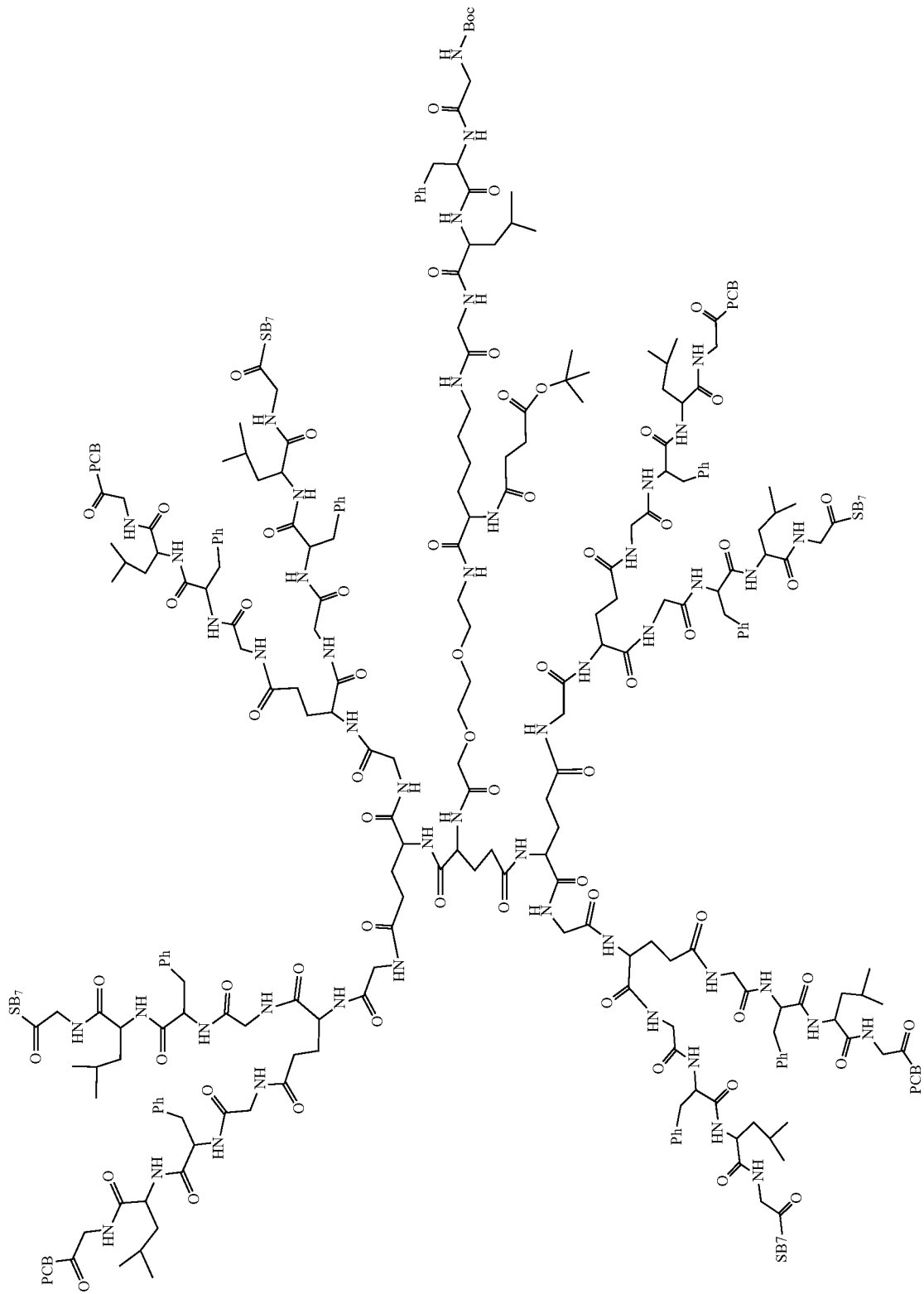

Compound 28-104 (6.3847 g, 3.3972 mmol), HBTU (1.5441 g, 4.0716 mmol), and HOBT (0.5502 g, 4.0716 mmol) were added to the DMF (120 mL) solution containing Product 28-107 (0.8791 g, 0.6786 mmol); the obtained solution was stirred at −5° C. for about 10 min to react, and then DIEA (3.1405 mL, 19.0008 mmol) was slowly added dropwise; the obtained solution further reacted at −5° C. for 60 min and then the reaction solution in the flask was stirred overnight at room temperature. At the end of the reaction, n-hexane (150 mL) and methyl tert-butyl ether (30 mL) were added to the reaction solution, and the resulting solution was then shaken and layered; supernatant was discarded, n-hexane (150 mL) and methyl tert-butyl ether (30 mL) were further added to the lower solution, and such operations were repeated four times to finally obtain a viscous oily product; dichloromethane (30 mL) and methyl tert-butyl ether (250 mL) were added to precipitate a solid product; suction filtering was then carried out and the filter cake was washed with methyl tert-butyl ether (100 mL×3) and then dissolved with a mixed solution of methanol (60 mL) and dichloromethane (240 mL); silica gel powder (30 g) was added to the obtained solution, and the solution was then evaporated to dryness to obtain a powdery solid; the operations of dry sample loading, column chromatography, and elution with a mixed solution (1% ammonia water:4%-7% methanol/dichloromethane) were carried out; the elution product was then collected, concentrated and evaporated to dryness. 3.1 g of Product 28-108 was obtained with a yield of 53%.

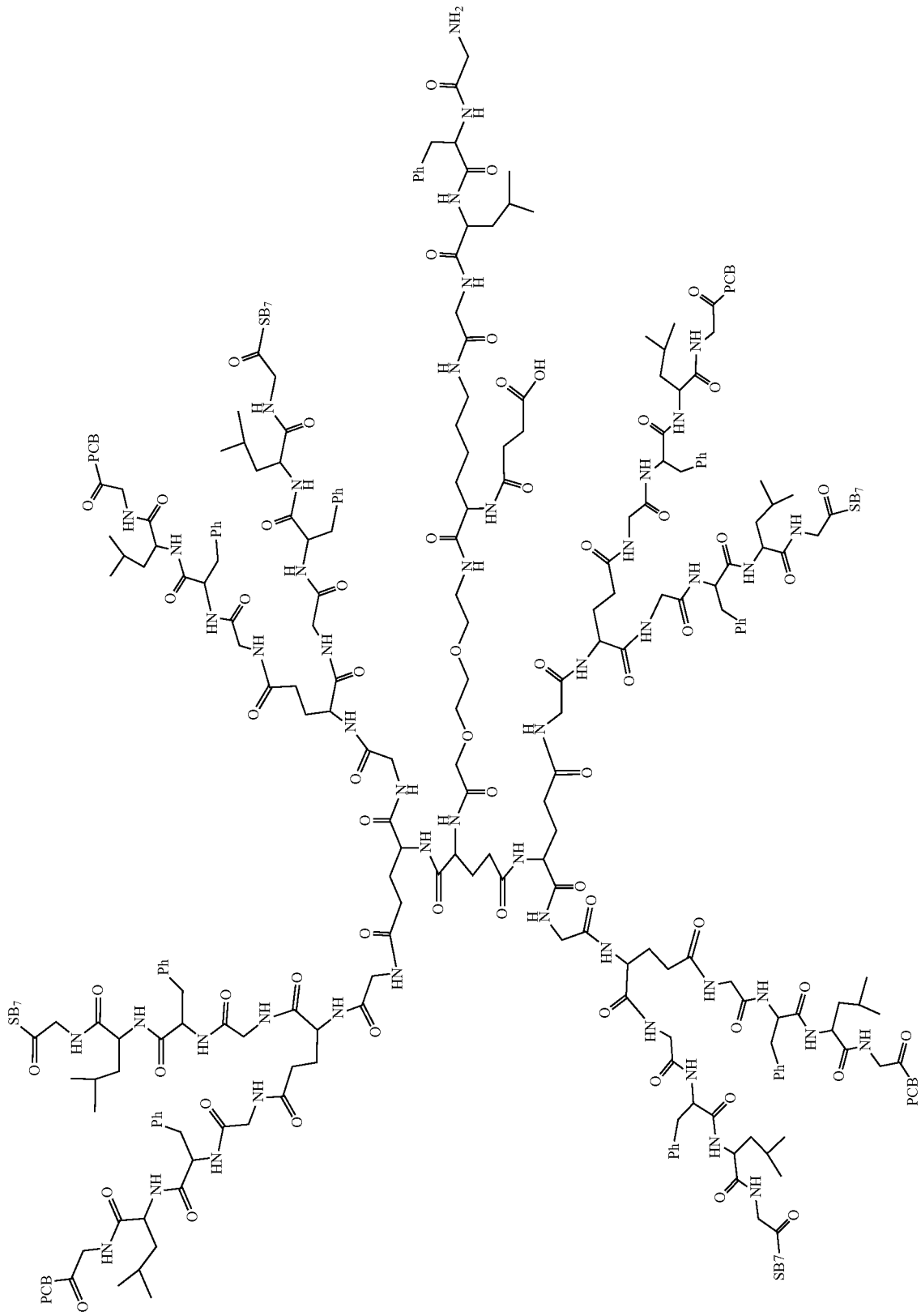

Compound 28-108 (3.1 g, 0.3578 mmol) was added in a 250 mL flask and then dissolved with dichloromethane (6 mL), TFA (1.06 mL, 14.3121 mmol) was then added in the flask, and the mixed solution was stirred overnight at room temperature to react. At the end of the reaction, the reaction solution was concentrated to a small amount and then precipitated with methyl tert-butyl ether (200 mL) to obtain a solid; suction filtering was then carried out, the filter cake was washed with methyl tert-butyl ether (50 mL×3) and then dissolved with a mixed solution of methanol (50 mL) and dichloromethane (200 mL), silica gel powder (30 g) was added to the obtained solution, and the solution was then evaporated to dryness to obtain a powdery solid; the operations of dry sample loading, column chromatography, and elution with a mixed solution (1% ammonia water:6%-7% methanol/dichloromethane) were carried out; the elution product was then collected, concentrated, evaporated to dryness to obtain a solid product, and the solid product was then dried. 2.4 g of Product 28-116 was obtained with a yield of 78%.

28-117
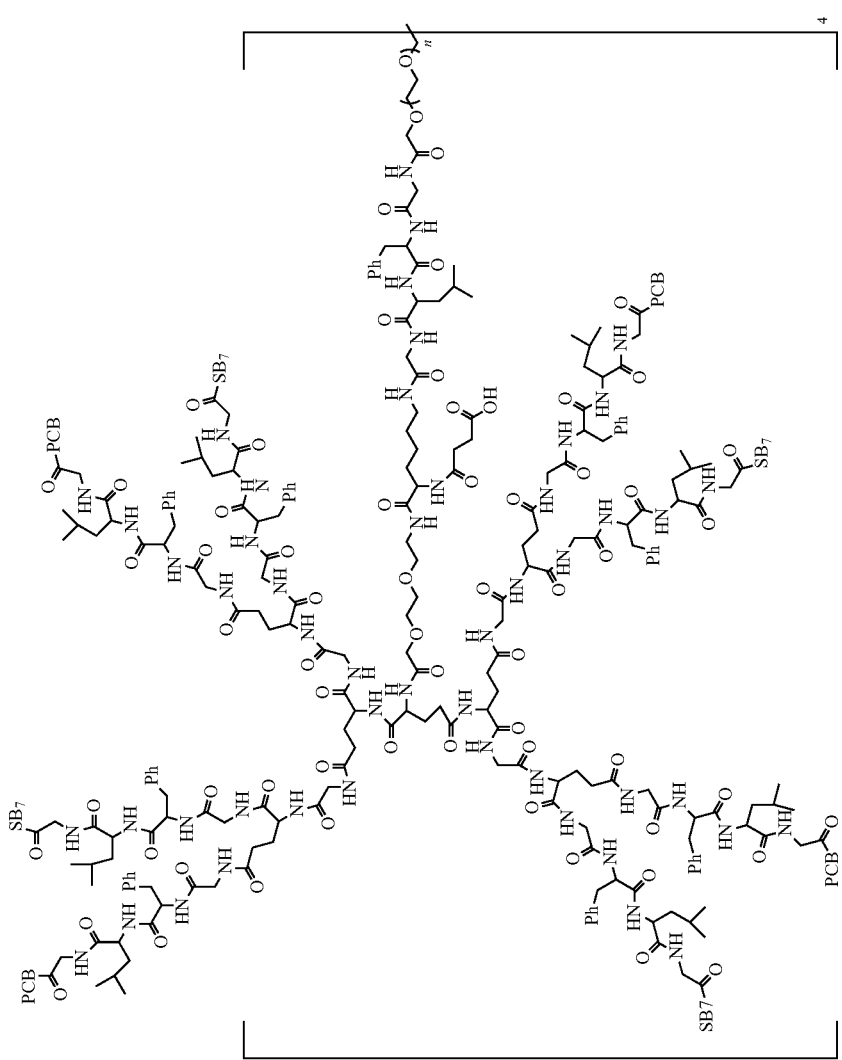

Product 28-116 (2.4 g, 0.2788 mmol) was added to a 500 mL flask and then dissolved with DMF (50 mL); the mixed solution was stirred at −5° C. at a low speed for about 10 min to react, DIEA (0.4611 mL, 2.7896 mmol) was slowly added dropwise, 4ARM-SCM-40K (2.6588 g, 0.0634 mmol, purchased from JenKem) was then added, and the obtained solution was stirred for a week in the dark at room temperature at a low speed to react. At the end of the reaction, n-hexane (200 mL) and methyl tert-butyl ether (50 mL) were added to layer the reaction solution, supernatant was discarded, n-hexane (200 mL) and methyl tert-butyl ether (50 mL) were further added to the lower oily solution, and such operations were repeated three times to obtain a viscous oily product; methyl tert-butyl ether (250 mL) was added to precipitate a solid product; filtering was then carried out and the filter cake was washed with methyl tert-butyl ether and methanol (50 mL×3) and then dissolved with a mixed solution of methanol (50 mL) and dichloromethane (200 mL); silica gel powder (30 g) was added to the obtained solution, and the solution was then evaporated to dryness to obtain a powdery solid; the operations of dry sample loading, column chromatography, and elution with a mixed solution (1% ammonia water:3%-6% methanol/dichloromethane) were carried out; the elution product was then collected, concentrated, evaporated to dryness to obtain a solid product, and the solid is product was then dried in a vacuum oven. 2.3 g of Product 28-117 was obtained with a yield of 48%.

$^1$H-NMR (400 MHz, DMSO-d$_6$) δ 10.14 (s, 9H), 8.94 (s, 10H), 8.18 (m, 63H), 8.07 (m, 144H), 7.87 (s, 26H), 7.50 (m, 48H), 7.23 (m, 302H), 7.13 (m, 59H), 5.79 (m, 20H), 5.32 (m, 12H), 4.54 (m, 111H), 4.30 (m, 232H), 3.53 (m, 3396H), 3.12 (m, 41H), 2.73 (m, 134H), 2.42-2.27 (m, 148H), 2.11 (s, 23H), 1.98-1.73 (m, 100H), 1.45 (m, 150H), 1.34-1.27 (m, 85H), 0.86 (m, 421H), 0.50 (s, 18H).

MALDI-TOF MS: 75029.43-76244.16

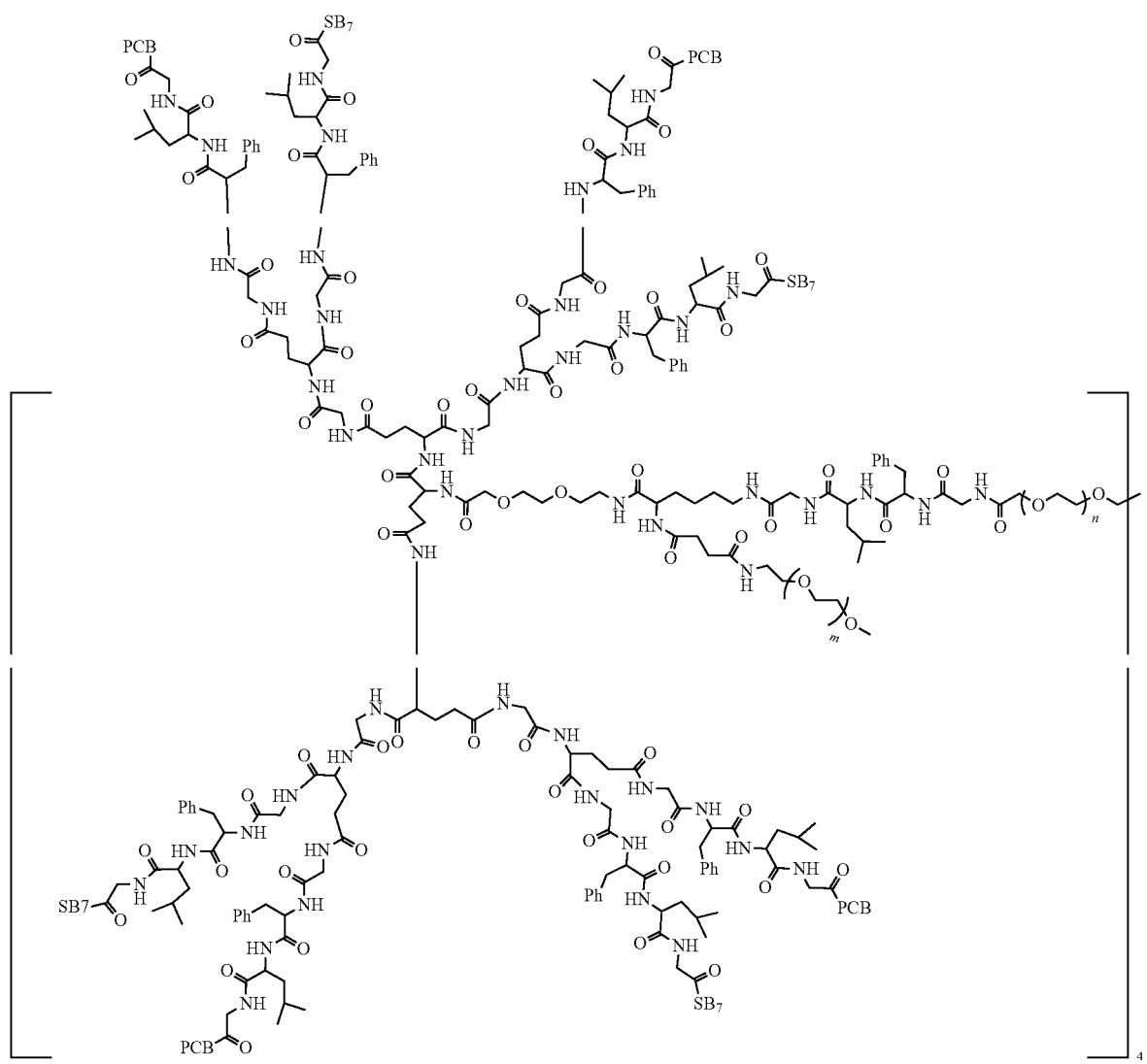

28-126

Compound 28-117 (2.3 g, 0.0302 mmol) was added to a 500 mL flask and then dissolved with DMF (40 mL), and M-NH$_2$·HCl-5K (0.9290 g, 0.1818 mmol, purchased from Jenkem), HBTU (0.0689 g, 0.1818 mmol), and HOBT (0.0246, 0.1818 mmol) were then added to the obtained solution; the mixed solution was slowly stirred at −5° C. for about 10 min to react, DIEA (0.1101 mL, 0.666 mmol) was then slowly added dropwise, and the obtained solution further reacted at −5° C. for 20 min; and the solution in the flask was stirred slowly in the dark at room temperature for 7 days. At the end of the reaction, n-hexane (100 mL) and methyl tert-butyl ether (30 mL) were added to the solution, the supernatant was discarded, and n-hexane (100 mL) and methyl tert-butyl ether (30 mL) were added to the lower liquid; such operations were repeated three times to obtain a viscous oily product; methyl tert-butyl ether (100 mL) was then added to precipitate a solid, the solid product was then filtered out and the filter cake was washed with methyl tert-butyl ether (30 mL×3) and then dissolved with a mixed solution of methanol (40 mL) and dichloromethane (160 mL); silica gel powder (15 g) was added to the obtained solution, and the solution was then evaporated to dryness to obtain a powdery solid; the operations of dry sample loading, column chromatography, and elution with a mixed solution (2% ammonia water:6%-8% methanol/dichloromethane) were carried out; the elution product was then collected, concentrated and evaporated to dryness to obtain a solid, and the solid was dried for 1 h in a vacuum oven; the product was dissolved with absolute ethanol (2 mL) and dichloromethane (30 mL), and methyl tert-butyl ether (200 mL) was added to the obtained solution to obtain a solid product by precipitation; the solution was filtered and the filter cake was washed with methyl tert-butyl ether (50 mL×2) and dried in the vacuum oven. 1.5 g of Product 28-126 was obtained with a yield of 52%.

$^1$H-NMR (400 MHz, DMSO-d$_6$) δ 10.15 (s, 9H), 8.95 (s, 10H), 8.19 (s, 63H), 8.15-7.85 (m, 170H), 7.52 (s, 41H), 7.18 (m, 361H), 5.76 (s, 28H), 4.46 (m, 111H), 4.14 (m, 235H), 3.51 (s, 5924H), 3.18 (nm, 40H), 2.76-2.67 (m, 134H), 2.43-2.25 (m, 157H), 2.18-2.03 (m, 23H), 1.81 (m, 84H), 1.52 (m, 166H), 1.05 (s, 85H), 0.84 (m, 418H), 0.49 (s, 22H).

MALDI-TOF MS: 96225-97497

Example 11: Synthesis of Compound 28-214

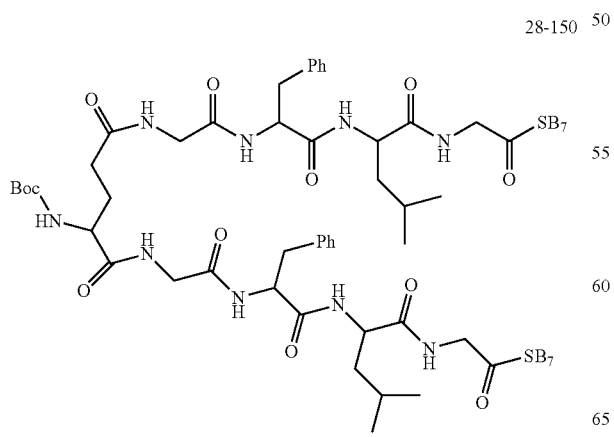

28-150

Compound 28-146 (home-made, 8.000 g, 15.4718 mmol), Boc-Glu-OH (0.6603 g, 2.6708 mmol), HBTU (3.0386 g, 8.0124 mmol), and HOBT (1.0827 g, 8.0124 mmol) were added in a 500 mL flask, the obtained solution was stirred for 10 min at −5° C. to react; then, DIEA (3.9729 mL, 24.0472 mmol) was slowly added dropwise and then the resulting solution further reacted at −5° C. for 1 h, and then the reaction solution was stirred overnight at room temperature to further react. At the end of the reaction, the reaction solution was transferred to a 1 L separatory funnel and then extracted with a saturated sodium chloride solution (200 mL) and ethyl acetate (300 mL); the obtained organic phase was washed with a saturated sodium chloride solution (200 mL×2) and then evaporated to dryness to obtain a solid product. 5.3 g of Product 28-150 was obtained with a yield of 100%.

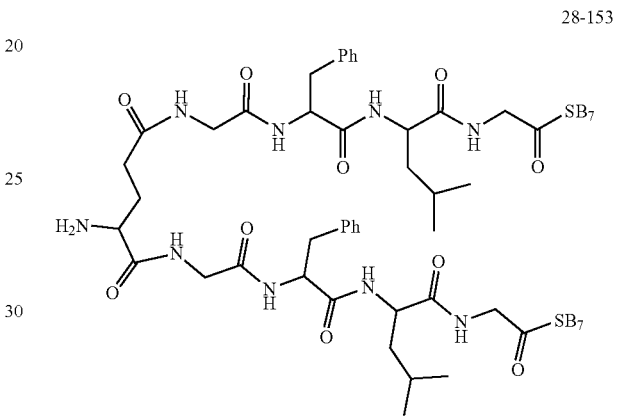

28-153

Compound 28-150 (5.3 g, 2.6708 mmol) was added in a 250 mL flask and then dissolved with dichloromethane (15 mL), TFA (3.967 mL, 53.416 mmol) was then added in the flask, and the mixed solution was stirred overnight at room temperature to react. At the end of the reaction, the reaction solution was concentrated, and methyl tert-butyl ether (200 mL) was added to precipitate a powdery solid; the solid was then filtered out by suction and the filter cake was washed with methyl tert-butyl ether (50 mL×3) and then dried in a vacuum oven. 5.1 g of Product 28-153 was obtained with a yield of 100%.

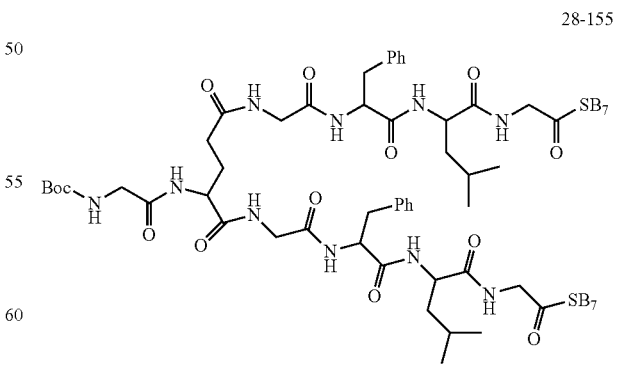

28-155

Compound 28-153 (5.0587 g, 2.6708 mmol), Boc-Gly-OH (0.6082 g, 3.4720 mmol), HBTU (1.5193 g, 4.0062 mmol), and HOBT (0.5414 g, 4.0062 mmol) were added in a 500 mL flask, the obtained solution was stirred for 10 min at −5° C. to react; then, DIEA (3.9729 mL, 24.0472 mmol) was slowly added dropwise and then the resulting solution further reacted at −5° C. for 1 h, and then the reaction solution was stirred overnight at room temperature to further react. At the end of the reaction, the reaction solution was transferred to a 1 L separatory funnel and then extracted with a saturated sodium chloride solution (200 mL) and ethyl acetate (250 mL); the obtained organic phase was washed with a saturated sodium chloride solution (200 mL×2) and then evaporated to dryness to obtain a solid product. 5.5 g of Product 28-155 was obtained with a yield of 100%.

Compound 28-155 (5.5 g, 2.6708 mmol) was added in a 500 mL flask, dichloromethane (20 mL) and TFA (3.9668 mL, 53.416 mmol) were then added, and the mixed solution was stirred overnight at room temperature to react. At the end of the reaction, the reaction solution was concentrated to a small amount and then precipitated with methyl tert-butyl ether (200 mL) to obtain a solid; suction filtering was then carried out, the filter cake was washed with methyl tert-butyl ether (50 mL×3) and then dissolved with a mixed solution of methanol (30 mL) and dichloromethane (120 mL), silica gel powder (20 g) was added to the obtained solution, and the solution was then evaporated to dryness to obtain a powdery solid; the operations of dry sample loading, column chromatography, and elution with a mixed solution (0.5% ammonia water:4%-6% methanol/dichloromethane) were carried out; the elution product was then collected, concentrated, evaporated to dryness, and dried. 4.0 g of Product 28-157 was obtained with a yield of 77%.

$^1$H-NMR (400 MHz, DMSO-$d_6$) δ 8.48-7.95 (m, 11H), 7.80 (s, 2H), 7.65-7.46 (m, is 4H), 7.38-6.93 (m, 27H), 5.74 (m, 1H), 4.50 (m, 3H), 4.35-4.15 (m, 5H), 3.89 (m, 4H), 3.77-3.47 (m, 11H), 3.16-2.99 (m, 4H), 2.92-2.66 (m, 6H), 2.31 (s, 5H), 2.10 (m, 3H), 1.86 (m, 1H), 1.77-1.69 (m, 1H), 1.63-1.43 (m, 7H), 1.41-1.21 (m, 4H), 1.11 (m, 2H), 0.99-0.77 (m, 18H), 0.52 (s, 4H).

MALDI-TOF MS: [M+Na$^+$] 1972.11

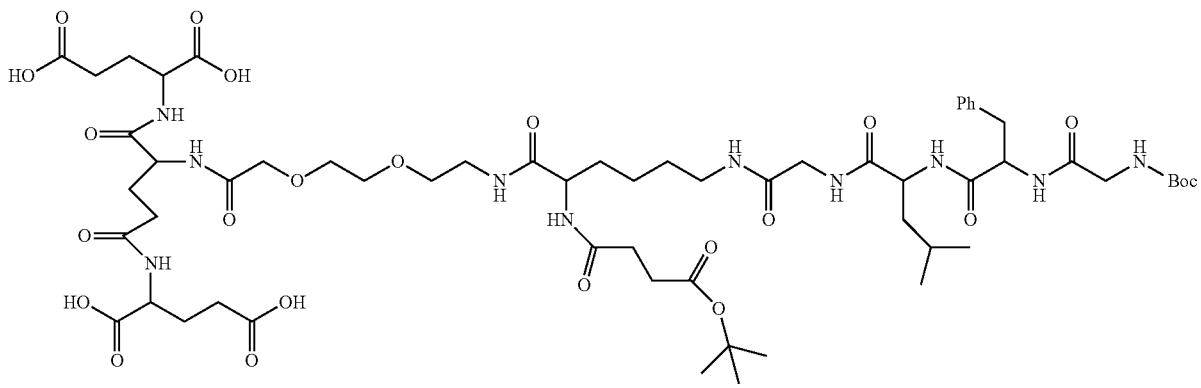

28-162

Product 28-83 (0.7380 g, 0.4457 mmol) and 10% Pd/C (0.030 g) were added in a reactor and then dissolved with DMF (30 mL); the air in the reactor was then pumped out to reach a vacuum state by a water pump; H$_2$ was introduced to a pressure of 1.8 MPa in the reactor, H$_2$ was then discharged, the reactor was pumped to reach a vacuum state by the water pump, H$_2$ was then introduced again, and such operations were repeated three times; finally, H$_2$ was introduced again into the reactor, and the mixed solution then was stirred overnight at room temperature to react. At the end of the reaction, the reaction solution was filtered with diatomaceous earth, the filter cake was washed with DMF (20 mL×3), and the filtrate was placed into a 500 mL round-bottomed flask as the raw material for the next step.

28-163
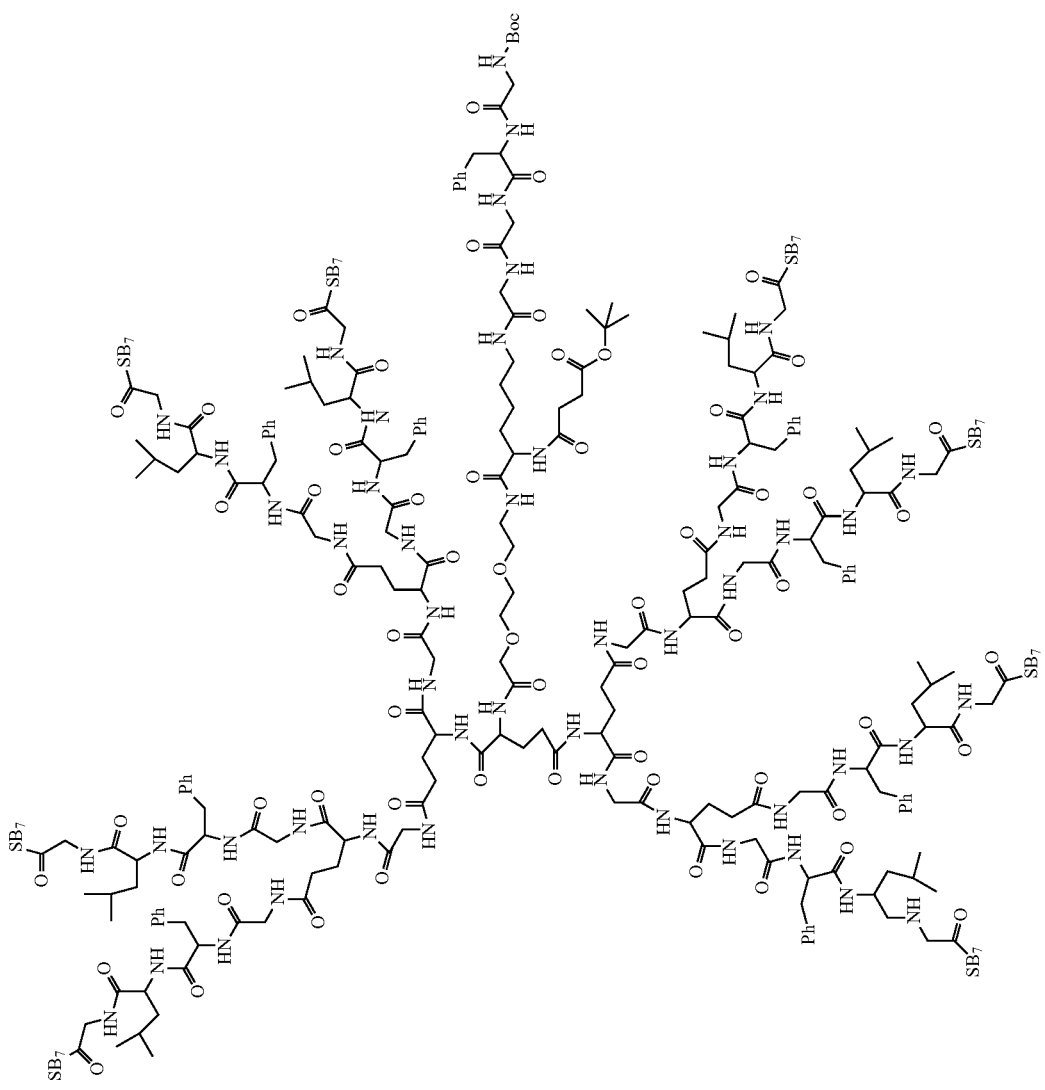

Compound 28-162 (0.5774 g, 0.4457 mmol), Compound 28-157 (4.0 g, 2.0502 mmol), HBTU (1.0142 g, 2.6742 mmol), and HOBT (0.3614 g, 2.6742 mmol) were added into a 500 mL flask and the mixed solution was stirred at −5° C. for about 15 min to react; DIEA is (1.3260 mL, 8.0226 mmol) was then slowly added dropwise, and the obtained solution further reacted at −5° C. for 1 h; and then the solution was stirred overnight at room temperature to react. At the end of the reaction, n-hexane (200 mL) and methyl tert-butyl ether (30 mL) were added for precipitation, supernatant was discarded, and n-hexane (150 mL) and methyl tert-butyl ether (50 mL) were further added to the lower oily solution; such operations were repeated three times to obtain an oily product; methyl tert-butyl ether (200 mL) was added to precipitate a solid product; suction filtering was then carried out and the filter cake was washed with methyl tert-butyl ether (50 mL×3) and then dried. 4.0 g of Product 28-163 was obtained with a yield of 100%.

$^1$H-NMR (400 MHz, DMSO-$d_6$) δ 8.37-7.97 (m, 56H), 7.74 (m, 13H), 7.53 (m, 16H), 7.38-7.08 (m, 113H), 5.76 (s, 6H), 5.11 (s, 2H), 4.53 (s, 13H), 4.38-4.10 (m, 32H), 3.68 (m, 76H), 3.17 (d, J=5.3 Hz, 3H), 2.96 (m, 19H), 2.81-2.64 (m, 30H), 2.26 (m, 34H), 1.80 (m, 14H), 1.50 (m, 31H), 1.35 (s, 18H), 1.27-1.06 (m, 17H), 0.85 (m, 78H), 0.50 (s, 16H).

MALDI-TOF MS: [M+H$^+$] 9033.17, [M+Na$^+$] 9055.73

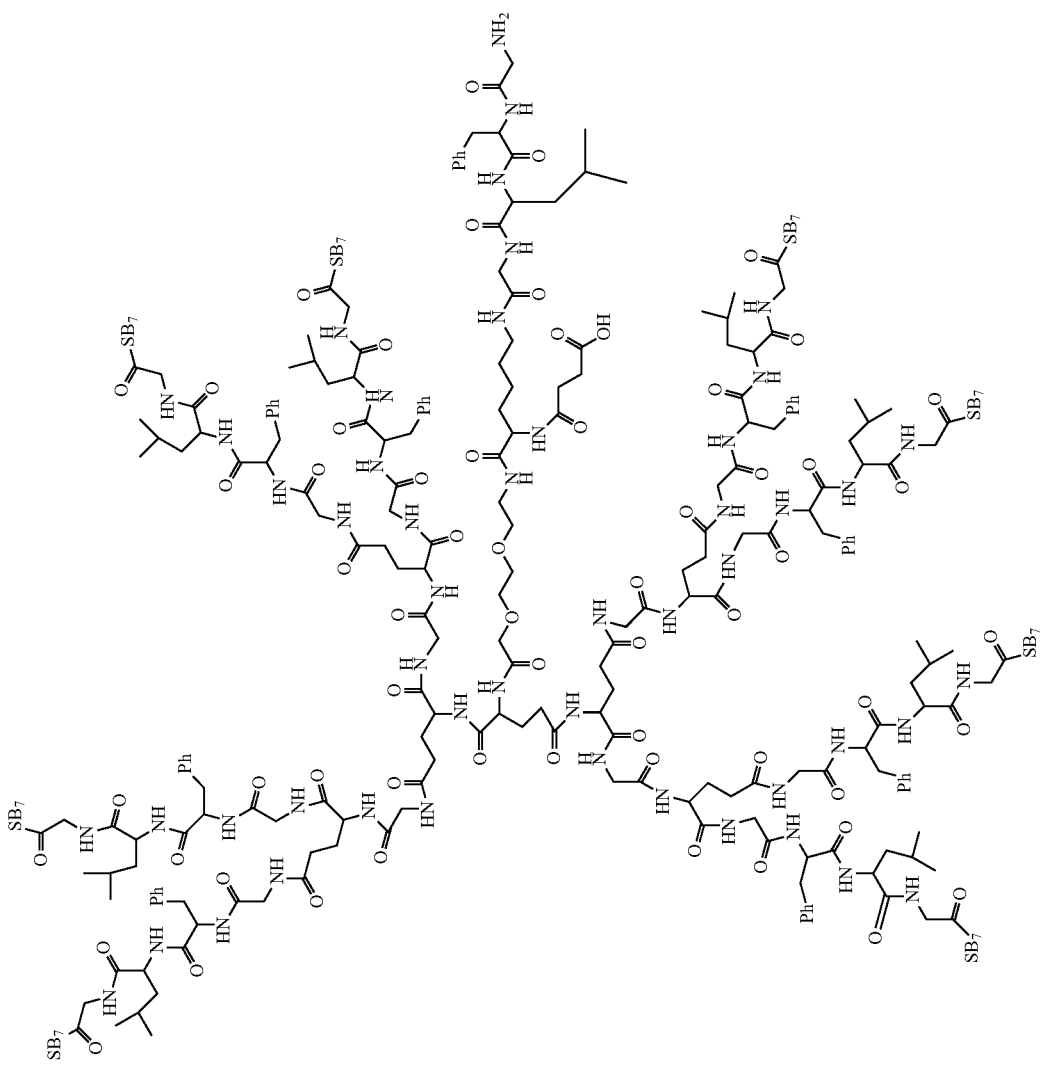
28-170

Compound 28-163 (3.3 g, 0.3650 mmol) was added in a 250 mL flask and then dissolved with dichloromethane (5 mL), TFA (1.355 mL, 18.25 mmol) was then added in the flask, and the mixed solution was stirred overnight at room temperature to react. At the end of the reaction, the reaction solution was concentrated and precipitated with methyl tert-butyl ether (200 mL) to obtain a solid; suction filtering was then carried out, the filter cake was washed with methyl tert-butyl ether (50 mL×3) and then dissolved with a mixed solution of methanol (30 mL) and dichloromethane (120 mL), silica gel powder (10 g) was added to the obtained solution, and the solution was then evaporated to dryness to obtain a powdery solid; the operations of dry sample loading, column chromatography, and elution with a mixed solution (1% ammonia water:4%-8% methanol/dichloromethane) were carried out; the elution product was then collected, concentrated, and evaporated to dryness to obtain a solid product, and the solid product was then dried in a vacuum oven. 0.91 g of Product 28-170 was obtained with a yield of 28%.

28-186
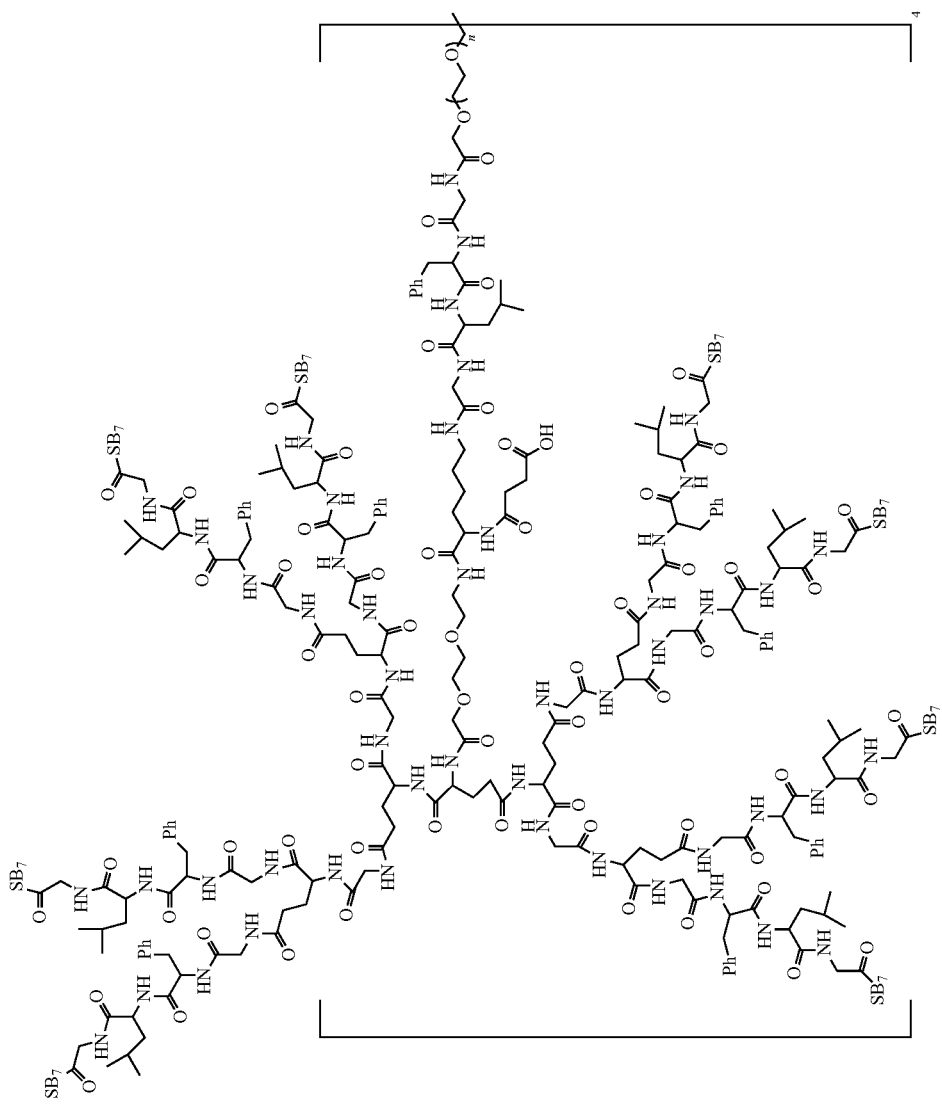

Product 28-170 (0.91 g, 0.1024 mmol) was added to a 250 mL flask and then dissolved with DMF (40 mL); the mixed solution was stirred at −5° C. at a low speed for about 10 min to react, DIEA (0.097 mL, 0.5899 mmol) was slowly added dropwise, 4ARM-SCM-40K (0.93 g, 0.0222 mmol, purchased from JenKem) was then added, and the obtained solution was slowly stirred for a week in the dark at room temperature to react. At the end of the reaction, n-hexane is (150 mL) and methyl tert-butyl ether (50 mL) were added to layer the reaction solution, supernatant was discarded, n-hexane (150 mL) and methyl tert-butyl ether (50 mL) were further added to the lower oily solution, and such operations were repeated four times to obtain an oily product; methyl tert-butyl ether (50 mL) was then added to obtain a viscous oily product and the obtained viscous oily product was then dissolved with a mixed solution of methanol (30 mL) and dichloromethane (120 mL); silica gel powder (15 g) was added to the obtained solution, and the solution was then evaporated to dryness to obtain a powdery solid; the operations of dry sample loading, column chromatography, and elution with a mixed solution (1% ammonia water:6%-8% methanol/dichloromethane) were carried out; the elution product was then collected, concentrated and evaporated to dryness to obtain a solid product, and the solid product was then dried in a vacuum oven. 1.26 g of Product 28-170 was obtained with a yield of 74%.

28-214
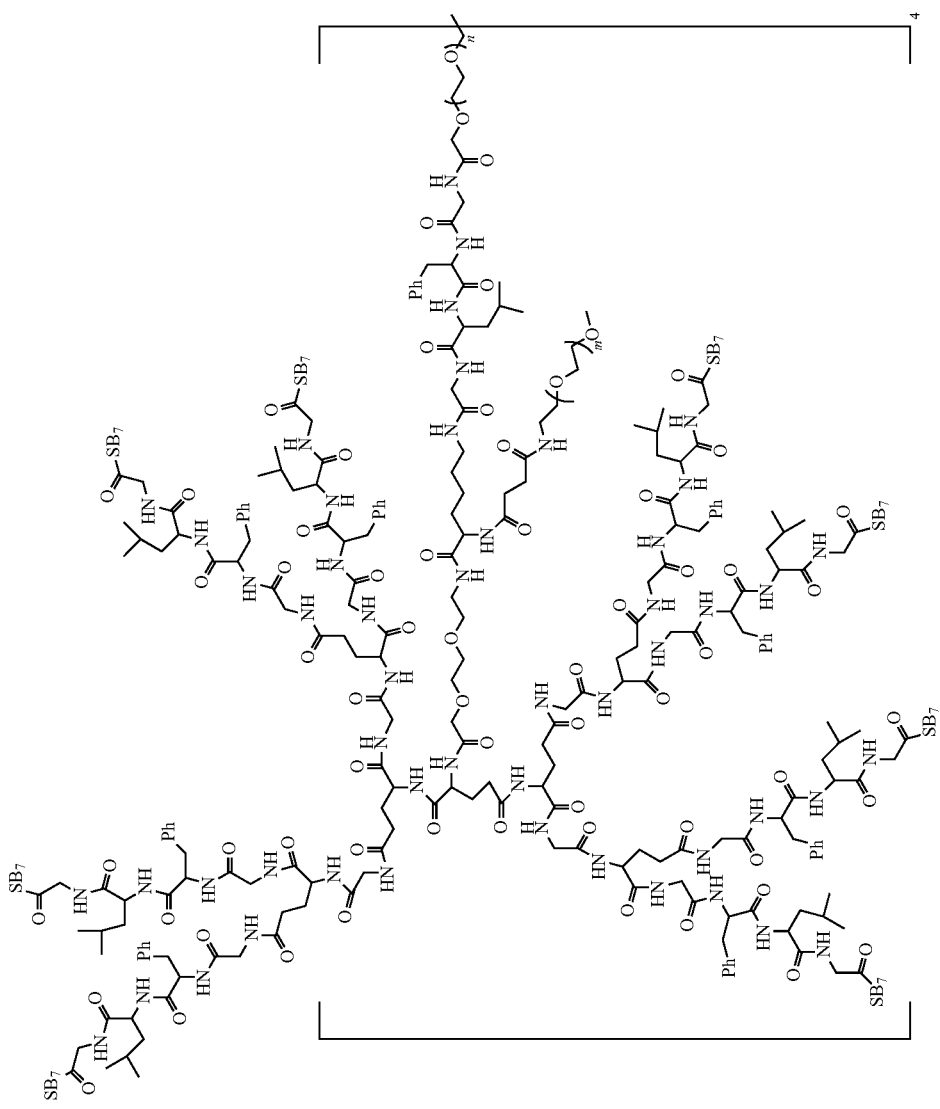

Compound 28-186 (1.26 g, 0.0164 mmol) was added to a 250 mL flask and then dissolved with DMF (20 mL), and M-NH$_2$·HCl-5K (0.5016 g, 0.0981 mmol, purchased from Jenkem), HBTU (0.0372 g, 0.0981 mmol), and HOBT (0.0133 g, 0.0981 mmol) were then added to the obtained solution; the mixed solution was slowly stirred at −5° C. for about 10 min to react, DIEA (0.1101 mL, 0.666 mmol) was then slowly added dropwise, and the obtained solution further reacted at −5° C. for 20 min; and the solution was then slowly stirred in the dark at room temperature for 7 days. At the end of the reaction, n-hexane (100 mL) and methyl tert-butyl ether (30 mL) were added to the solution, the supernatant was discarded, and n-hexane (110 mL) and methyl tert-butyl ether (30 mL) were added to the lower liquid; such operations were repeated six times to obtain a viscous oily product; methyl tert-butyl ether (100 mL) was then added to precipitate a solid, the solid product was then filtered out and the filter cake was washed with methyl tert-butyl ether (50 mL×3) and then dissolved with a mixed solution of methanol (30 mL) and dichloromethane (120 mL); silica gel powder (15 g) was added to the obtained solution, and the solution was then evaporated to dryness to obtain a powdery solid; the operations of dry sample loading, column chromatography, and elution with a mixed solution (1% ammonia water:5%-8% methanol/dichloromethane) were carried out; the elution product was then collected, concentrated and evaporated to dryness to obtain a solid, and the solid was dried for 1 h in a vacuum oven; the product was dissolved with absolute ethanol (2 mL) and dichloromethane (30 mL), and methyl tert-butyl ether (200 mL) was added to the obtained solution to obtain a solid product by precipitation; the solution was filtered and the filter cake was washed with methyl tert-butyl ether (50 mL×2) and dried in the vacuum oven. 1.5 g of Product 28-214 was obtained with a yield of 52%.

$^1$H-NMR (400 MHz, DMSO-d$_6$) δ 8.37-7.93 (m, 224H), 7.64 (m, 52H), 7.51 (m, 64H), 7.48-7.08 (m, 452H), 5.72 (s, 24H), 5.11 (s, 8H), 4.57 (s, 52H), 4.38-4.10 (m, 128H), 3.68 (m, 304H), 3.52 (s, 5547H), m 3.17 (d, J=5.3 Hz, 12H), 2.93 (m, 80H), 2.71-2.54 (m, 12H), 2.16 (m, 12H), 1.70 (m, 56H), 1.50 (m, 126H), 1.25-1.04 (m, 68H), 0.85 (m, 312H), is 0.46 (s, 64H).

MALDI-TOF MS: 95687.56-96552.52

Example 12: Synthesis of Compound 28-206

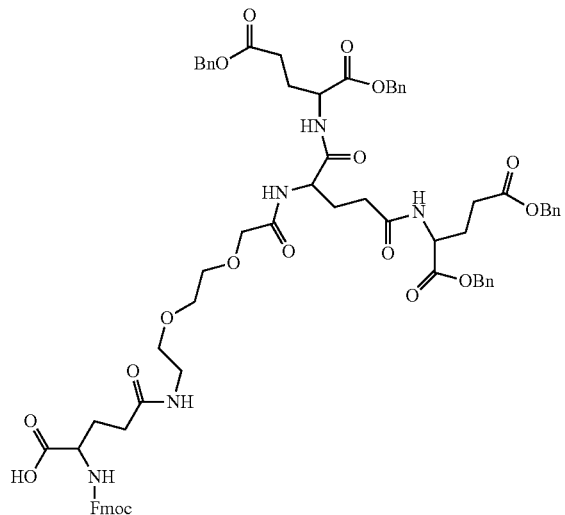

28-92

Compound 24-69 (1.7 g, 1.2894 mmol, home-made) was added in a 100 mL flask and then dissolved with dichloromethane (5 mL), TFA (1.4 mL, 19.3407 mmol) was then added in the flask, and the mixed solution was stirred overnight at room temperature to react. At the end of the reaction, the reaction solution was concentrated to a small amount and n-hexane (50 mL×3) was then added to layer the solution; the supernatant was discarded and n-hexane was further added to the lower oily solution; such operations were repeated three times to obtain an oily product and the oily product was then dried. 1.6 g of Product 28-92 was obtained with a yield of 100%.

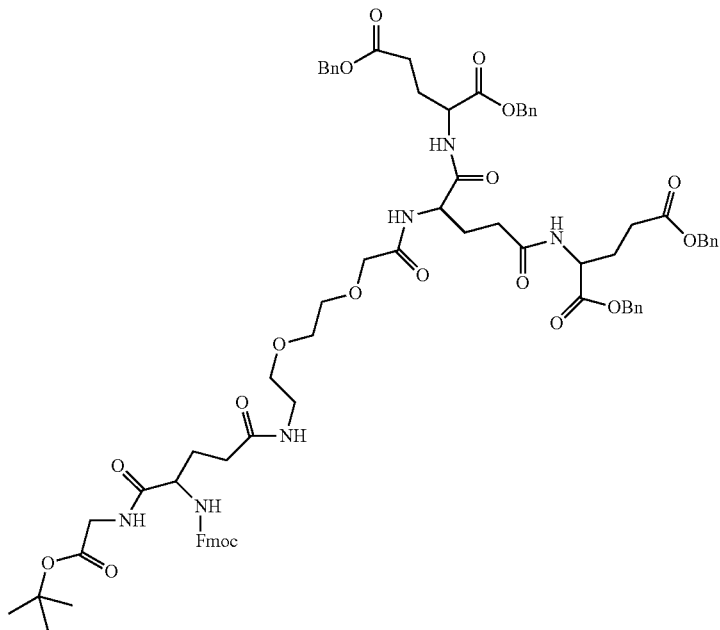

28-132

Compound 28-92 (1.6277 g, 12894 mmol), Boc-Gly-OH (0.2594 g, 1.5473 mmol), HBTU (0.7335 g, 1.9341 mmol), and HOBT (0.2614 g, 1.9341 mmol) were added in a 250 mL flask, and the obtained solution in the flask was stirred for about 20 min at 0° C.; then, DIEA (1.172 mL, 7.0917 mmol) was slowly added dropwise and then the resulting solution was stirred overnight at 0° C. to further react. At the end of the reaction, the reaction solution was transferred to a 1 L separatory funnel and then extracted with deionized water (200 mL) and ethyl acetate (250 mL); the obtained organic phase was washed with a saturated sodium chloride solution (200 mL×1) and then concentrated, evaporated to dryness and dried. 1.8 g of Product 28-132 was obtained with a yield of 100%.

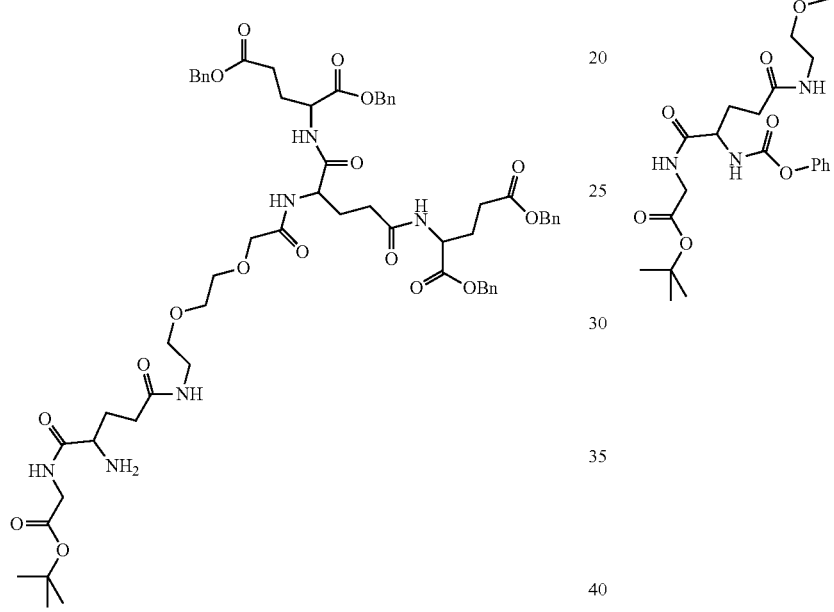

Compound 28-132 was added into a 100 mL flask and then dissolved with DMF; morpholine (3.37 mL, 38.682 mmol) was added to the obtained solution to react at room temperature for 1 h. At the end of the reaction, the reaction solution was transferred to a 1 L separatory funnel and extracted with a saturated sodium chloride solution (200 mL) and ethyl acetate (300 mL) to obtain an organic phase; the aqueous phase was washed with ethyl acetate (200 mL×1), and the obtained organic phases were combined, washed with a saturated sodium chloride solution (250 mL×1), then concentrated and evaporated to dryness; silica gel powder (10 g) was added to the obtained solution, and the solution was then evaporated to dryness to obtain a powdery solid; the operations of dry sample loading, column chromatography, and elution with a mixed solution (1% ammonia water:4%-6% methanol/dichloromethane) were carried out. 1.263 g of Product 28-135 was obtained with a yield of 85%.

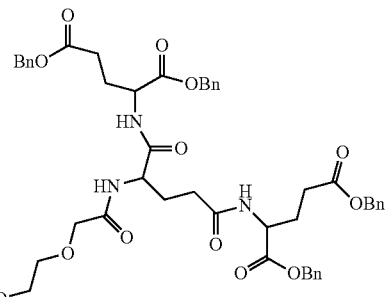

Compound 28-135 (1.163 g, 1.0084 mmol) was added into a 250 mL flask and then dissolved with dichloromethane (20 mL); triethylamine (0.5669 mL, 4.0337 mmol) was then added to the resulting solution, and the obtained solution was stirred at 0° C. for 15 min to react; then, phenyl chloroformate (0.2535 mL, 2.0169 mmol, purchased from damas-beta) was added dropwise to the reaction solution, and the resulting solution was further stirred overnight at 0° C. At the end of the reaction, the reaction solution was transferred to a 1 L separatory funnel and then extracted with dichloromethane (250 mL) and deionized water (200 mL) to obtain an organic phase; silica gel powder was added to the organic phase, and the obtained solution was then evaporated to dryness to obtain a powdery solid; the operations of dry sample loading, column chromatography, and elution with a mixed solution (5%-6% methanol/dichloromethane) were carried out. 0.57 g of Product 28-137 was obtained with a yield of 44%.

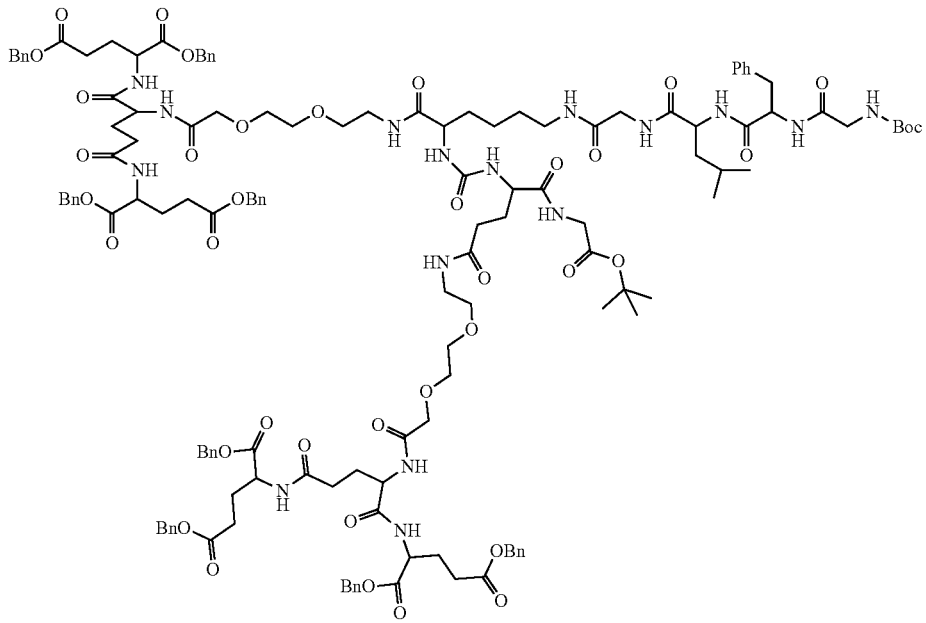

28-138

Compound 28-137 (0.57 g, 0.4476 mmol) and Compound 28-82 (0.7453 g, 0.4924 mmol) was added into a 100 mL flask and then dissolved with DMF (25 mL); the obtained solution was stirred overnight at 80° C. to react. At the end of the reaction, the reaction solution was transferred to a 1 L separatory funnel and extracted with ethyl acetate (200 mL) and a saturated sodium chloride solution (200 mL) to obtain an organic phase; the organic phase was washed with a saturated sodium chloride solution (150 mL); silica gel powder was then added to the obtained solution, and the solution was then evaporated to dryness to obtain a powdery solid; the operations of dry sample loading, column chromatography, and elution with a mixed solution (3%-5% methanol/dichloromethane) were carried out. 0.62 g of Product 28-138 was obtained with a yield of 52%.

$^1$H-NMR (400 MHz, DMSO-$d_6$) δ 8.51 (s, 2H), 8.30 (d, J=7.4 Hz, 2H), 8.08 (d, 2H), 7.89 (m, 4H), 7.68 (s, 3H), 7.35 (s, 45H), 6.61 (s, 1H), 6.59 (s, 2H), 4.35 (m, 6H), 4.15-4.00 (m, 3H), 3.90 (s, 4H), 3.71 (m, 5H), 3.59 (s, 18H), 3.39 (s, 6H), 3.28 (s, 7H), 3.16 (s, 5H), 2.41 (s, 9H), 2.18 (m, 9H), 2.03 (s, 6H), 1.89 (s, 11H), 1.39 (s, 18H), 1.34 (m, 3H), 1.23 (s, 5H), 0.85 (m, 2H).

MALDI-TOF MS: [M+H$^+$] 2690.54

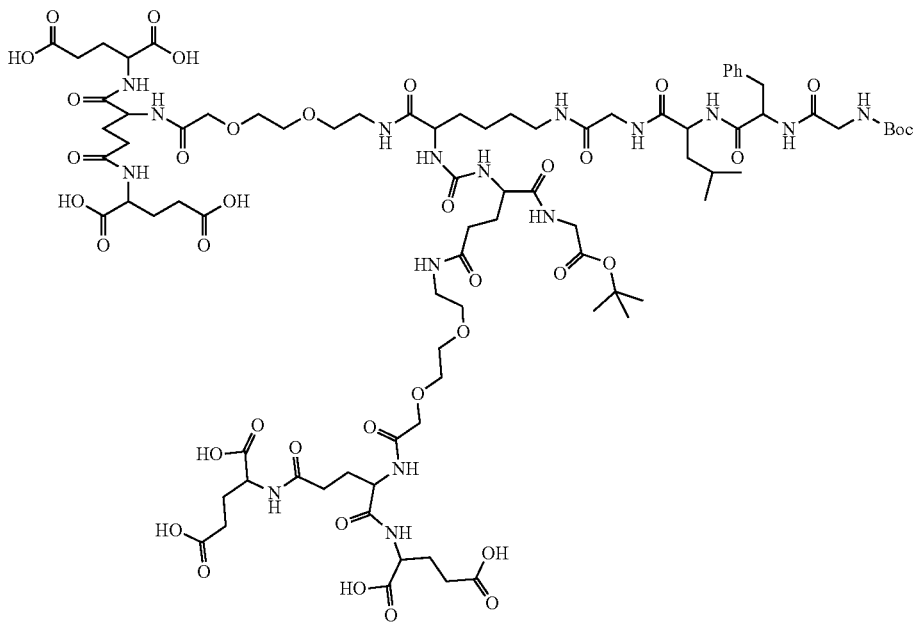

28-158

Compound 28-138 (0.5834 g, 0.2166 mmol) and 10% Pd/C (0.0300 g) were added in a reactor and then dissolved with DMF (45 mL); the reactor was then sealed and H₂ was introduced in the reactor to a pressure of 16 psi; and the mixed solution was then stirred for 3 days at room temperature to react. At the end of the reaction, the reaction solution was filtered with diatomaceous earth, the diatomaceous earth was washed with DMF (20 mL×3), and a DMF solution containing Product 28-158 was thus obtained.

at −5° C. to react and then the reaction solution was further stirred overnight at room temperature. At the end of the reaction, n-hexane (200 mL) and methyl tert-butyl ether (50 mL) were added to layer the reaction solution, supernatant was discarded, n-hexane (200 mL) and methyl tert-butyl ether (50 mL) were further added to the lower oily solution, and such operations were repeated four times to obtain a viscous oily product; methyl tert-butyl ether (200 mL) was added to precipitate a solid product; filtering was then 28-159

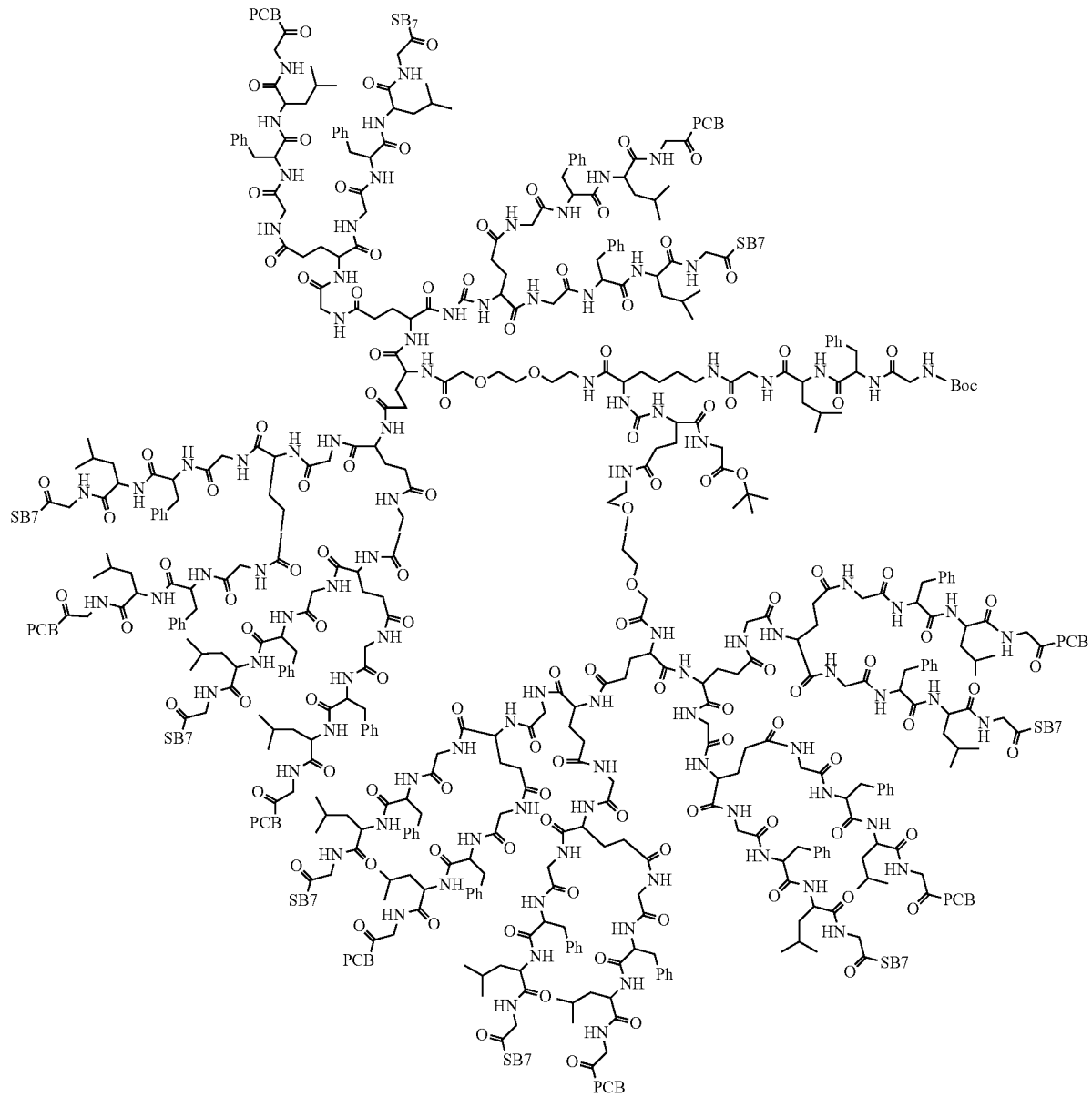

Compound 28-158 (0.4268 g, 0.2163 mmol), Compound 28-154 (3.5 g, 1.8601 mmol), HBTU (0.9843 g, 2.5956 mmol), and HOBT (0.3507 g, 2.5956 mmol) were added into a 500 mL flask and then dissolved with DMF (90 mL); the mixed solution was stirred at −5° C. for 20 min to react; DIEA (1.2870 mL, 7.7868 mmol) was then slowly added dropwise, the obtained solution was then stirred for 40 min carried out and the filter cake was washed with methyl tert-butyl ether and methanol (50 mL×3) and then dissolved with dichloromethane (160 mL) and methanol (40 mL); silica gel powder (30 g) was added to the obtained solution, and the solution was then evaporated to dryness to obtain a powdery solid; the operations of dry sample loading, column chromatography, and elution with a mixed solution (1% ammonia water:6%-7% methanol/dichloromethane) were carried out; the elution product was then collected, concentrated and dried. 2.6 g of Product 28-159 was obtained with a yield of 72%.

$^1$H-NMR (400 MHz, DMSO-$d_6$) δ 10.12 (s, 8H), 8.95 (s, 7H), 8.40-7.75 (m, 122H), 7.51 (m, 21H), 7.39-7.00 (m, 167H), 5.85-5.77 (m, 7H), 4.49 (m, 8H), 4.27 (m, 22H), 4.01 (m, 24H), 3.59 (m, 88H), 3.17 (d, J=5.2 Hz, 37H), 2.98 (m, 40H), 2.84-2.53 (m, 42H), 2.41 (s, 32H), 2.30 (s, 53H), 2.17 (m, 61H), 1.81 (m, 77H), 1.52 (m, 73H), 1.37 (s, 18H), 1.33-1.27 (m, 10H), 1.22 (m, 22H), 0.96-0.64 (m, 132H), 0.50 (s, 25H).

MALDI-TOF MS: [M+H$^+$] 16910.26

28-167
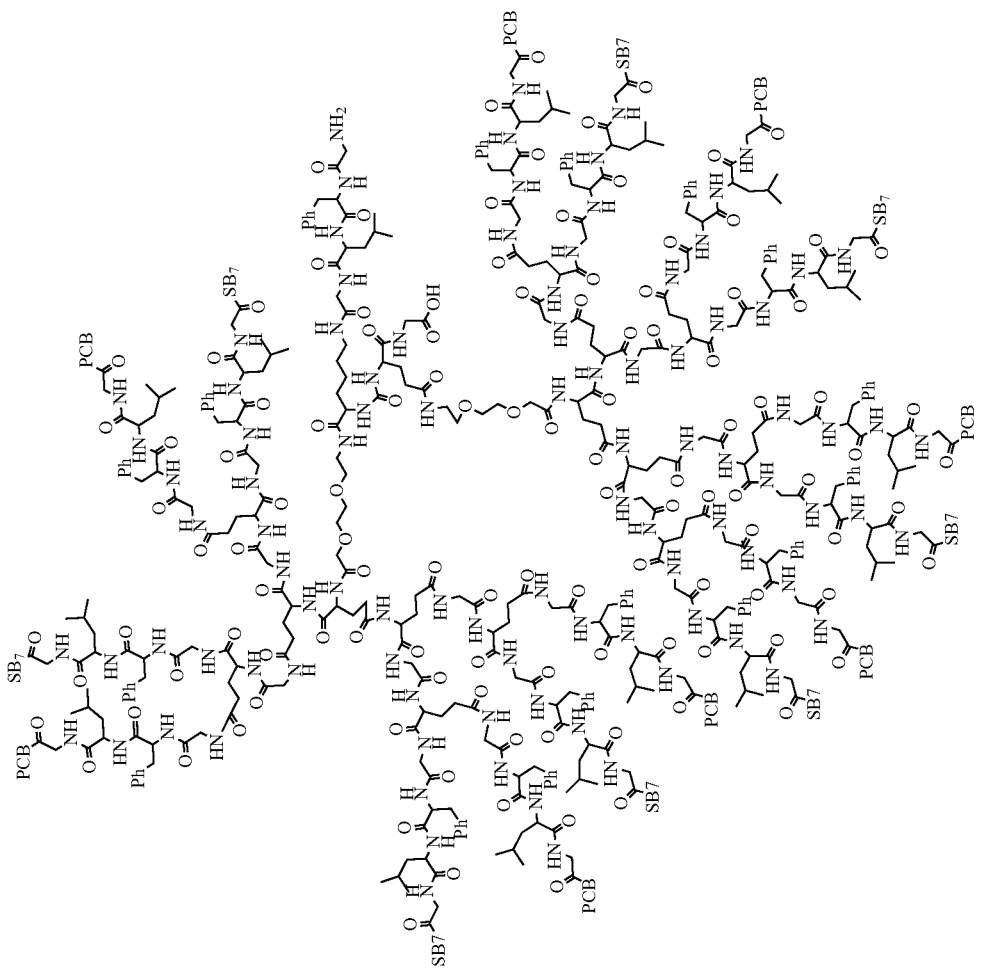

Compound 28-159 (2.6 g, 0.1537 mmol) was added in a 250 mL flask, dichloromethane (10 mL) and TFA (2.28 mL, 30.7476 mmol) were then added, and the mixed solution was stirred overnight at room temperature to react. At the end of the reaction, the reaction solution was concentrated to a small amount and then precipitated with methyl tert-butyl ether (150 mL) to obtain a solid; suction filtering was then carried out, the filter cake was washed with methyl tert-butyl ether (50 mL×3) and then dissolved with a mixed solution of methanol (40 mL) and dichloromethane (160 mL), silica gel powder (15 g) was added to the obtained solution, and the solution was then evaporated to dryness to obtain a powdery solid; the operations of dry sample loading, column chromatography, and elution with a mixed solution (1% ammonia water:6%-10% methanol/dichloromethane) were carried out; the elution product was then collected, concentrated, evaporated to dryness to obtain a solid product, and the solid product was then dried in a vacuum oven. 1.5 g of Product 28-167 was obtained with a yield of 60%.

$^1$H-NMR (400 MHz, DMSO-d$_6$) δ 10.12 (s, 8H), 8.95 (s, 7H), 8.12 (m, 93H), 7.87 (s, 26H), 7.51 (s, 21H), 7.34-6.97 (m, 167H), 5.83 (m, 6H), 5.75 (s, 7H), 4.56 (s, 8H), 4.23 (s, 22H), 3.99 (s, 9H), 3.89 (s, 8H), 3.55 (m, 91H), 3.18-2.92 (m, 94H), 2.78 (m, 40H), 2.41 (s, is 22H), 2.26 (m, 86H), 2.11 (s, 44H), 1.83 (m, 78H), 1.55 (m, 75H), 1.22 (s, 10H), 0.86 (m, 124H), 0.49 (s, 23H).

MALDI-TOF MS: [M+H$^+$] 16756.11, [M+Na$^+$] 16777.80

28-174

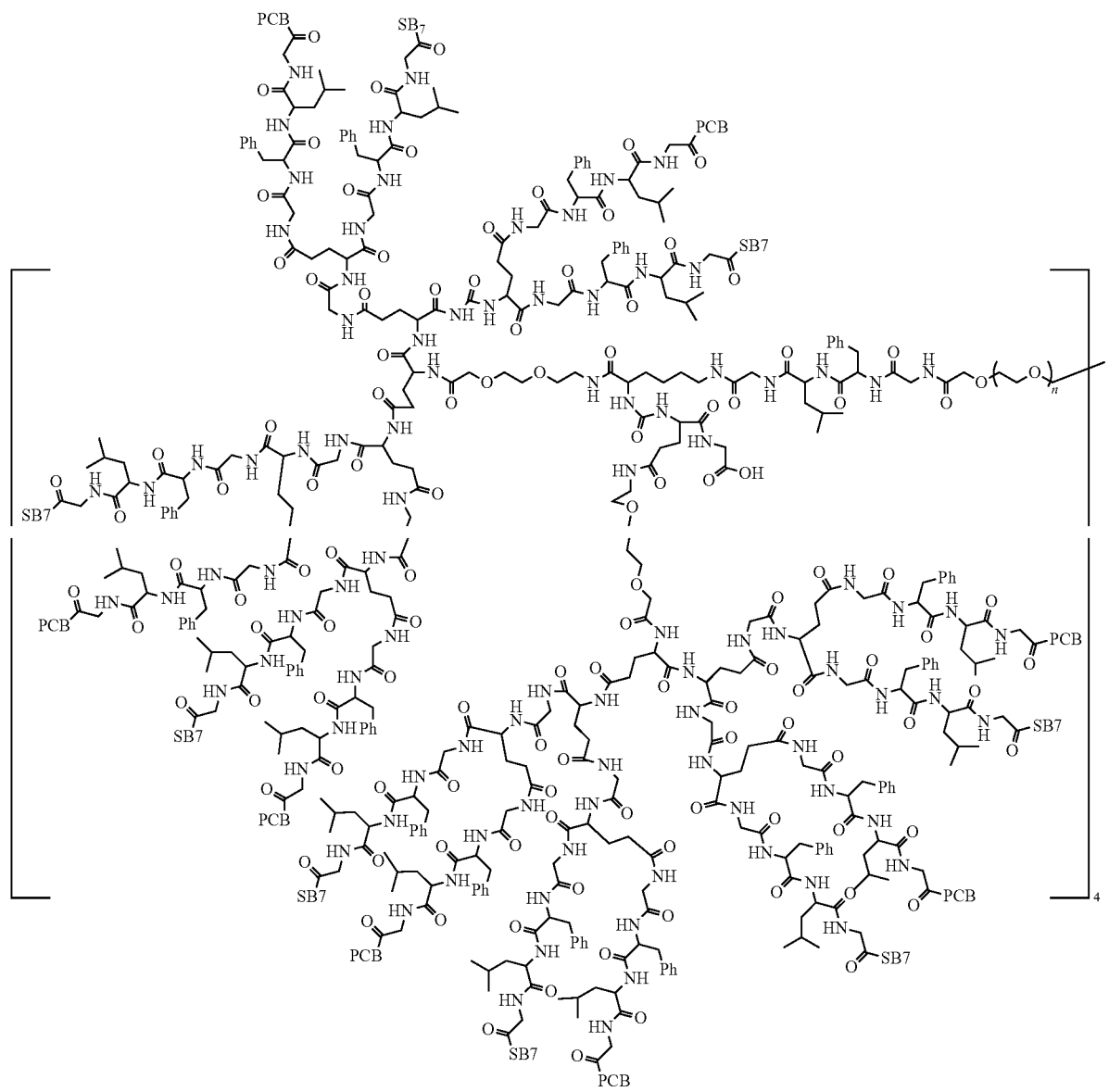

Product 28-167 (1.5 g, 0.0895 mmol) was added to a 250 mL flask and then dissolved with DMF (35 mL); the mixed solution was stirred at −5° C. at a low speed for about 10 m to react, DIEA (0.2284 mL, 1.3818 mmol) was slowly added dropwise, 4ARM-SCM-40K (0.8166 g, 0.0195 mmol, purchased from JenKem) was then added, and the obtained solution was stirred for a week in the dark at room temperature at a low speed to react. At the end of the reaction, n-hexane (120 mL) and methyl tert-butyl ether (50 mL) were added to layer the reaction solution, supernatant was discarded, n-hexane (150 mL) and methyl tert-butyl ether (50 mL) were further added to the lower oily solution, and such operations were repeated four times to obtain an oily product; methyl tert-butyl ether (150 mL) was then added to obtain a solid product; filtering was then carried out and the filter cake was then dissolved with a mixed solution of methanol (50 mL) and dichloromethane (200 mL); silica gel powder (20 g) was added to the obtained solution, and the solution was then evaporated to dryness to obtain a powdery solid; the operations of dry sample loading, column chromatography, and elution with a mixed solution (1% ammonia water:6% methanol/dichloromethane) were carried out; the elution product was then collected, concentrated and evaporated to dryness to obtain a solid product, and the solid product was then dried in a vacuum oven. 1.34 g of Product 28-174 was obtained with a yield of 70%.

$^1$H-NMR (400 MHz, DMSO-d$_6$) δ 10.15 (s, 32H), 8.95 (s, 28H), 8.08 (m, 389H), 7.95 (s, 38H), 7.91-7.82 (m, 66H), 7.53 (m, 90H), 7.38-6.83 (m, 672H), 5.82 (s, 32H), 5.75-5.69 (m, 20H), 4.47 (m, 188H), 4.24-3.90 (m, 363H), 3.51 (s, 4034H), 3.30-2.88 (m, 373H), 2.74 (m, 160H), 2.41 (s, 90H), 2.36-2.09 (m, 324H), 2.01-1.83 (m, 170H), 1.80-1.34 (m, 587H), 1.32-1.14 (m, 619H), 0.85 (m, 340H), 0.50 (s, 84H).

MALDI-TOF MS: 108487-109124

28-206
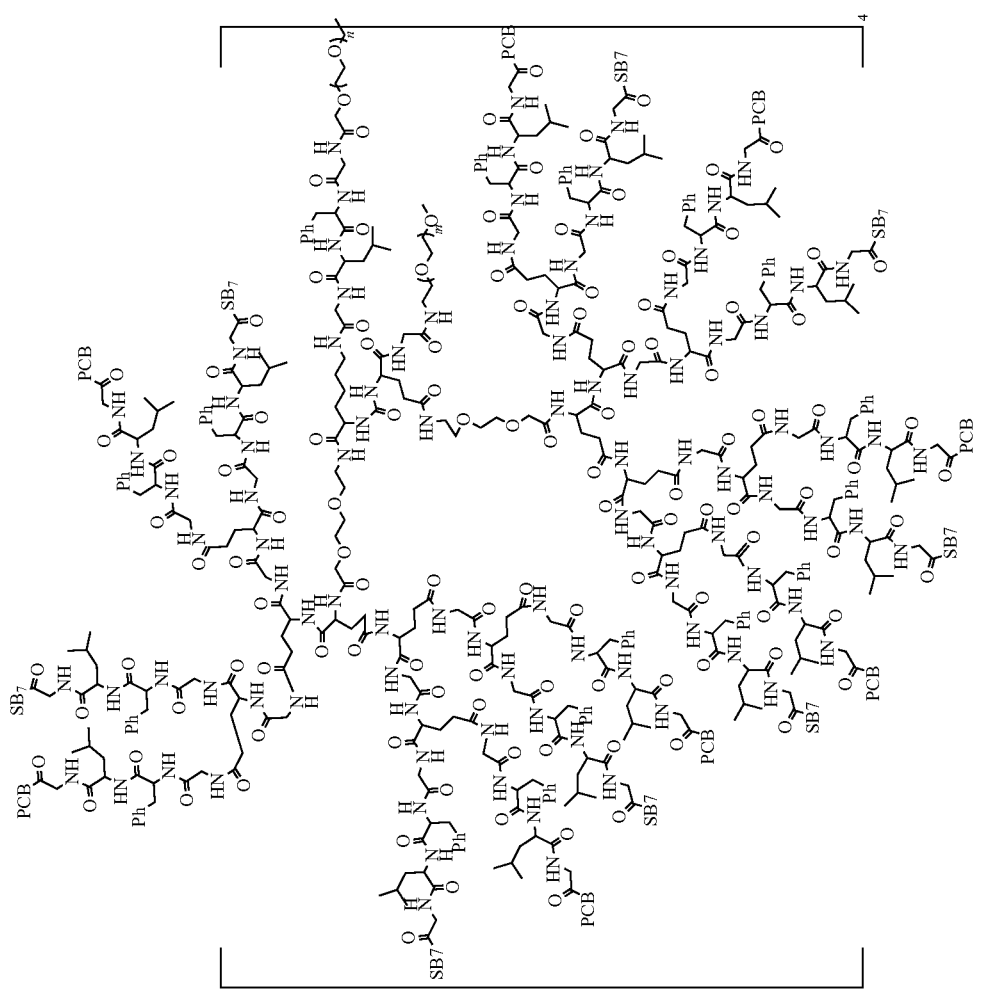

Compound 28-174 (1.3455 g, 0.0124 mmol) was added to a 250 mL flask and then dissolved with DMF (25 mL), and M-NH2·HCl-20K (1.5148 g, 0.0744 mmol, purchased from Jenkem), HBTU (0.0282 g, 0.0744 mmol), and HOBT (0.0101 g, 0.0744 mmol) were then added to the obtained solution; the mixed solution was slowly stirred at −5° C. for about 10 min to react, DIEA (0.045 mL, 0.2728 mmol) was then slowly added dropwise, and the obtained solution further reacted at −5° C. for 20 min; and the solution was then slowly stirred in the dark at room temperature for 7 days. At the end of the reaction, n-hexane (150 mL) and methyl tert-butyl ether (30 mL) were added to the solution, the supernatant was discarded, and n-hexane (150 mL) and methyl tert-butyl ether (30 mL) were added to the lower liquid; such operations were repeated four times to obtain a viscous oily product; methyl tert-butyl ether (200 mL) was then added to precipitate a solid, the solid product was then filtered out and the filter cake was is washed with methyl tert-butyl ether (40 mL×3) and then dissolved with a mixed solution of methanol (40 mL) and dichloromethane (160 mL); silica gel powder (20 g) was added to the obtained solution, and the solution was then evaporated to dryness to obtain a powdery solid; the operations of dry sample loading, column chromatography, and elution with a mixed solution (1% ammonia water:6%-7% methanol/dichloromethane) were carried out; the elution product was then collected, concentrated and evaporated to dryness to obtain a solid, and the solid was dried for 1 h in a vacuum oven; the product was dissolved with absolute ethanol (10 mL) and dichloromethane (15 mL), and methyl tert-butyl ether (200 mL) was added to the obtained solution to obtain a solid product by precipitation; the solution was filtered and the filter cake was washed with methyl tert-butyl ether (40 mL×3) and dried in the vacuum oven. 1.45 g of Product 28-206 was obtained with a yield of 63%.

$^1$H-NMR (400 MHz, DMSO-d$_6$) δ 10.15 (s, 31H), 8.95 (s, 28H), 8.13 (m, 390H), 7.95 (s, 38H), 7.88 (m, 66H), 7.52 (s, 90H), 7.21 (s, 672H), 5.82 (s, 32H), 5.76 (s, 20H), 4.55 (s, 188H), 3.70-3.66 (m, 363H), 3.51 (s, 12027H), 3.29-2.86 (m, 373H), 2.73 (s, 160H), 2.41 (s, 90H), 2.31 (m, 324H), 2.23-2.02 (m, 170H), 1.67 (m, 587H), 1.19 (m, 340H), 0.82 (s, 619H), 0.50 (s, 84H).

Example 13: Synthesis of Compound 25-276

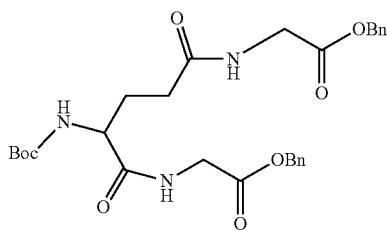

25-157

Boc-Glu-OH (5.0 g, 20.2224 mmol), HBTU (23.0075 g, 60.6673 mmol), HOBT (8.1974 g, 60.6673 mmol), and glycine benzyl ester hydrochloride (8.9713 g, 44.4894 mmol) were added in a 250 mL round-bottomed flask and dissolved with DMF (80 mL), and the obtained solution was stirred for about 30 min at −5° C.; then, DIEA (40.0 mL, 242.6694 mmol) was slowly added dropwise; the obtained solution was further stirred at −5° C. for 1 h, and then the reaction solution in the round-bottomed flask was stirred overnight at room temperature to further react.

At the end of the reaction, the reaction solution was transferred to a 2 L separatory funnel, a saturated sodium bicarbonate solution (300 mL) and ethyl acetate (200 mL) were then added, the obtained solution was then shaken and extracted and the aqueous phase was separated out. Next, a saturated sodium bicarbonate solution (300 mL) was further added to the organic phase, the obtained solution was then shaken and extracted and the aqueous phase was separated out. Then, a saturated sodium chloride solution (200 mL) was further added to the organic phase, the obtained solution was then shaken and extracted and the aqueous phase was separated out. Finally, the organic phase was concentrated and evaporated to dryness and then dried in a vacuum oven. 10.9522 g of Product 25-157 was obtained with a yield of 100%.

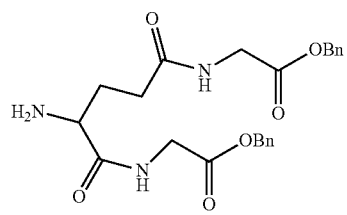

25-158

Compound 25-157 (10.9522 g, 20.2224 mmol) was added in a 500 mL round-bottomed flask and then dissolved with dichloromethane (5 mL), TFA (22.5 mL, 303.336 mmol) was then added with stirring, and the mixed solution in the reaction flask was stirred overnight at room temperature to react.

At the end of the reaction, the reaction solution was first concentrated under reduced pressure and evaporated to remove dichloromethane. The reaction solution was then transferred to a 2 L separatory funnel, a saturated sodium bicarbonate solution (400 mL) and ethyl acetate (300 mL) were then added, the obtained solution was then shaken and extracted and the aqueous phase was separated out. Then, a saturated sodium chloride solution (300 mL) was further added to the organic phase, the obtained solution was then shaken and extracted and the aqueous phase was separated out. Finally, the organic phase was concentrated and evaporated to dryness and then dried in a vacuum oven. 8.9278 g of Product 25-158 was obtained with a yield of 100%.

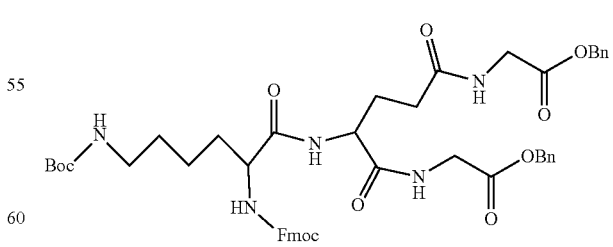

25-159

Fmoc-Lys(Boc)-OH (8.6136 g, 18.3840 mmol), HBTU (10.4579 g, 27.5760 mmol), HOBT (3.7261 g, 27.5760 mmol), and Compound 25-158 (8.9278 g, 20.2224 mmol) were added in a 500 mL round-bottomed flask and dissolved with DMF (80 mL), and the obtained solution was stirred for about 30 min at −5° C.; then, DIEA (13.7 mL, 82.7280 mmol) was slowly added dropwise; the reaction solution in the round-bottomed flask was stirred at −5° C. for 1 h to react and then the resulting reaction solution in the round-bottomed flask was stirred overnight at room temperature to further react At the end of the reaction, the reaction solution was transferred to a 2 L separatory funnel, a saturated sodium bicarbonate solution (300 mL) and ethyl acetate (200 mL) were then added, the obtained solution was then shaken and extracted and the aqueous phase was separated out. Next, a saturated sodium bicarbonate solution (300 mL) was further added to the organic phase, the obtained solution was then shaken and extracted and the aqueous phase was separated out. Then, a saturated sodium chloride solution (200 mL) was further added to the organic phase, the obtained solution was then shaken and extracted and the aqueous phase was separated out. Finally, the organic phase was concentrated and evaporated to dryness and then dried in a vacuum oven. 18.0384 g of Product 25-159 was obtained with a yield of 100%.

Compound 25-159 (18.0384 g, 18.3840 mmol) was added in a 100 mL round-bottomed flask and then dissolved with dichloromethane (10 mL), TFA (20.5 mL, 275.76 mmol) was then added with stirring, and the mixed solution in the reaction flask was stirred overnight at room temperature to react.

At the end of the reaction, the reaction solution was first concentrated under reduced pressure and evaporated to remove dichloromethane. N-hexane (150 mL) was then added to the reaction flask to precipitate the reaction solution; the supernatant was discarded; and then n-hexane (150 mL) was added to the lower solution again for precipitation, and the such operations were repeated five times to obtain an oily solid. Then, the oily solid was dissolved with dichloromethane (10 mL) and then precipitated with methyl tert-butyl ether (150 mL) to obtain a powdery solid, and the solid product was then filtered out and then dried in a vacuum oven. 14.5581 g of Product 25-197 was obtained with a yield of 100%.

MALDI-TOF MS: [M+H$^+$] 792.89, [M+Na$^+$] 814.72

25-197

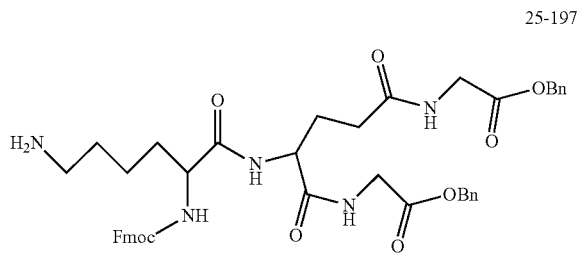

25-208

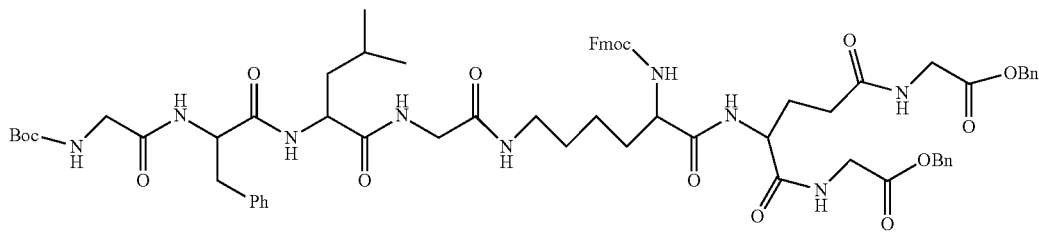

Compound 25-197 (14.5581 g, 18.3840 mmol), HBTU (10.4579 g, 27.5760 mmol), HOBT (3.7261 g, 27.5760 mmol), and Boc-GFLG-OH (10.8665 g, 22.0608 mmol, synthesized in the same way as Compound 30-28) were added in a 500 mL round-bottomed flask and then dissolved with DMF (100 mL), and the obtained solution in the reaction flask was stirred for about 30 min at −5° C.; then, DIEA (18.2 mL, 110.3040 mmol) was slowly added dropwise; and then the reaction solution was further stirred for 3 h at −5° C. to react.

At the end of the reaction, the reaction solution was transferred to a 1 L separatory funnel, a saturated sodium bicarbonate solution (300 mL) and ethyl acetate (300 mL) were then added, the obtained solution was then shaken and extracted and the organic phase was separated out. Ethyl acetate (200 mL) was then added to the aqueous phase, the obtained solution was then shaken and extracted and the organic phase was separated out. Then, the obtained organic phases were combined and a saturated sodium chloride solution (200 mL) was then added to the organic phase, the obtained solution was then shaken and extracted and the aqueous phase was separated out. Finally, the organic phase was concentrated and evaporated to dryness and then dried in a vacuum oven. 23.2767 g of Product 25-208 was obtained with a yield of 100%.

MALDI-TOF MS: [M+Na$^+$] 1288.92

25-217

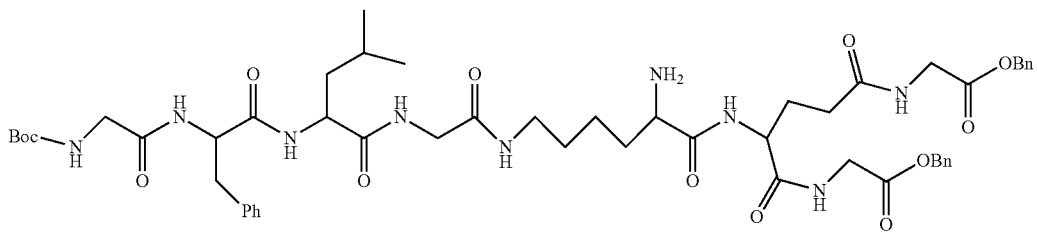

Compound 25-208 (23.2767 g, 18.3840 mmol) was added in a 500 mL round-bottomed flask and then dissolved with dichloromethane (30 mL), morpholine (24.0 mL, 275.7600 mmol) was then added with stirring, and the mixed solution was stirred for 2 h at room temperature to react. At the end of the reaction, the reaction solution was transferred to a 2 L separatory funnel, a saturated sodium bicarbonate solution (300 mL) and ethyl acetate (300 mL) were then added, the obtained solution was then shaken and extracted and the aqueous phase was separated out. Then, a saturated sodium chloride solution (200 mL) was then added to the organic phase, the obtained solution was then shaken and extracted and the aqueous phase was separated out. Finally, the organic phase was concentrated and evaporated to dryness and then dried in a vacuum oven. 19.1966 g of Product 25-217 was obtained with a yield of 100%.

MALDI-TOF MS: [M+H$^+$] 1044.62, [M+Na$^+$] 1066.49 organic phase was concentrated and evaporated to dryness. The organic phase was then dissolved with a mixed solvent (20% methanol/dichloromethane) (100 mL), 100 mL of silica gel powder was then added, and the obtained solution was then evaporated to dryness. The operations of dry sample loading, column chromatography, and elution with eluent (1%-4% methanol:99%-96% dichloromethane) were then carried out, and the elution solution was collected, concentrated, evaporated to dryness, and dried in a vacuum oven. 15.9076 g of Product 25-219 was obtained with a yield of 79.29%.

MALDI-TOF MS: [M+Na$^+$] 1222.52

25-219

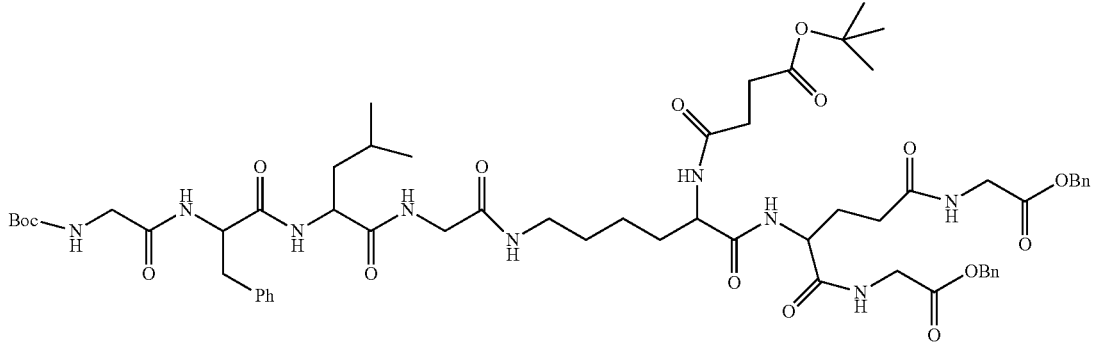

Compound 25-217 (19.1966 g, 18.3840 mmol), HBTU (9.5072 g, 25.0691 mmol), HOBT (3.3873 g, 25.0691 mmol) and mono-tert-butyl succinate (2.9112 g, 16.7127 mmol) were added in a 500 mL round-bottomed flask and dissolved with DMF (100 mL), and the obtained solution in the reaction flask was stirred for about 30 min at −5° C.; then, DIEA (12.4 mL, 75.2073 mmol) was slowly added dropwise; the obtained solution was further stirred at −5° C. for 1 h to react, and then the reaction solution was placed at room temperature to react overnight. At the end of the reaction, the reaction solution was transferred to a 2 L separatory funnel, a saturated sodium bicarbonate solution (400 mL) and ethyl acetate (300 mL) were then added, the obtained solution was then shaken and extracted and the aqueous phase was separated out. Then, a saturated sodium chloride solution (300 mL) was then added to the organic phase, the obtained solution was then shaken and extracted and the aqueous phase was separated out. Finally, the 25-198

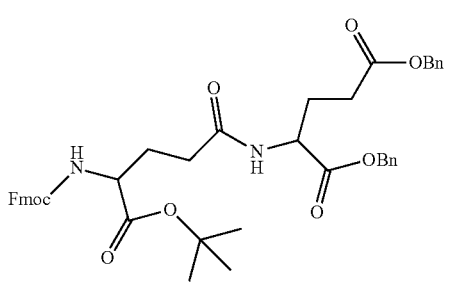

Fmoc-Glu-OtBu (5.6209 g, 13.2111 mmol), HBTU (6.8321 g, 18.0152 mmol), HOBT (2.4342 g, 18.0152 mmol), and H-Glu(OBzl)-OBzl·TosOH (6.0 g, 12.0101 mmol) were added in a 500 mL round-bottomed flask and dissolved with DMF (60 mL), and the obtained solution was stirred for about 30 min at −5° C.; then, DIEA (8.9 mL, 54.0455 mmol) was slowly added dropwise; and then the reaction solution was stirred for 3 h at −5° C. to further react. At the end of the reaction, the reaction solution was transferred to a 1 L separatory funnel, a saturated sodium bicarbonate solution (300 mL) and ethyl acetate (300 mL) were then added, the obtained solution was then shaken and extracted and the organic phase was separated out. Ethyl acetate (200 mL) was then added to the aqueous phase, the obtained solution was then shaken and extracted and the organic phase was separated out. Then, the obtained organic phases were combined and a saturated sodium chloride solution (200 mL) was then added to the organic phase; the obtained solution was then shaken and extracted and the aqueous phase was separated out. Finally, the organic phase was concentrated and evaporated to dryness. The organic phase was then dissolved with a mixed solvent (20% methanol/dichloromethane) (60 mL), 50 mL of silica gel powder was then added, and the obtained solution was then evaporated to dryness. The operations of dry sample loading, column chromatography, and elution with is eluent (20%-70% ethyl acetate: 80%-30% petroleum ether) were then carried out, and the elution solution was collected, concentrated, evaporated to dryness, and dried in a vacuum oven. 8.0 g of Product 25-198 was obtained with a yield of 90.65%.

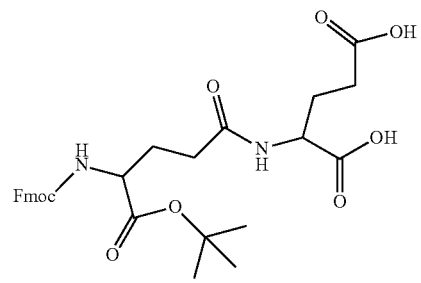

25-209

Compound 25-198 (1.2903 g, 1.7559 mmol) and 50 mg of 10% Pd/C were added into a hydrogenation reactor and then dissolved with DMF (30 mL); the hydrogenation reactor was sealed and H$_2$ was then introduced into the reactor until the pressure in the reactor reached 1.6 MPa; the obtained solution in the hydrogenation reactor was stirred overnight at room temperature.

At the end of the reaction, the hydrogenation reactor was taken out, the reaction solution was evenly added dropwise to a sand core funnel filled with compacted diatomaceous earth and suction filtering was carried out. The diatomaceous earth was washed three times with DMF (20 mL×3) until there was no product in the diatomaceous earth, and then the reaction product solution was obtained.

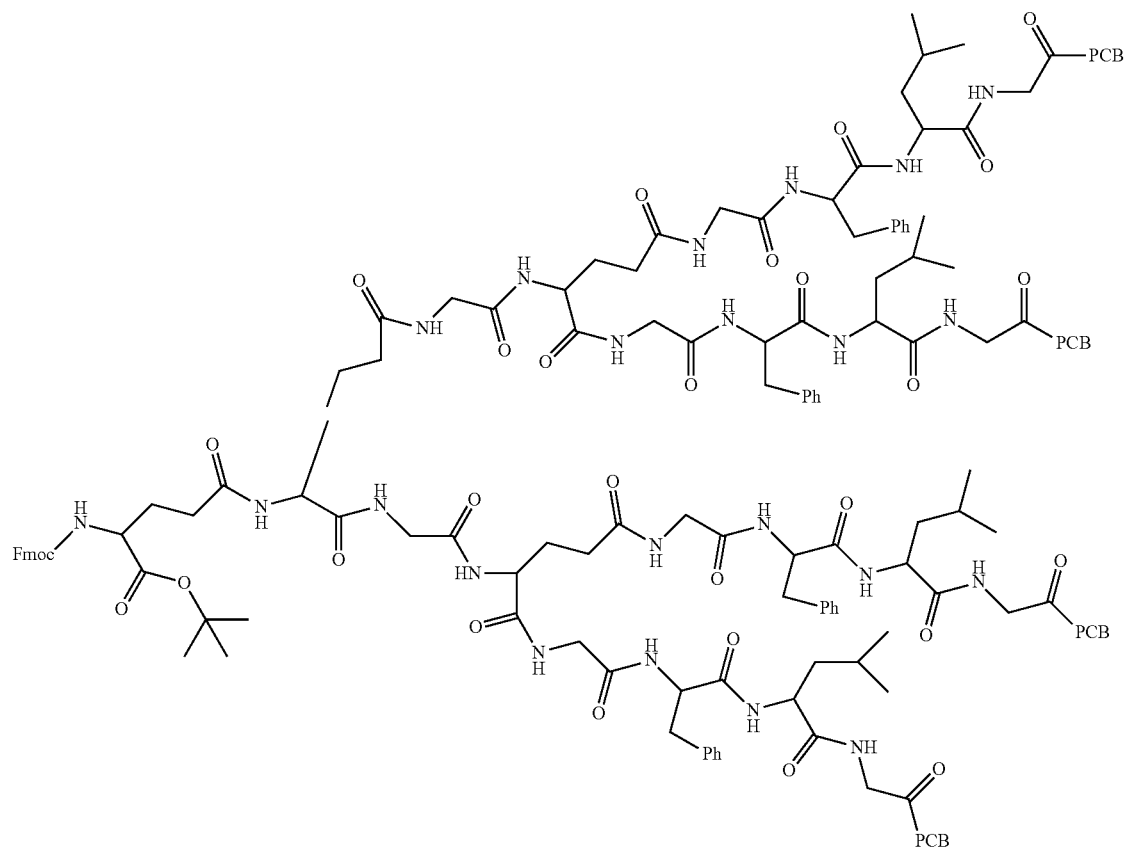

25-212

The solution of Compound 25-209 (0.9738 g, 1.7559 mmol), HBTU (1.9977 g, 5.2677 mmol), HOBT (0.7118 g, 5.2677 mmol), and Compound 30-33 (home-made) (7.0 g, 3.8630 mmol) were added in a 500 mL round-bottomed flask and then dissolved with DMF (30 mL), and the obtained solution was stirred for about 30 min at −5° C.; then, DIEA (2.6 mL, 15.8031 mmol) was slowly added dropwise; and then the reaction solution in the flask was further stirred for 3 h at −5° C.

At the end of the reaction, n-hexane (150 mL) and methyl tert-butyl ether (30 mL) were added to precipitate the reaction solution; the supernatant was discarded; and then n-hexane (150 mL) and methyl tert-butyl ether (30 mL) were added to the lower oily solution for precipitation, and the precipitation operation was repeated three times to obtain an oily solid. Then, the oily solid was dissolved with dichloromethane (10 mL) and then precipitated with methyl tert-butyl ether (150 mL) to obtain a powdery solid, and the solid product was then filtered out and dried. 7.2742 g of Product 25-212 was obtained with a yield of 100%.

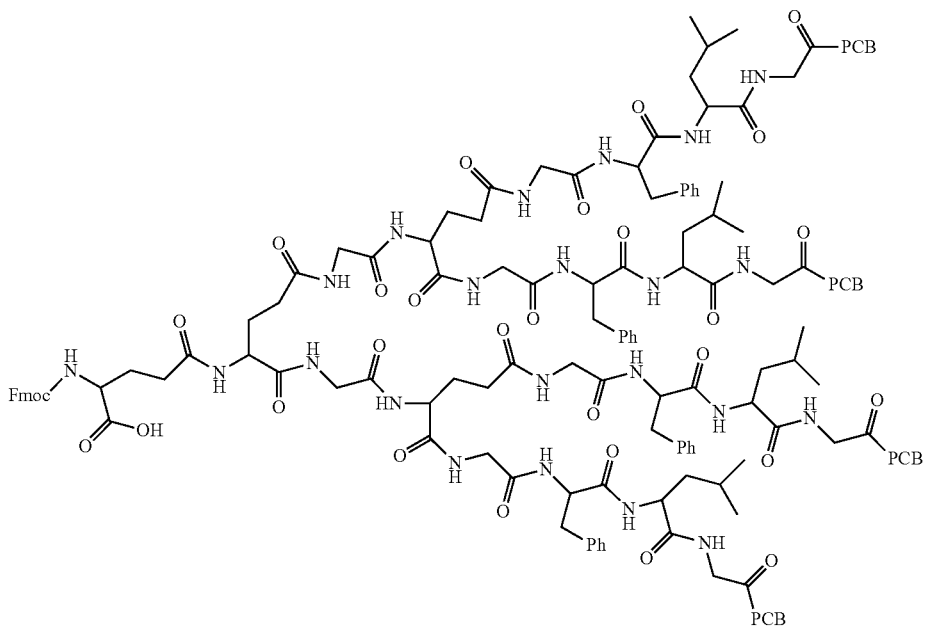

25-216

Compound 25-212 (7.2742 g, 1.7559 mmol) was added in a 100 mL round-bottomed flask and then dissolved with dichloromethane (10 mL), TFA (2.0 mL, 26.3385 mmol) was then added with stirring, and the mixed solution in the reaction flask was stirred overnight at room temperature to react.

At the end of the reaction, the reaction solution was first concentrated under reduced pressure and evaporated to remove dichloromethane. Then, methyl tert-butyl ether (150 mL) was added for precipitation to obtain a powdery solid, and the solid product was then filtered out. Then, the filter cake was dissolved with dichloromethane and then precipitated with methyl tert-butyl ether (150 mL) to obtain a powdery solid, and the solid product was then filtered out. The obtained solid product was then dissolved with a mixed solvent (20% methanol/dichloromethane) (100 mL), 80 mL of silica gel powder was then added, and the obtained solution was then evaporated to dryness. The operations of dry sample loading, column chromatography, and elution with eluent (3%-8% methanol:97%-92% dichloromethane) were then carried out, and the elution solution was collected, concentrated, evaporated to dryness, and dried in a vacuum oven. 3.4 g of Product 25-216 was obtained with a yield of 47.38%.

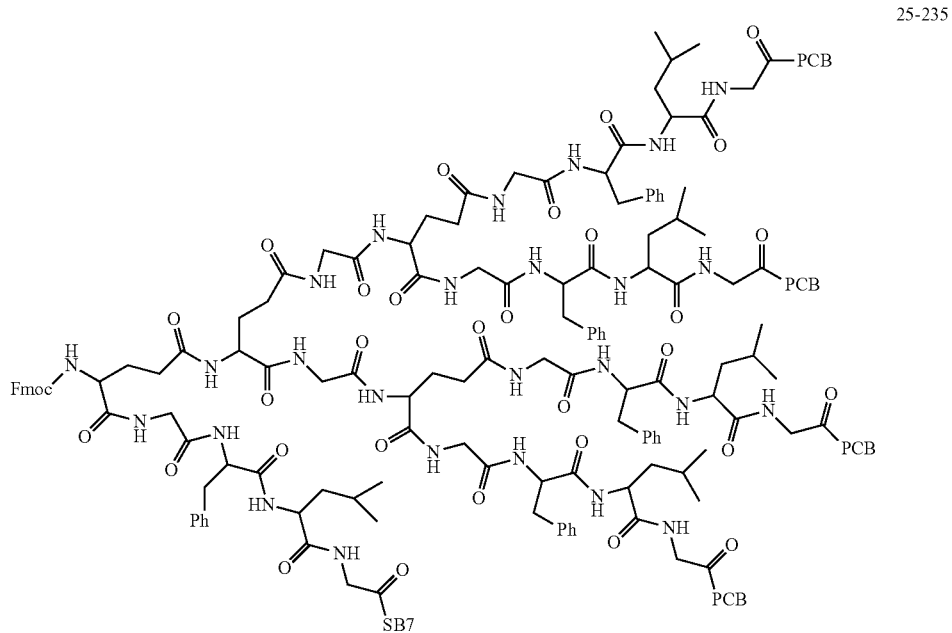

25-235

Compound 25-216 (3.4 g, 0.8320 mmol), HBTU (0.4733 g, 1.2480 mmol), HOBT (0.1686 g, 1.2480 mmol), and Compound 25-132 (0.7788 g, 0.8736 mmol, synthesized in the same way as Compound 28-146) were added in a 500 mL round-bottomed flask and then dissolved with DMF (30 mL), and the obtained solution was stirred for about 30 min at −5° C.; then, DIEA (0.6 mL, 3.7440 mmol) was slowly added dropwise; and then the reaction solution in the flask was further stirred for 3 h at −5° C. to react.

At the end of the reaction, n-hexane (150 mL) and methyl tert-butyl ether (30 mL) were first added to precipitate the reaction solution; the supernatant was discarded; and then n-hexane (150 mL) and methyl tert-butyl ether (30 mL) were added to the lower oily solution for precipitation, and the precipitation operation was repeated three times to obtain an oily solid. Then, the oily solid was dissolved with dichloromethane (10 mL) and then precipitated with methyl tert-butyl ether (150 mL) to obtain a powdery solid, and the solid product was then filtered out and dried. 4.1268 g of Product 25-235 was obtained with a yield of 100%.

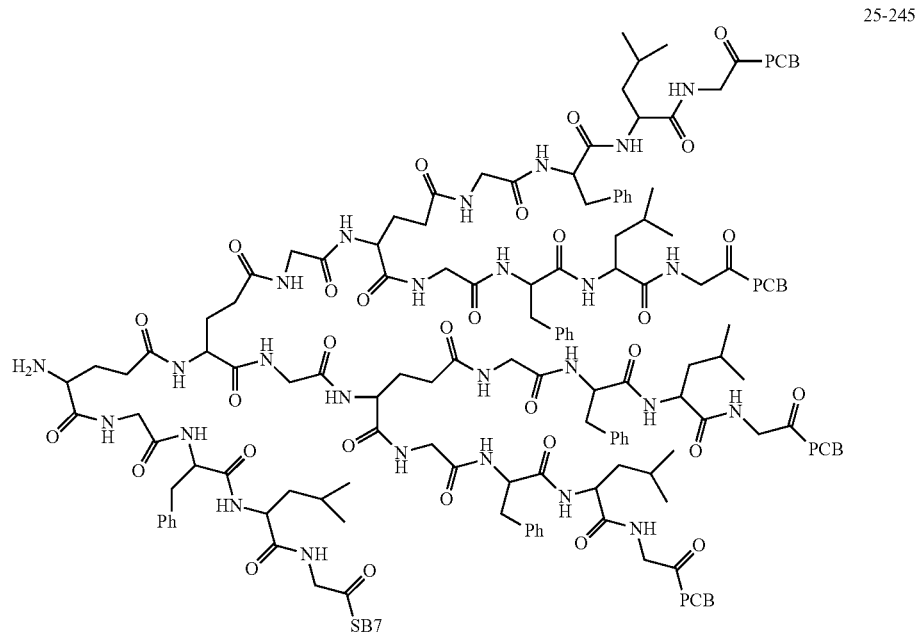

25-245

Compound 25-135 (4.1268 g, 0.8320 mmol) was added in a 500 mL round-bottomed flask and then dissolved with dichloromethane (20 mL), morpholine (1.1 mL, 12.4800 mmol) was then added with stirring, and the mixed solution was stirred for 2 h at room temperature to react.

At the end of the reaction, n-hexane (150 mL) and methyl tert-butyl ether (30 mL) were first added to precipitate the reaction solution; the supernatant was discarded; and then n-hexane (150 mL) and methyl tert-butyl ether (30 mL) were added to the lower oily solution for precipitation, and the precipitation operation was repeated three times to obtain an oily solid. Then, the oily solid was dissolved with dichloromethane (10 mL) and then precipitated with methyl tert-butyl ether (150 mL) to obtain a powdery solid, and the solid product was then filtered out. The solid product was then dissolved with a mixed solvent (20% methanol/dichloromethane) (60 mL), 50 mL of silica gel powder was then added, and the obtained solution was then evaporated to dryness. The operations of dry sample loading, column chromatography and elution with eluent (1% ammonia water:5%-8% methanol:94%-91% dichloromethane) were carried out, and the elution solution was then collected, concentrated, evaporated to dryness and dried. 3.0 g of Product 25-245 was obtained with a yield of 76.11%.

MALDI-TOF MS: [M+H⁺] 4736.35

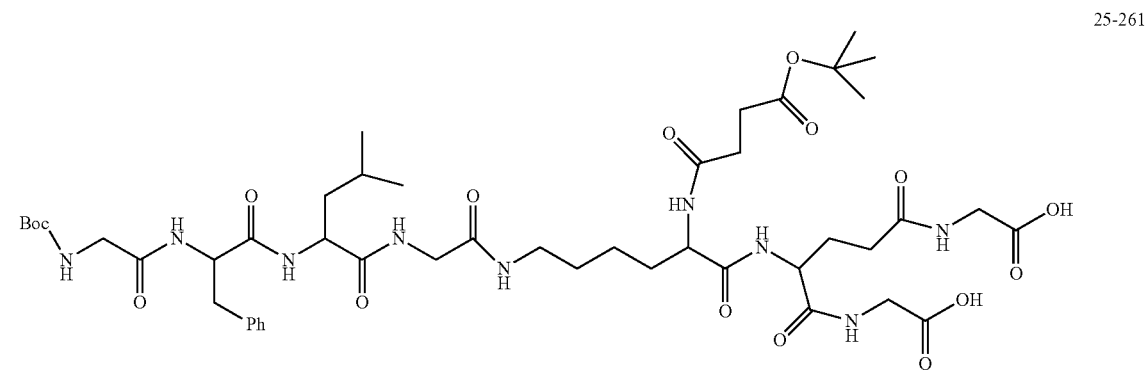 [SMILES: CC(C)CC(NC(=O)C(Cc1ccccc1)NC(=O)CNC(=O)OC(C)(C)C)C(=O)NCC(=O)NCCCCC(NC(=O)CCC(=O)OC(C)(C)C)C(=O)NC(CCC(=O)NCC(=O)O)C(=O)NCC(=O)O]

25-261

Compound 25-219 (0.3455 g, 0.2878 mmol) and 50 mg of 10% Pd/C were added into a hydrogenation reactor and then dissolved with DMF (20 mL); the hydrogenation reactor was sealed and $H_2$ was then introduced into the reactor until the pressure in the reactor reached 1.6 MPa; the obtained solution in the hydrogenation reactor was stirred overnight at room temperature.

At the end of the reaction, the hydrogenation reactor was taken out, the reaction solution was evenly added dropwise to a sand core funnel filled with compacted diatomaceous earth and suction filtering was carried out. The diatomaceous earth was washed three times with DMF (20 mL×3) until there was no product in the diatomaceous earth, and then the reaction product solution was obtained.

25-266

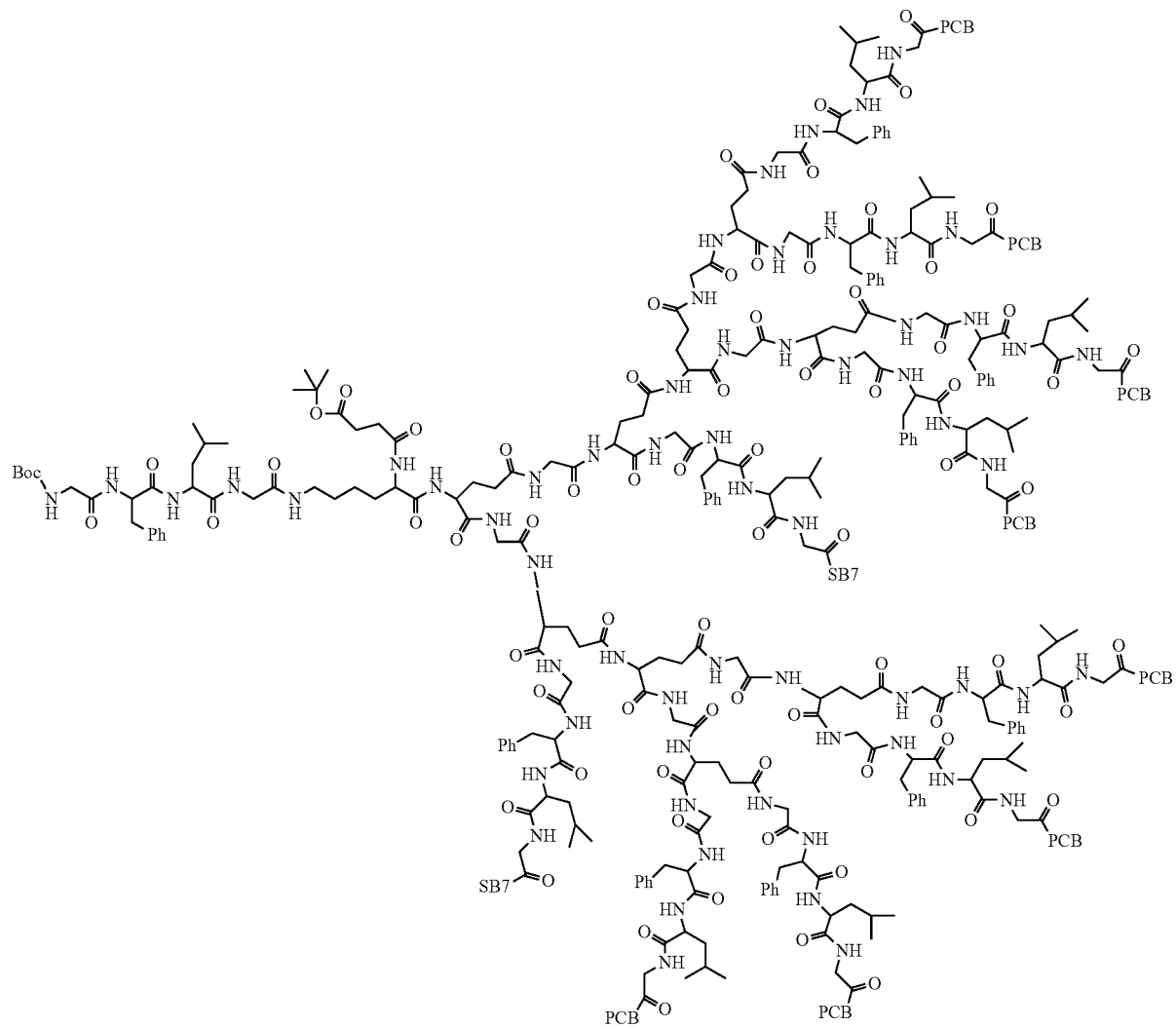

Compound 25-245 (3.0 g, 0.6332 mmol), HBTU (0.3274 g, 0.8634 mmol), HOBT (0.1167 g, 0.8634 mmol), and the solution of Compound 25-261 (0.2936 g, 0.2878 mmol) were added in a 500 mL round-bottomed flask and then dissolved with DMF (60 mL), and the obtained solution was stirred for about 30 min at −5° C.; then, DIEA (0.4 mL, 2.5902 mmol) was slowly added dropwise; and then the reaction solution in the flask was further stirred for 3 h at −5° C.

At the end of the reaction, n-hexane (150 mL) and methyl tert-butyl ether (30 mL) were first added to precipitate the reaction solution; the supernatant was discarded; and then n-hexane (150 mL) and methyl tert-butyl ether (30 mL) were added to the lower oily solution for precipitation, and the precipitation operation was repeated three times to obtain an oily solid. Then, the oily solid was dissolved with dichloromethane (10 mL) and then precipitated with methyl tert-butyl ether (150 mL) to obtain a powdery solid, and the solid product was then filtered out and dried. 3.0092 g of Product 25-266 was obtained with a yield of 100%.

25-268

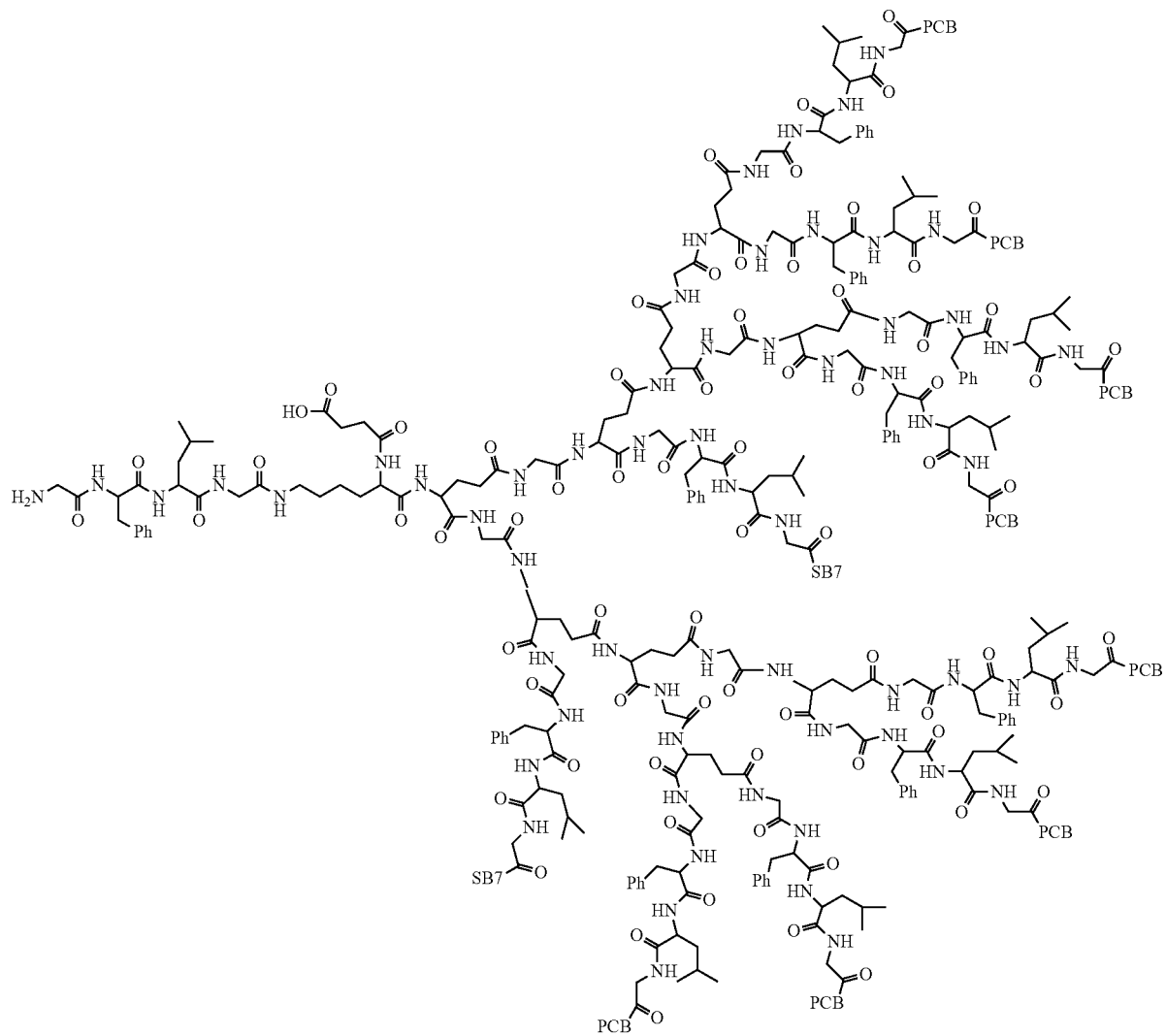

Compound 25-266 (3.0092 g, 0.2878 mmol) was added in a 100 mL round-bottomed flask and then dissolved with dichloromethane (10 mL), TFA (0.3 mL, 4.3170 mmol) was then added with stirring, and the mixed solution in the reaction flask was stirred overnight at room temperature to react.

At the end of the reaction, the reaction solution was first concentrated under reduced pressure and evaporated to remove dichloromethane. Then, methyl tert-butyl ether (100 mL) was added in the flask for precipitation to obtain a powdery solid, and the solid product was then filtered out. The solid product was then dissolved with a mixed solvent (20% methanol/dichloromethane) (50 mL), 80 mL of silica gel powder was then added, and the obtained solution was then evaporated to dryness. The operations of dry sample loading, column chromatography, and elution with eluent (1% ammonia water:3%-10% methanol:96%-89% dichloromethane) were then carried out, and the elution solution was collected, concentrated, evaporated to dryness, and dried in a vacuum oven. 1.8 g of Product 25-268 was obtained with a yield of 60.72%.

25-272

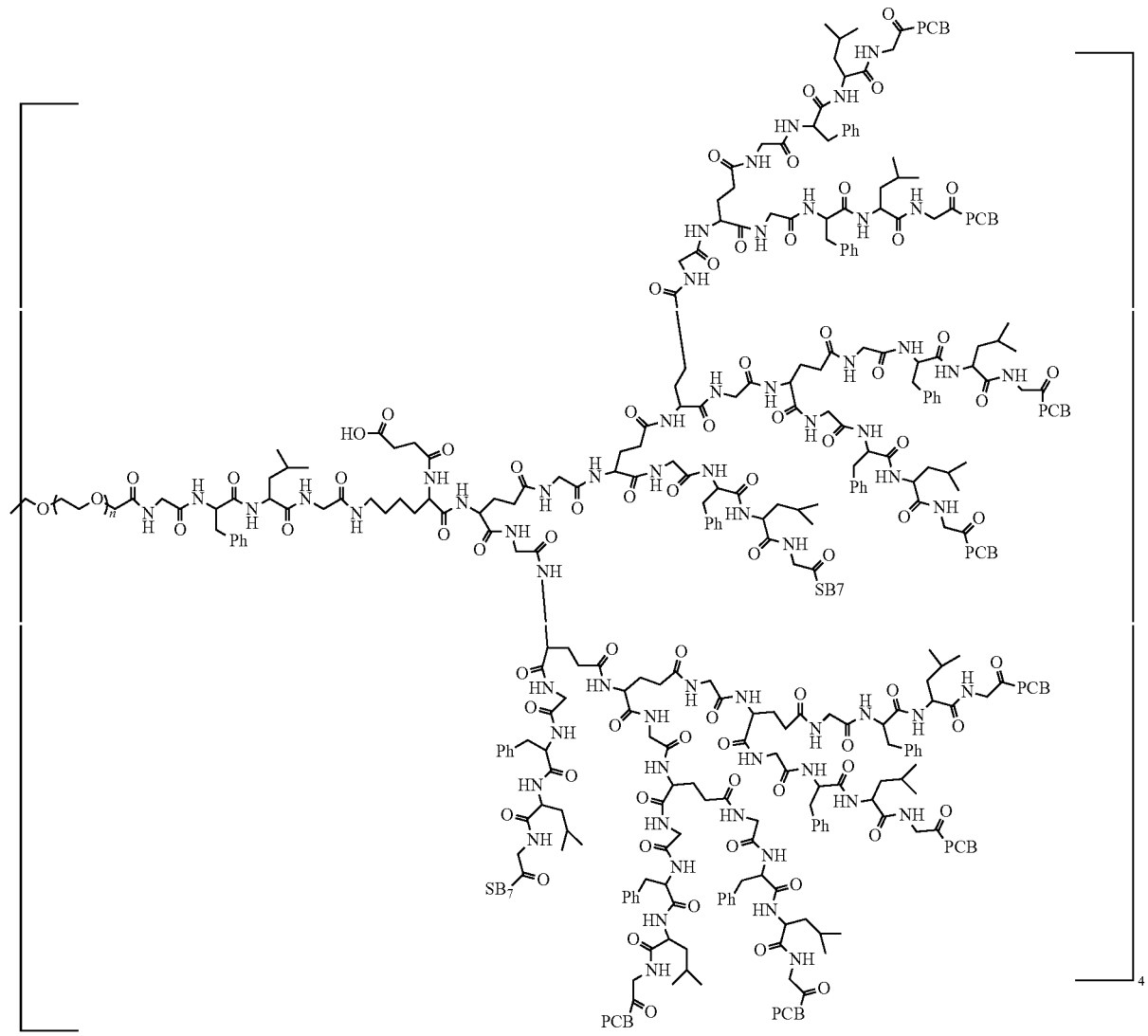

Compound 25-268 (1.8 g, 0.1748 mmol) was added in a 500 mL round-bottomed flask and dissolved with DMF (30 mL), and the obtained solution was stirred for about 30 min at −5° C.; then, DIEA (0.9 mL, 26.2200 mmol) was slowly added dropwise; the obtained solution was further stirred at −5° C. for 30 min to react, and then 4ARM-SCM-40K (MW: 41958, 1.5944 g, 0.0380 mmol) was added to the reaction solution and the resulting solution was slowly stirred for one week in the dark at room temperature to react.

At the end of the reaction, n-hexane (150 mL) and methyl tert-butyl ether (30 mL) were first added to precipitate the reaction solution; the supernatant was discarded; and then n-hexane (150 mL) and methyl tert-butyl ether (30 mL) were added to the lower oily solution for precipitation, and the precipitation operation was repeated three times to obtain an oily solid. Then, the oily solid was dissolved with dichloromethane (10 mL) and then precipitated with methyl tert-butyl ether (150 mL) to obtain a powdery solid, and the solid product was then filtered out.

The solid product was then dissolved with a mixed solvent (20% methanol/dichloromethane) (60 mL), 60 mL of silica gel powder was then added, and the obtained solution was then evaporated to dryness. The operations of dry sample loading, column chromatography and elution with eluent (1% ammonia water:4%-10% methanol:95%-89% dichloromethane) were carried out, and the elution solution was then collected, concentrated, evaporated to dryness and dried. 1.6 g of Product 25-272 was obtained with a yield of 50.91%.

25-276

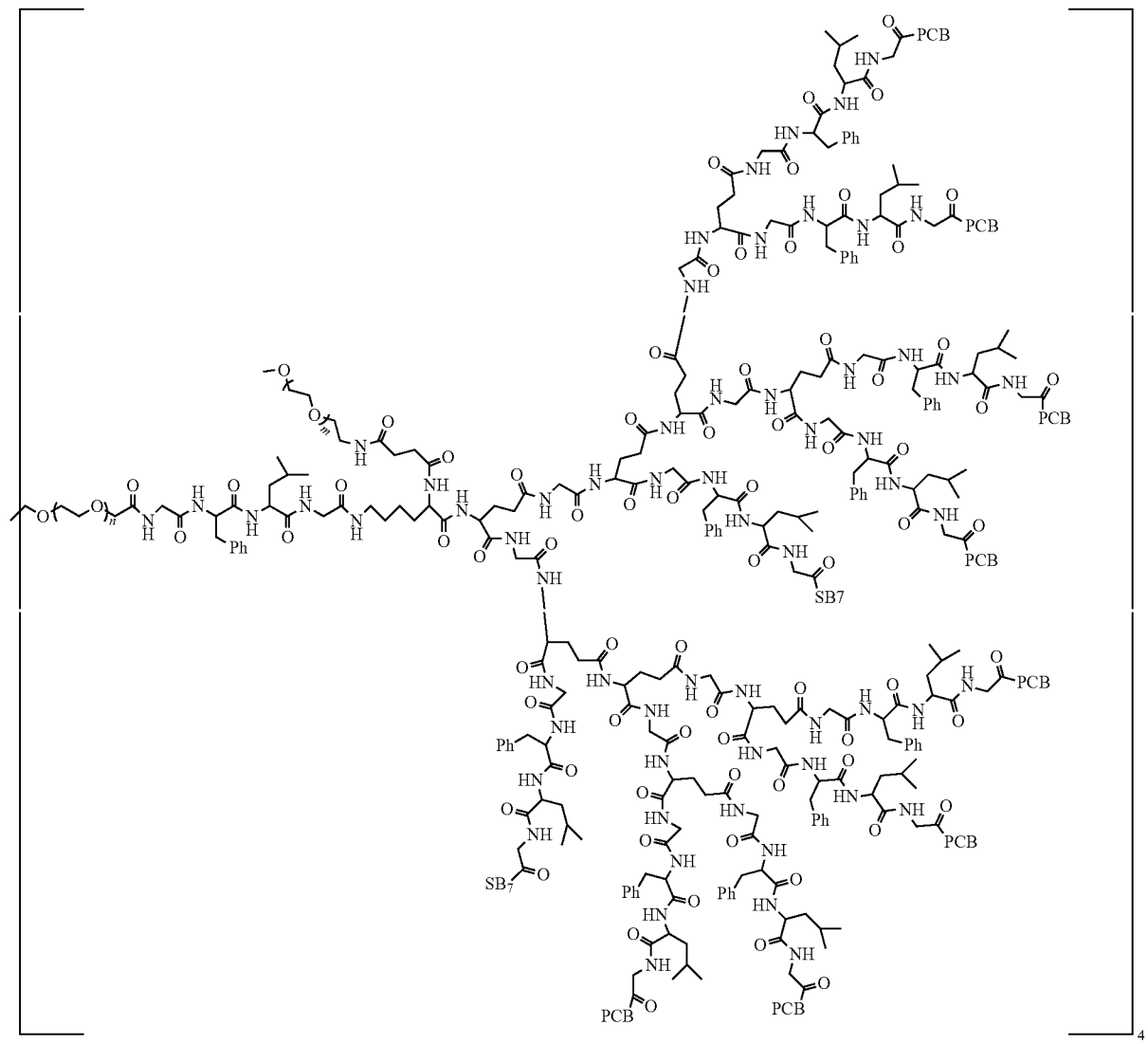

Compound 25-272 (1.6 g, 0.0193 mmol), HBTU (0.0066 g, 0.1741 mmol), HOBT (0.0023 g, 0.1741 mmol), and M-NH$_2$·HCl-10K (1.2210 g, 0.1161 mmol, purchased from JenKem) were added in a 500 mL round-bottomed flask and dissolved with DMF (10 mL), and the obtained solution was stirred for about 30 min at −5° C.; then, DIEA (0.2 mL, 1.0422 mmol) was slowly added dropwise; the obtained solution was further stirred at −5° C. for 10 min to react, and then the reaction solution was slowly stirred for one week in the dark at room temperature to react.

At the end of the reaction, n-hexane (150 mL) and methyl tert-butyl ether (30 mL) were first added to precipitate the reaction solution; the supernatant was discarded; and then n-hexane (150 mL) and methyl tert-butyl ether (30 mL) were added to the lower oily solution for precipitation, and the precipitation operation was repeated three times to obtain an oily solid. Then, the oily solid was dissolved with dichloromethane (10 mL) and then precipitated with methyl tert-butyl ether (150 mL) to obtain a powdery solid, and the solid product was then filtered out. The solid product was then dissolved with a mixed solvent (20% methanol/dichloromethane) (50 mL), 40 mL of silica gel powder was then added, and the obtained solution was then evaporated to dryness. The operations of dry sample loading, column chromatography and elution with eluent (1% ammonia water:4%-10% methanol:95%-89% dichloromethane) were carried out, and the elution solution was then collected, concentrated, evaporated to dryness and dried. 1.0 g of Product 25-276 was obtained with a yield of 41.60%.

$^1$H-NMR (400 MHz, DMSO-d$_6$) δ 10.16 (s, 209H), 8.95 (s, 176H), 8.46-7.85 (m, 675H), 7.70-7.05 (m, 757H), 5.21-5.13 (m, 94H), 4.86-4.14 (m, 840H), 4.13-3.45 (m, 5234H), 3.25 (m, 29H), 3.21-2.83 (m, 350H), 2.69 (m, 210H), 2.45-1.99 (m, 496H), 1.67 (m, 604H), 1.38-0.98 (m, 403H), 0.84 (m, 314H).

Example 14: Synthesis of Compounds 37-26 and 37-28

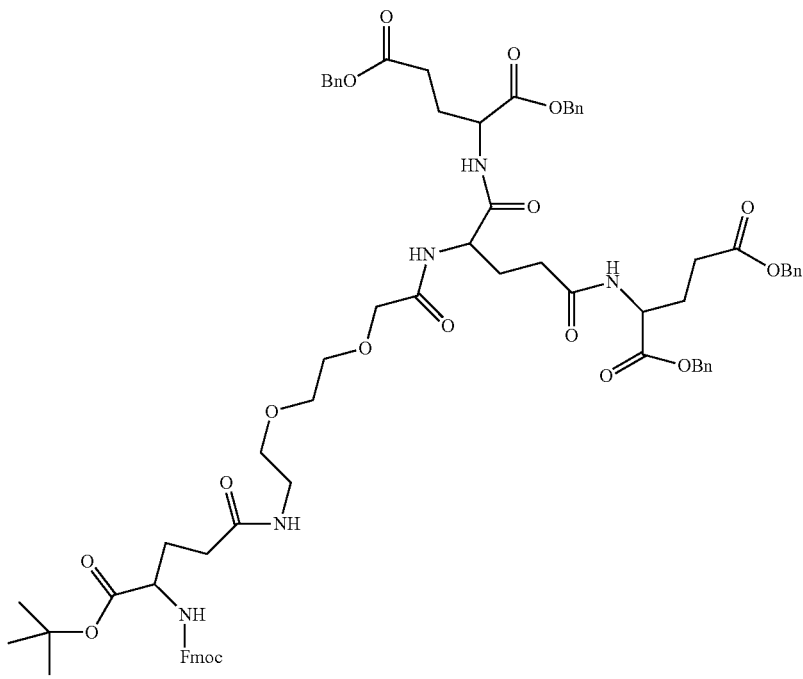

28-235

Fmoc-Glu-OtBu (1.262 g, 2.967 mmol, purchased from Ark pharm), Compound 22-181 (synthesized according to the synthesis method of Compound 24-90) (2.7 g, 2.967 mmol), HBTU (1.6878 g, 4.4505 mmol), and HOBT (0.6014 g, 4.4505 mmol) were added in a 250 mL flask, and the obtained solution was stirred for about 20 min at 0° C.; then, DIEA (2.2068 mL, 13.3515 mmol) was slowly added dropwise and then the resulting solution was stirred overnight at 0° C. to further react. At the end of the reaction, the reaction solution was transferred to a 1 L separatory funnel and then extracted with deionized water (200 mL) and ethyl acetate (250 mL); the obtained organic phase was washed with a saturated sodium chloride solution (200 mL×2) and then concentrated, and evaporated to dryness. 3.9 g of Product 28-235 was obtained.

28-238

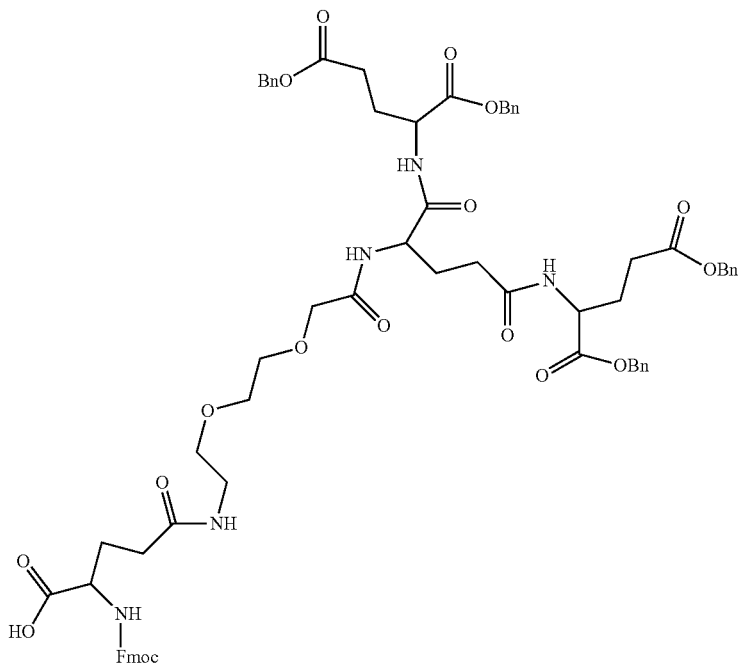

Compound 28-235 (3.9 g, 2.967 mmol) was added in a 100 mL flask and then dissolved with dichloromethane (5 mL), TFA (3.3 mL, 44.505 mmol) was then added in the flask, and the mixed solution was stirred overnight at room temperature to react. At the end of the reaction, the reaction solution was concentrated to a small amount, n-hexane (100 mL) was then added and the resulting solution was then shaken and layered; the supernatant was discarded and n-hexane (100 mL) was further added to the lower oily solution; such operations were repeated six times to obtain an oily product and the oily product was then dried. 3.6 g of Product 28-238 was obtained.

solution was transferred to a 1 L separatory funnel and then extracted with deionized water (200 mL) and ethyl acetate (150 mL); the obtained organic phase was washed with a saturated sodium chloride solution (150 mL×2) and then concentrated, and evaporated to dryness. 4.1 g of Product 28-241 was obtained.

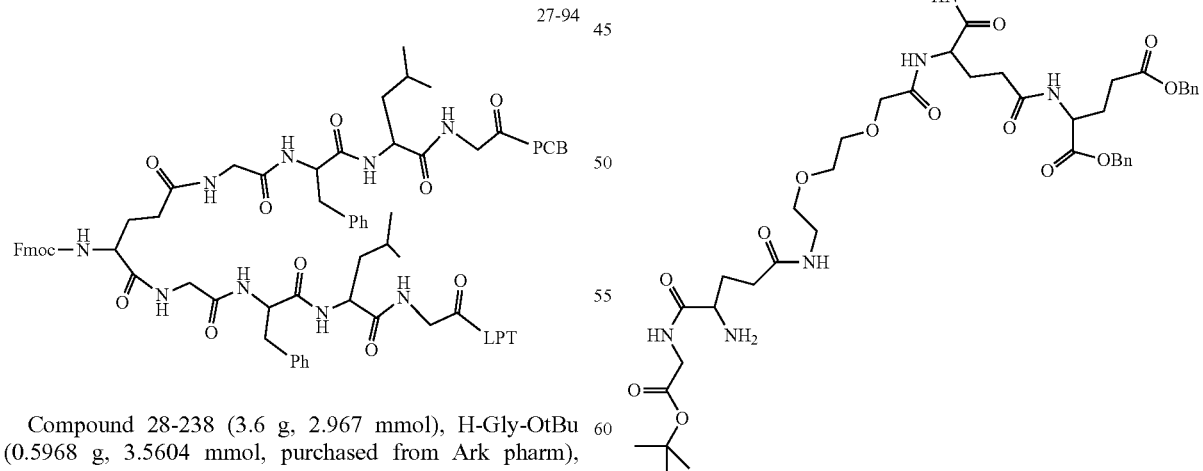

Compound 28-238 (3.6 g, 2.967 mmol), H-Gly-OtBu (0.5968 g, 3.5604 mmol, purchased from Ark pharm), HBTU (1.6878 g, 4.4505 mmol), and HOBT (0.6014 g, 4.4505 mmol) were added in a 250 mL flask, and the obtained solution was stirred for about 20 min at 0° C.; then, DIEA (2.697 mL, 16.3185 mmol) was slowly added dropwise and then the resulting solution was stirred overnight at 0° C. to further react. At the end of the reaction, the reaction Compound 28-241 (4.1 g, 2.967 mmol) was added into a 100 mL flask and then dissolved with DMF (15 mL); morpholine (5.17 mL, 59.34 mmol) was added to the obtained solution, and the obtained solution reacted at room temperature for 1 h. At the end of the reaction, the reaction solution was transferred to a 1 L separatory funnel and extracted with a saturated sodium chloride solution (150 mL) and ethyl acetate (250 mL) to obtain an organic phase; the aqueous phase was washed with ethyl acetate (200 mL×1), and the obtained organic phases were combined, washed with saturated sodium chloride solution (200 mL×2), then concentrated and evaporated to dryness; the solid product was then dissolved with methanol (30 mL) and dichloromethane (120 mL), silica gel powder (15 g) was added to the obtained solution, and the solution was then evaporated to dryness to obtain a powdery solid; the operations of dry sample loading, column chromatography, and elution with a mixed solution (3% methanol/dichloromethane) were carried out. 1.75 g of Product 28-244 was obtained with a yield of 46%.

Compound 28-244 (1.75 g, 1.517 mmol) was added into a 250 mL flask and then dissolved with dichloromethane (10 mL); triethylamine (0.4478 mL, 3.1857 mmol) was then added to the resulting solution, and the obtained solution was stirred at 0° C. for 15 min to react; then, phenyl chloroformate (0.2095 mL, 1.669 mmol) was added dropwise to the reaction solution, and the resulting solution was further stirred overnight at 0° C. At the end of the reaction, the reaction solution was transferred to a 1 L separatory funnel and then extracted with dichloromethane (200 mL) and deionized water (200 mL) to obtain an organic phase; the aqueous phase was washed with dichloromethane (200 mL×1), and the obtained organic phases were combined; silica gel powder (15 g) was added to the organic phase, and the obtained solution was then evaporated to dryness to obtain a powdery solid; the operations of dry sample loading, column chromatography, and elution with a mixed solution (3% methanol/dichloromethane) were carried out. 1.2004 g of Product 28-255 was obtained with a yield of 63%.

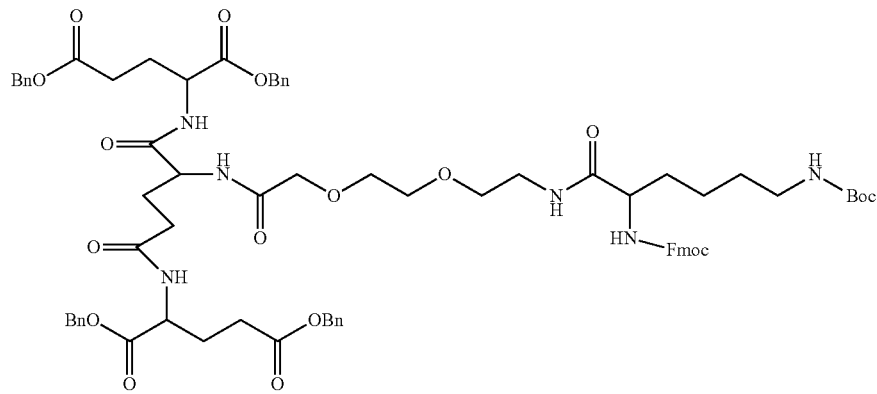

28-231

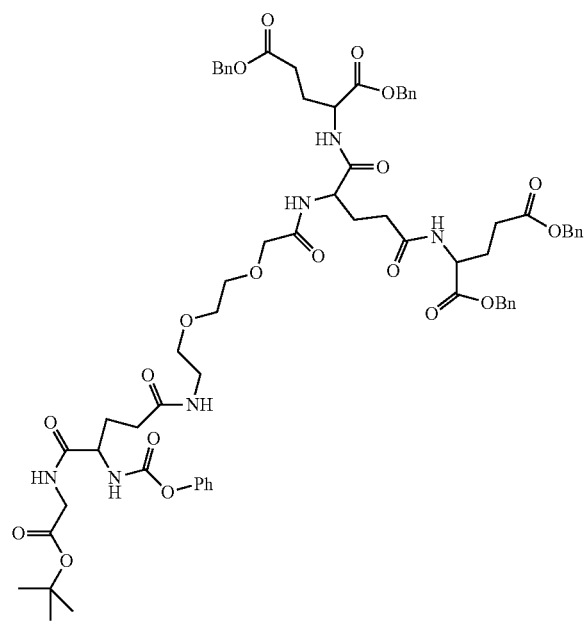

28-255

Fmoc-L-Lys(Boc)-OH (1.8825 g, 4.0177 mmol), Compound 22-181 (synthesized according to the synthesis method of Compound 24-90) (3.6601 g, 4.0177 mmol), HBTU (2.2855 g, 6.0266 mmol), and HOBT (0.8144 g, 6.0266 mmol) were added in a 100 mL flask, the obtained solution was stirred for 30 min at −5° C. to react; then, DIEA (2.9880 mL, 18.0797 mmol) was slowly added dropwise, the resulting solution further reacted at −5° C. for 1 h, and then the reaction solution was stirred overnight at room temperature to further react. At the end of the reaction, the reaction solution was transferred to a 1 L separatory funnel and then extracted with a saturated sodium bicarbonate solution (200 mL) and ethyl acetate (250 mL) to obtain an organic phase; the aqueous phase was washed with ethyl acetate (200 mL×1), and the obtained organic phases were combined and washed with a saturated sodium chloride solution (200 mL×2); the obtained solution was then concentrated and evaporated to dryness. 5.5 g of Product 28-233 was obtained.

28-233

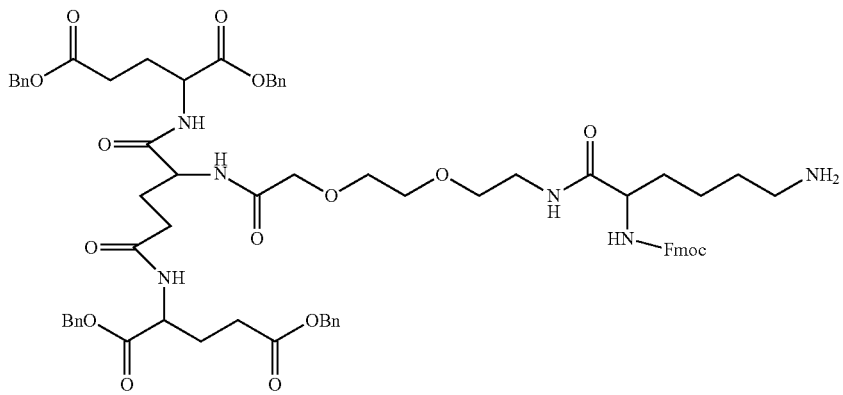

Compound 28-231 (3.0 g, 2.2034 mmol) was added in a 100 mL flask and then dissolved with dichloromethane (8 mL), TFA (2.45 mL, 33.1 mmol) was then added in the flask, and the mixed solution was stirred overnight at room temperature to react. At the end of the reaction, the reaction solution was concentrated to a small amount, n-hexane (150 mL) was then added and the resulting solution was then shaken and layered; the supernatant was discarded and n-hexane (150 mL) was further added to the lower oily solution; such operations were repeated six times to finally obtain an oily product and the oily product was then dried. 2.8 g of Product 28-233 was obtained.

28-239

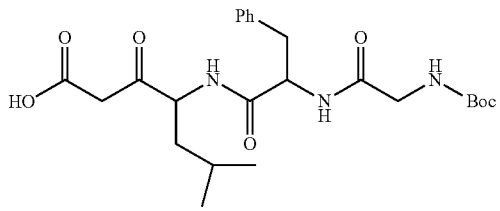

Boc-GFLG-OBn (1.54 g, 2.6441 mmol, home-made) and 10% Pd/C (0.0210 g) were added in a hydrogenation reactor and then dissolved with DMF (30 mL); $H_2$ was introduced in the reactor to a pressure of 1.6 Mpa; and the mixed solution was then stirred overnight at room temperature to react. At the end of the reaction, the reaction solution was filtered with diatomaceous earth, and the filter cake was washed three times with DMF (20 mL×3), and the obtained DMF solutions were combined as a raw material of the next reaction step.

28-240

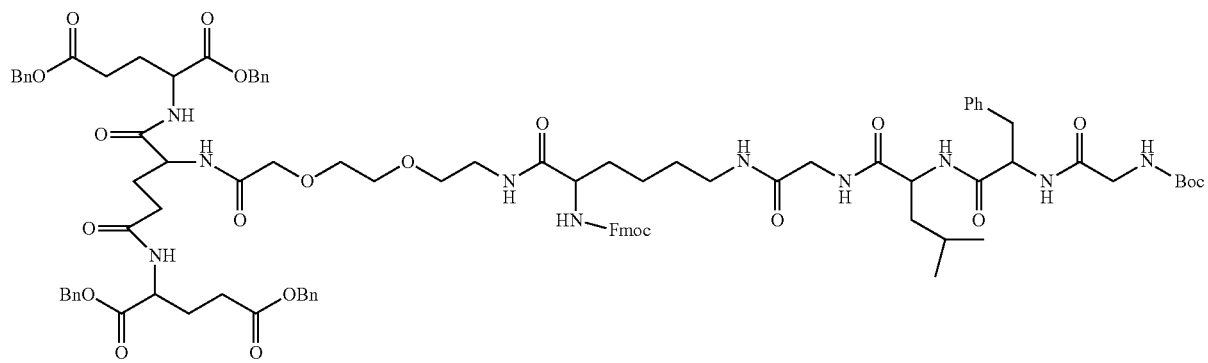

Compound 28-239 (1.3024 g, 2.6441 mmol), Compound 28-233 (2.779 g, 2.2034 mmol), HBTU (1.2534 g, 3.3051 mmol), and HOBT (0.4466 g, 3.3051 mmol) were added in a 100 mL flask, the obtained solution was stirred for 20 min at −5° C. to react; then, DIEA (1.6388 mL, 9.9153 mmol) was slowly added dropwise and then the resulting solution further reacted at 0° C. for 1 h, and then the reaction solution was stirred overnight at room temperature to further react. At the end of the reaction, the reaction solution was transferred to a 1 L separatory funnel and then extracted with deionized water (200 mL) and ethyl acetate (250 mL) to obtain an organic phase; the aqueous phase was washed with ethyl acetate (150 mL×1), and the obtained organic phases were combined and washed with a saturated sodium chloride solution (200 mL×1); the obtained solution was then concentrated and evaporated to dryness. 3.8 g of Product 28-240 was obtained with a yield of 100%.

28-251

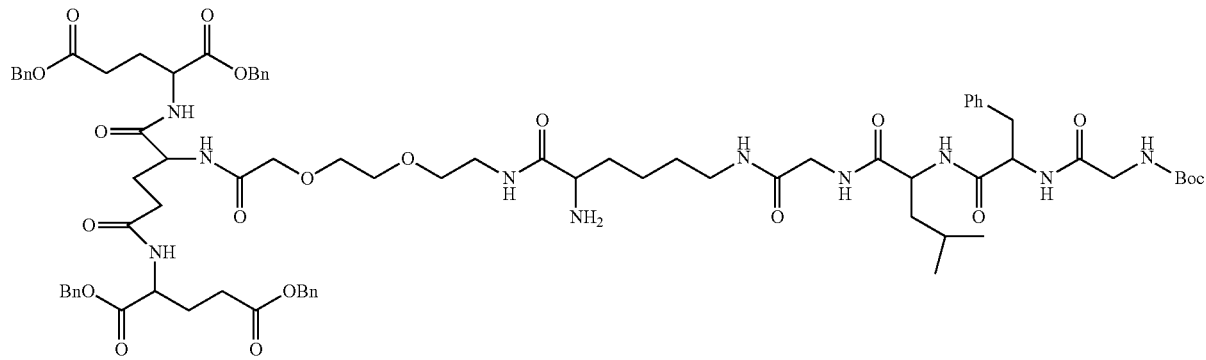

Compound 28-240 (3.8 g, 2.2034 mmol) was added into a 250 mL flask and then dissolved with DMF (10 mL); morpholine (5.758 mL, 66.102 mmol) was added to the obtained solution, and the obtained solution was stirred at room temperature for 1 h to react. At the end of the reaction, the reaction solution was transferred to a 1 L separatory funnel and extracted with deionized water (200 mL) and ethyl acetate (200 mL) to obtain an organic phase; the aqueous phase was washed with ethyl acetate (200 mL×1), and the obtained organic phases were combined, washed with saturated sodium chloride solution (200 mL×1), then concentrated and evaporated to dryness; the solid product was then dissolved with methanol (20 mL) and dichloromethane (80 mL), silica gel powder (10 g) was added to the obtained solution, and the solution was then evaporated to dryness to obtain a powdery solid; the operations of dry sample loading, column chromatography, and elution with a mixed solution (3%-7% methanol/dichloromethane) were carried out. 1.9 g of Product 28-251 was obtained with a yield of 58%.

28-259

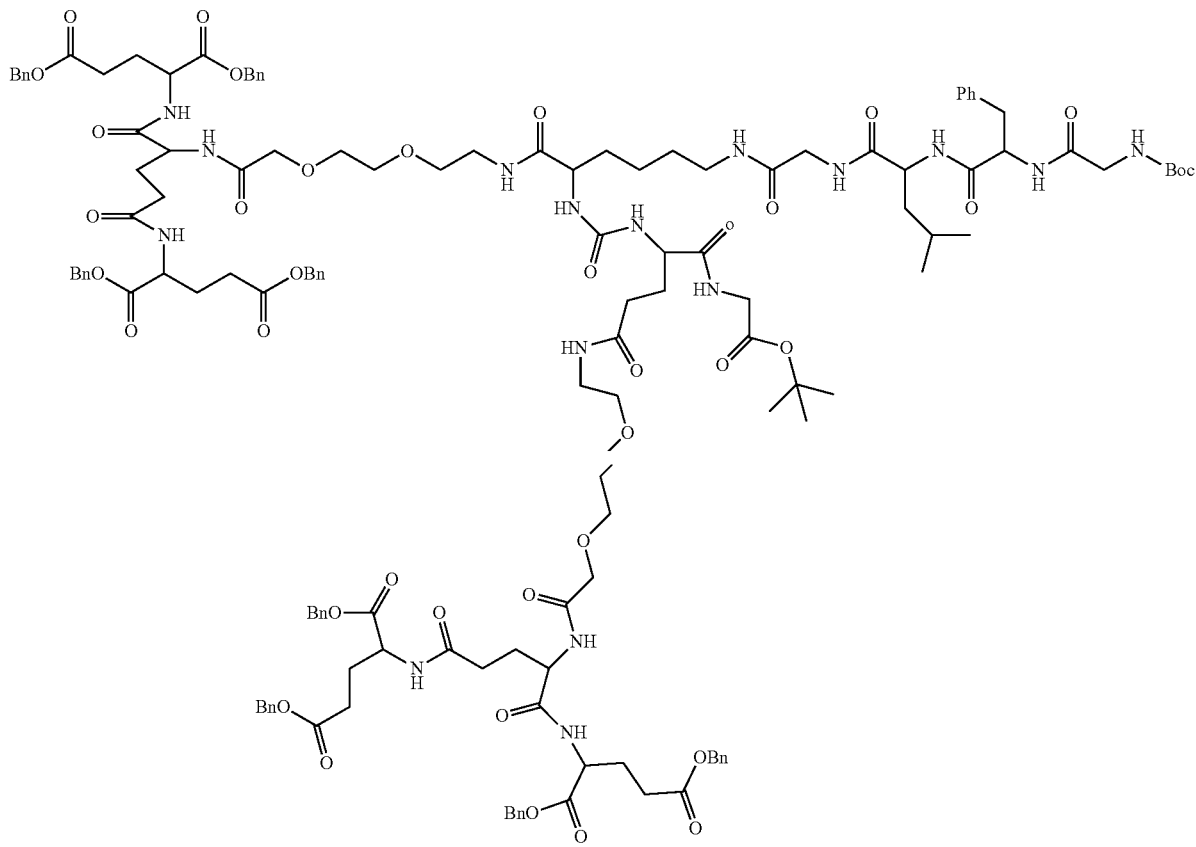

Compound 28-251 (1.4265 g, 0.9424 mmol) and Compound 28-255 (1.2 g, 0.9424 mmol) was added into a 100 mL flask and then dissolved with DMF (25 mL); the obtained solution was stirred overnight at 80° C. to react. At the end of the reaction, the reaction solution was transferred to a 1 L separatory funnel and extracted with ethyl acetate (200 mL) and a saturated sodium chloride solution (200 mL) to obtain an organic phase; the organic phase was washed with a saturated sodium chloride solution (150 mL); silica gel powder was then added to the obtained solution, and the solution was then evaporated to dryness to obtain a powdery solid; the operations of dry sample loading, column chromatography, and elution with a mixed solution (3%-5% methanol/dichloromethane) were carried out. 0.85 g of Product 28-259 was obtained with a yield of 33%.

37-10

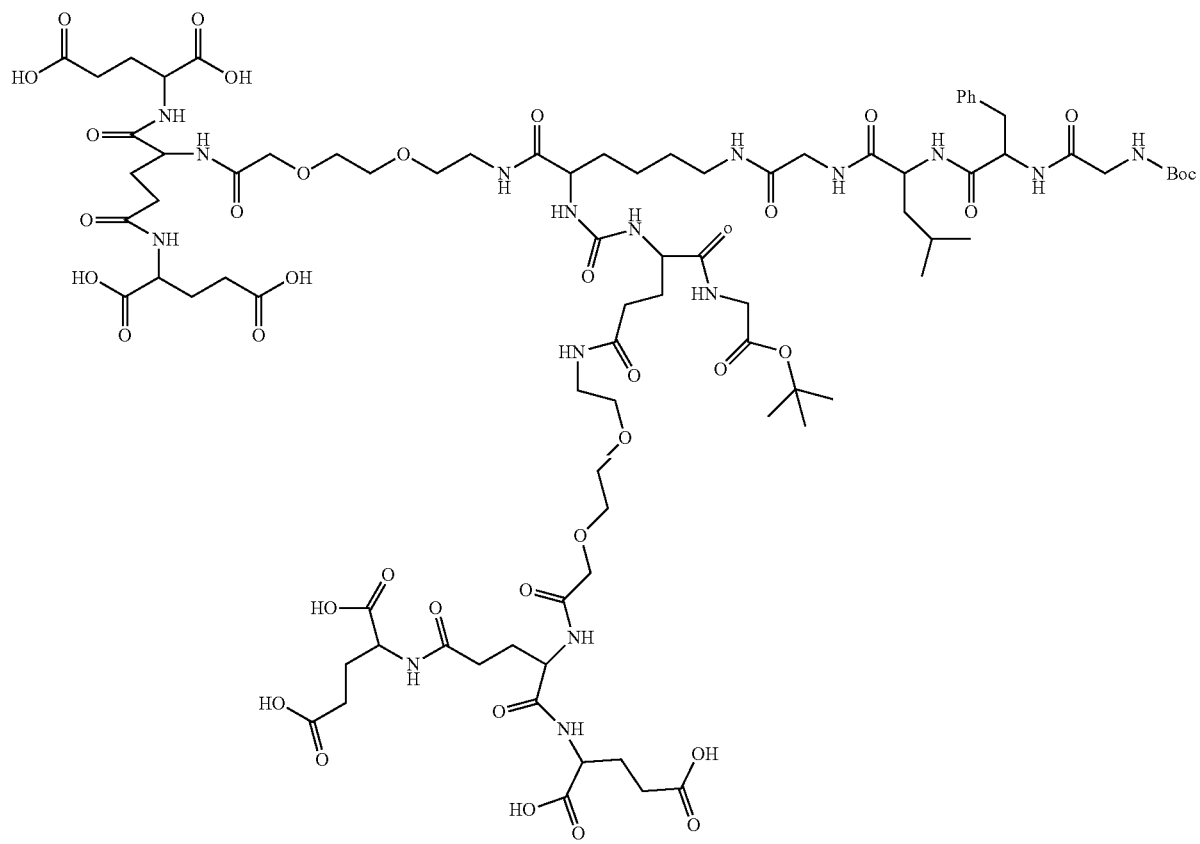

Compound 28-259 (0.49923 g, 0.1854 mmol) and 10% Pd/C (0.0300 g) were added in a reactor and then dissolved with DMF (30 mL); the reactor was then sealed and H$_2$ as introduced in the reactor to a pressure of 1.6 MPa; and the mixed solution was then stirred for 3 days at room temperature to react. At the end of the reaction, the reaction solution was filtered with diatomaceous earth, and the filter cake was washed three times with DMF (20 mL×3), and the obtained DMF solutions were combined as a raw material of the next reaction step.

37-11

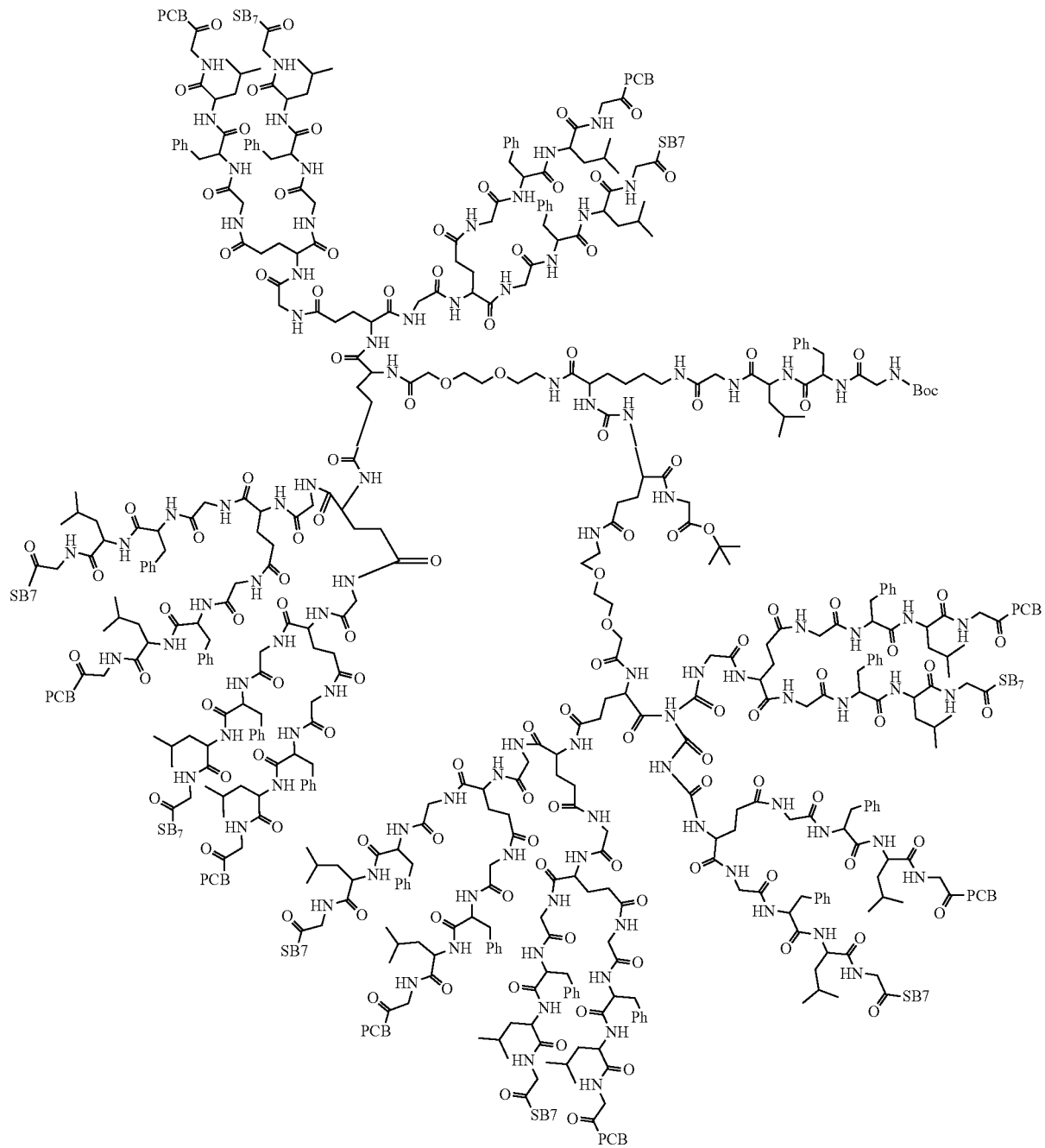

Compound 37-10 (0.3656 g, 0.1854 mmol), Compound 37-2 (3.0 g, 1.5943 mmol, synthesized according to the synthesis method of Compound 24-90) HBTU (0.8437 g 2.2248 mmol), and HOBT (0.3006 g, 2.2248 mmol) were added into a 250 mL flask and then dissolved with DMF (95 mL); the mixed solution was stirred at −5° C. for 20 m to react; DIEA (1.1 mL, 6.6744 mmol) was then slowly added dropwise, the obtained solution was then stirred for 40 min at −5° C. to react and then the reaction solution was further stirred overnight at room temperature. At the end of the reaction, n-hexane (150 mL) and methyl tert-butyl ether (40 me) were added to carried out precipitation four times to obtain a viscous oily product; methyl tert-butyl ether (200 mL) was added to precipitate a solid product; filtering was then carried out and the filter cake was washed with methyl tert-butyl ether (50 mL×3) and then dissolved with dichloromethane (160 mL) and methanol (40 mL); silica gel powder (15 g) was added to the obtained solution, and the solution was then evaporated to dryness to obtain a powdery solid; the operations of dry sample loading, column chromatography, and elution with a mixed solution (1% ammonia water:6%-7% methanol/dichloromethane) were carried out; the elution product was then collected, concentrated and dried. 2.1 g of Product 37-11 was obtained with a yield of 68%.

37-16

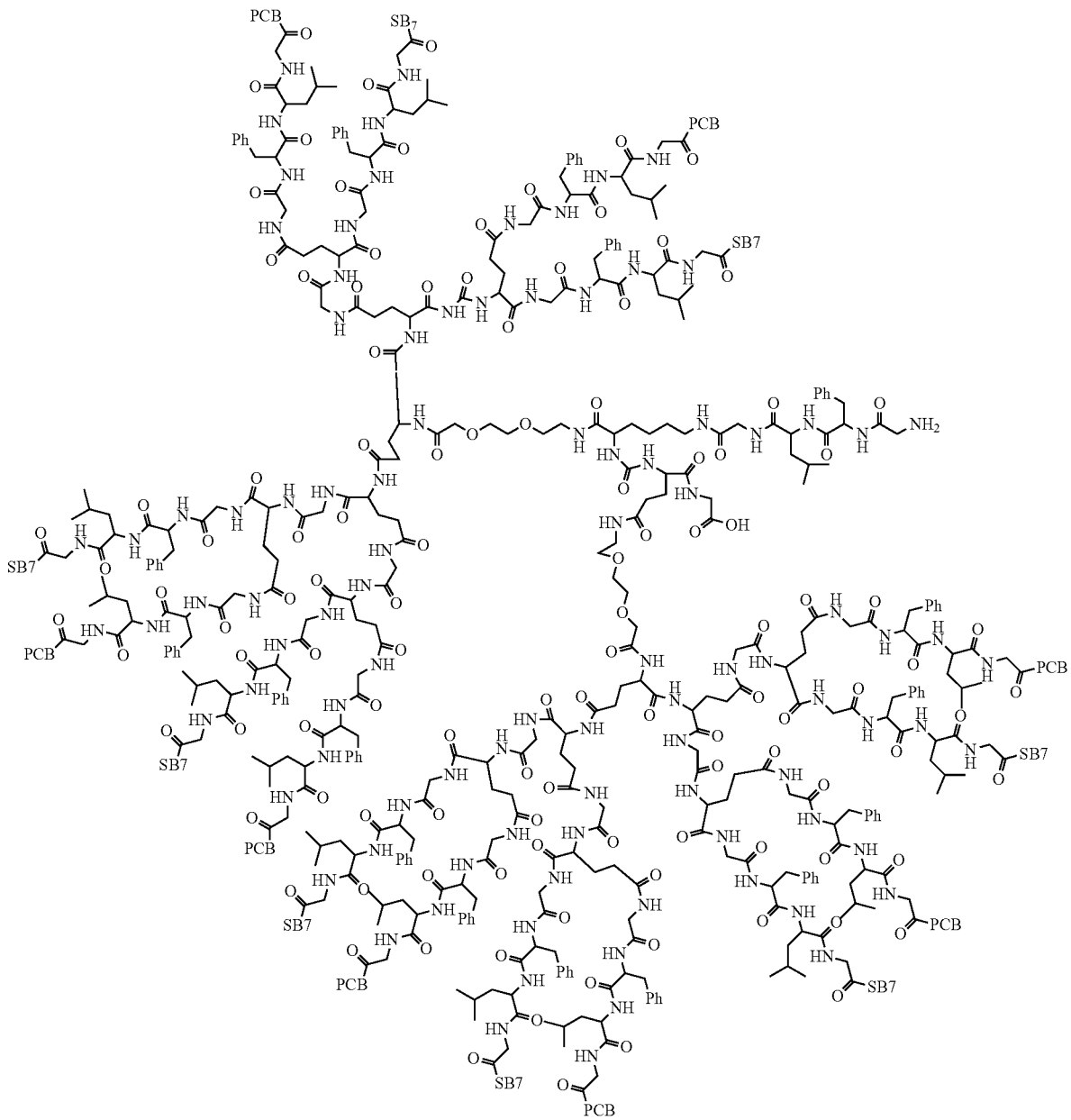

Compound 37-11 (2.1 g, 0.1244 mmol) was added in a 250 mL flask and then dissolved with dichloromethane (10 mL), TFA (8 mL, 107.7260 mmol) was then added in the flask, and the mixed solution was stirred overnight at room temperature to react. At the end of the reaction, the reaction solution was concentrated to a small amount and then precipitated with methyl tert-butyl ether (150 mL) to obtain a solid; suction filtering was then carried out, the filter cake was washed with methyl tert-butyl ether (50 mL×2) and then dissolved with a mixed solution of methanol (30 mL) and dichloromethane (120 mL), silica gel powder (15 g) was added to the obtained solution, and the solution was then evaporated to dryness to obtain a powdery solid; the operations of dry sample loading, column chromatography, and elution with a mixed solution (1% ammonia water:5%-8% methanol/dichloromethane) were carried out; the elution product was then collected, concentrated, evaporated to dryness to obtain a solid product, and the solid product was then dried in a vacuum oven. 1.6457 g of Product 37-16 was obtained with a yield of 79%.

$^1$H-NMR (400 MHz, DMSO-$d_6$) δ 10.12 (s, 8H), 8.95 (s, 7H), 8.12 (m, 93H), 7.87 (s, 26H), 7.51 (s, 21H), 7.34-6.97 (m, 167H), 5.83 (m, 6H), 5.75 (s, 7H), 4.56 (s, 23H), 4.23 (s, 54H), 4.09-3.97 (m, 23H), 3.94-3.65 (m, 79H), 3.23-3.28 (m, 27H), 3.18-2.92 (m, 21H), 2.78 (m, 40H), 2.41 (s, 22H), 2.26 (m, 86H), 2.11 (s, 44H), 1.83 (m, 78H), 1.55 (m, 75H), 1.22 (s, 10H), 0.86 (m, 124H), 0.49 (s, 23H).

MALDI-TOF MS: [M+H$^+$] 16710.99, [M+Na$^+$] 16733.99

37-18

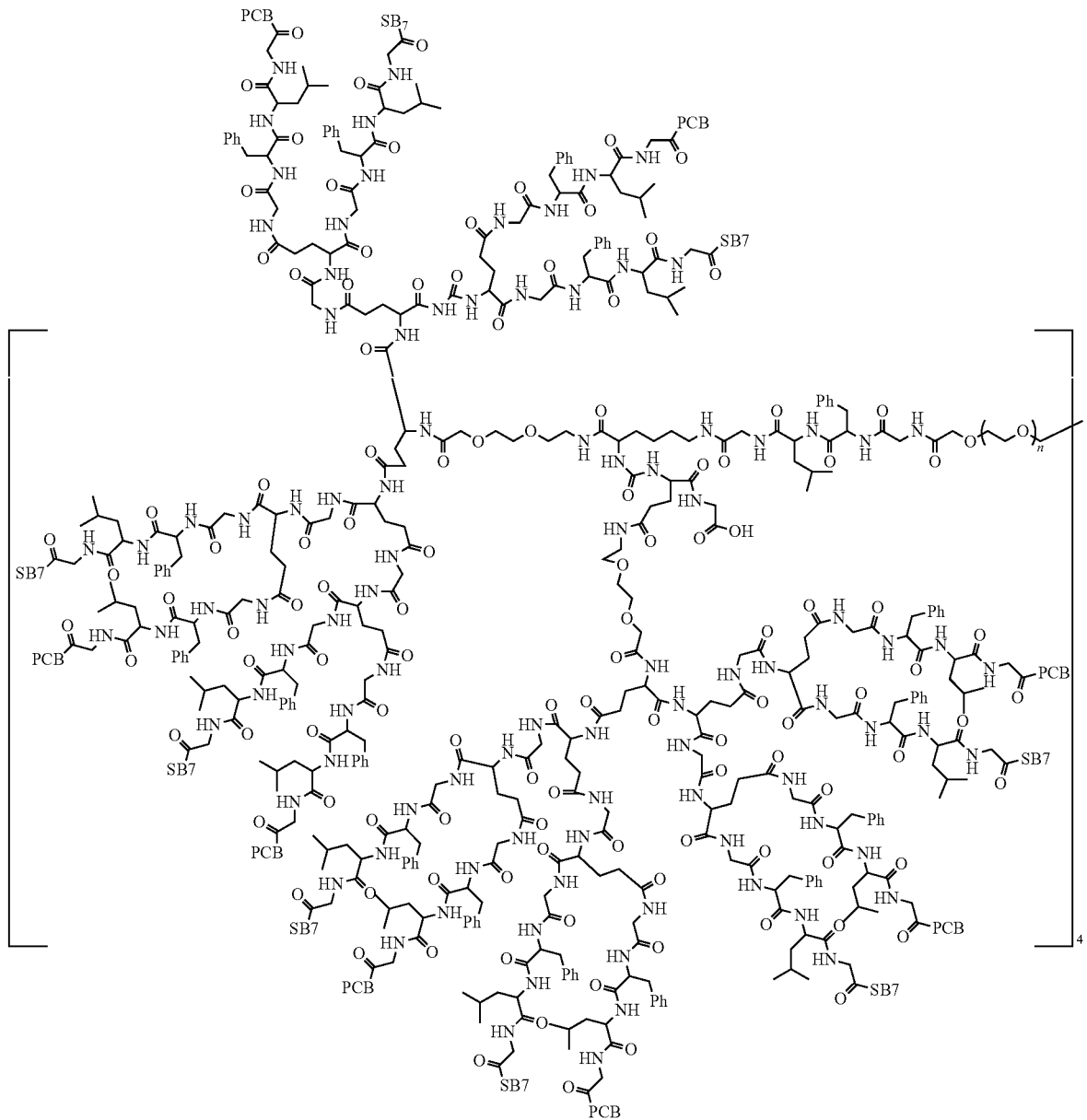

Product 37-16 (1.6457 g, 0.0984 mmol) was added to a 250 mL flask and then dissolved with DMF (35 mL); the mixed solution was stirred at −5° C. at a low speed for about 20 min to react, DIEA (0.1626 mL, 0.9838 mmol) was slowly added dropwise, 4ARM-SCM-5K (0.1311 g, 0.0224 mmol, purchased from JenKem) was then added, and the obtained solution was slowly stirred for 7 days in the dark at room temperature to react. At the end of the reaction, n-hexane (150 mL) and methyl tert-butyl ether (30 mL) were added to layer the reaction solution, supernatant was discarded, n-hexane (150 mL) and methyl tert-butyl ether (50 mL) were further added to the lower oily solution, and such operations were repeated four times to obtain an oily product; the oily product was then dissolved with a mixed solution of methanol (30 mL) and dichloromethane (120 mL); silica gel powder (10 g) was added to the obtained solution, and the solution was then evaporated to dryness to obtain a powdery solid; the operations of dry sample loading, column chromatography, and elution with a mixed solution (1% ammonia water:6%-8% methanol/dichloromethane) were carried out; the elution product was then collected, concentrated and evaporated to dryness to obtain a solid product, and the solid product was then dried in a vacuum oven. 1.4803 g of Product 37-18 was obtained with a yield of 88%.

$^1$H-NMR (400 MHz, DMSO-$d_6$) δ 10.16 (s, 34H), 8.95 (s, 28H), 8.11 (m, 376H), 7.99-7.83 (m, 105H), 7.51 (s, 84H), 7.20 (m, 680H), 5.88-5.74 (m, 41H), 4.55 (s, 41H), 4.40-4.12 (m, 124H), 4.03 (m, 59H), 3.75 (m, 379H), 3.53-3.48 (s, 473H), 3.15 (m, 110H), 3.02 (s, 84H), 2.80-2.63 (m, 159H), 2.42 (s, 88H), 2.27 (m, 344H), 2.18-1.94 (m, 177H), 1.92-1.62 (m, 317H), 1.50-1.22 (m, 342H), 1.01-0.72 (m, 496H), 0.50 (s, 92H).

37-26

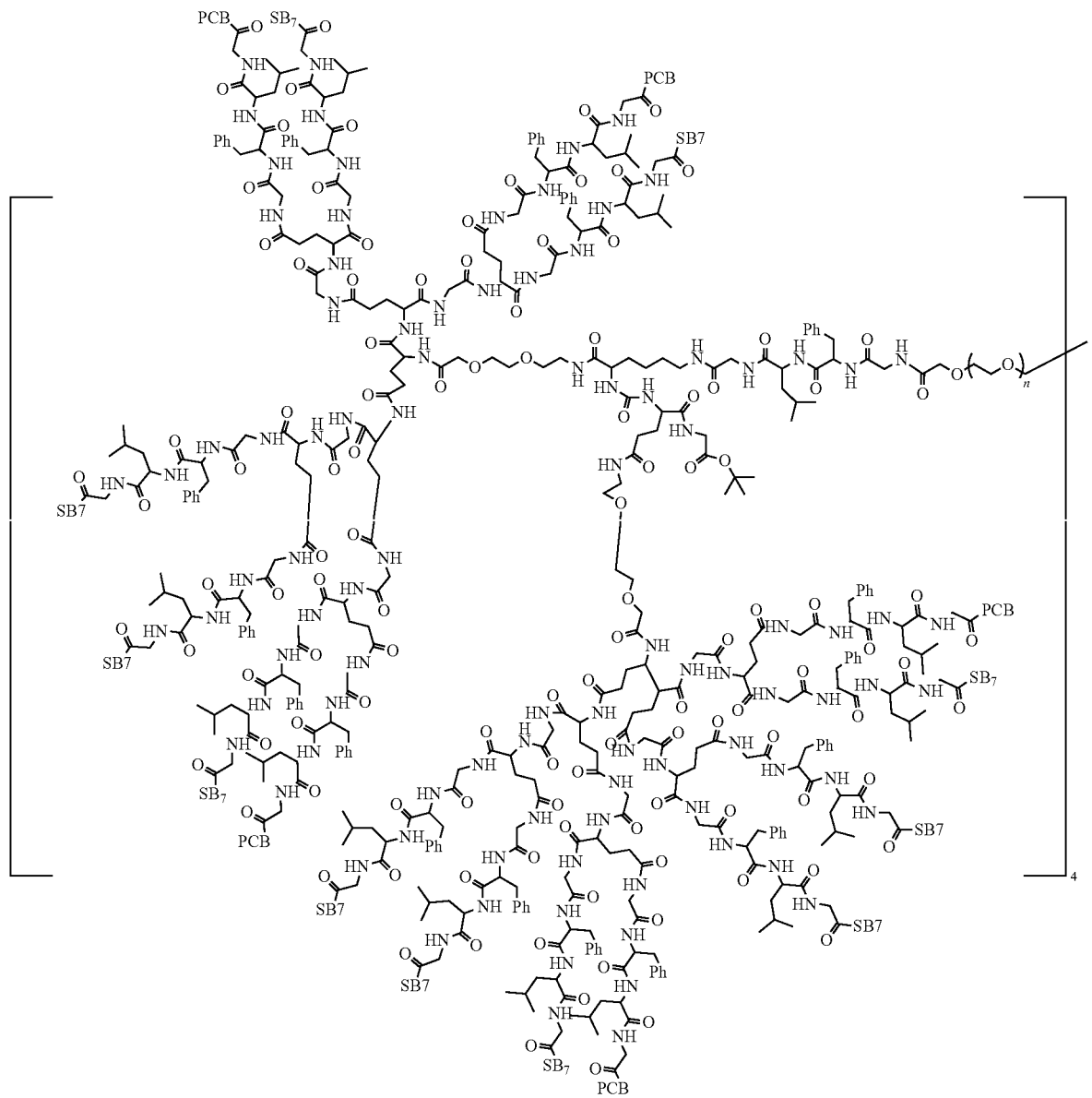

Compound 37-18 (0.8011 g, 0.0111 mmol) was added to a 250 mL flask and then dissolved with DMF (35 mL), and M-NH2·HCl-10K (1.0878 g, 0.0528 mmol, purchased from Jenkem), HBTU (0.0257 g, 0.0664 mmol), and HOBT (0.0091 g, 0.0664 mmol) were then added to the obtained solution; the mixed solution was slowly stirred at −5° C. for about 15 min to react, DIEA (0.0987 mL, 0.5975 mmol) was then slowly added dropwise, and the obtained solution further reacted at −5° C. for 20 min; and the solution was then slowly stirred in the dark at room temperature for 7 days to react. At the end of the reaction, n-hexane (150 mL) and methyl tert-butyl ether (40 mL) were added to the solution, the supernatant was discarded, and n-hexane (150 mL) and methyl tert-butyl ether (40 mL) were added to the lower liquid; such operations were repeated four times to obtain a viscous oily product and methyl tert-butyl ether (100 mL) was then added to the viscous oily product to obtain a viscous product; the viscous product was then dissolved with a mixed solution of methanol (20 mL) and dichloromethane (100 mL); silica gel powder (15 g) was added to the obtained solution, and the solution was is then evaporated to dryness to obtain a powdery solid; the operations of dry sample loading, column chromatography, and elution with a mixed solution (1% ammonia water:5%-7% methanol/dichloromethane) were carried out; the elution product was then collected, concentrated and evaporated to dryness to obtain a solid, and the solid was dried for 1 h in a vacuum oven; the product was dissolved with absolute ethanol (10 mL) and dichloromethane (15 mL), and methyl tert-butyl ether (200 mL) was then added to the obtained solution to separate out a solid product by precipitation; the solution was filtered and the filter cake was washed with methyl tert-butyl ether (50 mL×3) and dried in the vacuum oven. 0.75 g of Product 37-26 was obtained with a yield of 84%.

¹H-NMR (400 MHz, DMSO-d₆) δ 10.15 (s, 28H), 8.95 (s, 29H), 8.08 (m, 379H), 7.92-7.75 (m, 106H), 7.51 (s, 107H), 7.36-6.89 (m, 680H), 5.83 (m, 29H), 5.74 (m, 12H), 4.55 (s, 42H), 4.27 (m, 125H), 3.96 (m, 59H), 3.91 (m, 379H), 3.51 (s, 4329H), 3.15 (m, 119H), 3.03 (m, 87H), 2.72 (m, 157H), 2.41 (s, 88H), 2.37-2.21 (m, 338H), 2.11 (s, 179H), 1.81 (m, 317H), 1.54-1.11 (m, 334H), 0.94-0.74 (m, 499H), 0.49 (s, 88H).

further reacted at −5° C. for 20 min; and the solution was then slowly stirred in the dark at room temperature for 7 days to react. At the end of the reaction, n-hexane (120 mL) and methyl tert-butyl ether (30 mL) were added to the solution, the supernatant was discarded, and n-hexane (120 mL) and methyl tert-butyl ether (30 mL) were added to the lower liquid; such operations were repeated three times to obtain a viscous oily product; methyl tert-butyl ether (150

37-28

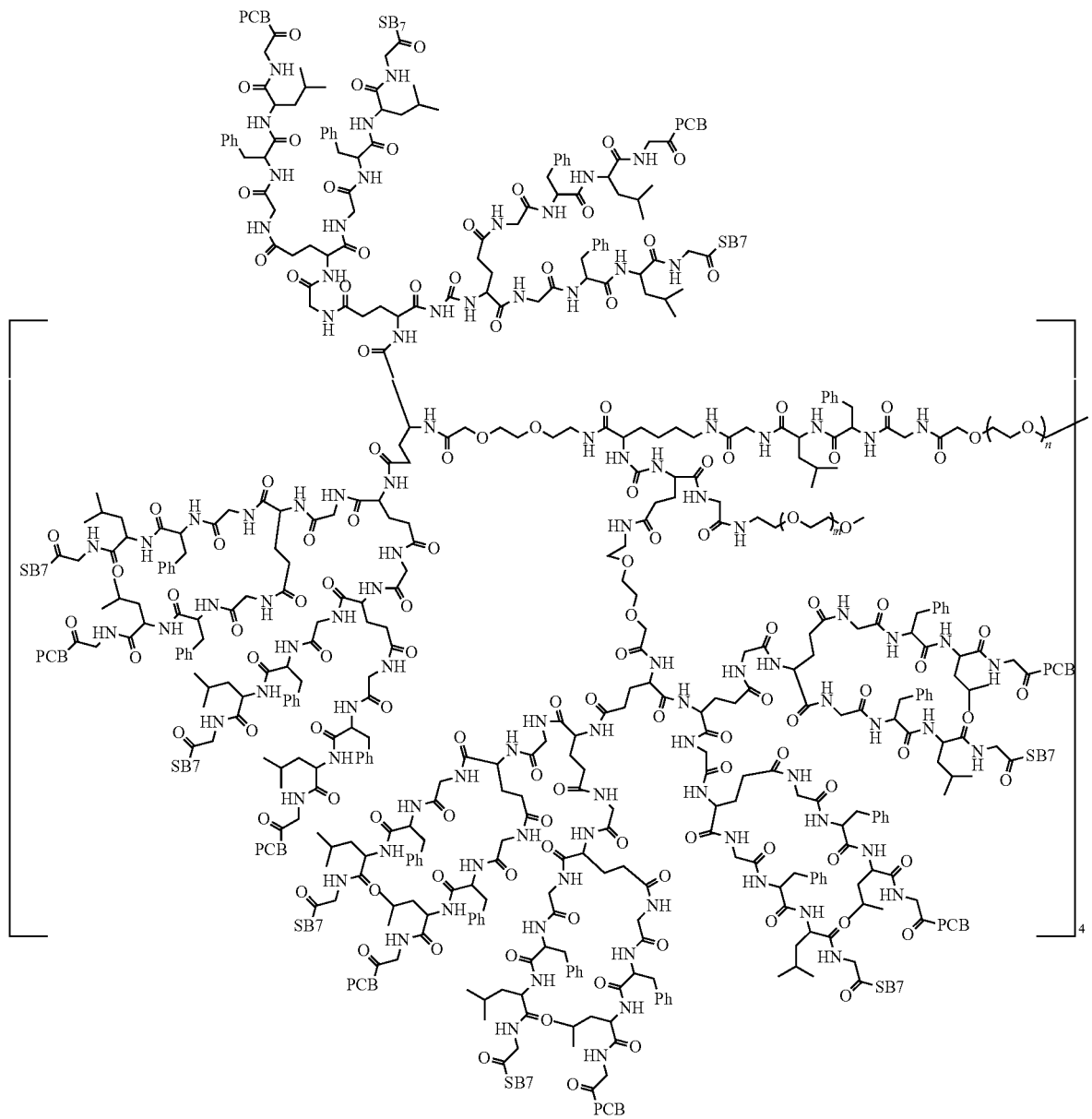

Compound 37-18 (0.68 g, 0.0088 mmol) was added to a 250 mL flask and then dissolved with DMF (25 mL), and M-NH₂·HCl-20K (1.0878 g, 0.0528 mmol, purchased from Jenkem), HBTU (0.0200 g, 0.0528 mmol), and HOBT (0.0071 g, 0.0528 mmol) were then added to the obtained solution; the mixed solution was slowly stirred at −5° C. for about 15 min to react, DIEA (0.0785 mL, 0.475 mmol) was then slowly added dropwise, and the obtained solution mL) was then added to precipitate a solid, the solid product was then filtered out and the filter cake was washed with methyl tert-butyl ether (50 mL×3) and then dissolved with a mixed solution of methanol (30 mL) and dichloromethane (120 mL); silica gel powder (15 g) was added to the obtained solution, and the solution was then evaporated to dryness to obtain a is powdery solid; the operations of dry sample loading, column chromatography, and elution with a mixed solution (1% ammonia water:6%-8% methanol/dichloromethane) were carried out; the elution product was then collected, concentrated and evaporated to dryness to obtain a solid, and the solid was dried for 1 h in a vacuum oven; the product was dissolved with absolute ethanol (10 mL) and dichloromethane (15 mL), and methyl tert-butyl ether (150 mL) was added to the obtained solution to obtain a solid product by precipitation; the solution was filtered and the filter cake was washed with methyl tert-butyl ether (50 mL×3) and dried in the vacuum oven. 0.8 g of Product 37-28 was obtained with a yield of 57%.

$^1$H-NMR (400 MHz, DMSO-d$_6$) δ 10.14 (m, 28H), 8.94 (m, 29H), 8.41-8.10 (m, 389H), 8.02 (m, 62H), 7.88 (m, 45H), 7.52 (m, 111H), 7.41-7.08 (m, 680H), 5.79 (m, 40H), 4.24 (m, 104H), 4.12-3.96 (m, 115H), 3.94-3.73 (m, 357H), 3.51 (s, 7936H), 3.15 (m, 119H), 3.01 (s, 26H), 2.89-2.70 (m, 85H), 2.41 (m, 155H), 2.41-2.40 (m, 90H), 2.39-2.26 (m, 336H), 2.12 (s, 179H), 1.81 (m, 320H), 1.61-1.10 (m, 340H), 0.93-0.74 (m, 503H), 0.42 (m, 83H).

Example 15: Synthesis of Compound 27-117

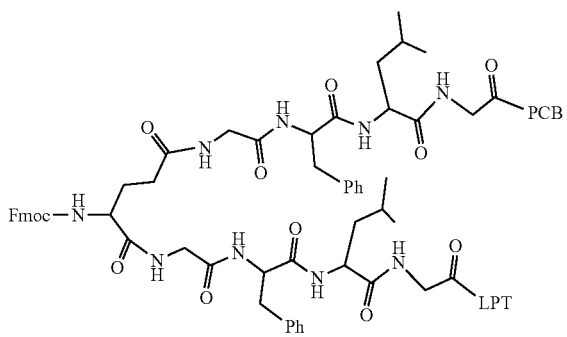

27-94

Product 14-128 (4.64 g, 4.8580 mmol), HBTU (2.91 g, 7.6705 mmol), and HOBT (1.04 g, 7.6705 mmol) were added to a flask containing Product 28-98 (6 g, 5.1137 mmol) and then dissolved with an appropriate amount of DMF; the obtained solution was stirred at −5° C. for 30 min, and then DIEA (3.8 mL, 23.0117 mmol) was slowly added dropwise to react for 30 min; then, the reaction solution was stirred overnight at room temperature to further react. At the end of the reaction, 250 mL of a mixed solution of methyl tert-butyl ether and n-hexane (1:5) was added to the reaction solution and the resulting solution was then oscillated; the mixed solution was then rested and the supernatant was discarded; then, methyl tert-butyl ether and n-hexane were added again; suction operations were repeated three times. Next, 200 mL of methyl tert-butyl ether was added to separate out a solid by precipitation and suction filtering was then carried out. The filter cake was washed with methyl tert-butyl ether (40 mL×3), collected, and dried in a vacuum oven. 10.25 g of the product was obtained with a yield of 100%.

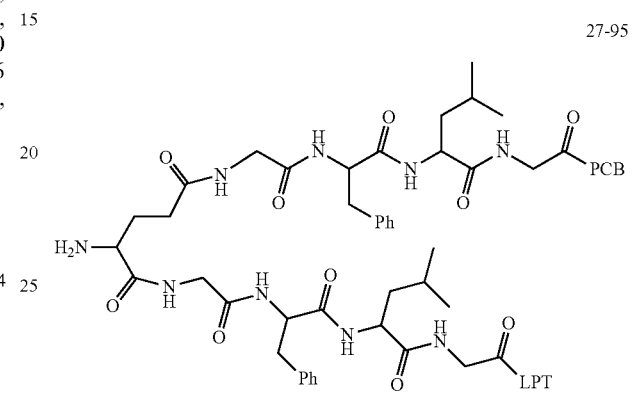

27-95

DMF was added into a flask with Compound 27-94 (10.25 g, 4.8580 mmol), the resulting solution was oscillated by ultrasonic until Compound 27-94 was completely dissolved, morpholine (4.23 mL, 48.580 mmol) was then added, and the mixed solution was stirred at room temperature for 2 h to react. At the end of the reaction, 250 mL of a mixed solution of methyl tert-butyl ether and n-hexane (1:5) was added to the reaction solution; the mixed solution was then rested and the supernatant was discarded; then, methyl tert-butyl ether and n-hexane were added again; suction operations were repeated three times. Next, 200 mL of methyl tert-butyl ether was added to separate out a solid by precipitation and suction filtering was then carried out. The filter cake was washed with methyl tert-butyl ether (40 mL×3), collected, and dried. 9.17 g of the product was obtained with a yield of 100%.

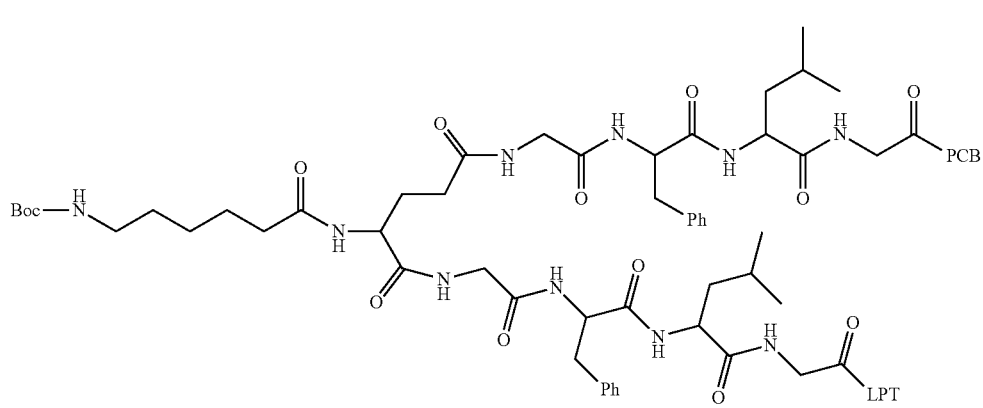

27-96

Product 27-95 (9.17 g, 4.8580 mmol), HBTU (2.76 g, 7.287 mmol), and HOBT (0.98 g, 7.287 mmol) were added to a flask containing Boc-AH-OH (1.68 g, 7.287 mmol) and then dissolved with an appropriate amount of DMF; the obtained solution was stirred at −5° C. for 30 min, and then DIEA (3.61 mL, 21.861 mmol) was slowly added dropwise to react for 30 min; then, the reaction solution was stirred overnight at room temperature to further react. At the end of the reaction, 250 mL of a mixed solution of methyl tert-butyl ether and n-hexane (1:5) was added to the reaction solution; the mixed solution was then rested and the supernatant was discarded; then, methyl tert-butyl ether and n-hexane were added again; suction operations were repeated three times. Next, 200 mL of methyl tert-butyl ether was added to separate out a solid by precipitation and suction filtering was then carried out. The filter cake was washed with methyl tert-butyl ether (40 mL×3), collected, and dried. 10.21 g of the product was obtained with a yield of 100%.

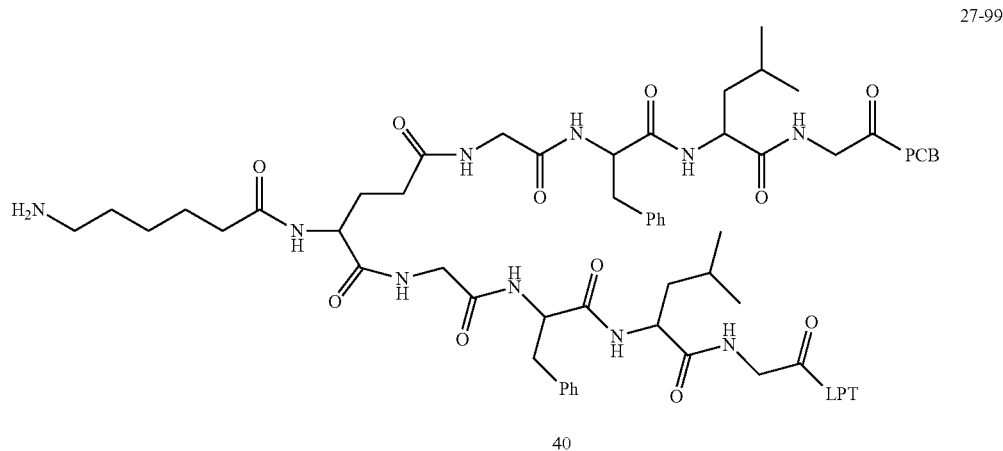

27-99

Dichloromethane was added into a flask with Compound 27-96 (10.21 g, 4.8580 mmol), the resulting solution was treated by ultrasonic until Compound 27-96 was completely dissolved, TFA (3.61 mL, 48.58 mmol) was then added, and the mixed solution was stirred overnight at room temperature to react. At the end of the reaction, the dichloromethane in the reaction solution was evaporated out, and methyl tert-butyl ether (200 mL) was then added for precipitation until a solid was separated out; suction filtering was then carried out, the filter cake was dissolved with a methanol/dichloromethane (1:4) solution (200 mL), silica gel powder (200 mL) was added to the obtained solution, and the solution was then evaporated to dryness to obtain a powdery solid; the operations of dry sample loading, column chromatography, and elution with a mixed solution (1% ammonia water:5% methanol/dichloromethane) were carried out; the elution product was then collected, concentrated, and dried. 6.935 g of the product was obtained with a yield of 71.36%.

27-102

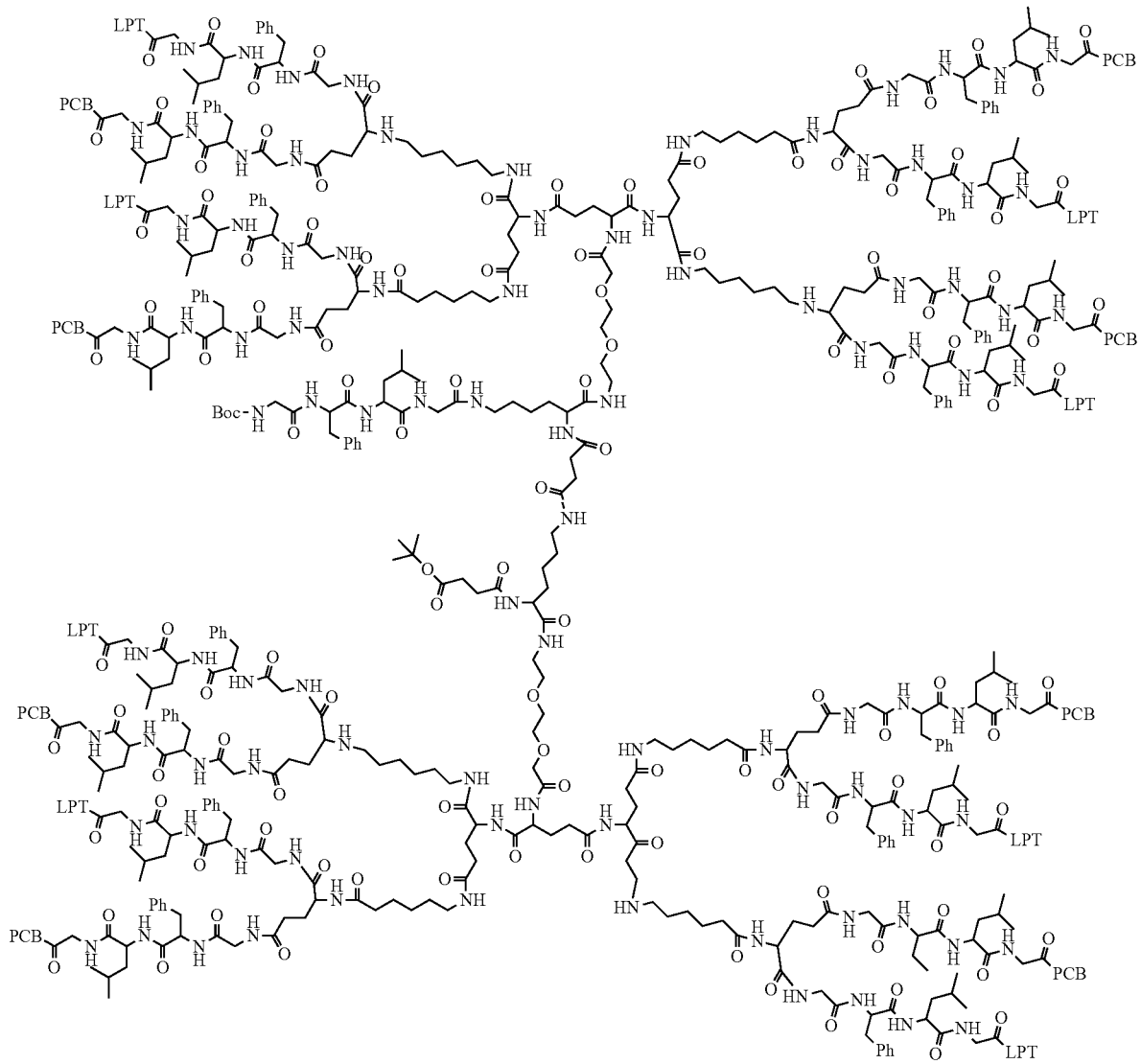

Product 22-268 (0.2298 g, 0.1110 mmol), HBTU (0.57 g, 1.4985 mmol), and HOBT (0.2 g, 1.4985 mmol) were added to a flask containing Product 27-99 (2 g, 0.9991 mmol) and then dissolved with an appropriate amount of DMF; the obtained solution was stirred at −5° C. for 30 min, and then DIEA (0.74 mL, 4.4955 mmol) was slowly added dropwise to react for 30 min; then, the reaction solution was stirred overnight at room temperature to further react. At the end of the reaction, 250 mL of a mixed solution of methyl tert-butyl ether and n-hexane (1:5) was added to the reaction solution; the mixed solution was then rested and the supernatant was discarded; then, methyl tert-butyl ether and n-hexane were added again for precipitation; suction operations were repeated three times. Next, 200 mL of methyl tert-butyl ether was added to separate out a solid by precipitation and suction filtering was then carried out. The filter cake was dissolved with a methanol/dichloromethane (1:4) solution (100 mL), silica gel powder (100 mL) was added to the obtained solution, and the solution was then evaporated to dryness to obtain a powdery solid; the operations of dry sample loading, column chromatography, and elution with a mixed solution (1% ammonia water:8% methanol/dichloromethane) were carried out; the elution product was then collected, concentrated, and evaporated to dryness. 1.9737 g of Product 27-102 was obtained with a yield of 99%.

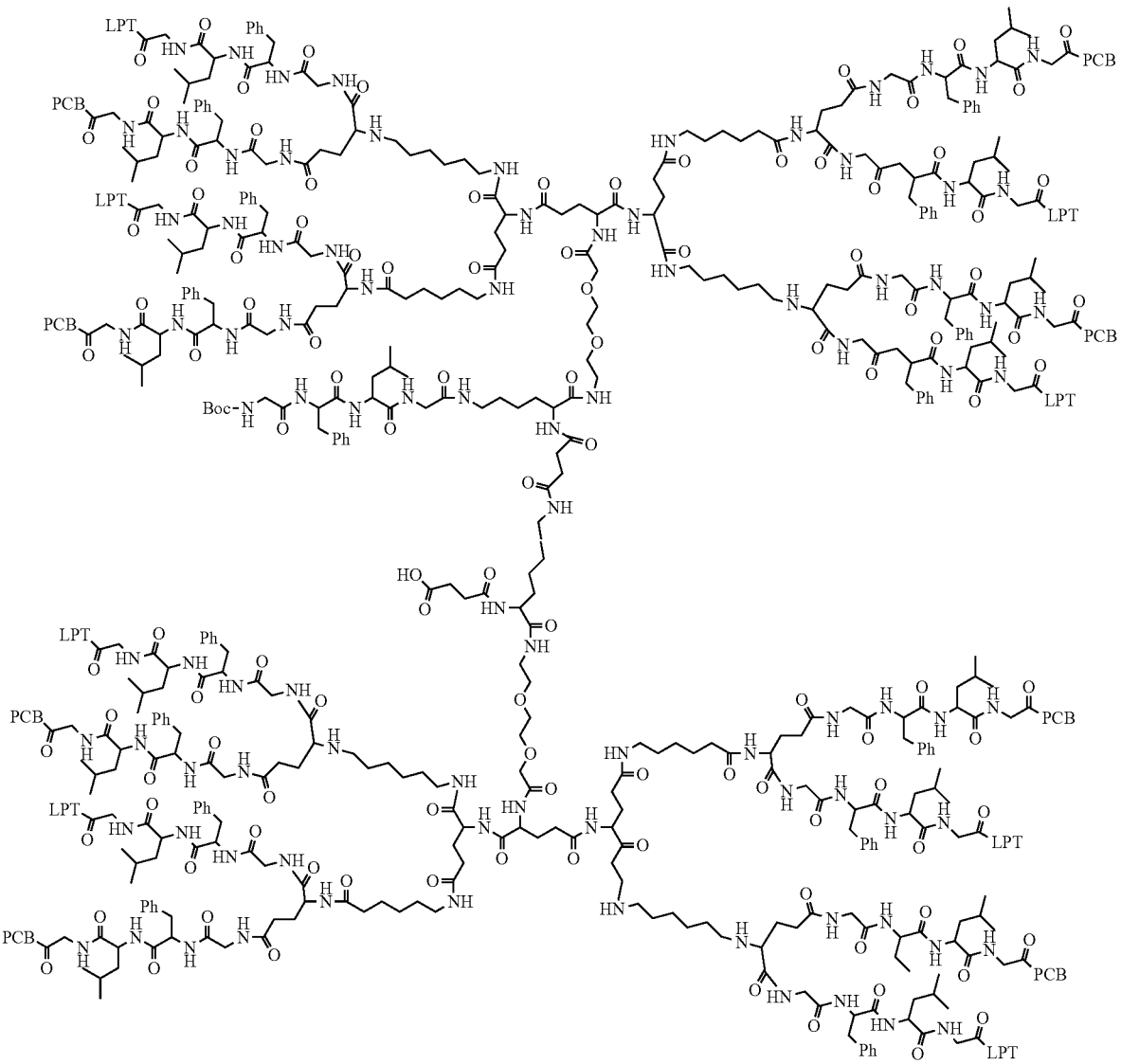

27-108

Dichloromethane was added into a flask with Compound 27-102 (1.9737 g, 0.1100 mmol), the resulting solution was oscillated by ultrasonic until Compound 27-102 was completely dissolved, TFA (0.082 mL, 1.1100 mmol) was then added, and the mixed solution was stirred overnight at room temperature to react. At the end of the reaction, the reaction solution was evaporated to be oily, and methyl tert-butyl ether (200 mL) was then added for precipitation until a solid was separated out; suction filtering was then carried out, the filter cake was dissolved with a methanol/dichloromethane (1:4) solution (100 mL), silica gel powder was added to the obtained solution, and the solution was then evaporated to dryness to obtain a powdery solid; the operations of dry sample loading, column chromatography, and elution with a mixed solution (1% ammonia water:8% methanol/dichloromethane) were carried out; the elution product was then collected, concentrated, and dried in a vacuum oven. 0.8963 g of Product 27-108 was obtained with a yield of 45.96%.

27-115

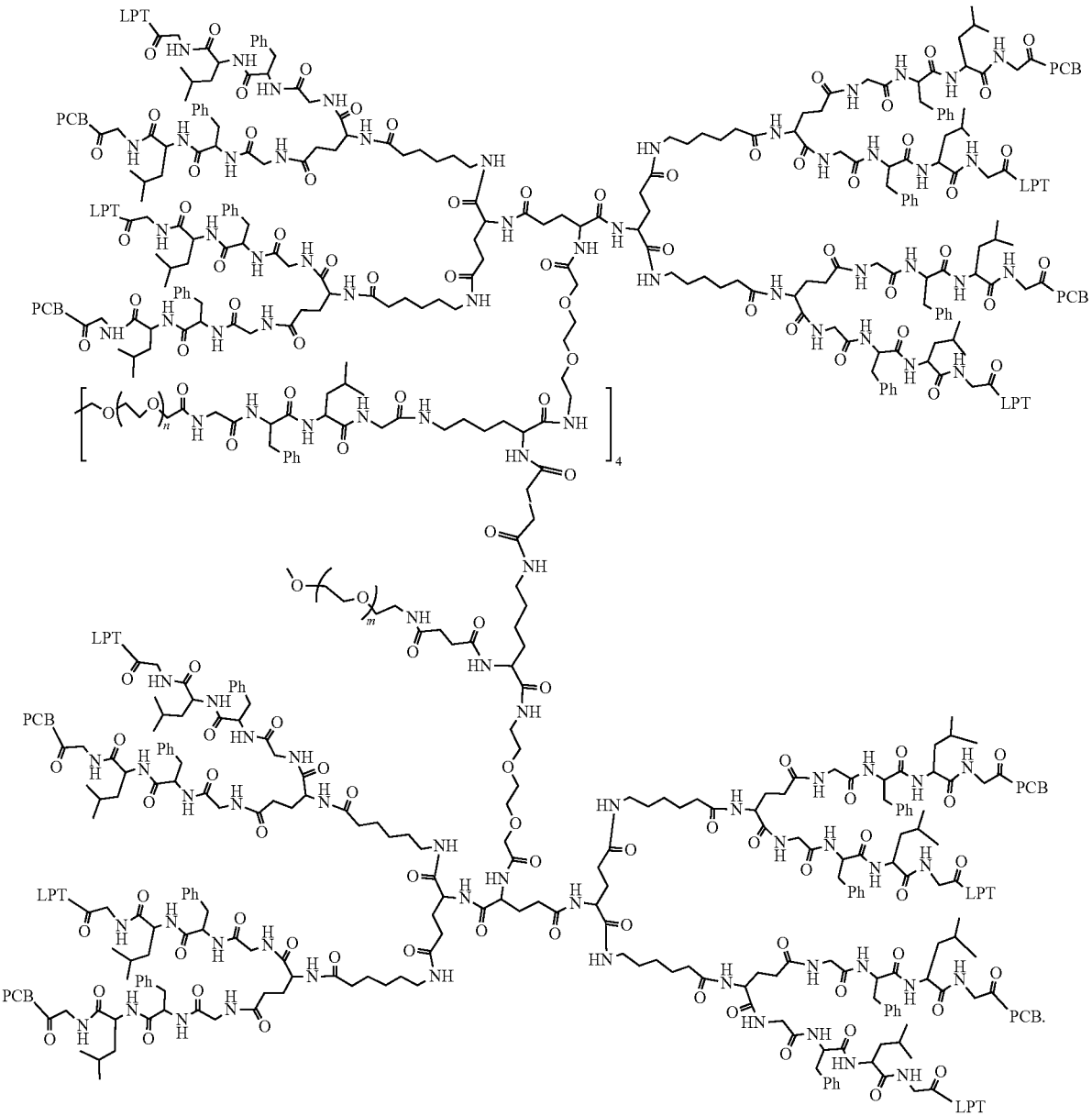

Product 27-108 (0.8963 g, 0.0504 mmol) was added in a 250 mL flask and dissolved with DMF (20 mL), the resulting solution was stirred at −5° C. for 30 min to react, and DIEA (0.142 mL, 0.8568 mmol) was then slowly added dropwise over 5 min. The obtained solution was further stirred at a low temperature for 30 min, 4ARM-SCM-40K (0.44 g, 0.0105 mmol, purchased from JenKem) was added and then dissolved with dichloromethane (10 mL), and the reaction solution was further stirred for 20 min at −5° C.; and then the reaction solution was stirred for one week in the dark at a low speed at room temperature to react. At the end of the reaction, the dichloromethane in the reaction solution was evaporated out, and methyl tert-butyl ether (200 mL) and n-hexane (70 mL) were then added to separate out a solid by precipitation; suction filtering was then carried out, the filter cake was washed with methyl tert-butyl ether (40 mL×3) and then dissolved with a methanol/dichloromethane (1:4) solution (100 mL), silica gel powder (50 mL) was added to the obtained solution, and the solution was then evaporated to dryness to obtain a powdery solid; the operations of dry sample loading, column chromatography, and elution with a mixed solution (1% ammonia water:7% methanol/dichloromethane) were carried out; the elution product was then collected, concentrated, and dried in a vacuum oven. 0.4545 g of Product 27-115 was obtained with a yield of 38.45%.

27-117

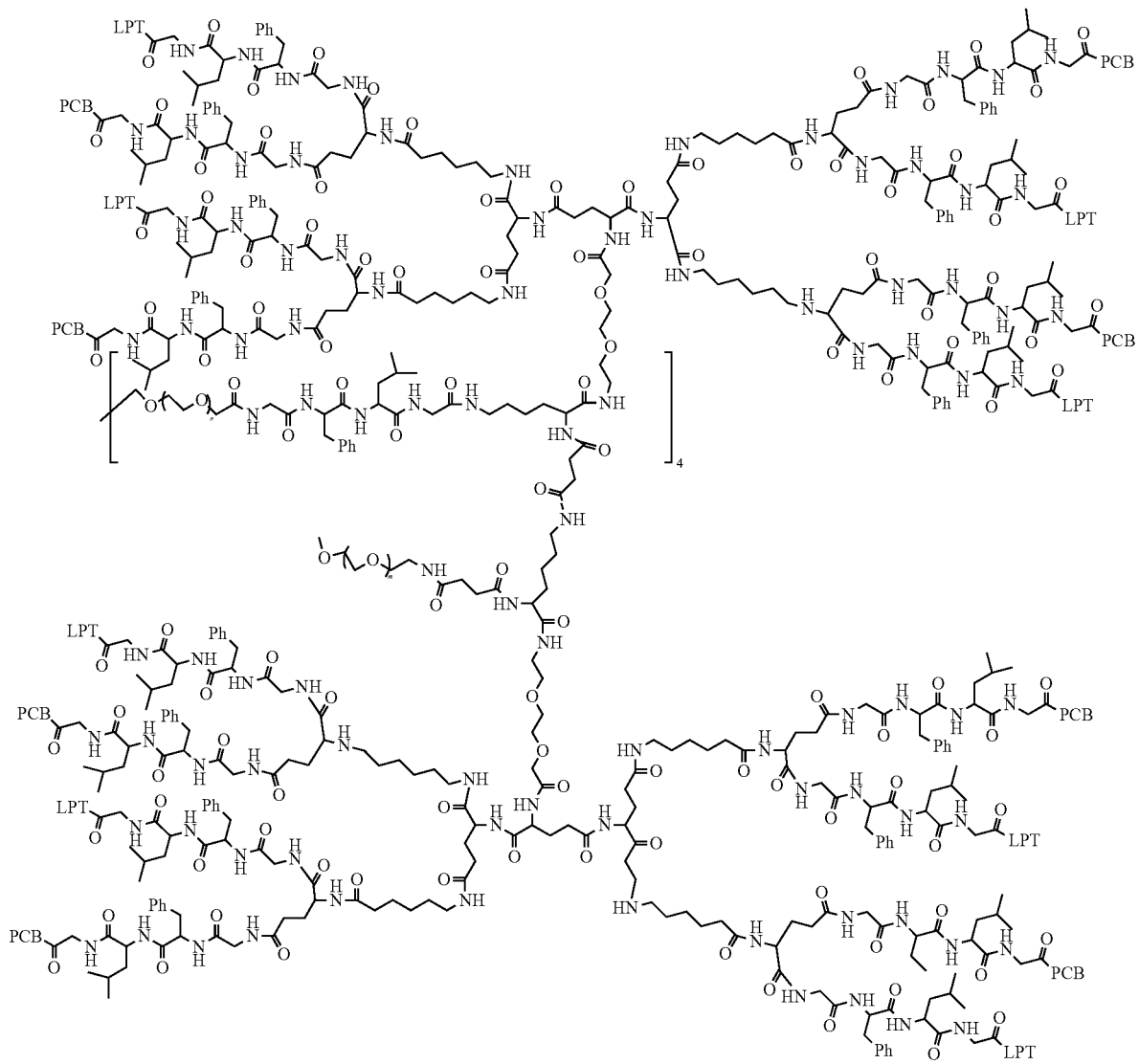

M-NH$_2$·HCl-20K (0.4929 g, 0.02421 mmol, purchased from KenJem), HBTU (0.009 g, 0.02421 mmol), and HOBT (0.003 g, 0.02421 mmol) were added to a flask containing Product 27-115 (0.4545 g, 0.00404 mmol) and then dissolved with an appropriate amount of DMF; the obtained solution was stirred at −5° C. for 30 min, and then DIEA (0.018 mL, 0.10908 mmol) was slowly added dropwise to react for 30 min; then, the reaction solution was stirred overnight at room temperature to further react. At the end of the reaction, the reaction solution was transferred to a 2 L flask, n-hexane (300 mL) and methyl tert-butyl ether (100 mL) were then added, and the resulting solution was then oscillated; the supernatant was discarded; suction operations were repeated three times. Next, methyl tert-butyl ether (300 mL) and a small amount of n-hexane (100 mL) were added and the resulting solution was then oscillated to separate out a solid by precipitation; suction filtering was then carried out, the filter cake was washed with methyl tert-butyl ether (40 mL×3) and then dissolved with a methanol/dichloromethane (1:4) solution (100 mL), silica gel powder (200 mL) was added to the obtained solution, and the solution was then evaporated to dryness to obtain a powdery solid; the operations of dry sample loading, column chromatography, and elution with a mixed solution (1% ammonia water:7% methanol/dichloromethane) were carried out; the elution product was then collected, concentrated, and evaporated to dryness to obtain a solid, and then the solid was dried in a vacuum oven. 0.5521 g of Product 27-117 was obtained with a yield of 70.50%.

$^1$H-NMR (400 MHz, DMSO-d$_6$) δ 10.14 (s, 8H), 9.97 (s, 8H), 8.89 (m, 18H), 8.54 (s, 7H), 8.28-7.70 (m, 87H), 7.55-7.02 (m, 157H), 6.79-6.64 (m, 16H), 6.53 (s, 5H), 5.53 (s, 8H), 5.25 (s, 14H), 4.83-4.45 (m, 57H), 4.25-3.37 (m, 3214H), 3.21-2.96 (m, 30H), 2.89 (s, 23H), 2.82-2.63 (m, 30H), 2.28 (m, 22H), 2.10 (s, 18H), 1.81 (m, 28H), 1.53 (m, 38H), 1.22 (t, m, 41H), 0.84 (m, 40H).

Example 16: Synthesis of Compound 24-239

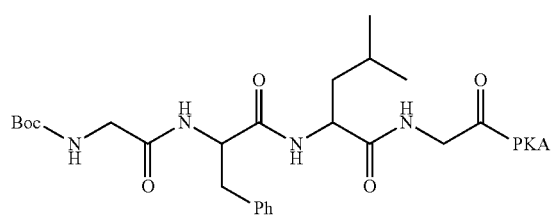

24-58

PKA (18.3 g, 31.2028 mmol), HBTU (17.75 g, 46.8042 mmol), and HOBT (6.3241 g, 46.8042 mmol) were added in a round-bottomed flask and then dissolved with the DMF solution of Boc-GFLG-OH; the obtained solution was then stirred for 30 min at −5° C. and DIEA (23.2076 mL, 140.4126 mmol) was then slowly added dropwise to the mixed solution to react for 2 h; then, the reaction solution was stirred overnight at room temperature to react At the end of the reaction, methyl tert-butyl ether and n-hexane were added to the reaction solution and the obtained solution was then rested; the supernatant was discarded and there was no product in the supernatant. A small amount of ethyl acetate was added to the oily product, the mixed solution was treated by ultrasonic and then precipitated with methyl tert-butyl ether and n-hexane, and the process of dissolution and precipitation by using ethyl acetate, methyl tert-butyl ether and n-hexane was repeated four times, and the product was evaporated to dryness. 40 g of product was obtained, 7 g being extra-quota product. The obtained product was directly used for the next reaction step.

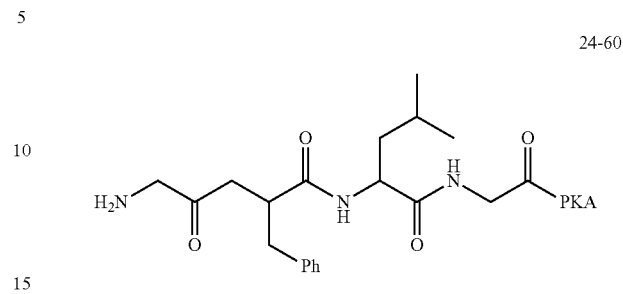

24-60

Compound 24-58 (33 g, 31.2028 mmol) was weighed, dichloromethane (20 mL) and TFA (69.5279 mL, 936.084 mmol) were then added sequentially, and the reactant was completely dissolved by ultrasonic treatment; the mixed solution was stirred at room temperature to react. At the end of the reaction, the reaction solution was evaporated to dryness and dichloromethane was removed; n-hexane (200 mL) was then added; the supernate was discarded; methyl tert-butyl ether was then added to obtain separate out a solid by precipitation, and suction filtering was then carried out; next, methyl tert-butyl ether was added and the obtained solution was treated by ultrasonic, and then suction filtering was carried out; washing with methyl tert-butyl ether was carried out four times; the obtained solution was filtered by suction. 35 g of the product was obtained with a yield of 100%.

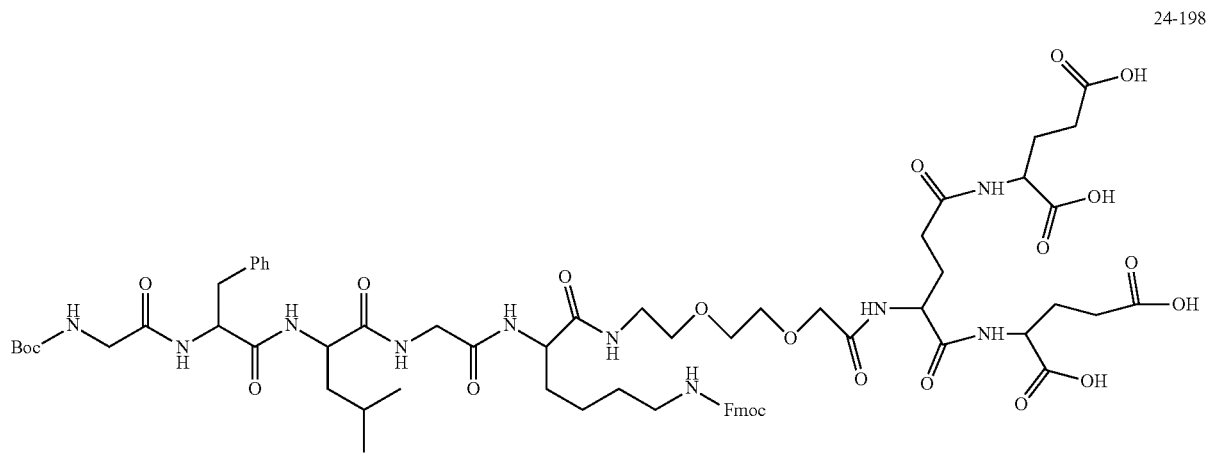

24-198

The reactant Compound 24-144 (synthesized according to the synthesis route of Compound 24-95, 1.12 g, 0.6496 mmol) and 10% Pd/C (70 mg) were added in a micro-reactor and then dissolved with DMF (30 mL); $H_2$ (20 psi) was introduced in the reactor, and the mixed solution was stirred overnight to react. At the end of the reaction, the reaction solution was filtered by suction with diatomaceous earth as a filter cake to remove Pd/C; the diatomaceous earth was washed three to four times with DMF to obtain the DMF solution of Compound 24-198 for the next reaction step.

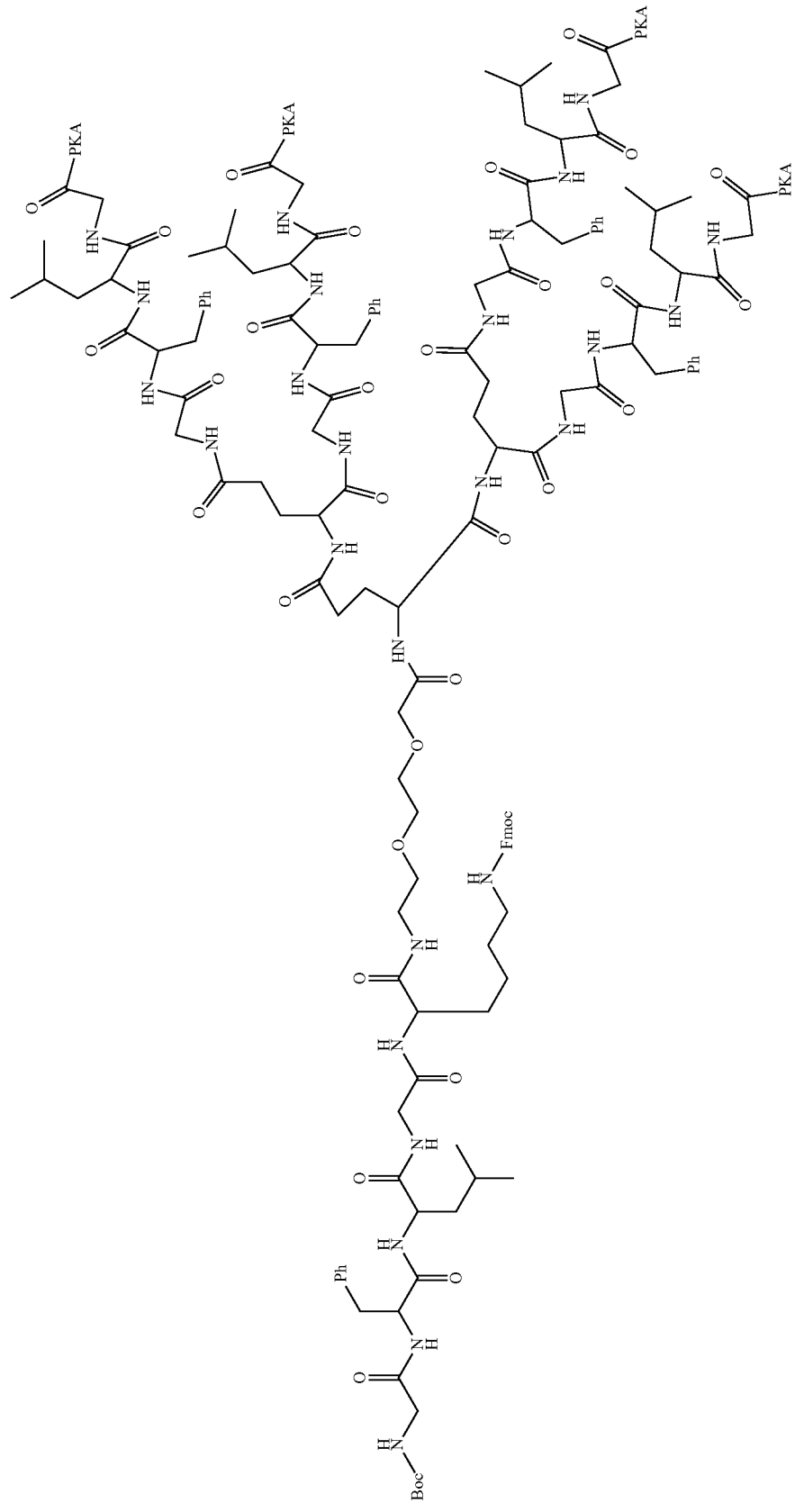

Compound 24-60 (3 g, 3.1181 mmol), HBTU (1.4400 g, 3.8976 mmol), and HOBT (0.5268 g, 3.8976 mmol) were weighed and added into a 250 mL flask and then completely dissolved with the DMF solution of Compound 24-198 by ultrasonic, the resulting solution was then stirred at −5° C. for 30 min, DIEA (1.9328 mL, 11.6928 mmol) was slowly added dropwise, and the mixed solution reacted at a low temperature. At the end of the reaction, methyl tert-butyl ether (200 mL) and n-hexane (100 mL) were added to the reaction solution, the resulting solution was rested in the refrigerator for 30 min, the supernatant was discarded and there was no product in the supernatant; ethyl acetate (20 mL) was added to the lower liquid, and the obtained solution was treated to be uniform by ultrasonic; n-hexane (200 mL) was added to the solution and the resulting solution was rested for 30 min; the supernatant was discarded, and the lower product was dissolved with a solvent (20% methanol/dichloromethane); silica gel powder (12.4 g) was then added to the obtained solution and the operations of evaporation, column chromatography, and gradient elution with 7%-13% methanol/dichloromethane were carried out. 3.7 g of the product was obtained with a yield of 100%, 0.4 g being extra-quota.

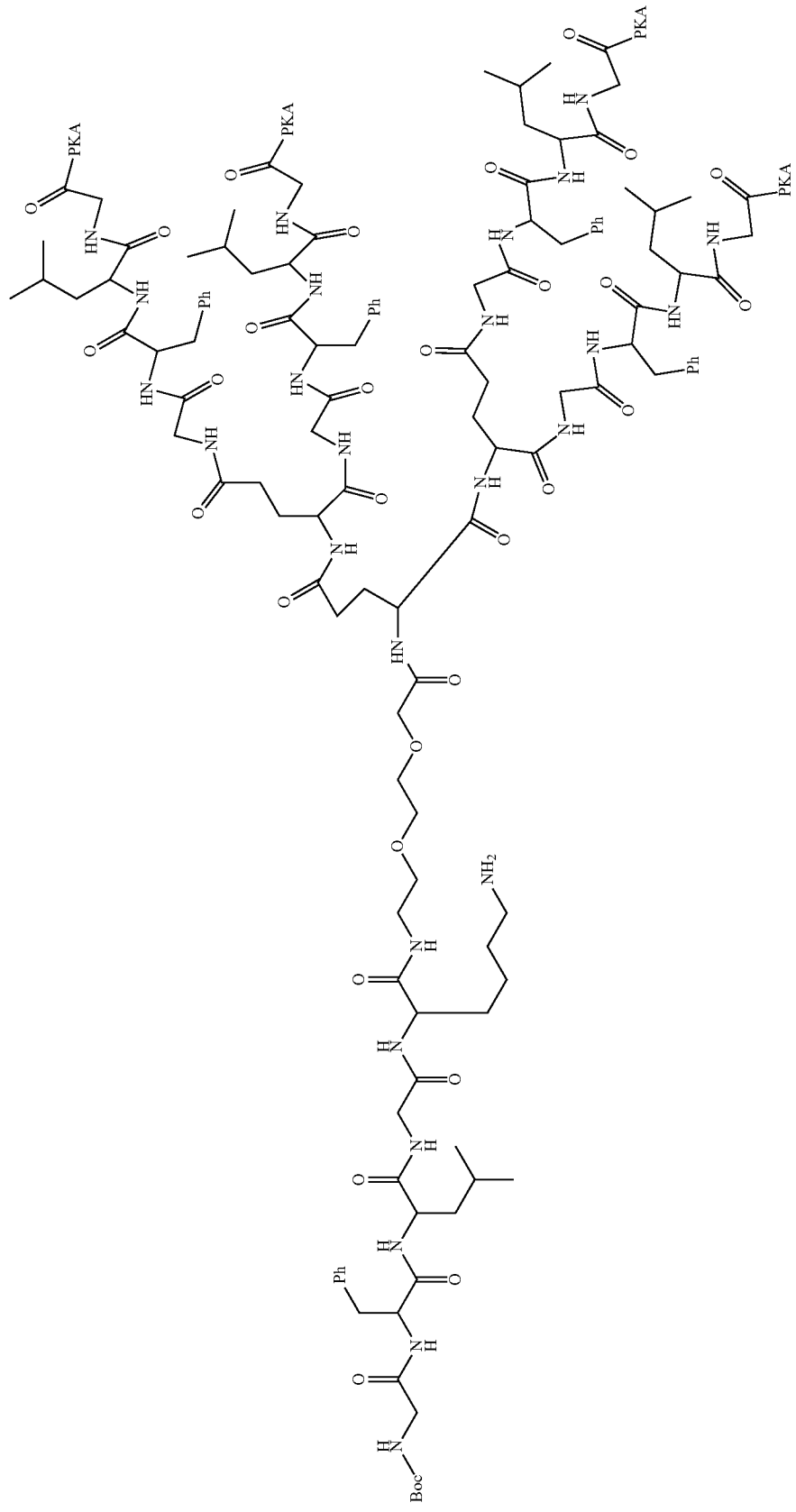

The reactant Compound 24-199 (3.3 g, 0.6405 mmol) was added into a 250 mL round-bottomed flask and then dissolved with DMF (20 mL), morpholine (1.3950 mL, 16.0125 mmol) was then added to the resulting solution, and the mixed solution was stirred at room temperature to react; 2.5 h later, the reaction ended, methyl tert-butyl ether (200 mL) and n-hexane (50 mL) were added to the reaction solution and the resulting solution was then rested in a refrigerator for 30 min to separate out a solid by precipitation; suction filtering and washing with ethyl acetate (50 mL) were carried out; suction filtering and drying in vacuum were carried out. 2 g of the product was obtained with a yield of 64%.

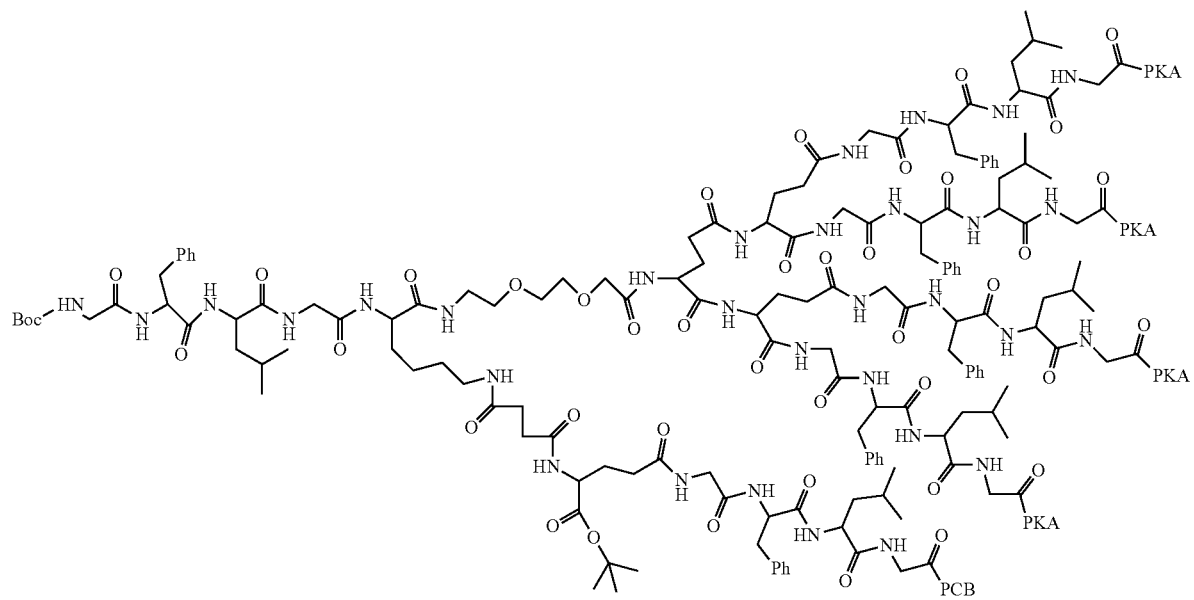

24-212

Compound 24-211 (2 g, 0.4057 mmol), Compound 24-210 (synthesized according to the synthesis method of Compound 19-175) (0.5389 g, 0.4869 mmol), HBTU (0.2307 g, 0.6086 mmol), and HOBT (0.0822 g, 0.6086 mmol) were weighed and added into a 250 mL flask and then completely dissolved with DMF (50 mL) in a condition of ultrasonic. The obtained solution was stirred at −5° C. for 30 min. DIEA (0.3018 mL, 1.8257 mmol) was then slowly added dropwise, and the mixed solution was stirred at a low temperature for 2 h and then placed at room temperature to react. At the end of the reaction, methyl tert-butyl ether (100 mL) and n-hexane (100 mL) were then added to the reaction solution for precipitation to separate out a solid product; suction filtering was then carried out and ethyl acetate (200 mL) was added to the solid product and the resulting solution was treated by ultrasonic; suction filtering and drying in vacuum were carried out. 2.5 g of the product was obtained with a yield of 100%, 0.1 g being extra-quota product.

24-214

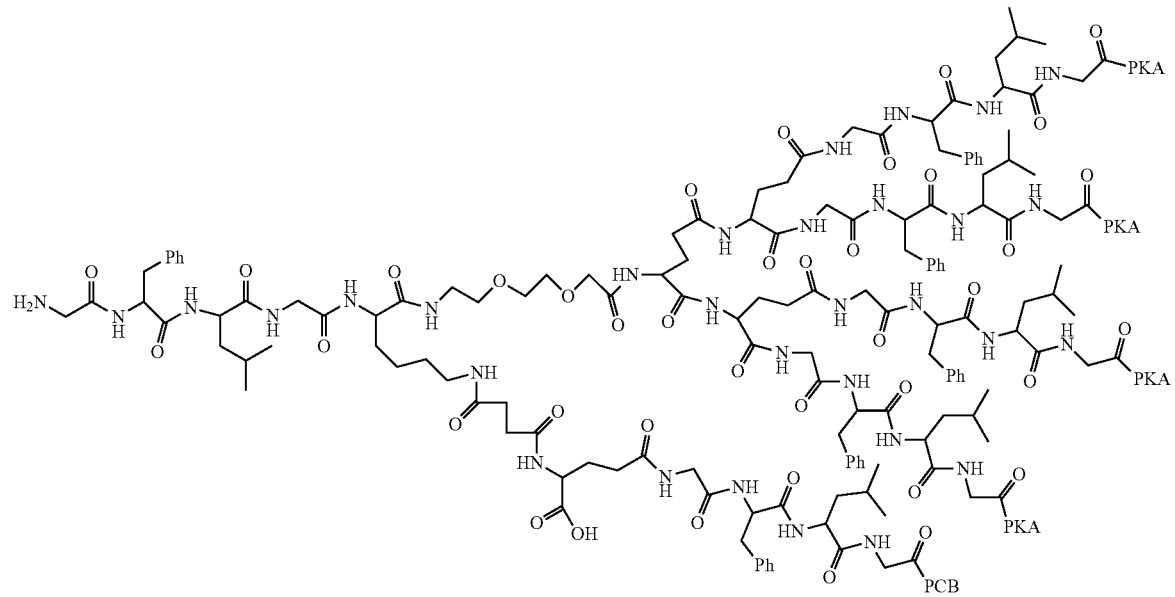

Compound 24-212 (0.8 g, 0.0701 mmol) was weighed, dichloromethane (20 mL) and TFA (1.2 mL, 16.228 mmol) were then added sequentially, and the obtained solution was treated by ultrasonic until Compound 24-212 was completely dissolved; the mixed solution was then stirred at room temperature to react. At the end of the reaction, the reaction solution was evaporated to dryness and dichloromethane was removed; then, methyl tert-butyl ether (150 mL) was added to the reaction solution and the obtained solution was treated by ultrasonic for 2 min to separate out a solid product by precipitation; the solid product was then filtered out by suction and dissolved with a solvent (20% methanol/dichloromethane); silica gel powder was then added to the obtained solution; the obtained solution was then evaporated to dryness with a rotary evaporator and the operations of column chromatography and gradient elution with 1% ammonia water+5%-20% methanol/dichloromethane were carried out. 0.7 g of the product was obtained with a yield of 30%.

24-220

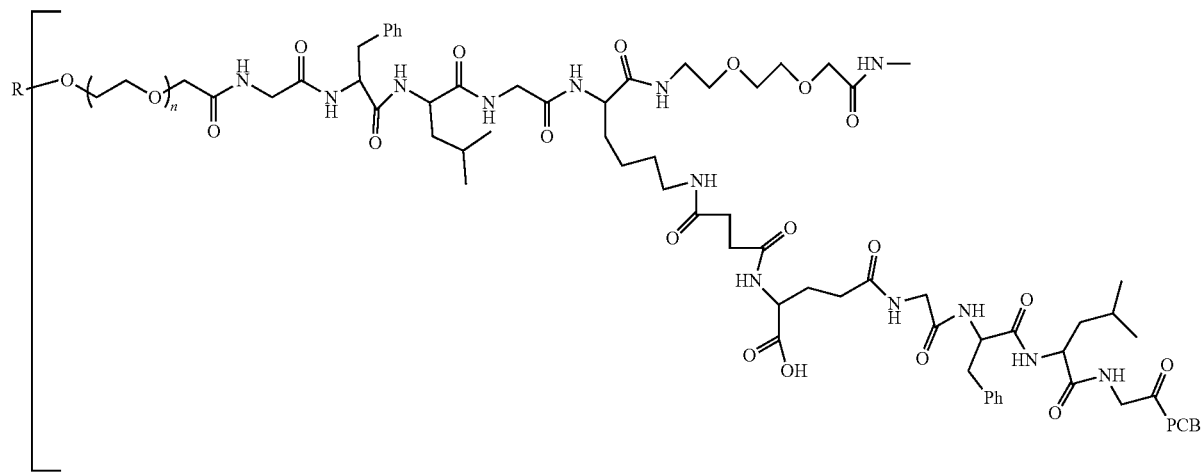

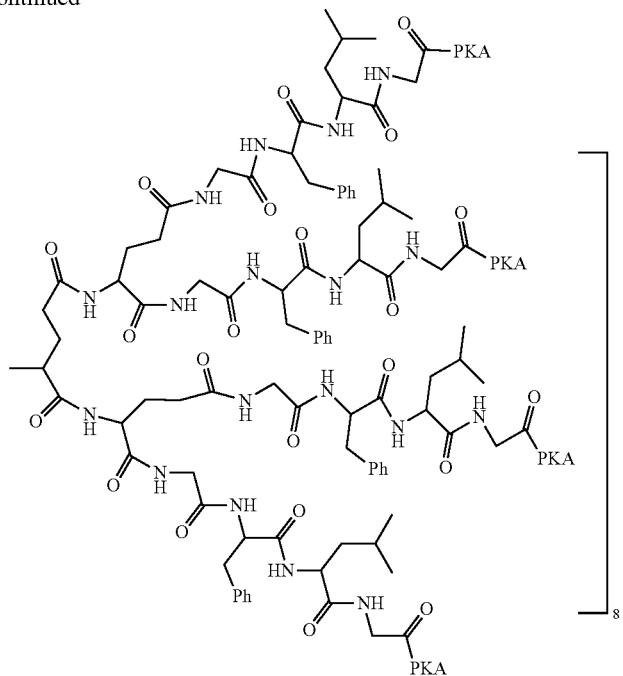

Compound 24-214 (0.7 g, 0.1194 mmol) was weighed and then dissolved with DMF (20 mL), DIEA (0.0791 mL, 0.4788 mmol) and 8ARM-SCM-40K (0.5738 g, 0.0133 mmol, purchased from Jenkem, hexaglycerol core) were added sequentially to the resulting solution and dissolved by ultrasonic. The obtained solution was slowly stirred in the dark to react. At the end of the reaction, methyl tert-butyl ether (150 mL) and n-hexane (100 mL) were added to the reaction solution; the supernatant was discarded; ethyl acetate (10 mL) was added to the lower solution; methyl tert-butyl ether (100 mL) and n-hexane (100 mL) were added to the mixed solution to separate out a solid product by precipitation; suction filtering was carried out and the filter cake was dissolved with 20% methanol/dichloromethane; silica gel powder (3 g) was then added, and the obtained solution was evaporated to dryness and then subjected to is column chromatography. Gradient elution with 100 ammonia water+70%-10% methanol/dichloromethane was carried out. 0.3 g of the product was obtained with a yield of 30%.

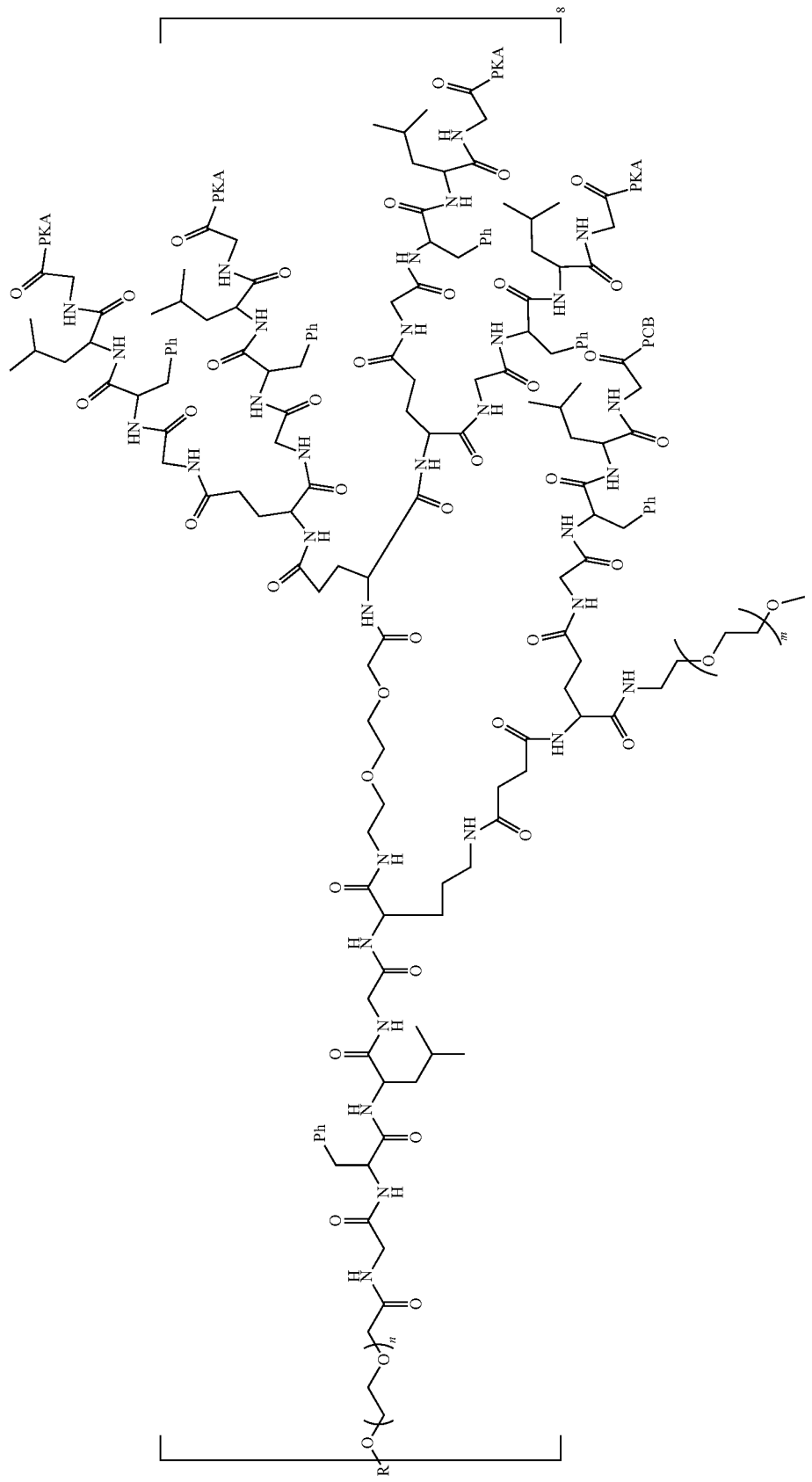

The reactants, Compound 24-220 (0.3 g, 0.0034 mmol), M-NH$_2$HCL-5K (0.2135 g, 0.0408 mmol), HBTU (0.0232 g, 0.0612 mmol), and HOBT (0.0232 g, 0.0612 mmol) were weighed and added into a 250 mL reaction flask and then dissolved with DMF (20 mL) by ultrasonic; the obtained solution was stirred at −5° C. for 30 min; DIEA (0.0281 mL, 0.1700 mmol) was slowly added dropwise and the obtained solution was stirred for 1 h and then slowly stirred in the dark at room temperature to react. At the end of the reaction, methyl tert-butyl ether (150 mL) and n-hexane (100 mL) were added to the reaction solution; the supernatant was discarded; ethyl acetate (10 mL) was added to the lower solution; methyl tert-butyl ether (100 mL) was added to the mixed solution to separate out a solid product by precipitation; suction filtering was carried out and the filter cake was dissolved with 20% methanol/dichloromethane; silica gel powder (3 g) was then added, and the obtained solution was evaporated to dryness and then subjected to column chromatography. Gradient elution with 1% ammonia water+6%-7% methanol/dichloromethane was carried out. 0.35 g of the product was obtained with a yield of 80%.

$^1$H-NMR (400 MHz, DMSO-d$_6$) δ 11.15-10.90 (m, 4H), 10.28-10.08 (m, 4H), 9.01 (d, J=42.4 Hz, 4H), 8.11 (m, 105H), 7.51 (m, 36H), 7.04 (m, 182H), 4.54 (s, 12H), 4.18 (m, 64H), 3.51 (s, 4546H), 3.15 (s, 87H), 2.86 (m, 116H), 2.64 (m, 37H), 2.34 (s, 20H), 1.76 (m, 12H), 1.48 (m, 36H), 1.35-1.12 (m, 697H), 0.86 (s, 105H).

Example 17: Synthesis of Compound 26-234

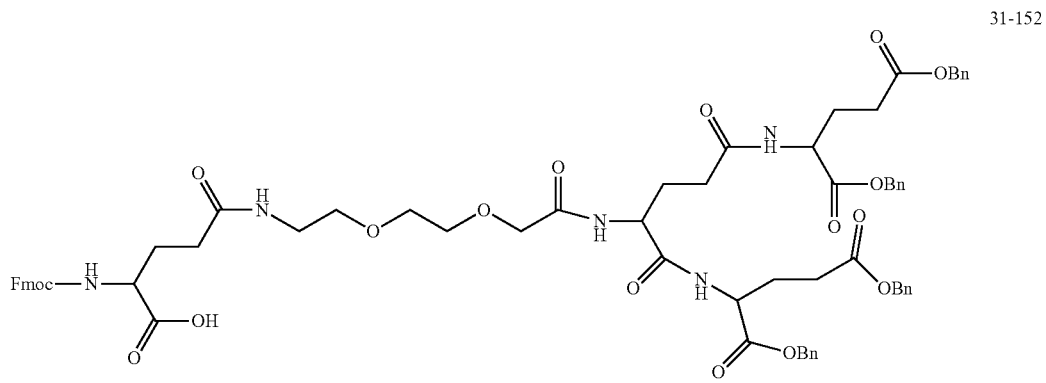

Compound 31-145 (synthesized according to the synthesis method of Compound 24-69) (7.9 g, 5.99 mmol) was added in a 250 mL round-bottomed flask and then dissolved with dichloromethane (10 mL). Then, TFA (6.67 mL, 89.85 mmol) was added to the resulting solution and the mixed solution was then stirred at room temperature to react. At the end of the reaction, the reaction solution was evaporated to dryness and dried in an oven for later use. The theoretical weight of the obtained product was 7.56 g.

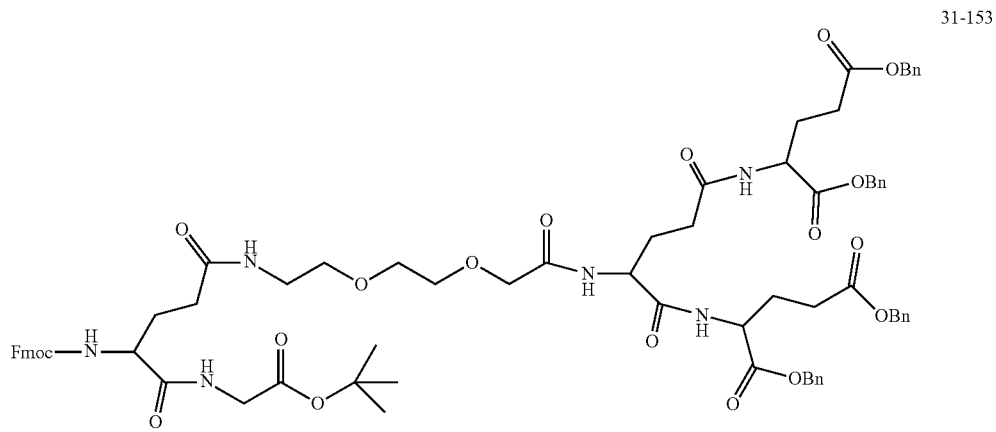

Compound 31-152 (7.56 g, 5.99 mmol), NH₂-Gly-OtBu·HCl (1.20 g, 7.19 mmol, purchased from Innochem), HOBT (1.21 g, 8.98 mmol), and HBTU (3.41 g, 8.98 mmol) were added in a 500 mL round-bottomed flask and then dissolved with DMF (30 mL), and the mixed solution was stirred at 0° C. for 30 min. Then DIEA (4.46 mL, 26.96 mmol) was slowly added dropwise and then the solution in the reaction flask was stirred overnight at a low temperature is (0° C.). At the end of the reaction, the reaction solution was washed with a saturated sodium chloride solution (200 mL) and then extracted three times with ethyl acetate (100 mL). The organic phases were combined and washed once with pure water (100 mL). The organic phase was evaporated to dryness with a rotary evaporator and dried in an oven to obtain a crude product. The theoretical weight of the obtained product was 8.24 g.

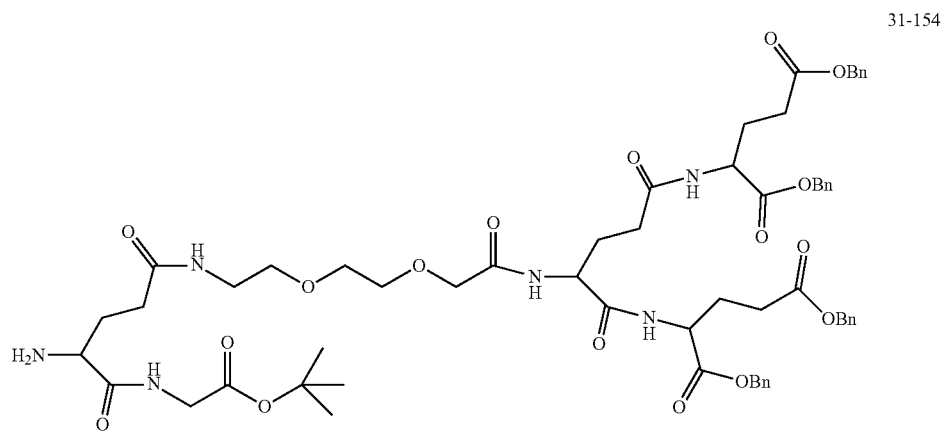 [SMILES: CC(C)(C)OC(=O)CNC(=O)C(N)CCC(=O)NCCOCCOCC(=O)NC(CCC(=O)NC(CCC(=O)OCc1ccccc1)C(=O)OCc1ccccc1)C(=O)NC(CCC(=O)OCc1ccccc1)C(=O)OCc1ccccc1]

31-154

Compound 31-153 (8.24 g, 5.99 mmol) was added in a 250 mL round-bottomed flask and then dissolved with DMF (25 mL), and the mixed solution was stirred at room temperature. Morpholine (15.66 mL, 179.7 mmol) was then added dropwise, and the mixed solution reacted at room temperature for 1 h. At the end of the reaction, the reaction solution was extracted twice with a saturated sodium bicarbonate solution (150 mL) and ethyl acetate (100 mL), the organic phases were combined and then extracted twice with a saturated sodium chloride solution (100 mL) and ethyl acetate (500 mL); the organic phase was then concentrated; silica gel powder was then added and the obtained solution was evaporated to become powder; the operations of dry sample loading, column chromatography, and gradient elution with 3% methanol/dichloromethane-3% methanol/0.5% ammonia water/dichloromethane were carried out, and then the elution product was collected, concentrated, evaporated to dryness, and dried in a vacuum oven. 3.71 g of the product was obtained with a yield of 1.72%.

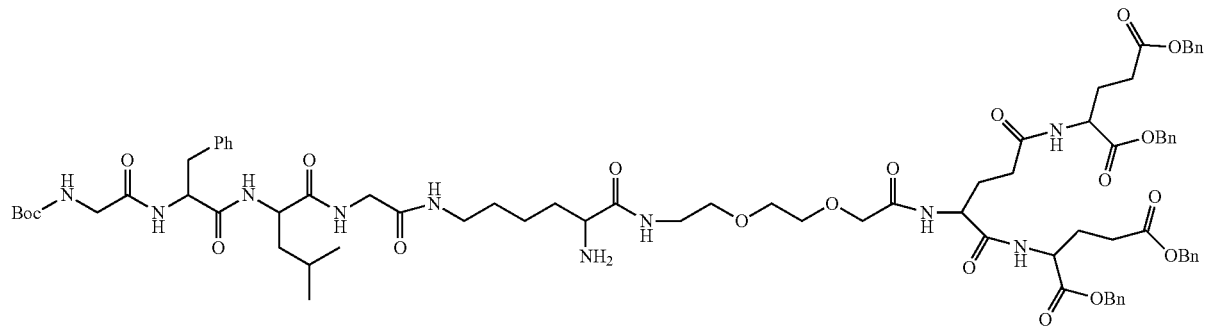

31-181

Compound 31-170 (2.52 g, 1.76 mmol) (synthesized according to the synthesis method of Compound 30-84) was added in a 250 mL round-bottomed flask and then dissolved with DMF (15 mL), and the mixed solution was stirred at room temperature. Morpholine (4.58 mL, 52.6 mmol) was then added dropwise, and the mixed solution reacted at room temperature for 2 h. At the end of the reaction, the reaction solution was transferred to a 500 mL separatory funnel and extracted three times with a saturated sodium bicarbonate solution (100 mL) and ethyl acetate (100 mL), the organic phase was then evaporated to dryness with a rotary evaporator and then dried in an oven for later use. The theoretical weight of the obtained product was 2.66 g.

31-186

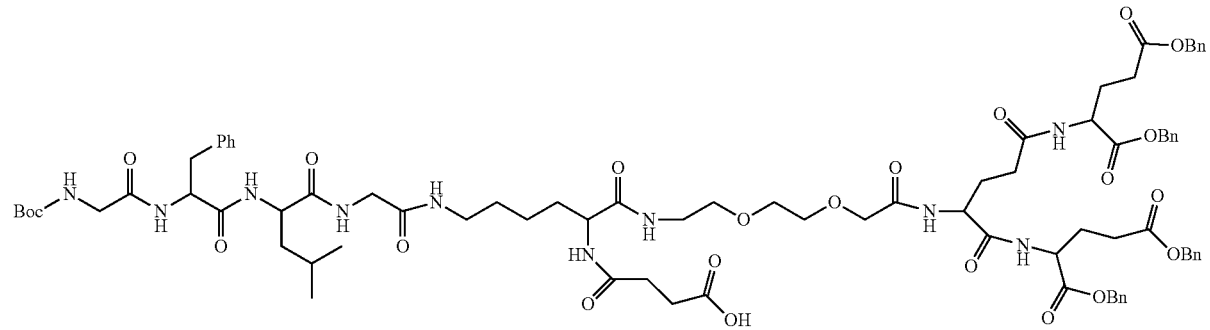

Compound 31-181 (2.66 g, 1.76 mmol) was added in a 250 mL round-bottomed flask and then dissolved with DMF (30 mL), and the mixed solution was then stirred at 0° C. to react; 0.5 h later, DIEA (0.34 mL, 2.08 mmol) was slowly added dropwise and then the resulting solution further reacted for 0.5 h; then, the reaction solution was stirred at room temperature to react and then succinic anhydride (0.53 g, 5.28 mmol) was added quickly; the resulting solution reacted overnight. At the end of the reaction, the reaction solution was extracted three times with a saturated sodium chloride solution (200 mL) and ethyl acetate (100 mL), the organic phase was then concentrated; silica gel powder was then added and the obtained solution was evaporated to become powder. The operations of dry sample loading, column chromatography, and gradient elution with 5% methanol/dichloromethane-10% methanol/dichloromethane were carried out. The elution product was collected and concentrated. 2.44 g of the product was obtained with a yield of 85.9%.

31-190

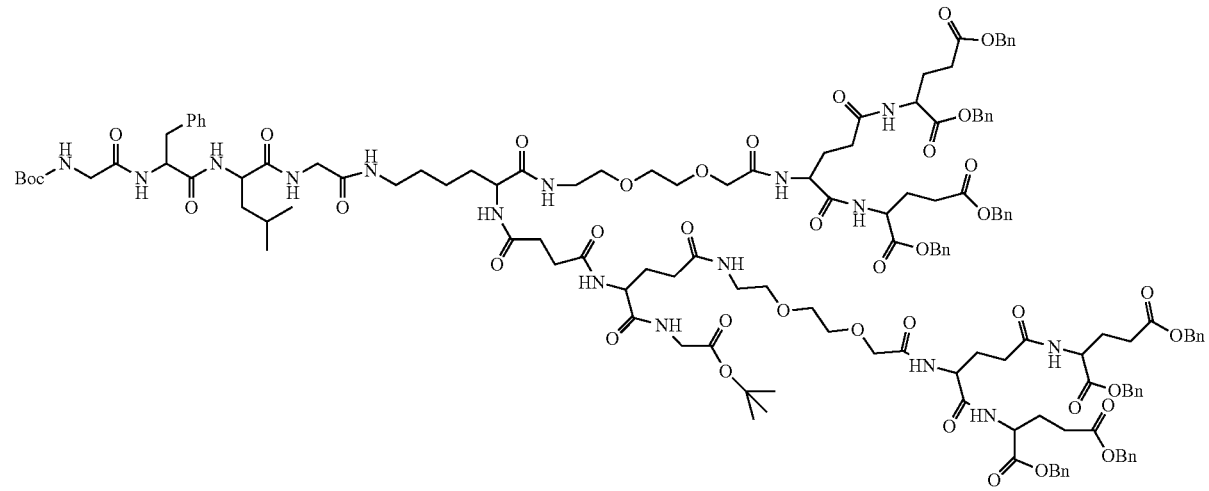

Compound 31-186 (2.44 g, 1.51 mmol), Compound 31-154 (1.83 g, 1.59 mmol), HOBT (0.31 g, 2.27 mmol) and HBTU (0.86 g, 2.27 mmol) were added in a 500 mL round-bottomed flask and then dissolved with DMF (20 mL), and the mixed solution was stirred at −5° C. for 30 min. Then DIEA (1.12 mL, 6.80 mmol) was slowly added dropwise, and then the mixed solution reacted at −5° C. for 2 h; then, the reaction solution in the reaction flask was stirred overnight at room temperature. At the end of the reaction, the reaction solution was transferred to a 1 L separatory funnel, extracted twice with a saturated sodium bicarbonate solution (150 mL) and ethyl acetate (100 mL), and then extracted once with a saturated sodium chloride solution (100 mL) and ethyl acetate (100 mL); the organic phase was then concentrated; silica gel powder was then added and the obtained solution was evaporated to become powder; the operations of dry sample loading, column chromatography, and gradient elution with 3% methanol/0.5% ammonia water/dichloromethane-4% methanol/0.5% ammonia water/dichloromethane were carried out, and then the elution product was collected, concentrated, evaporated to dryness, and dried in a vacuum oven. 2.74 g of the product was obtained with a yield of 66.0%.

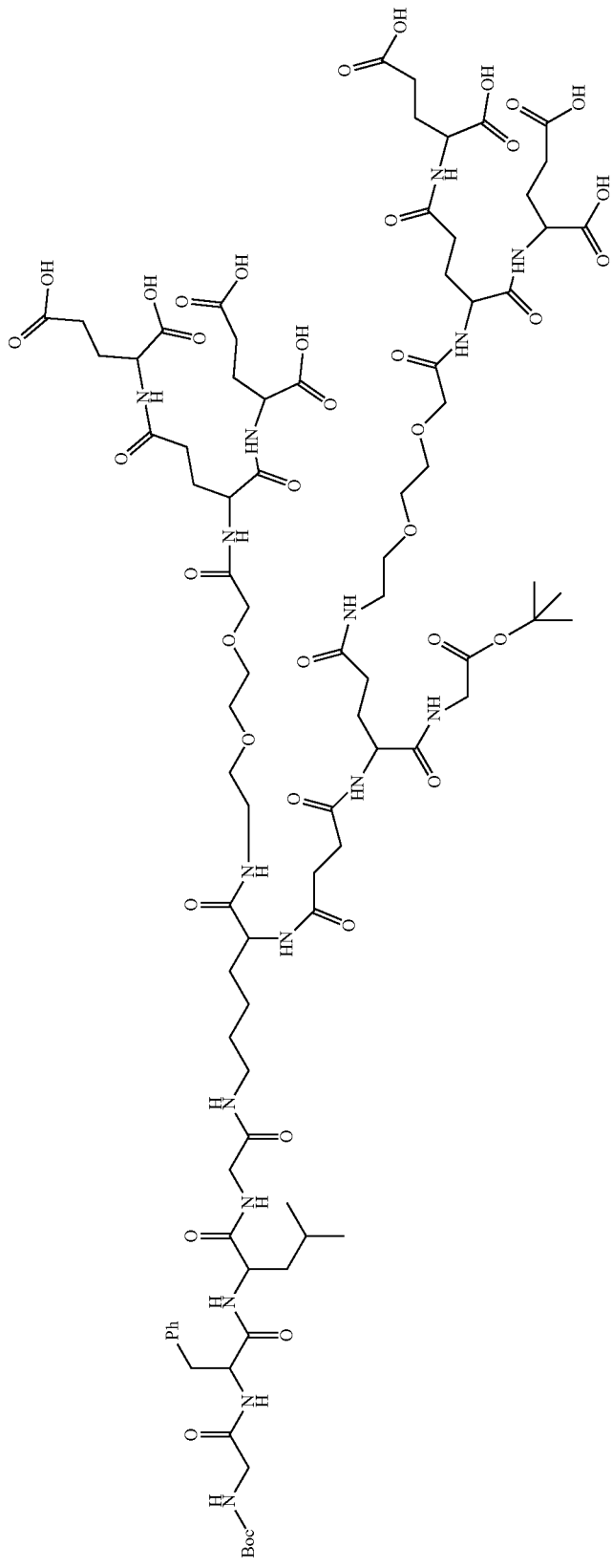

Raw material Compound 31-190 (0.74 g, 0.27 mmol) and 10% Pd/C catalyst (100 mg) were added into a hydrogenation reaction device and then dissolved with DMF (40 mL). The hydrogenation reaction device was then sealed and $H_2$ was introduced so that the pressure of the hydrogenation reaction device was read as 18 Psi. The mixed solution was stirred overnight at room temperature. After the reaction was found to be completed from the monitoring of the TLC, the reaction solution was taken out and evenly dropwise added to a sand core funnel filled with compacted diatomaceous earth and suction filtering was carried out; the diatomaceous earth was then washed with DMF (90 mL) until there was no product in the diatomaceous earth. The reaction product solution was thus obtained.

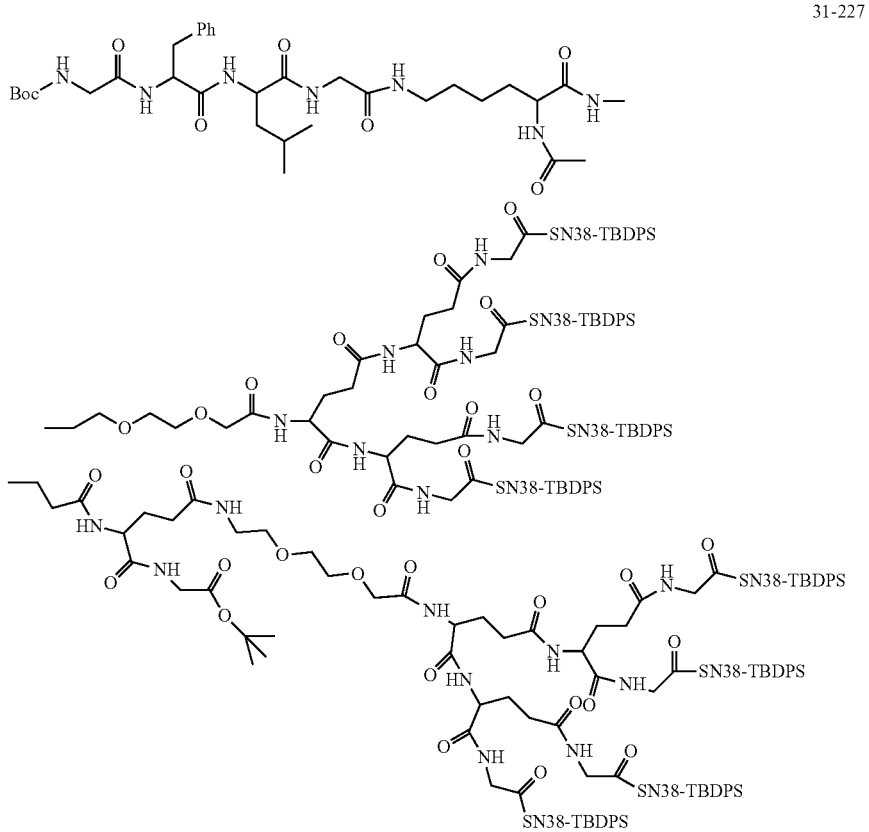

31-227

G-SN38-TBDPS (1.5 g, 2.18 mmol) was dissolved with DMF (10 mL) and the resulting solution was then stirred at −5° C. for 30 min; DIEA (1.60 mL, 9.72 mmol) was then is slowly added dropwise to the solution; the resulting solution was denoted as solution 1.

HOBT (0.44 g, 3.24 mmol) and HBTU (1.23 g, 3.24 mmol) were dissolved in the Compound 31-226 (0.27 mmol) (70 mL), and the resulting solution was then stirred at −5° C. for 30 min. Then solution 1 (10 mL) was slowly added dropwise, and then the mixed solution reacted at −5° C. for 2 h; then, the reaction solution in the reaction flask was stirred overnight at room temperature. At the end of the reaction, n-hexane (300 mL) and methyl tert-butyl ether (500 mL) were added for precipitation to separate out a solid; the solid product was then filtered out and the filter cake was dissolved; silica gel powder was then added and the obtained solution was evaporated to become powder; the operations of dry sample loading, column chromatography, and gradient elution with 6% methanol/dichloromethane-15% methanol/dichloromethane were carried out; the elution product was collected, concentrated, evaporated to dryness, and dried in a vacuum oven. 1.0 g of the product was obtained with a yield of 50.0%.

31-229

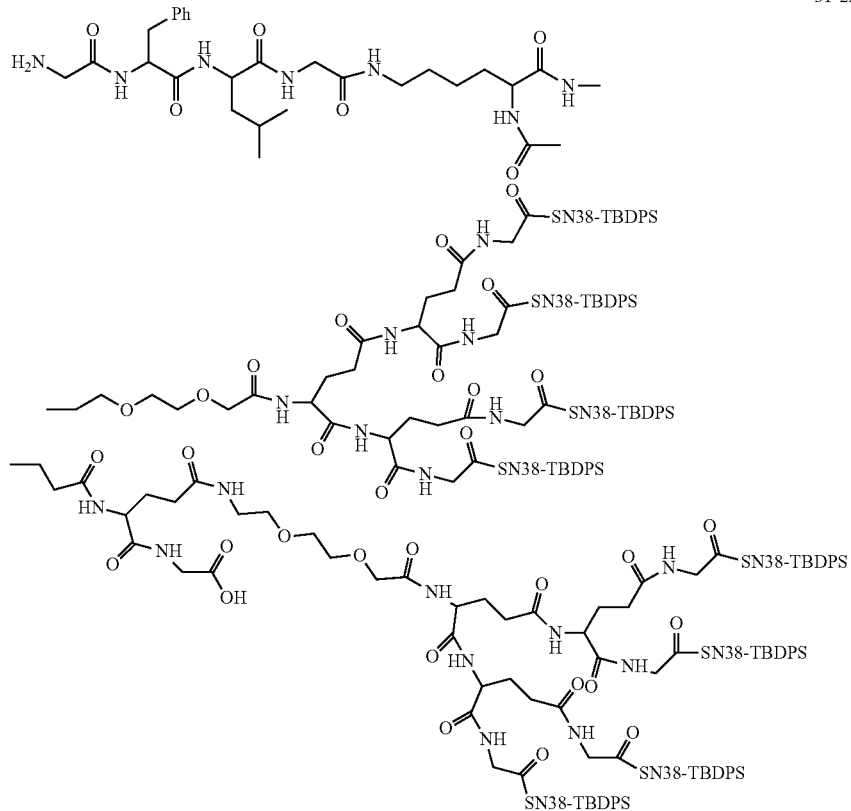

Compound 31-227 (1.0 g, 0.14 mmol) was added in a 500 mL round-bottomed flask and then dissolved with dichloromethane (10 mL), TFA (0.15 mL, 2.03 mmol) was then added and the obtained solution was stirred for 2 h at room temperature to react; at the end of the reaction, the reaction solution was evaporated to dryness with a rotary evaporator, then precipitated with methyl tert-butyl ether (100 mL) and filtered by suction to obtain a solid product; the obtained solid product was dissolved with dichloromethane (100 mL) and methanol (10 mL); silica gel powder was then added and the obtained solution was evaporated to become powder; the operations of dry sample loading, column chromatography and gradient elution with 6% methanol/dichloromethane-15% methanol/dichloromethane were carried out; the elution product was then collected, concentrated, evaporated to dryness, and dried in a vacuum oven. 0.50 g of the product was obtained with a yield of 55.0%. The product was moistened with dichloromethane (5 mL), and then dissolved with toluene (20 mL); the obtained solution was evaporated to dryness with a rotary evaporator, and then dried in an oven. 0.50 g of the product was obtained.

31-231

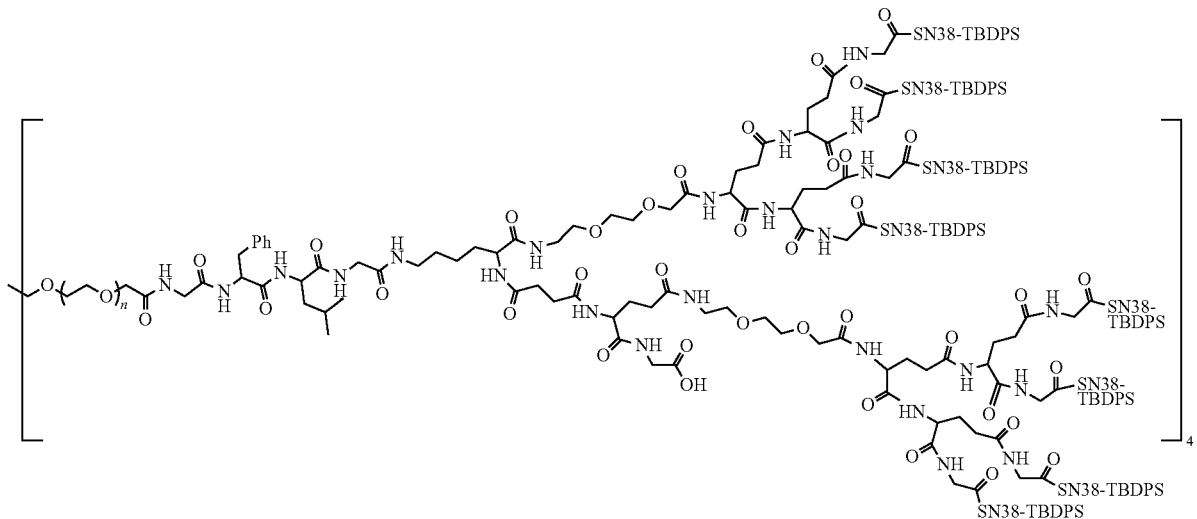

Compound 31-229 (0.5 g, 0.069 mmol) was dissolved with DMF (10 mL) and the resulting solution was denoted as solution 1.

4ARM-SCM-40K (0.72 g, 0.017 mmol, purchased from JenKem) was stirred at 0° C. for 30 min and DIEA (0.20 mL, 1.21 mmol) was slowly added dropwise to further react for 30 min. Then solution 1 (10 mL) was slowly added dropwise to the reaction solution, and then the mixed solution reacted at 0° C. for 0.5 h; then, the reaction solution was stirred for one week in the dark at room temperature. At the end of the reaction, methyl tert-butyl ether (300 mL) was then added to the reaction solution, and the resulting solution was then rested in a refrigerator for 30 min and then taken out to precipitate a solid; suction filtering was then carried out. The obtained solid product was dissolved with dichloromethane (100 mL) and methanol (10 mL); silica gel powder was then added and the obtained solution was evaporated to dryness to become powder. The operations of dry sample loading, column chromatography, and elution with 6% methanol/dichloromethane-15% methanol/dichloromethane were carried out. The elution product was then collected, concentrated, evaporated to dryness with a rotary evaporator, and dried in an oven. 0.6 g of the product was obtained. The product was moistened with dichloromethane (5 mL), and then dissolved with toluene (20 mL); the obtained solution was evaporated to dryness with a rotary evaporator, and then dried in an oven. 0.60 g of the product was obtained.

31-221

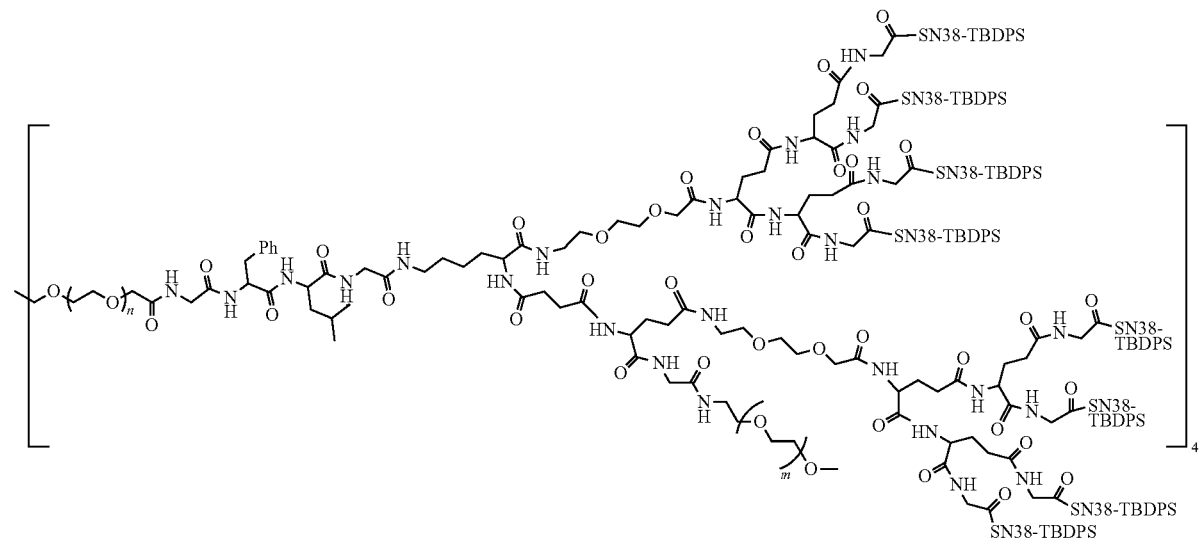

M-NH$_2$-10K (0.36 g, 0.034 mmol) (purchased from Jen-Kem) was dissolved with DMF (10 mL) and the resulting solution was then stirred at 0° C. for 30 min; DIEA (0.20 mL, 1.21 mmol) was then slowly added dropwise to the solution; the resulting solution was denoted as solution 1.

HOBT (0.01 g, 0.077 mmol), HBTU (0.03 g, 0.077 mmol) and Compound 31-231 (0.60 g, 0.0085 mmol) were dissolved with DMF (10 mL), and the resulting solution was then stirred at −5° C. for 30 min. Then solution 1 (10 mL) was slowly added dropwise, and then the mixed solution reacted at −5° C. for 2 h; then, the reaction solution in the reaction device was stirred overnight at room temperature. At the end of the reaction, methyl tert-butyl ether (90 mL) was then added to the reaction solution, and the resulting solution was then rested in a refrigerator for 30 min and then taken out to precipitate a solid; suction filtering was then carried out. The obtained solid product was dissolved with dichloromethane (100 mL) and methanol (10 mL); silica gel powder was then added and the obtained solution was evaporated to dryness to become powder. The operations of dry sample loading, column chromatography, and elution with 6% methanol/dichloromethane-20% methanol/dichloromethane were carried out. The elution product was then collected, concentrated, evaporated to dryness with a rotary evaporator, and dried in an oven. 0.23 g of the product was obtained. The product was moistened with dichloromethane (5 mL), and then dissolved with toluene (20 mL); the obtained solution was evaporated to dryness with a rotary evaporator, and then dried in an oven. 0.23 g of the product was obtained.

$^1$H-NMR (400 MHz, DMSO-d$_6$) δ 9.04 (s, 83H), 7.95 (s, 46H), 7.22-7.12 (m, 159H), 7.01-6.95 (m, 96H), 6.89 (s, 61H), 6.73-6.65 (m, 163H), 5.36-5.27 (m, 152H), 3.99-3.95 (m, 76H), 3.69-3.66 (m, 145H), 3.50 (s, 7655H), 2.89 (s, 166H), 2.75-2.66 (m, 247H), 0.88-0.80 (m, 424H).

to obtain a solid product. The solid product was precipitated with DMF (30 mL) first and then with 20 mL of isopropanol, and such precipitation operation was repeated three times; the obtained solution was then evaporated to dryness. Then, the obtained solid was dissolved with dichloromethane (20 mL) and precipitated with methyl tert-butyl ether; suction filtering was then carried out and the filter cake was collected and dried in a vacuum oven. 0.15 g of the final product 26-234 was obtained with a yield of 65%.

$^1$H-NMR (400 MHz, DMSO-d$_6$) δ 9.00 (s, 83H), 7.93 (s, 46H), 7.03-6.92 (m, 96H), 6.85 (s, 63H), 5.36-5.27 (m, 154H), 3.97-3.94 (m, 76H), 3.67-3.60 (m, 145H), 3.50 (s, 8103H), 2.87 (s, 167H), 2.73-2.64 (m, 240H), 0.89-0.78 (m, 136H).

Example 18: Synthesis of Compound 27-113

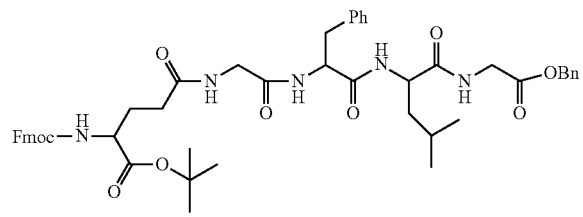

27-33

Fmoc-Glu-Otbu (1.85 g, 4.3517 mmol), HBTU (2.36 g, 6.2167 mmol), and HOBT (0.84 g, 6.2167 mmol) were added into a flask with Compound 27-32 (2 g, 4.1444 mmol), and then dissolved with an appropriate amount of DMF, the resulting solution was then rested at −5° C., and

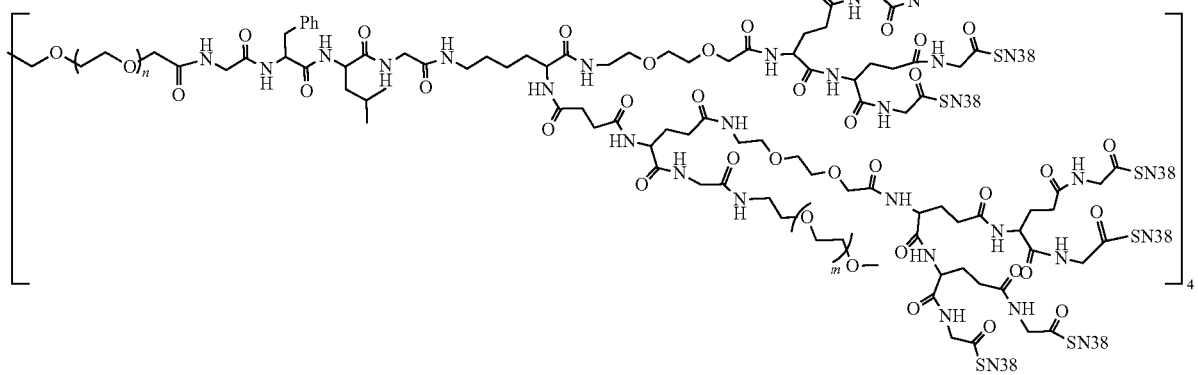

26-234

THF (20 mL), concentrated hydrochloric acid (20 mL, 0.05 mol/L), and TBAF (34 mg, 0.1309 mmol) were added into a 250 mL flask with Compound 31-221 (0.23 g), and the obtained solution reacted overnight at room temperature. At the end of the reaction, the reaction solution was first evaporated to dryness, and absolute ethanol was then added to remove water, and such operation was repeated three times; then, the obtained solution was evaporated to dryness DIEA (3.08 mL, 18.6501 mmol) was slowly added dropwise; the mixed solution reacted for 30 min and then taken out and stirred overnight at room temperature. At the end of the reaction, excessive saturated sodium bicarbonate solution was added to the reaction solution until the solution became alkaline; ethyl acetate (300 mL) was then added to the obtained solution; the resulting solution was then extracted, the extraction solution was then rested to be layered, and the organic phase was collected; the aqueous phase was washed with ethyl acetate (300 mL) three times; the obtained organic phases were combined, evaporated to dryness and concentrated to about 100 mL; the concentrated solution was then taken out and washed with a saturated sodium chloride solution (100 mL×3); the organic phase was collected, evaporated to dryness, and then dissolved with the methanol/dichloromethane (1:4) solution (150 mL); silica gel powder (60 mL) was then added and the obtained solution was evaporated to dryness to obtain a powdery solid; the operations of dry sample loading, column chromatography, and elution with a mixed solution (1% ammonia water:1-2% methanol/dichloromethane) were is carried out, and the elution product was then collected, concentrated, and evaporated to dryness to obtain a solid product, and the solid product was then dried in a vacuum oven. 2.6051 g of Compound 27-33 was obtained with a yield of 70.79%.

27-36

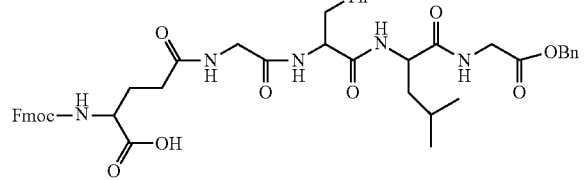

Dichloromethane was added into a flask with Compound 27-33 (2.6 g, 2.9212 mmol), the resulting solution was oscillated by ultrasonic until Compound 27-33 was completely dissolved, TFA (3.25 mL, 43.8187 mmol) was then added, and the mixed solution was stirred overnight at room temperature to react. At the end of the reaction, the dichloromethane in the reaction solution was evaporated out, excessive saturated sodium bicarbonate solution was added to the reaction solution until the solution became alkaline; ethyl acetate (200 mL) was then added to the obtained solution; the resulting solution was then extracted, the extraction solution was then rested to be layered, and the organic phase was collected; the aqueous phase was washed again with ethyl acetate (200 mL×3); the obtained organic phases were combined and evaporated to dryness to obtain a solid product, and the solid product was then dried in a vacuum oven. 6.8784 g of Compound 27-36 was obtained with a yield of 100%.

27-38

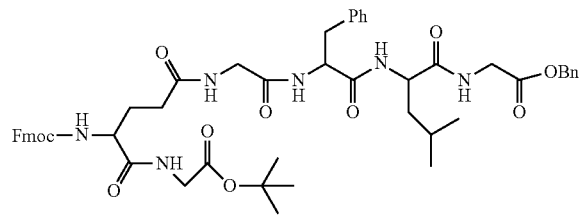

H-Glu-OtBu (0.54 g, 3.2133 mmol, purchased from Innochem), HBTU (1.66 g, 4.3818 mmol), and HOBT (0.59 g, 4.3818 mmol) were added into a flask with Compound 27-36 (2.44 g, 2.9212 mmol), and then dissolved with an appropriate amount of DMF, the resulting solution was then rested at −5° C., and DIEA (2.17 mL, 13.1454 mmol) was slowly added dropwise; the mixed solution reacted for 30 min and then taken out and stirred overnight at room temperature. At the end of the reaction, pure water (100 mL) and ethyl acetate (80 mL) were added to the reaction solution and extraction was carried out; the extraction solution was rested to be layered and then the organic phase was collected; the aqueous phase was washed with ethyl acetate (80 mL×3), the obtained organic phases were combined, evaporated to dryness and concentrated to about 100 mL; the concentrated solution was then taken out and washed with a saturated sodium chloride solution (100 mL×3); the organic phase was collected, evaporated to dryness, concentrated, and dried in a vacuum oven. 7.92 g of Product is 27-38 was obtained with a yield of 100%.

27-39

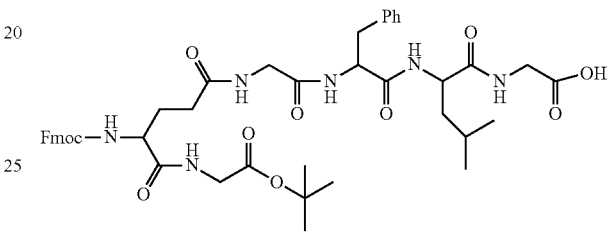

Compound 27-38 (2.76 g, 2.9212 mmol) and 10% Pd/C (0.1 g) were added into a hydrogenation reactor and then dissolved with DMF (20 mL); the air in the hydrogenation reactor was pumped out, and $H_2$ gas was introduced until the pressure of $H_2$ was 14 psi. The mixed solution was then stirred overnight at room temperature to react. At the end of the reaction, the reaction solution was filtered with diatomaceous earth, the filter cake was washed three times with DMF (20 mL×3), and the filtrate was placed into a 500 mL round-bottomed flask. Product 27-39 was thus obtained and used as the raw material for the next step.

27-40

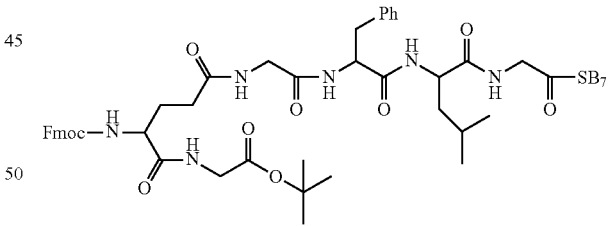

$SB_7$ (1.51 g, 2.9212 mmol, purchased from Innochem), HBTU (1.66 g, 4.3818 mmol), and HOBT (0.59 g, 4.3818 mmol) were weighed and then added into a flask with Compound 27-39 (2.5 g, 2.9212 mmol), and then dissolved with an appropriate amount of DMF, the resulting solution was then rested at −5° C., and DIEA (2.17 mL, 13.1454 mmol) was slowly added dropwise; the mixed solution reacted for 30 min and then taken out and stirred overnight at room temperature. At the end of the reaction, pure water (100 mL) and ethyl acetate (80 mL) were added to the reaction solution and extraction was carried out; the extraction solution was rested to be layered and then the organic phase was collected; the aqueous phase was washed with ethyl acetate (80 mL×3), the obtained organic phases were combined, evaporated to dryness and concentrated to about 100 mL; the concentrated solution was then taken out and washed with a saturated sodium chloride solution (100 mL×3); the organic phase was collected, evaporated to dryness, concentrated, and dried in a vacuum oven. 9 g of Product 27-40 was obtained with a yield of 100%.

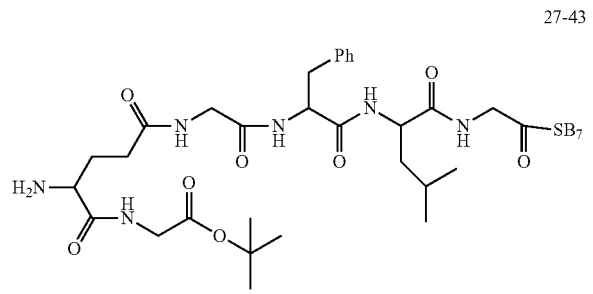

27-43

DMF was added into a flask with Compound 27-40 (3.96 g, 2.9212 mmol), the resulting solution was oscillated by ultrasonic until Compound 27-40 was completely dissolved, morpholine (87.12 mL, 29.212 mmol) was then added, and the mixed solution was stirred at room temperature for 2 h to react. At the end of the reaction, pure water (100 mL) and ethyl acetate (80 mL) were added to the reaction solution; the resulting solution was then extracted, the extraction solution was then rested to be layered and the organic phase was collected; the aqueous phase was washed with ethyl acetate (80 mL×3); the obtained organic phases were combined, evaporated to dryness and concentrated to about 100 mL; the concentrated solution was then taken out and then washed with a saturated sodium chloride solution (100 mL×3); the organic phase was collected, evaporated to dryness, and then dissolved with the methanol/dichloromethane (1:4) solution (100 mL); silica gel powder (50 mL) was then added and the obtained solution was evaporated to dryness to obtain a powdery solid; the operations of dry sample loading, column chromatography, and elution with a mixed solution (1% ammonia water:6% methanol/dichloromethane) were carried out, and the elution product was then collected, concentrated, and evaporated to dryness to obtain a solid product, and the solid product was then dried in a vacuum oven. 1.2 g of Compound 27-43 was obtained with a yield of 36.36%.

An appropriate amount of DMF was added in a flask with Compound 27-43 (1.2 g, 1.0584 mmol) to dissolve the Compound 27-43, and the resulting solution was rested at −5° C.; DIEA (33.07 mL, 200.065 mmol) was then slowly added dropwise and the resulting solution reacted for 30 min; then, the reaction solution was taken out, succinic anhydride (0.32 g, 3.1753 mmol) was quickly added to the reaction solution, and the resulting solution was stirred overnight at room temperature to react. At the end of the reaction, pure water (100 mL) and ethyl acetate (80 mL) were added to the reaction solution; the resulting solution was then extracted, the extraction solution was then rested to be layered and the organic phase was collected; the aqueous phase was then washed with ethyl acetate (80 mL×3); the obtained organic phases were combined, evaporated to dryness and concentrated to about 100 mL; the concentrated solution was then taken out and then washed with a saturated sodium chloride solution (100 mL×3); the organic phase was collected, evaporated to dryness, and then dissolved with the methanol/dichloromethane (1:4) solution (100 mL); silica gel powder (50 mL) was then added and the obtained solution was evaporated to dryness to obtain a powdery solid; the operations of dry sample loading, column chromatography, and elution with a mixed solution (1% ammonia water:6-8% methanol/dichloromethane) were carried out, and the elution product was then collected, concentrated, and then dried in a vacuum oven. 1.2731 g of Compound 27-45 was obtained with a yield of 97.48%.

$^1$H-NMR (400 MHz, DMSO-$d_6$) δ 8.33 (m, 1H), 8.25-8.05 (m, 5H), 8.03-7.93 (m, 3H), 7.82 (s, 1H), 7.62-7.45 (m, 2H), 7.42-7.02 (m, 11H), 4.50 (m, 1H), 4.23 (m, 2H), 3.95-3.79 (m, 2H), 3.11 (m, 3H), 3.03-2.96 (m, 1H), 2.45-2.36 (m, 5H), 2.32 (s, 2H), 2.16 (m, 1H), 1.92 (m, 2H), 1.69 (m, 2H), 1.49 (d, J=7.0 Hz, 2H), 1.42-1.35 (m, 9H), 1.29-1.21 (m, 13H), 0.87 (m, 8H), 0.51 (m, 2H).

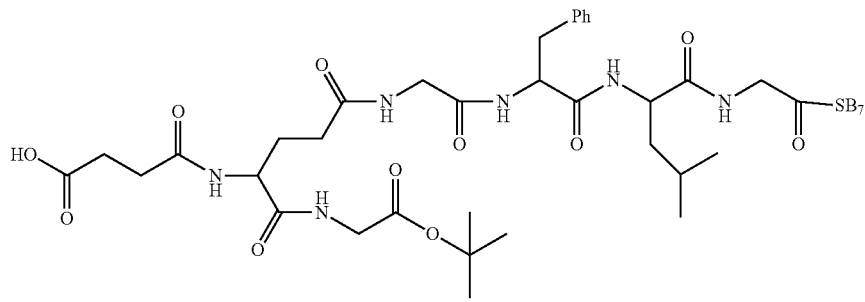

27-45

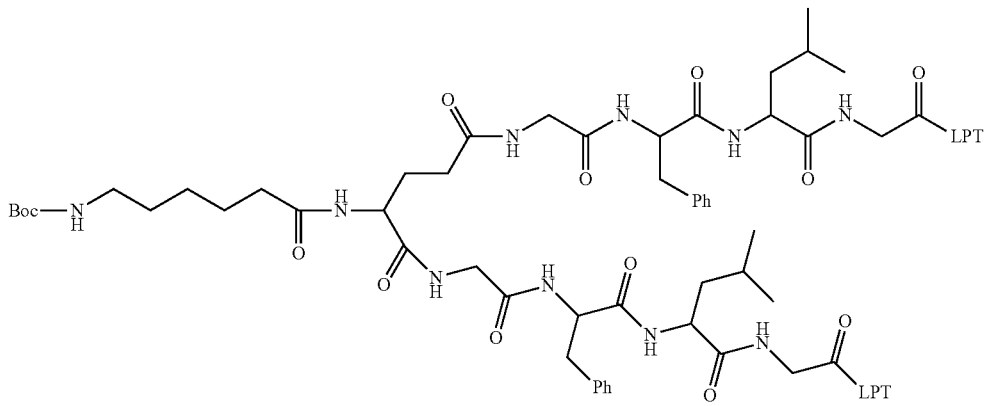

27-83

Compound 24-138 (home-made) (3.68 g, 1.8201 mmol), HBTU (1.04 g, 2.7301 mmol), and HOBT (0.37 g, 2.7301 mmol) were added to a flask with Compound 22-225 (0.46 g, 2.0021 mmol) and then dissolved with an appropriate amount of DMF; the obtained solution was stirred at −5° C., and then DIEA (1.35 mL, 8.1905 mmol) was slowly added dropwise to react for 30 min; then, the reaction solution was taken out and stirred overnight at room temperature. At the end of the reaction, 250 mL of a mixed solution of methyl tert-butyl ether and n-hexane (1:5) was added to the reaction solution and the resulting solution was then oscillated; the mixed solution was then rested and the supernatant was discarded; such operations were repeated three times; then, methyl tert-butyl ether (200 mL) was added for precipitation to obtain a solid and suction filtering was then carried out; the filter cake was collected and dried in a vacuum oven. 6.3466 g of Product 27-83 was obtained with a yield of 100%.

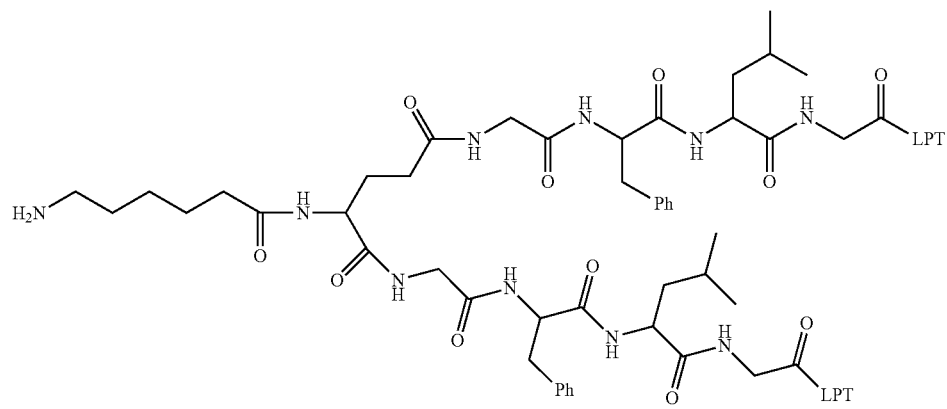

27-86

Dichloromethane was added into a flask with Compound 27-83 (4.06 g, 1.8201 mmol), the resulting solution was oscillated by ultrasonic until Compound 27-83 was completely dissolved, TFA (1.35 mL, 18.201 mmol) was then added, and the mixed solution was stirred overnight at room temperature to react. At the end of the reaction, the dichloromethane in the reaction solution was evaporated out; methyl tert-butyl ether (70 mL) was then added and the resulting solution was oscillated to separate out a solid by precipitation; suction filtering was then carried out, the filter cake was washed with methyl tert-butyl ether (40 mL×3) and then dissolved with a methanol/dichloromethane (1:4) solution (100 mL), silica gel powder (200 mL) was added to the obtained solution, and the solution was then evaporated to dryness to obtain a powdery solid; the operations of dry sample loading, column chromatography, and elution with a mixed solution (1% ammonia water:3-5% methanol/dichloromethane) were carried out; the elution product was then collected, concentrated, and dried in a vacuum oven. 2.7342 g of Product 27-86 was obtained with a yield of 70.35%.

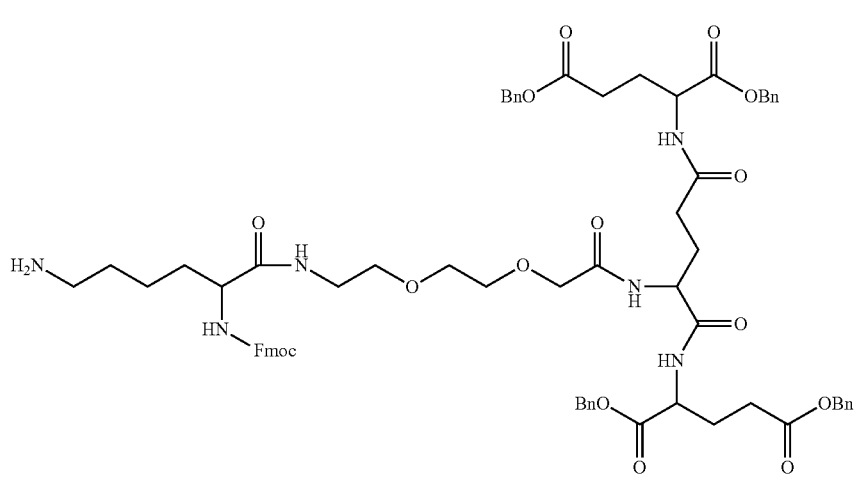

22-235

Product 30-75 (6 g, 4.4068 mmol) was added in a 250 mL flask and then dissolved with dichloromethane (5 mL), TFA (3.3 mL, 44.0681 mmol) was then added in the flask, and the mixed solution was stirred overnight at room temperature to react. At the end of the reaction, the dichloromethane was evaporated out, and 200 mL of methyl tert-butyl ether was then added for precipitation to obtain a viscous solid; the viscous solid was then dissolved with 3 mL of dichloromethane, and 100 mL of methyl tert-butyl ether was then added for precipitation; the previous two steps were repeated four to five times; the solid product was then dried. 3.66 g of Product 22-235 was obtained with a yield of 65.8%

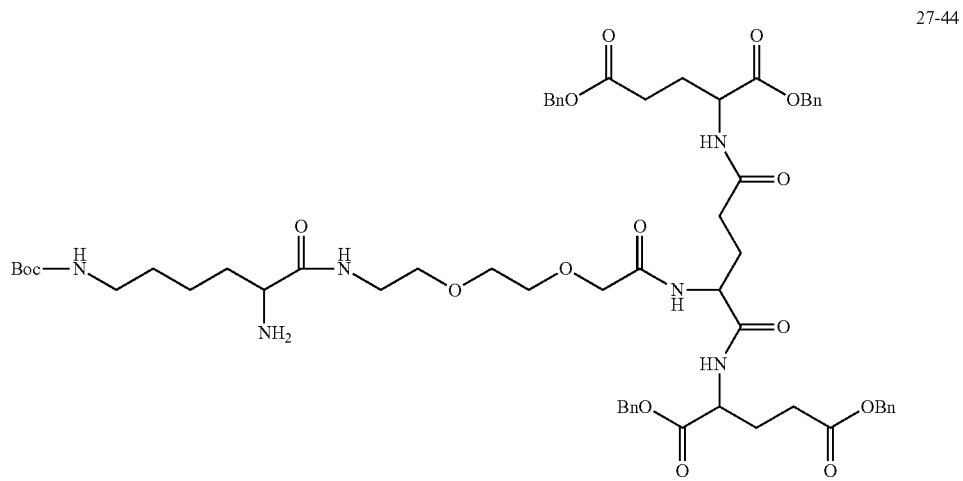 [SMILES: CC(C)(C)OC(=O)NCCCCC(N)C(=O)NCCOCCOCC(=O)NC(CCC(=O)NC(CCC(=O)OCc1ccccc1)C(=O)OCc1ccccc1)C(=O)NC(CCC(=O)OCc1ccccc1)C(=O)OCc1ccccc1]

27-44

Product 30-75 (6 g, 4.4068 mmol) was added in a 250 mL flask and then dissolved with DMF and morpholine (3.84 mL, 44.068 mmol) was then added, and the mixed solution in the reaction flask was stirred for 1 h at room temperature to react. At the end of the reaction, the reaction solution was transferred to a 1 L separatory funnel and a sodium bicarbonate solution (300 mL) and ethyl acetate (200 mL) were added; the obtained solution was then shaken and rested and the organic phase was then separated; the aqueous phase was extracted twice with ethylacetate (200 mL×2), and the obtained organic phases were combined and washed twice with saturated sodium chloride solution (200 mL×2); the obtained solution was then concentrated and evaporated to dryness. 6.05 g of Product 27-44 was obtained with a yield of 100%.

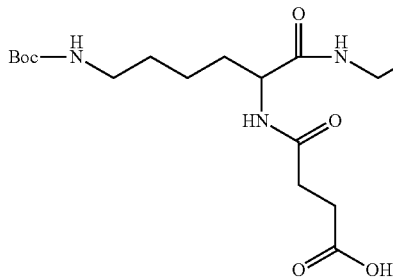
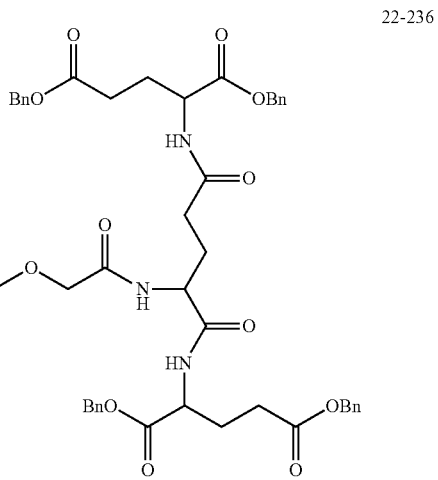

22-236

Compound 27-44 (5 g, 4.4068 mmol) was added into a 250 mL flask and dissolved with 40 mL of DMF, the resulting solution was stirred for 30 min at −5° C., and then DIEA (3.64 mL, 22.034 mmol) was slowly added dropwise; when the temperature of the reaction solution reached room temperature, succinic anhydride (1.3 g, 13.2204 mmol) was then added, and the mixed solution was then stirred overnight at room temperature. At the end of the reaction, the reaction solution was transferred to a 1 L separatory funnel, and a saturated sodium bicarbonate solution (300 mL) and ethyl acetate (200 mL) were added to the reaction solution; the resulting solution was shaken and then rested, the organic phase was separated, and the aqueous phase was extracted twice with ethyl acetate (200 mL×2); the obtained organic phases were combined, washed twice with saturated sodium chloride solution (200 mL×2), evaporated to dryness, and then dissolved with a methanol/dichloromethane (1:5) solution; silica gel powder was added to the obtained solution, and the solution was then evaporated to dryness; the operations of dry sample loading, column chromatography, and gradient elution with a mixed solution (2%-10% methanol/dichloromethane) were carried out; the elution product was then collected, concentrated, and dried. 5.4 g of Product 22-236 was obtained with a yield of 68.5%.

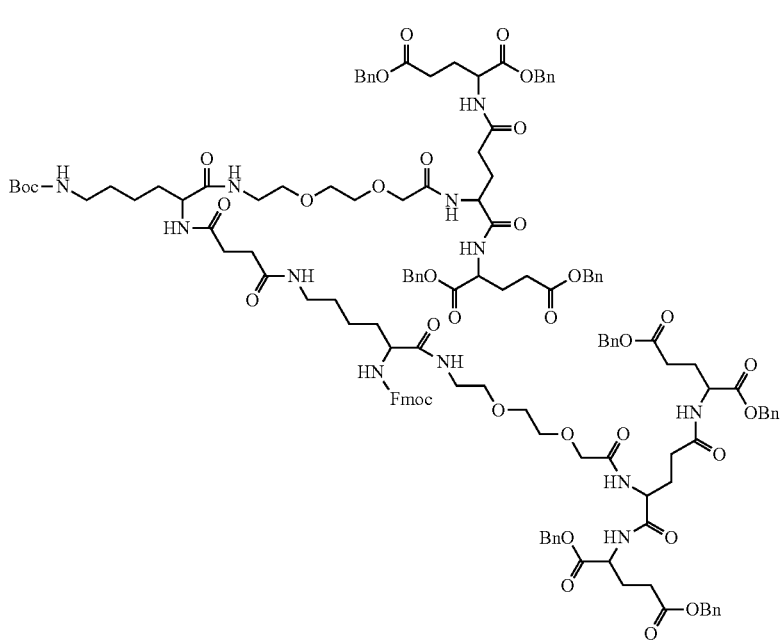

22-238

Compound 22-236 (3.77 g, 3.0466 mmol), Compound 22-235 (3.66 g, 2.9015 mmol), HBTU (1.7 g, 4.3523 mmol), and HOBT (0.6 g, 4.3523 mmol) were added in a 250 mL flask and then dissolved with 30 mL of DMF; the obtained solution was stirred at −5° C. for 30 min to react, and DIEA (2.6 mL, 15.9583 mmol) was then slowly added dropwise; the obtained solution was stirred at −5° C. for 1 h to further react, and then the reaction solution in the reaction flask was stirred overnight at room temperature to react. At the end of the reaction, the reaction solution was transferred to a 1 L separatory funnel and then deionized water (200 mL) and ethyl acetate (200 mL) was added to the reaction solution; the resulting solution was shaken and then rested, the organic phase was separated, and the aqueous phase was extracted twice with ethyl acetate (200 mL×2); the obtained organic phases were combined, washed twice with a saturated sodium chloride solution (200 mL×2), evaporated to dryness, and then dissolved with a methanol/dichloromethane (1:5) solution; silica gel powder was added to the obtained solution, and the solution was then evaporated to dryness; the operations of dry sample loading, column chromatography, and elution with a mixed solution (1%-6% methanol:99%-94% dichloromethane) were carried out; the elution product was then collected, concentrated, and dried. 6.86 g of Product 22-238 was obtained with a yield of 95.3%.

$^1$H-NMR (400 MHz, DMSO-d$_6$) δ 8.54 (s, 2H), 8.31 (m, 2H), 7.95 (s, 3H), 7.87 (s, 2H), 7.81 (s, 1H), 7.69 (s, 5H), 7.45 (s, 4H), 7.38-7.25 (m, 40H), 6.74 (d, J=5.4 Hz, 1H), 5.08 (m, 16H), 4.29 (m, 13H), 3.89 (s, 6H), 3.51 (m, 9H), 3.21 (s, 4H), 2.99 (s, 3H), 2.86 (s, 3H), 2.43 (s, 7H), 2.32 (s, 5H), 2.17 (s, 4H), 1.87 (m, 14H), 1.35 (s, 9H), 1.23 (s, 6H), 0.84 (s, is 1H).

MALDI-TOF MS: [M+Na$^+$] 2504.75

22-244

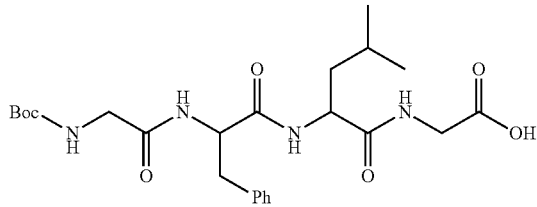

BOC-GFLG-OBn (2 g, 3.3157 mmol, home-made) and 0.1 g of 10% Pd/C were added into a hydrogenation reactor and then dissolved with DMF (30 mL); H$_2$ was then introduced in the reactor until the H$_2$ pressure reached 16 psi. Then, the mixed solution was stirred overnight at room temperature. At the end of the reaction, the reaction solution was filtered with a sand core funnel filled with diatomaceous earth, and the filter cake was washed three times with DMF (20 mL×3), and the obtained DMF solutions were combined as a raw material of the next reaction step.

22-245

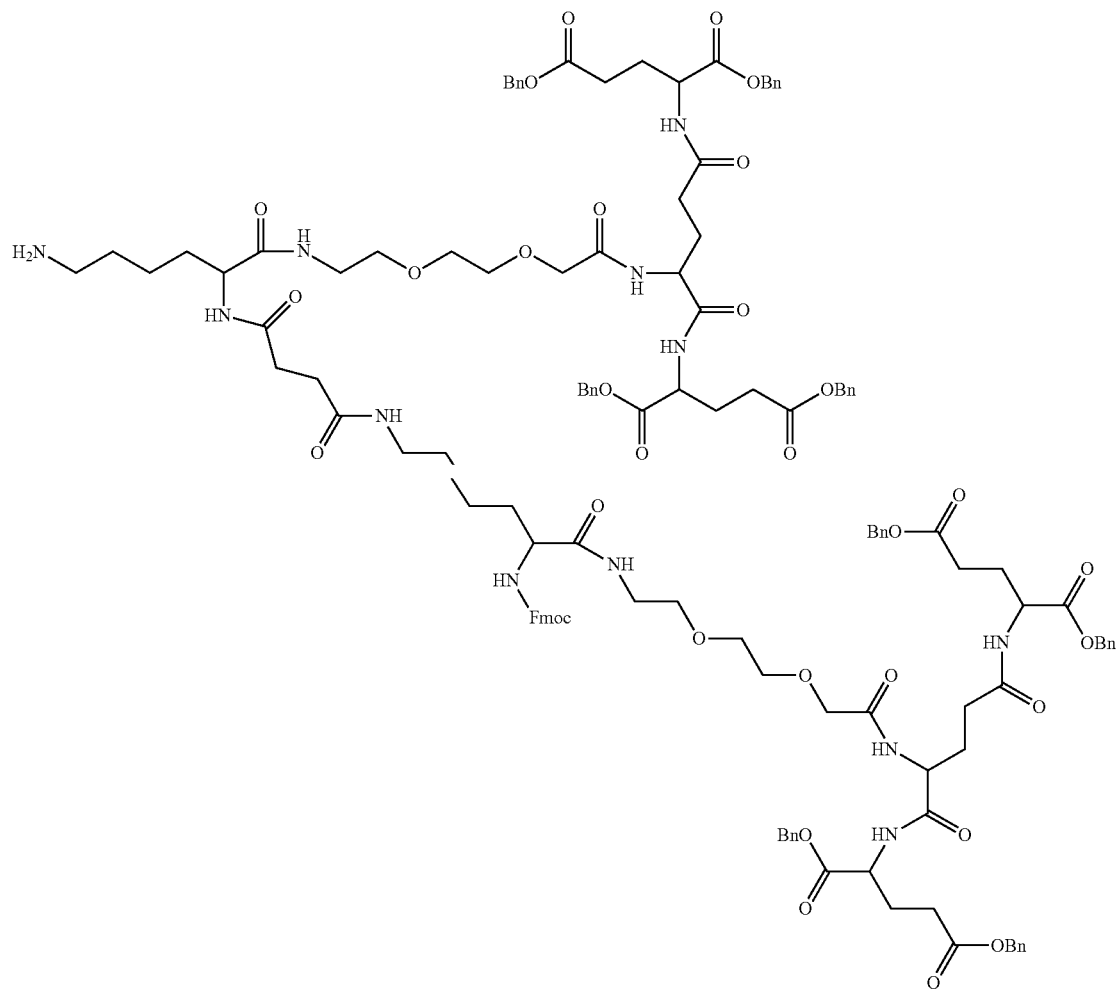

Compound 22-238 (6.86 g, 2.7631 mmol) was added in a 250 mL flask and then dissolved with dichloromethane (5 mL), TFA (2 mL, 27.6305 mmol) were then added to the obtained solution, and the mixed solution in the reaction flask was stirred overnight at room temperature to react. At the end of the reactor, the dichloromethane in the reaction flask was pumped out and then methyl tert-butyl ether (100 mL) was added to the reaction solution to obtain a viscous liquid by precipitation; dichloromethane (3 mL) was then added to the viscous liquid, and methyl tert-butyl ether was then added to precipitate the mixed solution; the previous steps were repeated twice, and the obtained product was then dissolved with a methanol/dichloromethane (1:5) solution; the obtained solution was then concentrated and evaporated to dryness. 7.2 g of Product 22-245 was obtained with a yield of 100%.

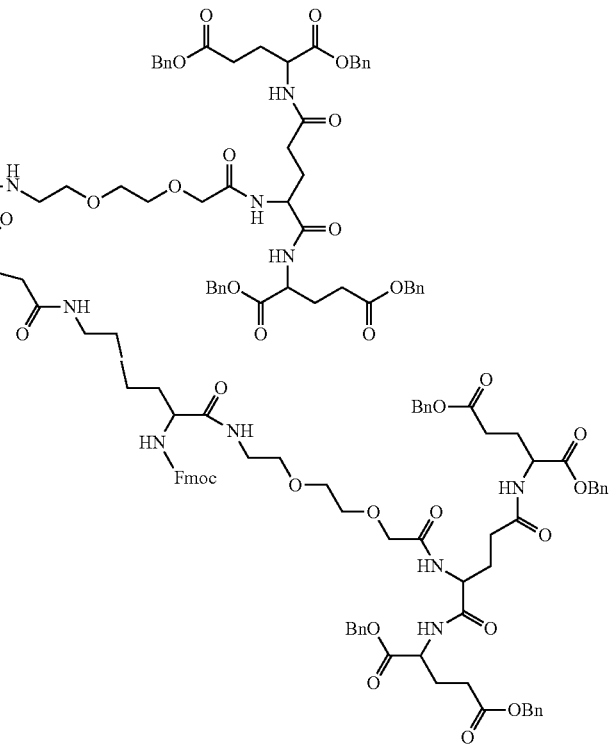

22-246

Compound 22-245 (6.58 g, 2.7631 mmol), Compound 22-244 (1.69 g, 3.4324 mmol), HBTU (1.6 g, 4.1447 mmol), and HOBT (0.6 g, 4.1447 mmol) were added into a 250 mL flask and stirred for 30 min at −5° C., and DIEA (3 mL, 12.434 mmol) was then slowly added dropwise; the obtained solution was further stirred at −5° C. for 1 h, and the reaction solution in the reaction flask was then stirred overnight at room temperature. At the end of the reaction, the reaction solution was transferred to a 1 L separatory funnel and then deionized water (200 mL) and ethyl acetate (200 mL) was added to the reaction solution; the resulting solution was shaken and then rested, the organic phase was separated, and the aqueous phase was extracted twice with ethyl acetate (200 mL×2); the obtained organic phases were combined, washed twice with a saturated sodium chloride solution (200 mL×2), evaporated to dryness, and then dissolved with a methanol/dichloromethane (1:5) solution; silica gel powder was added to the obtained solution, and the solution was then evaporated to dryness; the operations of dry sample loading, column chromatography, and gradient elution with a mixed solution (2%-5% methanol:98%-95% dichloromethane) were carried out; the elution product was then collected, concentrated, and dried. 6.14 g of Product 22-246 was obtained with a yield of 77.8%.

$^1$H-NMR (400 MHz, DMSO-$d_6$) δ 8.54 (s, 2H), 8.30 (s, 2H), 8.17 (s, 1H), 7.90 (m, 9H), 7.70 (s, 5H), 7.33 (s, 43H), 7.21 (s, 5H), 6.93 (s, 1H), 5.08 (m, 15H), 4.28 (m, 12H), 3.89 (s, 5H), 3.53 (m, 13H), 3.19 (s, 5H), 2.99 (s, 5H), 2.43 (s, 6H), 2.31 (s, 5H), 2.17 (s, 4H), 1.94 (m, 14H), 1.47 (s, 10H), 1.35 (s, 10H), 1.23 (s, 9H), 0.85 (m, 6H).

MALDI-TOF MS: [M+Na$^+$] 2878.87

22-274

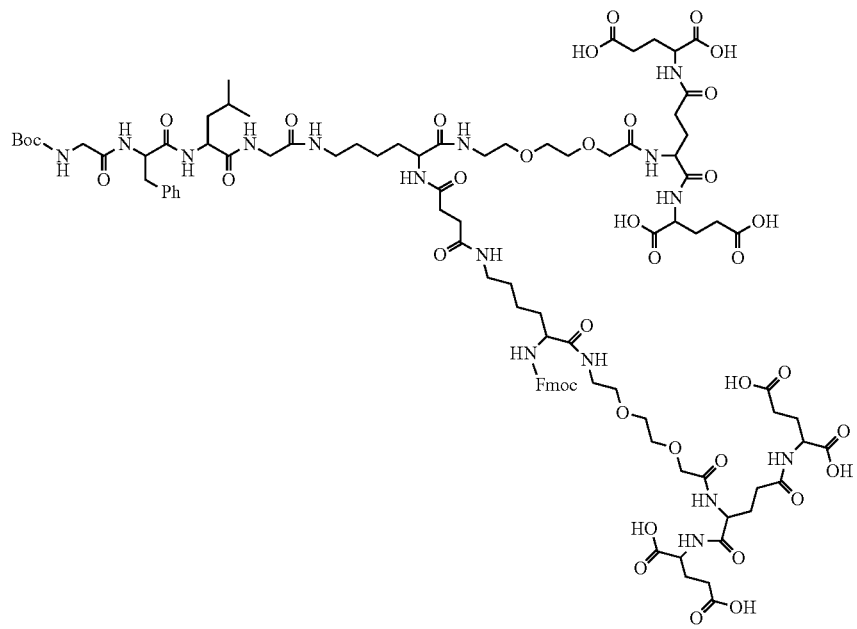

Compound 22-246 (1.27 g, 0.4461 mmol) and 10% Pd/C (0.0200 g) were added in a reactor and then dissolved with DMF (30 mL); H$_2$ was introduced in the reactor to a pressure of 16 Psi; and the mixed solution was then stirred overnight at room temperature to react. At the end of the reaction, the reaction solution was filtered with a funnel filled with diatomaceous earth, and the filter cake was washed three times with DMF (20 mL×3), and the obtained DMF solutions were combined as a raw material of the next reaction step.

27-90

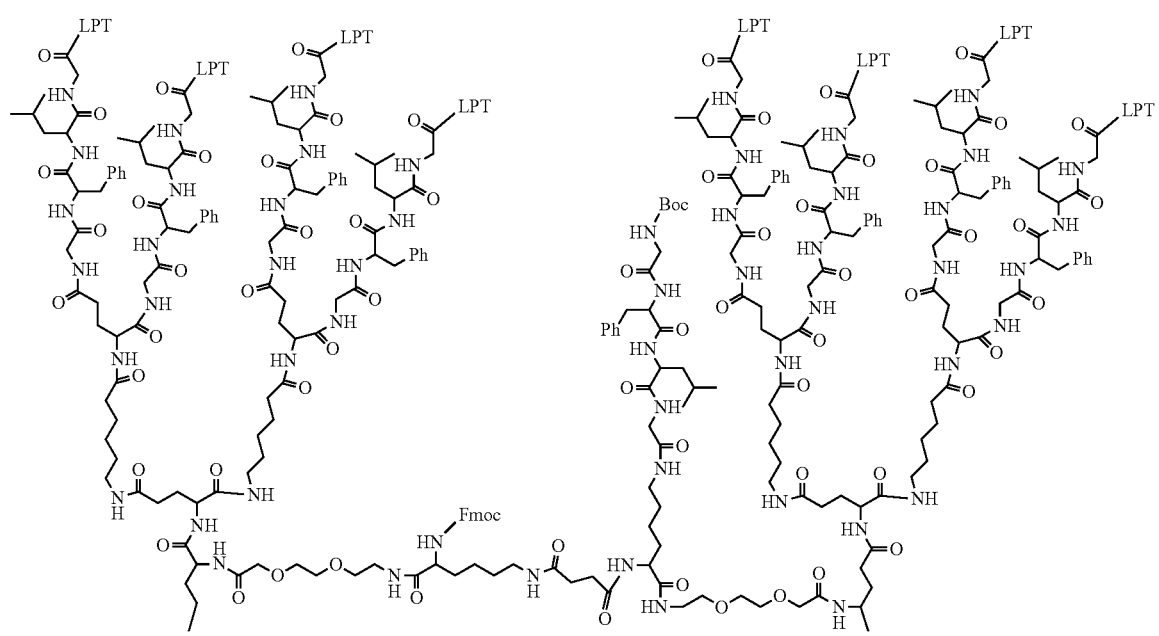

503

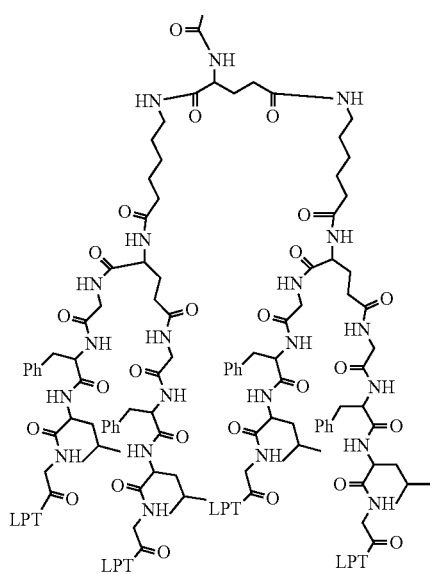

504

-continued

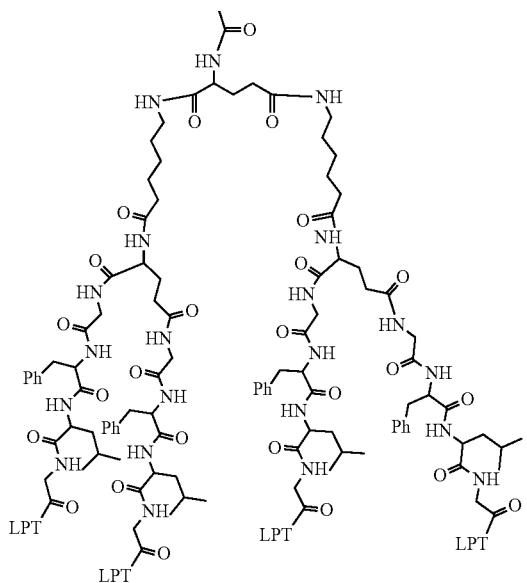

Compound 27-86 (0.2879 g, 0.1348 mmol), HBTU (0.7668 g, 2.022 mmol), and HOBT (0.27 g, 2.022 mmol) were added to a flask with Compound 22-274 (0.2879 g, 0.1348 mmol, home-made) and then dissolved with an appropriate amount of DMF; the obtained solution was stirred at −5° C., and then DIEA (1.0 mL, 6.066 mmol) was slowly added dropwise to react for 30 min; then, the reaction solution was taken out and stirred overnight at room temperature to react. At the end of the reaction, 250 mL of a mixed solution of methyl tert-butyl ether and n-hexane (1:5) was added to the reaction solution and the resulting solution was then oscillated; the mixed solution was then rested and the supernatant was discarded; such operations were repeated three times; then, methyl tert-butyl ether (200 mL) was added for precipitation to obtain a solid and suction filtering was then carried out; the filter cake was collected and dried in a vacuum oven. 4.7726 g of Product 27-90 was obtained with a yield of 100%.

27-92

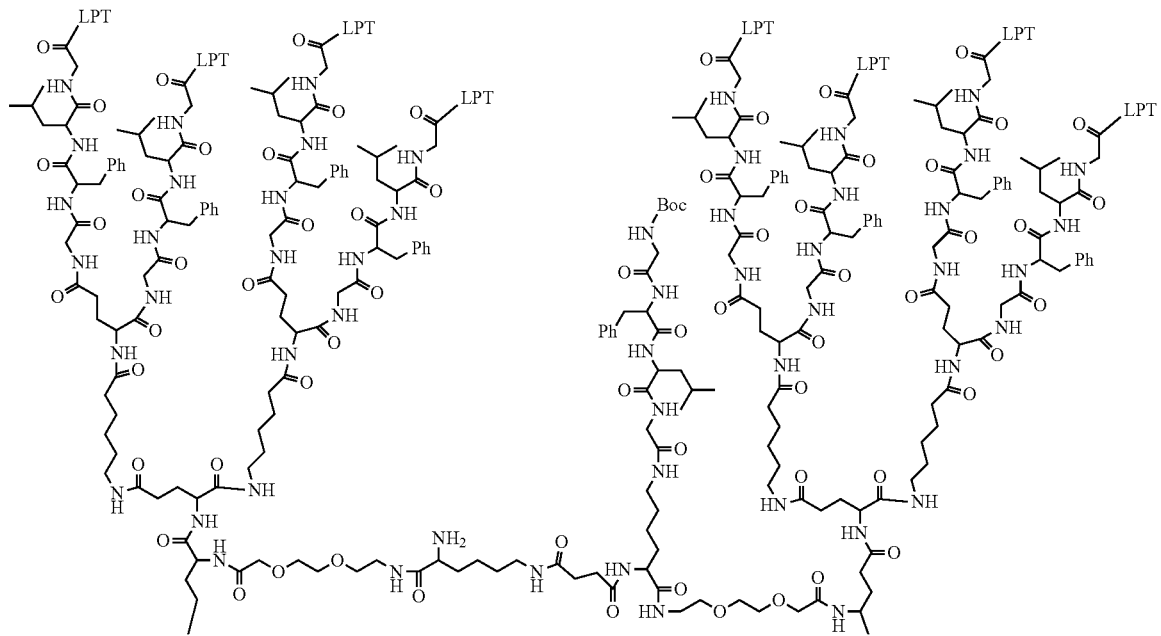

505

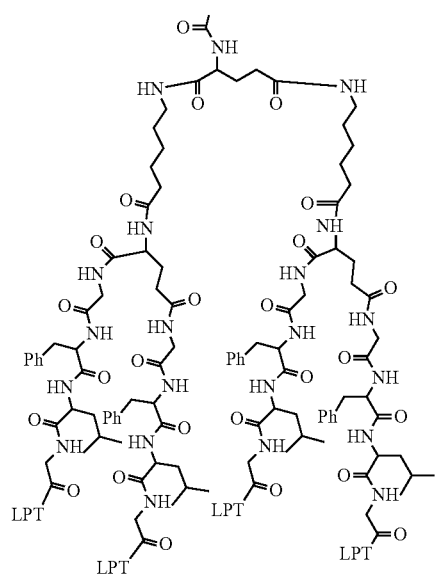

506

-continued

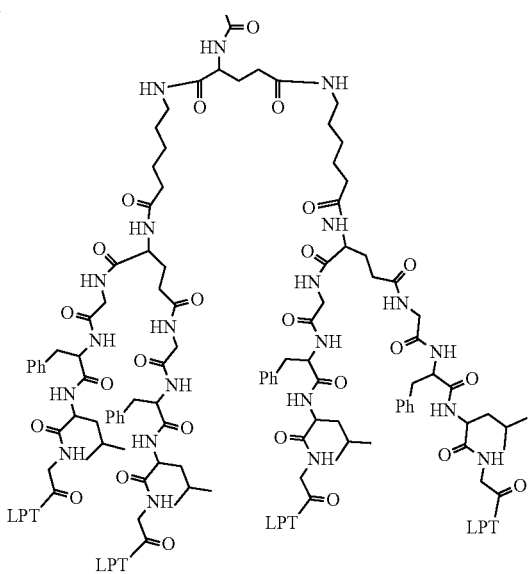

DMF was added into a flask with Compound 27-90 (2.57 g, 0.1348 mmol), the resulting solution was oscillated by ultrasonic until Compound 27-90 was completely dissolved, morpholine (0.117 mL, 1.348 mmol) was then added, and the mixed solution was stirred at room temperature for 2 h to react. At the end of the reaction, 250 mL of a mixed solution of methyl tert-butyl ether and n-hexane (1:5) was added to the reaction solution; the mixed soliton was oscillated and then rested and the supernatant was discarded; and such operations were repeated three times. Next, 200 mL of methyl tert-butyl ether was added to the mixed solution to obtain a solid by precipitation and suction filtering was then carried out. The filter cake was dissolved with a methanol/dichloromethane (1:4) solution (100 mL), silica gel powder (100 mL) was added to the obtained solution, and the solution was then evaporated to dryness to obtain a powdery solid; the operations of dry sample loading, column chromatography, and elution with a mixed solution (1% ammonia water:7-8% methanol/dichloromethane) were carried out; the elution product was then collected, is concentrated, and dried in a vacuum oven. 1.5175 g of Product 27-92 was obtained with a yield of 59.74%.

27-97

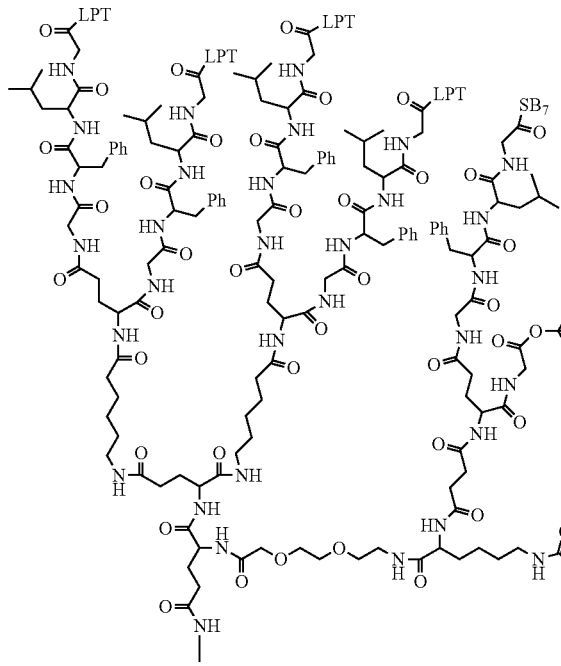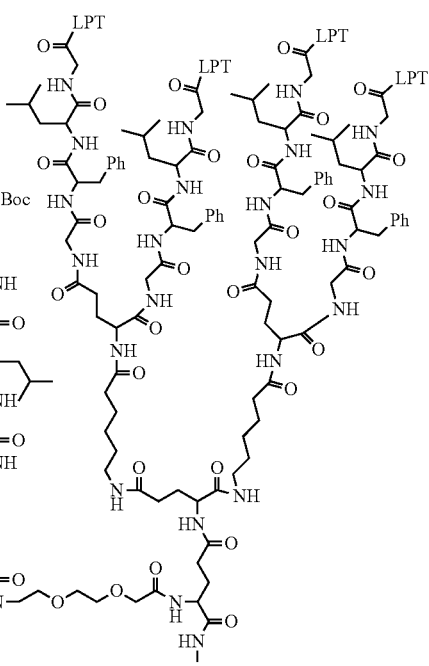

507

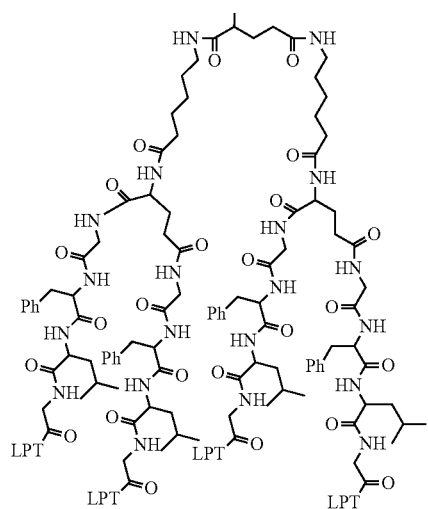

508

-continued

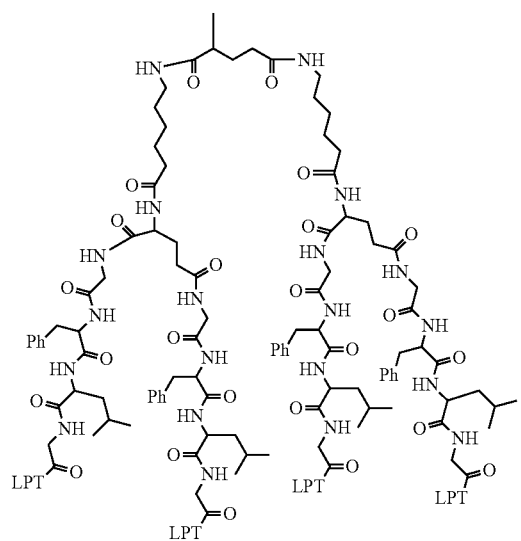

Compound 27-45 (0.1490 g, 0.1207 mmol), HBTU (0.061 g, 0.1609 mmol), and HOBT (0.0217 g, 0.1609 mmol) were added to a flask with Compound 27-92 (1.518 g, 0.0805 mmol) and then dissolved with an appropriate amount of DMF; the obtained solution was stirred at −5° C., and then DIEA (0.0798 m, 0.4829 mmol) was slowly added dropwise to react for 30 min; then, the reaction solution was taken out and stirred overnight at room temperature. At the end of the reaction, 250 mL of a mixed solution of methyl tert-butyl ether and n-hexane (1:5) was added to the reaction solution; the mixed solution was oscillated and then rested and the supernatant was discarded; and such operations were repeated three times. Next, 200 mL of methyl tert-butyl ether was added to the mixed solution to obtain a solid by precipitation and suction filtering was then carried out. The filter cake was dissolved with a methanol/dichloromethane (1:4) solution (100 mL), silica gel powder (100 mL) was added to the obtained solution, and the solution was then evaporated to dryness to obtain a powdery is solid; the operations of dry sample loading, column chromatography, and elution with a mixed solution (1% ammonia water:5-6% methanol/dichloromethane) were carried out; the elution product was then collected, concentrated, and dried in a vacuum oven. 0.9888 g of Product 27-97 was obtained with a yield of 61.41%.

27-100

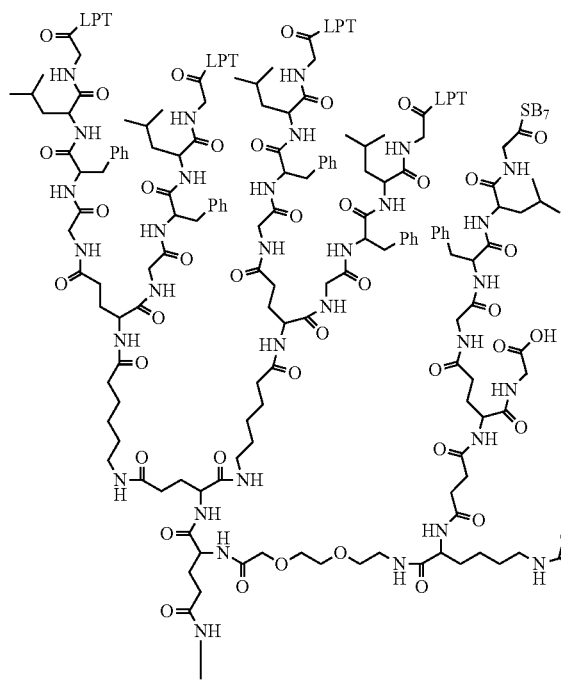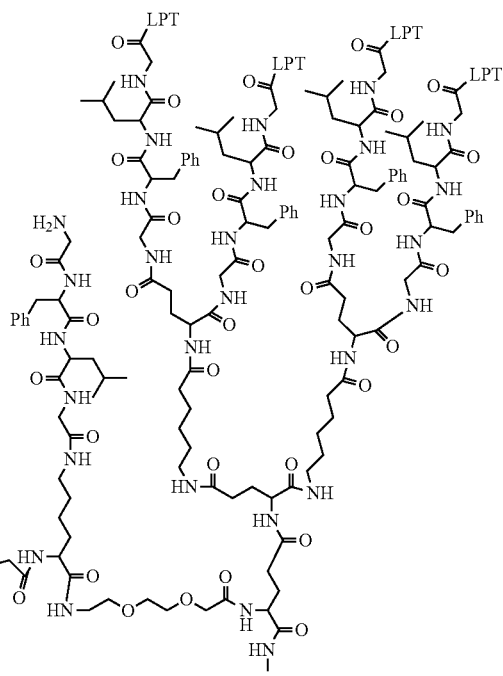

509

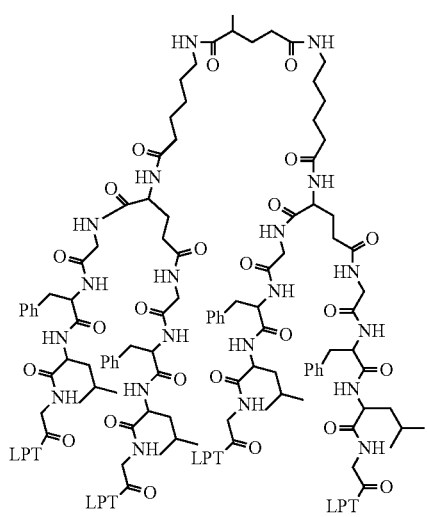

510

-continued

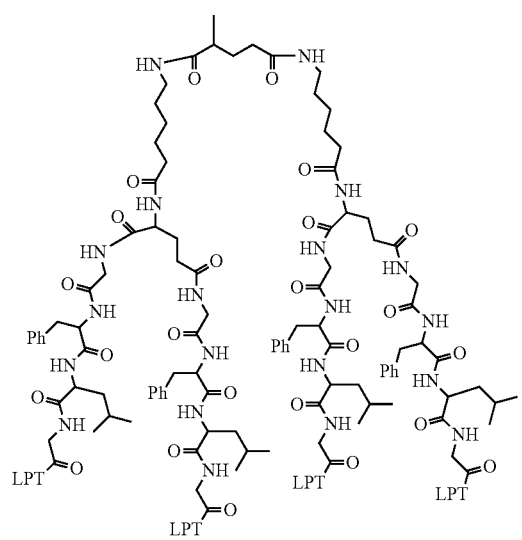

Dichloromethane and TFA (0.03659 mL, 0.4927 mmol) were added to a flask with Compound 27-97 (0.9888 g, 0.04927 mmol) and the mixed solution was then oscillated by ultrasonic until Compound 27-97 was completely dissolve; then, the solution was stirred overnight at room temperature. At the end of the reaction, the dichloromethane in the reaction solution was evaporated out; methyl tert-butyl ether (70 mL) was then added and the resulting solution was oscillated to separate out a solid by precipitation; suction filtering was then carried out, the filter cake was dissolved with a methanol/dichloromethane (1:4) solution (100 mL), silica gel powder (60 mL) was added to the obtained solution, and the solution was then evaporated to dryness to obtain a powdery solid; the operations of dry sample loading, column chromatography, and elution with a mixed solution (1% ammonia water:5-6% methanol/dichloromethane) were carried out; the elution product was then collected, concentrated, and dried in a vacuum oven. 0.7831 g of Product 27-100 was obtained with a yield of 79.83%.

27-106

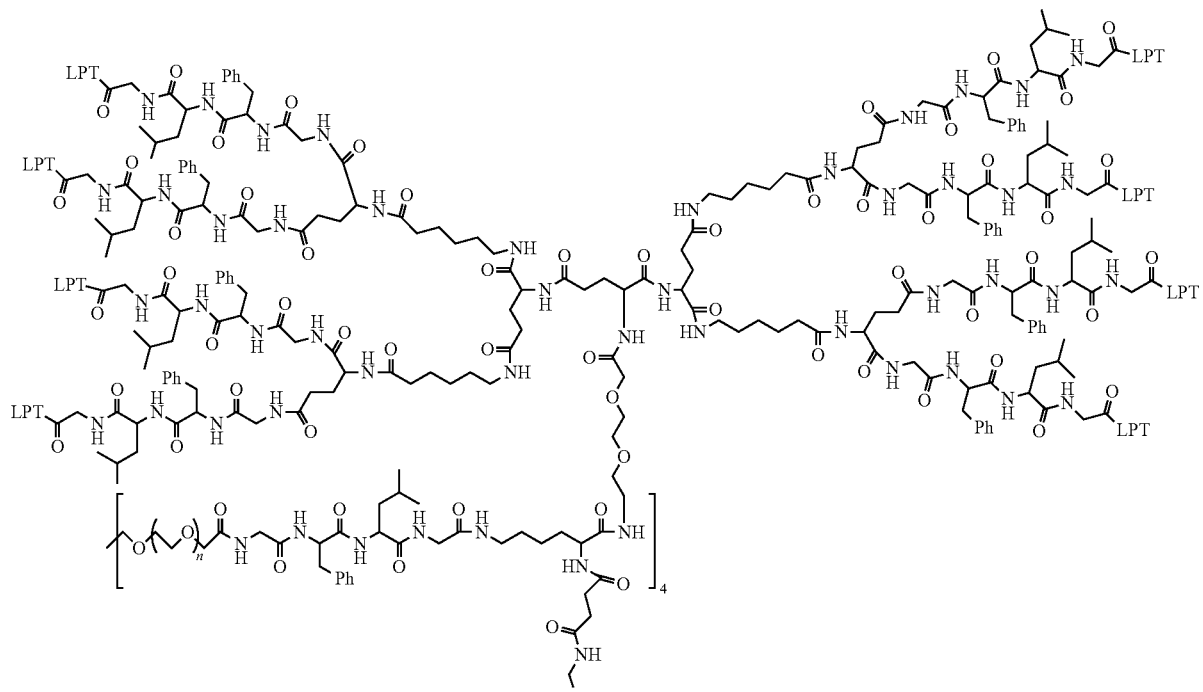

-continued

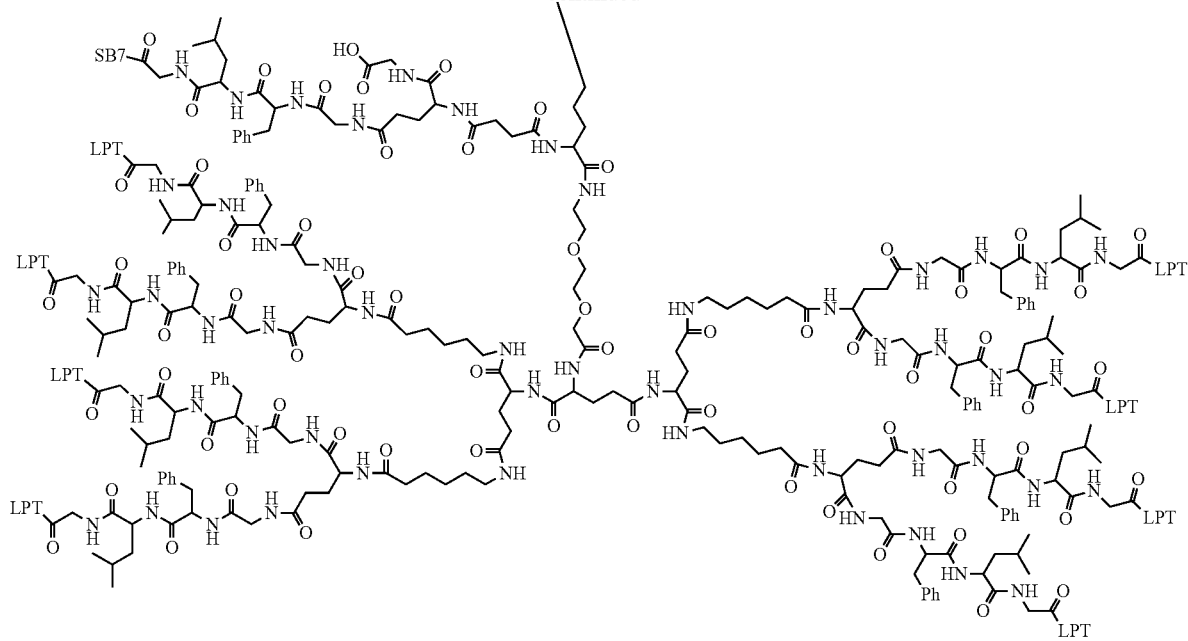

Compound 27-100 (0.7831 g, 0.03933 mmol) was added in a 250 mL flask and dissolved with DMF (20 mL), the reaction solution was stirred at −5° C. for 30 min, and DIEA (0.21 mL, 1.2996 mmol) was then slowly added dropwise over 5 min. The obtained solution was further stirred at −5° C. for 30 min, 4ARM-SCM-40K (0.3587 g, 0.00855 mmol, purchased from JenKem) was added and then dissolved with dichloromethane (10 mL), and the reaction solution was further stirred for 20 min at −5° C.; and then the reaction solution was slowly stirred for one week in the dark at room temperature to react. At the end of the reaction, the dichloromethane in the reaction solution was evaporated out, and methyl tert-butyl ether (200 mL) and n-hexane (70 mE) were then added to separate out a solid by precipitation; suction filtering was then carried out, the filter cake was washed with methyl tert-butyl ether (40 mL× 3) and then dissolved with a methanol/dichloromethane (1:4) solution (100 mL), silica gel powder (50 mL) was added to the obtained solution, and the solution was then evaporated to dryness to obtain a powdery solid; the operations of dry sample loading, column chromatography, and elution with a mixed solution (1% ammonia water:6% methanol/dichloromethane) were carried out; the elution product was then collected, concentrated, and dried in a vacuum oven. 0.6335 g of Product 27-106 was obtained with a yield of 61.16%.

27-113

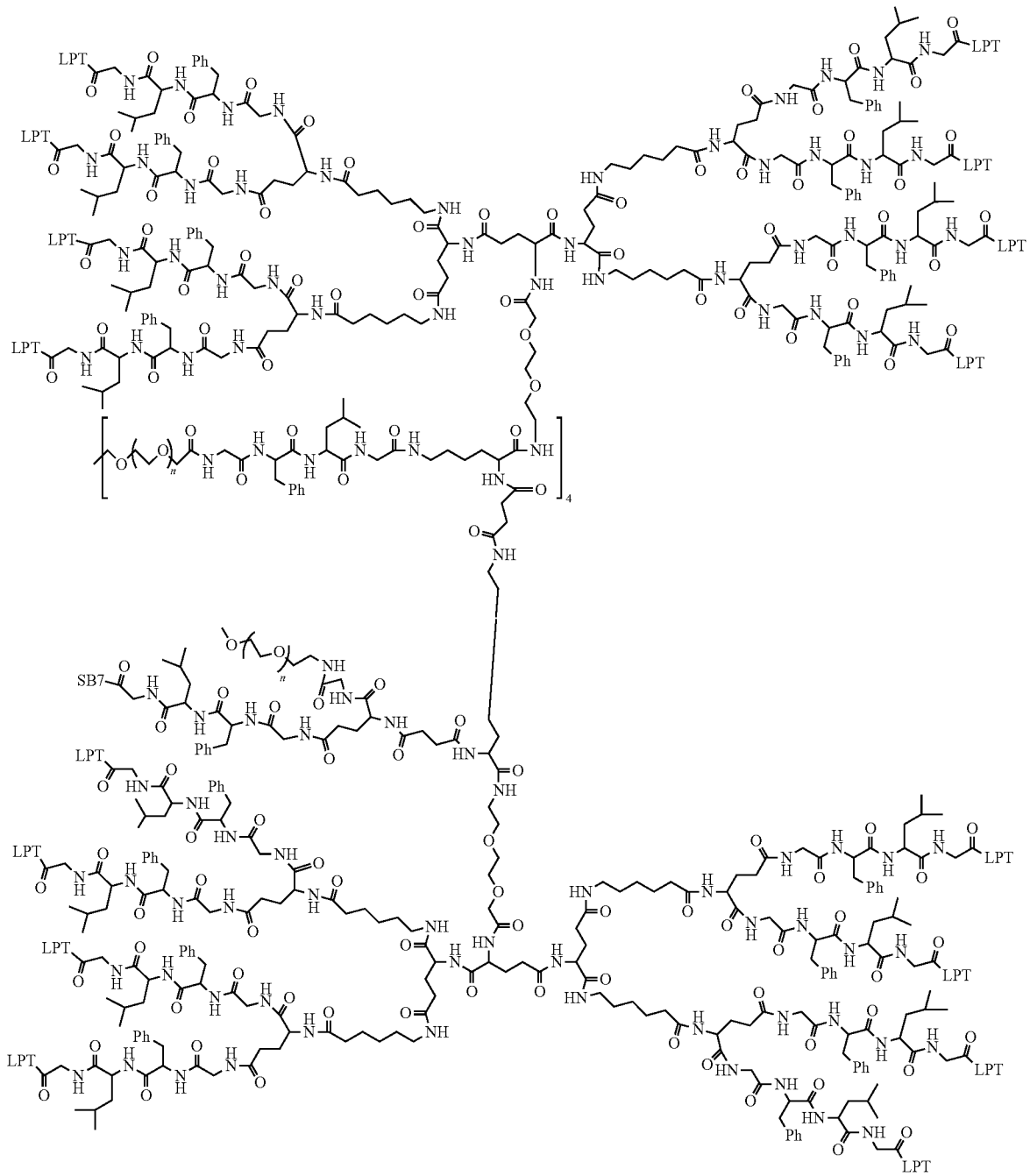

M-NH₂·HCl-20K (0.6399 g, 0.03138 mmol, purchased from JenKem), HBTU (0.012 g, 0.03138 mmol), and HOBT (0.0042 g, 0.03138 mmol) were weighed and then added into a flask with Compound 27-106 (0.6335 g, 0.00523 mmol), and then dissolved with an appropriate amount of DMF, the resulting solution was then rested at −5° C., and DIEA (0.023 mL, 0.14121 mmol) was slowly added dropwise; the mixed solution reacted for 30 min and then taken out and stirred overnight at room temperature to react. At the end of the reaction, the reaction solution was transferred to a 2 L flask, n-hexane (300 mL) and methyl tert-butyl ether (100 mL) were then added, and the resulting solution was then oscillated; the supernatant was discarded; suction operations were repeated three times. Next, methyl tert-butyl ether (300 mL) and a small amount of n-hexane (100 mL) were added and the resulting solution was then oscillated to separate out a solid by precipitation; suction filtering was then carried out, the filter cake was washed with methyl tert-butyl ether (40 mL×3) and then dissolved with a methanol/dichloromethane (1:4) solution (100 mL), silica gel powder (200 mL) was added to the obtained solution, and the solution was then evaporated to dryness to obtain a powdery solid; the operations of dry sample loading, column chromatography, and elution with a mixed solution (1% ammonia water:8% methanol/dichloromethane) were carried out; the elution product was then collected, concentrated, and evaporated to dryness to obtain a solid, and then the solid was dried in a vacuum oven. 0.4836 g of Product 27-113 was obtained with a yield of 45.70%.

$^1$H-NMR (400 MHz, DMSO-d$_6$) δ 9.99 (s, 62H), 9.05 (s, 22H), 8.82 (m, 56H), 8.78-8.61 (m, 72H), 8.31-7.92 (m, 338H), 7.87-7.63 (m, 136H), 7.22 (s, 619H), 7.06-6.95 (m, 43H), 6.90 (s, 12H), 6.73-6.69 (m, 55H), 6.61-6.55 (m, 29H), 5.26 (s, 107H), 4.82-4.73 (m, 104H), 4.55 (s, 63H), 4.42-4.19 (m, 142H), 3.51 (s, 11316H), 3.13-2.96 (m, 250H), 2.94-2.69 (m, 411H), 2.32-2.08 (m, 115H), 1.53-1.42 (m, 209H), 1.40-1.14 (m, 705H), 0.86 (m, 355H).

Example 19: Synthesis of Compound 27-138

27-104

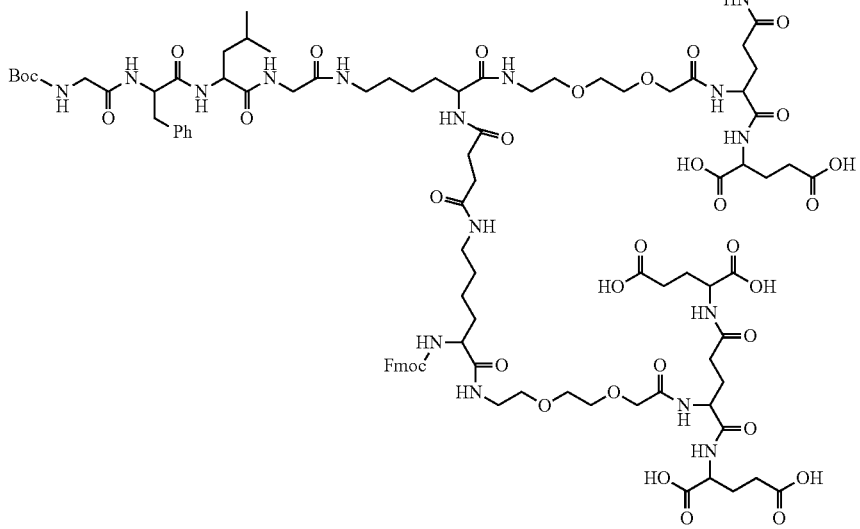

Compound 22-246 (home-made) (1.4 g, 0.4900 mmol) and Pd/C (0.1 g) were added in a hydrogenation reactor and then dissolved with DMF (20 mL); H$_2$ was introduced in the reactor to a pressure of 14 psi; and the mixed solution was then stirred overnight at room temperature to react. At the end of the reaction, the reaction solution was filtered with diatomaceous earth, the filter cake was washed three times with DMF (15 mL×3), and the filtrate was placed into a 250 mL round-bottomed flask. Product 27-104 was thus obtained and used as the raw material for the next step.

27-111

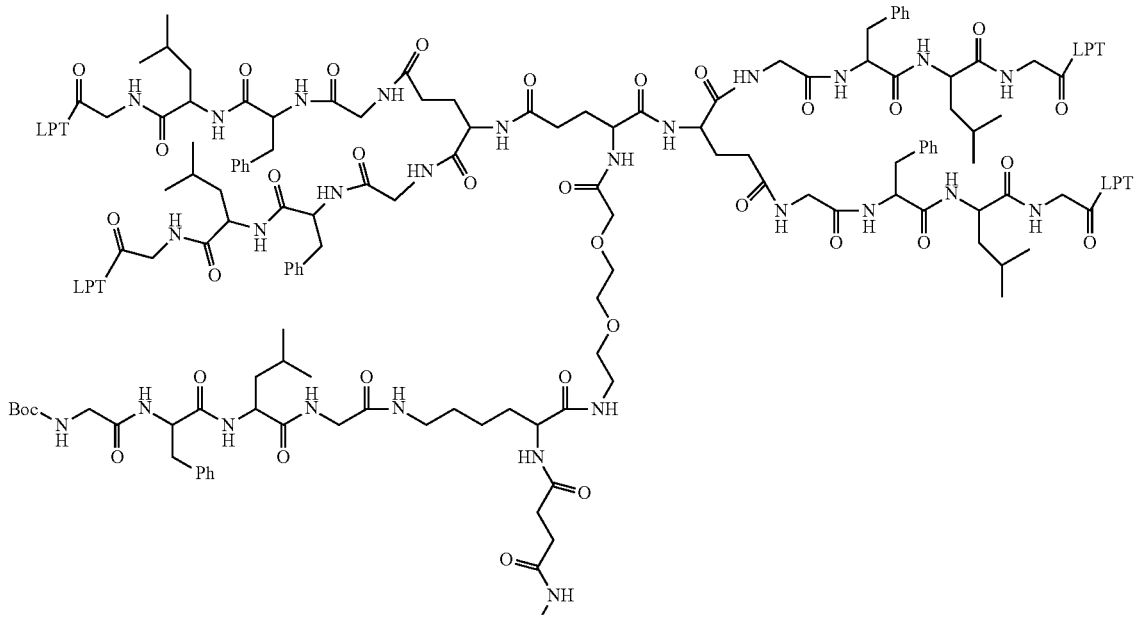

-continued

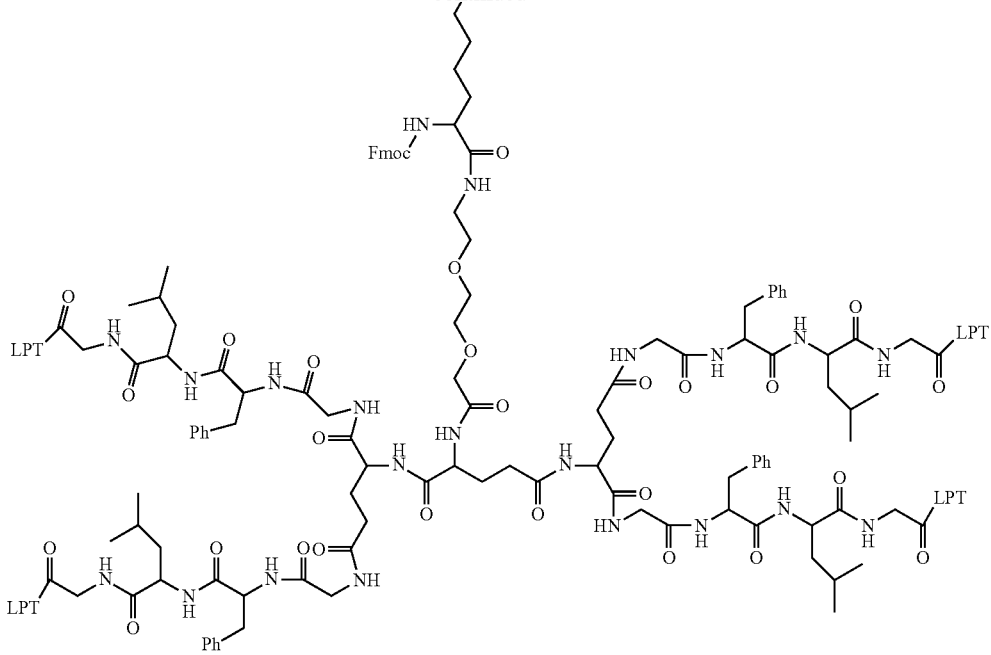

Compound 14-128 (home-made) (3 g, 2.8644 mmol), HBTU (1.48 g, 3.906 mmol), and HOBT (0.53 g, 3.906 mmol) were added to a flask with Compound 27-104 (0.6953 g, 0.3255 mmol) and then dissolved with an appropriate amount of DMF; the obtained solution was stirred at −5° C., and then DIEA (1.94 mL, 11.72 mmol) was slowly added dropwise to react for 30 min; then, the reaction solution was taken out and stirred overnight at room temperature. At the end of the reaction, 250 mL of a mixed solution of methyl tert-butyl ether and n-hexane (1:5) was added to the reaction solution; the mixed solution was oscillated and then rested and the supernatant was discarded; and such operations were repeated three times. Next, 200 mL of methyl tert-butyl ether was added to the mixed solution to obtain a solid by precipitation and suction filtering was then carried out. The filter cake was dissolved with a methanol/dichloromethane (1:4) solution (100 mL), silica gel powder (200 mL) was added to the obtained solution, and the solution was then evaporated to dryness to obtain a powdery solid; the operations of dry sample loading, column chromatography, and elution with a mixed solution (1% ammonia water:6%-8% methanol/dichloromethane) were carried out; the elution product was then collected, concentrated, and dried in a vacuum oven. 1.7 g of Product 27-111 was obtained with a yield of 54.31%.

27-124

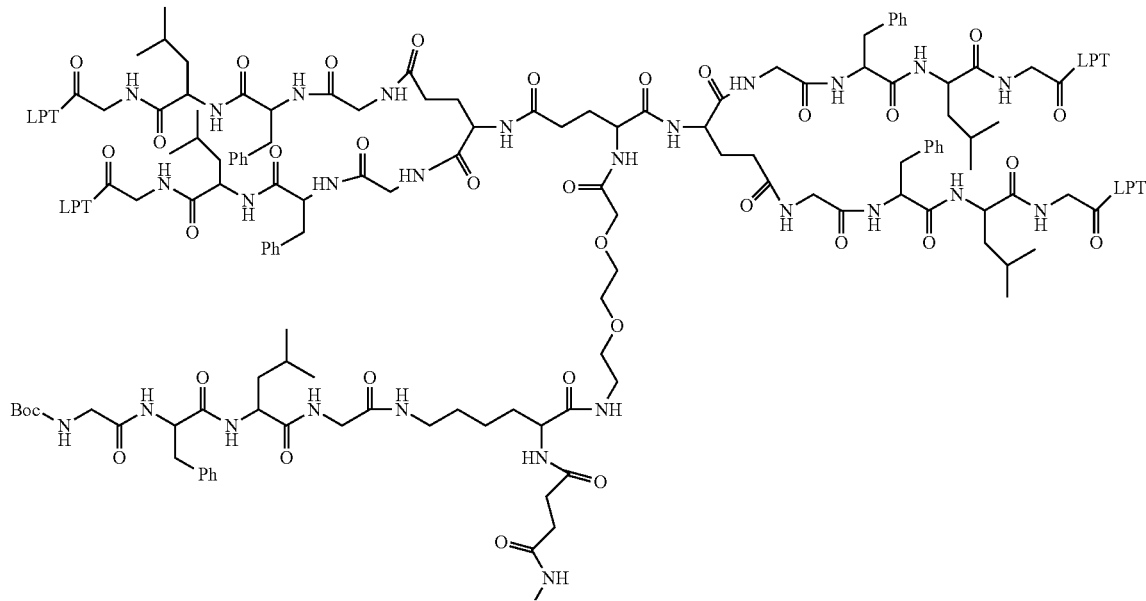

-continued

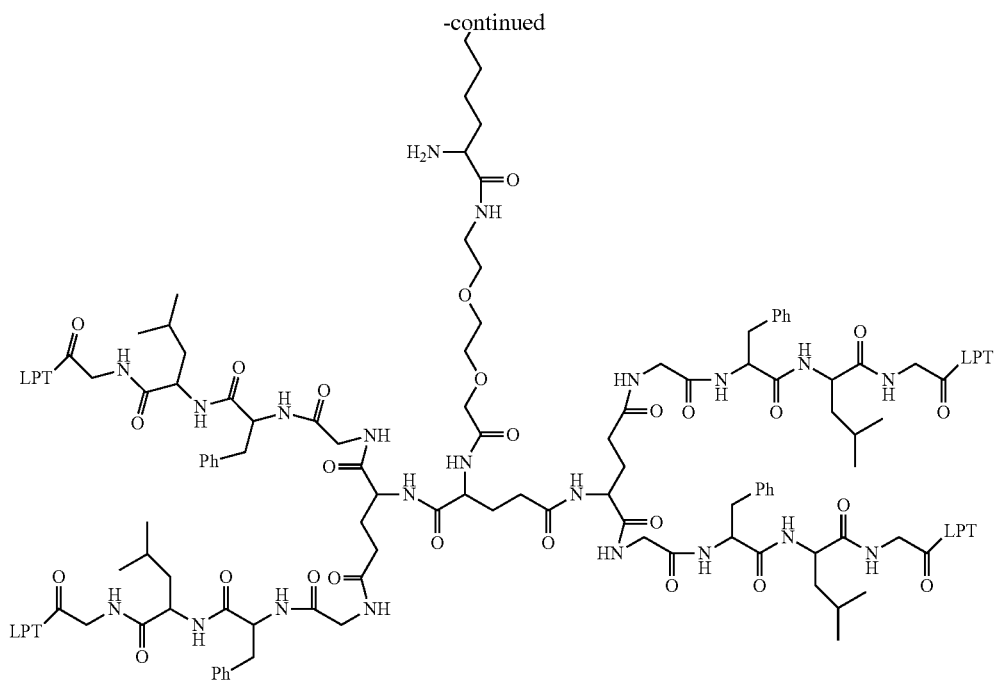

DMF was added into a flask with Compound 27-111 (1.7 g, 0.1764 mmol), the resulting solution was oscillated by ultrasonic until Compound 27-111 was completely dissolved, morpholine (0.23 mL, 2.6463 mmol) was then added, and the mixed solution was stirred at room temperature for 2 h to react. At the end of the reaction, 250 mL of a mixed solution of methyl tert-butyl ether and n-hexane (1:5) was added to the reaction solution; the mixed solution was oscillated and then rested and the supernatant was discarded; and such operations were repeated three times. Next, 200 mL of methyl tert-butyl ether was added to the mixed solution to obtain a solid by precipitation and suction filtering was then carried out. The filter cake was dissolved with a methanol/dichloromethane (1:4) solution (100 mL), silica gel powder (100 mL) was added to the obtained solution, and the solution was then evaporated to dryness to obtain a powdery solid; the operations of dry sample loading, column chromatography, and elution with a mixed solution (1% ammonia water:7%-8% methanol/dichloromethane) were carried out; the elution product was then collected, concentrated, and dried in a vacuum oven. 1.4 g of Product 27-124 was obtained with a yield of 84.34%.

27-126

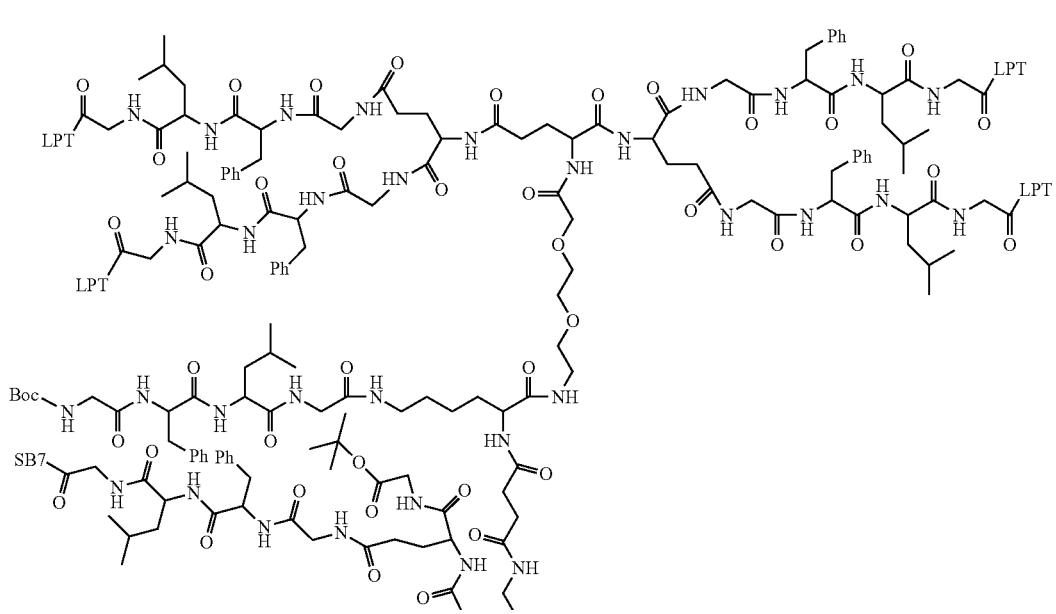

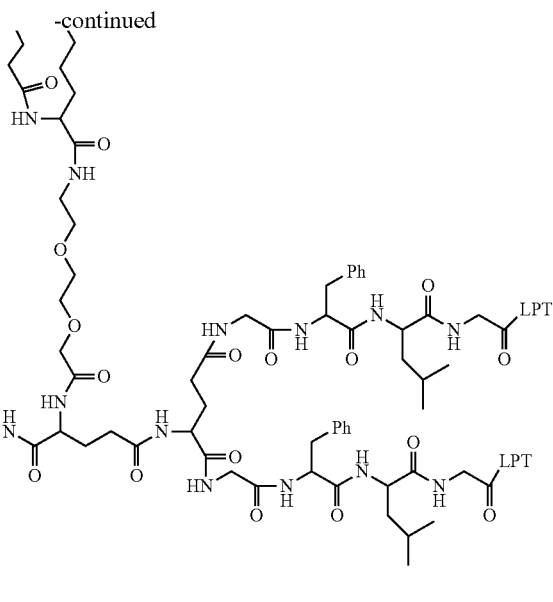

Compound 27-45 (0.22 g, 0.17844 mmol), HBTU (0.084 g, 0.22305 mmol), and HOBT (0.03 g, 0.22305 mmol) were added to a flask with Compound 27-124 (1.4 g, 0.1487 mmol) and then dissolved with an appropriate amount of DMF; the obtained solution was stirred at −5° C., and then DIEA (0.037 mL, 0.66915 mmol) was slowly added dropwise to react for 30 min; then, the reaction solution was taken out and stirred overnight at room temperature. At the end of the reaction, 250 mL of a mixed solution of methyl tert-butyl ether and n-hexane (1:5) was added to the reaction solution; the mixed solution was oscillated and then rested and the supernatant was discarded; and such operations were repeated three times. Next, 200 mL of methyl tert-butyl ether was added to the mixed solution to obtain a solid by precipitation and suction filtering was then carried out. The filter cake was dissolved with a methanol/dichloromethane (1:4) solution (100 mL), silica gel powder (200 mL) was added to the obtained solution, and the solution was then evaporated to dryness to obtain a powdery solid; the operations of dry sample loading, column chromatography, and elution with a mixed solution (1% ammonia water:6% methanol/dichloromethane) were carried out; the elution product was then collected, concentrated, and dried in a vacuum oven. 0.8701 g of Product 27-126 was obtained with a yield of 55.05%.

27-130

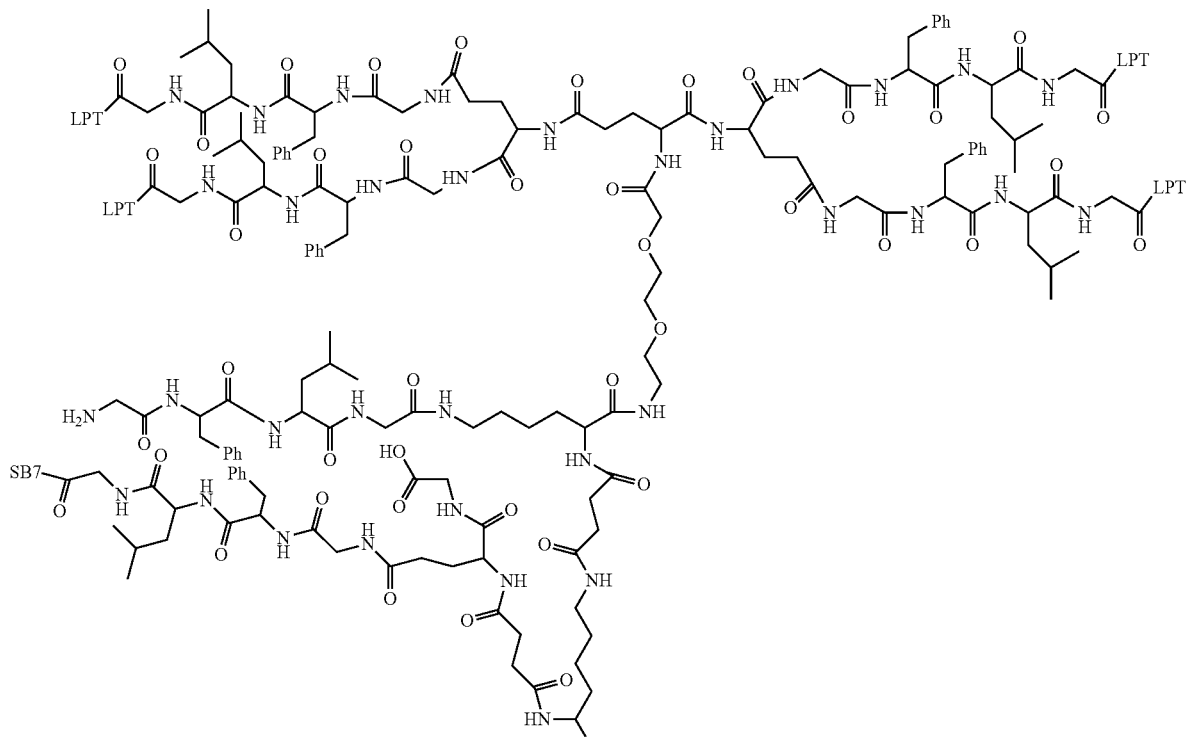

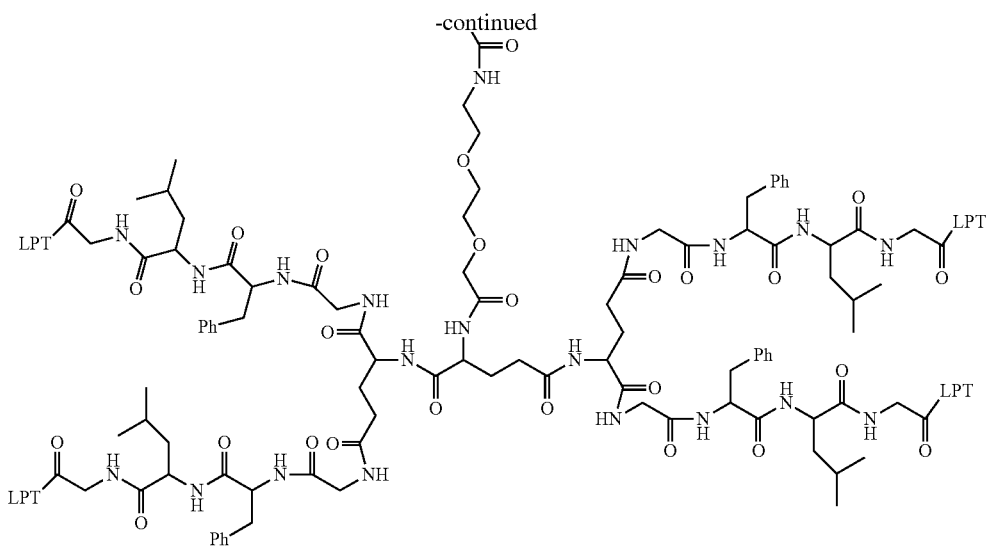

Dichloromethane and TFA (0.091 mL, 1.2278 mmol) were added to a flask with Compound 27-126 (0.8701 g, 0.0819 mmol) and the mixed solution was then oscillated by ultrasonic until Compound 27-126 was completely dissolve; then, the solution was stirred overnight at room temperature. At the end of the reaction, the dichloromethane in the reaction solution was evaporated out; methyl tert-butyl ether (70 mL) was then added and the resulting solution was oscillated to separate out a solid by precipitation; suction filtering was then carried out, the filter cake was dissolved with a methanol/dichloromethane (1:4) solution (100 mL), silica gel powder (60 mL) was added to the obtained solution, and the solution was then evaporated to dryness to obtain a powdery solid; the operations of dry sample loading, column chromatography, and elution with a mixed solution (1% ammonia water:6%-8% methanol/dichloromethane) were carried out; the elution product was then collected, concentrated, and dried in a vacuum oven. 0.6536 g of Product 27-130 was obtained with a yield of 76.20%.

$^1$H-NMR (400 MHz, DMSO-$d_6$) δ 9.85 (s, 8H), 9.05 (s, 5H), 8.74 (s, 10H), 8.55 (s, 9H), 8.10 (m, 56H), 7.76 (m, 20H), 7.46 (m, 11H), 7.38-6.96 (m, 73H), 6.90 (s, 3H), 6.67 (s, 9H), 6.54 (s, 4H), 5.28 (m, 16H), 5.04 (s, 3H), 4.72 (m, 13H), 4.56 (s, 10H), 4.29 (m, 31H), 3.61 (m, 53H), 3.03 (m, 33H), 2.89 (s, 5H), 2.73 (s, 16H), 2.12 (s, 14H), 1.99 (s, 27H), 1.54 (m, 37H), 1.34 (s, 32H), 0.81 (m, 90H).

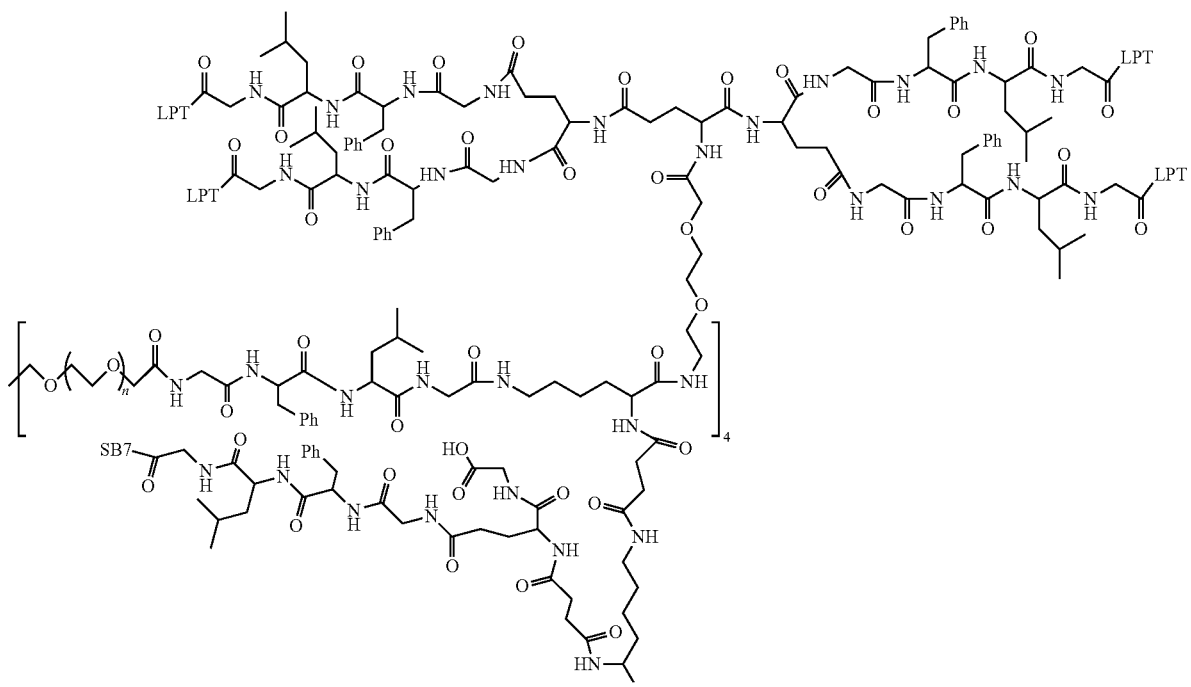

27-136

-continued

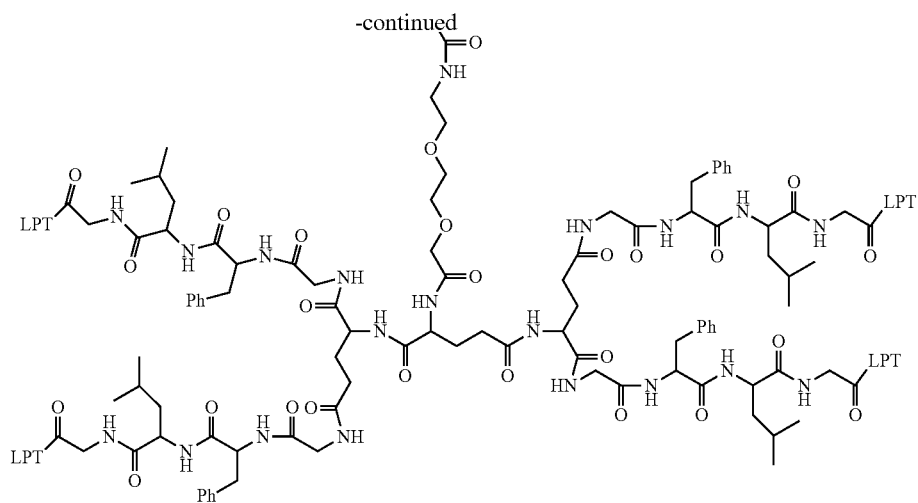

Compound 27-130 (0.6536 g, 0.0624 mmol) was added in a 250 mL flask and dissolved with DMF (20 mL), the reaction solution was stirred at −5° C. for 30 min, and DIEA (0.74 mL, 4.4928 mmol) was then slowly added dropwise over 5 min. The obtained solution was further stirred at a low temperature for 30 min, 4ARM-SCM-40K (0.5692 g, 0.01356 mmol, purchased from JenKem) was added and then dissolved with dichloromethane (10 mL), and the reaction solution was further stirred for 20 min at −5° C.; and then the reaction solution was stirred for one week in the dark at a low speed at room temperature to react. At the end of the reaction, the dichloromethane in the reaction solution was evaporated out, and methyl tert-butyl ether (200 mL) and n-hexane (70 mL) were then added to separate out a solid by precipitation; suction filtering was then carried out, the filter cake was washed with methyl tert-butyl ether (40 mL×3) and then dissolved with a methanol/dichloromethane (1:4) solution (100 mL), silica gel powder (50 mL) was added to the obtained solution, and the solution was then evaporated to dryness to obtain a powdery solid; the operations of dry sample loading, column chromatography, and elution with a mixed solution (1% ammonia water:7% methanol/dichloromethane) were carried out; the elution product was then collected, concentrated, and dried in a vacuum oven. 0.6956 g of Product 27-136 was obtained with a yield of 61.56%.

27-138

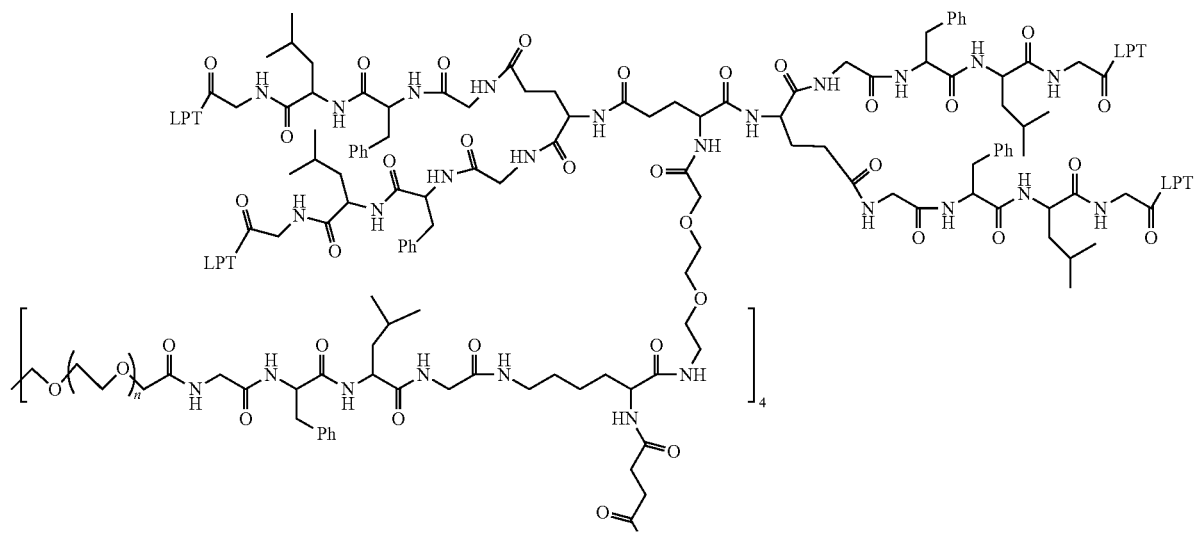

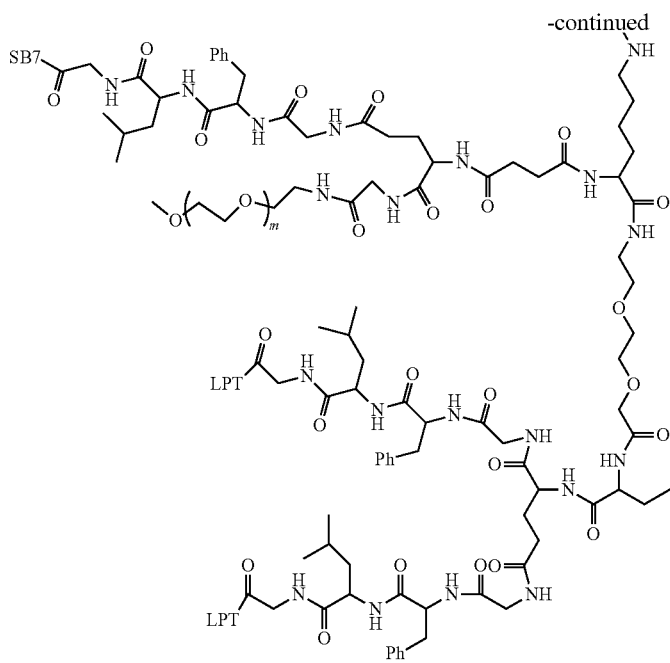
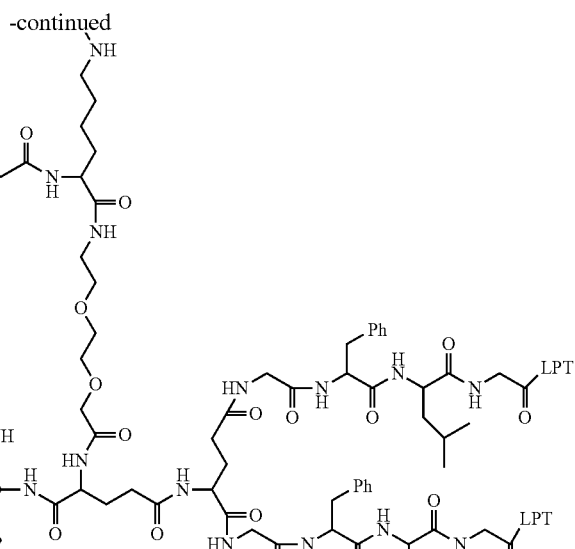

M-NH$_2$·HCl-20K (1.018 g, 0.05004 mmol, purchased from JenKem), HBTU (0.0189 g, 0.05004 mmol), and HOBT (0.00646 g, 0.05004 mmol) were weighed and then added into a flask with Compound 27-115 (0.6956 g, 0.00834 mmol), and then dissolved with an appropriate amount of DMF, the resulting solution was then rested at −5° C., and DIEA (0.0372 mL, 0.22518 mmol) was slowly added dropwise; the mixed solution reacted for 30 min and then taken out and stirred overnight at room temperature to react. At the end of the reaction, the reaction solution was transferred to a 2 L flask, n-hexane (300 mL) and methyl tert-butyl ether (100 mL) were then added, and the resulting solution was then oscillated; the supernatant was discarded; suction operations were repeated three times. Next, methyl tert-butyl ether (300 mL) and a small amount of n-hexane (100 mL) were added and the resulting solution was then oscillated to separate out a solid by precipitation; suction filtering was then carried out, the filter cake was washed with methyl tert-butyl ether (40 mL×3) and then dissolved with a methanol/dichloromethane (1:4) solution (100 mL), silica gel powder (200 mL) was added to is the obtained solution, and the solution was then evaporated to dryness to obtain a powdery solid; the operations of dry sample loading, column chromatography, and elution with a mixed solution (1% ammonia water:8% methanol/dichloromethane) were carried out; the elution product was then collected, concentrated, and evaporated to dryness to obtain a solid, and then the solid was dried in a vacuum oven. 0.6958 g of Product 27-138 was obtained with a yield of 50.68%.

$^1$H-NMR (400 MHz, DMSO-d$_6$) δ 8.87 (s, 40H), 8.74 (s, 45H), 8.38-7.91 (m, 220H), 7.84 (s, 54H), 7.67 (m, 60H), 7.55-7.41 (m, 57H), 7.41-7.04 (m, 249H), 6.96 (s, 27H), 6.70 (s, 32H), 6.55 (s, 26H), 5.28 (s, 82H), 4.72 (m, 86H), 4.57 (s, 69H), 4.18 (m, 260H), 3.99-3.42 (m, 9310H), 3.22 (m, 75H), 2.99 (m, 185H), 2.71 (m, 84H), 2.33 (s, 51H), 2.12 (s, 68H), 1.53 (m, 115H), 1.37-1.09 (m, 100H), 0.83 (m, 164H).

Example 20: Synthesis of Compound 36-23

22-275

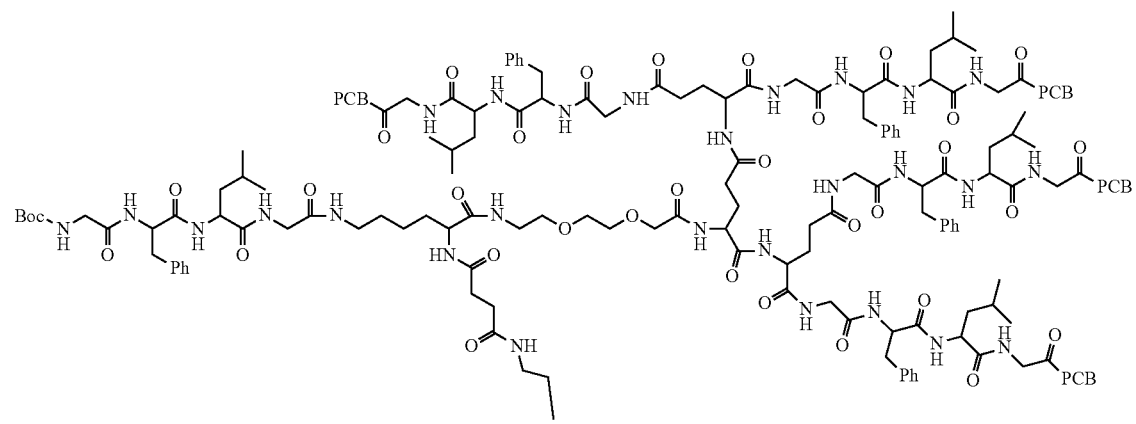

-continued

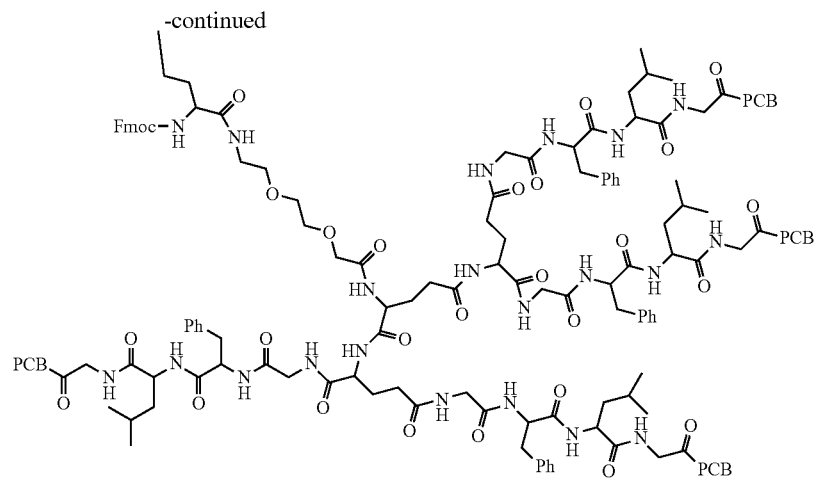

Compound 22-274 (0.953 g, 0.4461 mmol), Compound 30-33 (3.3 g, 4.0148 mmol, home-made), HBTU (2.1 g, 5.3532 mmol), and HOBT (0.7 g, 5.3532 mmol) were added into a 500 mL flask and then dissolved with an appropriate amount of DMF; the mixed solution in the reaction flask was stirred at −5° C. for about 20 min to react; DIEA (2.7 mL, 16.0596 mmol) was then slowly added dropwise, and the obtained solution further reacted at −5° C. for 1 h; and then the solution in the reaction flask was stirred overnight at room temperature to react. At the end of the reaction, n-hexane (150 mL) and methyl tert-butyl ether (30 mL) were added for precipitation, supernatant was discarded, and n-hexane (150 mL) and methyl tert-butyl ether (50 mL) were further added to the lower oily solution; such operations were repeated three times to obtain an oily product; methyl tert-butyl ether (200 mL) was added to precipitate a solid product; suction filtering was then carried out and the filter cake was washed with methyl tert-butyl ether (50 mL×3). The filter cake was then dissolved with a methanol/dichloromethane (1:5) solution, silica gel powder (40 mL) was added to the obtained solution, the obtained solution was then evaporated to dryness, and the operations of dry sample loading, column chromatography, and gradient elution with an eluent (4%-7% methanol:96%-93% dichloromethane) were carried out; the elution solution was then collected, concentrated, and dried. 2.5 g of Product 22-275 was obtained with a yield of 65.79%.

531  532
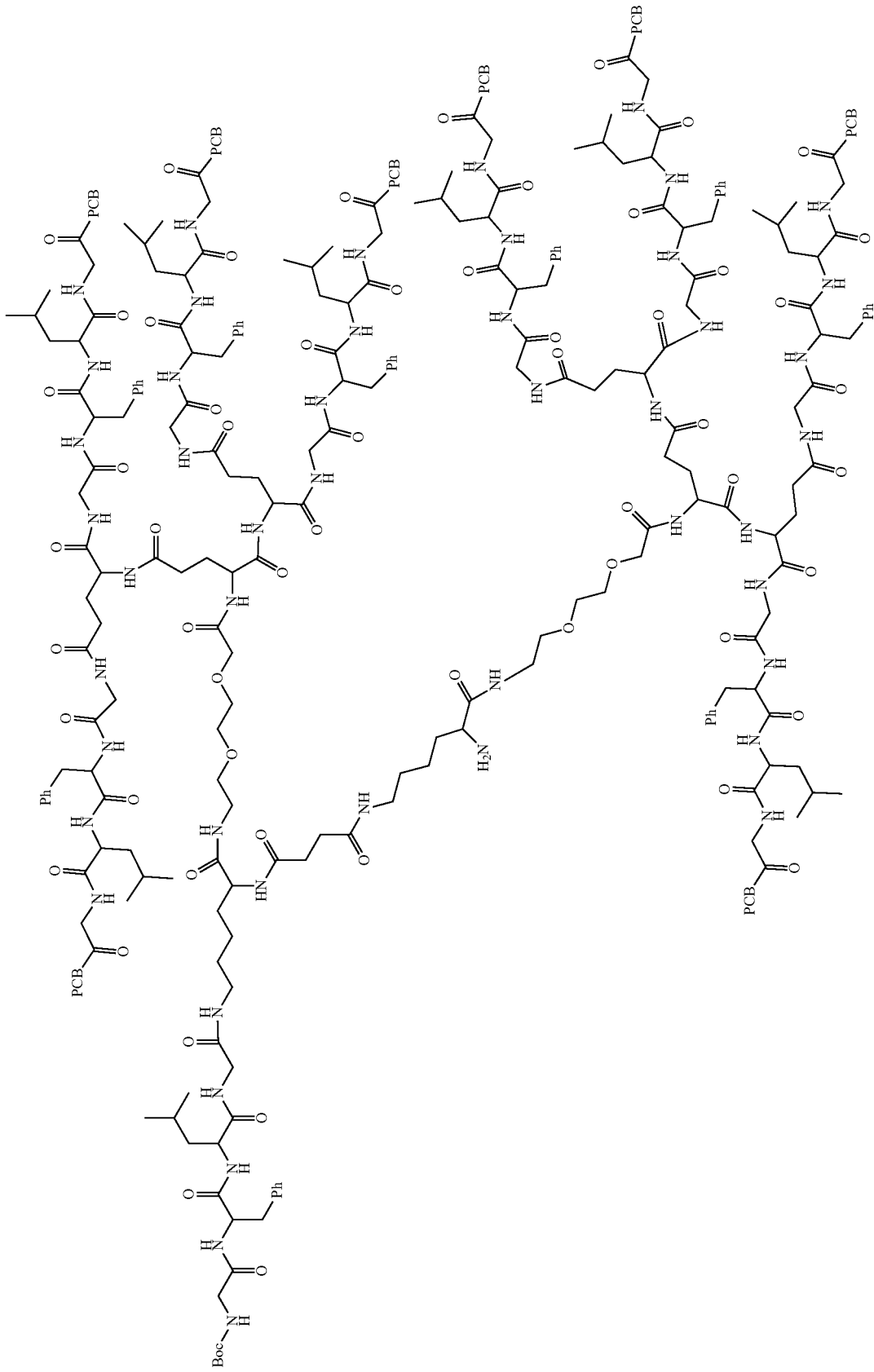

Compound 22-275 (2.5 g, 0.2918 mmol) was added in a 250 mL flask and then dissolved with 10 mL of DMF, morpholine (0.25 mL, 2.9179 mmol) was then added, and the mixed solution in the reaction flask was stirred for 1 h at room temperature to react. At the end of the reaction, n-hexane (150 mL) and methyl tert-butyl ether (30 mE) were added for precipitation, supernatant was discarded, and n-hexane (150 mL) and methyl tert-butyl ether (50 mL) were further added to the lower oily solution; such operations were repeated three times to obtain an oily product; methyl tert-butyl ether (200 mL) was added to precipitate a solid product; suction filtering was then carried out and the filter cake was washed with methyl tert-butyl ether (50 mL×3). The filter cake was then dissolved with a methanol/dichloromethane (1:5) solution, silica gel powder (40 mL) was added to the obtained solution, the obtained solution was then evaporated to dryness, and the operations of dry sample loading, column chromatography, and gradient elution with an eluent (1% ammonia water:4%-6.5% methanol:95%-92.5% dichloromethane) were carried out; the elution solution was then collected, concentrated, and evaporated to dryness. 1.1 g of Product 22-282 was obtained with a yield of 45%.

Compound 22-282 (1.1 g, 0.1318 mmol), Compound 27-45 (0.21 g, 0.1714 mmol), HBTU (0.075 g, 0.1977 mmol), and HOBT (0.027 g, 0.1977 mmol) were added into a 250 mL flask and then dissolved with an appropriate amount of DMF; the mixed solution in the reaction flask was stirred at −5° C. for about 20 min to react; DIEA (0.1 mL, 0.5931 mmol) was then slowly added dropwise, and the obtained solution further reacted at −5° C. for 1 h; and then the solution in the reaction flask was stirred overnight at room temperature to react. At the end of the reaction, n-hexane (150 mL) and methyl tert-butyl ether (30 mL) were added for precipitation, supernatant was discarded, and n-hexane (150 mL) and methyl tert-butyl ether (50 mL) were further added to the lower oily solution; such operations were repeated three times to obtain an oily product; methyl tert-butyl ether (200 mL) was added to precipitate a solid product; suction filtering was then carried out and the filter cake was washed with methyl tert-butyl ether (50 mL×3). The filter cake was then dissolved with a methanol/dichloromethane (1:5) solution, 40 mL of silica gel powder was added to the obtained solution, the obtained solution was then evaporated to dryness, and the operations of dry sample loading, column chromatography, and gradient elution with an eluent (1% ammonia water:5%-8% methanol:94%-91% dichloromethane) were carried out; the elution solution was then collected, concentrated, and dried. 0.9 g of Product 36-9 was obtained with a yield of 71.4%.

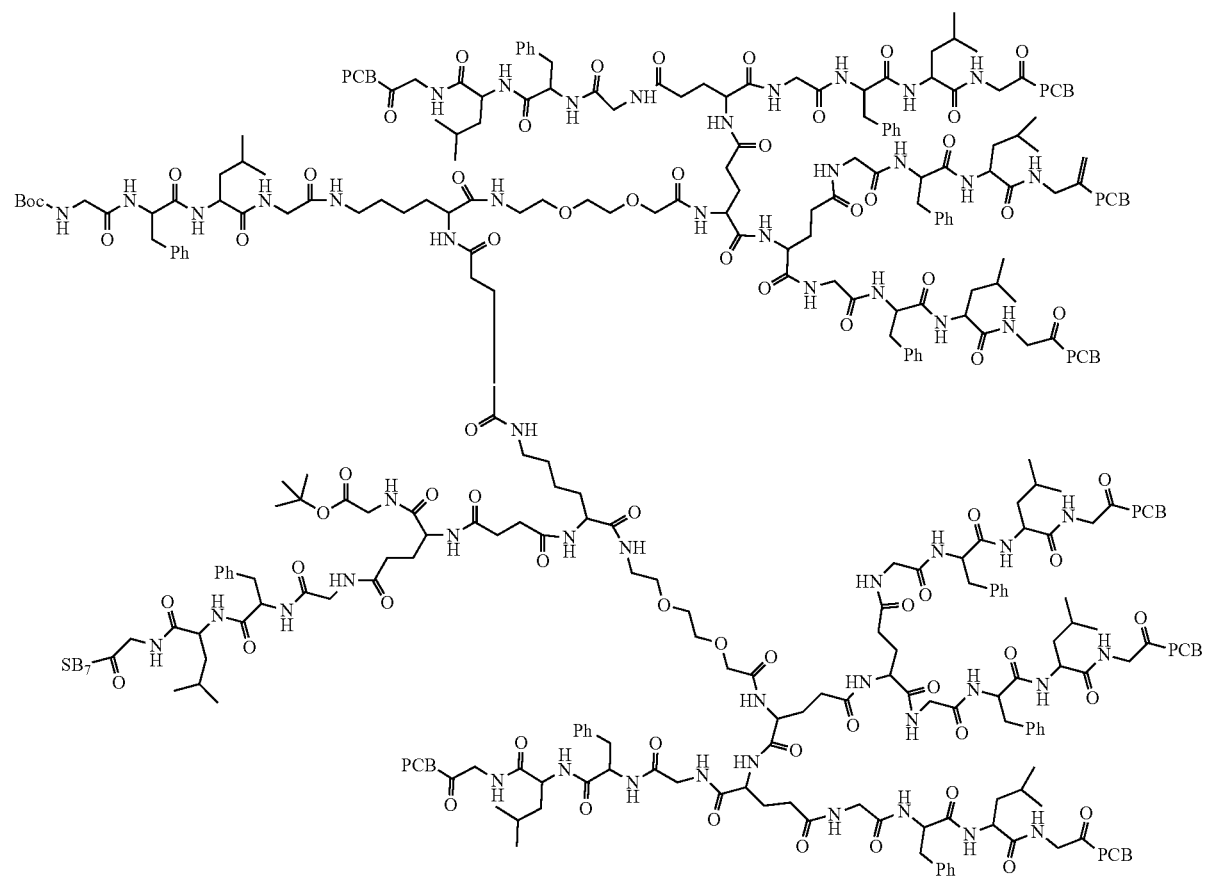

36-9

36-11

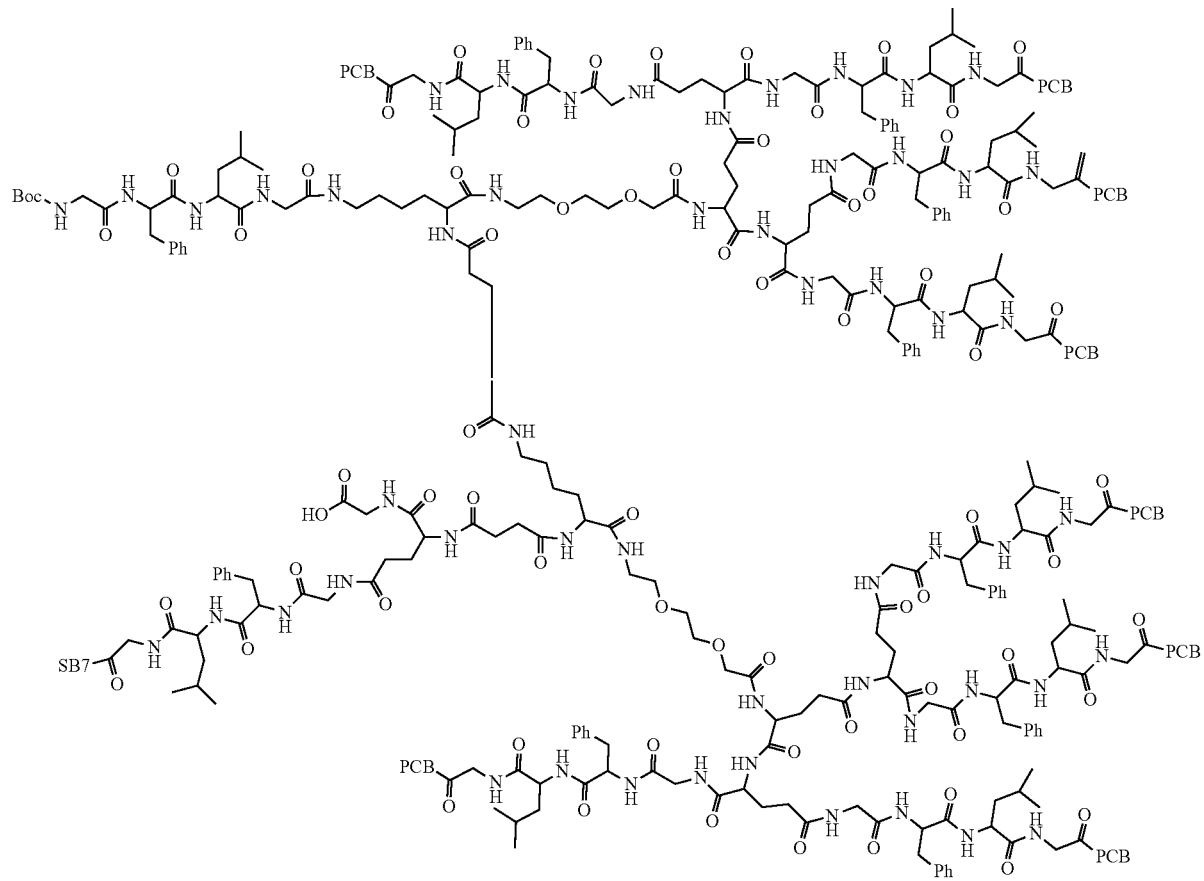

Product 36-9 (0.9 g, 0.09413 mmol) was added in a 250 mL flask and then dissolved with dichloromethane (5 mL), TFA (0.07 mL, 0.9413 mmol) was then added in the flask, and the mixed solution was stirred overnight at room temperature to react. At the end of the reaction, the dichloromethane was pumped out and then 200 mL of methyl tert-butyl ether was added to the reaction solution to obtain powder by precipitation; the powder was then filtered out and dissolved with a methanol/dichloromethane (1:5) solution, 30 mL of silica gel powder was added to the obtained solution, the obtained solution was then evaporated to dryness, and the operations of dry sample loading, column chromatography, and gradient elution with an eluent (1% ammonia water:6%-10% methanol:93%-89% dichloromethane) were carried out; the elution solution was then collected, concentrated, and dried. 0.3 g of Product 36-11 was obtained with a yield of 33.9%.

36-13

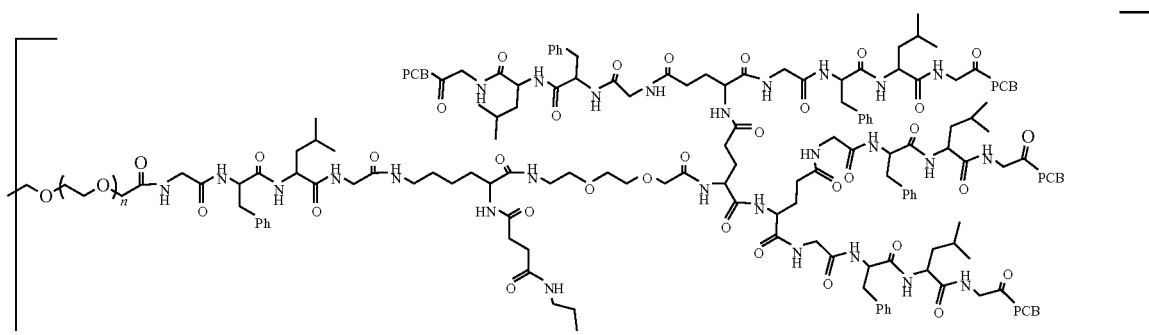

-continued

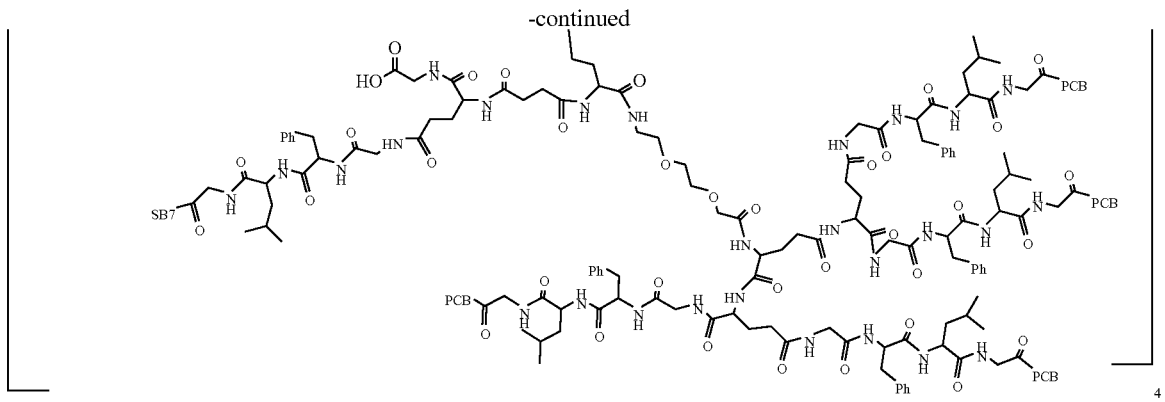

Compound 36-11 (0.3 g, 0.0319 mmol) was added to a 500 mL flask and then dissolved with 10 mL of DMF, the obtained solution was stirred for 30 min at −5° C. to react, and DIEA (0.02 mL, 0.1450 mmol) was then slowly added dropwise; then, 4ARM-SCM-40K (0.3 g) was added, and the obtained solution was slowly stirred for a week in the dark at room temperature to react. At the end of the reaction, n-hexane (50 mL×3) was first added; and when there was little lower oily product, methyl tert-butyl ether (20 mL) was added for precipitation, and a solid product was precipitated; the filter cake was then dissolved with a methanol/dichloromethane (1:5) solution, 30 mL of silica gel powder was then added to the obtained solution, and the solution was then evaporated to dryness; the operations of dry sample loading, column chromatography, and elution with an eluent (1% ammonia water:5%-8% methanol:94%-91% dichloromethane) were carried out; the filtrate was then collected, concentrated and evaporated to dryness. 0.36 g of Product 36-13 was obtained with a yield of 63%.

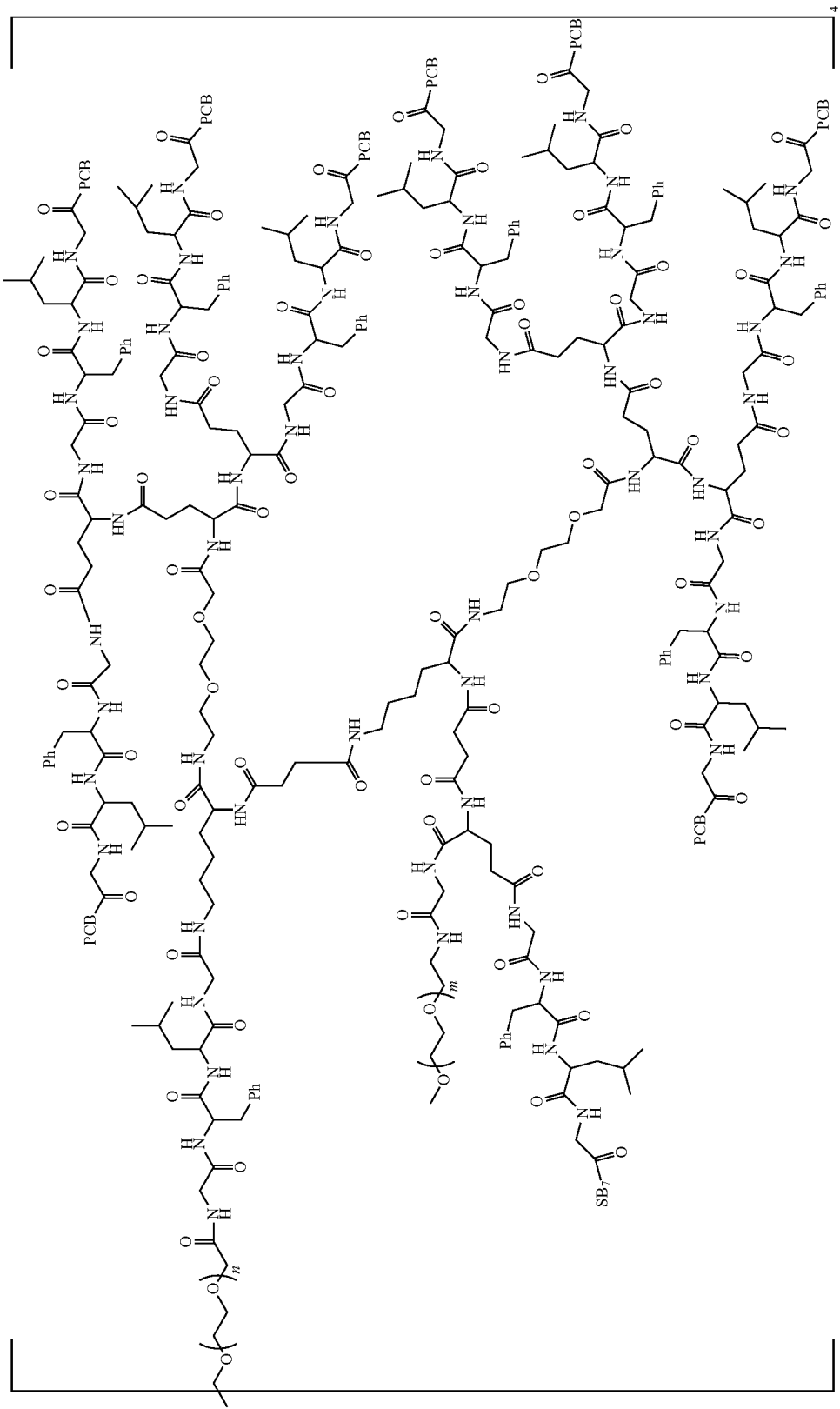

Product 36-13 (0.36 g, 0.00455 mmol), M-NH$_2$·HCl-5K (0.17 g, 0.03185 mmol, purchased from JenKem), HBTU (0.01 g, 0.0273 mmol), and HOBT (0.004 g, 0.0273 mmol) were added in a 250 mL flask and dissolved with an appropriate amount of DMF; the obtained solution was stirred for 30 min at −5° C. to react, and DIEA (0.16 mL, 0.0819 mmol) was then slowly added dropwise; the obtained solution further reacted for 1 h, and then stirred overnight at room temperature to react. At the end of the reaction, n-hexane (100 mL×3) was first added for precipitation; and when there was little lower oily product, methyl tert-butyl ether was added to separate out a solid product by precipitation; the filter cake was then dissolved with a methanol/dichloromethane (1:5) solution, 30 mL of silica gel powder was then added to the obtained solution, and the solution was then evaporated to dryness; the operations of dry sample loading, column chromatography, and elution with an eluent (1% ammonia water:5%-12% methanol:94%-87% dichloromethane) were carried out; the filtrate was then collected, concentrated and evaporated to dryness. 0.27 g of Product 36-23 was obtained with a yield of 60%.

MALDI-TOF MS: [M+H$^+$] 99859.26

Example 21: Synthesis of Compound 36-33

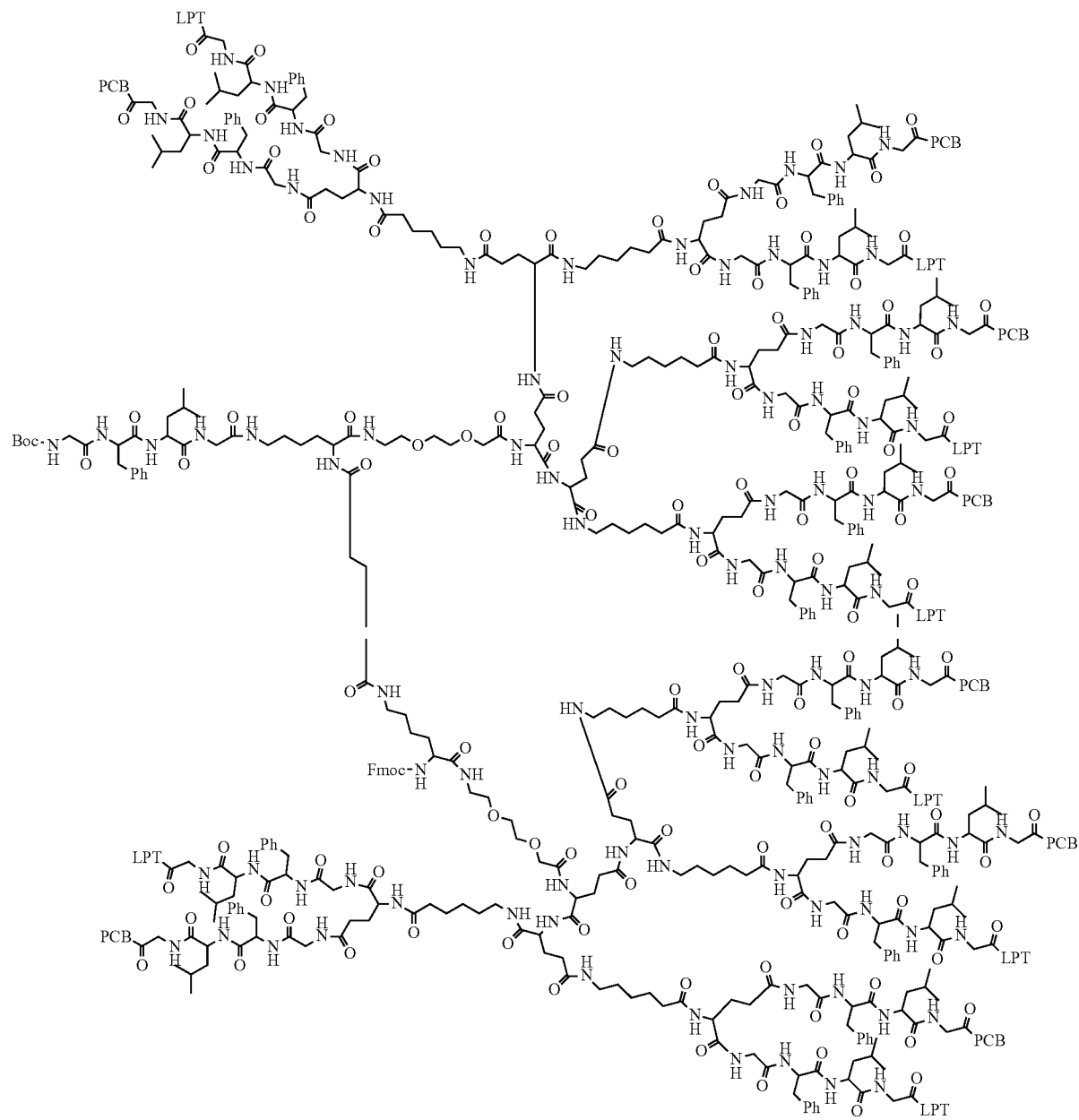

22-280

Compound 22-274 (0.356 g, 0.1665 mmol), Compound 27-99 (3 g, 1.4987 mmol), HBTU (0.8 g, 1.9983 mmol), and HOBT (0.3 g, 1.9983 mmol) were added into a 250 mL flask; the mixed solution in the reaction flask was stirred at −5° C. for 20 min to react; DIEA (1 mL, 5.9949 mmol) was then slowly added dropwise, and the obtained solution further reacted at −5° C. for 1 h; and then the solution in the reaction flask was stirred overnight at room temperature to react. At the end of the reaction, n-hexane (150 mL) and methyl tert-butyl ether (30 mL) were added for precipitation, supernatant was discarded, and n-hexane (150 mL) and methyl tert-butyl ether (50 mL) were further added to the lower oily solution; such operations were repeated three times to obtain an oily product; methyl tert-butyl ether (200 mL) was added to precipitate a solid product; suction filtering and drying were then carried out. 2.3 g of Product 22-280 was obtained with a yield of 76.72%.

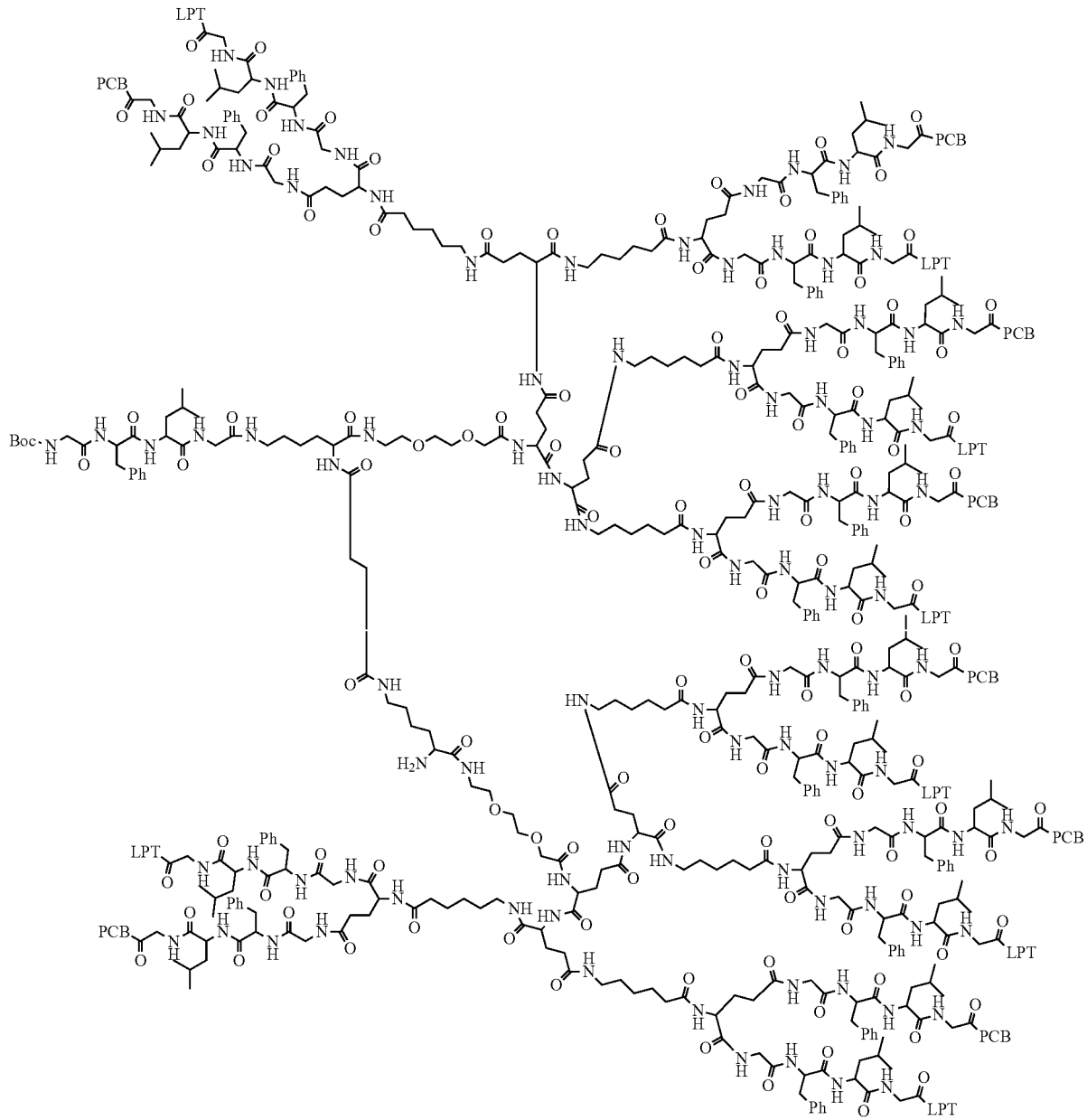

36-1

Product 22-280 (2.3 g, 0.12774 mmol) was added in a 250 mL flask and then dissolved with 10 mL of DMF and morpholine (0.01 mL, 1.2774 mmol) was then added, and the mixed solution was stirred for 1 h at room temperature to react. At the end of the reaction, n-hexane (150 mL) and methyl tert-butyl ether (30 mL) were added for precipitation, supernatant was discarded, and n-hexane (150 mL) and methyl tert-butyl ether (50 mL) were added to the lower oily solution; such operations were repeated three times to obtain an oily product; methyl tert-butyl ether (200 mL) was then added to precipitate a solid product; suction filtering was then carried out and the filter cake was washed with methyl tert-butyl ether (50 mL×3) and then dissolved with a methanol/dichloromethane (1:5) solution, 30 mL of silica gel powder was then added to the obtained solution, and the solution was then evaporated to dryness; the operations of dry sample loading, column chromatography, and gradient elution with a mixed solution (1% ammonia water:3%-10% methanol:96%-89% dichloromethane) were carried out; the elution product was then collected, concentrated, and dried in an oven. 1.9 g of Product 36-1 was obtained with a yield of 82.6%.

20 min to react; DIEA (0.08 mL, 0.4808 mmol) was then slowly added dropwise, and the obtained solution further reacted at −5° C. for 1 h; and then the solution in the reaction flask was stirred overnight at room temperature to react. At the end of the reaction, n-hexane (150 mL) and methyl tert-butyl ether (30 mL) were added for precipitation, supernatant was discarded, and n-hexane (150 mL) and methyl tert-butyl ether (50 mL) were added to the lower oily solution; such operations were repeated three times to obtain an oily product; methyl tert-butyl ether (200 mL) was then

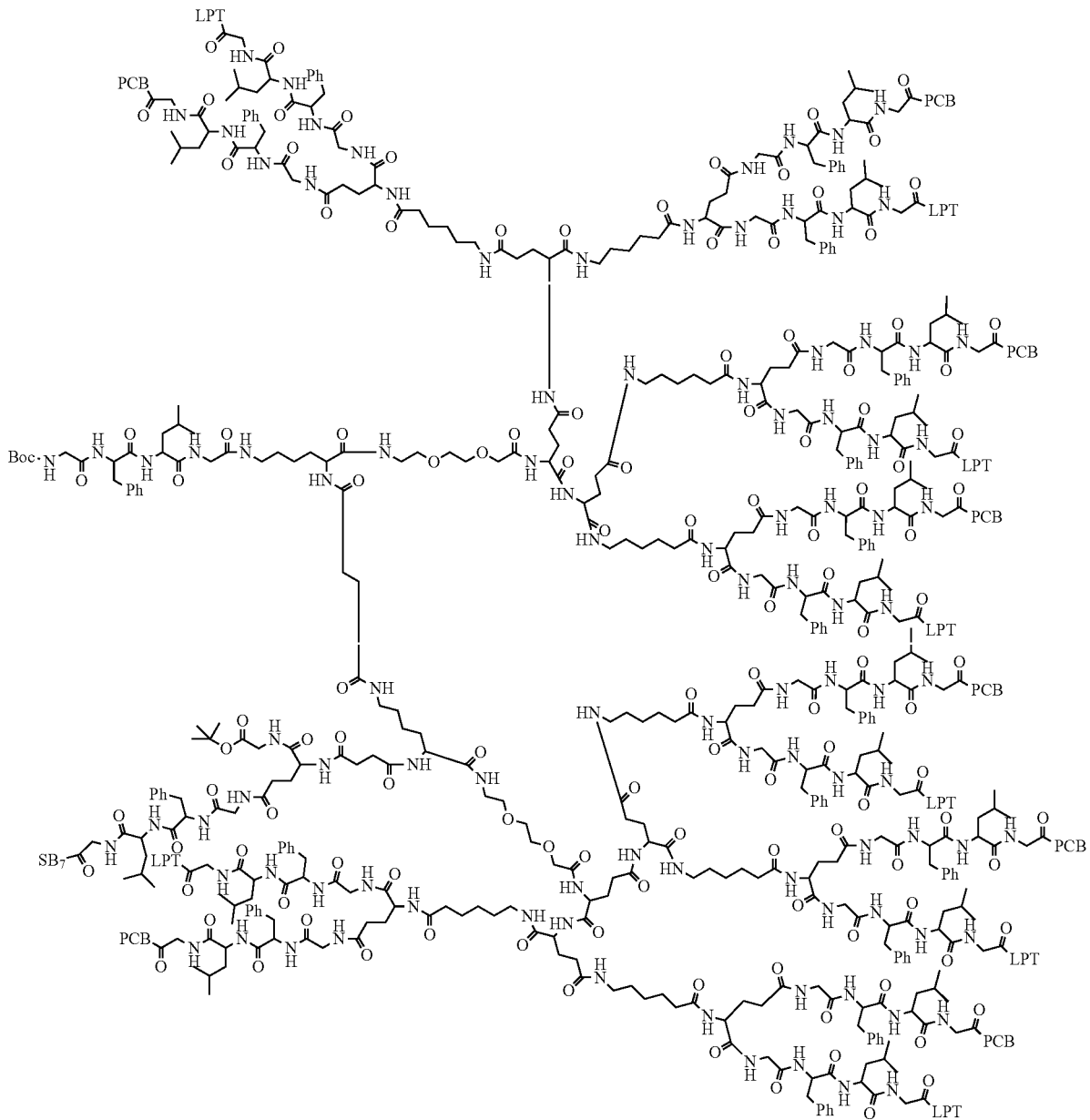

36-5

Compound 36-1 (1.9 g, 0.10684 mmol), Compound 27-45 (0.145 g, 0.1175 mmol), HBTU (0.06 g, 0.1603 mmol), and HOBT (0.02 g, 0.1603 mmol) were added into a 250 mL flask and then dissolved with 20 mL of DMF; the mixed solution in the reaction flask was stirred at −5° C. for about added to precipitate a solid product; suction filtering was then carried out and the filter cake was washed with methyl tert-butyl ether (50 mL×3) and then dissolved with a methanol/dichloromethane (1:5) solution, 40 mL of silica gel powder was then added to the obtained solution, and the solution was then evaporated to dryness; the operations of dry sample loading, column chromatography, and gradient elution with a mixed solution (1% ammonia water:4%-8% methanol:95%-91% dichloromethane) were carried out; the elution product was then collected, concentrated, and dried in an oven. 1 g of Product 36-5 was obtained with a yield of 50%.

reaction, the dichloromethane was pumped out and then 200 mL of methyl tert-butyl ether was added to the reaction solution to obtain powder by precipitation; the powder was then filtered out and dissolved with a methanol/dichloromethane (1:5) solution, 30 mL of silica gel powder was added to the obtained solution, the obtained solution was then evaporated to dryness, and the operations of dry sample 36-29

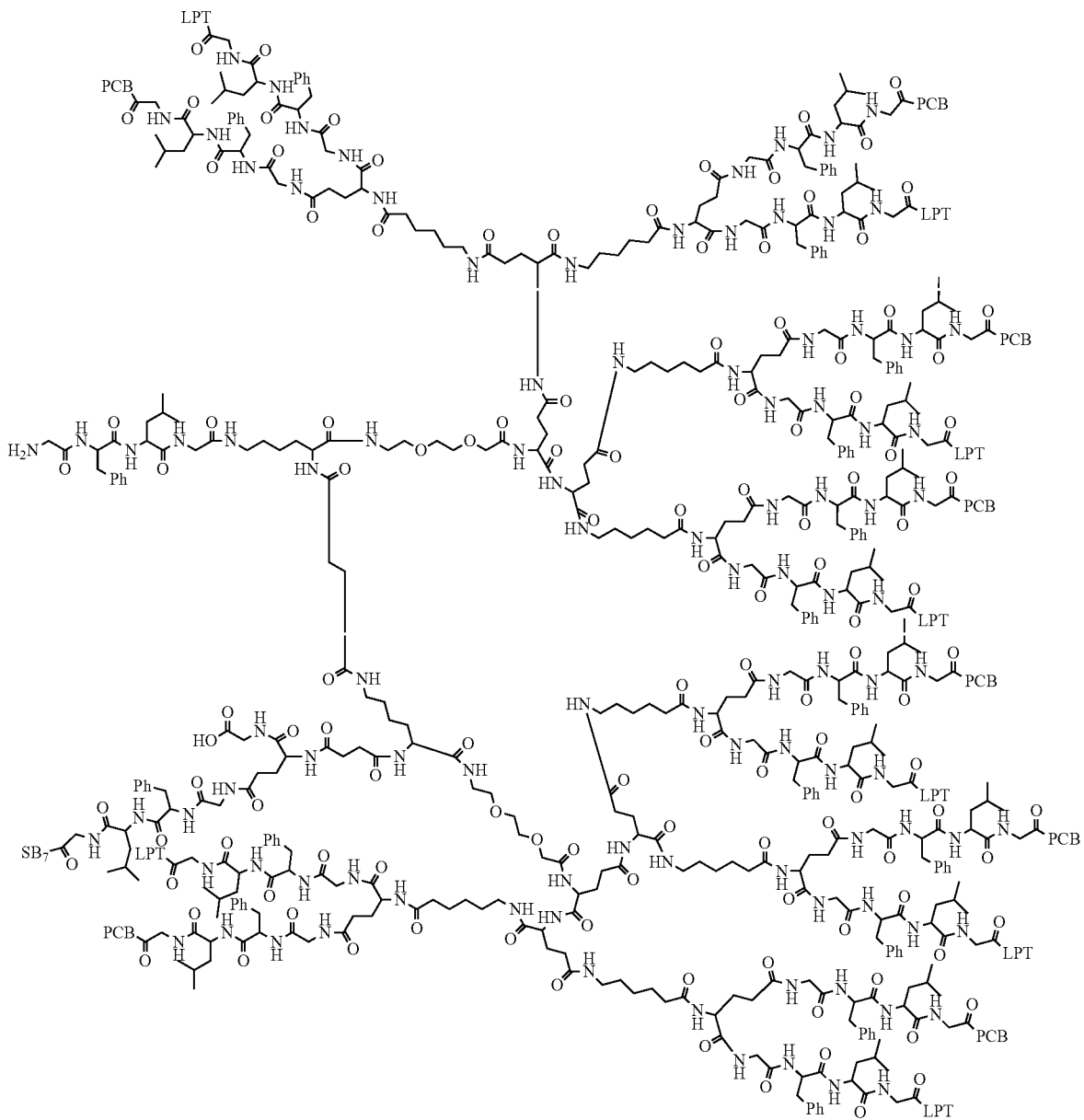

Compound 36-9 (1 g, 0.05263 mmol) was added in a 250 mL flask and then dissolved with 3 mL of dichloromethane, TFA (0.078 mL, 1.0527 mmol) was then added in the flask, and the mixed solution in the reaction flask was stirred overnight at room temperature to react. At the end of the loading, column chromatography, and gradient elution with an eluent (1% ammonia water:5%-10% methanol:94%-89% dichloromethane) were carried out; the elution solution was then collected, concentrated, and dried. 0.6 g of Product 36-29 was obtained with a yield of 60.6%.

36-31

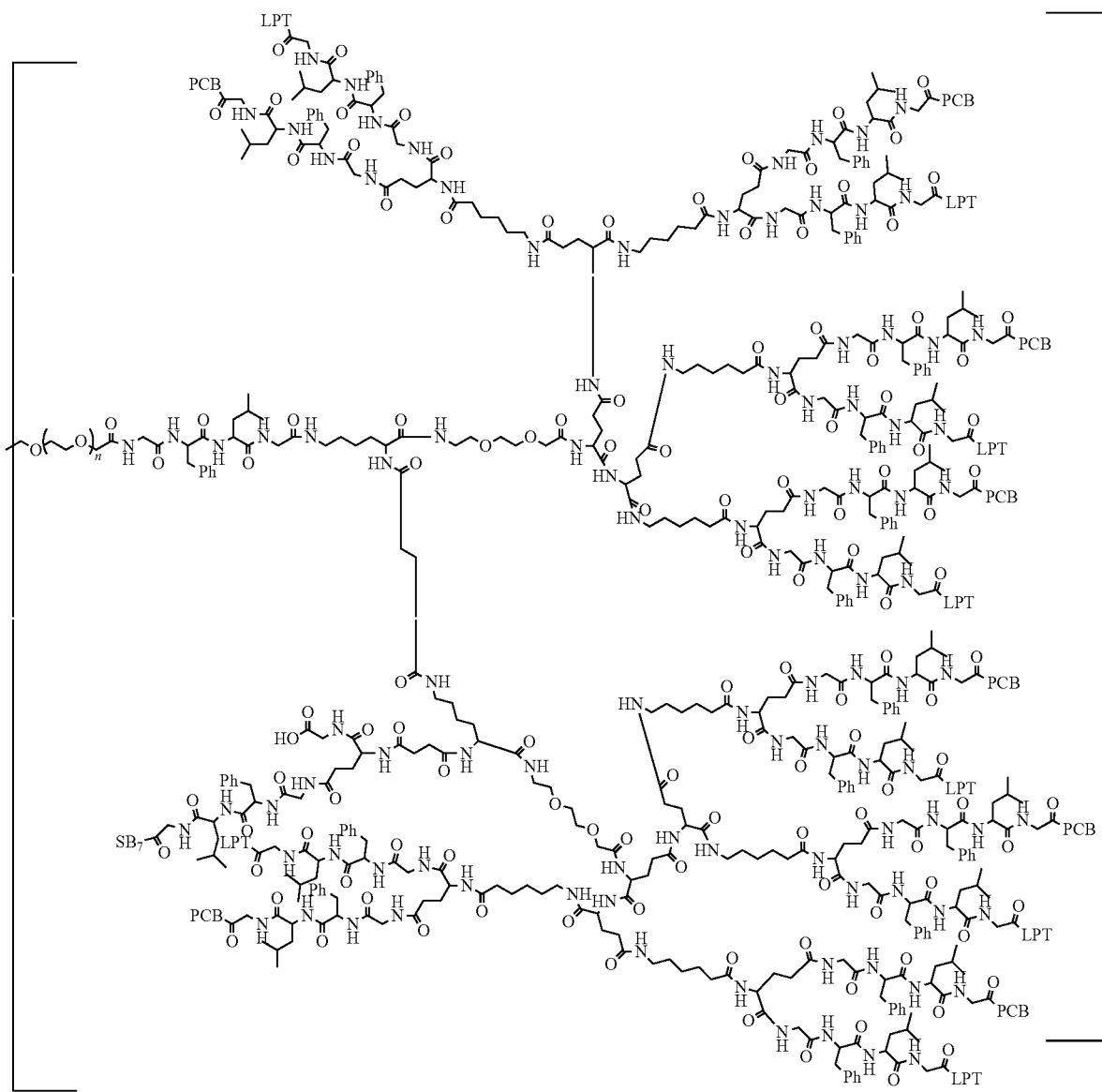

Compound 36-29 (0.6 g, 0.0318 mmol) was added to a 250 mL flask and then dissolved with 10 mL of DMF, the obtained solution was stirred for 30 mi at −5° C. to react, and DIEA (0.024 mL, 0.14474 mmol) was then slowly added dropwise; then, 4ARM-SCM-40K (0.04 g) was added, and the obtained solution was slowly stirred for a week in the dark at room temperature to react. At the end of the reaction, n-hexane (50 mL×3) was first added; and when there was little lower oily product, methyl tert-butyl ether (20 mL) was added for precipitation, and a solid product was precipitated; the filter cake was then dissolved with a methanol/dichloromethane (1:5) solution, 30 mL of silica gel powder was then added to the obtained solution, and the solution was then evaporated to dryness; the operations of dry sample loading, column chromatography, and elution with an eluent (1% ammonia water:5%-10% methanol:94%-89% dichloromethane) were carried out; the filtrate was then collected, concentrated and evaporated to dryness. 0.35 g of Product 36-31 was obtained with a yield of 60%.

36-33

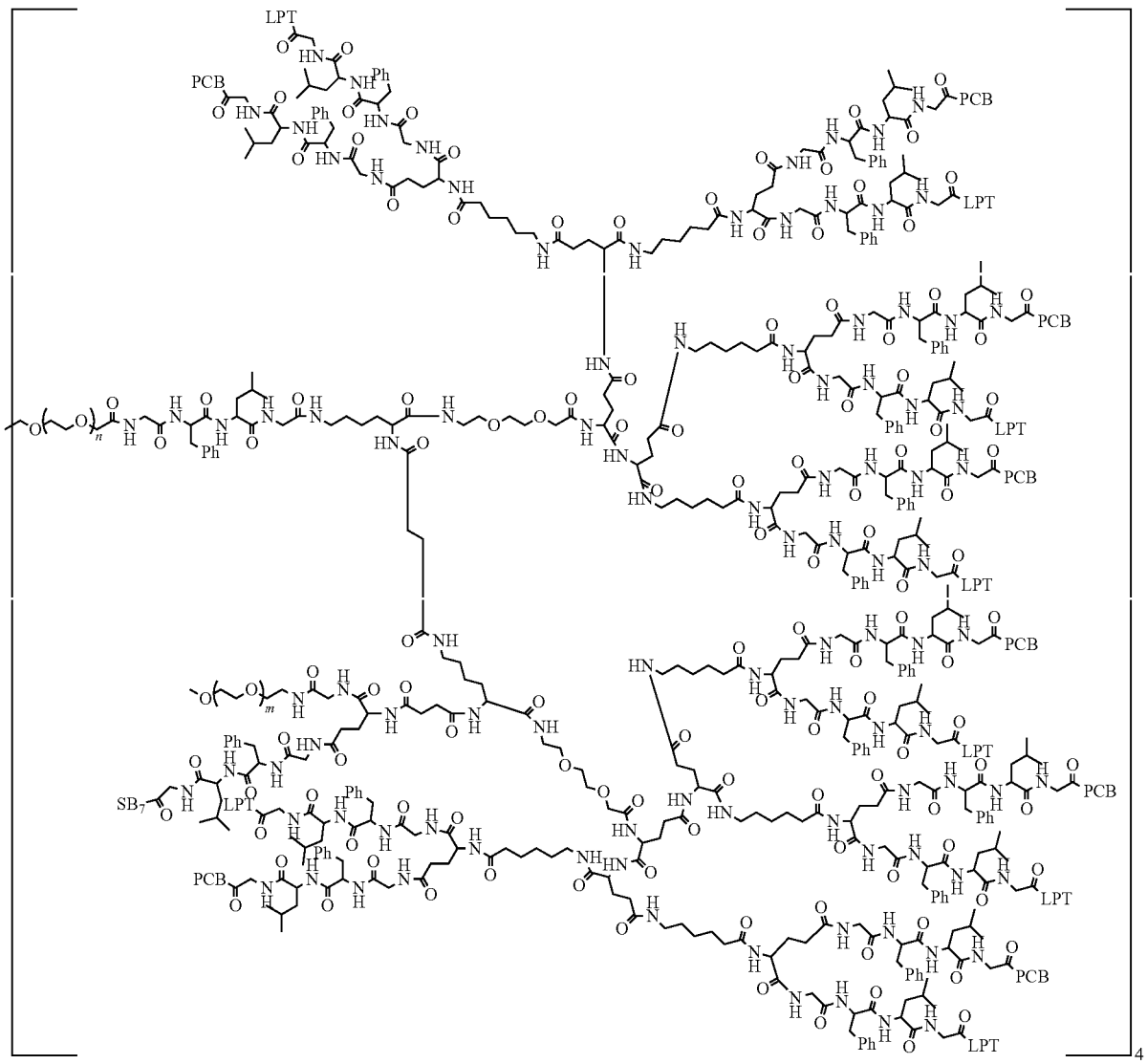

Product 36-31 (0.35 g, 0.00433 mmol), M-NH$_2$·HCl-20K (0.53 g, 0.026 mmol), HBTU (0.01 g, 0.026 mmol), and HOBT (0.0035 g, 0.026 mmol) were added in a 250 mL flask and dissolved with an appropriate amount of DMF; the obtained solution was stirred for 30 min at −5° C. to react, and DIEA (0.16 mL, 0.09532 mmol) was then slowly added dropwise; the obtained solution in the reaction flask further reacted at −5° C. for 1 h and was then stirred overnight at room temperature to react. At the end of the reaction, n-hexane (100 mL×3) was first added for precipitation; and when there was little lower oily product, methyl tert-butyl ether was added to separate out a solid product by precipitation; the filter cake was then dissolved with a methanol/dichloromethane (1:5) solution, 30 mL of silica gel powder was then added to the obtained solution, and the solution was then evaporated to dryness; the operations of dry sample loading, column chromatography, and elution with an eluent (1% ammonia water:5%-11% methanol:94%-88% dichloromethane) were carried out; the filtrate was then collected, concentrated and evaporated to dryness. 0.456 g of Product 36-33 was obtained with a yield of 65%.

MALDI-TOF MS: [M+Na$^+$] 199062.23

Example 22: Synthesis of Compound 26-168

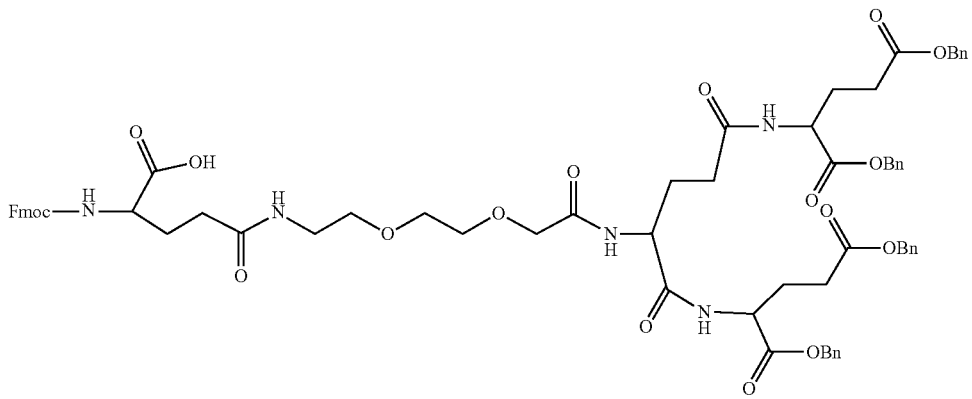

26-123

Compound 24-69 (8.0 g, 6.0677 mmol) was added in a 500 mL flask and then dissolved with dichloromethane (10 mL) and TFA (6.7590 mL, 9.1015 mmol), and the mixed solution was stirred overnight at room temperature to react. At the end of the reaction, the reaction solution was transferred to a 2 L separatory funnel, a saturated sodium bicarbonate solution (300 mL) was then added to adjust the pH of the reaction solution to alkaline, and then ethyl acetate (200 mL) was added for extraction to obtain an organic phase; the aqueous phase was extracted with ethyl acetate (200 mL×3), and the obtained organic phases were combined and washed with a saturated sodium chloride solution (150 mL×3); the obtained solution was then concentrated, evaporated to dryness, and dried in a vacuum oven. 7.66 g of Product 26-12 was obtained with a yield of 100%.

27.3046 mmol) was then slowly dropwise over 10 min. The reaction solution was stirred for 1 h at −5° C., and then stirred overnight at room temperature. At the end of the reaction, the reaction solution was transferred to a 2 L separatory funnel and extracted with pure water (300 mL) and ethyl acetate (200 mL) to obtain the organic phase; the aqueous phase was extracted with ethyl acetate (200 mL×3), and the obtained organic phases were combined, washed with saturated sodium chloride solution (150 mL×3), then concentrated and evaporated to dryness, the solid was dissolved with a methanol/dichloromethane (1:4) solution (200 mL), silica gel powder (30 g) was added to the obtained solution, and the solution was then evaporated to dryness to obtain a powdery solid; the operations of dry sample load-

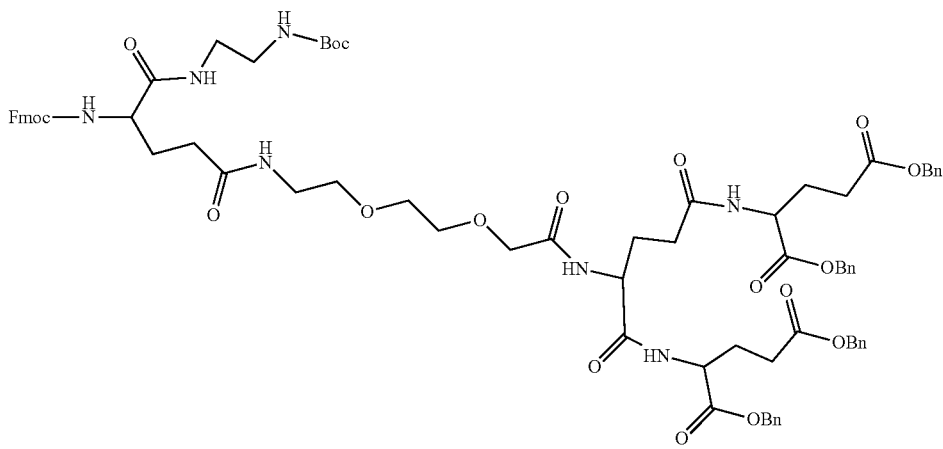

32-26

Compound 26-123 (7.66 g, 6.0677 mmol), Boc-ethylenediamine (1.02 g, 6.3710 mmol, purchased from Innochem), HBTU (3.45 g, 9.1015 mmol), and HOBT (1.23 g, 0.6497 mmol) were added in a 500 mL flask and then dissolved with a proper amount of DMF (100 mL), and the mixed solution was stirred for 30 min at −5° C. to react. DIEA (4.5 mL, ing, column chromatography, and gradient elution with a mixed solution (1% ammonia water:3% methanol/dichloromethane) were carried out; the elution product was then collected, concentrated and evaporated to obtain a solid, and the solid was dried in a vacuum oven. 7.1 g of Product 32-26 was obtained with a yield of 84%.

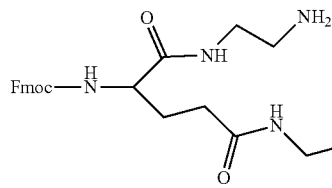
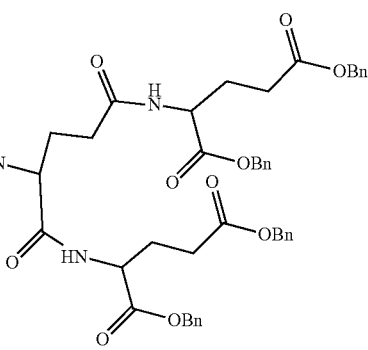

26-124

Compound 32-26 (7.1 g, 5.0550 mmol) was added in a 500 mL flask and then dissolved with dichloromethane (10 mL) and TFA (5.6308 mL, 75.8244 mmol), and the mixed solution was stirred overnight at room temperature to react. At the end of the reaction, the reaction solution was transferred to a 2 L separatory funnel, a saturated sodium bicarbonate solution (300 mL) was then added to adjust the pH of the reaction solution to alkaline, and then ethyl acetate (200 mL) was added for extraction to obtain an organic phase; the aqueous phase was extracted with ethyl acetate (200 mL×3), and the obtained organic phases were combined and washed with a saturated sodium chloride solution (150 mL×3); the obtained solution was then concentrated, evaporated to dryness, and dried in a vacuum oven. 6.6 g of Product 26-12 was obtained with a yield of 100%.

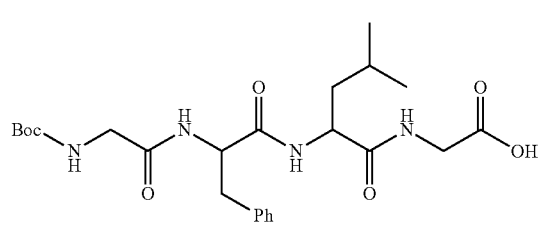

26-116

The Boc-GFLG-OBn (4.1 g, 7.077 mmol, home-made) and 10% Pd/C catalyst (0.05 g) were added into a hydrogenation reactor and then dissolved with DMF (30 mL); the hydrogenation reactor was then sealed and H₂ was charged until the pressure on the hydrogenation reaction device was read as 18 Psi, and then the obtained solution was stirred overnight at room temperature. At the end of the reaction, the reaction solution was filtered with a buchner funnel filled with diatomaceous earth, and the filter cake was washed with DMF (20 mL×3). Product 26-116 was obtained with a yield of 100%.

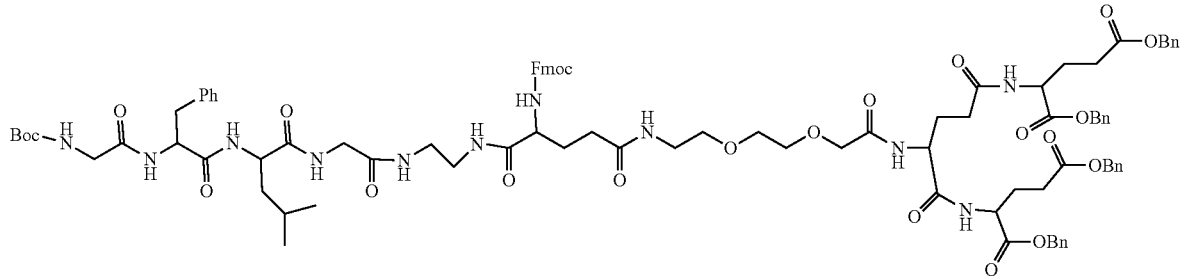

26-125

Compound 26-124 (6.6 g, 5.0550 mmol), Compound 26-116 (3.485 g, 7.077 mmol), HBTU (2.8756 g, 7.5825 mmol), and HOBT (1.0246 g, 7.5825 mmol) were added in a 500 mL flask and then dissolved with a proper amount of DMF (80 mL), and the mixed solution was stirred for 30 min at 0° C. to react. DIEA (3.7597 mL, 22.7475 mmol) was then slowly dropwise over 8 min. The reaction solution was further stirred overnight at 0° C. to react. At the end of the reaction, n-hexane (100 mL) was added, the reaction solution was then oscillated, and the supernatant was discarded; the above operations were repeated three times. Methyl tert-butyl ether (80 mL) and a small amount of n-hexane (10 mL) were then added, the obtained solution was then oscillated, and the supernatant was discarded; the above operations were repeated three times. The reaction solution precipitated to obtain a powdery solid; then, suction filtering was carried out, the filter cake was washed with methyl tert-butyl ether (40 mL×3) and then collected and dissolved with a methanol/dichloromethane (1:4) solution (100 mL); silica gel powder (30 g) was then added to the obtained solution and the solution was evaporated to be powder; the operations of dry sample loading, column chromatography and gradient elution with a mixed solution (3%-7% methanol/dichloromethane) were carried out; the elution product was collected, concentrated and dried in a vacuum oven. 4.3 g of product 26-125 was obtained with a yield of 48%.

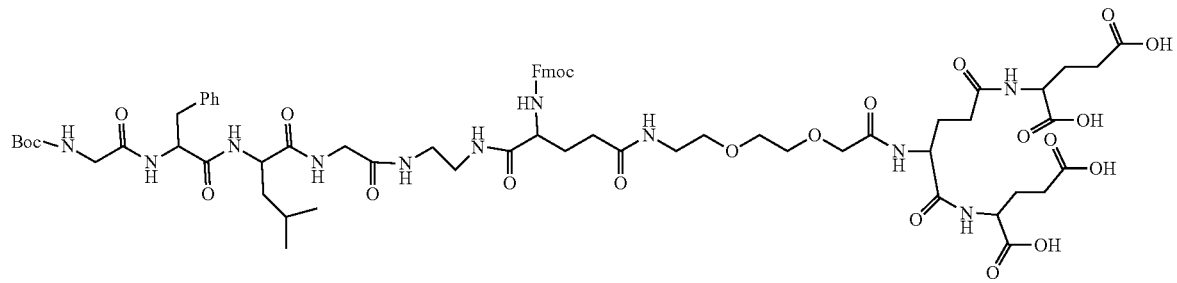

26-127

Compound 26-125 (0.5825 g, 0.3274 mmol) and 10% Pd/C catalyst (0.02 g) were added into a hydrogenation reactor and then dissolved with DMF (30 mL); the hydrogenation reactor was then sealed and $H_2$ was then charged until the pressure on the hydrogenation reaction device was read as 18 Psi, and then the obtained solution was stirred overnight at room temperature. At the end of the reaction, the reaction solution was filtered with a buchner funnel filled with diatomaceous earth, and the filter cake was washed with DMF (20 mL×3). Product 26-127 was obtained with a yield of 100%.

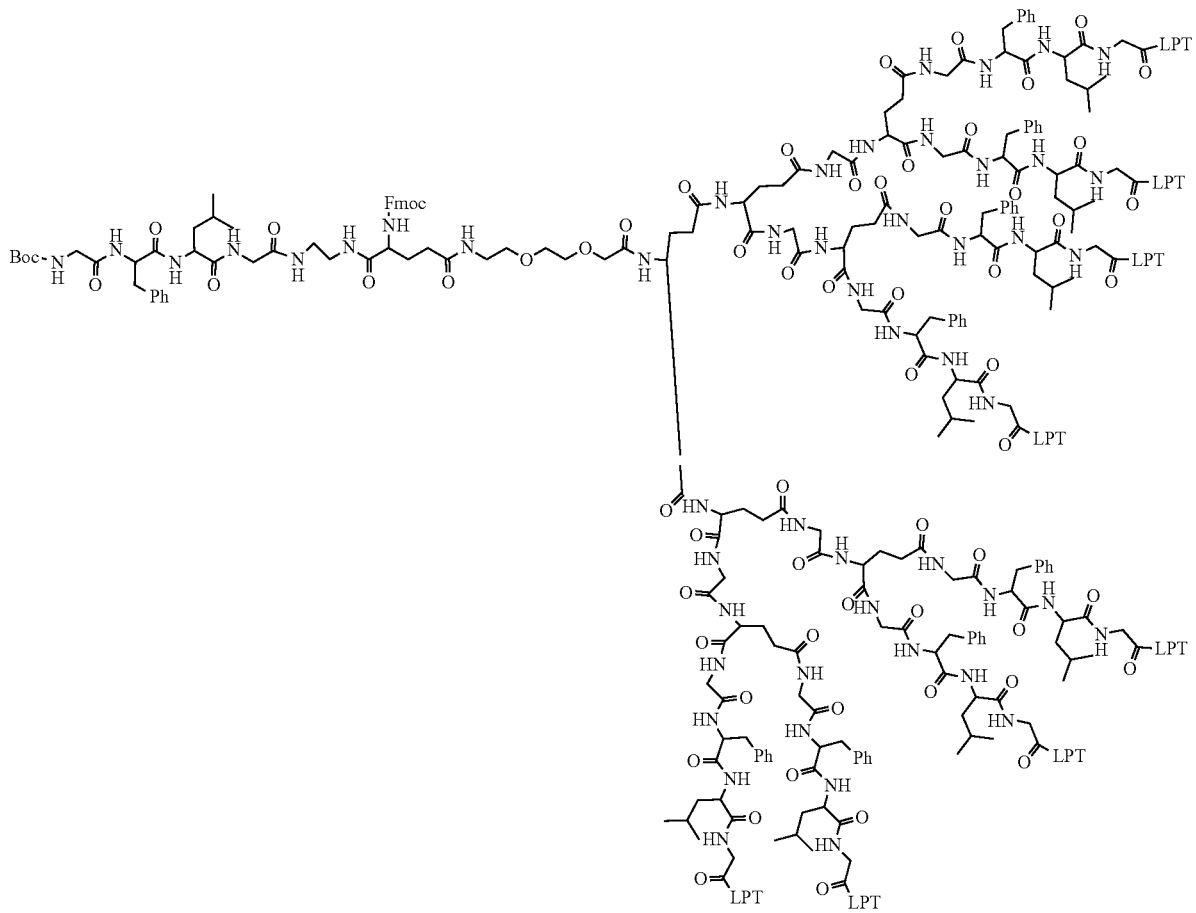

26-128

Compound 26-127 (0.4645 g, 0.3275 mmol), Compound 27-42 (synthesized according to the synthesis method of Compound 24-115) (2.9275 g, 1.4080 mmol), HBTU (0.7452 g, 1.965 mmol), and HOBT (0.2655 g, 1.965 mmol) were added in a 500 mL flask and then dissolved with a proper amount of DMF (50 mL), and the mixed solution was stirred for 30 min at 0° C. to react. DIEA (0.9743 mL, 5.895 mmol) was then slowly dropwise over 3 min. The reaction solution was further stirred overnight at 0° C. to react. At the end of the reaction, n-hexane (100 mL) was added, the reaction solution was then oscillated, and the supernatant was discarded; the above operations were repeated three times. Methyl tert-butyl ether (80 mL) and a small amount of n-hexane (10 mL) were then added, the obtained solution was then oscillated, and the supernatant was discarded; the above operations were repeated three times, and the reaction solution was precipitated to obtain a powdery solid; then, suction filtering was carried out, the filter cake was washed with methyl tert-butyl ether (40 mL×3) and then collected and dissolved with a methanol/dichloromethane (1:4) solution (100 mL); silica gel powder (10 g) was then added to the obtained solution and the solution was evaporated to be powder; the operations of dry sample loading, column chromatography and gradient elution with a mixed solution (1% ammonia water/5%-8% methanol/dichloromethane) were carried out; the elution product was collected, concentrated and dried in a vacuum oven. 1.6 g of product 26-128 was obtained with a yield of 52%.

MALDI-TOF MS: [M+Na$^+$] 9630.62

Product 26-128 (1.6 g, 0.1656 mmol) was added in a 250 mL flask and then dissolved with DMF (30 mL), morpholine (0.2164 mL, 2.4837 mmol) was then added to the obtained solution, and the mixed solution was stirred for 1 h at room temperature to react. At the end of the reaction, n-hexane (100 mL) was added, the reaction solution was then oscillated, and the supernatant was discarded; the above operations were repeated three times. Methyl tert-butyl ether (80 mL) and a small amount of n-hexane (10 mL) were then added, the obtained solution was then oscillated, and the supernatant was discarded; the above operations were repeated three times, and the reaction solution was precipitated to obtain a powdery solid; then, suction filtering was carried out, the filter cake was washed with methyl tert-butyl ether (40 mL×3) and then collected and dissolved with a methanol/dichloromethane (1:4) solution (100 mL); silica gel powder (15 g) was then added to the obtained solution and the solution was evaporated to be powder; the operations of dry sample loading, column chromatography and gradient elution with a mixed solution (1% ammonia water/5%-7% methanol/dichloromethane) were carried out; the elution product was collected, concentrated and dried in a vacuum oven. 1.2 g of Product 26-130 was obtained with a yield of 77%.

MALDI-TOF MS: [M+Na$^+$] 9451.93

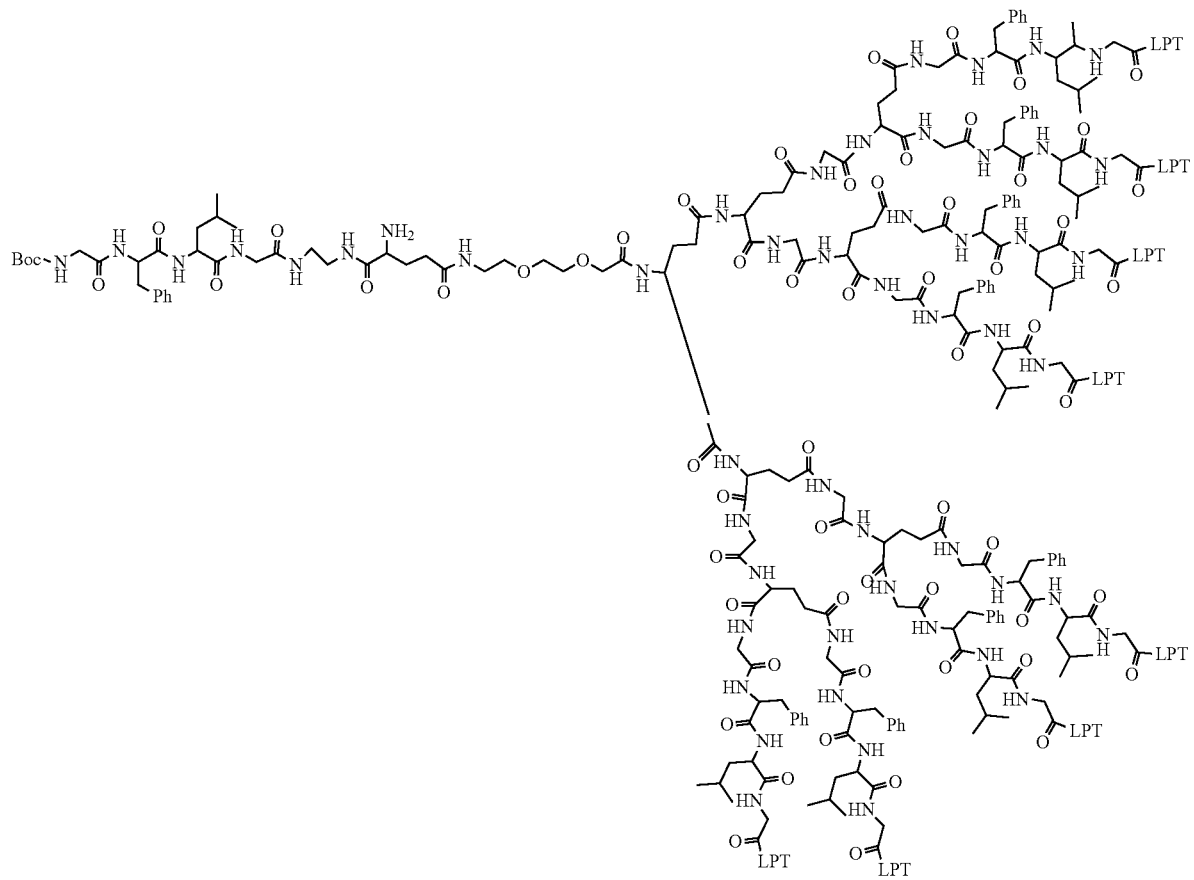

26-130

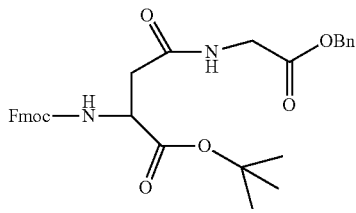

32-16

Fmoc-Asp-OtBu (3.0 g, 7.2917 mmol), H-Gly-OBn (1.26 g, 7.6559 mmol), HBTU (4.15 g, 10.9369 mmol), and HOBT (1.48 g, 10.9369 mmol) were added in a 500 mL flask and then dissolved with DMF (40 mL), and the mixed solution was stirred for 30 min at −5° C. to react. Then DIEA (5.4 mL, 32.8109 mmol) was slowly added dropwise to further react, and 1 h later, the reaction solution was stirred overnight at room temperature to react. At the end of the reaction, the reaction solution was transferred to a 2 L separatory funnel, a saturated sodium bicarbonate solution (300 mL) was then added to adjust the pH of the reaction solution to alkaline, and then ethyl acetate (200 mL) was added for extraction to obtain an organic phase; the aqueous phase was extracted with ethyl acetate (200 mL×3), and the obtained organic phases were combined and washed with a saturated sodium chloride solution (150 mL×3); the obtained solution was then concentrated, evaporated to dryness, and dried in a vacuum oven. The reaction solution was transferred to a 2 L separatory funnel. 10.1 g of Product 32-14 was obtained with a yield of 100%.

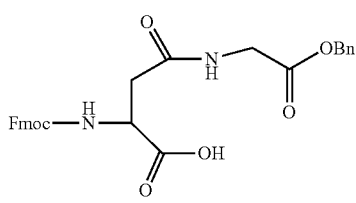

32-18

Compound 32-16 (7.9 g, 14.5826 mmol) was added in a 500 mL flask and then dissolved with dichloromethane (8 mL) and TFA (10.8 mL, 145.8260 mmol), and the mixed solution was stirred overnight at room temperature to react. At the end of the reaction, a saturated sodium bicarbonate solution (300 mL) was added to adjust the pH to alkaline, and the obtained solution was then extracted with ethyl acetate (200 mL) to obtain the organic phase; the aqueous phase was extracted with ethyl acetate (200 mL×3), and the obtained organic phases were combined, washed with a saturated sodium chloride solution (150 mL×3), then concentrated and evaporated to dryness, the solid was dissolved with a methanol/dichloromethane (1:4) solution (100 mL), silica gel powder (20 g) was added to the obtained solution, and the solution was then evaporated to become powder; the operations of dry sample loading, column chromatography, and gradient elution with a mixed solution with 1%-4% methanol/dichloromethane were carried out; the elution product was then collected, concentrated and dried in a vacuum oven. 6.1 g of Product 32-18 was obtained with a yield of 86%.

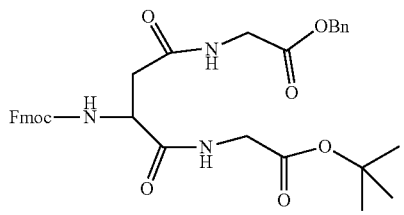

32-20

Compound 32-18 (6.1 g, 12.4864 mmol), H-Gly-OtBu (2.2 g, 13.1107 mmol), HBTU (7.1 g, 18.7296 mmol), and HOBT (2.5 g, 18.7296 mmol) were added in a 500 mL flask and then dissolved with DMF (80 mL), and the mixed solution was stirred for 30 min at −5° C. to react. Then DIEA (9.2 mL, 56.1888 mmol) was slowly added dropwise to further react, and 1 h later, the reaction solution was stirred overnight at room temperature. At the end of the reaction, the reaction solution was transferred to a 2 L separatory funnel and extracted with a saturated sodium bicarbonate solution (300 mL×3) and ethyl acetate (200 mL×3); the aqueous phase was extracted with ethyl acetate (200 mL×3), and the obtained organic phases were combined, washed with a saturated sodium chloride solution (150 mL×3), then concentrated and evaporated to dryness, the solid was then dissolved with a methanol/dichloromethane (1:4) solution (100 mL), silica gel powder (20 g) was added to the obtained solution, and the solution was then evaporated to dryness to obtain a powdery solid; the operations of dry sample loading, column chromatography, and gradient elution with a mixed solution (0.1%-0.2% methanol/dichloromethane) were carried out; the elution product was then collected, concentrated and dried in a vacuum oven. 6.1 g of Product 32-20 was obtained with a yield of 79%.

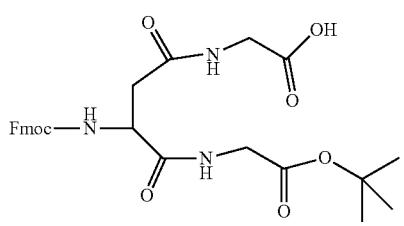

32-54

Compound 32-20 (0.357 g, 0.58 mmol) and 10% Pd/C catalyst (0.02 g) were added into a hydrogenation reactor and then dissolved with DMF (30 mL); the hydrogenation reactor was then sealed and $H_2$ was then charged until the pressure on the hydrogenation reaction device was read as 18 Psi, and then the obtained solution was stirred overnight at room temperature. At the end of the reaction, the reaction solution was filtered with a buchner funnel filled with diatomaceous earth, and the filter cake was washed with DMF (20 mL×3). Product 32-54 was obtained with a yield of 100%.

32-46

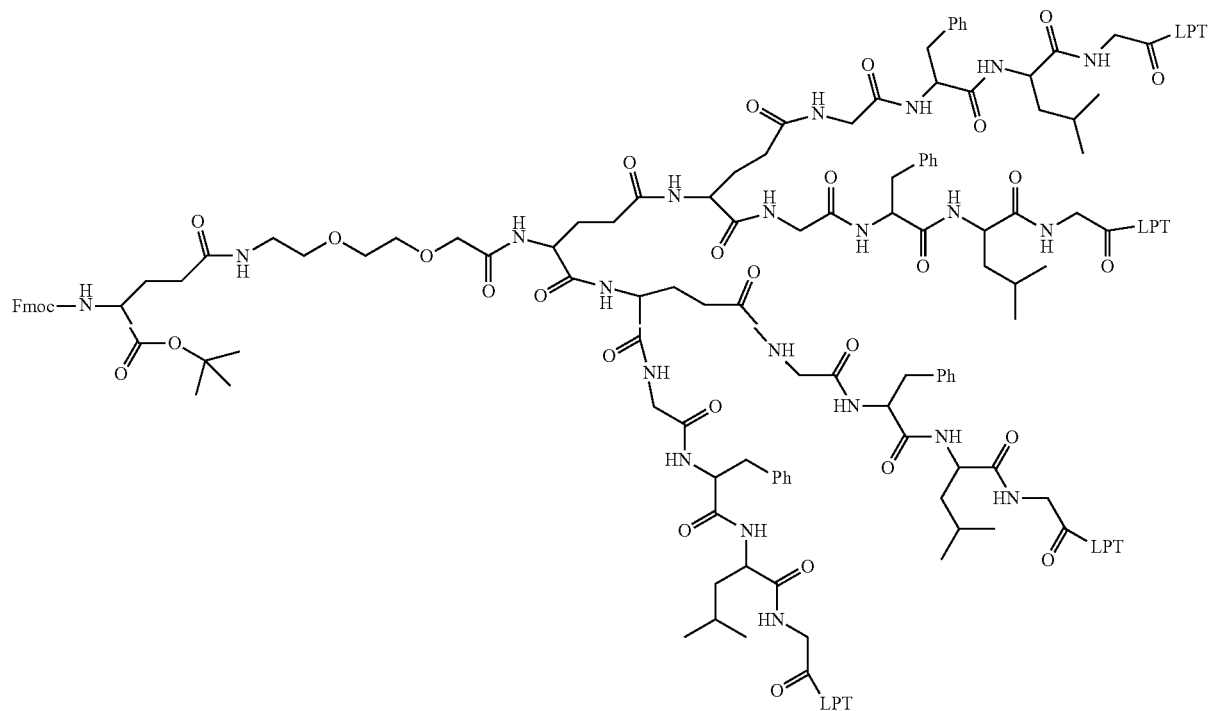

Compound 33-7 (1.0 g, 1.0941 mmol), GFLG-LPT (synthesized according to the synthesis route of Compound 14-128) (4.6 g, 4.8142 mmol), HBTU (2.49 g, 6.5649 mmol), HOBT (0.89 g, 6.5649 mmol) were added in a 500 mL flask and then dissolved with a proper amount of DMF (80 mL), and the mixed solution was stirred for 30 min at 0° C. to react. DIEA (3.3 mL, 19.6946 mmol) was then slowly dropwise over 5 min and the obtained solution was stirred overnight at 0° C. to further react. At the end of the reaction, n-hexane (100 mL) was added, the reaction solution was then oscillated, and the supernatant was discarded; the above operations were repeated three times. Methyl tert-butyl ether (80 mL) and a small amount of n-hexane (10 mL) were then added, the obtained solution was then oscillated, and the supernatant was discarded; the above operations were repeated three times, and the reaction solution was precipitated to obtain a solid; then, suction filtering was carried out, the filter cake was washed with methyl tert-butyl ether (40 mL×3) and then collected and dissolved with a methanol/dichloromethane (1:4) solution (100 mL); silica gel powder (20 g) was then added to the obtained solution and the solution was evaporated to be powder; the operations of dry sample loading, column chromatography and gradient elution with a mixed solution (1% ammonia water/2%-3% methanol/dichloromethane) were carried out; the elution product was collected, concentrated and dried in a vacuum oven. 3.5 g of Product 32-46 was obtained with a yield of 70%.

32-48

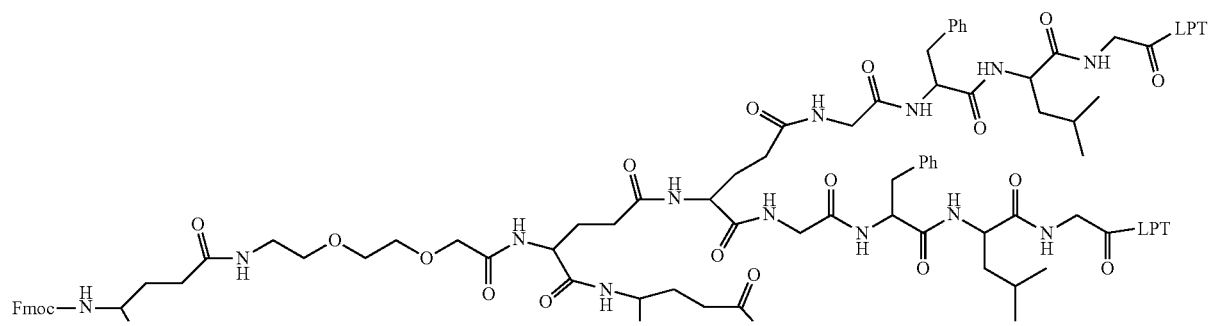

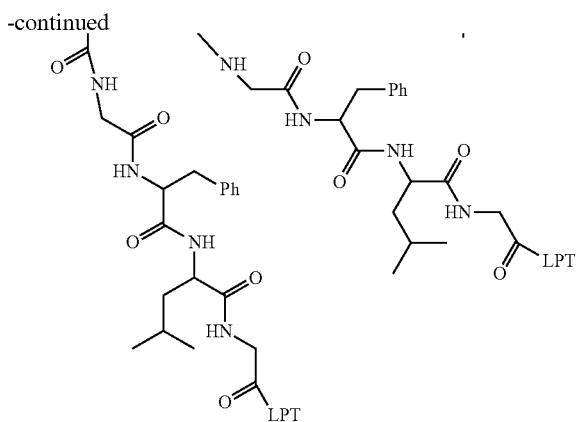

-continued

Compound 32-46 (2.7 g, 0.5794 mmol) was added in a 250 mL flask and then dissolved with dichloromethane (8 mL) and TFA (3 mL, 8.6913 mmol), and the mixed solution was stirred overnight at room temperature to react. At the end of the reaction, the reaction solution was evaporated with a rotary evaporator to obtain an oily product. Methyl tert-butyl ether (60 mL) was then added; the reaction solution was precipitated to obtain a powdery solid; suction filtering was carried out, the filter cake was washed with methyl tert-butyl ether (40 mL×3) and then collected, and dried in a vacuum oven. 3.1 g of crude product 32-48 was obtained with a yield of 100%.

Compound 32-48 (2.67 g, 0.5794 mmol), Compound 28-146 (synthesized according to the synthesis method of Compound 16-159) (0.52 g, 0.5794 mmol), HBTU (0.33 g, 0.8691 mmol), and HOBT (0.12 g, 0.8691 mmol) were added in a 500 mL flask and then dissolved with DMF (40 mL), and the mixed solution was stirred for 30 min at −5° C. to react. Then DIEA (0.43 mL, 2.6073 mmol) was slowly added dropwise to further react, and 1 h later, the reaction solution was stirred overnight at room temperature. At the end of the reaction, n-hexane (100 mL×8) and a small amount of methyl tert-butyl ether (30 ml×8) were added to precipitate the reaction solution to obtain a solid, and the solid was then filtered by suction and then dried in a vacuum oven. 3.17 g of Product 32-49 was obtained with a yield of 100%.

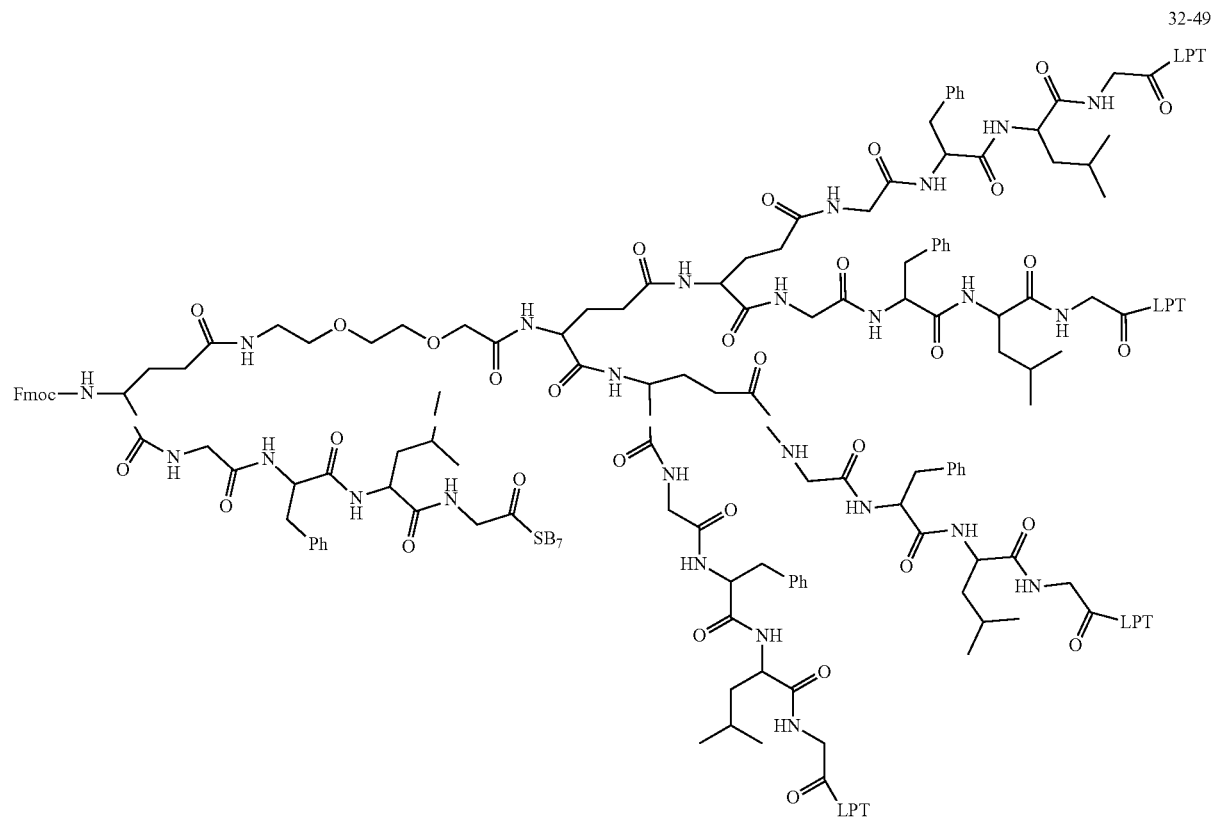

26-55

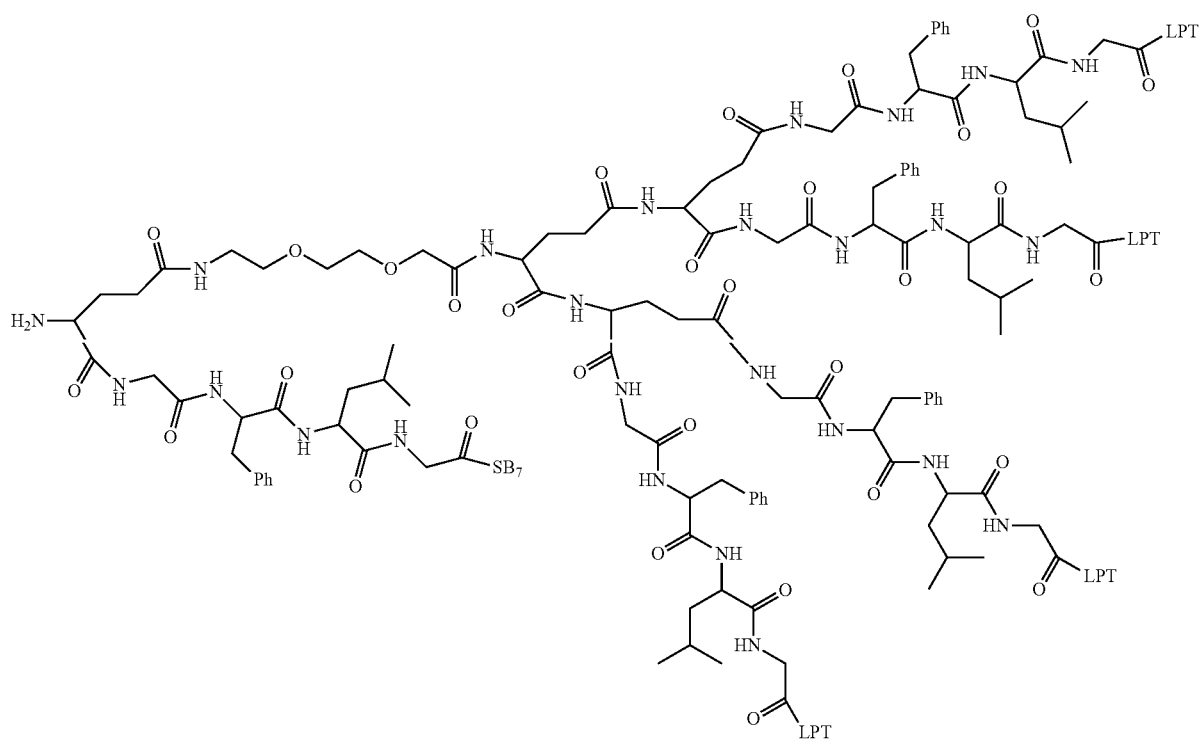

Compound 32-49 (3.17 g, 2.0625 mmol) was added in a 250 mL flask and then dissolved with DMF (15 mL), morpholine (1.5 mL, 17.382 mmol) was then added to the obtained solution, and the mixed solution was stirred at room temperature to react for 1 h. At the end of the reaction, n-hexane (100 mL) was added, the reaction solution was then oscillated, and the supernatant was discarded; the above operations were repeated three times. Methyl tert-butyl ether (80 mL) and a small amount of n-hexane (10 mL) were then added, the obtained solution was then oscillated, and the supernatant was discarded; the above operations were repeated three times, and the reaction solution was precipitated to obtain a powdery solid; then, suction filtering was carried out, the filter cake was washed with methyl tert-butyl ether (40 mL×3) and then collected and dissolved with a methanol/dichloromethane (1:4) solution (100 mL); silica gel powder (20 g) was then added to the obtained solution and the solution was evaporated to be powder; the operations of dry sample loading, column chromatography and gradient elution with a mixed solution (1% ammonia water/ 4%-10% methanol/dichloromethane) were carried out; the elution product was collected, concentrated and dried in a vacuum oven. 2.1 g of Product 26-55 was obtained with a yield of 70.4%.

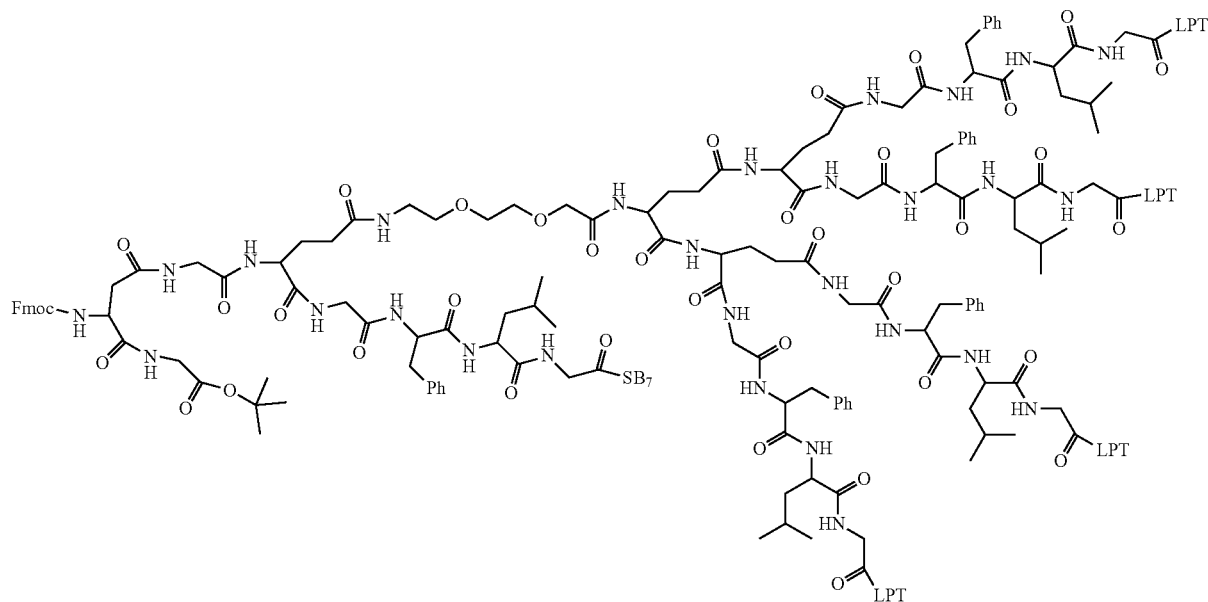

32-57

Compound 32-54 (0.2 g, 0.4036 mmol), Compound 26-55 (2.1 g, 0.3996 mmol), HBTU (0.23 g, 0.5994 mmol), and HOBT (0.08 g, 0.5994 mmol) were added in a 500 mL flask and then dissolved with DMF (30 mL), and the mixed solution was stirred for 30 min at −5° C. to react. Then DIEA (0.3 mL, 0.5994 mmol) was slowly added dropwise to further react, and 1 h later, the reaction solution was stirred overnight at room temperature. At the end of the reaction, methyl tert-butyl ether (80 mL) was added to the reaction solution; the obtained solution was then rested in a refrigerator and 30 min later, the solution was taken out and has solid precipitates; suction filtering was carried out, the filter cake was washed with methyl tert-butyl ether (40 mL×3) and then collected, and dried in a vacuum oven. 1.9 g of Product 32-57 was obtained with a yield of 82.9%.

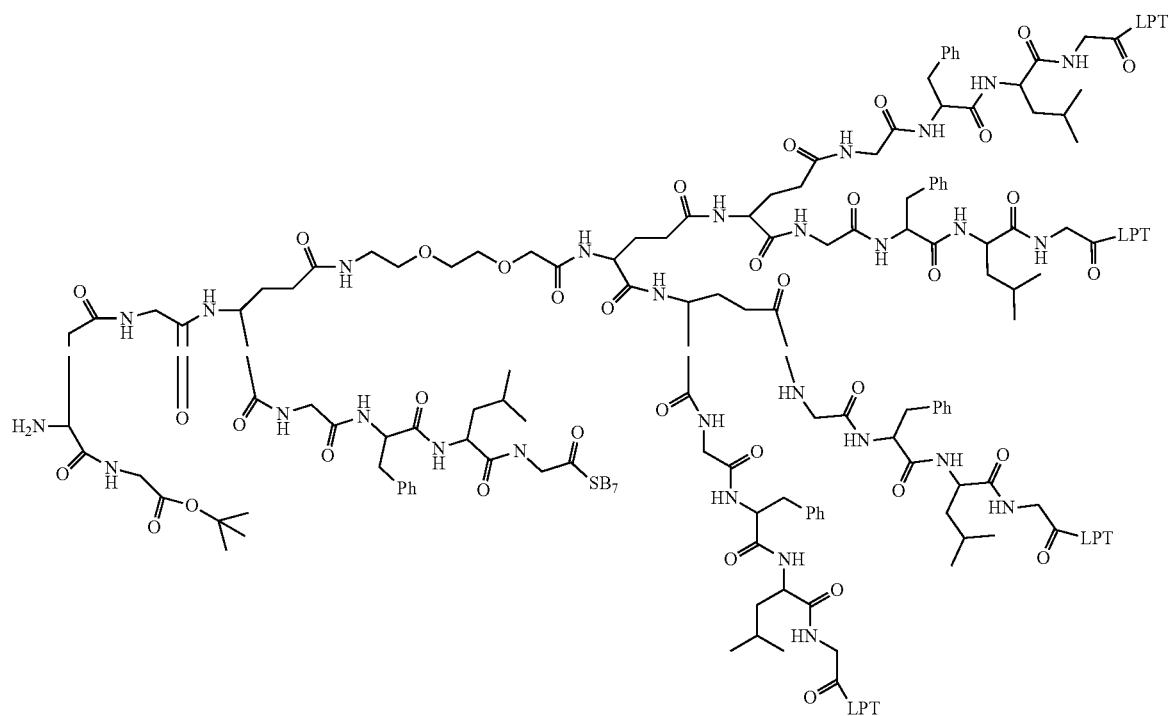

32-61

Compound 32-57 (1.9 g, 0.3306 mmol) was added in a 250 mL flask and then dissolved with DMF (10 mL), morpholine (0.8 mL, 9.9174 mmol) was then added to the obtained solution, and the mixed solution was stirred for 1 h at room temperature to react. At the end of the reaction, n-hexane (100 mL) was added, the reaction solution was then oscillated, and the supernatant was discarded; the above operations were repeated three times. Methyl tert-butyl ether (80 mL) and a small amount of n-hexane (10 mL) were then added, the obtained solution was then oscillated, and the supernatant was discarded; the above operations were repeated three times, and the reaction solution was precipitated to obtain a powdery solid; then, suction filtering was carried out, the filter cake was washed with methyl tert-butyl ether (40 mL×3) and then collected and dissolved with a methanol/dichloromethane (1:4) solution (100 mL); silica gel powder (10 g) was then added to the obtained solution and the solution was evaporated to be powder; the operations of dry sample loading, column chromatography and gradient elution with a mixed solution (1% ammonia water/2%-7% methanol/dichloromethane) were carried out; the elution product was collected, concentrated and dried in a vacuum oven. 0.9 g of Product 32-55 was obtained with a yield of 51%.

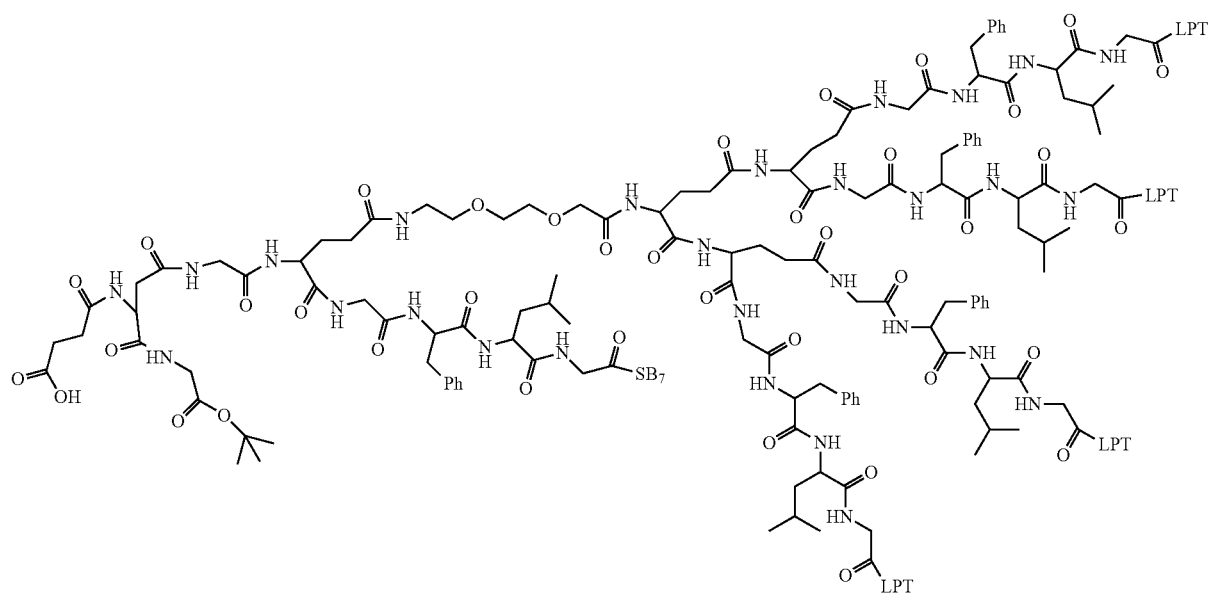

32-63

Compound 32-61 (0.9 g, 0.1624 mmol) was added to a 500 mL flask and then dissolved with DMF (10 mL), and then DIEA (0.1 mL, 0.6499 mmol) and succinic anhydride (0.049 g, 0.4873 mmol) were slowly added dropwise to further react, and the reaction was stirred overnight at room temperature to react. At the end of the reaction, n-hexane (100 mL) was added, the reaction solution was then oscillated, and the supernatant was discarded; the above operations were repeated three times. Methyl tert-butyl ether (80 mL) and a small amount of n-hexane (10 mL) were then added, the obtained solution was then oscillated, and the supernatant was discarded; the above operations were repeated three times. The reaction solution precipitated to obtain a powdery solid; then, suction filtering was carried out, the filter cake was washed with methyl tert-butyl ether (40 mL×3) and then collected and dissolved with a methanol/dichloromethane (1:4) solution (100 mL); silica gel powder (10 g) was then added to the obtained solution and the solution was evaporated to be powder; the operations of dry sample loading, column chromatography and gradient elution with a mixed solution (1% ammonia water/5%-7% methanol/dichloromethane) were carried out; the elution product was collected, concentrated and dried in a vacuum oven. 0.91 g of product 32-63 was obtained with a yield of 68%.

26-151

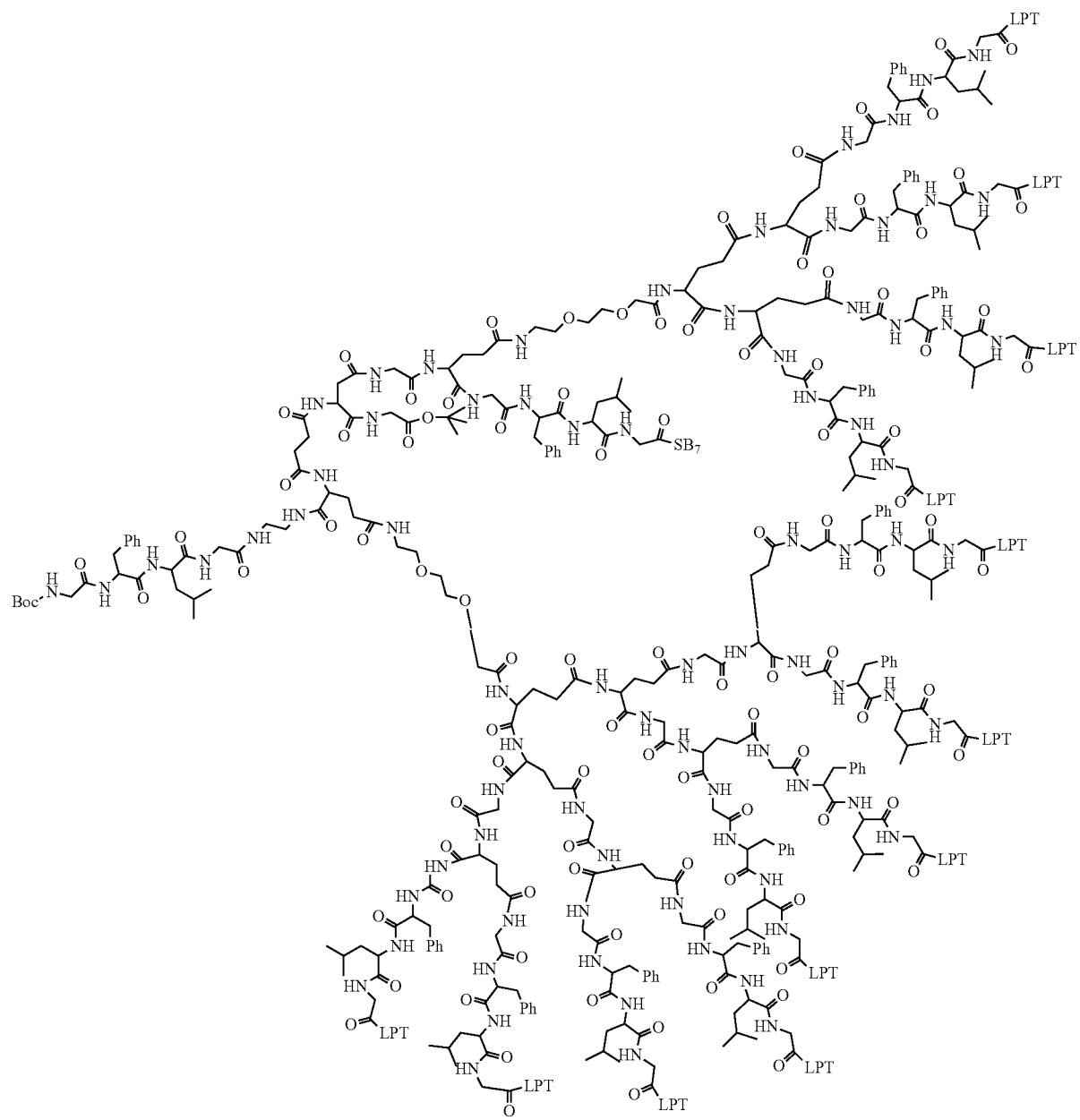

Compound 32-63 (0.65 g, 0.1152 mmol), Compound 26-130 (0.9891 g, 0.1048 mmol), HBTU (0.0596 g, 0.1571 mmol), and HOBT (0.0212 g, 0.1571 mmol) were added in a 500 mL flask and then dissolved with an appropriate amount of DMF (30 mL), and the mixed solution was stirred for 30 min at −5° C. to react. Then DIEA (0.08 mL, 0.4715 mmol) was slowly added dropwise to further react, and 1 h later, the reaction solution was stirred overnight at room temperature. At the end of the reaction, n-hexane (100 mL) was added, the reaction solution was then oscillated, and the supernatant was discarded; the above operations were repeated three times. Methyl tert-butyl ether (80 mL) and a small amount of n-hexane (10 mL) were then added, the obtained solution was then oscillated, and the supernatant was discarded; the above operations were repeated three times. The reaction solution precipitated to obtain a powdery solid; then, suction filtering was carried out, the filter cake was washed with methyl tert-butyl ether (40 mL×3) and then collected and dissolved with a methanol/dichloromethane (1:4) solution (100 mL); silica gel powder (10 g) was then added to the obtained solution and the solution was evaporated to be powder; the operations of dry sample loading, column chromatography and gradient elution with a mixed solution (1% ammonia water/3%-6% methanol/dichloromethane) were carried out; the elution product was collected, concentrated and dried in a vacuum oven. 1.2 g of product 26-151 was obtained with a yield of 80%.

MALDI-TOF MS: [M+Na$^+$] 15005.63

26-156

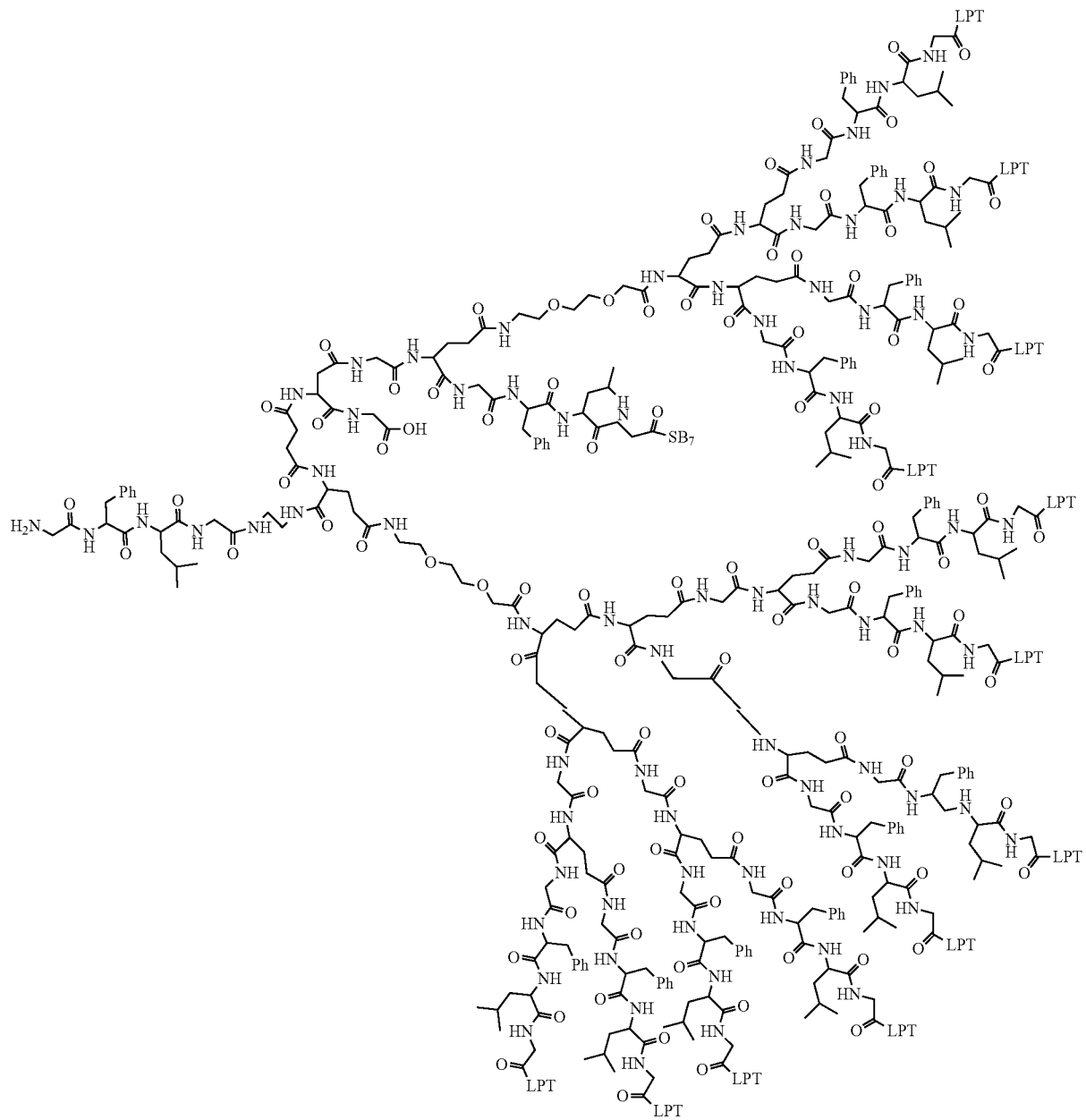

Compound 26-151 (1.2 g, 0.0008 mmol) was added in a 250 mL flask and then dissolved with dichloromethane (8 mL) and TFA (0.088 mL, 0.001 mmol), and the mixed solution was stirred overnight at room temperature to react. At the end of the reaction, the reaction solution was evaporated with a rotary evaporator to obtain an oily product. Methyl tert-butyl ether (60 mL) was then added; the reaction solution was precipitated to obtain a powdery solid; suction filtering was carried out, the filter cake was washed with methyl tert-butyl ether (40 mL×3) and then collected and dissolved with a methanol/dichloromethane (1:4) solution (100 mL); silica gel powder (10 g) was then added to the obtained solution and the solution was evaporated to be powder; the operations of dry sample loading, column chromatography and gradient elution with a mixed solution (1% ammonia water/5%-7% methanol/dichloromethane) were carried out; the elution product was collected, concentrated and dried in a vacuum oven. 0.45 g of product 26-156 was obtained with a yield of 41%.

$^1$H-NMR (400 MHz, DMSO-$d_6$) δ 9.83 (s, 15H), 8.76-8.50 (d, 36H), 8.20-7.93 (m, 85H), 7.82-7.69 (m, 27H), 7.50-7.05 (m, 148H), 6.75-6.45 (m, 20H), 5.31-5.18 (m, 25H), 4.77-4.14 (m, 106H), 3.84-3.56 (m, 82H), 3.11-2.68 (m, 81H), 2.33-2.03 (m, 36H), 1.64-1.42 (m, 43H), 1.29-1.18 (m, 36H), 0.95-0.69 (m 84H).

26-158

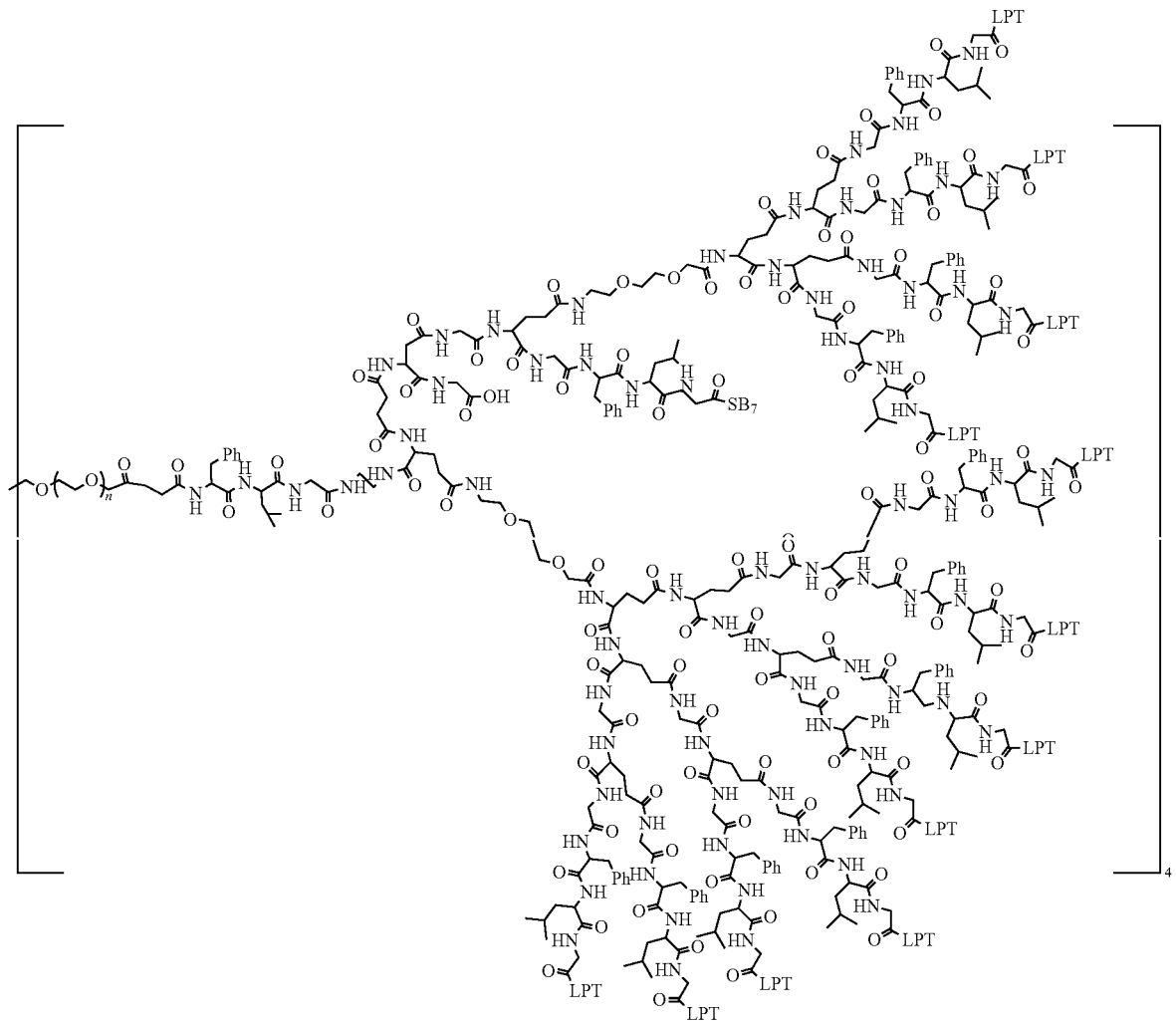

Product 26-156 (0.45 g, 0.003 mmol) was added in a 250 mL flask and dissolved with DMF (10 mL), the resulting solution was stirred at −5° C. for 30 min to react, and DIEA (0.034 is mL, 0.2058 mmol) was then slowly added dropwise over 3 min. The obtained solution was further stirred for 30 min 4ARM-SCM-40K (0.2879 g, 0.0006 mmol, purchased from JenKem) was added, and the reaction solution was further stirred for 20 min at −5° C.; and then the reaction solution was slowly stirred in the dark for one week at room temperature to react. At the end of the reaction, methyl tert-butyl ether (40 mL) was then added to separate out a solid by precipitation; suction filtering was then carried out, the filter cake was washed with methyl tert-butyl ether (40 mL×3) and then dissolved with a methanol/dichloromethane (1:4) solution (100 mL), silica gel powder (10 g) was added to the obtained solution, and the solution was then evaporated to dryness to obtain a powdery solid; the operations of dry sample loading, column chromatography, and gradient elution with a mixed solution (1% ammonia water:5%-7% methanol/dichloromethane) were carried out; the elution product was then collected, concentrated, evaporated to obtain a solid, and the solid was dried in a vacuum oven. 0.2 g of Product 26-158 was obtained with a yield of 29%.

$^{1}$H-NMR (400 MHz, DMSO-d$_6$) δ 8.76-8.50 (m, 188H), 8.22-7.95 (m, 341H), 7.80-7.67 (m, 137H), 7.34-7.07 (m, 476H), 6.71-6.51 (m, 182H), 5.38-5.20 (m, 199H), 4.82-4.46 (m, 415H), 3.55-3.50 (m, 3814H), 3.12-2.64 (m, 582H), 2.37-2.25 (m, 122H), 1.41-1.36 (m, 26H), 1.35-1.32 (m, 65H), 1.24-1.18 (m, 223H), 0.89-0.682 (m, 336H).

26-168

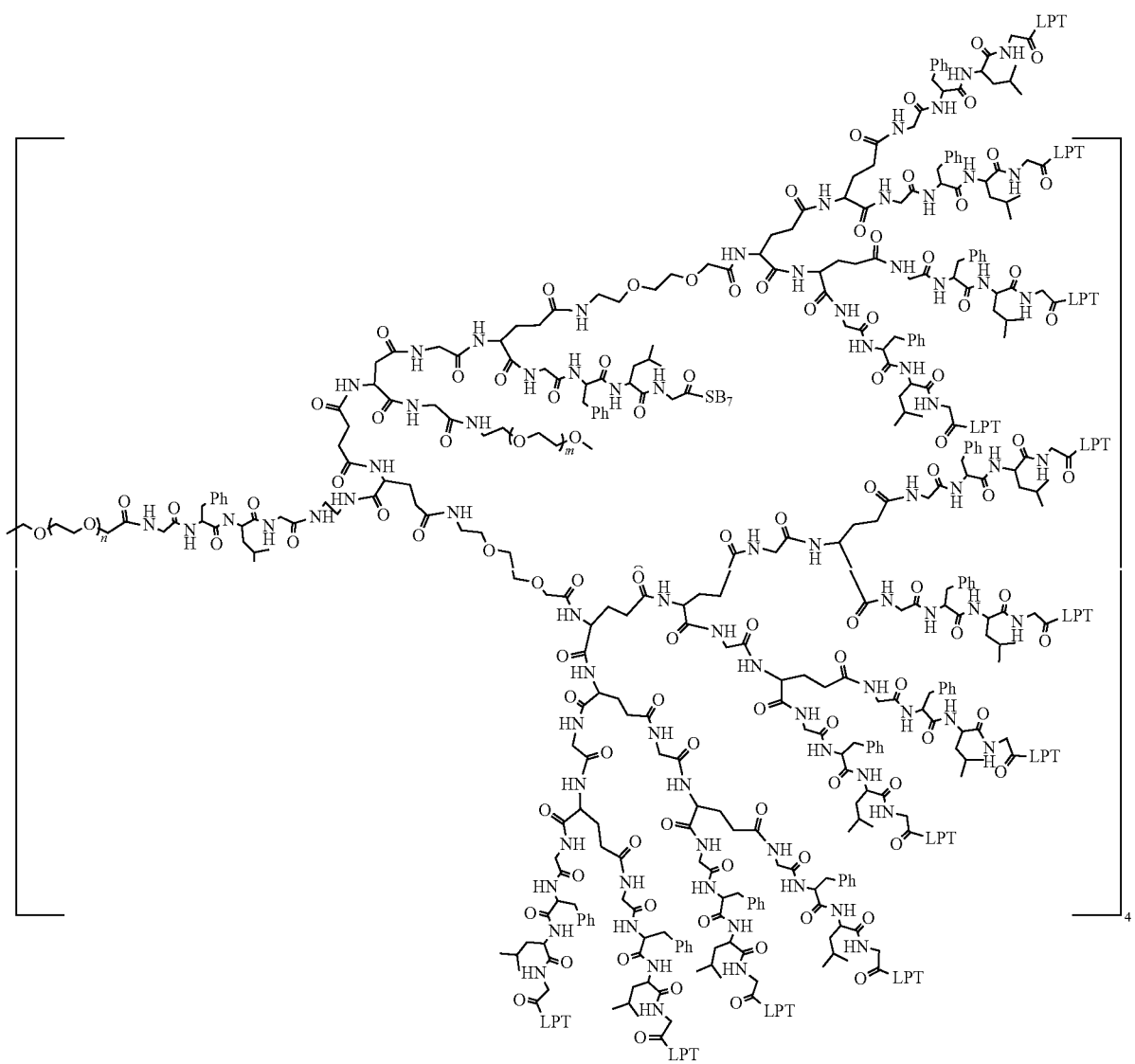

Compound 26-158 (0.21 g, 0.002 mmol), M-NH$_2$-10K·HCl (0.1311 g, 0.001 mmol, purchased from JenKem), HBTU (0.0017 g, 0.001 mmol), and HOBT (0.0047 g, 0.001 mmol) were added in a 250 mL flask and then dissolved with DMF (40 mL), and the mixed solution was stirred at −5° C. for 30 min. DIEA (0.1 mL) was then slowly dropwise over 3 min. The reaction solution was first stirred for 1 h at −5° C. to react, and then slowly stirred for one week in the dark at room temperature to further react. At the end of the reaction, methyl tert-butyl ether (30 mL) were added, the reaction solution was then oscillated and then precipitated to obtain a solid product; suction filtering was then carried out, the filter cake was washed with methyl tert-butyl ether (40 mL×3) and dissolved with a methanol/dichloromethane (1:4) solution (100 mL), silica gel powder (10 g) was added to the obtained solution, and the solution was then evaporated to dryness to obtain a powdery solid; the operations of dry sample loading, column chromatography, and gradient elution with a mixed solution (1% ammonia water/5%-7% methanol/dichloromethane) were carried out; the elution product was then collected, concentrated, and evaporated into a solid, and the solid was dried in a vacuum oven, thus obtaining a crude product; the crude product was then dissolved with absolute ethanol (15 mL) and dichloromethane (5 mL), and methyl tert-butyl ether (100 mL×3) was added and a powdery solid was then precipitated; the suction filtering was carried out and the filter cake was washed with methyl tert-butyl ether (40 mL×3) and dried in the vacuum oven. 31 mg of Product 26-168 was obtained with a yield of 11%.

Example 23: Synthesis of Compound X

X-1

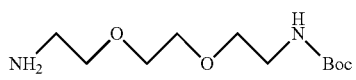

1,2-bis(2-aminoethoxy)ethane (20 mL, 136 mmol) was measured and then dissolved with dichloromethane (80 mL) and triethylamine (37.9 mL, 272 mmol) was then added to the resulting solution. Di-tert-butyl dicarbonyl (29 g, 136 mmol) was then slowly added with stirring. At the end of the reaction, 90 g of silica gel powder was added to the reaction solution, and the obtained solution was then evaporated to dryness. The operations of dry sample loading, column chromatography and gradient elution with dichloromethane-1% ammonia water:5% methanol were then carried out. The elution solution was then evaporated to dryness. 6 g of the product was obtained with a yield of 18%.

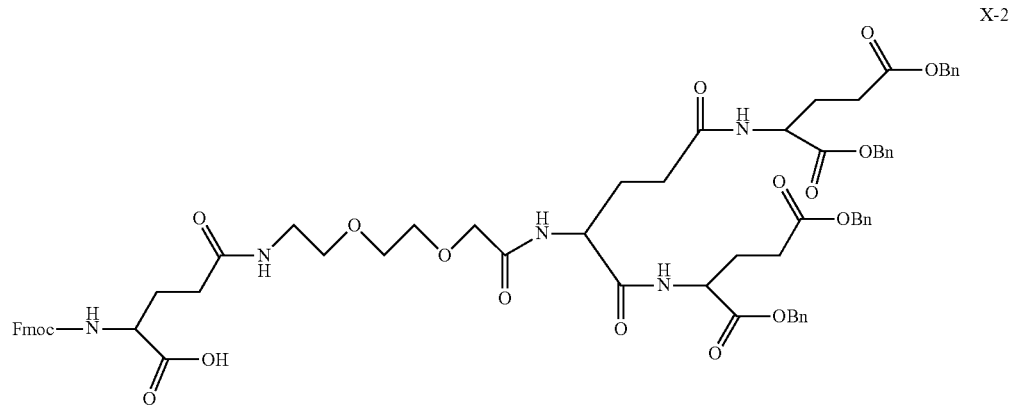

X-2

Compound 24-69 (5.5 g, 4.17 mmol) was weighed, dichloromethane (5 mL) and TFA (6.19 mL, 83.4 mmol) were added sequentially, and the resulting solution was then treated by ultrasonic until Compound 24-69 was dissolved; the mixed solution was stirred to react. At the end of the reaction, the reaction solution was concentrated and the concentrated product was then dissolved with ethyl acetate (100 mL) and extracted with a saturated sodium bicarbonate solution (500 mL) and the aqueous phase became alkaline; then, the organic phase was separated, and the aqueous phase was extracted three times with ethyl acetate (50 mL×3) until there was no product in the aqueous phase; the organic phases were combined, and washing with a saturated sodium chloride solution (50 mL) was carried out once; the organic phase was concentrated and evaporated to dryness to obtain the product.

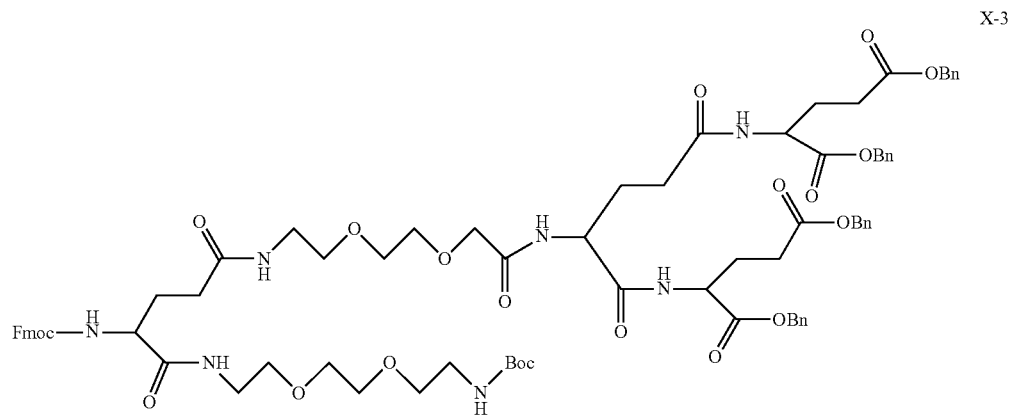

X-3

The reactants, Compound X-1 (1.08 g, 4.37 mmoL), Compound X-2 (4.17 mmoL), HBUT (2.37 g, 6.25 mmoL), and HOBT (0.84 g, 6.25 mmoL) were added into a 250 mL reaction flask and then dissolved with DMF (40 mL); the resulting solution was then stirred for 0.5 h at 0° C.; DIEA (3.1 mL, 18.76 mmoL) was then slowly added dropwise, and the mixed solution was then stirred to react. At the end of the reaction, the reaction solution was extracted with deionized water (100 mL) and ethyl acetate (100 mL), the organic phase was then separated, the aqueous phase was extracted three times with ethyl acetate (50 mL×3), and the obtained organic phases were then combined, washed twice with a saturated sodium chloride solution (50 mL×2), and then evaporated to dryness to obtain the product.

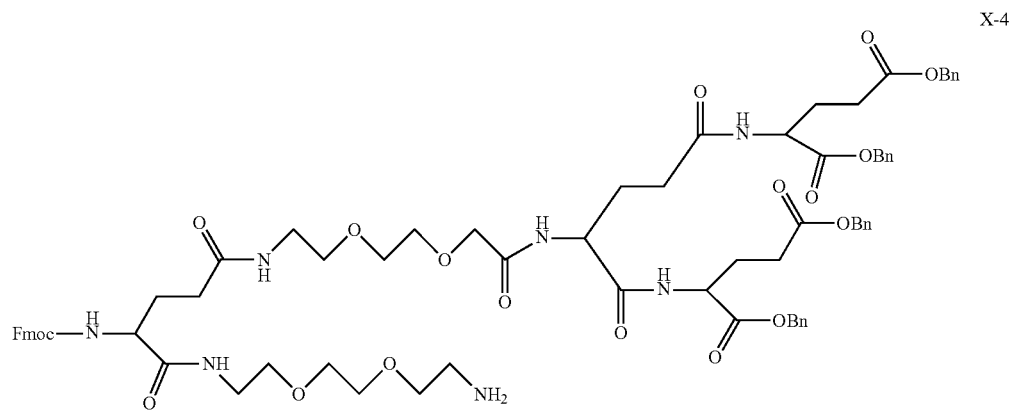

X-4

Compound X-3 (4.17 mmol) was weighed, dichloromethane (5 mL) and TFA (6.19 mL, 83.4 mmol) were added sequentially, and the resulting solution was then treated by ultrasonic until Compound 24-69 was dissolved; the mixed solution was stirred to react. At the end of the reaction, the reaction solution was concentrated and the concentrated product was then dissolved with ethyl acetate (100 mL); a saturated sodium bicarbonate solution was then added until the aqueous phase became alkaline; then, the organic phase was separated, and the aqueous phase was extracted three times with ethyl acetate (50 mL×3) until there was no product in the aqueous phase; the organic phases were combined, and washing with a saturated sodium chloride solution (50 mL) was carried out once; the organic phase was concentrated and evaporated to dryness. The product was obtained with a yield of 100%.

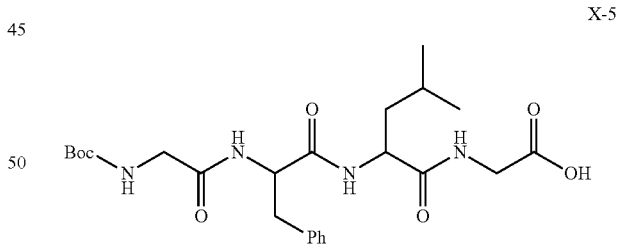

X-5

The reactant Boc-GFLG-OBn (home-made, 5 g, 8.58 mmoL) was weighed and added into a hydrogenation device and then dissolved with DMF (30 mL) and then 10% Pd/C (0.04 g) was then added to the resulting solution; the hydrogenation device was then sealed and $H_2$ was introduced in the device to a pressure of 18 psi. The mixed solution was then stirred overnight at room temperature. After the reaction was found to be completed from the monitoring of the TLC, the reaction solution was taken out and evenly dropwise added to a sand core funnel filled with compacted diatomaceous earth and suction filtering was carried out; the diatomaceous earth was then washed with DMF (90 mL) until there was no product in the diatomaceous earth. A reaction product solution was thus obtained.

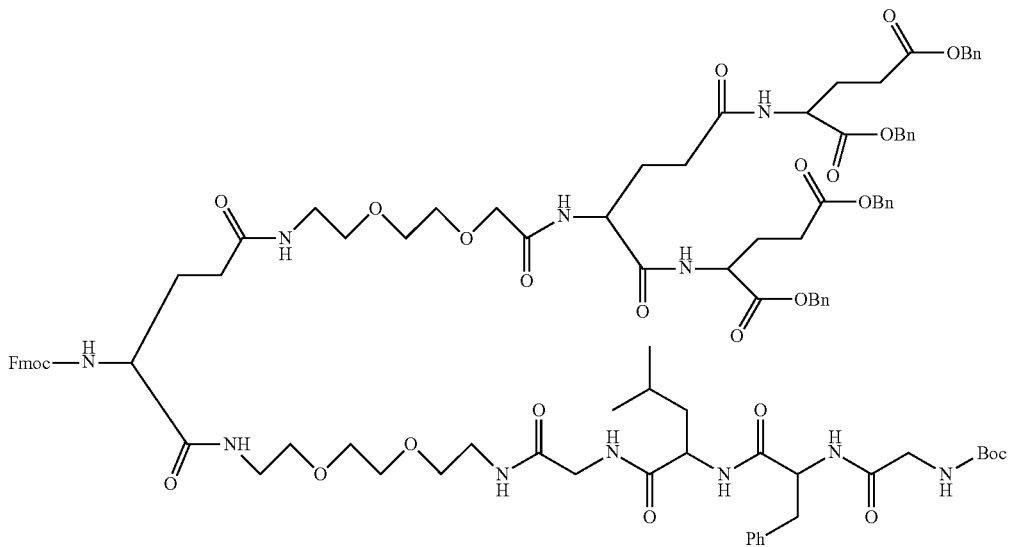

X-6

Reactants, the solution of Compound X-5 (4.37 mmoL), Compound X-4 (4.17 mmoL), HBUT (2.37 g, 6.25 mmoL), and HOBT (0.84 g, 6.25 mmoL) were added into a 250 mL reaction flask and then dissolved with DMF (40 mL); the resulting solution was then stirred for 0.5 h at 0° C.; DIEA (3.1 mL, 18.76 mmol) was then slowly added dropwise, and the mixed solution was then stirred to react. At the end of the reaction, the reaction solution was extracted with deionized water (100 mL) and ethyl acetate (100 mL), the organic phase was then separated, the aqueous phase was extracted three times with ethyl acetate (50 mL×3), and the obtained organic phases were then combined, washed twice with a saturated sodium chloride solution (50 mL×2), and then evaporated to dryness. The product was obtained with a yield of 100%.

Reactant Compound X-6 was added into a 250 mL flask and then a DMF solution (20 mL) and morpholine (7.2 mL, 83.7 mmol) were added sequentially; the resulting solution was stirred at room temperature to react. 3 h later, the reaction ended. The reaction solution was precipitated with methyl tert-butyl ether (100 mL) and n-hexane (200 mL) to obtain a powder; suction filtering was then carried out; then, the obtained solid product was dissolved with dichloromethane (50 mL), silica gel powder was then added, and the obtained solution was evaporated to dryness. The operations of dry sample loading, column chromatography, and gradient elution with 1% ammonia water:2% methanol/dichloromethane-1% ammonia water:6% methanol/dichloromethane were carried out. The elution product was evaporated to dryness and then dried in vacuum. 5 g of the product was obtained.

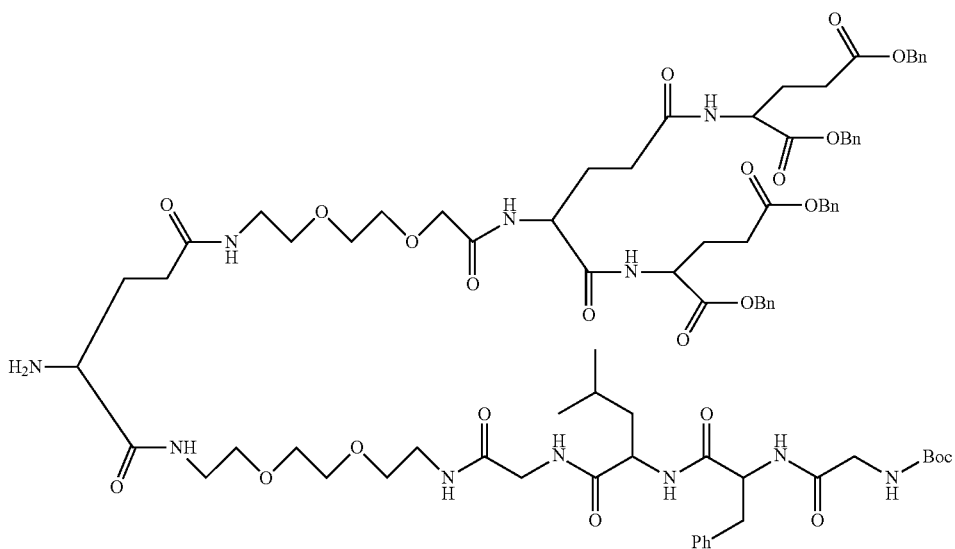

X-7

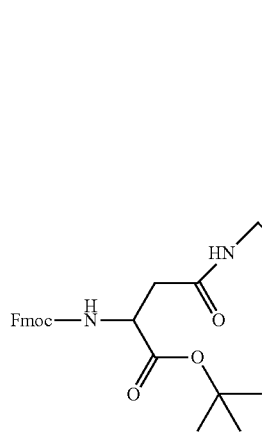 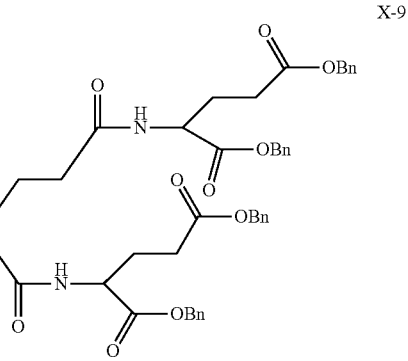

X-9

The reactant Compound 30-74 (3.8 g, 4.16 mmoL), Fmoc-Asp (otBu)-OH (1.8 g, 4.56 mmoL), HBUT (2.36 g, 6.25 mmoL), and HOBT (0.84 g, 6.25 mmoL) were added into a 250 mL reaction flask and then dissolved with DMF (40 mL); the resulting solution was then stirred for 0.5 h at 0° C.; DIEA (3.1 mL, 18.76 mmoL) was then slowly added dropwise, and the mixed solution was then stirred to react. At the end of the reaction, the reaction solution was extracted with deionized water (300 mL) and ethyl acetate (100 mL), the organic phase was then separated, the aqueous phase was extracted three times with ethyl acetate (50 mL×3), and the obtained organic phases were then combined, washed twice with a saturated sodium chloride solution (50 mL×2), and then evaporated to dryness. The operations of column chromatography, dry sample loading and gradient elution with 1% methanol/dichloromethane-5% methanol/dichloromethane were carried out. The elution product was evaporated to dryness. 3.9 g of the product was obtained finally with a yield of 72%.

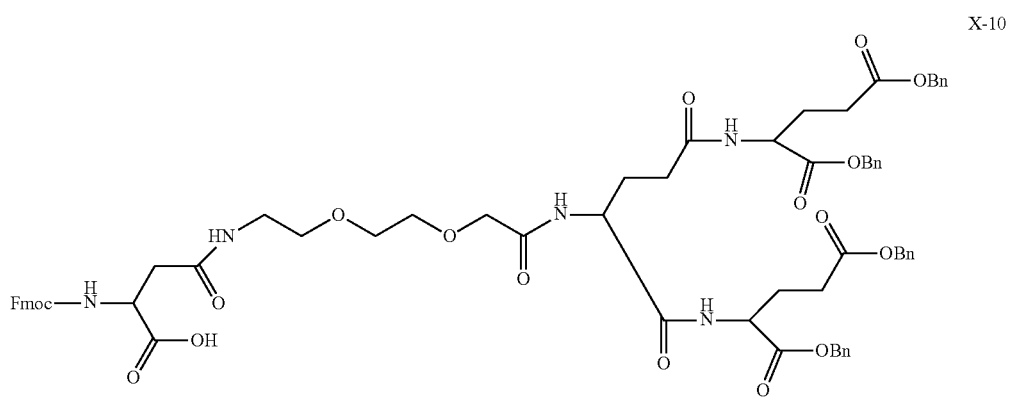

X-10

Compound X-9 (2.98 mmol) was weighed, dichloromethane (5 mL) and TFA (6.63 mL, 89.4 mmol) were added sequentially, and the resulting solution was then treated by ultrasonic until Compound X-9 was dissolved; the mixed solution was stirred to react. At the end of the reaction, the reaction solution was concentrated and the concentrated product was then dissolved with ethyl acetate (100 mL); a saturated sodium bicarbonate solution was then added until the aqueous phase became alkaline; then, the organic phase was separated, and the aqueous phase was extracted three times with ethyl acetate (50 mL×3) until there was no product in the aqueous phase; the organic phases were combined, and washing with a saturated sodium chloride solution (50 mL) was carried out once; the organic phase was concentrated and evaporated to dryness. The product was obtained with a yield of 89%.

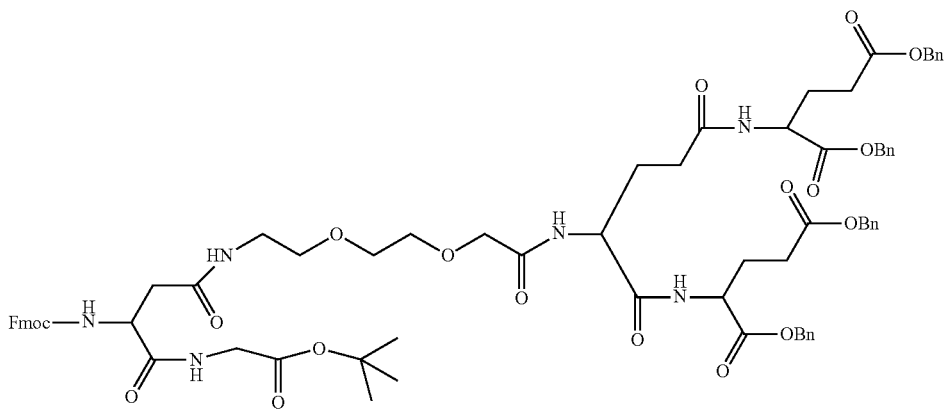

X-11

The reactant Compound X-10 (3.3 g, 2.64 mmoL), H-Gly-otBu (0.46 g, 2.77 mmoL), HBUT (1.50 g, 3.96 mmoL), and HOBT (0.53 g, 3.96 mmoL) were added into a 250 mL reaction flask and then dissolved with DMF (40 mL); the resulting solution was then stirred for 0.5 h at 0° C.; DIEA (1.96 mL, 11.88 mmoL) was then slowly added dropwise, and the mixed solution was then stirred to react. At the end of the reaction, the reaction solution was extracted with deionized water (300 mL) and ethyl acetate (100 mL), the organic phase was then separated, the aqueous phase was extracted three times with ethyl acetate (50 mL×3) until there was no product in the aqueous phase, and the obtained organic phases were then combined, washed twice with a saturated sodium chloride solution (50 mL×2), and then evaporated to dryness. The product was obtained with a yield of 100%.

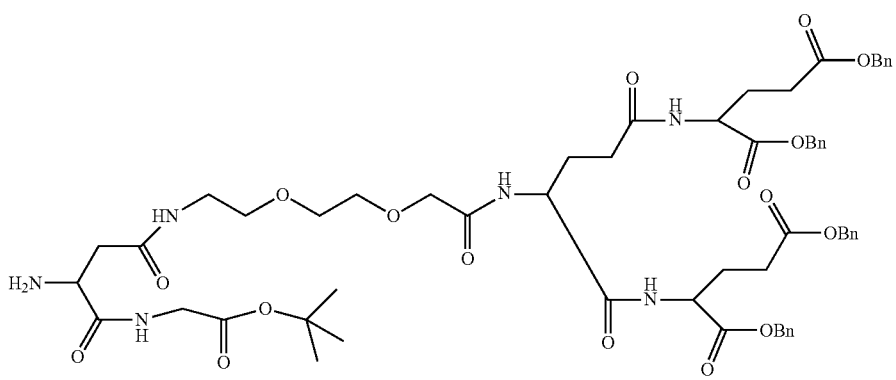

X-12

Compound X-11 was added in a 250 mL flask and then dissolved with DMF solution is (20 mL) and then morpholine (6.9 mL, 79.2 mmoL) was added, and the obtained solution was stirred at room temperature to react for 3 h. At the end of the reaction, the reaction solution was extracted with deionized water (300 mL) and ethyl acetate (100 mL), the organic phase was separated, and the aqueous phase was extracted three times with ethyl acetate (50 mL×3) until there was no product in the aqueous phase; and then the obtained organic phases were combined. The operations of column chromatography, dry sample loading and gradient elution with 1% ammonia water:2% methanol/dichloromethane-11 % ammonia water:6% methanol/dichloromethane were carried out. 2.5 g of the product was obtained with a yield of 83%.

X-13

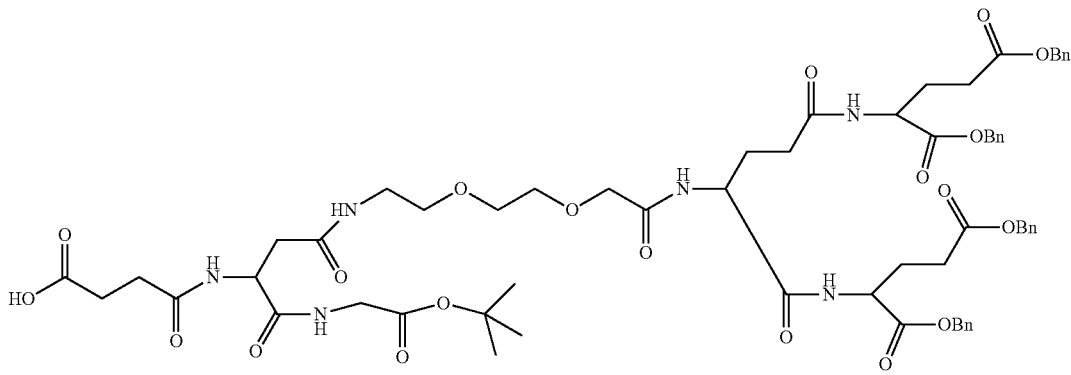

The reactant Compound X-12 (1 g, 0.87 mmol) was dissolved with DMF (20 mL). DIEA (0.58 mL, 3.51 mmol) was added dropwise to the resulting solution. 30 min later, succinic anhydride (0.26 g, 2.16 mmol) was added to the mixed solution. At the end of the reaction, the reaction solution was extracted with deionized water (300 mL) and ethyl acetate (100 mL), the organic phase was then separated, the aqueous phase was extracted three times with ethyl acetate (50 mL×3), and the obtained organic phases were then combined and then evaporated to dryness. The product was obtained with a yield of 100%.

Reactants, Compound X-13 (0.87 mmoL), Compound X-7 (1.43 g, 0.87 mmoL), HBUT (0.49 g, 1.3 mmoL), and HOBT (0.175 g, 1.3 mmoL) were added into a 250 mL reaction flask and then dissolved with DMF (40 mL); the resulting solution was then stirred for 0.5 h at −5° C.; DIEA (0.64 mL, 3.9 mmoL) was then slowly added dropwise, and the mixed solution was then stirred to react. At the end of the reaction, the reaction solution was extracted with deionized water (300 mL) and ethyl acetate (100 mL), the organic phase was then separated, the aqueous phase was extracted three times with ethyl acetate (50 mL×3), and the obtained

X-14

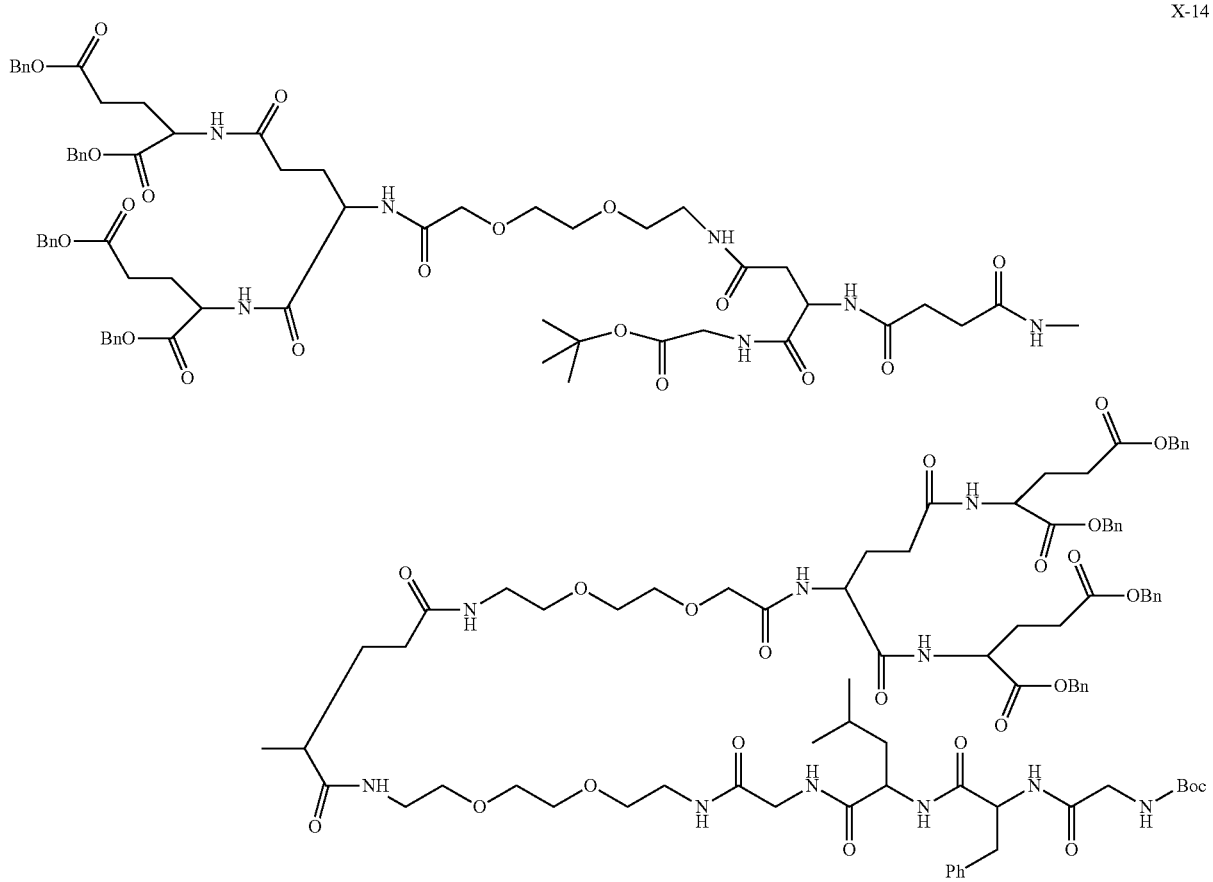

organic phases were then combined, washed twice with a saturated sodium chloride solution (50 mL×2), and then evaporated to dryness. The operations of column chromatography, dry sample loading and gradient elution with 2% methanol/dichloromethane-8% methanol/dichloromethane were carried out. The elution solution was evaporated to dryness. 1.87 g of the product was obtained with a yield of 75%.

phase was then separated, the aqueous phase was extracted three times with ethyl acetate (50 mL×3), and the obtained organic phases were then combined, washed twice with a saturated sodium chloride solution (50 mL×2), and then evaporated to dryness. 4.6 g of the product was obtained with a yield of 100%.

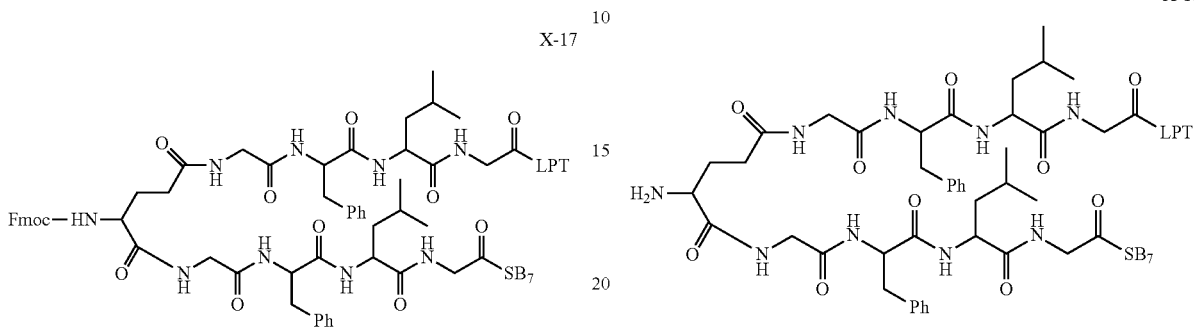

Reactants, Compound 30-77 (2.8 g, 2.14 mmoL), GFLG-SB7 (synthesized according to the synthesis method of Compound 28-146) (2 g, 2.247 mmoL), HBUT (1.21 g, 3.21 mmoL), and HOBT (0.43 g, 3.21 mmoL) were added into a 250 mL reaction flask and then dissolved with DMF (30 mL); the resulting solution was then stirred for 0.5 h at −5° C.; DIEA (1.59 mL, 9.63 mmoL) was then slowly added dropwise, and 1 h later, the mixed solution was taken out and then stirred at room temperature to react. At the end of the reaction, the reaction solution was extracted with deionized water (300 mL) and ethyl acetate (100 mL), the organic Compound X-17 (2.14 mmol) was added in a 250 mL flask and then dissolved with DMF solution (20 mL) and then morpholine (5.59 mL, 64.2 mmoL) was added, and the obtained solution was stirred at room temperature to react for 3 h. At the end of the reaction, the reaction solution was extracted with deionized water (300 mL) and ethyl acetate (150 mL), the organic phase was separated, and the aqueous phase was extracted three times with ethyl acetate (50 mL×3); and then the obtained organic phases were combined and evaporated to dryness. The product was obtained with a yield of 100%.

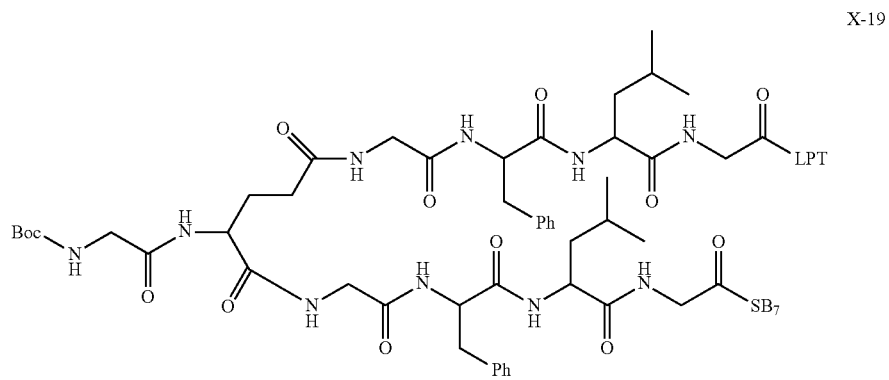

Reactants, Compound X-18 (2.14 mmoL), Boc-Gly-OH (0.39, 2.247 mmoL), HBUT (1.21 g, 3.21 mmoL), and HOBT (0.43 g, 3.21 mmoL) were added into a 250 mL reaction flask and then dissolved with DMF (50 mL); the resulting solution was then stirred for 0.5 h at −5° C.; DIEA (1.59 mL, 9.63 mmoL) was then slowly added dropwise, and 1 h later, the mixed solution was taken out and then stirred at room temperature to react. At the end of the reaction, the reaction solution was extracted with deionized water (300 mL) and ethyl acetate (150 mL), the organic phase was then separated, the aqueous phase was extracted three times with ethyl acetate (50 mL×3), and the obtained organic phases were then combined, washed twice with a saturated sodium chloride solution (50 mL×2), and then evaporated to dryness. The product was obtained with a yield of 100%.

X-20

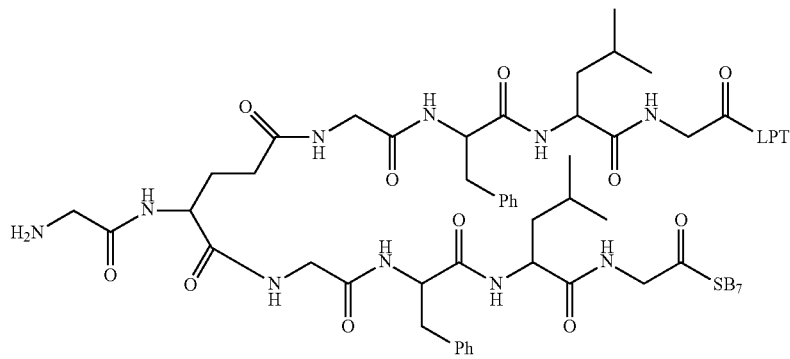

Compound X-19 (2.14 mmol) was weighed, dichloromethane (5 mL) and TFA (4.7 mL, 64.2 mmol) were added sequentially, and the resulting solution was then treated by ultrasonic; the mixed solution was stirred to react. At the end of the reaction, the reaction solution was concentrated, and methyl tert-butyl ether (100 mL) and n-hexane (200 mL) were added sequentially to precipitate the concentrated solution to obtain powder; the suction filtering was then carried out to obtain a solid product. The operations of column chromatography, dry sample loading and elution with 1% ammonia water:3% methanol/dichloromethane-1% ammonia water:6% methanol/dichloromethane were carried out. 3 g of the product was obtained with a yield of 69%.

X-21

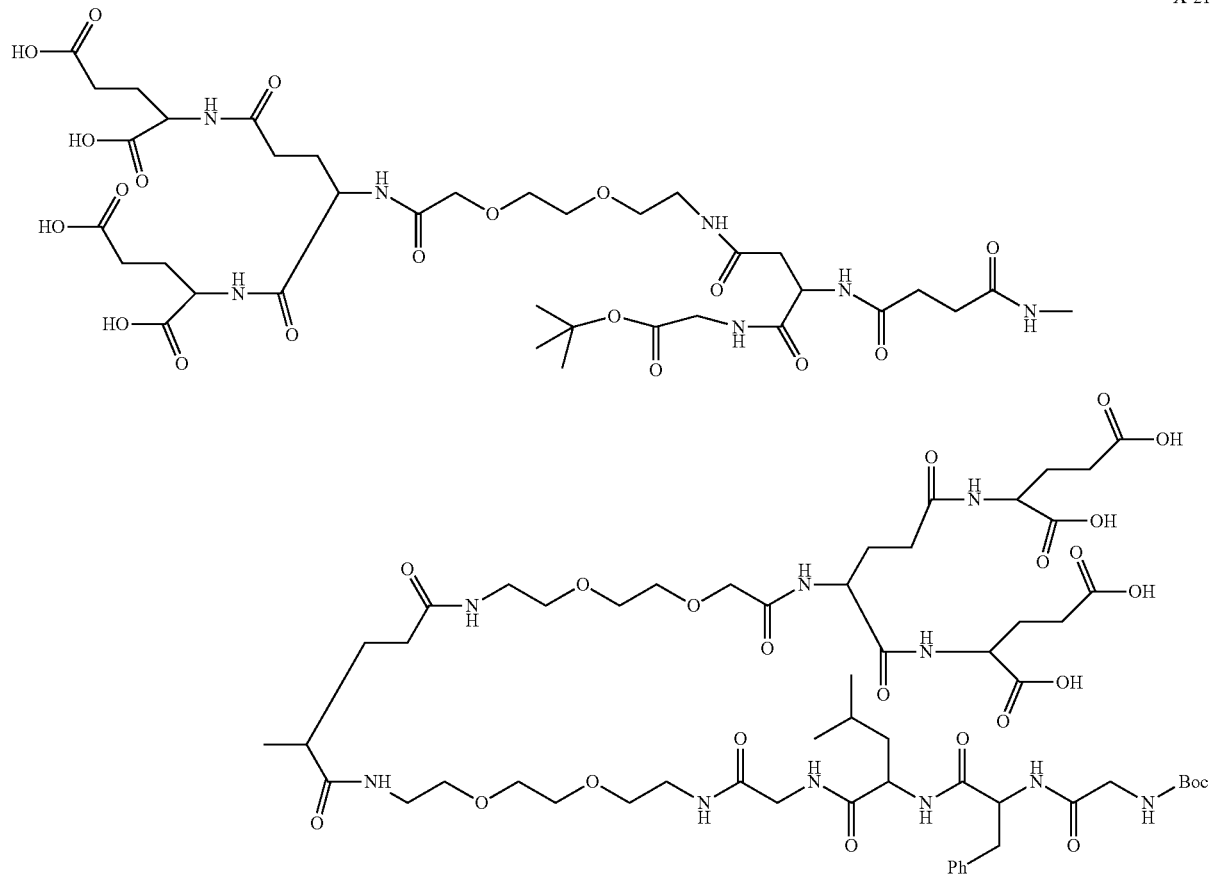

The reactant Compound X-14 (0.5 g, 0.175 mmoL) was weighed and added into a hydrogenation device and then dissolved with DMF (30 mL) and then 10% Pd/C (0.1 g) was added to the resulting solution; the hydrogenation device was then sealed and H₂ was introduced in the device to a pressure of 18 psi. The mixed solution was then stirred overnight at room temperature. After the reaction was found to be completed from the monitoring of the TLC, the reaction solution was taken out and evenly dropwise added to a sand core funnel filled with compacted diatomaceous earth and suction filtering was carried out; the diatomaceous earth was then washed with DMF (90 mL) until there was no product in the diatomaceous earth. A reaction product solution was thus obtained.

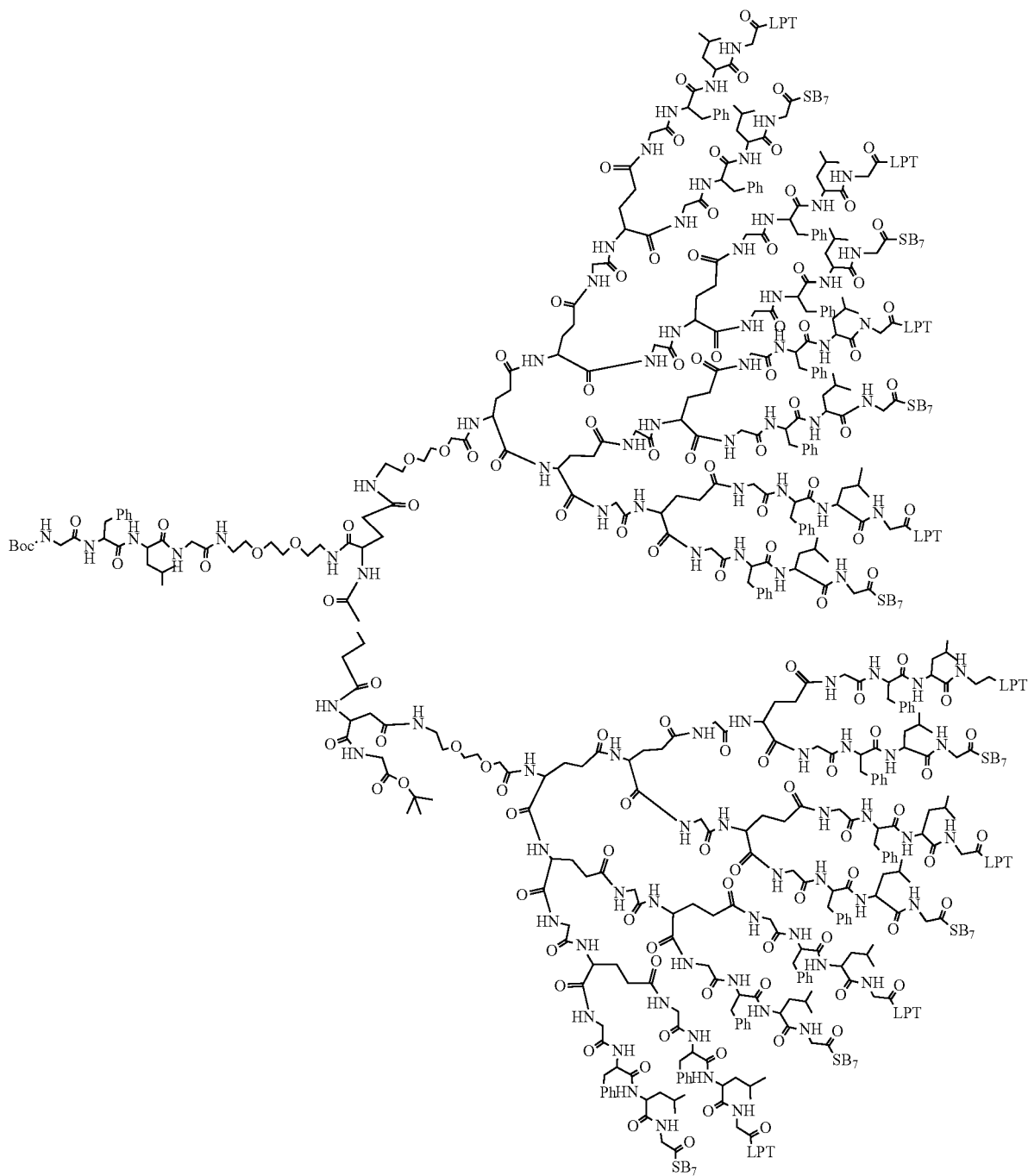

X-22

Reactants, Compound X-20 (3 g, 1.48 mmoL), Compound X-21 (0.175 mmoL), HBUT (0.79 g, 2.1 mmoL), and HOBT (0.28 g, 2.1 mmoL) were added into a 250 mL reaction flask and then dissolved with DMF (50 mL); the resulting solution was then stirred for 0.5 h at −5° C.; DIEA (1.04 mL, 6.3 mmoL) was then slowly added dropwise, and 1 h later, the mixed solution was taken out and then stirred at room temperature to react. At the end of the reaction, methyl tert-butyl ether (100 mL) and n-hexane (200 mL) were added sequentially to precipitate the reaction solution to obtain powder; the suction filtering was then carried out to obtain a solid product. The operations of column chromatography, dry sample loading and elution with 1% ammonia water:4% methanol/dichloromethane-1% ammonia water:10% methanol/dichloromethane were carried out. The elution solution was evaporated to dryness. 1.5 g of the product was obtained with a yield of 50%.

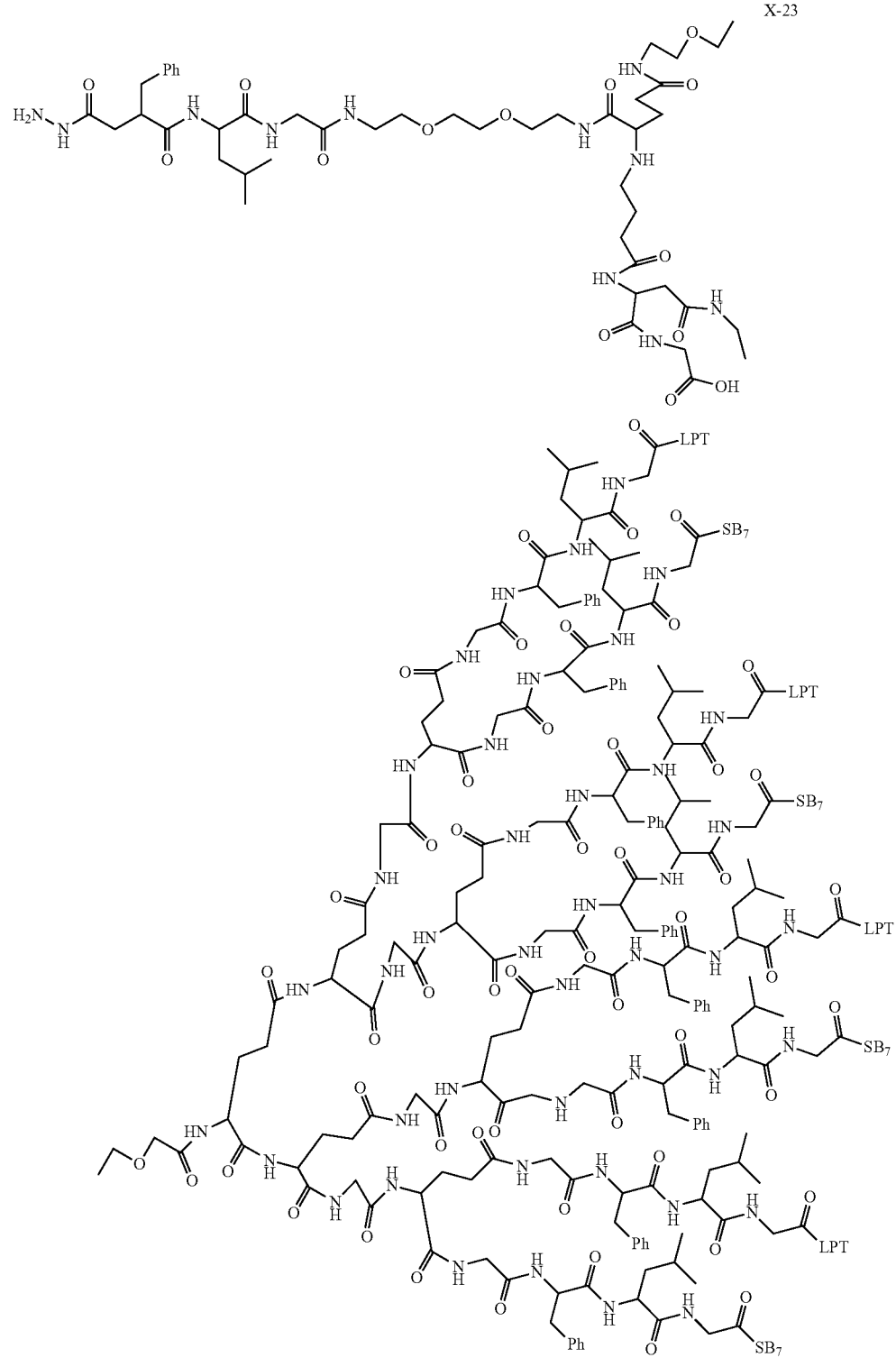

X-23

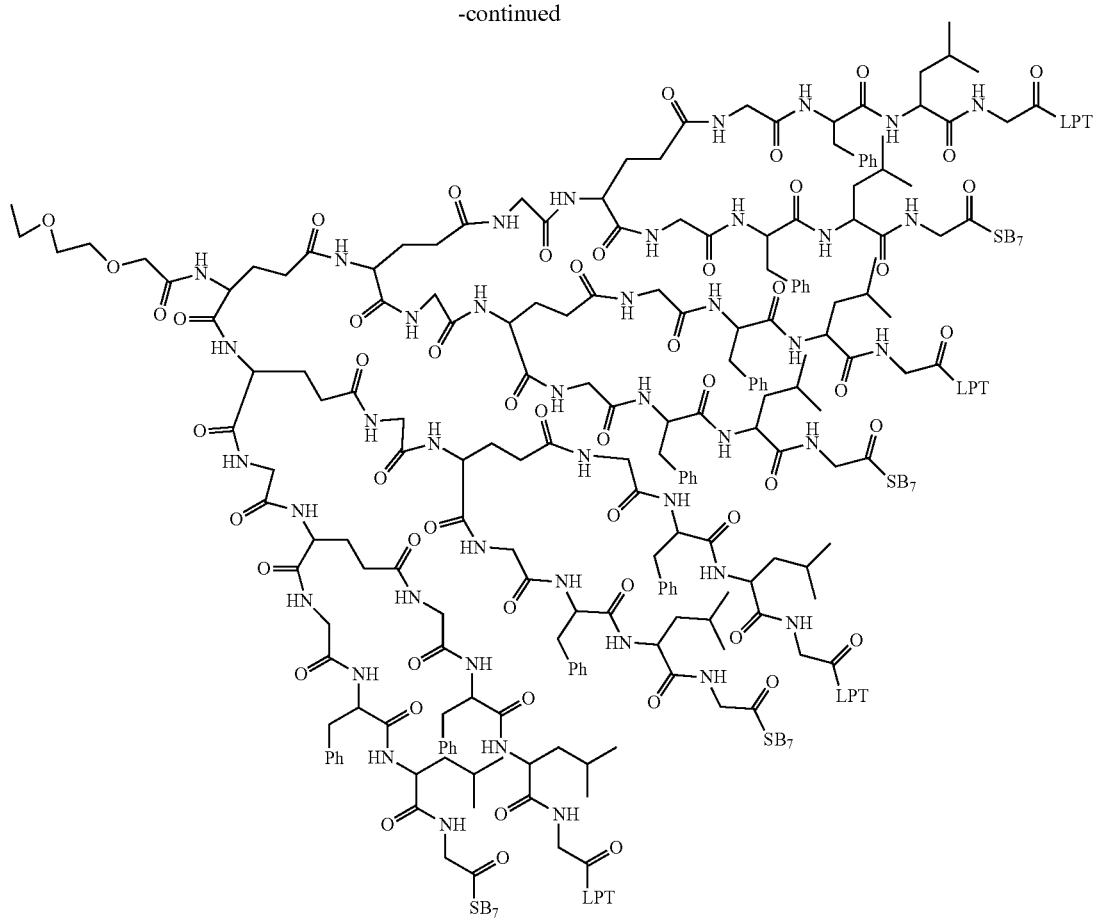

Compound X-22 (1.5 g) was weighed, dichloromethane (5 mL) and TFA (4.7 mL, 64.2 mmol) were added sequentially, and the resulting solution was then treated by ultrasonic; the mixed solution was stirred to react. At the end of the reaction, the reaction solution was concentrated, and methyl tert-butyl ether (100 mL) and n-hexane (200 mL) were added sequentially to precipitate the concentrated solution to obtain powder; the suction filtering was then carried out to obtain a solid product. The operations of column chromatography, dry sample loading and elution with 1 h ammonia water:5% methanol/dichloromethane-1% ammonia water:100% methanol/dichloromethane were carried out. 1 g of the product was obtained with a yield of 66%.

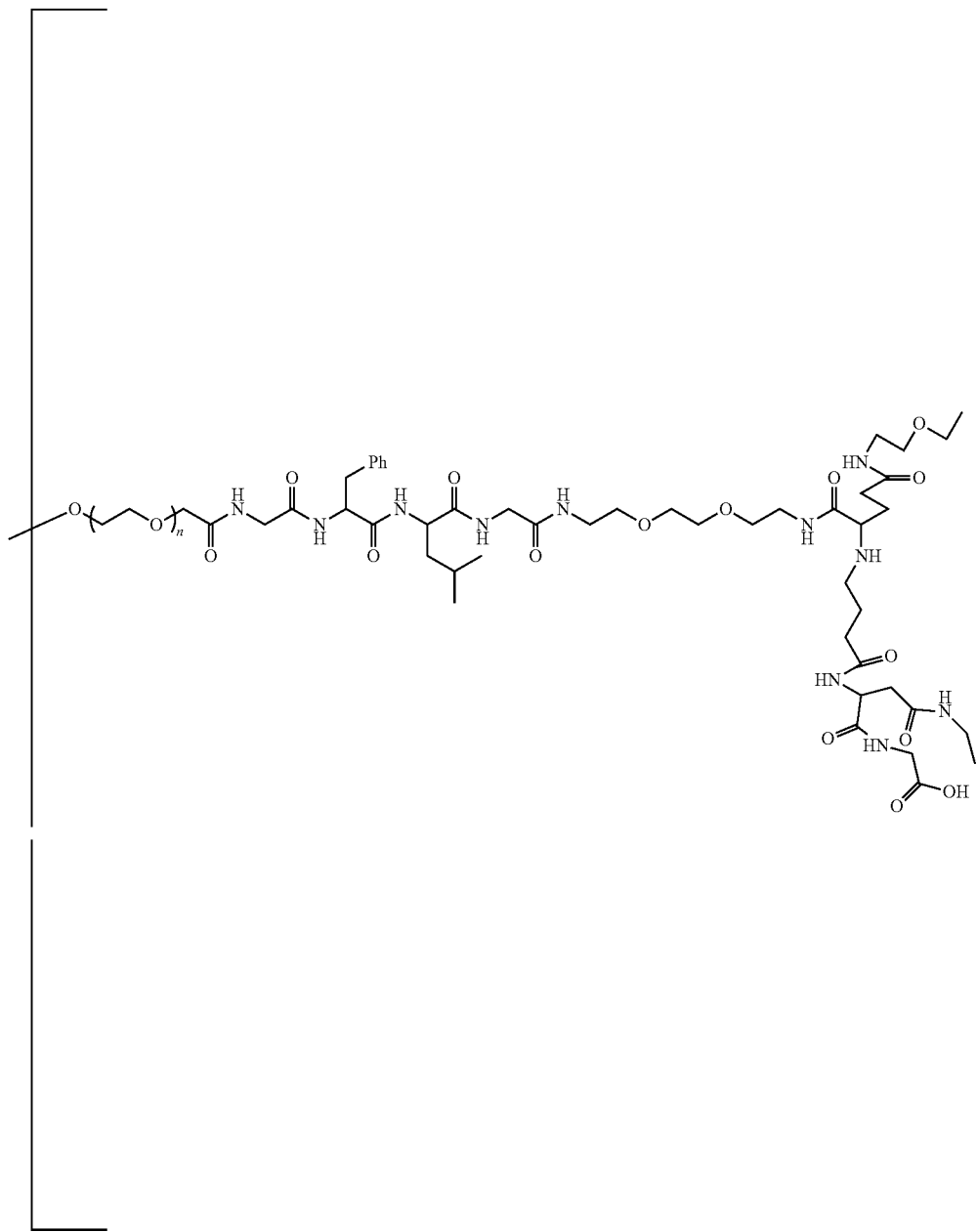

-continued
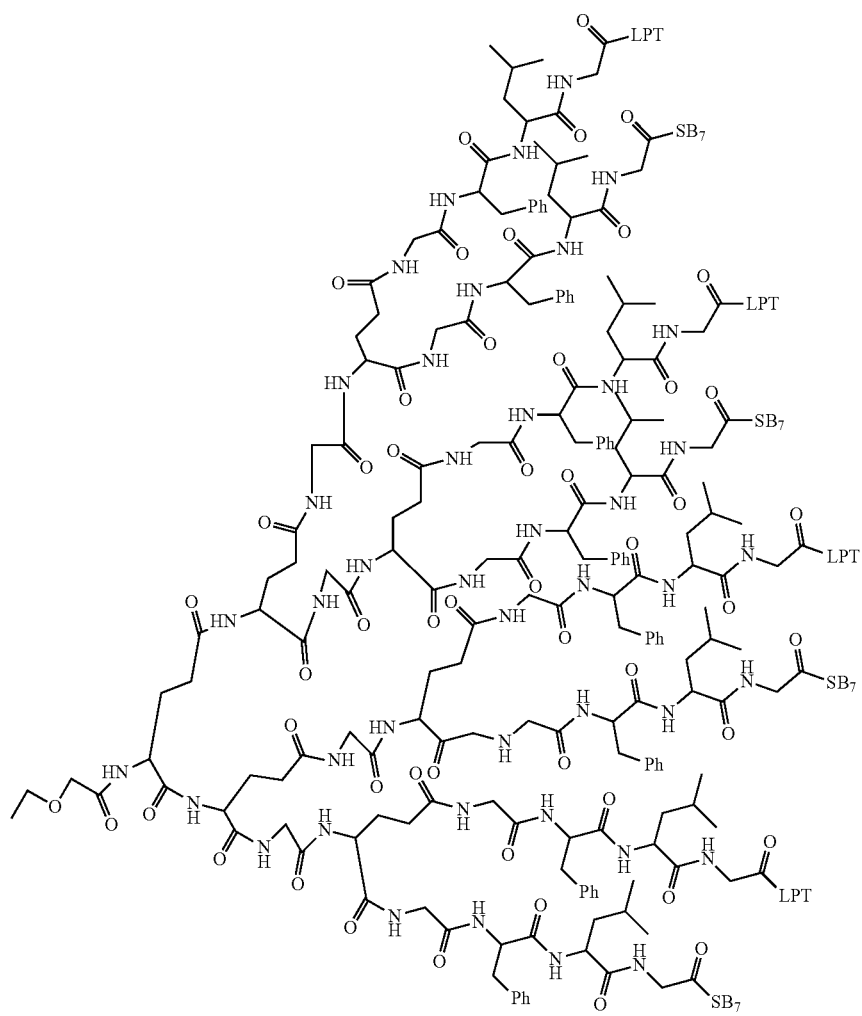

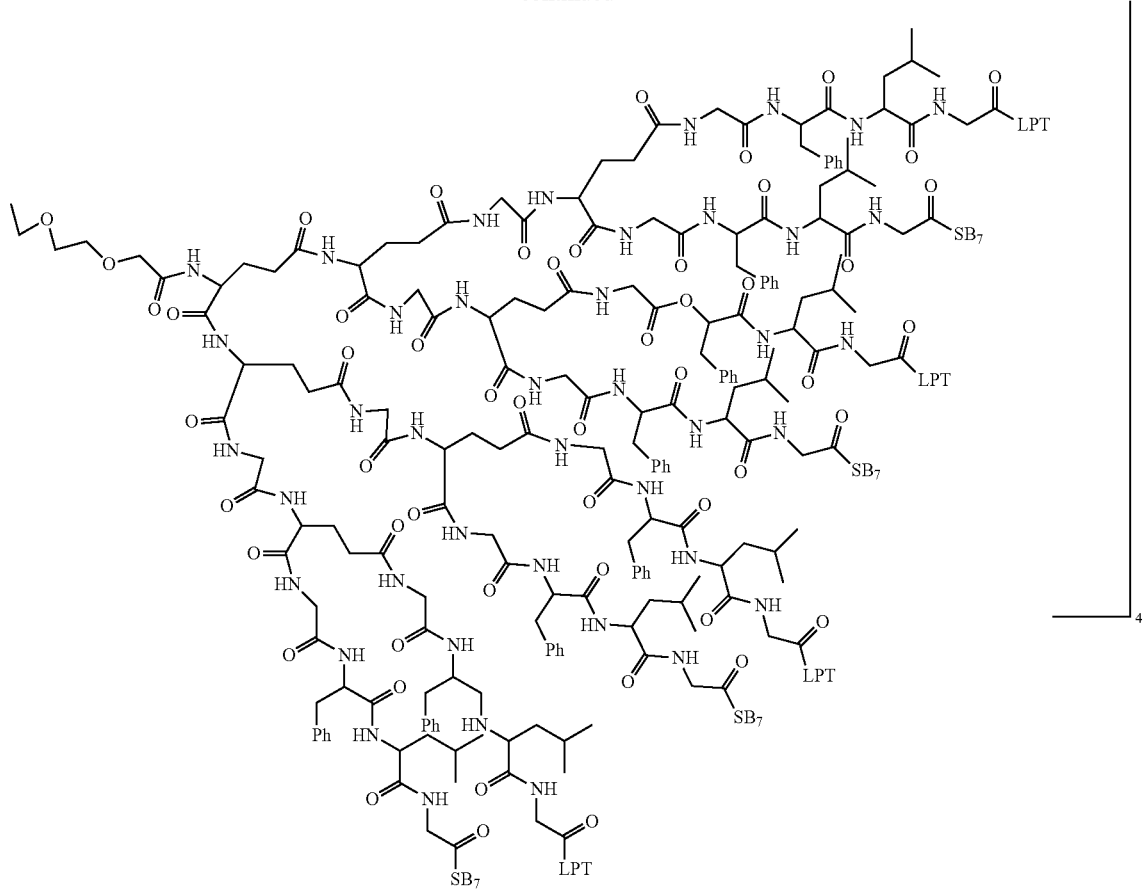

The reactant Compound X-23 (1 g) was dissolved in DMF (20 mL) in a 250 mL flask, and then the flask was placed in a low-temperature constant temperature bath (−5° C.). The mixed solution was stirred for 30 min and DIEA (0.1 mL) was then added dropwise to the solution. 4ARM-SCM-50K (0.05 g, 0.0115 mmol) was then added and dissolved in the above solution and the resulting solution was then stirred slowly at room temperature in the dark to react. At the end of the reaction, methyl tert-butyl ether (150 mL) was added in a conical flask, the reaction solution was poured into the conical flask, and then n-hexane (200 mL) was added. The product was separated out by precipitation. Suction filtering was carried out. The operations of column chromatography and dry sample loading were carried out; with the column height of 5 cm, gradient elution with an eluent (7% methanol/dichloromethane-1% ammonia water:10% methanol/dichloromethane was carried out, and the elution product was evaporated to dryness. 0.3 g of the product was obtained.

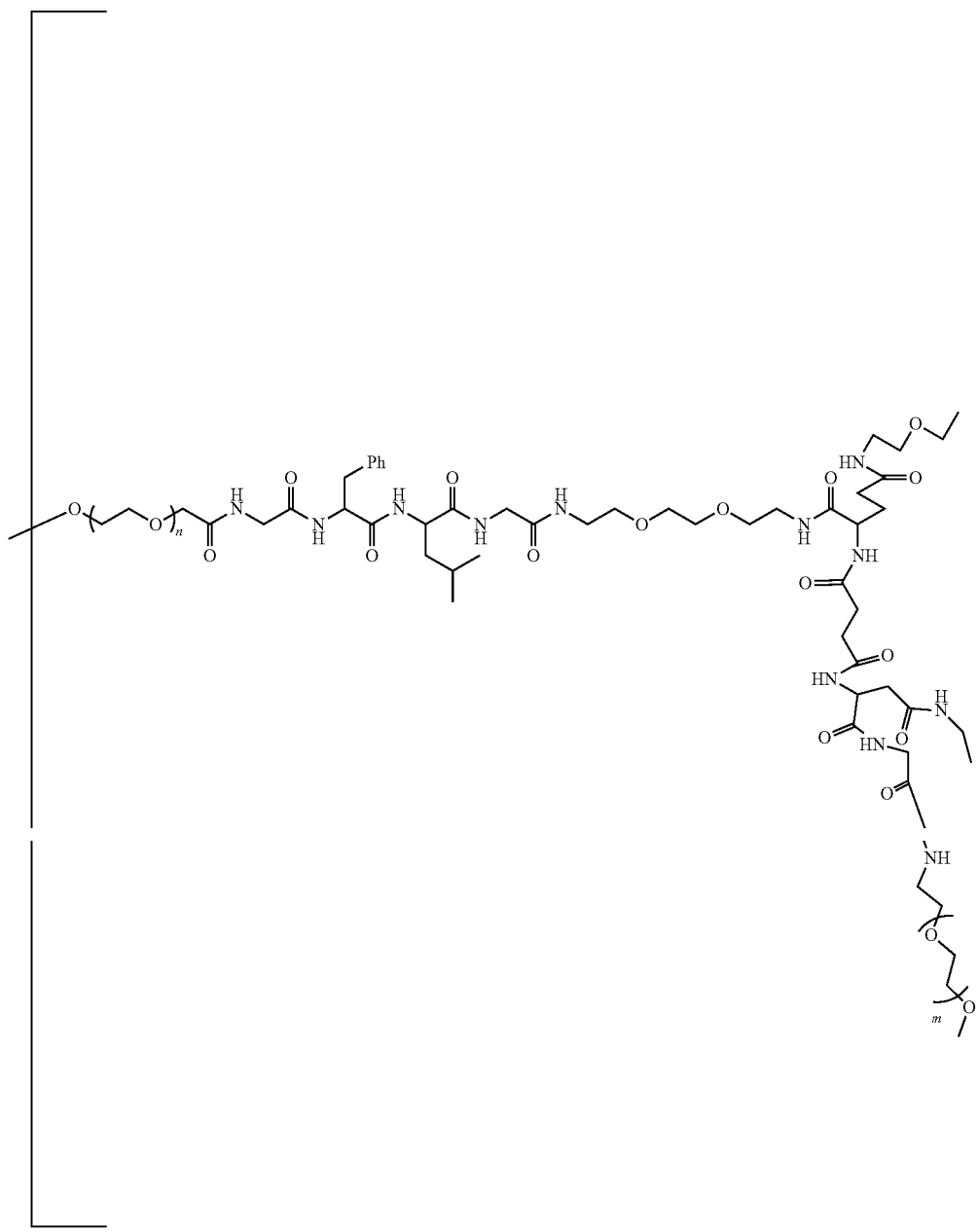

-continued
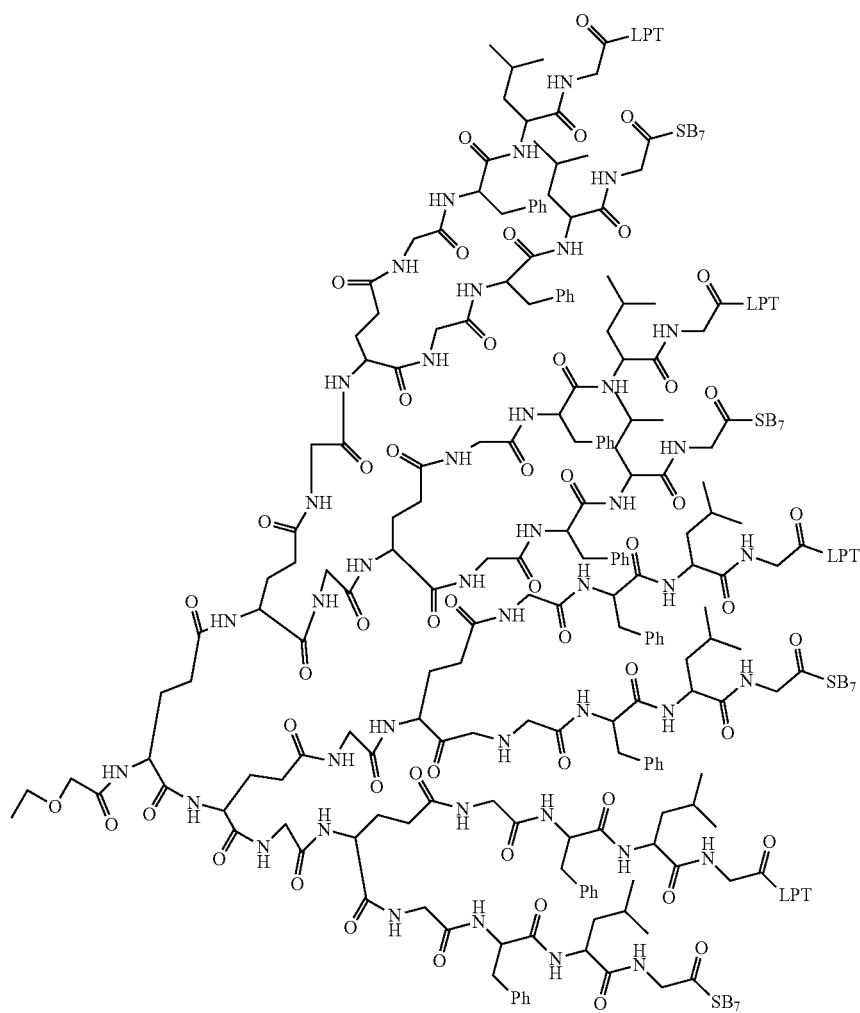

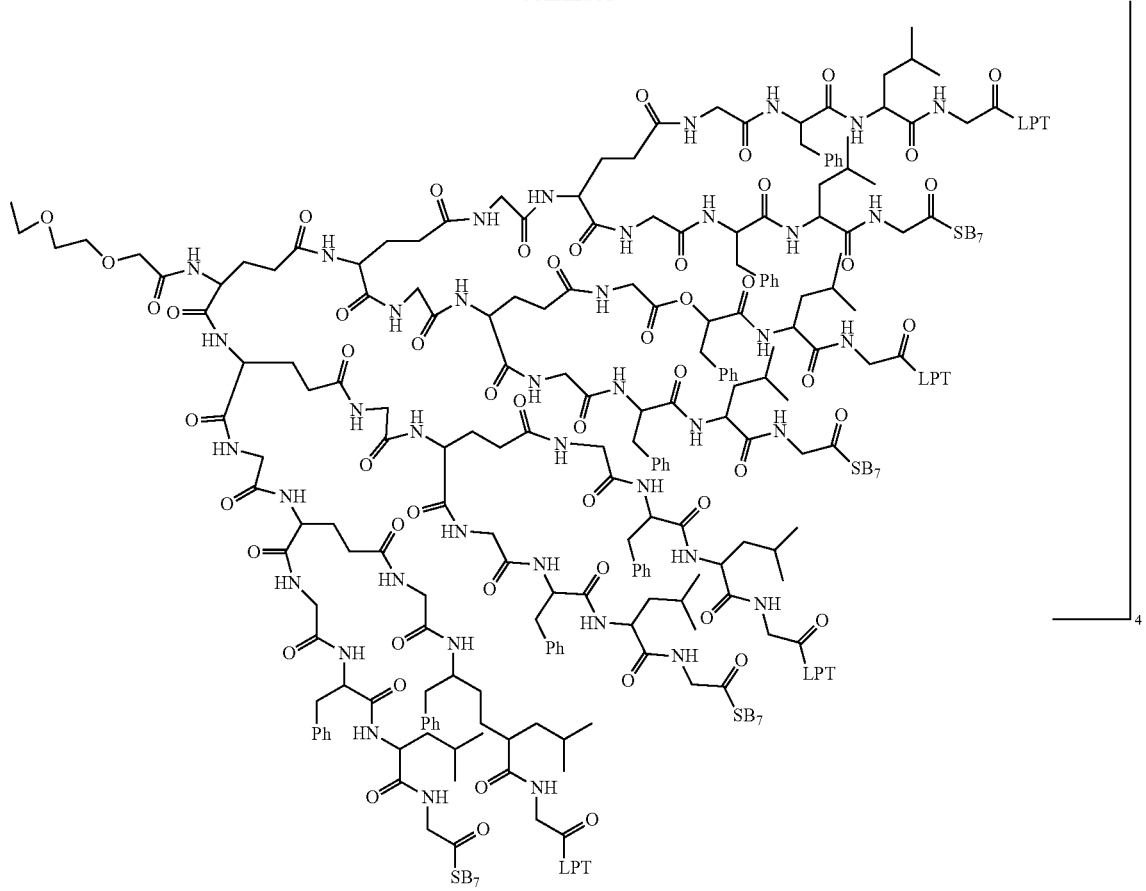

M-NH2·HCL-15K (0.34 g, 0.0234 mmoL), Compound X-24 (0.3 g, 0.0039 mmoL), HOBT (0.0045 g, 0.0335 mmoL), and HBTU (0.0127 g, 0.0335 mmoL) were added into a 250 mL flask and a DMF solution (20 mL) was then added; the resulting solution was then placed in a low-temperature constant temperature bath; 30 min later, DIEA (0.020 mL) was then added dropwise; 1 h later, the mixed solution was taken out and slowly stirred in the dark at a room temperature to react. At the end of the reaction, methyl tert-butyl ether (50 mL) and n-hexane (150 mL) were then added to the reaction solution to precipitate a solid. The suction filtering was then carried out. The obtained solid was dissolved with a solution (20% methanol:80% dichloromethane) (50 mL); and then the operations of dry sample loading and column chromatography were carried out. With the column height of 5 cm, gradient elution with 5% methanol/dichloromethane-1% ammonia water:10% methanol/dichloromethane was carried out, the elution product was evaporated to dryness and then dissolved with absolute ethanol (5 mL) and dichloromethane (2 mL); the obtained solution was treated by ultrasonic to obtain a homogeneous phase; n-hexane (100 mL) was added and then suction filtering was carried out. The process of dissolution and precipitation was repeated three times. The obtained product was dried in vacuum. 0.4 g of the product was finally obtained.

Example 24: Dissolution Experiments of Compounds 24-184

0.1 g of Compound 24-184 was weighed and put into a sample bottle; 2 mL of PEG3000 and absolute ethanol (0.2 mL) were then added to the sample bottle, the resulting solution was treated for 40 min by ultrasonic; normal saline (0.3 mL) was added and the resulting solution was then treated for 10 min by ultrasonic, the mixed solution was then filtered with a 0.45 μm microporous filter membrane; the filter membrane was then washed with normal saline; the obtained solution was then diluted to volume of 10 mL with a 10 ml volumetric flask. The solution preparation process was repeated three times, and the resulting solution was then transferred into a 50 mL sample bottle and treated for 20 s by ultrasonic, and then stored in a refrigerator with a temperature of 0° C. The state of the solution was shown in FIG. 1.

28-126

Figure 2:
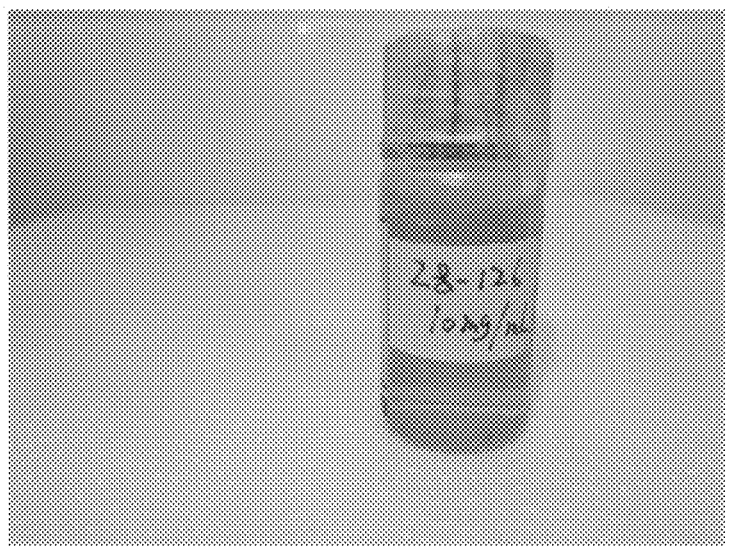
FIG. 2 shows the state of a 10 mg/mL solution of Compound 28-126 in Example 25.

100 mg of Compound 28-126 was weighed and then dissolved with 2 mL of PEG300 and 2 mL of ethanol by ultrasonic; 3 mL of normal saline was then added and the resulting solution was mixed well by ultrasonic and filtered with a 0.45 μm microporous filter membrane; the solution was diluted with normal saline to the scale mark in a 10 mL volumetric flask and then transferred to a 10 mL glass bottle and ultrasonically sterilized; the glass bottle was sealed and stored at 2 to 8° C. The state of the solution was shown in FIG. 2.

28-206

Figure 3:
FIG. 3 shows the state of a 10 mg/mL solution of Compound 28-206 in Example 25.

100 mg of Compound 28-206 was weighed and then dissolved with 2 mL of PEG300 and 2 mL of ethanol by ultrasonic; 3 mL of normal saline was then added and the resulting solution was mixed well by ultrasonic and filtered with a 0.45 μm microporous filter membrane; the solution was diluted with normal saline to the scale mark in a 10 mL volumetric flask and then transferred to a 10 mL glass bottle and ultrasonically sterilized; the glass bottle was sealed and stored at 2 to 8° C. The state of the solution was shown in FIG. 3.

33-8

Figure 4:
FIG. 4 shows the state of a 10 mg/mL solution of Compound 33-8 in Example 25.

50 mg of Compound 33-8 was weighed and then dissolved with 2 mL of PEG300 and 2 mL of absolute ethanol by ultrasonic to obtain a perfect solution, and the solution was then diluted with normal saline to the volume of 10 mL and filtered with 0.45 μm microporous filter membrane. The state of the solution was shown in FIG. 4.

Experimental Example 1 In vivo anti-tumor efficacy test of the compound of the disclosure on subcutaneously transplanted tumor model of human colon cancer COLO-205 cells in BALB/c nude mice I. Experimental Purpose A subcutaneously transplanted tumor model of human colon cancer COLO-205 cells in BALB/c nude mice was established to investigate the anti-tumor effect of the test samples on the subcutaneously transplanted tumor.

II. Information of Test Sample and Control

1. Test Sample
Compound 37-26, Compound 28-126, and Compound 28-206
2. Control
Component 1: SB7 HCL (PharmaBlock Sciences (Nanjing), Inc.)
Component 2: Palbociclib (PCB, purity: 99.5%, Tianjin Pharmacn Medical Technology Co., Ltd)
3. Solvent/Negative Control
Sodium chloride injection (Shandong Qidu Pharmaceutical Co., Ltd., batch number: 4B19030803, concentration: 0.9%, specification: 100 mL: 0.9 g)

III. Preparation of Test Sample/Control

1. Diluent of test sample: normal saline was added to an appropriate amount of PEG300 and anhydrous ethanol so that the content of PEG300 and anhydrous ethanol reached 20% (v/v).
2. Test Sample:
An appropriate amount of Compound 37-26 was weighed, an appropriate amount of the diluent of the test sample was added to Compound 37-26 to prepare a solution with a concentration of 2.79 mg/mL.
An appropriate volume of Compound 28-126 or Compound 28-206 was weighed, an appropriate amount of normal saline was added to the compound to prepare a solution with a concentration of 4.65 mg/mL and a solution with a concentration of 4.59 mg/mL, respectively.
3. Small-Molecule Control:
An appropriate amount of SB7 (conversion coefficient: 93.4%) was weighed and dissolved with a certain volume of ethanol (5%, V/V); after SB7 was completely dissolved, an appropriate amount of sodium chloride injection was added to prepare a solution with a concentration of 0.4 mg/mL.

An appropriate amount of PCB was weighed and a certain volume of 0.5% CMC-Na solution were added; the obtained solution was then well stirred by a magnetic stirrer to prepare a solution with a concentration of 0.35 mg/mL.

4. Negative Control: Normal Saline was Used Directly.

IV. Experiment System

1. Information of Tumor Cell Line

Human colon cancer cell COLO-205: sourced from Cell Resource Center, Institute of Basic Medical Sciences, Chinese Academy of Medical Sciences, and the culture conditions were RPMI1640+10% FBS, 37° C., 5% $CO_2$.

2. Experimental Animals

SPF-level male BALB/c nude mice, 4 weeks old, with weight of 11.0-14.9 g

Laboratory animal source: Beijing Vitalstar Biotechnology Co., Ltd, production license number: SCXK (Beijing) 2016-0011, certificate number: No. 1100111911049640.

3. Animal Rearing and Management

Rearing environment: SPF-level environmental animal facility

Animal use license number: SYXK (Beijing) 2016-0029

Feed: Animals were given qualified feed (provided by Beijing Keao Xieli Feed Co., Ltd., batch numbers: 19063113, 19063123, 19073113, production license number: SCXK (Beijing) 2014-0010), and the animals were allowed to eat the feed freely.

Drinking water: during the quarantine and test process, animals were given purified water (filtered with secondary reverse osmosis RO membrane), supplied with a drinking bottle. The animals were allowed to drink the water freely.

Rearing condition: Animals were raised in an independent air supply system (IVC), with 3 to 5 animals in each cage. The environmental conditions temperature: 20° C. to 26° C.; relative humidity: 40% to 70%; actual temperature: 22° C. to 26° C.: actual relative humidity: 42% to 59%. The animals were raised under light and in the dark alternately for about 12 h.

V. Experimental Design

COLO-205 cells were thawed for cell subculture and amplification. When the cells were amplified to a sufficient number, the cells in the logarithmic growth phase were collected for cell inoculation. The cell concentration was adjusted to $5 \times 10^7$ cells/mL, and the cells were inoculated subcutaneously in the right axilla of mice with a dose of 0.2 mL/mouse. After the animals were inoculated, the tumor growth was observed, and 30 qualified tumor-bearing mice within tumor volume in the range of 162.96 $mm^3$ to 470.56 $mm^3$ were screened and grouped randomly according to the tumor size.

According to the size of the tumor, the mice were randomly divided into 5 groups with 6 animals in each group. The dosage and animal number of each group were shown in Table 1. Negative control, SB7, and test samples were injected intravenously, and PCB was given by intragastric administration. Administration was consecutively carried out for two weeks, once a week.

TABLE 1

Animal grouping and dosage

| Test sample/Control | Administration dose (mg/kg) | Administration concentration (mg/kg) | Administration capacity (mL/kg) | Number of animals |
|---|---|---|---|---|
| Negative control | — | — | 10 | 6 |
| SB7 + PCB | 4 + 3.5 | 0.4 + 0.35 | 10 + 10 | 6 |
| 37-26 | 27.9 | 2.79 | 10 | 6 |
| 28-126 | 46.5 | 4.65 | 10 | 6 |
| 28-206 | 45.9 | 4.59 | 10 | 6 |

VI. Indicator Measurement

1. During the administration period, general clinical observations were performed twice a day, and body weight and tumor diameter measurements were performed twice a week. After euthanasia of the animal, the tumor was removed and weighed. After the animal was euthanized, gross anatomy was performed to observe the changes in the main organs.

2. Tumor Diameter Measurement

Tumor diameters were measured in all animals with a vernier caliper on the grouping date (the is day of the first administration was regarded as D1), twice a week after the first administration and the day before euthanasia; long and short diameters of the tumors were recorded, the tumor volumes were calculated, and the tumor growth curves were made according to the tumor volumes. The tumor volume was calculated as follows: $V = \frac{1}{2} \times \text{long diameter} \times \text{short diameter}^2$ 3. Evaluation of Curative Effect Based on Tumor Volume Relative tumor volume (RTV) and relative tumor proliferation rate T/C % were calculated as follows:

$$RTV = V_t/V_0$$

$V_t$: Tumor volume obtained by measuring the tumor every day $V_0$: initial tumor volume (before administration)

T/C %=average RTV of the treatment group/average RTV of the control group×100%

If T/C %≤40% and P≤0.05 in statistics for the RTV of the experimental group and the RTV of the model group, it means effective in tumor growth inhibition; on the contrary, if T/C %>40%, it means ineffective in tumor growth inhibition.

4. Evaluation of Curative Effect Based on Tumor Weight

At the end of the experiment on D16, the tumor nodules were taken and weighed, and the difference in tumor weight between the groups was compared to further calculate the tumor inhibition rate $IR_{TW}$. $IR_{TW} \geq 60\%$ was used as a reference indicator for effectiveness. The calculation formula was as follows:

$$IR_{TW}(\%) = (W_{model\ group} - W_{treatment\ group})/W_{model\ group} \times 100\%$$

VII. Statistical Analysis

The statistical software SPSS13.0 was used to process the data, and the measurement data were expressed in the form of "mean±standard error". The specific analysis process was as follows: one-way analysis of variance (ANOVA) was adopted for statistical analysis, if ANOVA was statistically significant (P≤0.05) and the variance was homogeneous, Tukey test was carried out for comparative analysis between groups; if the variance was not homogeneous, Dunnett's T3 test was adopted for comparative analysis between groups.

VIII. Results

1. Body Weight and Clinical Observation:

The animals in the experiment showed no obvious abnormalities. Throughout the experiment, the body weights of mice in the negative control group were significantly lower than those before the grouping, and the animal weights of the other groups were slightly higher than those before the grouping. Body weights of animals in each group are shown in Table 2.

TABLE 2

Statistical data of body weight (x ± s)

| Test sample/Control | Weight (g) | | | | |
|---|---|---|---|---|---|
| | D1 | D5 | D8 | D12 | D15 |
| Negative control | 17.7 ± 1.7 | 17.0 ± 1.9 | 16.2 ± 1.4 | 15.3 ± 1.3 | 15.5 ± 1.2 |
| SB7 + PCB | 18.3 ± 1.0 | 18.4 ± 1.3 | 18.7 ± 1.9 | 18.4 ± 1.7$^a$ | 19.3 ± 1.9 |
| 37-26 | 18.1 ± 1.5 | 18.6 ± 1.5 | 19.5 ± 2.0$^a$ | 19.5 ± 1.9$^a$ | 20.8 ± 1.9$^a$ |
| 28-126 | 18.6 ± 1.4 | 19.4 ± 1.7 | 20.5 ± 2.0$^a$ | 20.2 ± 2.1$^a$ | 21.5 ± 2.2$^a$ |
| 28-206 | 17.5 ± 0.6 | 17.6 ± 0.9 | 18.2 ± 1.2 | 18.9 ± 1.4$^a$ | 20.1 ± 1.8$^a$ |

Note:
$^a$means P ≤ 0.05 relative to group 1

2. Tumor Volume

Figure 5:
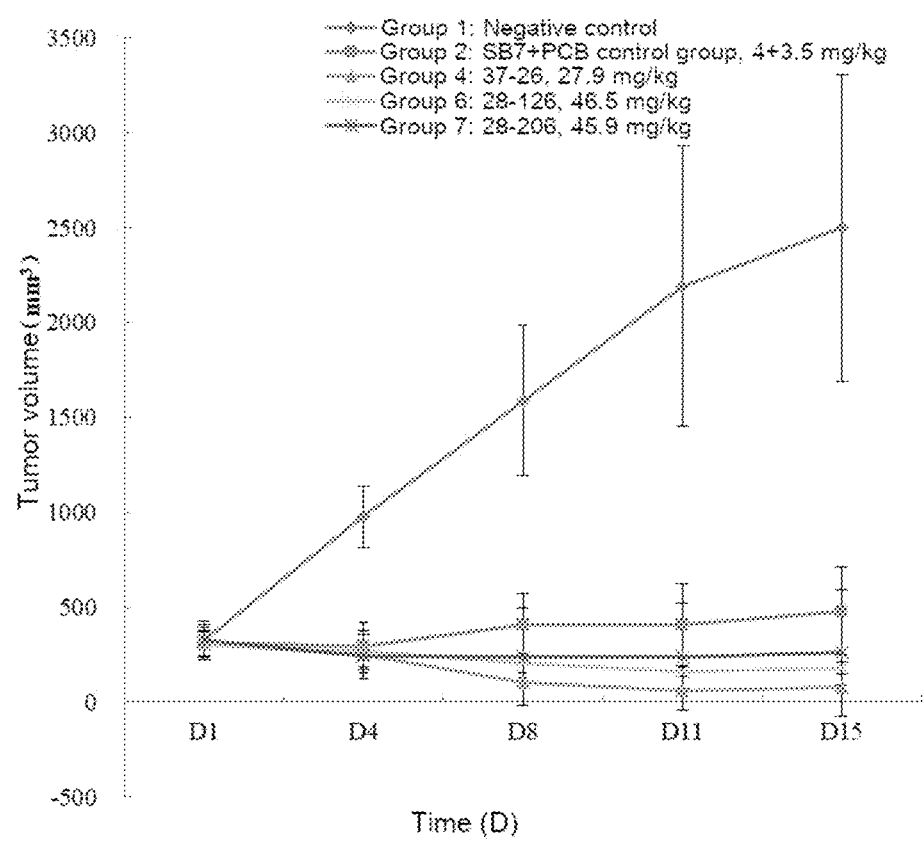
FIG. 5 shows an average tumor volume growth trend of each group in Experimental Example 1.

There was no significant difference in tumor volume among the groups in grouping on D1 (P>0.05). The average tumor volume and average RTV of groups 2-10 were lower than those of the negative control group at each time point after administration. The tumor nodules in the negative control group maintained stable growth. The tumor volume and RTV of each group changed with time. The changes and the statistical differences among groups are shown in Table 3. The trend of average tumor volume growth of each group is shown in FIG. 5.

TABLE 3

Statistical data of tumor volume and RTV

| Test sample/ Control | Tumor volume (mm³) | | | | |
|---|---|---|---|---|---|
| | D1 | D5 | D8 | D12 | D15 |
| Negative control | 323.10 | 978.16 | 1590.65 | 2191.65 | 2498.27 |
| RTV | — | 3.30 | 5.43 | 7.41 | 8.32 |
| SB7 + PCB | 326.47 | 297.00$^a$ | 405.97$^a$ | 407.50$^a$ | 479.71$^a$ |
| RTV | — | 0.89 | 1.21 | 1.21 | 1.43$^a$ |
| 37-26 | 321.94 | 251.97$^a$ | 106.05$^a$ | 62.22$^a$ | 76.60$^a$ |
| RTV | — | 0.76 | 0.33$^{ab}$ | 0.20$^a$ | 0.24$^{ab}$ |
| 28-126 | 325.81 | 266.22$^a$ | 203.83$^a$ | 163.24$^a$ | 179.38$^a$ |
| RTV | — | 0.82 | 0.61$^a$ | 0.49 | 0.53$^a$ |
| 28-206 | 324.33 | 242.42$^a$ | 239.02$^a$ | 239.45$^a$ | 259.57$^a$ |
| RTV | — | 0.74 | 0.73$^b$ | 0.73 | 0.80$^a$ |

Note:
$^a$means P ≤ 0.05 relative to group 1; $^b$means P ≤ 0.05 relative to group 2.

It can be seen from Table 3 and FIG. 5 that SB7+PCB group and the 37-26, 28-126 and 28-206 groups have obvious inhibitory effect on tumor growth. The anti-tumor effects of the 37-26, 28-126 and 28-206 groups are better than the anti-tumor effect of the SB7+PCB combination group.

3. Relative Tumor Proliferation Rate T/C %

The statistical data of tumor T/C % and IR$_{TV}$ % are shown in Table 4 and Table 5.

TABLE 4

Statistical data of Relative tumor proliferation rate (T/C %)

| Test sample/ Control | Relative tumor proliferation rate (T/C %) | | | |
|---|---|---|---|---|
| | D5 | D8 | D12 | D15 |
| SB7 + PCB | 26.96 | 22.35 | 16.40 | 17.22* |
| 37-26 | 23.00 | 6.02* | 2.66* | 2.87* |
| 28-126 | 24.79 | 11.32* | 6.59 | 6.40* |
| 28-206 | 22.49 | 13.47 | 9.88 | 9.58* |

Note:
*means that T/C % ≤40%, and for RTV, P ≤ 0.05 relative to group 1.

TABLE 5

Statistical data of tumor volume inhibition rate (IR$_{TV}$, %)

| Test sample/ Control | Tumor volume inhibition rate (IR$_{TV}$, %) | | | |
|---|---|---|---|---|
| | D5 | D8 | D12 | D15 |
| SB7 + PCB | 73.04 | 77.65 | 83.60 | 82.78* |
| 37-26 | 77.00 | 93.98* | 97.34* | 97.13* |
| 28-126 | 75.21 | 88.68* | 93.41 | 93.60* |
| 28-206 | 77.51 | 86.53 | 90.12 | 90.42* |

Note:
*means that T/C % ≤40%, and for RTV, P ≤ 0.05 relative to group 1.

It can be seen from Table 4 and Table 5 that on D15 (the day before euthanasia), the T/C % values of 37-26 group, 28-126 group and 28-206 group were 17.22%, 2.87%, 6.40%, and 9.58%, respectively and their IR$_{TV}$ % values were 82.78%, 97.13%, 93.60%, and 90.42%, respectively.

The T/Cf the 28-206 group on D15, the T/C % the 37-26 group during the period of D8 to D15, and the T/C % the 28-126 group on D8 and D15 fell below 40%, and their mean RTV values were significantly lower than the mean RTV of the negative control group (P≤0.05).

4. Tumor Weight

Figure 6:
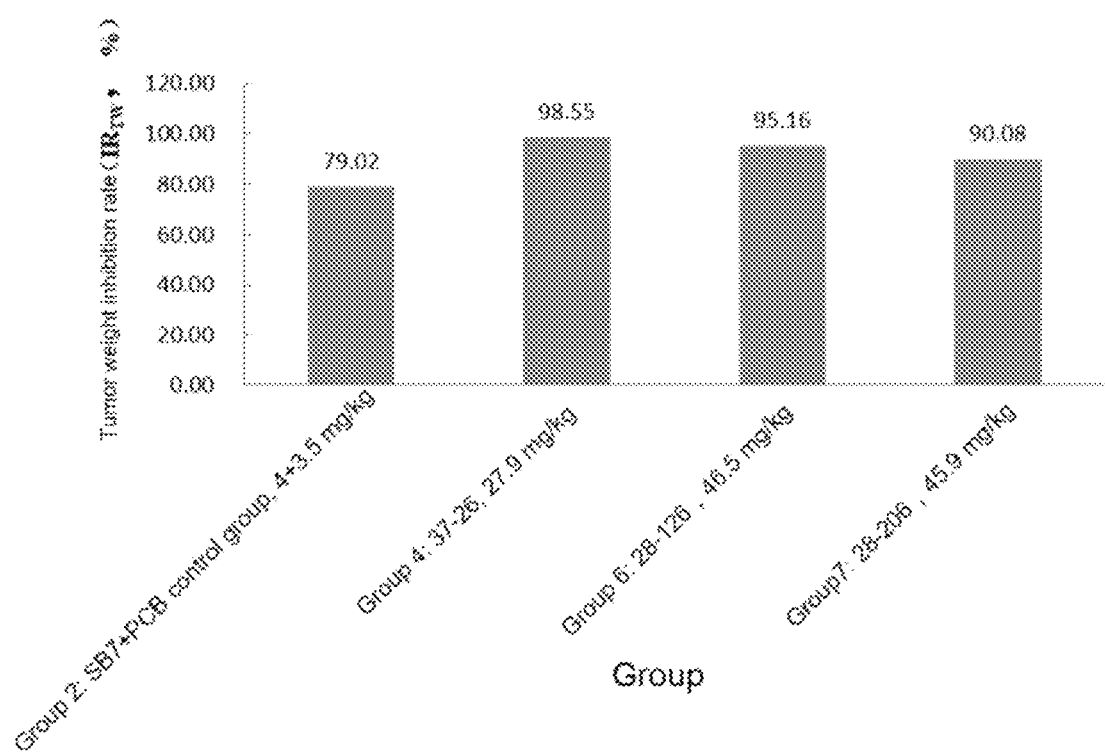
FIG. 6 shows a schematic diagram showing a tumor weight inhibition rate of each group in Experimental Example 1.

The animals were euthanized on D16 and the tumor weights were weighed. The statistical data of tumor weight and inhibition rate are shown in Table 6, and the schematic diagram of tumor weight inhibition rate is shown in FIG. 6.

TABLE 6

Statistical data of tumor weight (x ± s) and tumor weight inhibition rate (IR$_{TW}$, %)

| Test sample/ control | Tumor weight (g) | IR$_{TW}$ (%) |
|---|---|---|
| Negative control | 1.844 ± 0.475 | — |
| SB7 + PCB | 0.387 ± 0.227$^a$ | 79.01▲ |
| 37-26 | 0.027 ± 0.022$^a$ | 98.54▲ |
| 28-126 | 0.089 ± 0.114$^a$ | 95.17▲ |
| 28-206 | 0.183 ± 0.116$^a$ | 90.08▲ |

Notes:
1. IR$_{TW}$ (%) = (W$_{solvent}$ − W$_{treatment\ group}$)/W$_{solvent}$ × 100%
2. ▲means that IR$_{TW}$ % ≥60%, and as for tumor weight, P ≤ 0.05 relative to group 1.
3. $^a$means P ≤ 0.05 relative to group 1

It can be seen from Table 6 and FIG. 6 that the tumor weights of the SB7+PCB group and the 37-26, 28-126, and 28-206 groups are significantly lower than the tumor weight of the negative control group and the IR$_{TW}$ % is greater than 60%.

Conclusion: Under the experimental conditions, compound 37-26, compound 28-126, and compound 28-206 administered by tail vein injection at a dose of 27.9 mg/kg, 46.5 mg/kg, and 45.9 mg/kg respectively have a significant tumor growth inhibitory effect on the subcutaneously transplanted tumor model of human colon cancer cell COLO-205. The combination of PCB at a dose of 3.5 mg/kg by intragastric administration and SB7 administered by tail vein injection at a dose of 4.0 mg/kg also has a significant growth inhibitory effect on the tumor model. The anti-tumor effects of compound 37-26, compound 28-126, and is compound 28-206 are better than the anti-tumor effect of the SB7+PCB combination group. Although the specific embodiments of the disclosure have been described in detail, those skilled in the art will understand that various modifications and changes can be made to the details according to all the teachings that have been disclosed, and these changes are within the protection scope of the disclosure. The full scope of the disclosure is given by the appended claims and any equivalents thereof.

The invention claimed is:

1. A polyethylene glycol conjugated drug of formula (I) or a pharmaceutically acceptable salt thereof;

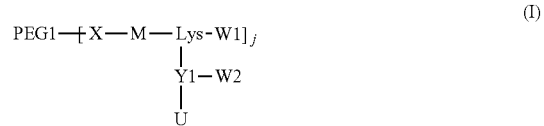

wherein Lys represents a lysine residue, PEG1 is a single-arm, four-arm or eight-arm polyethylene glycol segment, and j represents the number of arms of PEG1;

X represents carbonyl; M represents GFLG; wherein G of M is linked to an α-amino group or an ε-amino group on Lys;

Y1 is selected from:

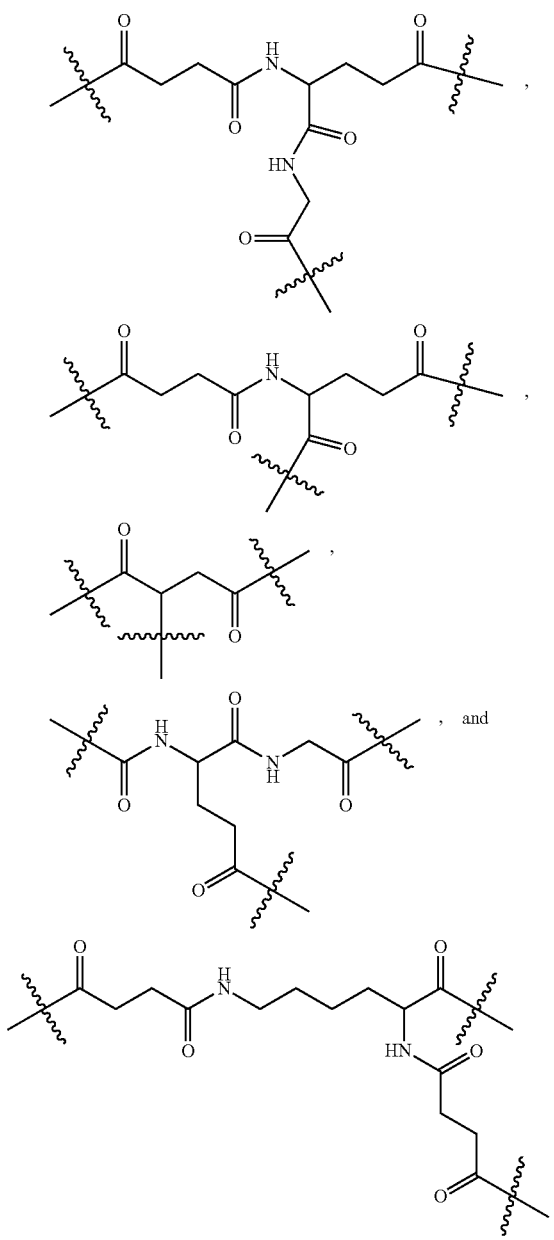

when j is 4 or 8, there are 4 or 8 Y1s at the same time, and in this case, the Y1s are the same or different;

W1 is selected from:

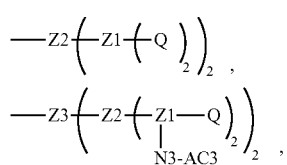

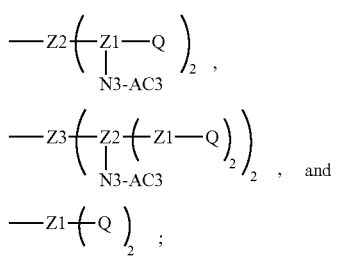

when j is 4 or 8, there are 4 or 8 W1s at the same time, and in this case, the W1s are the same or different;

Q represents

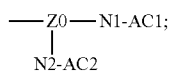

each of Z0, Z1, Z2 and Z3 is independently selected from

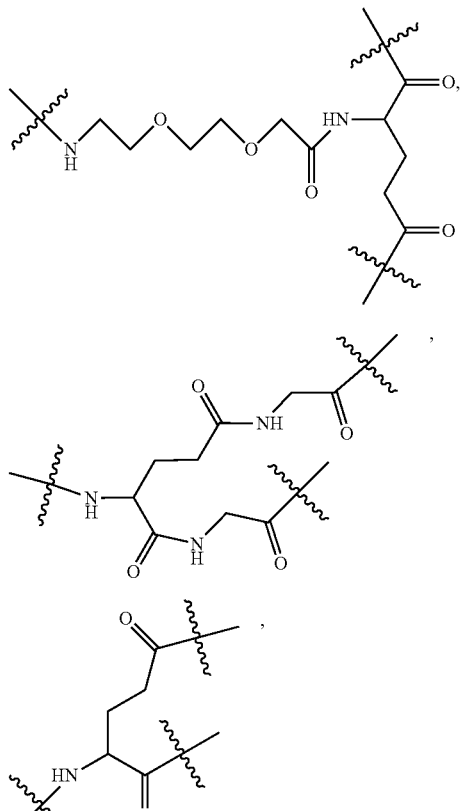

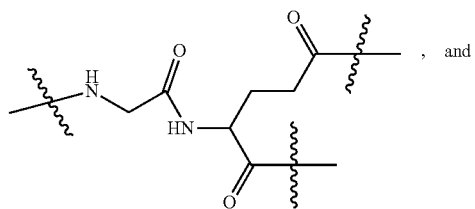

623
-continued

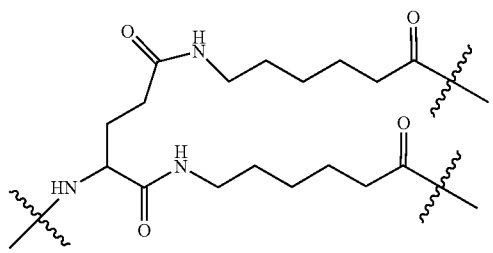
;

Z0, Z1, Z2, and Z3 may be the same or different, and when there are multiple Z0s, multiple Z1s, multiple Z2s, or multiple Z3s at the same time, the Z0s are the same or different, the Z1s are the same or different, the Z2s are the same or different, or the Z3s are the same or different;

each of N1, N2 and N3 independently is G or GFLG; N1, N2 and N3 are the same or different, and when there are multiple N1s, multiple N2s or multiple N3s at the same time, the N1s are the same or different, the N2s are the same or different, or the N3s are the same or different;

AC1, AC2 and AC3 are drug molecules with anti-tumor activity; AC1, AC2 and AC3 are the same or different, and when there are multiple AC1s, multiple AC2s or multiple AC3s at the same time, the AC1s are the same or different, the AC2s are the same or different, or the AC3s are the same or different;

W2 is selected from H, N1'-AC1', Q',

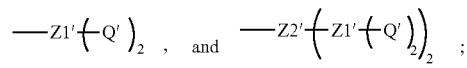

when j is 4 or 8, there are 4 or 8 W2s at the same time, and in this case, the W2s are the same or different;

Q' represents

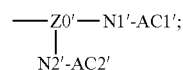

each of Z0', Z1' and Z2' is independently selected from:

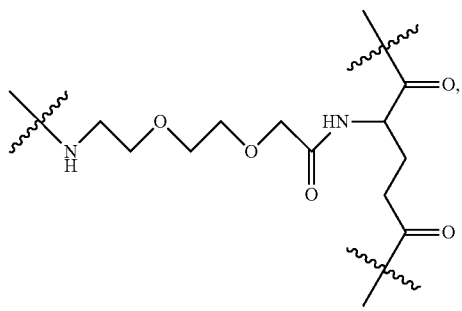

624
-continued

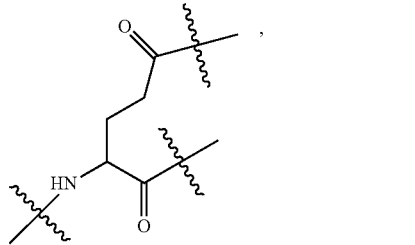
,

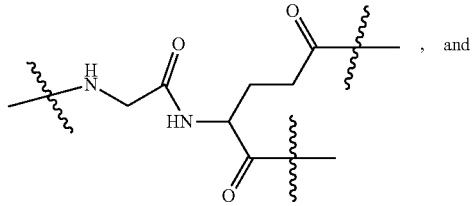
, and

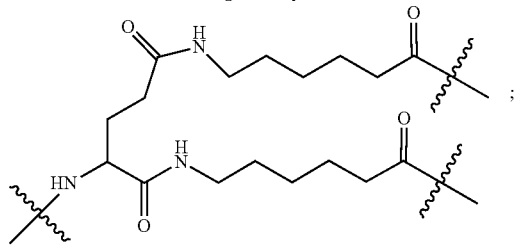
;

Z0', Z1' and Z2' are the same or different, and when there are multiple Z0's, multiple Z1's or multiple Z2's at the same time, the Z0's are the same or different, the Z1's are the same or different, or the Z2's are the same or different;

each of N1' and N2' independently is G or GFLG; N1' and N2' are the same or different, and when there are multiple N1's or multiple N2's at the same time, the N1's are the same or different or the N2's are the same or different;

AC1' and AC2' are drug molecules with anti-tumor activity; AC1' and AC2' are the same or different, and when there are multiple AC1's or multiple AC2's at the same time, the AC1's are the same or different or the AC2's are the same or different;

U represents PEG2 or

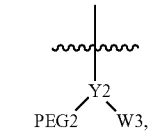

wherein PEG2 represents a single-arm polyethylene glycol segment, which is linked to Y1 or Y2 through an amide bond;

Y2 represents

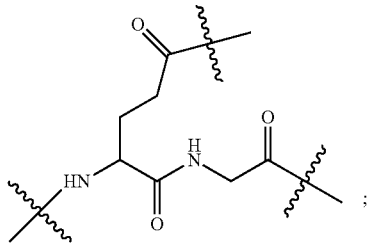 [SMILES: *NC(CCC(*)=O)C(=O)NCC(*)=O]

W3 represents N1"-AC1", wherein N1" is GFLG and AC1" is a a drug molecule with anti-tumor activity).

2. The polyethylene glycol conjugated drug or a pharmaceutically acceptable salt thereof according to claim 1, characterized in one or more of the following:
(1) PEG1 is a four-arm or eight-arm polyethylene glycol segment;
(2) PEG1 has a number-average molecular weight of 5 k-10 k, 10 k-20 k or 20 k-40 k;
(3) PEG2 has a number-average molecular weight of 5 k-10 k or 10 k-20 k;
(4) each of AC1, AC2, AC3, AC1', AC2', and AC1" is independently selected from MK2, LPT, PCB, SB7, PKI, and NPB; wherein MK2 is MK-2206·2HCl, LPT is Lapatinib, PCB is Palbociclib, SB7 is SB-743921, PKI is allosteri PKI-587, and NPB is Niraparib;
PKI has a structure of

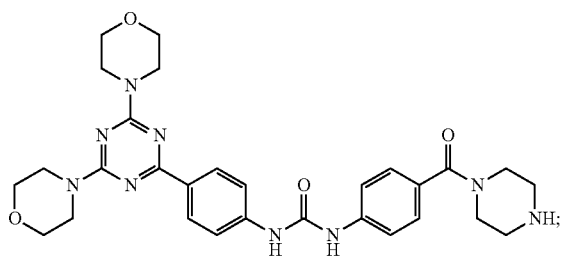 [SMILES: O=C(Nc1ccc(C(=O)N2CCNCC2)cc1)Nc1ccc(-c2nc(N3CCOCC3)nc(N3CCOCC3)n2)cc1]

(5) N1, N2 and N3 are all GFLG;
(6) N1 and N2 are both GFLG;
(7) N1 and N2 are both G; and
(8) N1' and N2' are both GFLG.

3. The polyethylene glycol conjugated drug or a pharmaceutically acceptable salt thereof according to claim 1, wherein AC1 and AC2 are selected from:
(1) a combination in which AC1 is MK2 and AC2 is PCB,
(2) a combination in which AC1 and AC2 are both PCB;
(3) a combination in which AC1 and AC2 are both LPT;
(4) a combination in which AC1 is PCB and AC2 is SB7;
(5) a combination in which AC1 and AC2 are both SB7;
(6) a combination in which AC1 and AC2 are both PKA;
(7) a combination in which AC1 and AC2 are both SN38; and
(8) a combination in which AC1 is LPT and AC2 is PCB;
wherein MK2 is MK-2206·2HCl, LPT is Lapatinib, PCB is Palbociclib, SB7 is SB-743921, SN38 is 7-ethyl-10-hydroxycamptothecin, and PKA is de-terminal-dimethyl PKI-587; PKA has a structure of

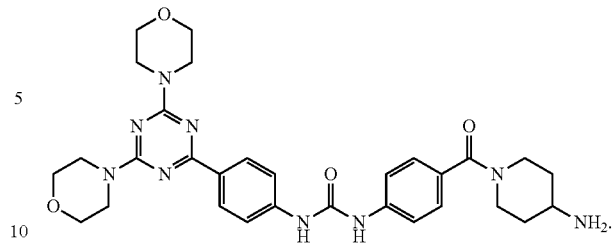

4. The polyethylene glycol conjugated drug or a pharmaceutically acceptable salt thereof according to claim 1, wherein AC1, AC2 and AC3 are selected from:
(1) a combination in which AC1, AC2 and AC3 are all LPT; and
(2) a combination in which AC1 and AC2 are both PCB and AC3 is SB7,
wherein LPT is Lapatinib, and SB7 is SB-743921.

5. The polyethylene glycol conjugated drug or a pharmaceutically acceptable salt thereof according to claim 1, wherein AC1' and AC2' are selected from:
(1) a combination in which AC1' and AC2' are both PCB;
(2) a combination in which AC1' is PCB and AC2' is SB7;
(3) a combination in which AC1' and AC2' are both LPT; and
(4) a combination in which AC1' is LPT and AC2' is PCB;
wherein LPT is Lapatinib, PCB is Palbociclib, and SB7 is SB-743921.

6. The polyethylene glycol conjugated drug or a pharmaceutically acceptable salt thereof according to claim 1, wherein the polyethylene glycol conjugated drug has a structure of formula (II):

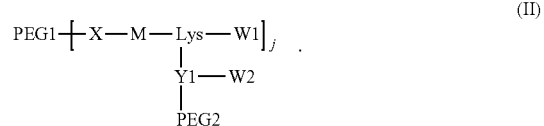

7. The polyethylene glycol conjugated drug or a pharmaceutically acceptable salt thereof according to claim 6, wherein
Y1 is

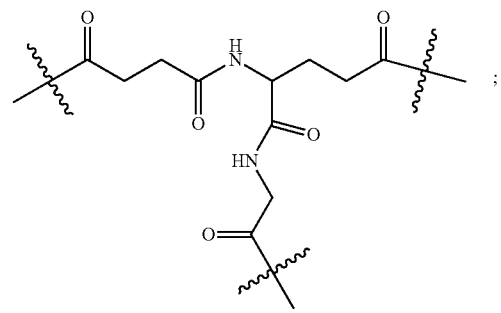 [SMILES: *C(=O)CCC(=O)NC(CCC(*)=O)C(=O)NCC(*)=O]

W1 is selected from

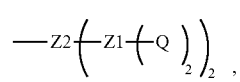

-continued

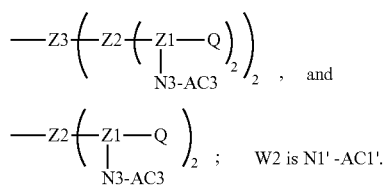
, and

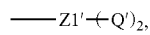; W2 is N1'-AC1'.

8. The polyethylene glycol conjugated drug or a pharmaceutically acceptable salt thereof according to claim 6, wherein
Y1 is

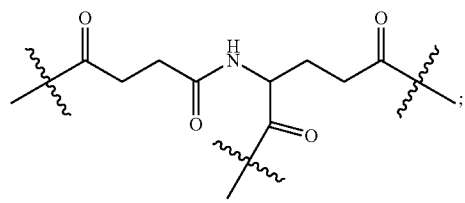 [SMILES: *C(=O)CCC(=O)NC(CCC(*)=O)C(*)=O]
;

W1 is selected from

—Z2—(Z1—(Q)₂)₂    and    —Z1—(Q)₂;

W2 is selected from N1'-AC1',

—Z1'—(Q')₂, and Q'.

9. The polyethylene glycol conjugated drug or a pharmaceutically acceptable salt thereof according to claim 6, wherein
Y1 is

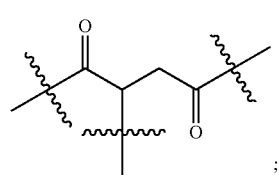 [SMILES: *C(=O)CC(*)C(*)=O]
;

W1 is selected from

—Z2—(Z1—(Q)₂)₂  and  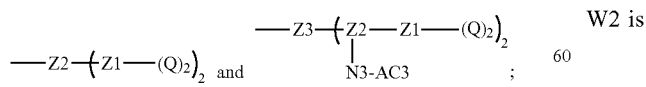;

and W2 is H.

10. The polyethylene glycol conjugated drug or a pharmaceutically acceptable salt thereof according to claim 6, wherein Y1 is

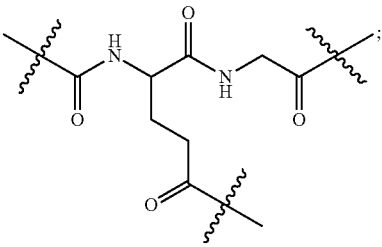 [SMILES: *C(=O)CCC(NC(*)=O)C(=O)NCC(*)=O]
;

W1 is

—Z2—(Z1—(Q)₂)₂;

W2 is

—Z2'—(Z1'—(Q')₂)₂.

11. The polyethylene glycol conjugated drug or a pharmaceutically acceptable salt thereof according to claim 6, wherein
Y1 is

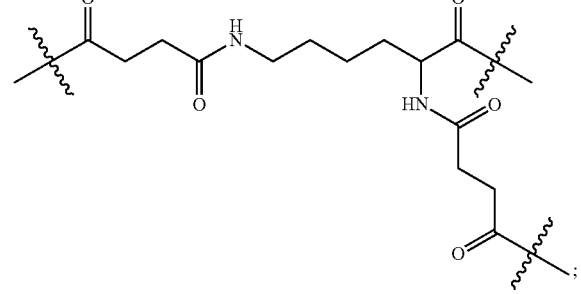
;

W1 is

—Z2—(Z1—(Q)₂)₂;

W2 is

—Z2'—(Z1'—(Q')₂)₂.

12. The polyethylene glycol conjugated drug or a pharmaceutically acceptable salt thereof according to claim 6, wherein Y1 is

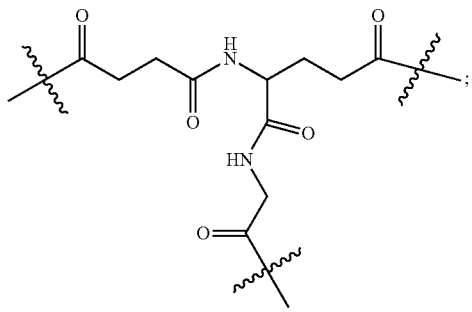 [SMILES: *C(=O)CCC(=O)NC(CCC(*)=O)C(=O)NCC(*)=O]

W1 is

—Z1─(Q)₂;

W2 is

—Z1'─(Q')₂.

13. The polyethylene glycol conjugated drug or a pharmaceutically acceptable salt thereof according to claim 1, wherein the polyethylene glycol conjugated drug has a structure of formula (III):

$$\begin{array}{c} \text{PEG1}\!-\!\!\left[\text{X}-\text{M}-\text{Lys-W1}\right]_j \\ | \\ \text{Y1}-\text{W2.} \\ | \\ \text{Y2} \\ \diagup \diagdown \\ \text{PEG2} \quad \text{W3} \end{array} \quad (III)$$

14. The polyethylene glycol conjugated drug or a pharmaceutically acceptable salt thereof according to claim 1, the polyethylene glycol conjugated drug being selected from

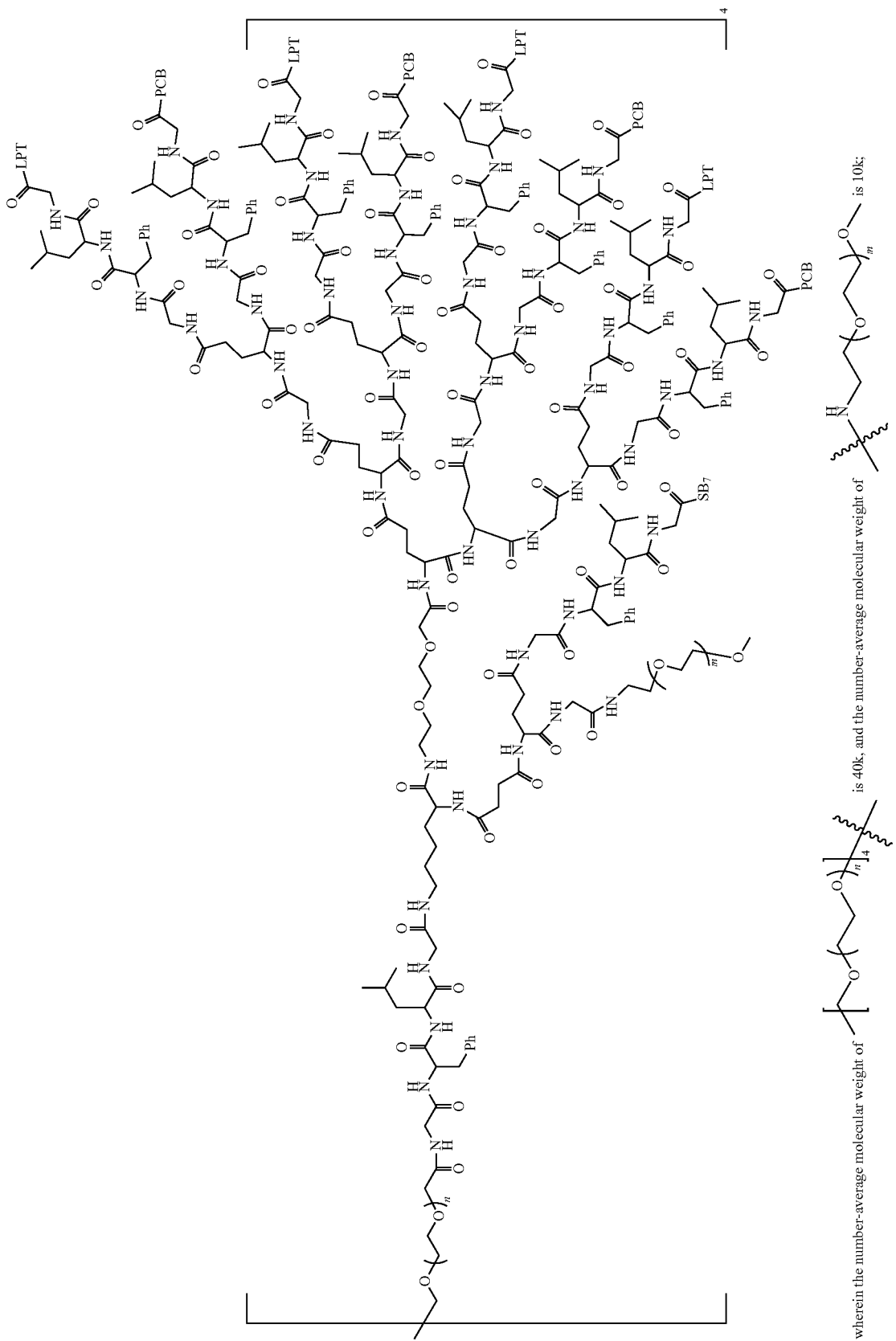

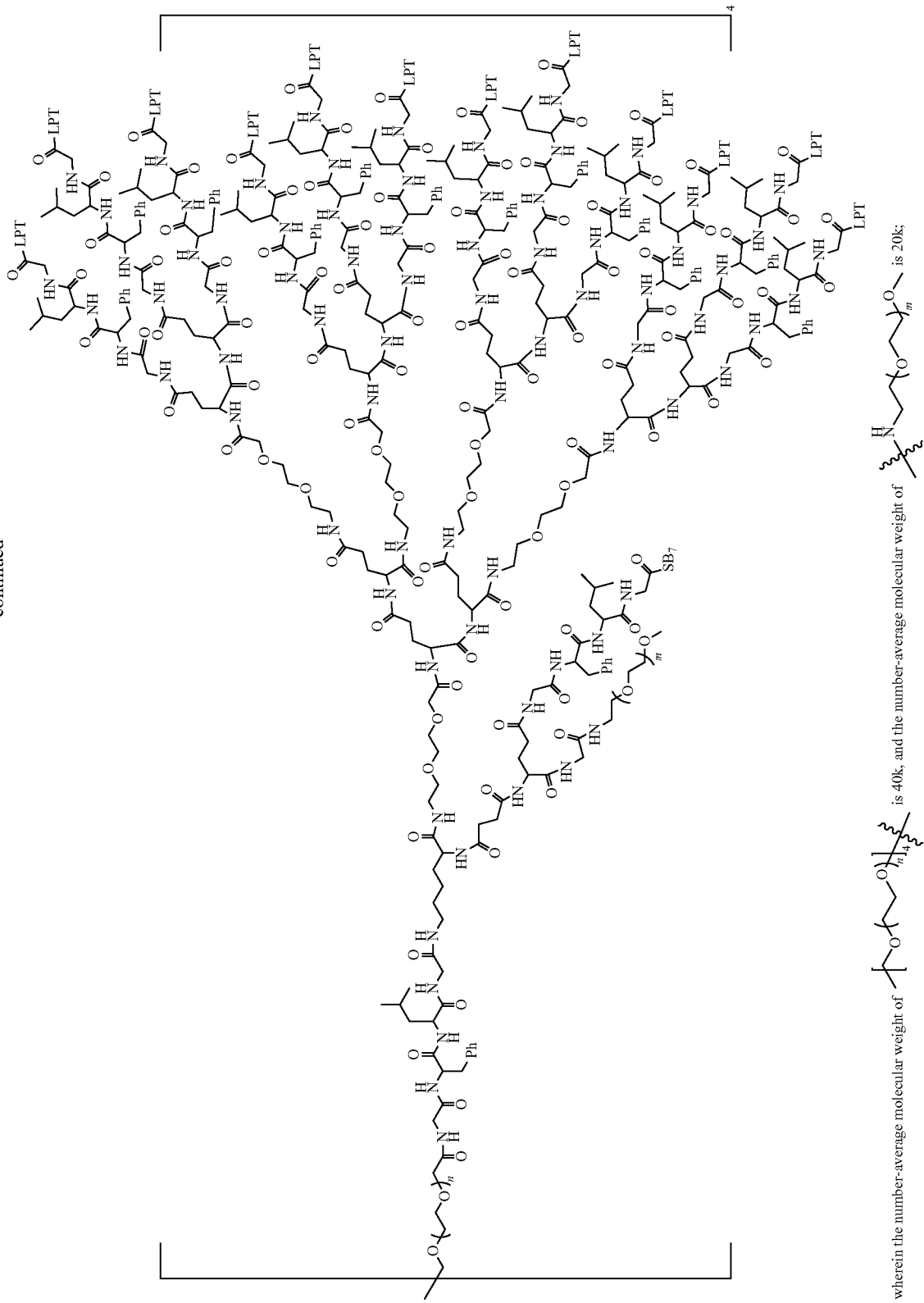

-continued
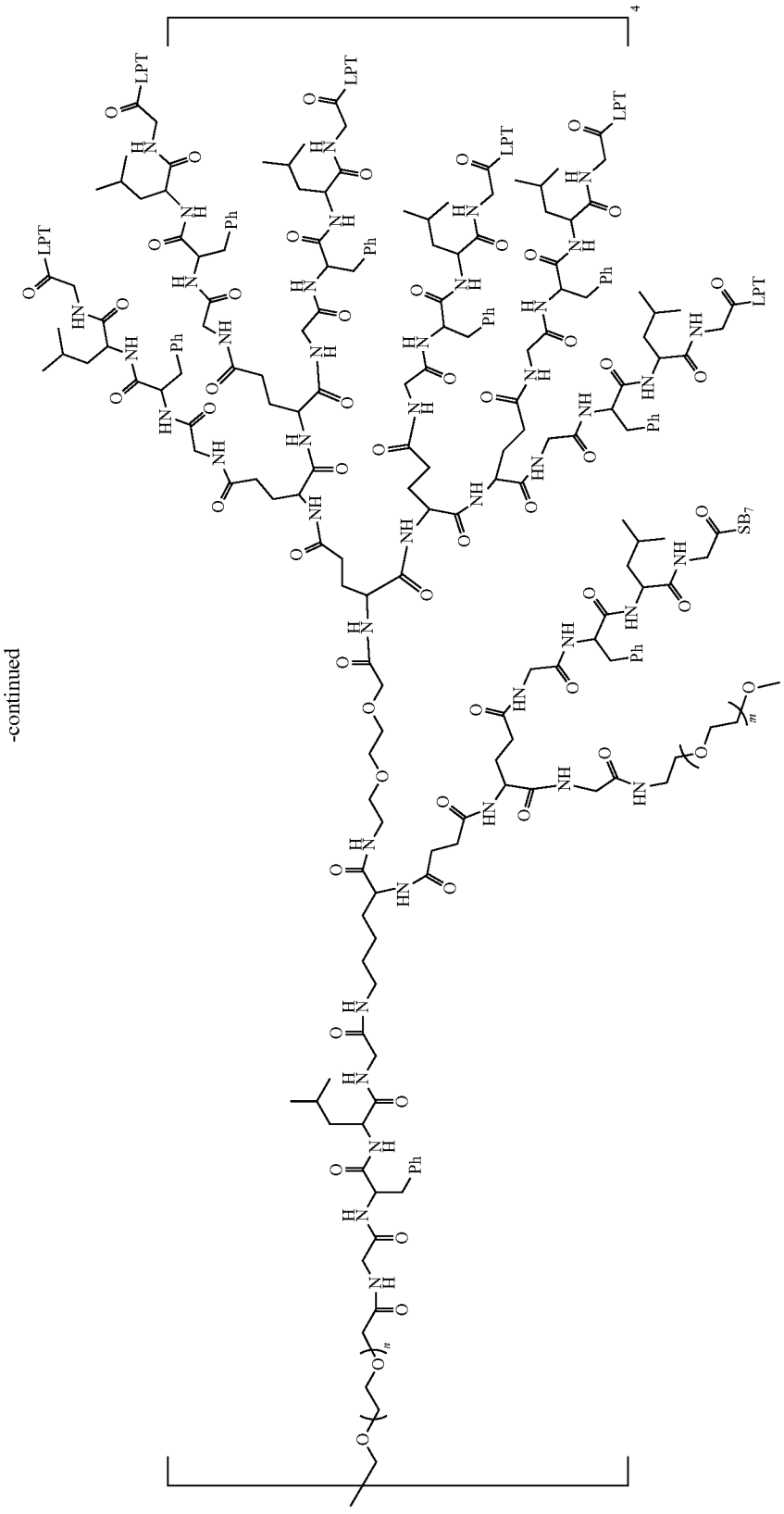
wherein the number-average molecular weight of  is 40k, and the number-average molecular weight of the PEG is 10k;

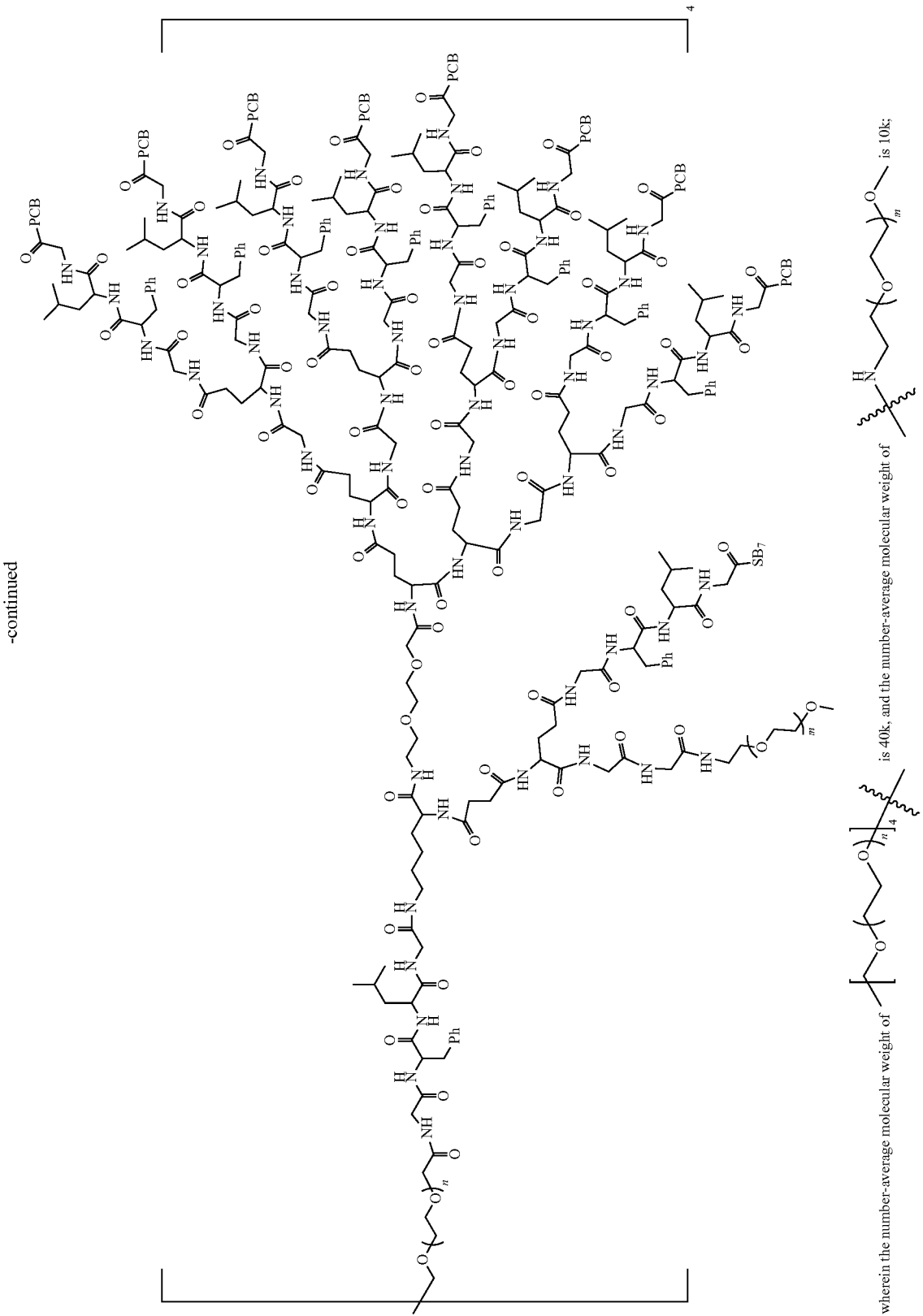

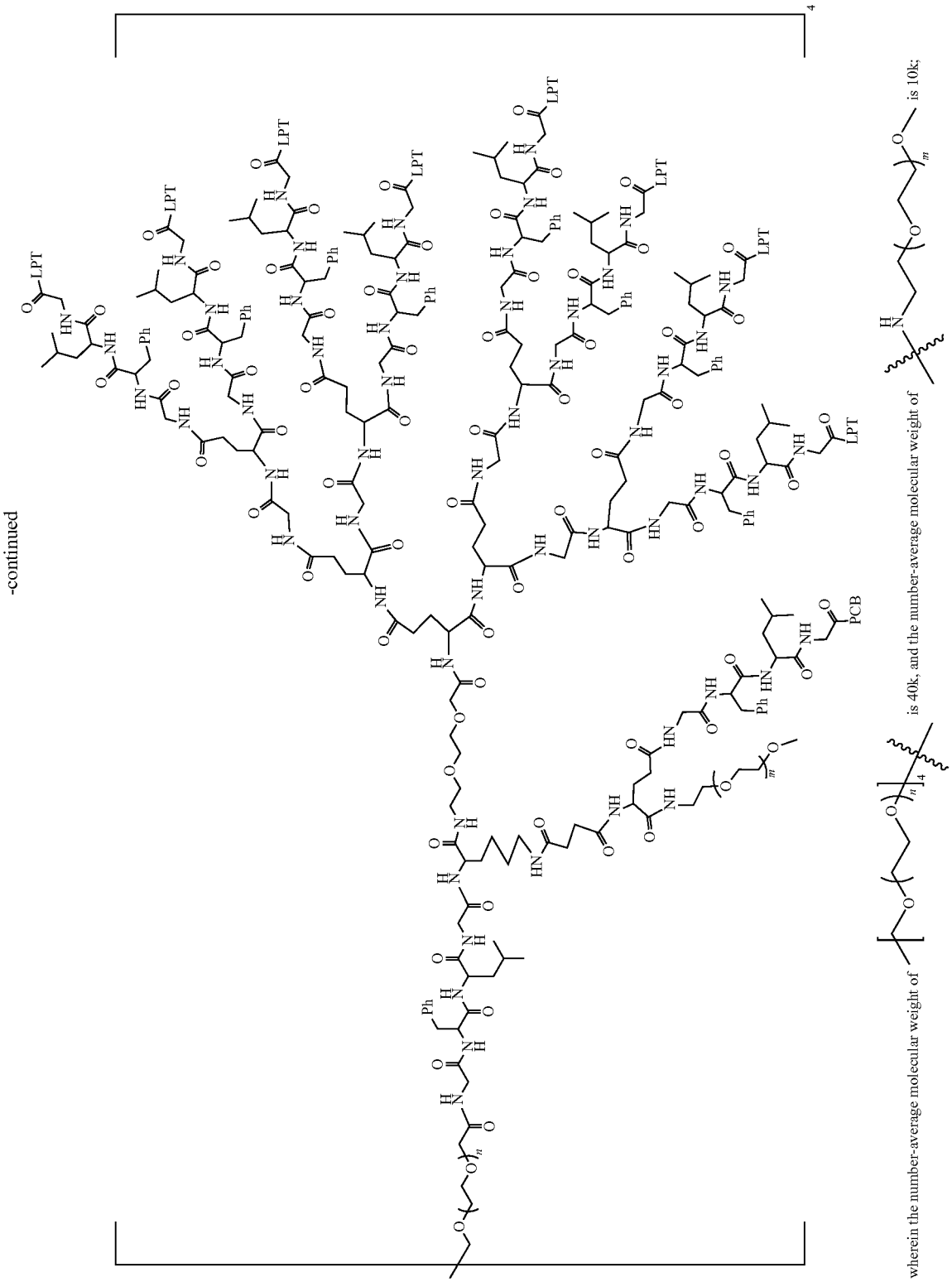

-continued
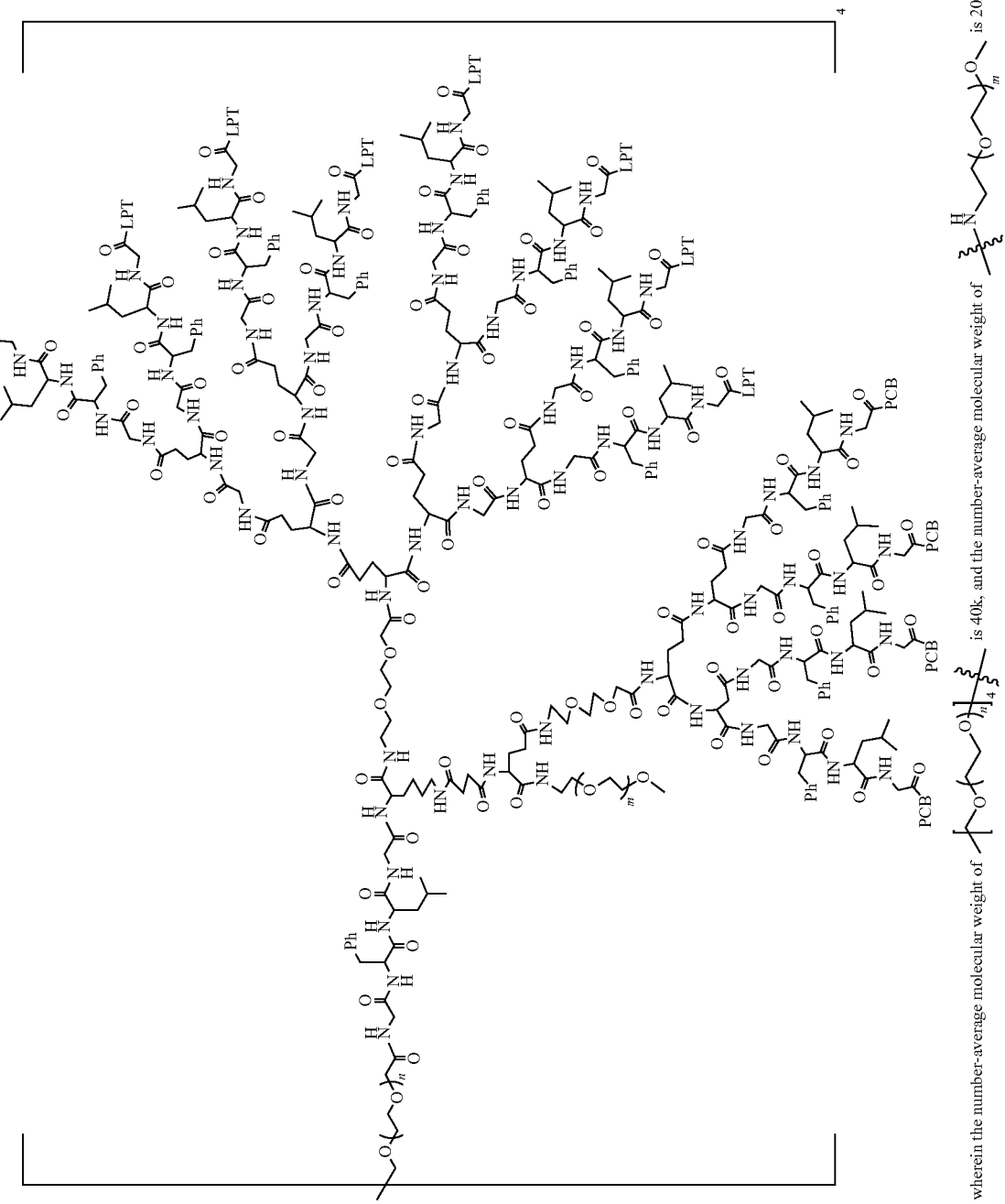

-continued

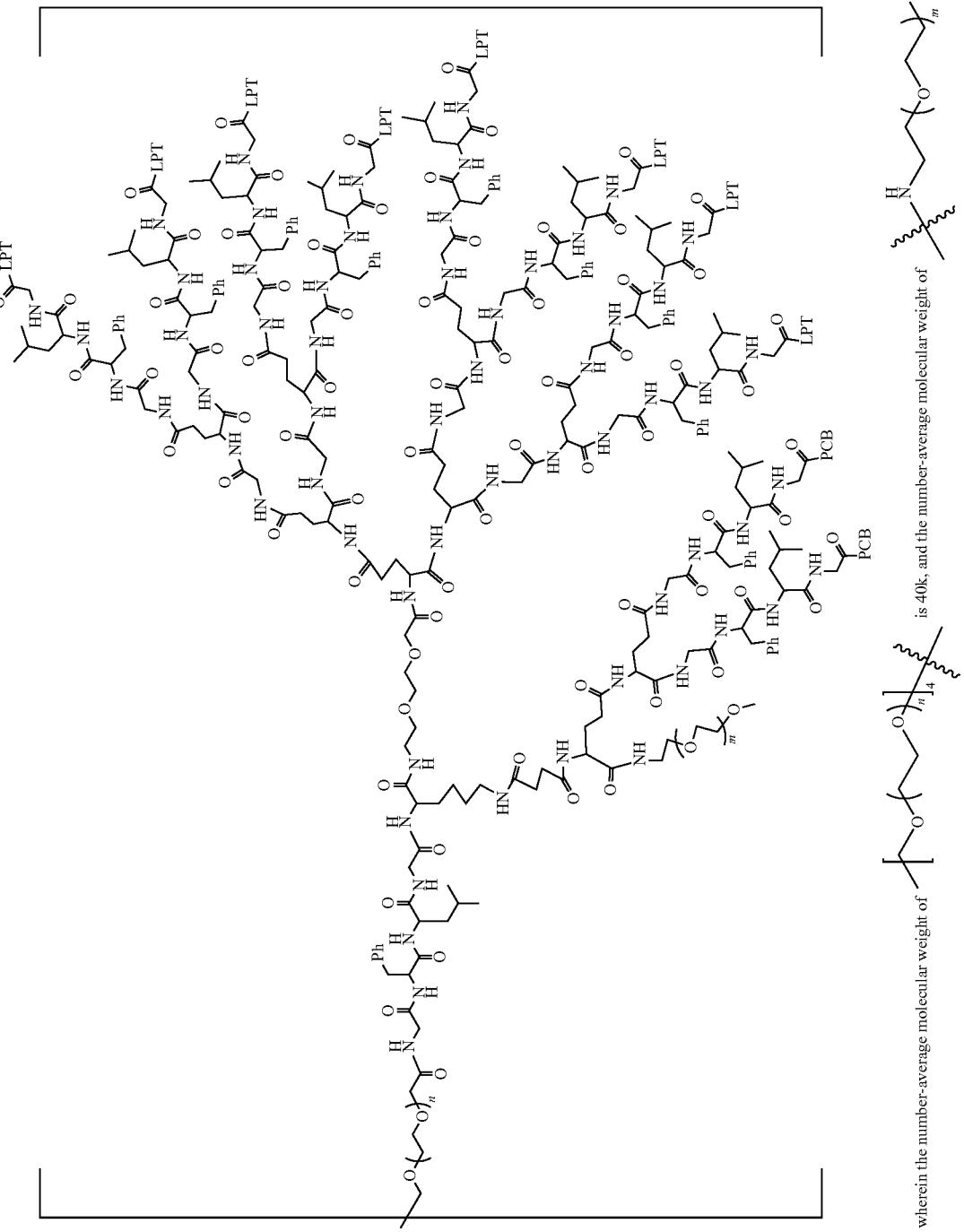

wherein the number-average molecular weight of $\underset{\substack{\text{\Large/}\\O}}{\overset{\substack{\text{\Large\textbackslash}}}{\phantom{O}}}\!\!\left(\!\!\diagup\!\!\diagdown\!\!\mathrm{O}\right)_{\!\!n}\!\!\diagup$ is 40k, and the number-average molecular weight of $\underset{H}{N}\!\!\diagup\!\!\diagdown\!\!\left(\mathrm{O}\!\!\diagup\!\!\diagdown\right)_{\!\!m}\!\!\mathrm{O}\diagdown$ is 20k;

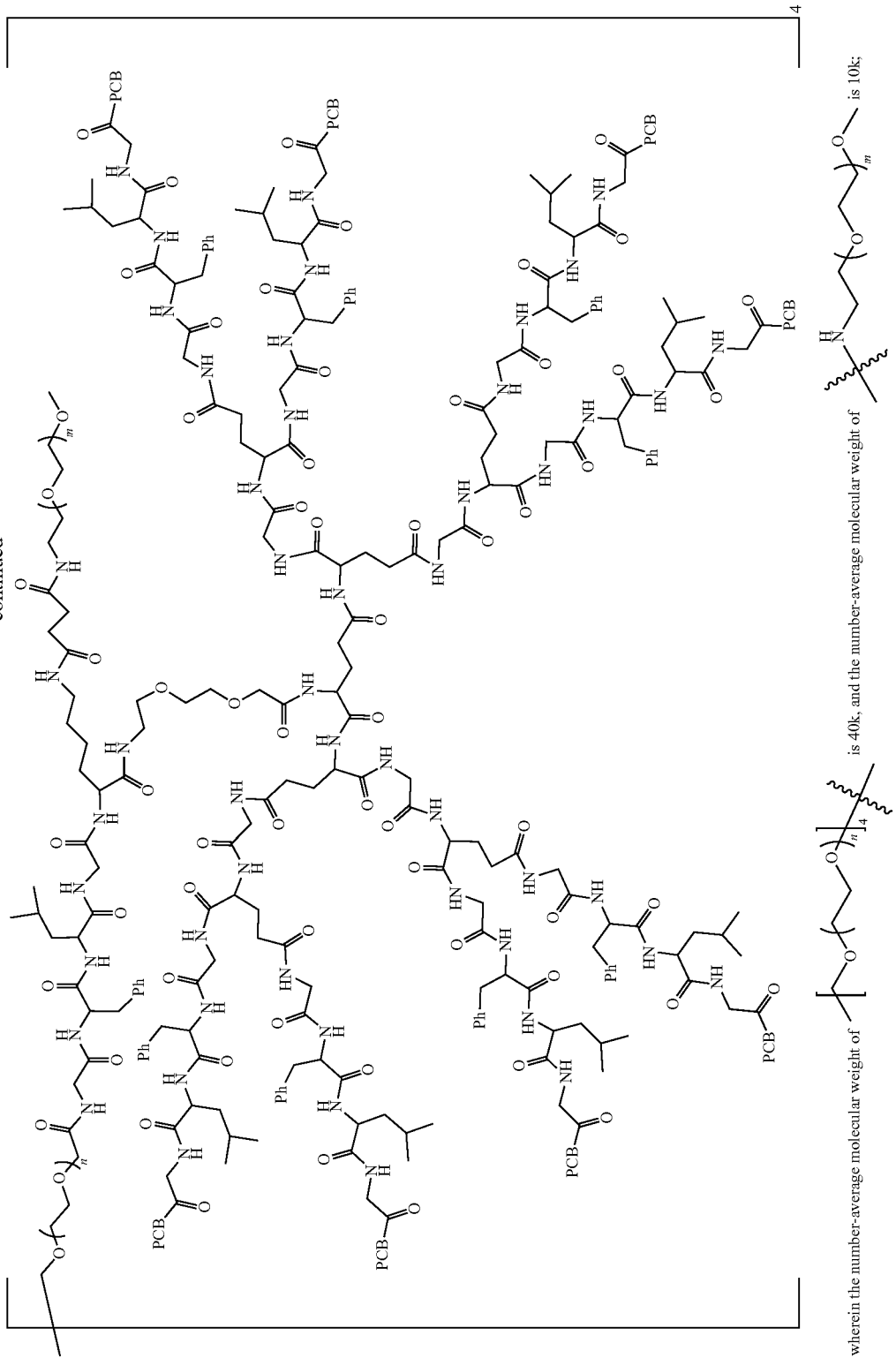

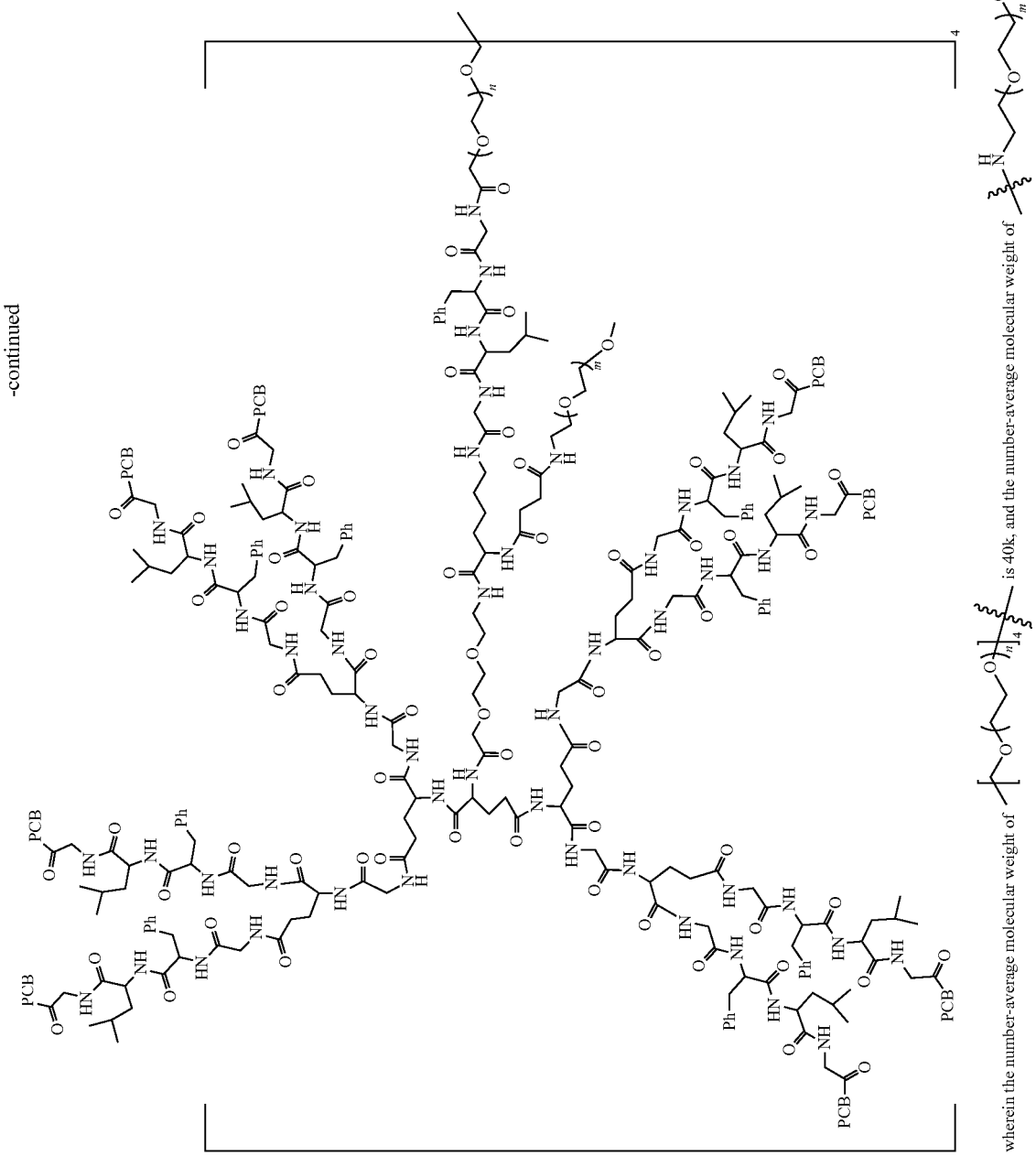

wherein the number-average molecular weight of $\underset{n14}{\sim\!\!\!\!\!\sim\!\!\!\!\!\sim\!\!\!\!\!\!\sim}\!\!-\!\!O\!\!\left(\!\!\begin{array}{c}\\ \\ \end{array}\!\!\!\!\!\!\!\!O\!\!\right)_{n14}$ is 40k, and the number-average molecular weight of $\underset{}{\sim\!\!\!\!\!\sim\!\!\!\!\!\sim\!\!\!\!\!\!\sim}\!\!-\!\!N\!\!\!\!H\!\!\left(\!\!\begin{array}{c}\\ \\ \end{array}\!\!\!\!\!\!\!\!O\!\!\right)_{m}\!\!-\!\!O\!\!-\!\!$ is 10k;

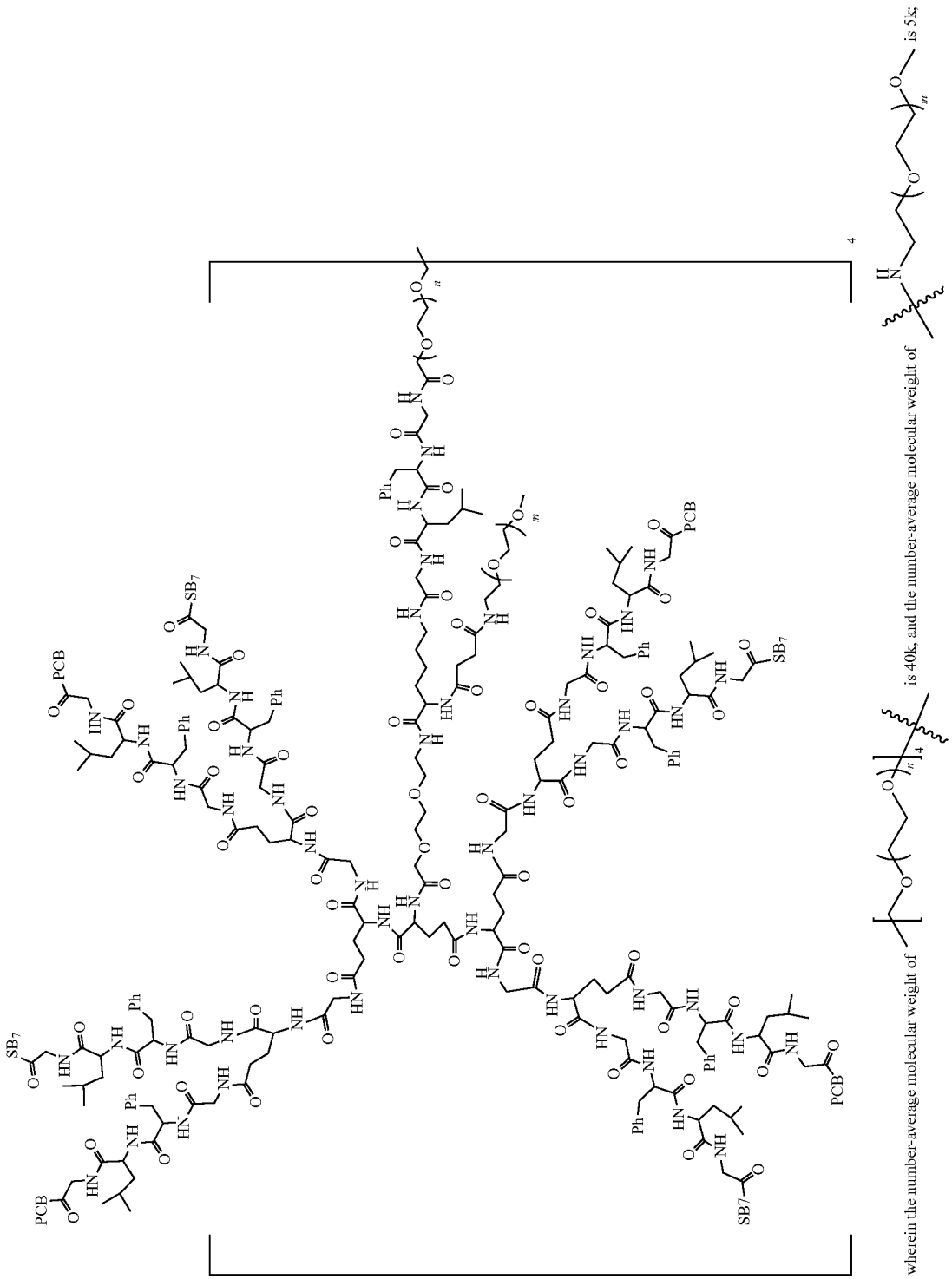

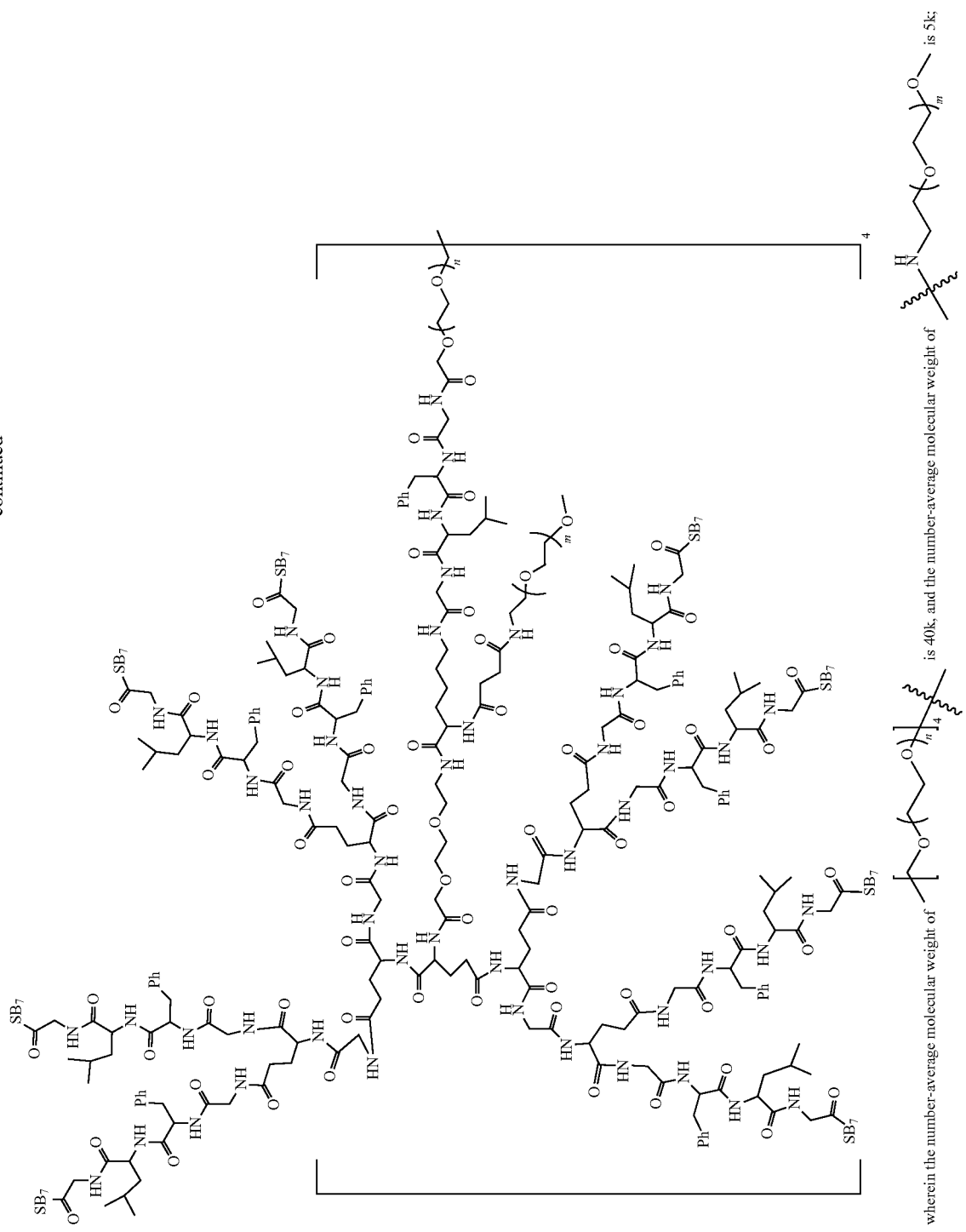

-continued
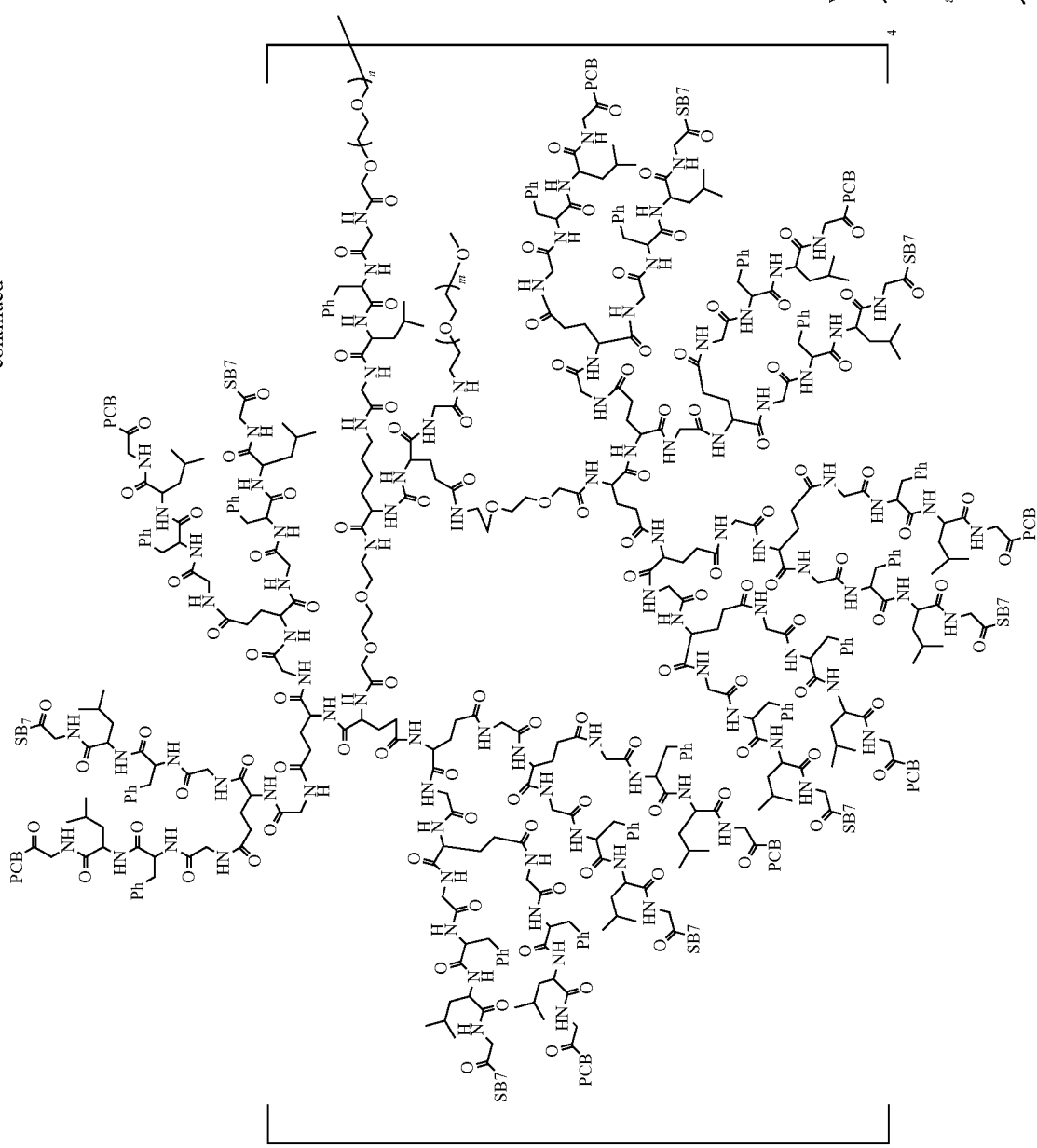
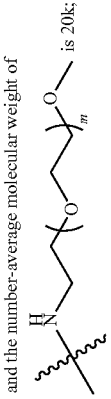
wherein the number-average molecular weight of $[\text{structure}]_4$ is 40k, and the number-average molecular weight of $[\text{structure}]_m$ is 20k;

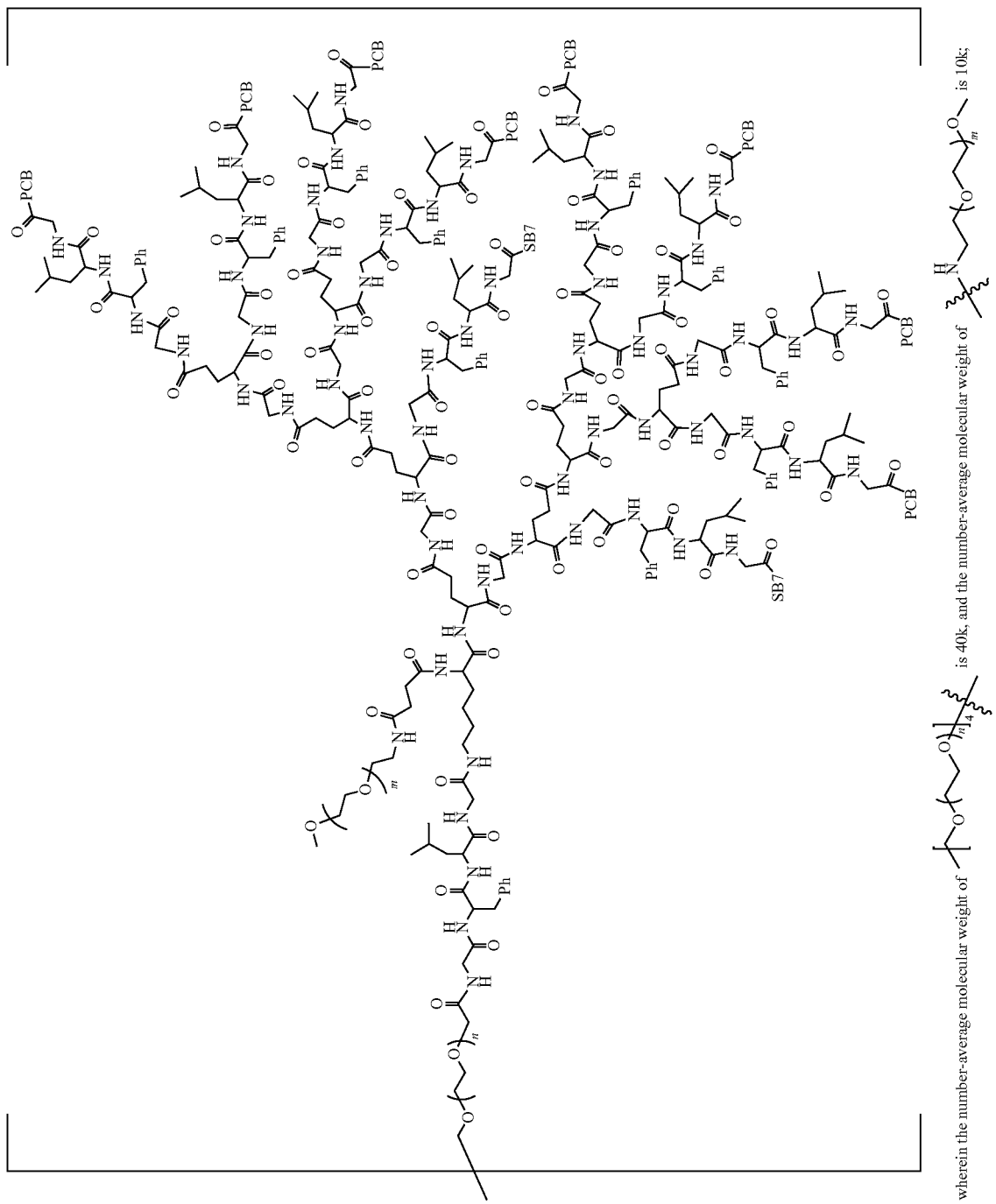

-continued
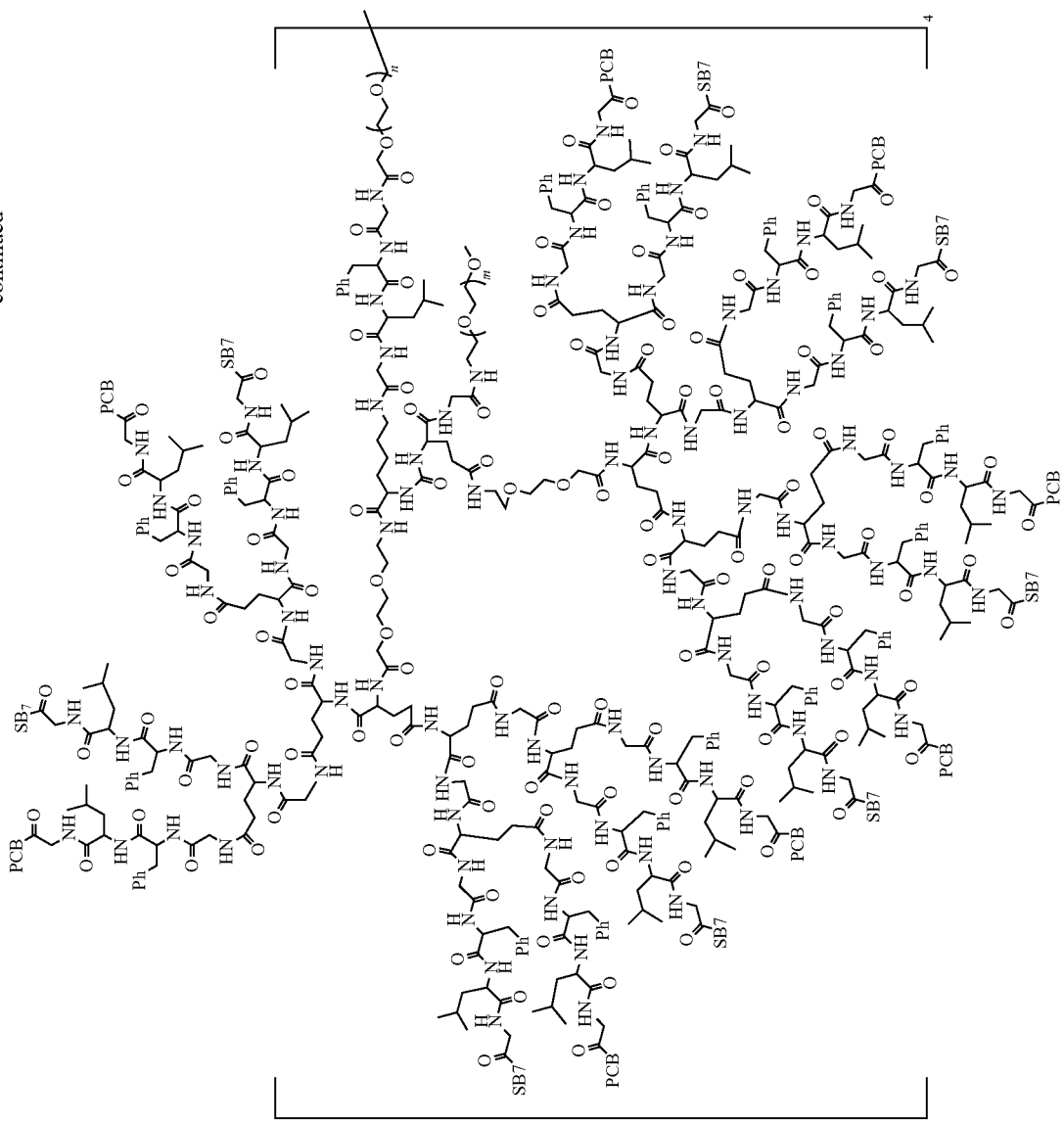

-continued
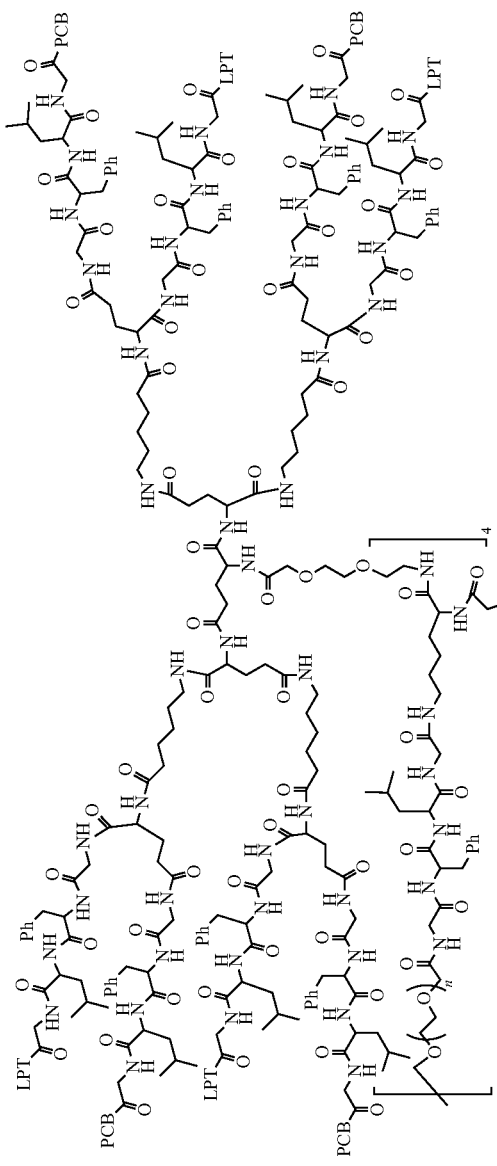
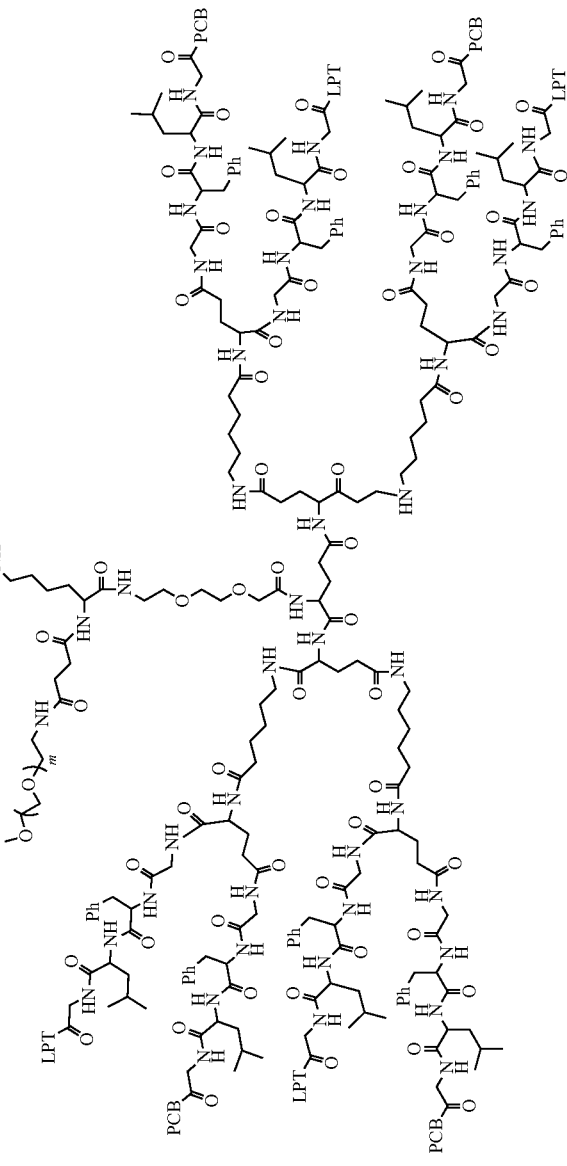
wherein the number-average molecular weight of $\begin{bmatrix}\phantom{x}\end{bmatrix}_n$ is 40k, and the number-average molecular weight of $\begin{bmatrix}\phantom{x}\end{bmatrix}_m$ is 20k;

-continued
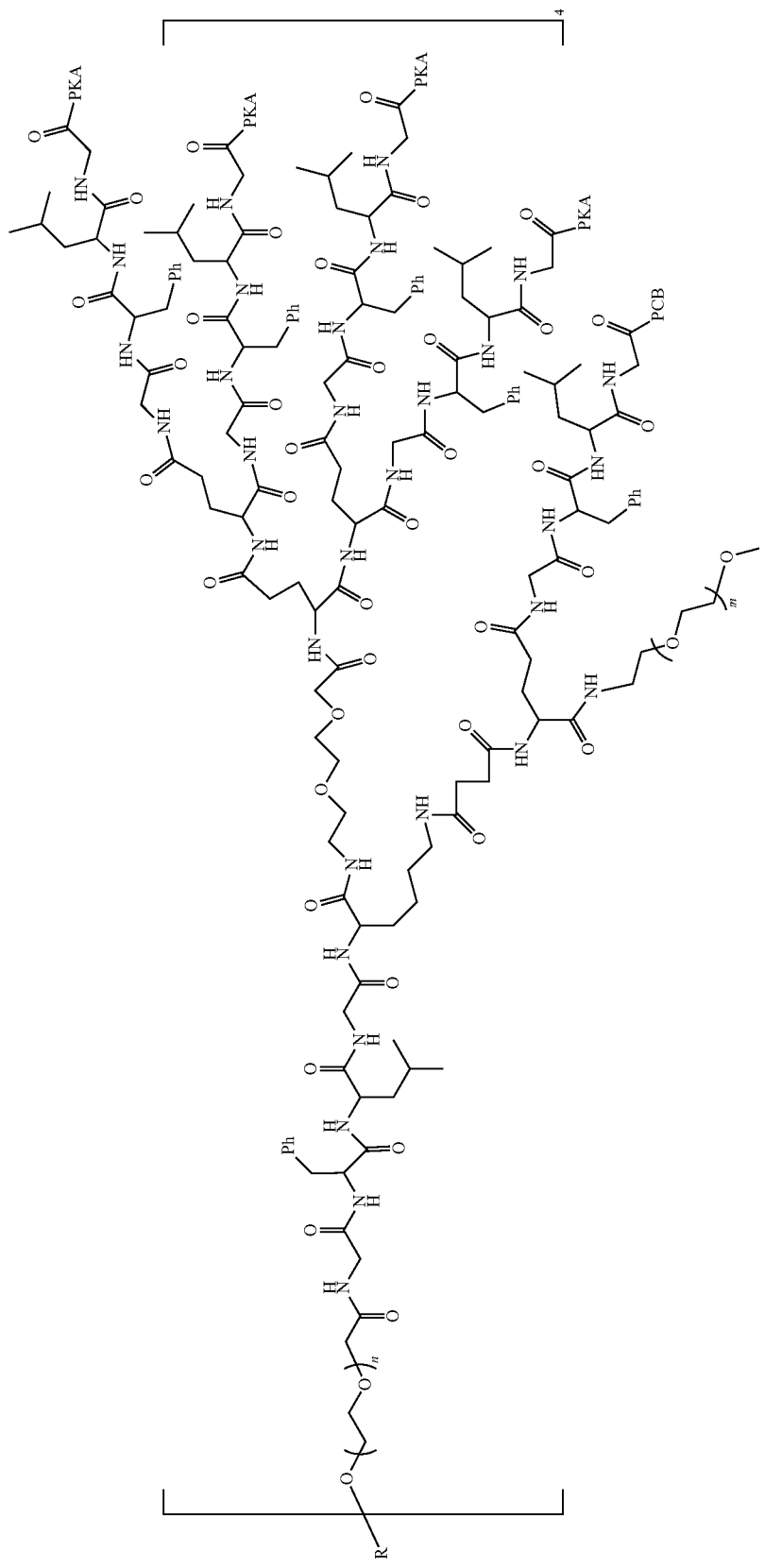
wherein R is a core structure of an eight-arm polyethylene glycol; the number-average molecular weight of  is 40k, and the number-average molecular weight of R is 5k;

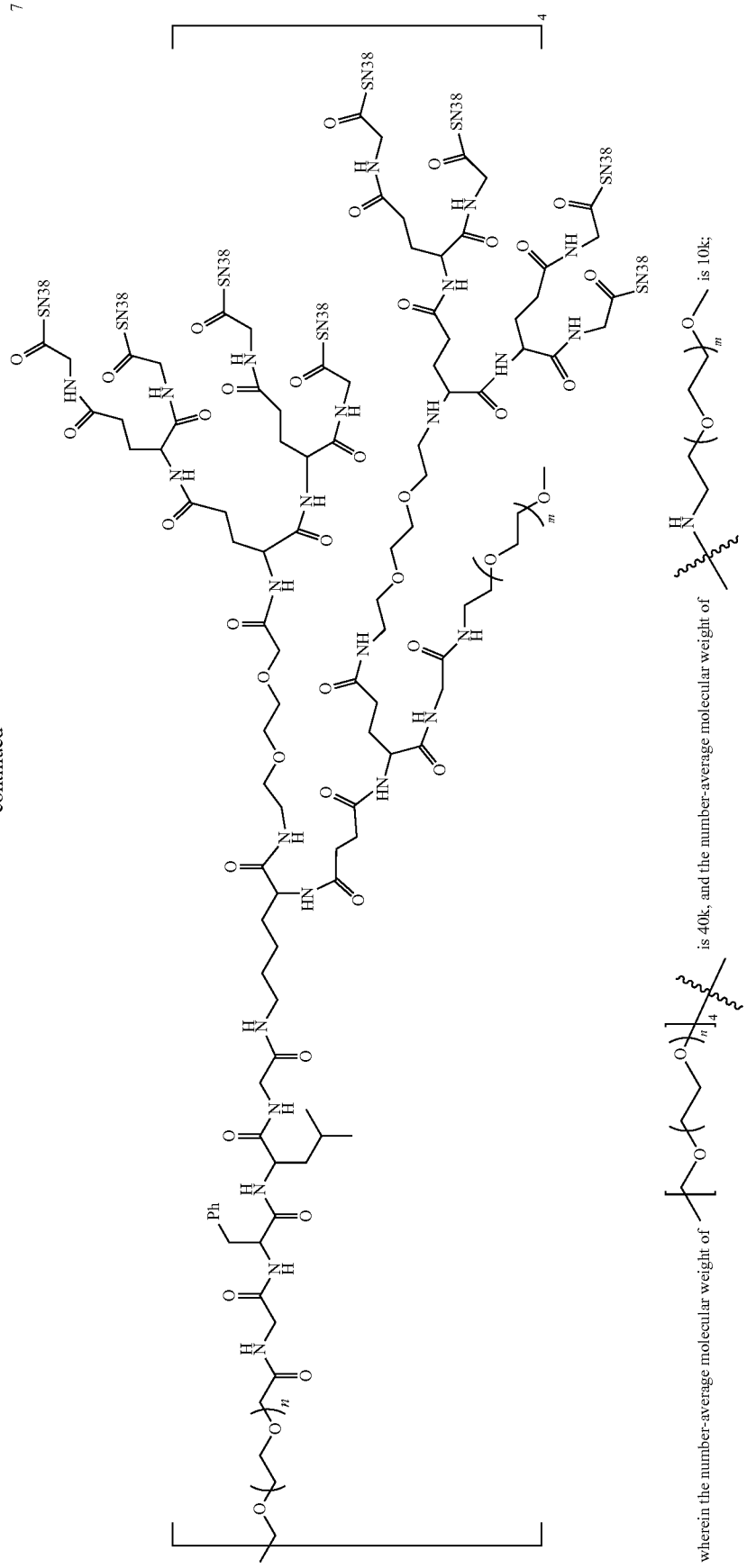

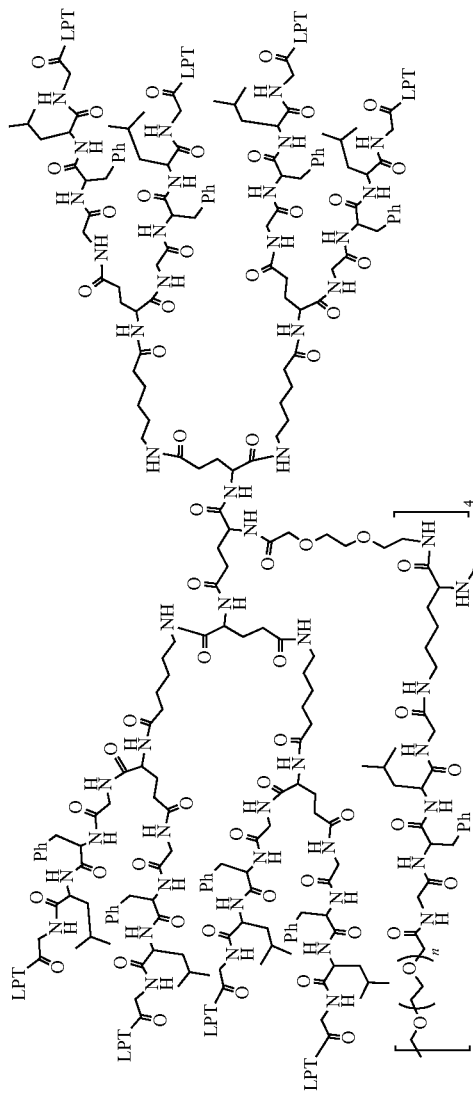
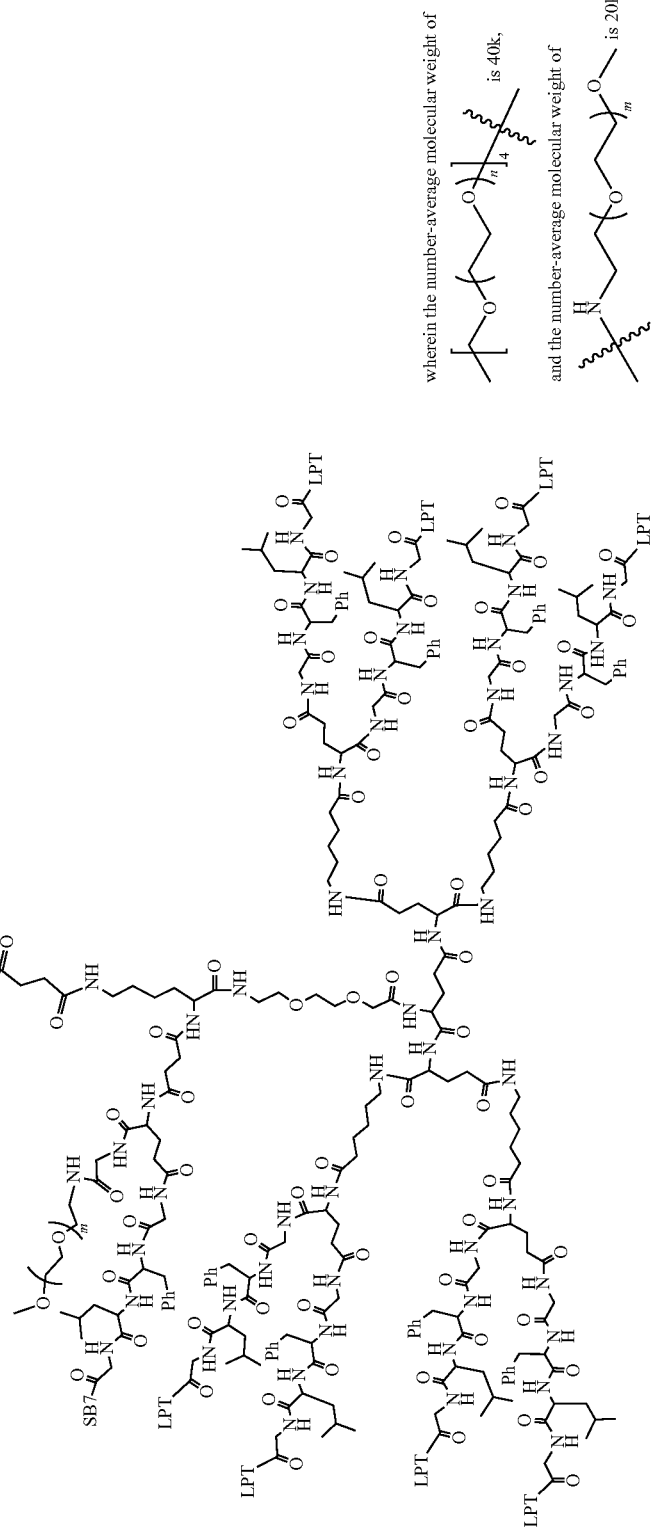

-continued
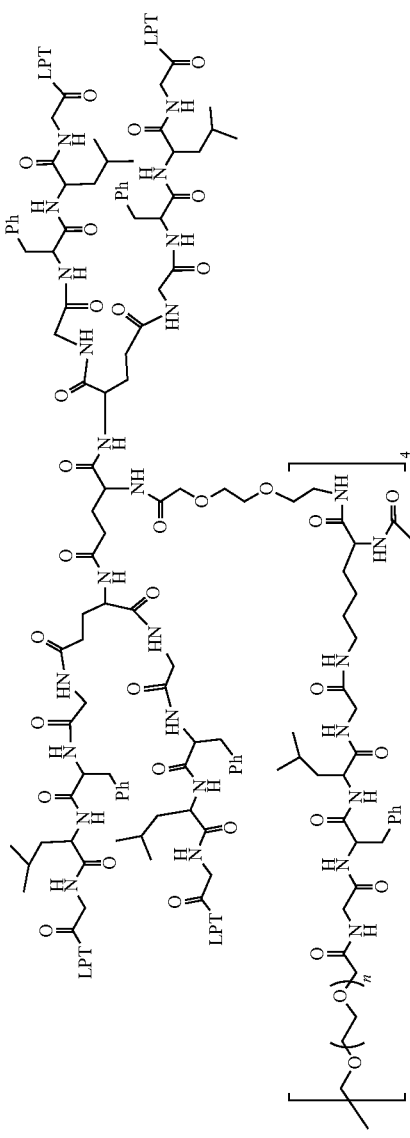
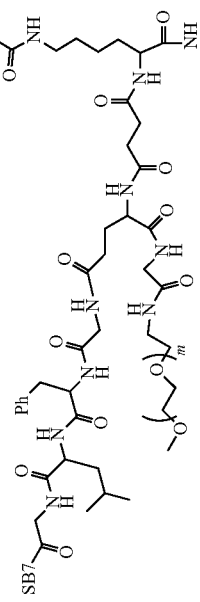
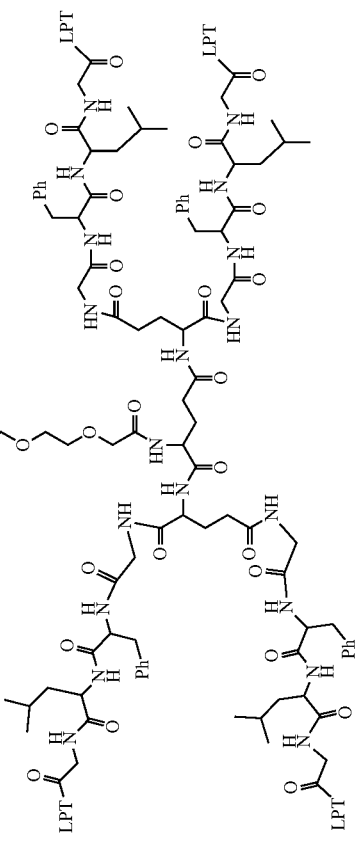
wherein the number-average molecular weight of $\left(\!\!\begin{array}{c}\\ \\ \end{array}\!\!O\!\!\begin{array}{c}\\ \\ \end{array}\!\!\right)_{\!n}$ is 40k, and the number-average molecular weight of $\left(\!\!\begin{array}{c}\\ \\ \end{array}\!\!O\!\!\begin{array}{c}\\ \\ \end{array}\!\!\right)_{\!m}$ is 20k;

-continued
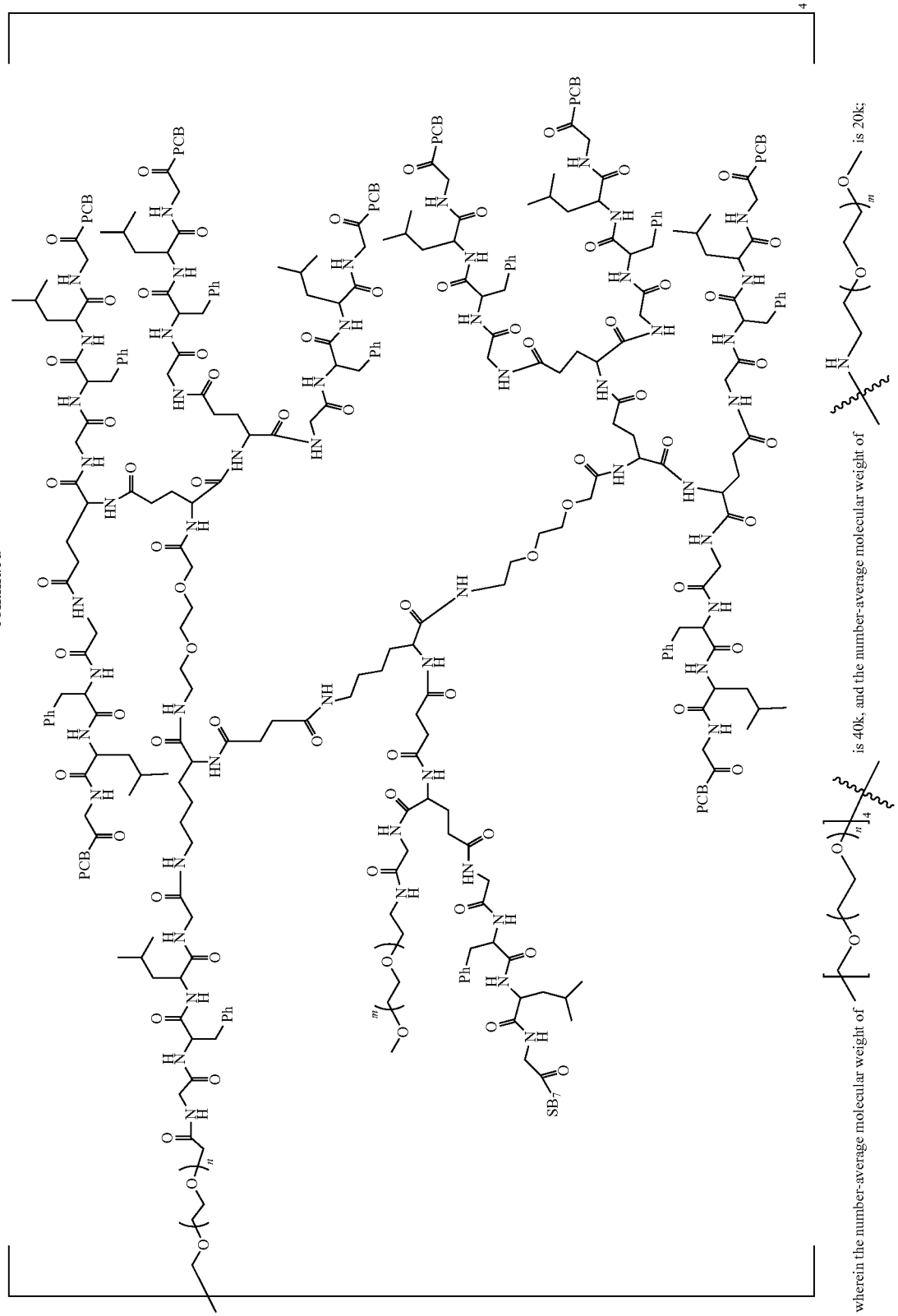
wherein the number-average molecular weight of PEG is 40k, and the number-average molecular weight of PEG is 20k;

-continued
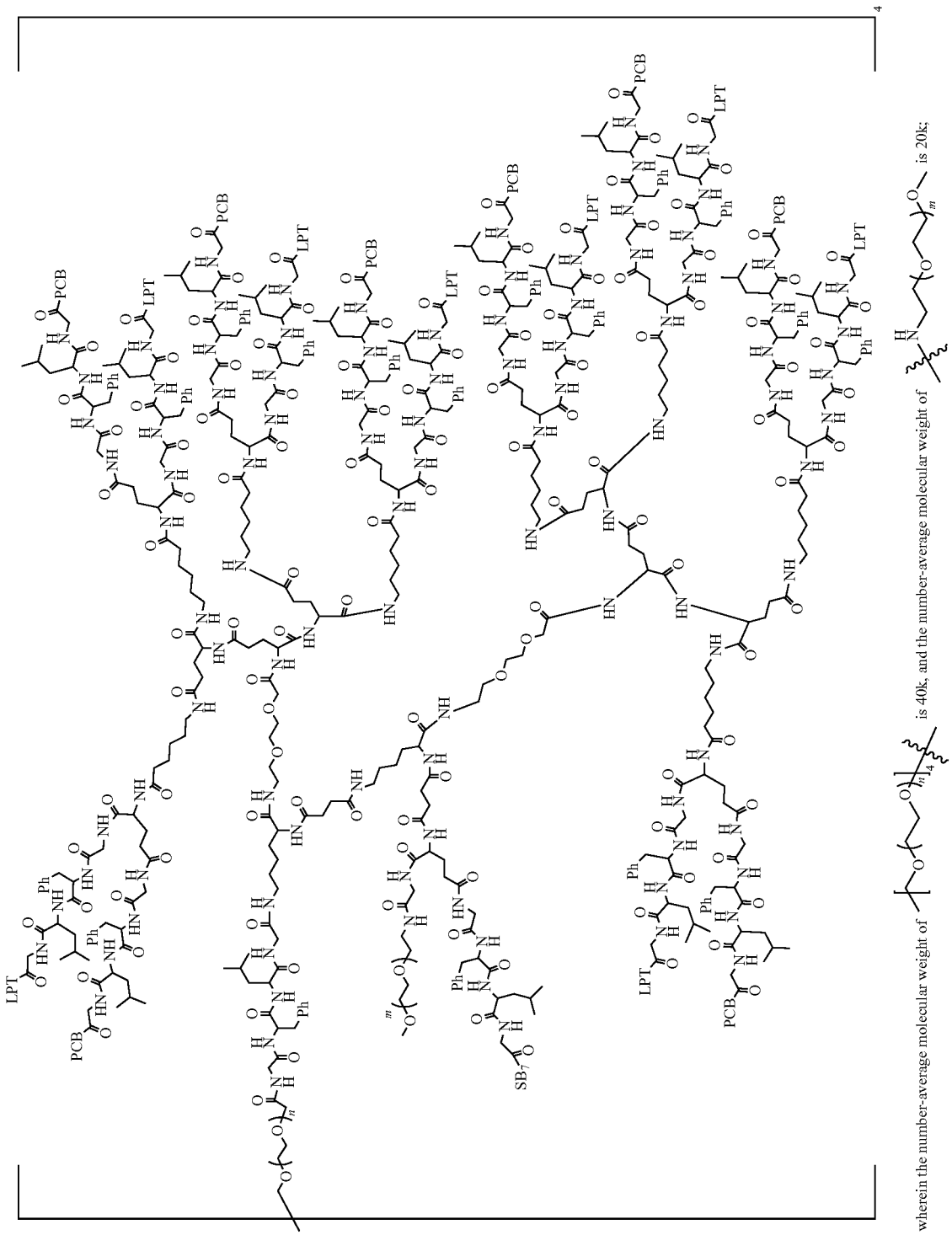
wherein the number-average molecular weight of ⌇⌇O—ᵐ is 20k; the number-average molecular weight of ⌇⌇O—₁₄ is 40k; and

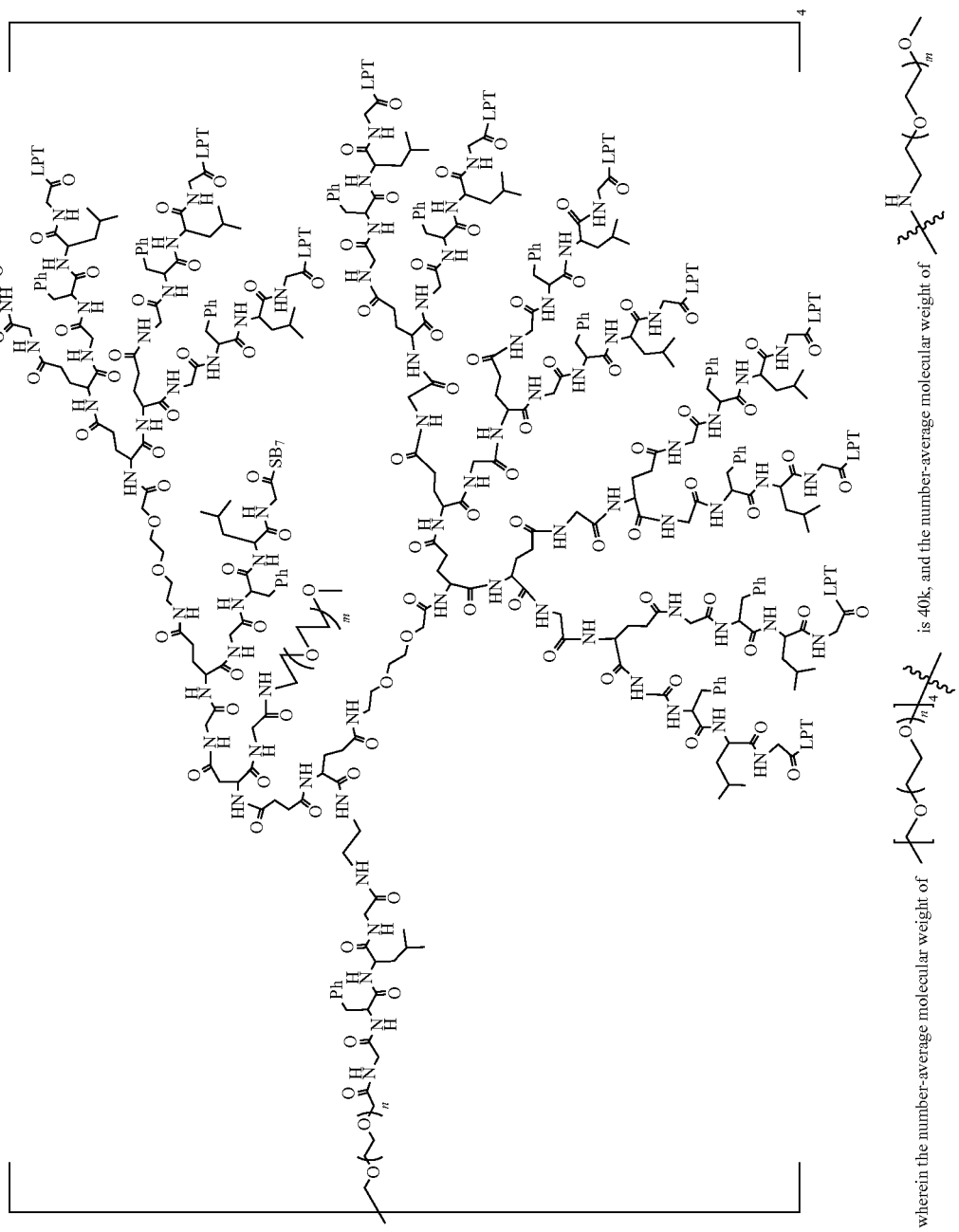

-continued
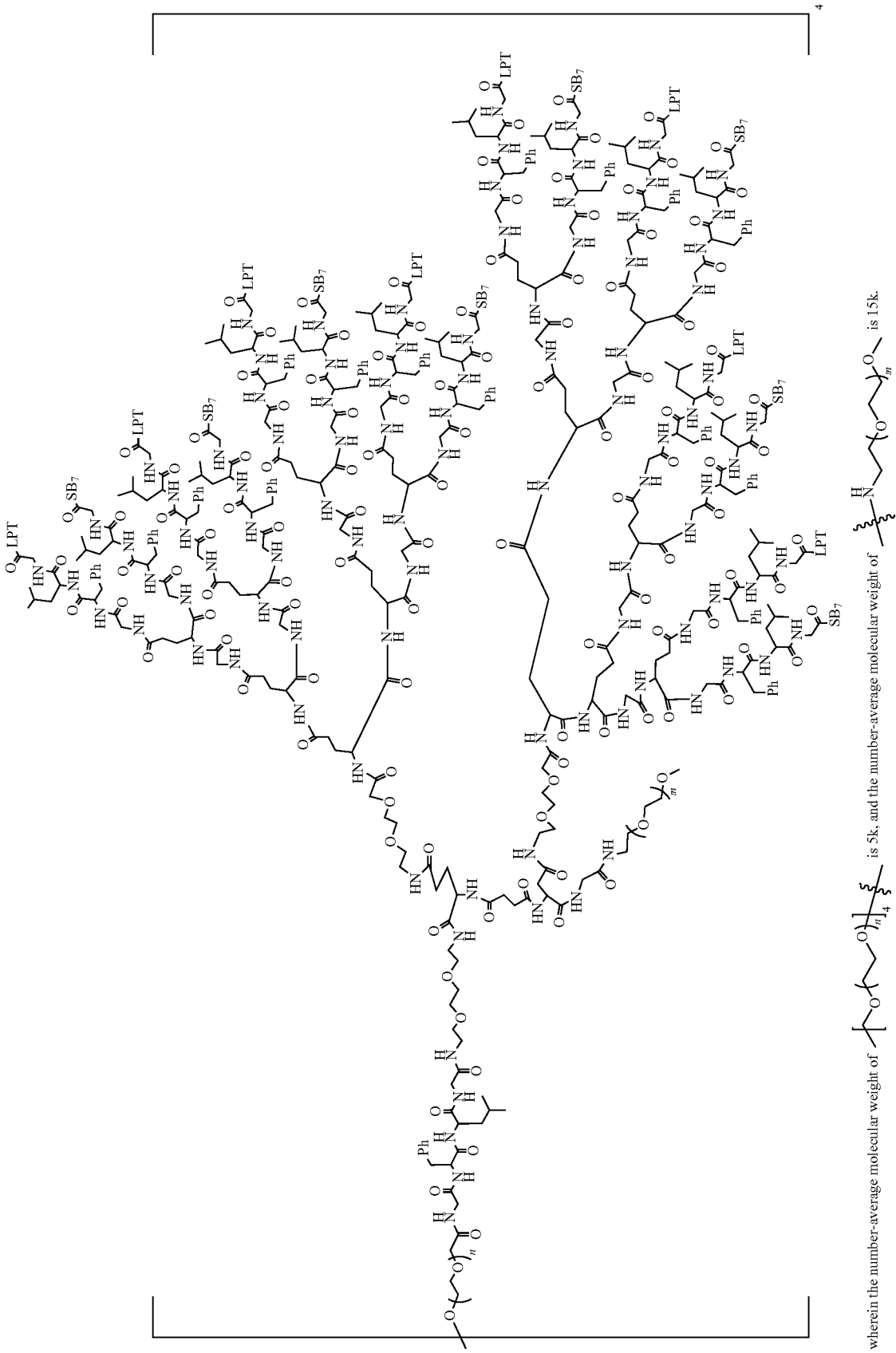

15. A pharmaceutical composition, comprising a therapeutically effective amount of the polyethylene glycol conjugated drug or a pharmaceutically acceptable salt thereof according to claim 1.

16. A method for treating cancer, including administering an effective amount of the polyethylene glycol conjugated drug or a pharmaceutically acceptable salt thereof according to claim 1.

17. An injection solution, comprising the polyethylene glycol conjugated drug or a pharmaceutically acceptable salt thereof according to claim 1, or comprising a pharmaceutical composition, comprising a therapeutically effective amount of the polyethylene glycol conjugated drug or a pharmaceutically acceptable salt thereof according to claim 1.

18. A method for preparing the polyethylene glycol conjugated drug of formula (II) or a pharmaceutically acceptable salt thereof according to claim 6, comprising the following steps:

step 1: preparing an intermediate

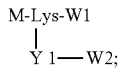

step 2: carrying out an amidation reaction so that PEG1 with carboxyl group(s) or activated carboxyl group(s) is linked to M to obtain an intermediate

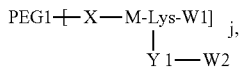

wherein Y1 has a free carboxyl group; and step 3: carrying out an amidation reaction so that PEG2 with free amino group(s) or activated amino group(s) is linked to Y1 in the intermediate

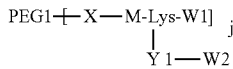

to obtain a polyethylene glycol conjugated drug of formula (II);

wherein PEG1, PEG2, Lys, X, Y1, W1, W2, M, and j are as defined in claim 6.

19. A method for preparing the polyethylene glycol conjugated drug of formula (III) or a pharmaceutically acceptable salt thereof according to claim 6, comprising the following steps:

step 1: preparing an intermediate

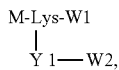

wherein an amino group on a glycine residue in M is protected, and Y1 has a free amino group; preparing an intermediate Y2-W3, wherein Y2 has a free carboxyl group and a protected carboxyl group;

step 2: carrying out an amidation reaction between the free amino group on Y1 and the free carboxyl group on Y2 so that the intermediate

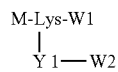

linked to Y2-W3 to obtain an intermediate

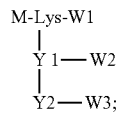

step 3: removing a protecting group of carboxyl on Y2 and a protecting group of amino on M in the intermediate

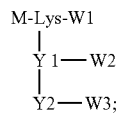

step 4: carrying out an amidation reaction so that the intermediate

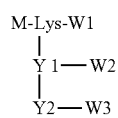

from step 3 is linked to PEG1 with free carboxyl group(s) or activated carboxyl group(s) to obtain an intermediate

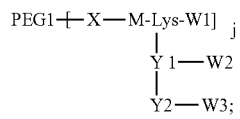

and step 5: carrying out an amidation reaction so that the intermediate

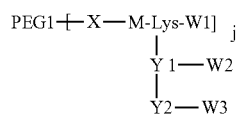

is linked to PEG2 with free amino group(s) or activated amino group(s) to obtain a polyethylene glycol conjugated drug of formula (III);

wherein PEG1, PEG2, Lys, X, Y1, Y2, W1, W2, W3, M, and j are as defined in claim 6.

20. The polyethylene glycol conjugated drug according to claim 1, wherein the polyethylene glycol conjugated drug has a structure selected from:

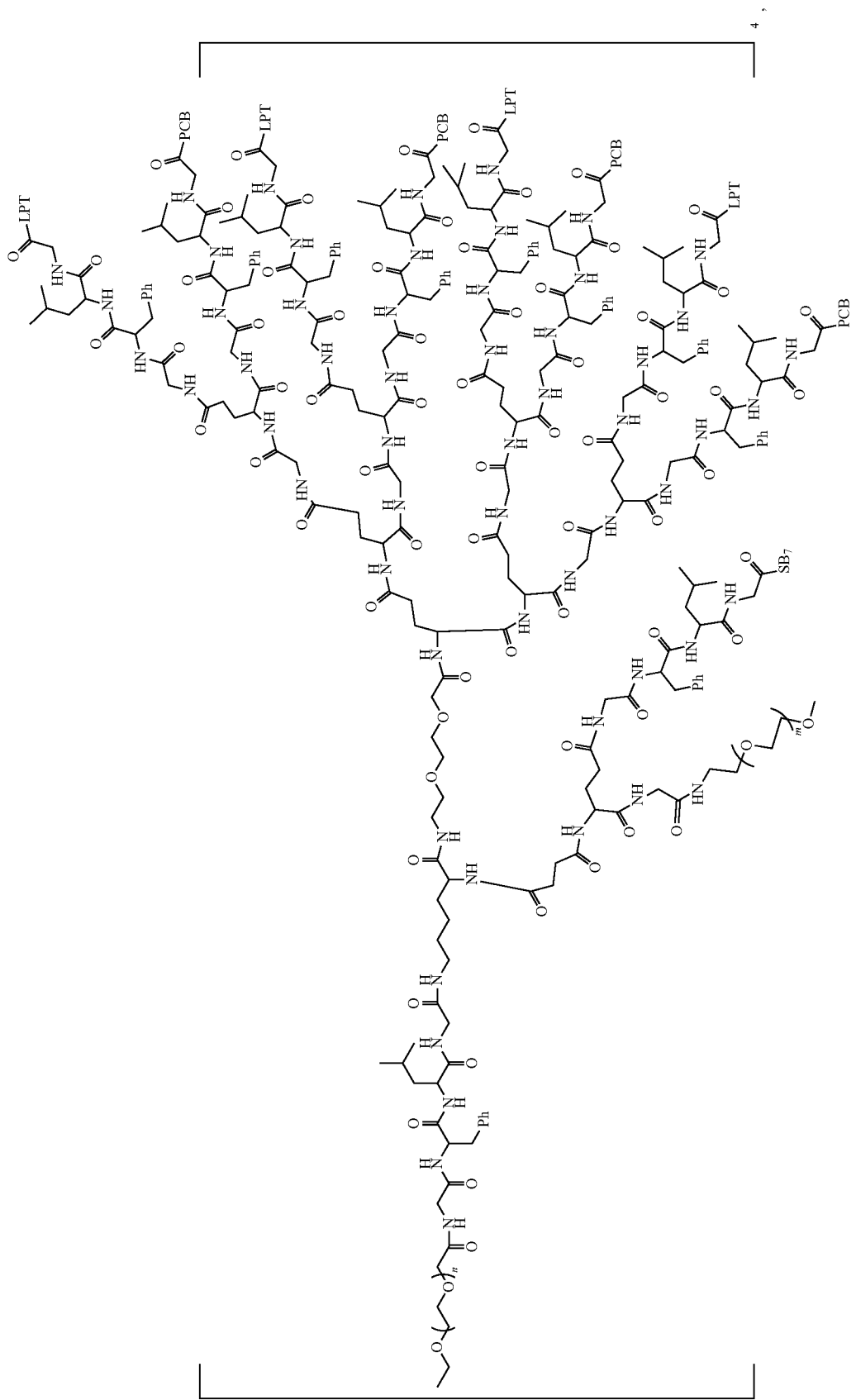

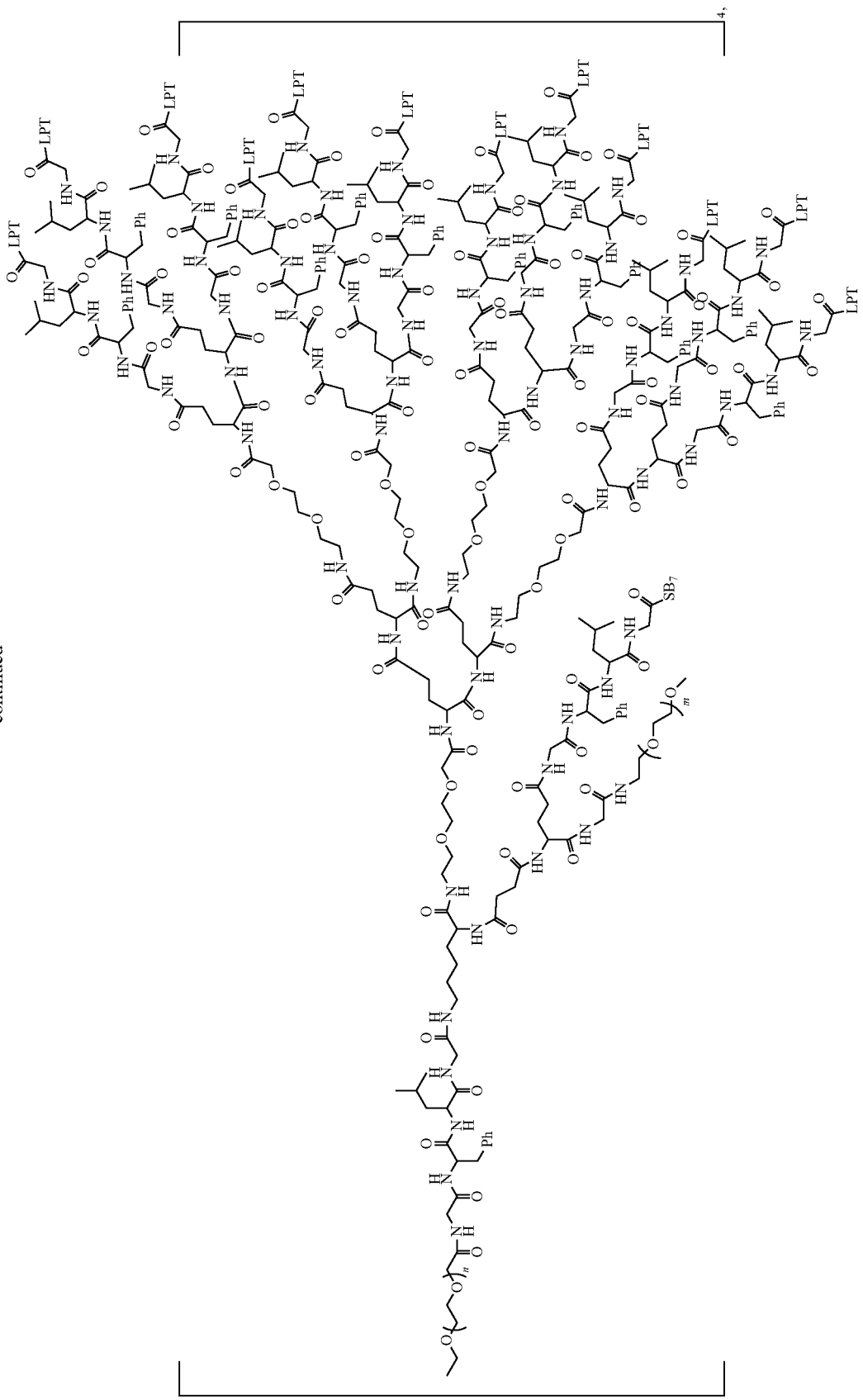

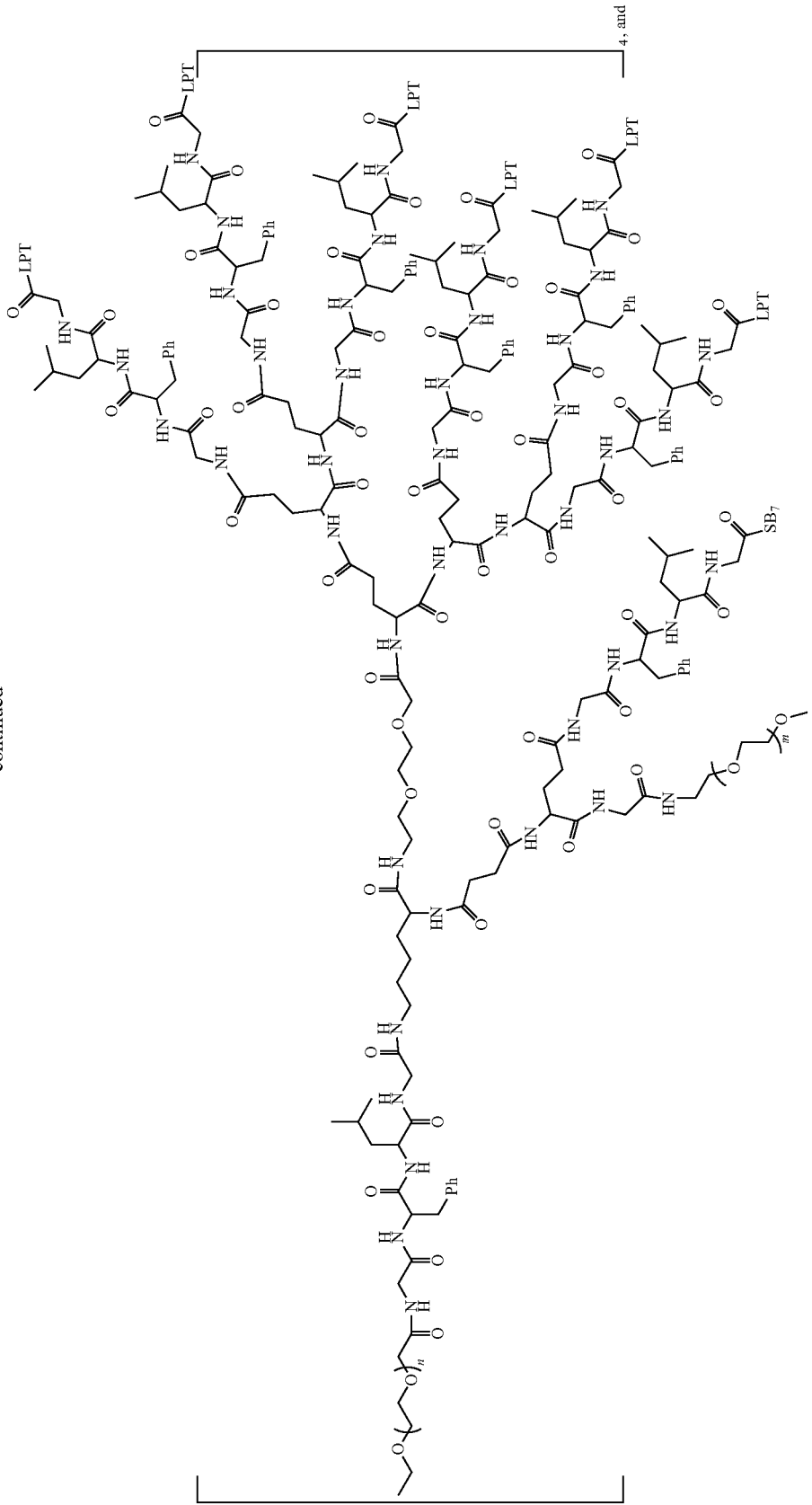

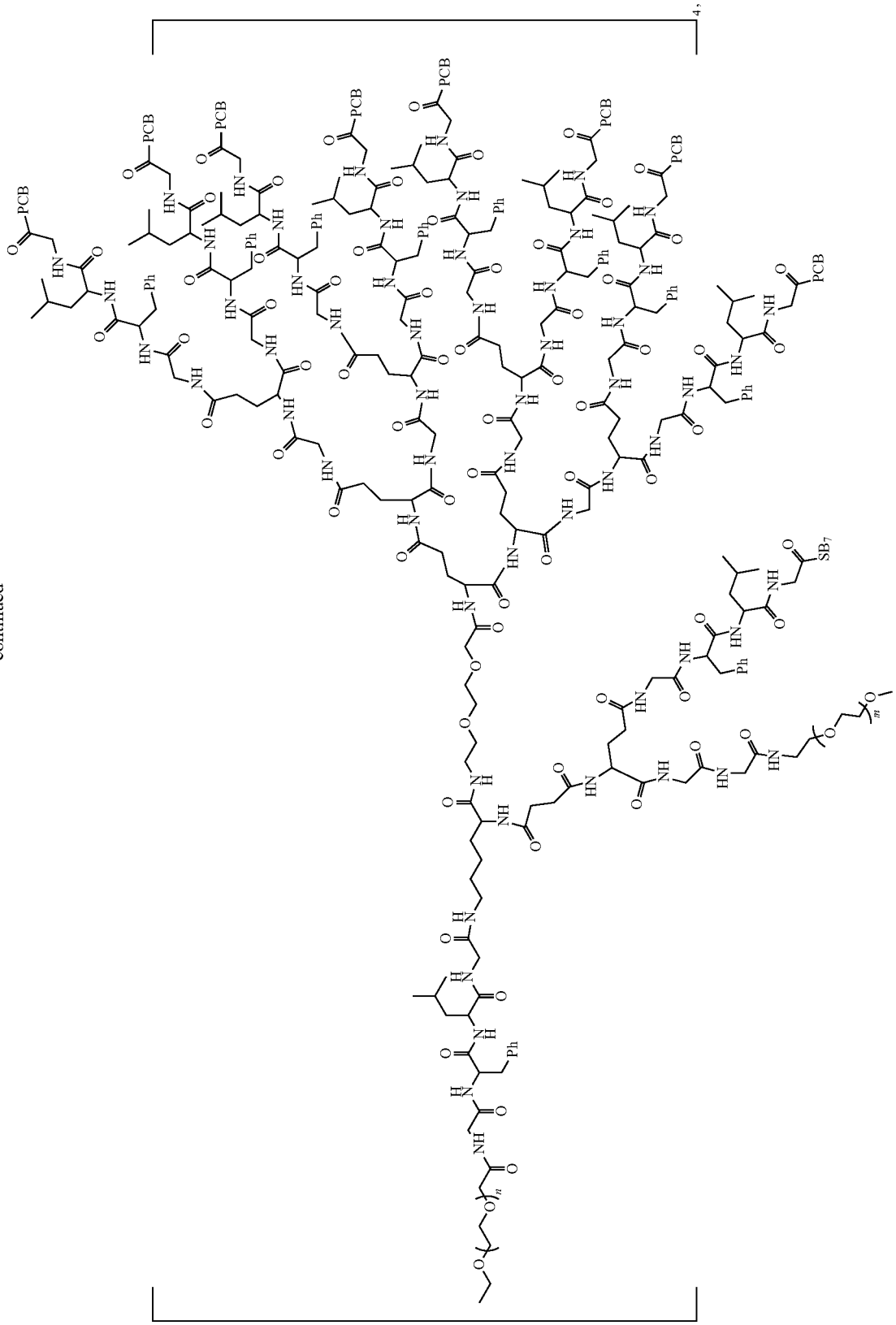

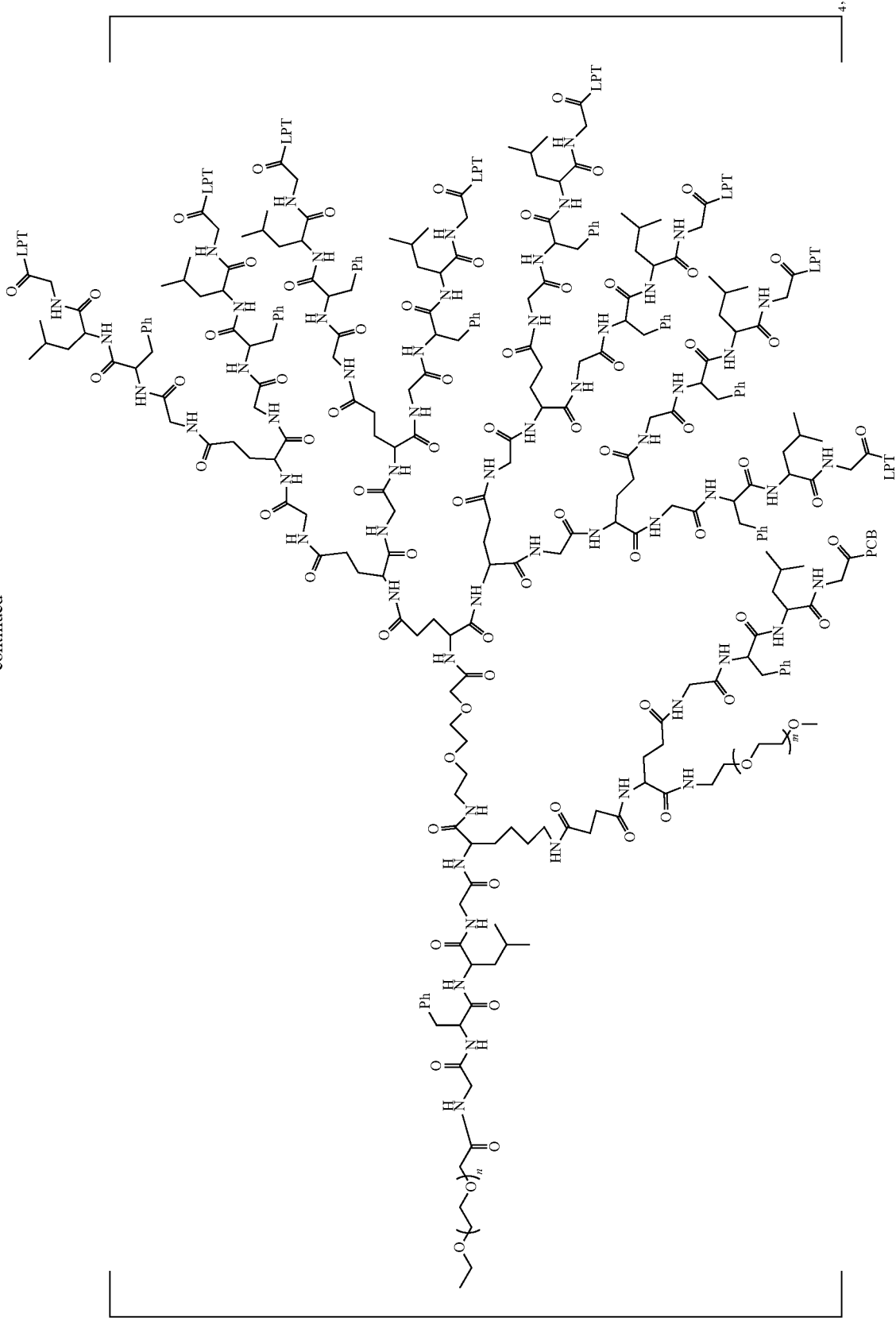

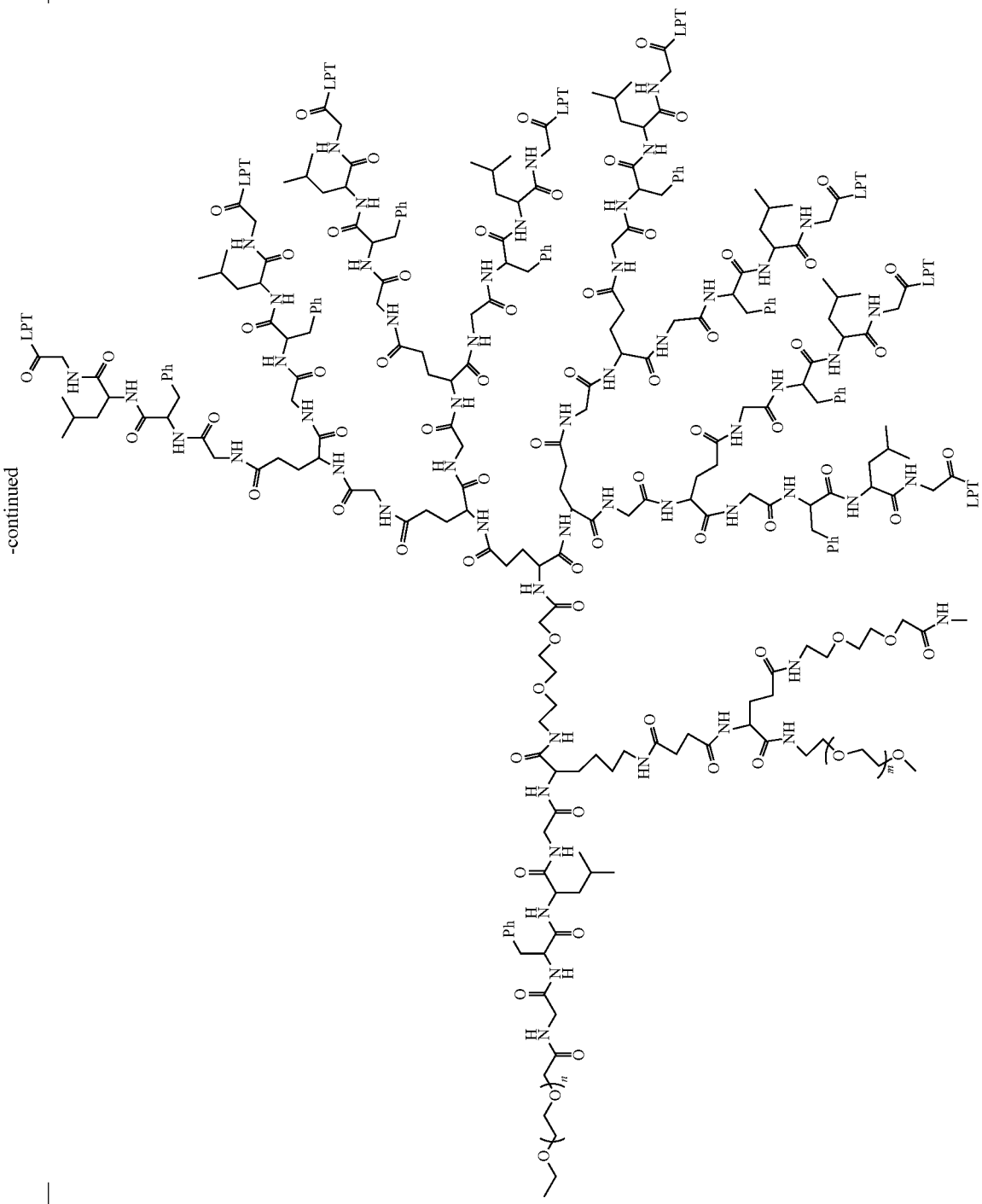

-continued
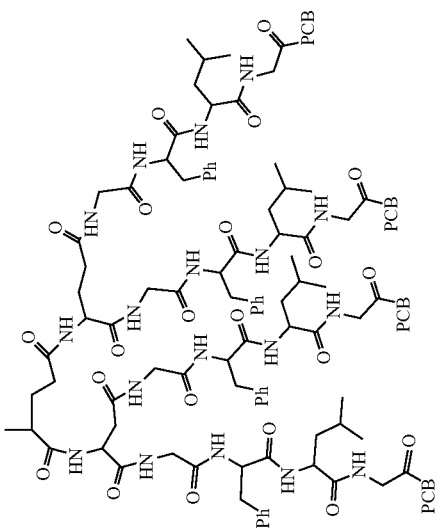

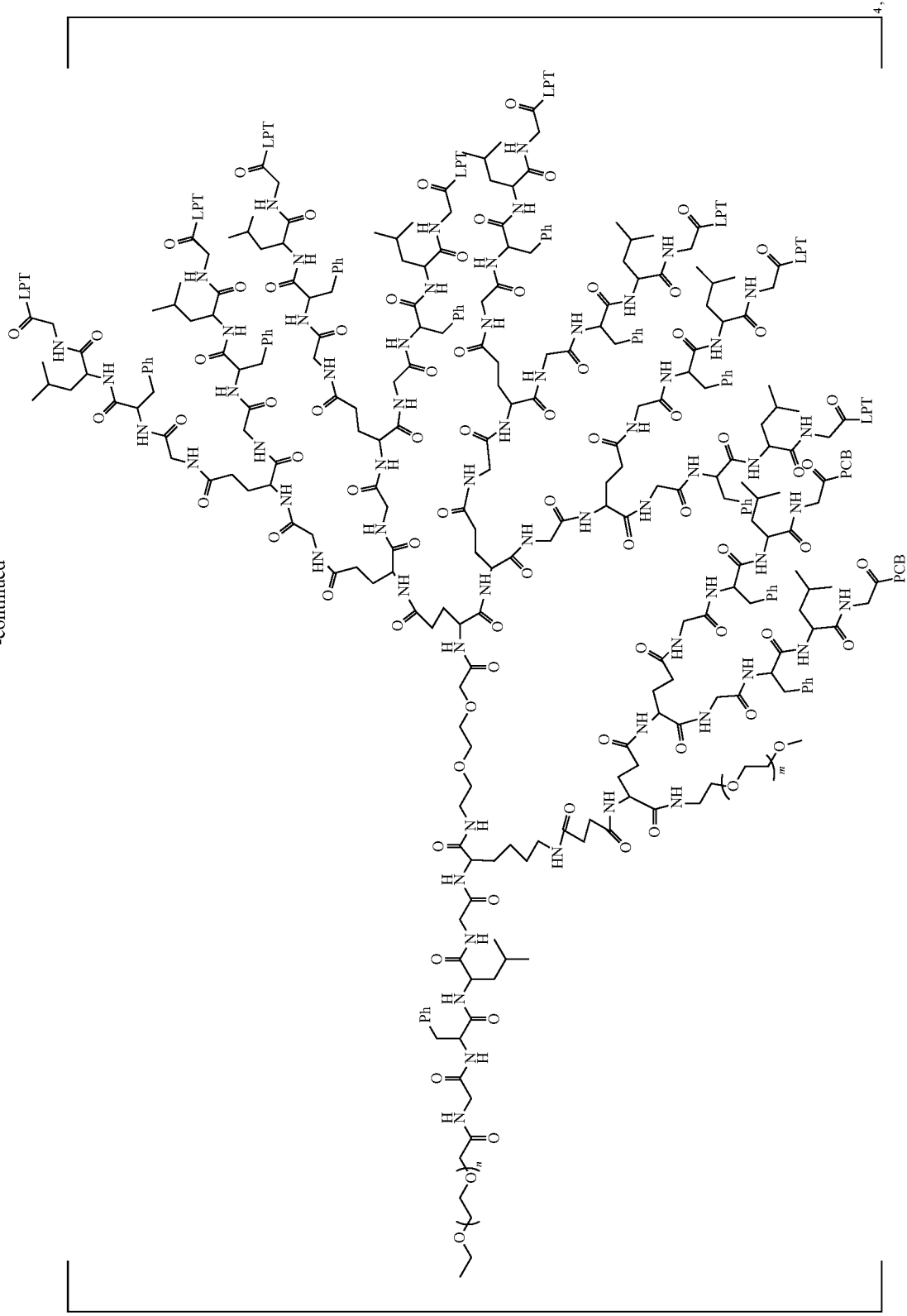

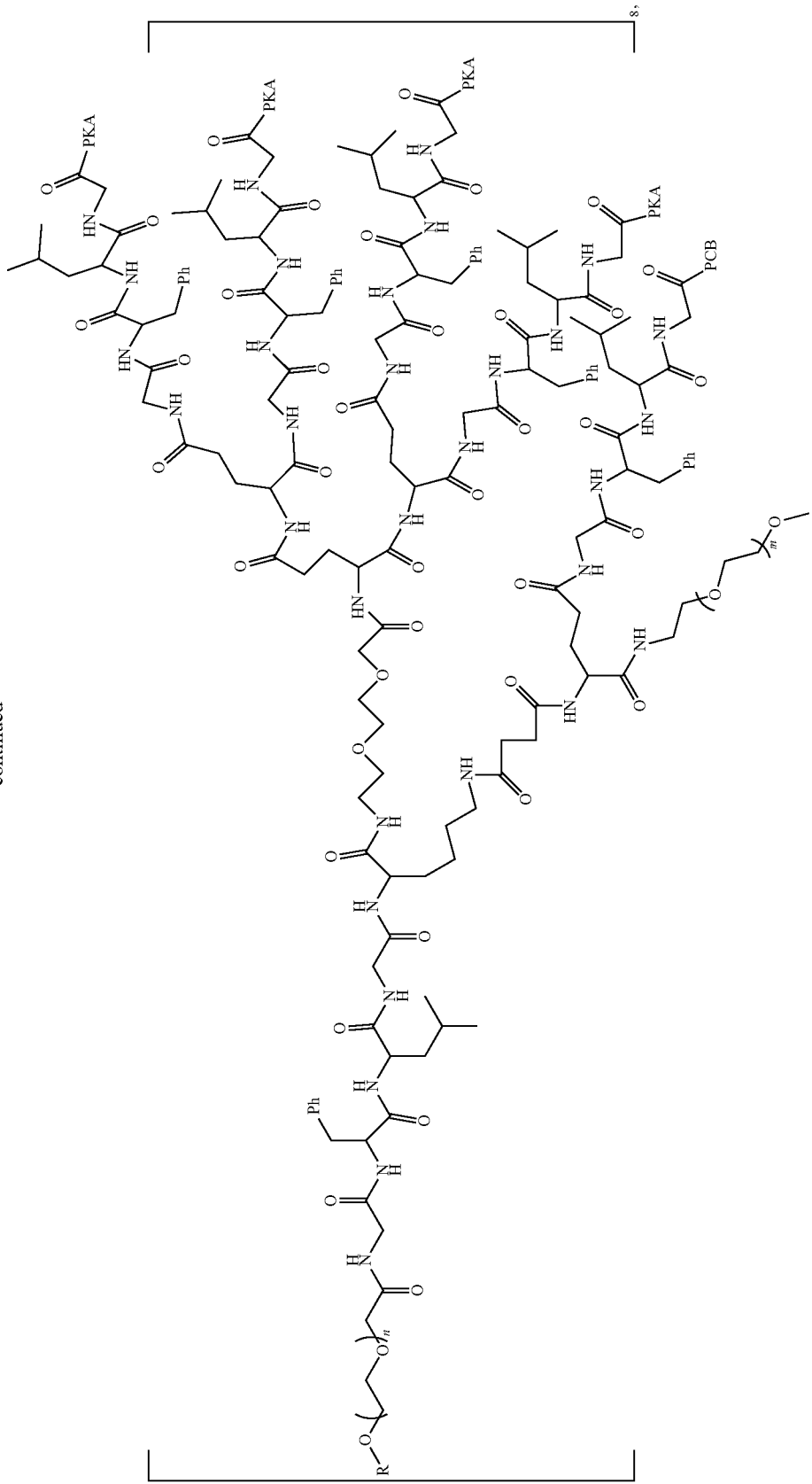

wherein R is a core structure of an eight-arm polyethylene glycol,

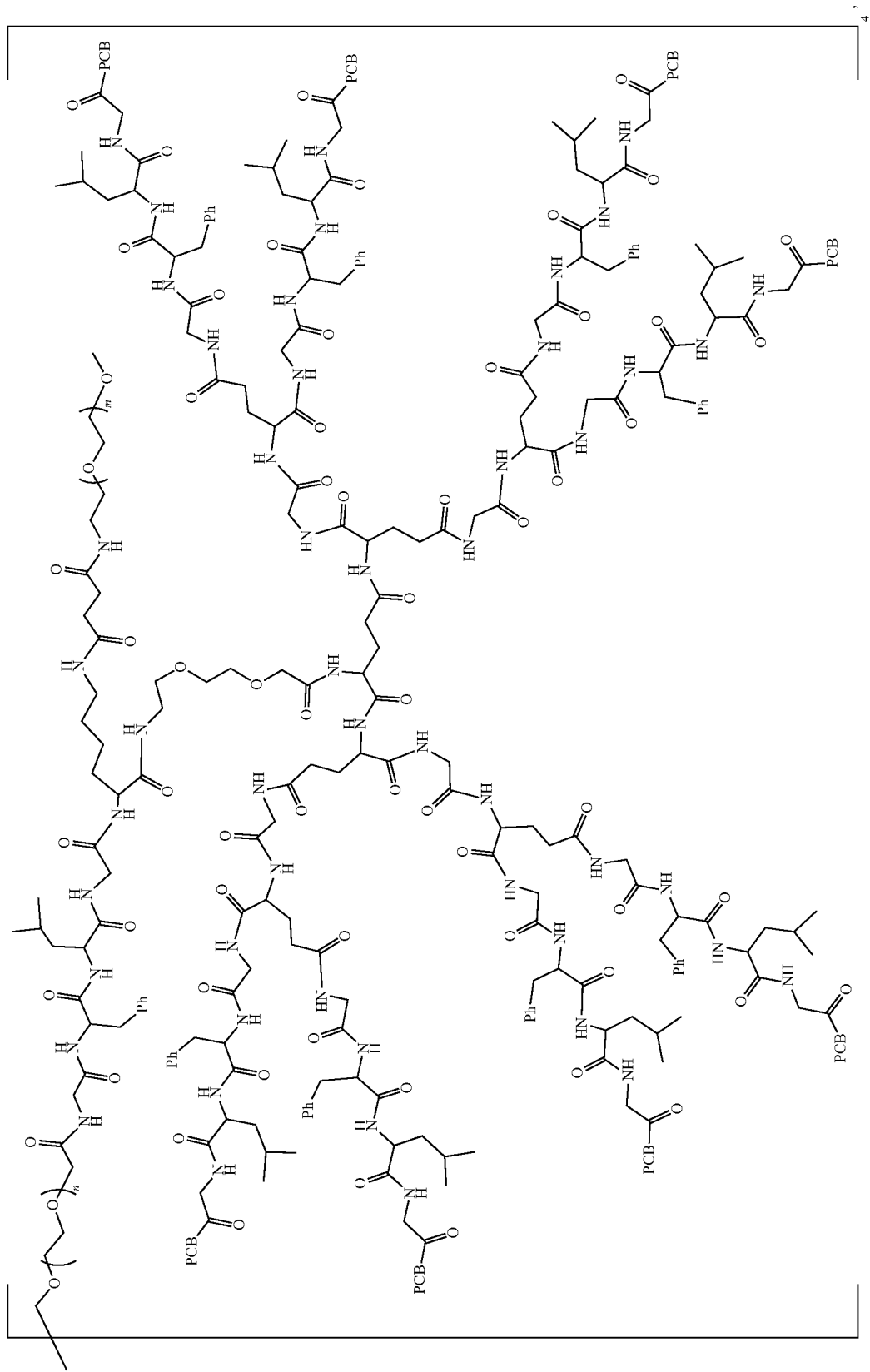

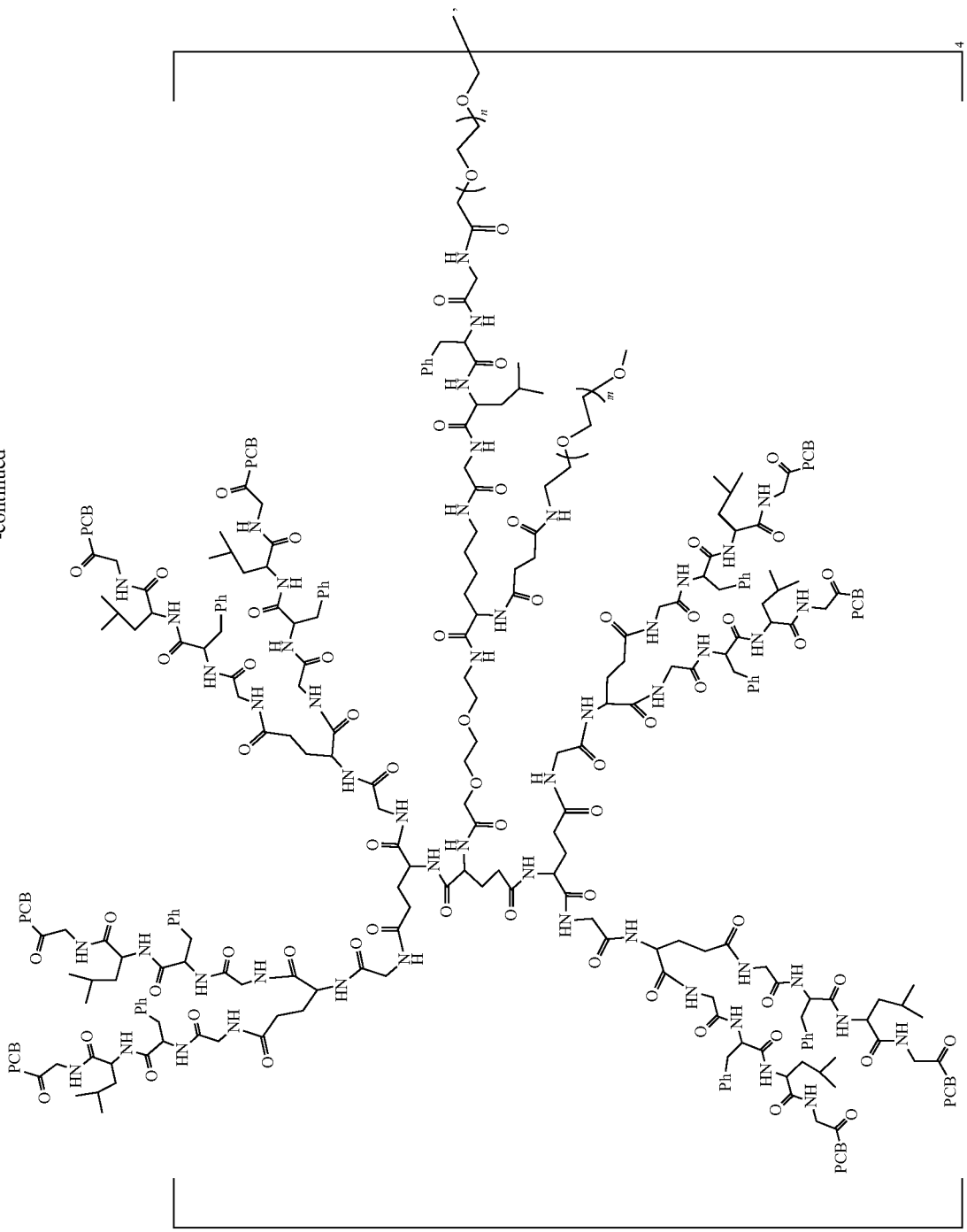

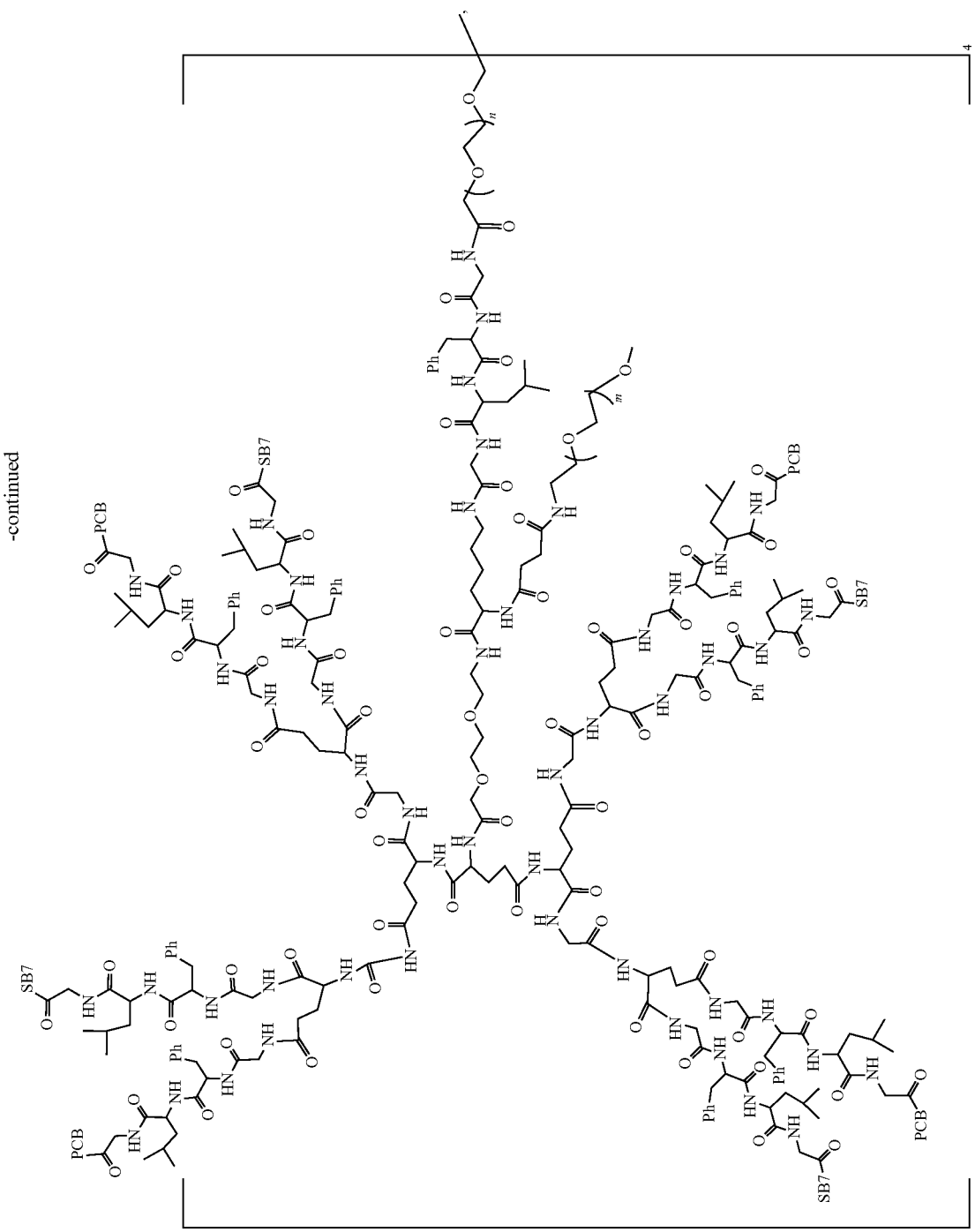

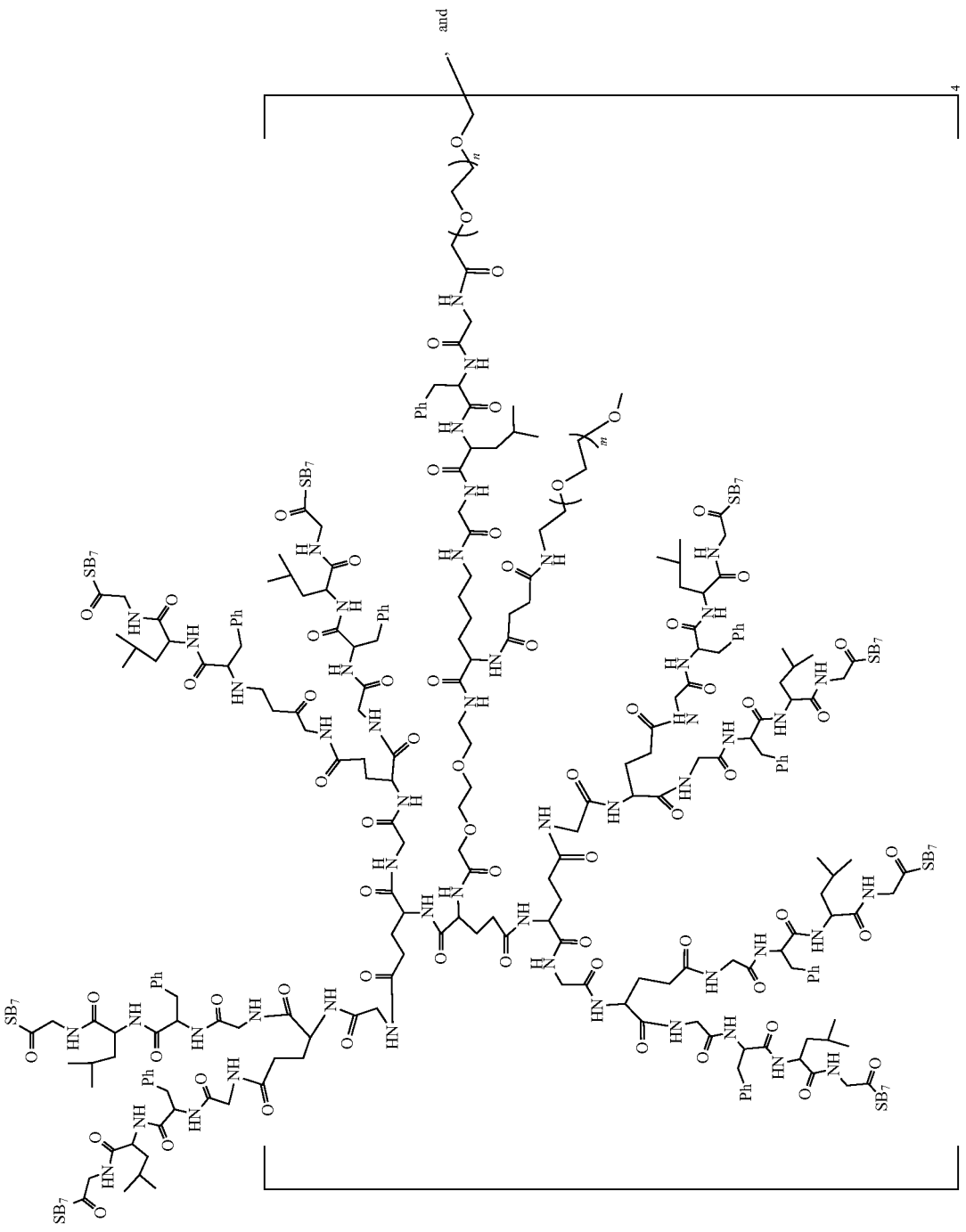

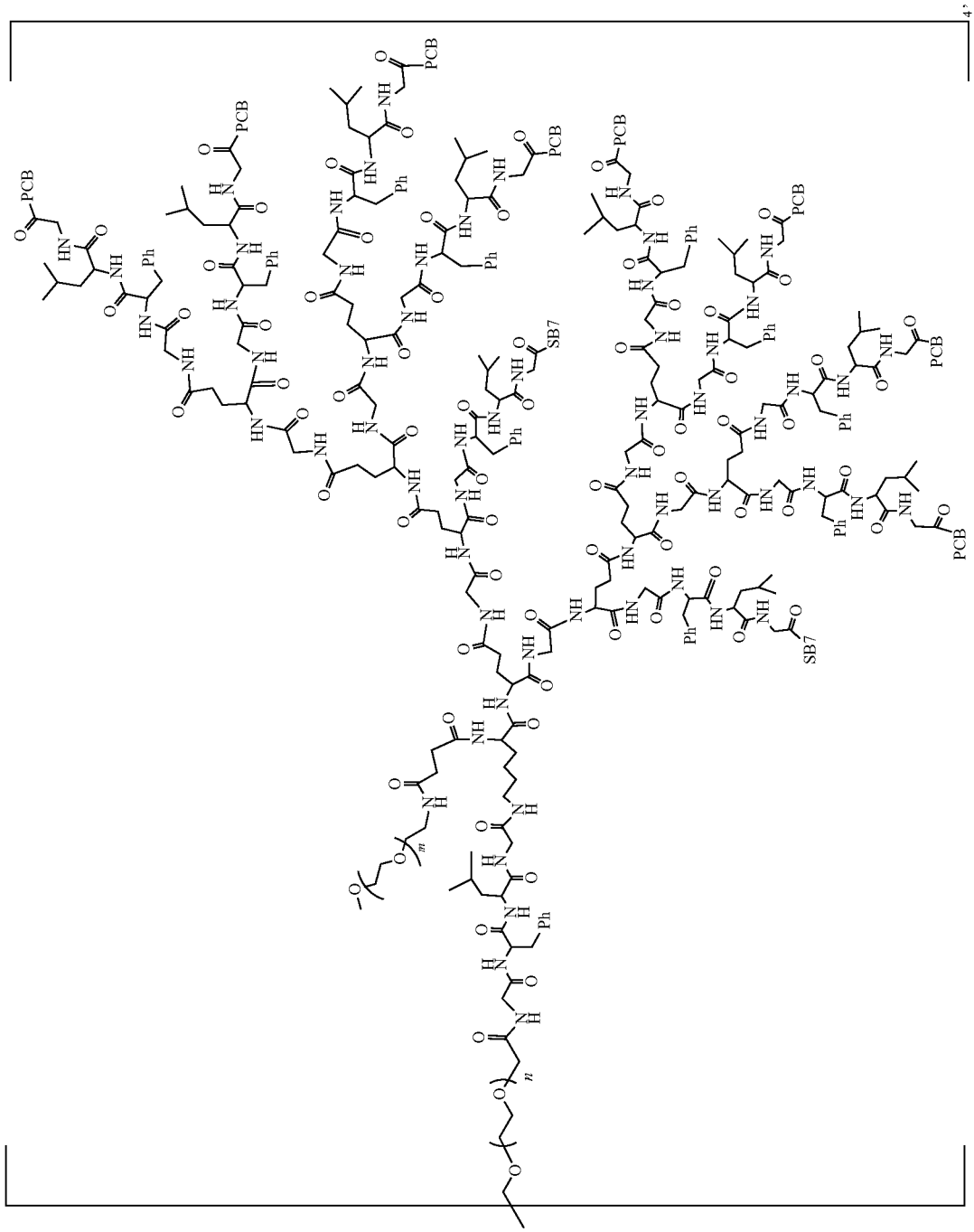

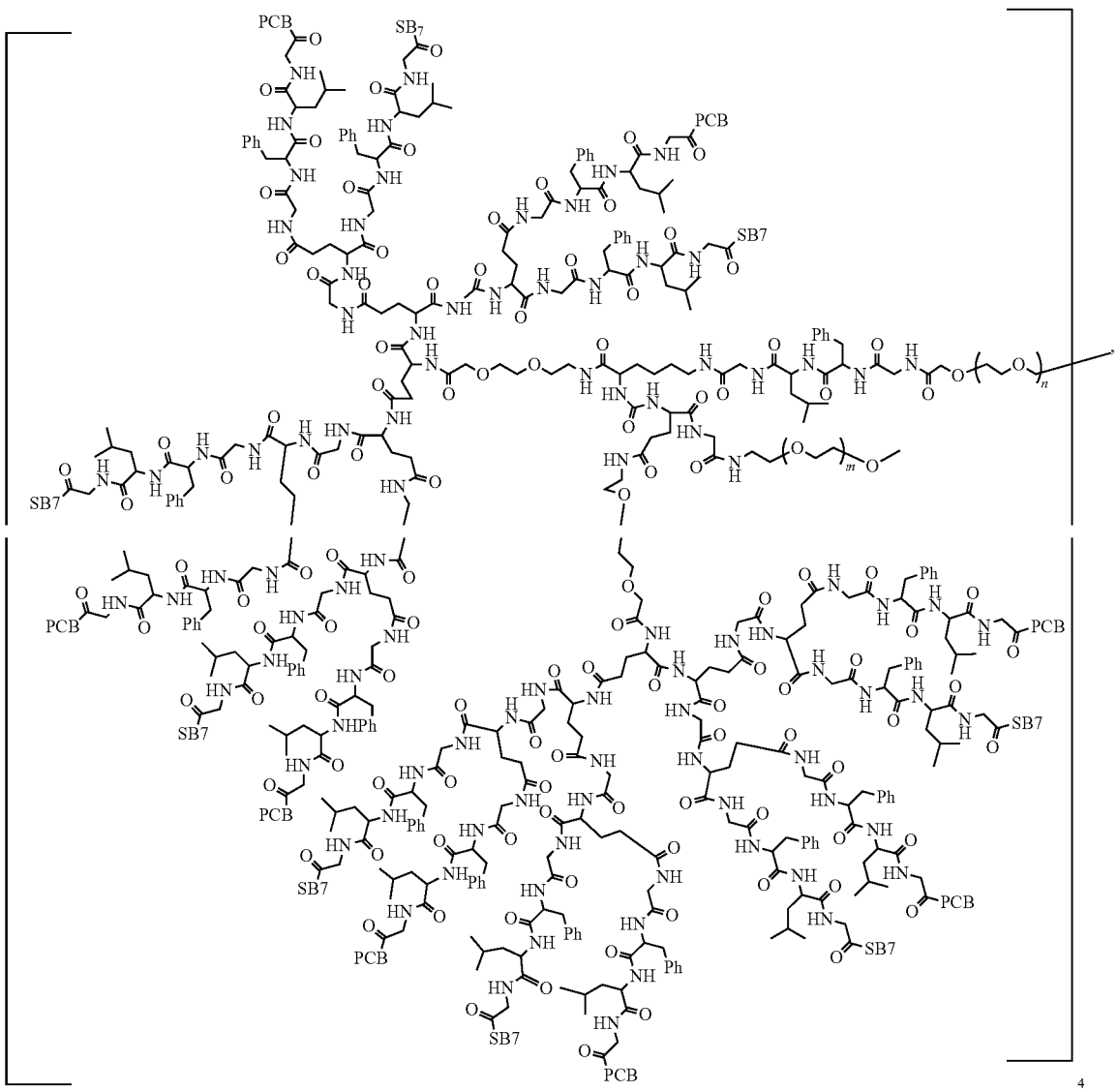
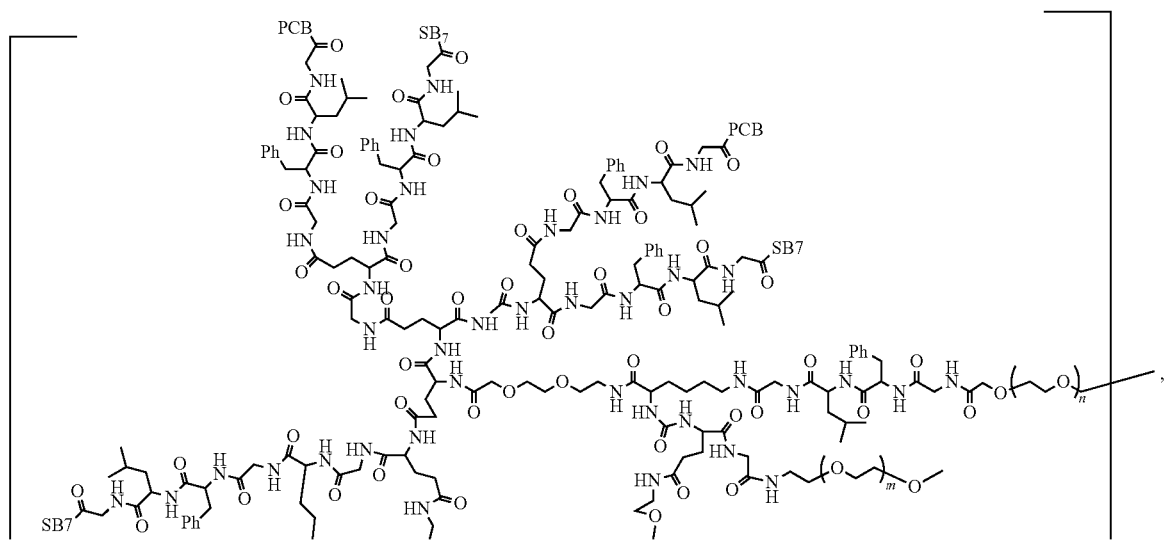

-continued
711
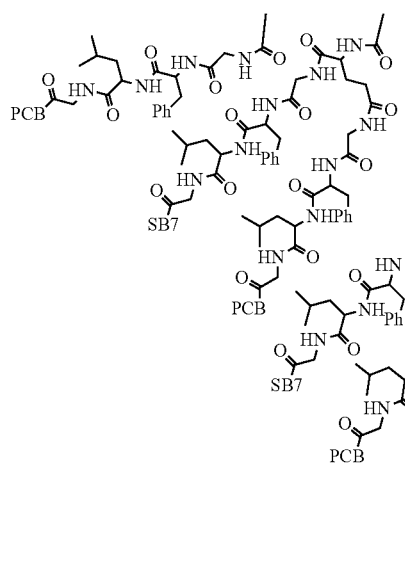
712
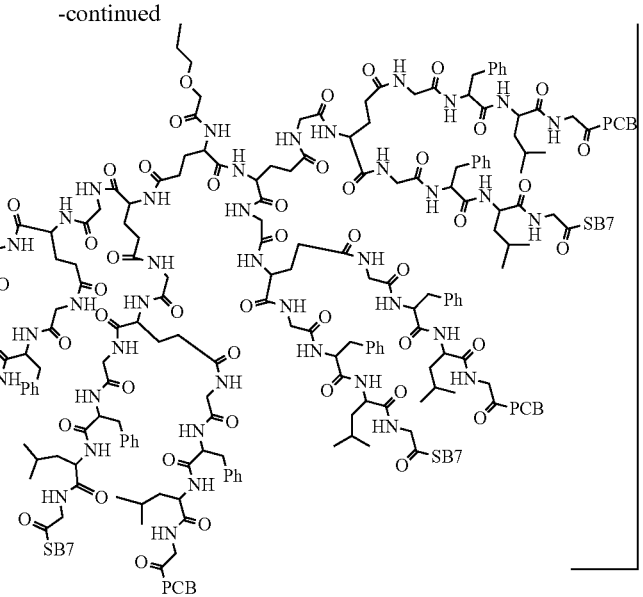

713 714
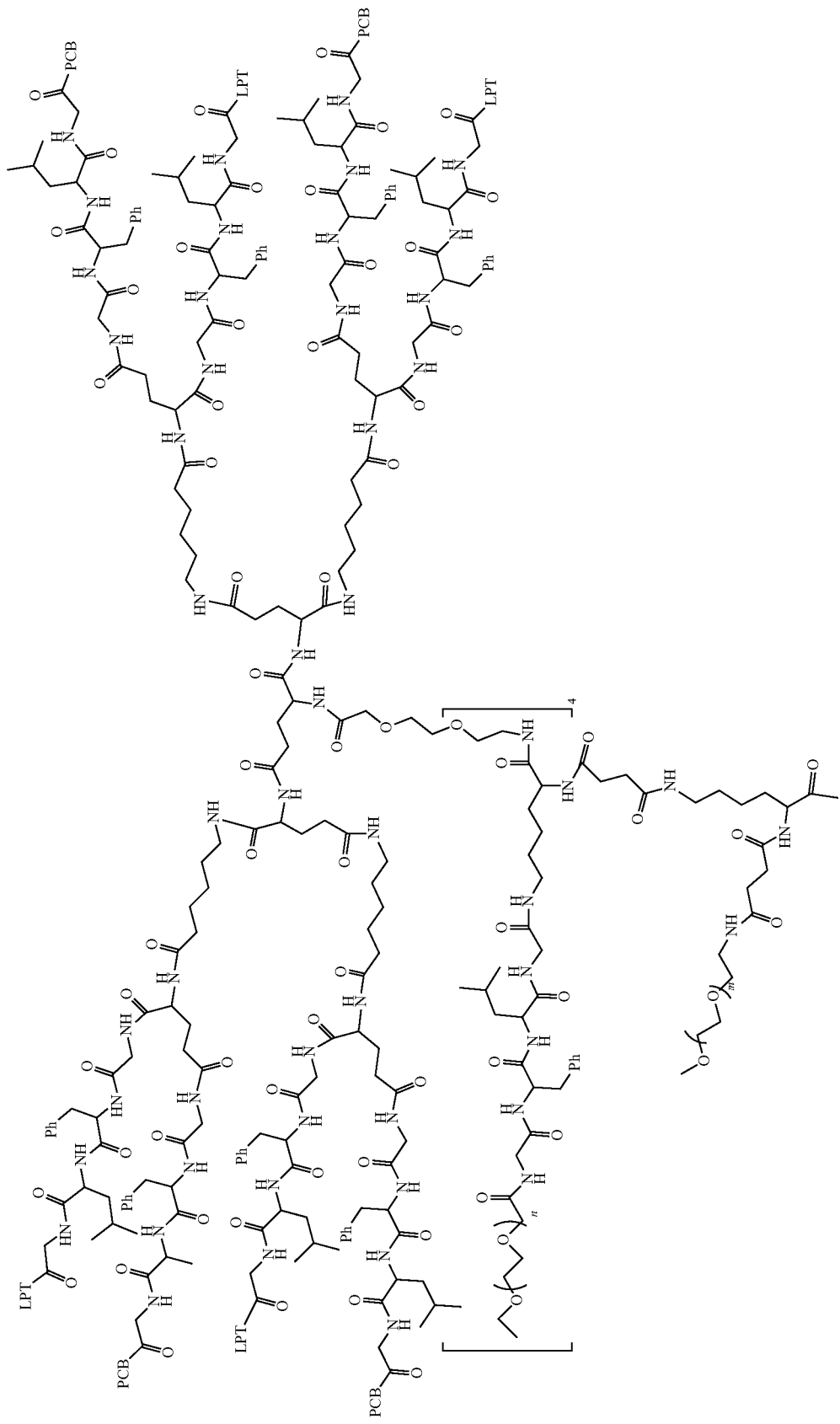

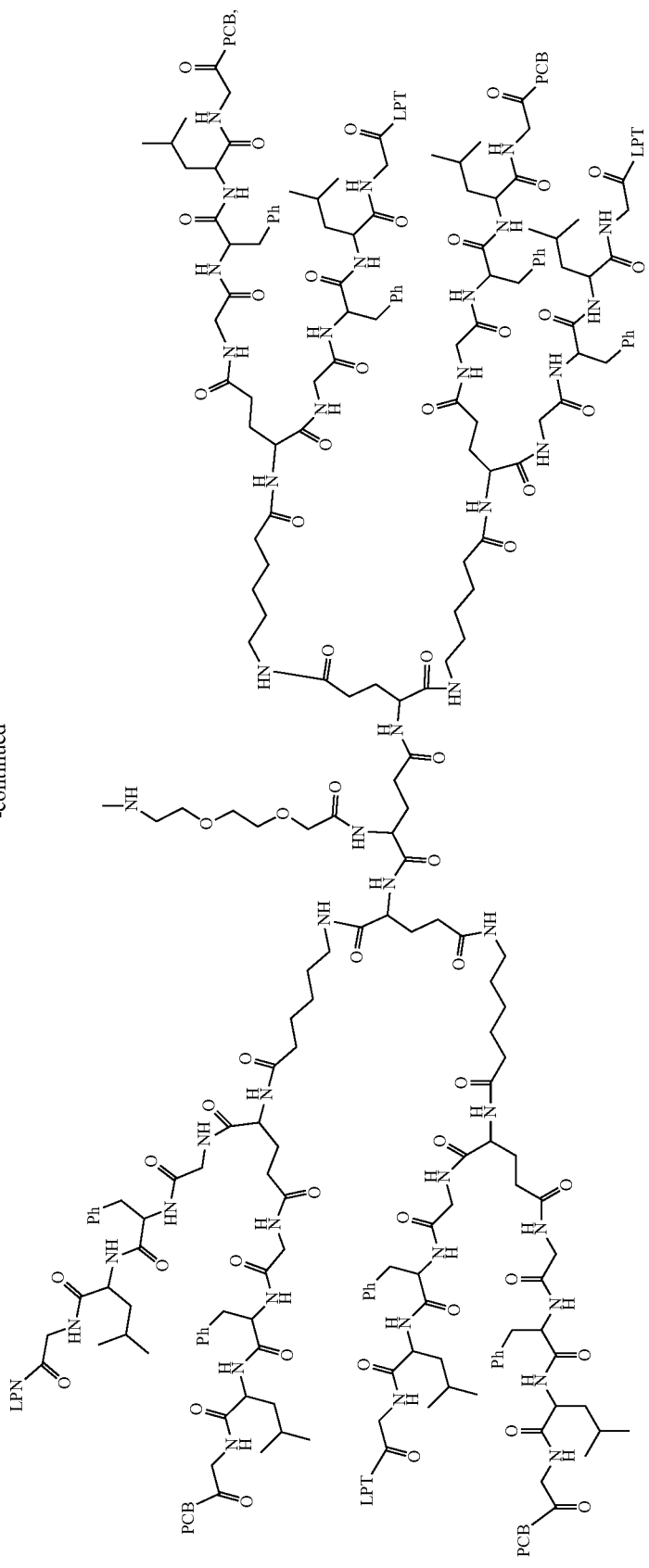

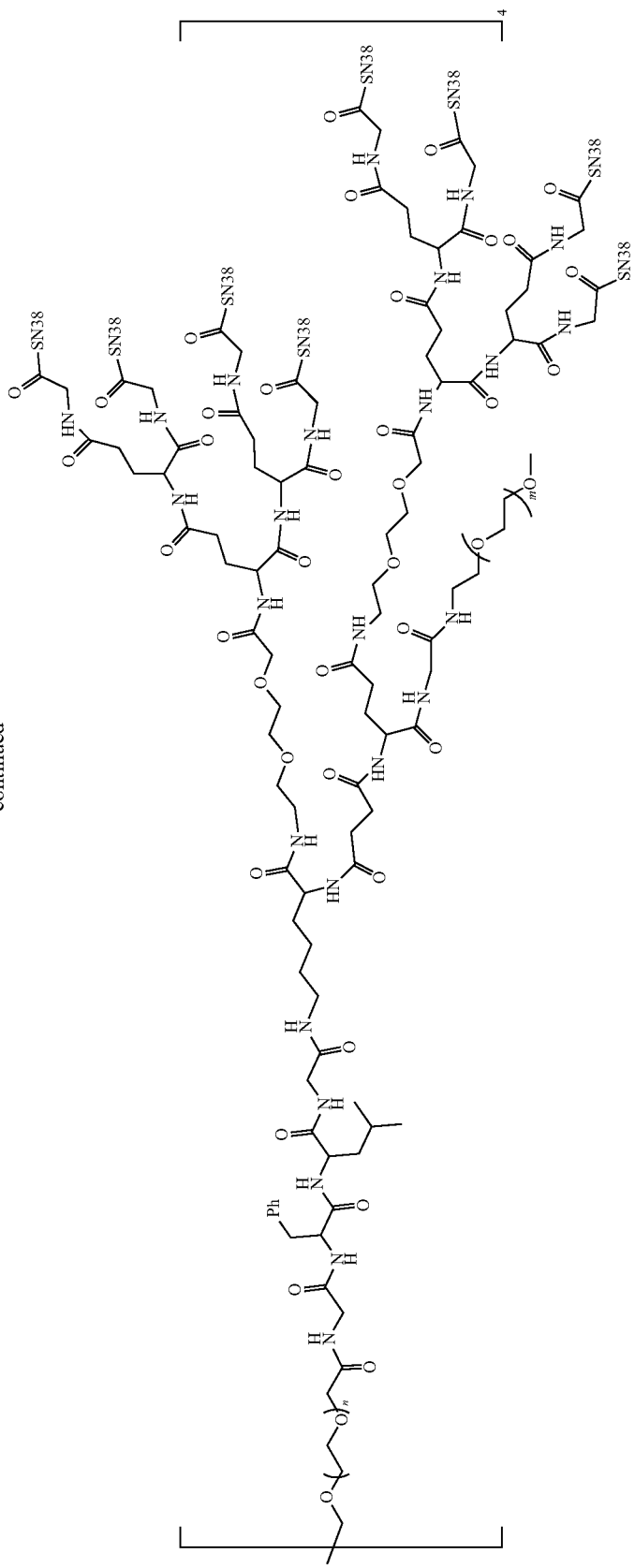

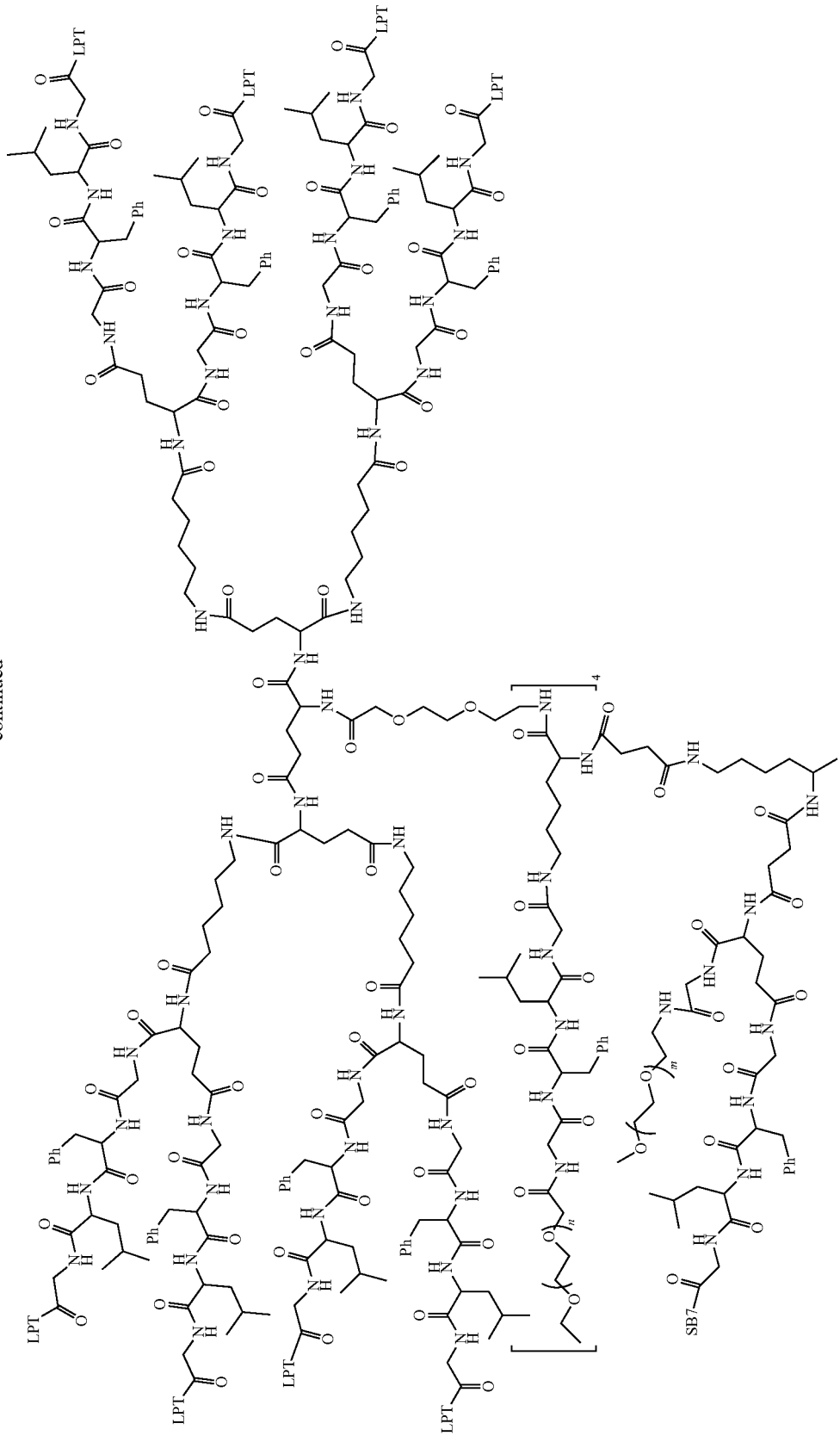

-continued
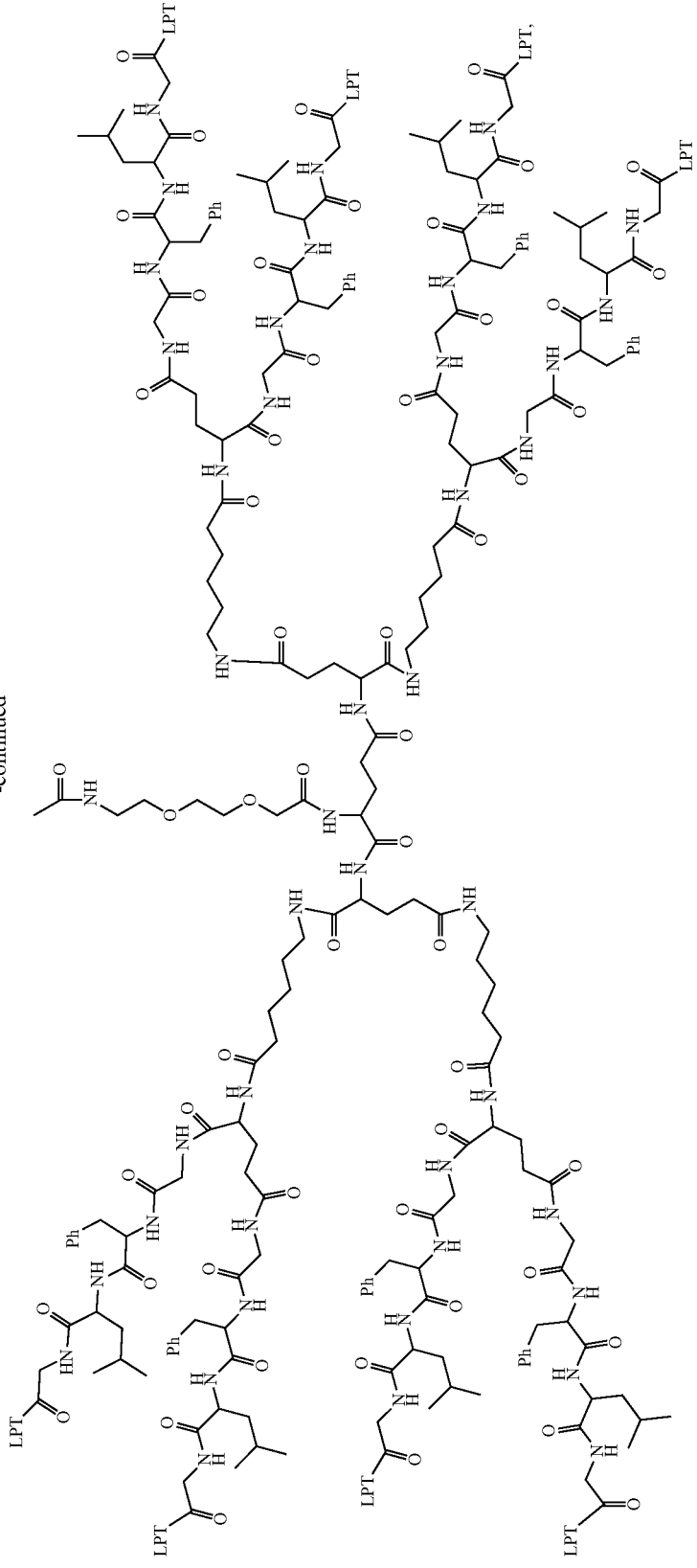

723 724
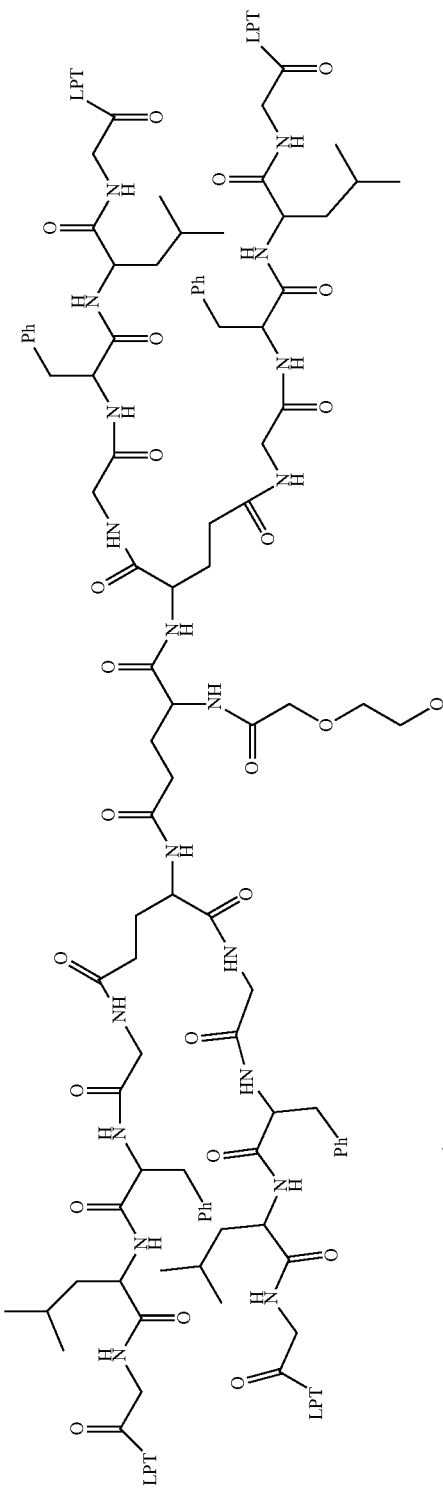
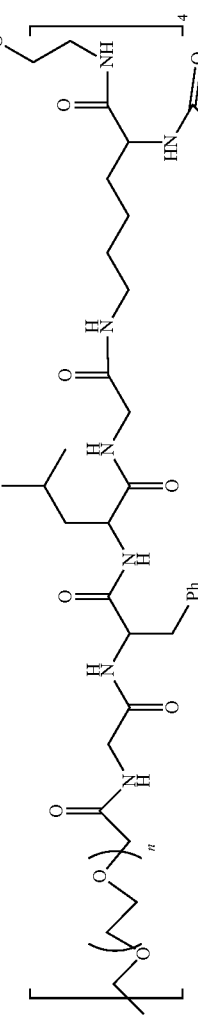
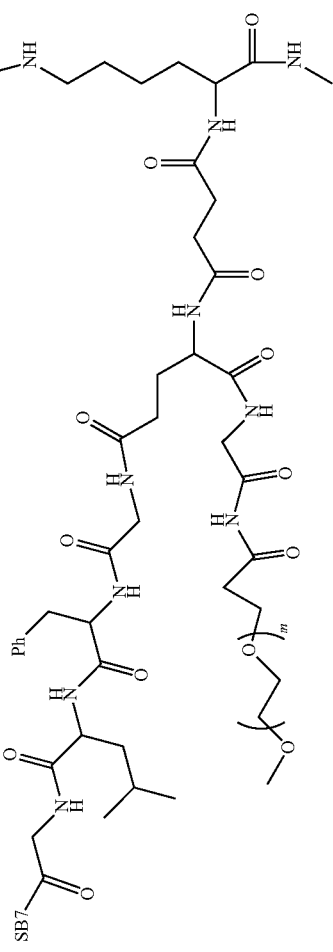

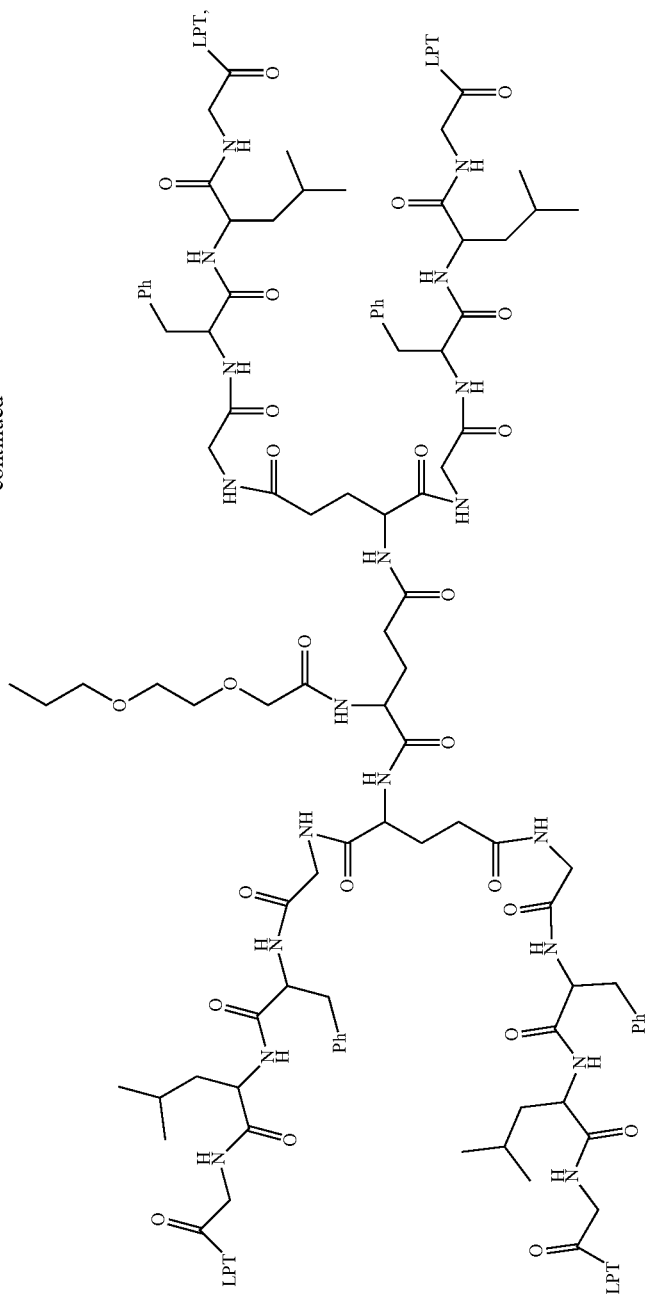

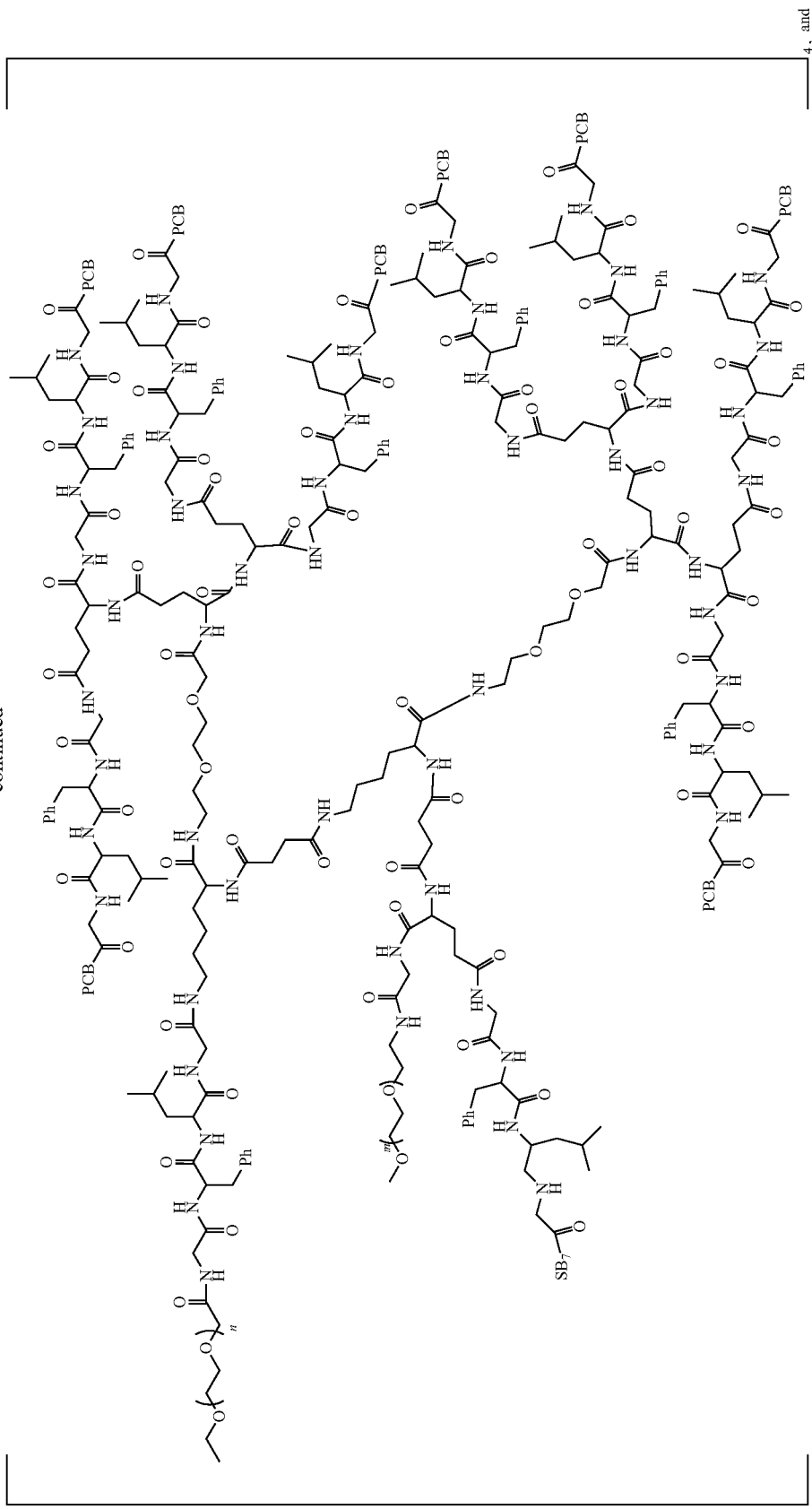

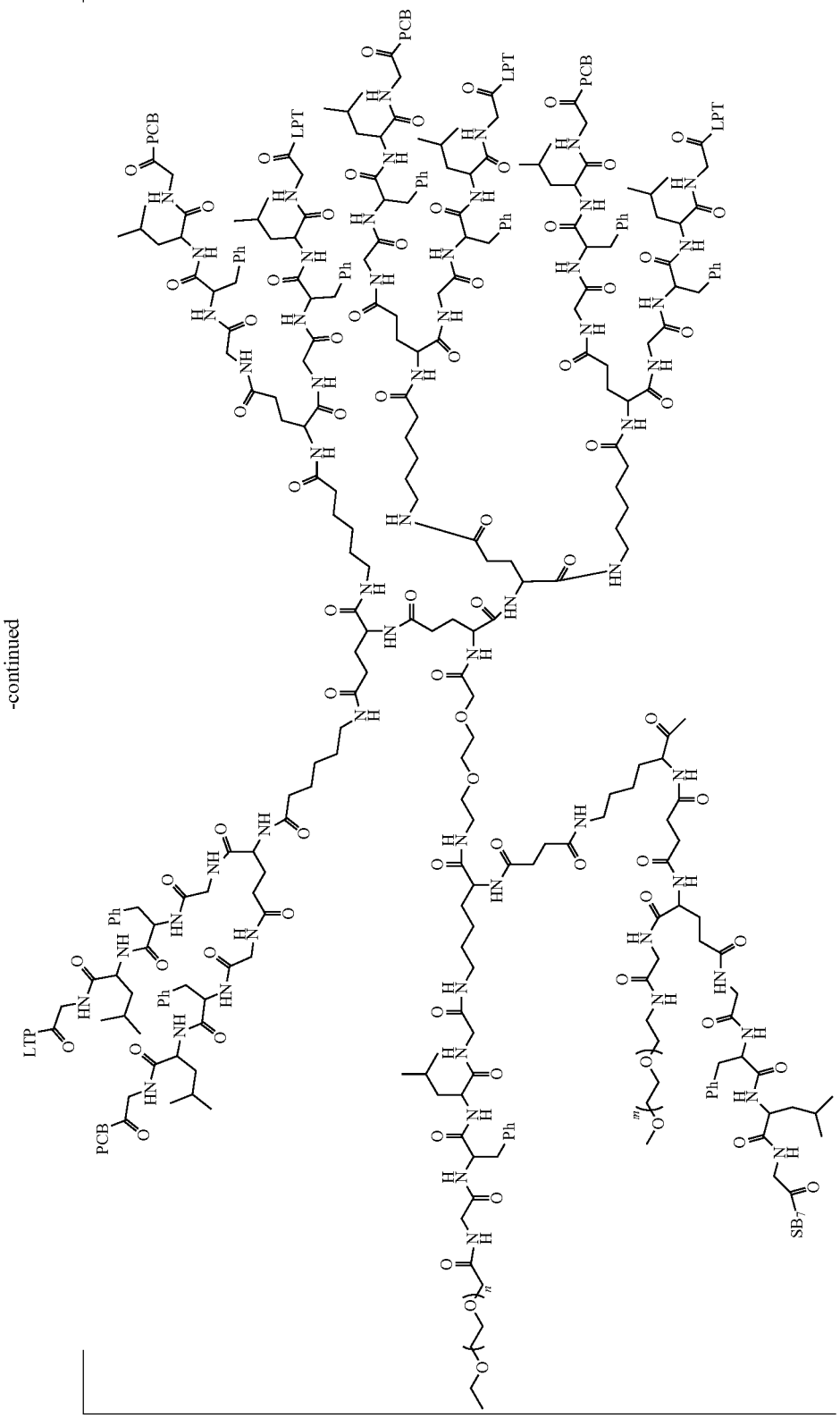

-continued
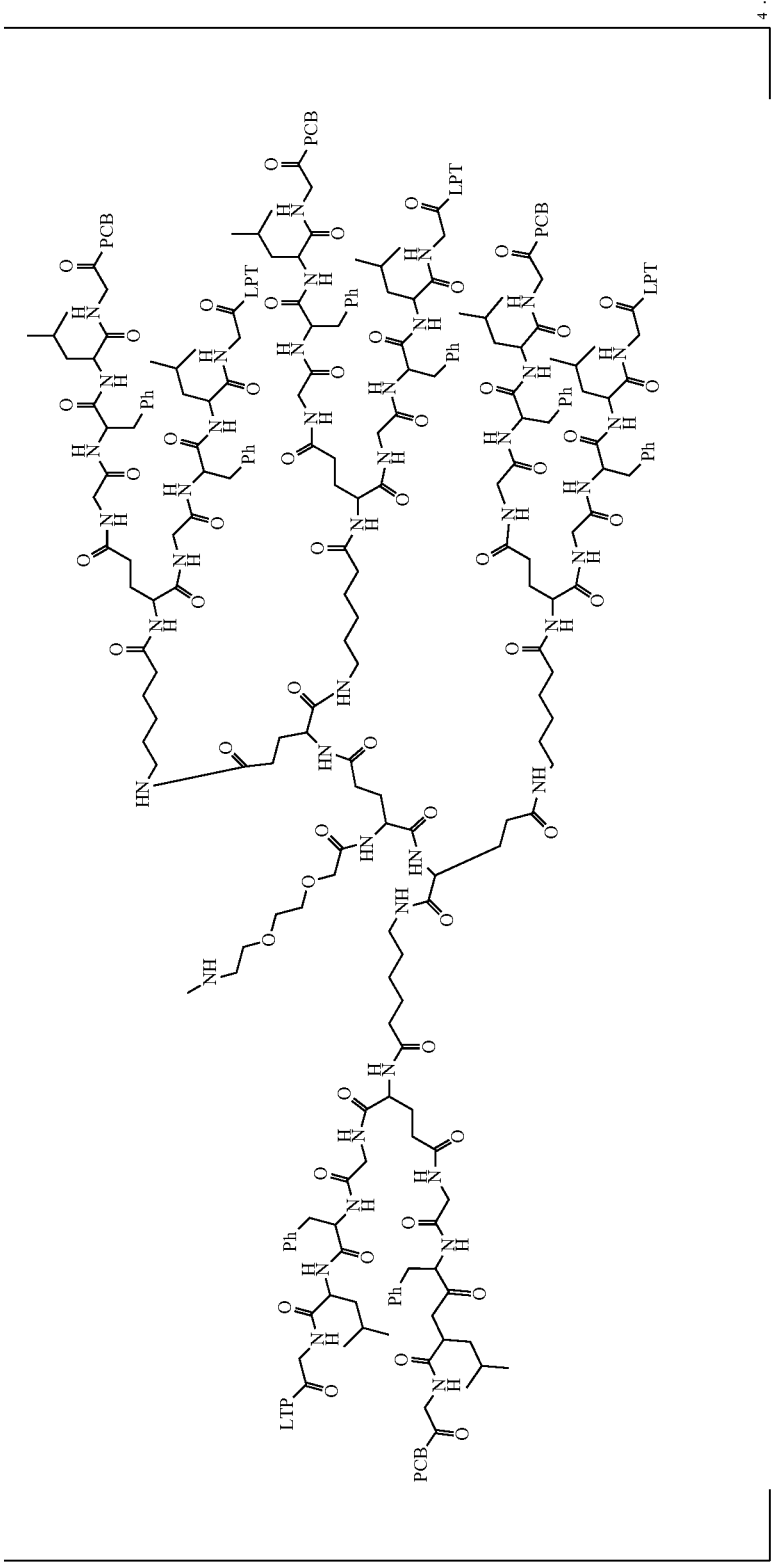

21. The pharmaceutical composition according to claim 15, wherein the pharmaceutical composition is made into an injection preparation.

22. The method according to claim 16, wherein the cancer is selected from colon cancer, leukemia, lymphoma, bladder cancer, bone cancer, brain tumor, medulloblastoma, glioma, breast cancer, adenoma/carcinoid, adrenal cortical cancer, pancreatic islet cell cancer, cervical cancer, endometrial cancer, ovarian cancer, colorectal cancer, skin cancer, esophageal cancer, eye cancer, gallbladder cancer, stomach cancer, head and neck cancer, liver cancer, melanoma, Kaposi's sarcoma, kidney cancer, oral cancer, lung cancer, nasopharyngeal cancer, neuroblastoma, ovarian cancer, pancreatic cancer, thyroid cancer, parathyroid penile cancer, prostate cancer, urethral cancer, vaginal cancer, vulvar cancer, anal cancer, and sarcoma, as well as metastasis of these cancers.

23. The injection solution according to claim 17, wherein the injection solution uses saline as a carrier.

* * * * *